US011484581B2

(12) United States Patent
Johnston et al.

(10) Patent No.: US 11,484,581 B2
(45) Date of Patent: Nov. 1, 2022

(54) METHOD TO CREATE PERSONALIZED CANINE CANCER VACCINES

(71) Applicant: ARIZONA BOARD OF REGENTS ON BEHALF OF ARIZONA STATE UNIVERSITY, Scottsdale, AZ (US)

(72) Inventors: Stephen Albert Johnston, Tempe, AZ (US); Luhui Shen, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 57 days.

(21) Appl. No.: 16/617,889

(22) PCT Filed: Jun. 1, 2018

(86) PCT No.: PCT/US2018/035744
§ 371 (c)(1),
(2) Date: Nov. 27, 2019

(87) PCT Pub. No.: WO2018/223094
PCT Pub. Date: Dec. 6, 2018

(65) Prior Publication Data
US 2021/0196805 A1    Jul. 1, 2021

Related U.S. Application Data

(60) Provisional application No. 62/514,689, filed on Jun. 2, 2017, provisional application No. 62/514,679, filed on Jun. 2, 2017.

(51) Int. Cl.
| A61K 39/00 | (2006.01) |
| A61P 35/00 | (2006.01) |
| A61K 9/00 | (2006.01) |
| G01N 33/50 | (2006.01) |
| G01N 33/574 | (2006.01) |
| A61K 39/39 | (2006.01) |

(52) U.S. Cl.
CPC ........ *A61K 39/0011* (2013.01); *A61K 9/0019* (2013.01); *A61K 39/39* (2013.01); *A61P 35/00* (2018.01); *G01N 33/505* (2013.01); *G01N 33/5011* (2013.01); *G01N 33/574* (2013.01); *A61K 2039/53* (2013.01); *A61K 2039/545* (2013.01); *A61K 2039/552* (2013.01)

(58) Field of Classification Search
CPC .......... C12N 2760/18122; C12N 15/86; C12N 2760/18144; A61K 2039/552; A61K 39/155; A61K 39/0011; A61K 2300/00; A61K 39/39; A61K 2039/70; A61K 2039/53; A61K 45/06; A61P 31/14; A61P 35/00; A61P 37/04; C07K 16/30; C07K 14/4748; C07K 2317/34; G01N 33/5011;
G01N 33/5047; G01N 33/505; G01N 33/54306; G01N 33/574; G01N 33/6878; C12Q 1/6897; C12Q 1/701
See application file for complete search history.

(56) References Cited

U.S. PATENT DOCUMENTS

| 5,601,989 | A | 2/1997 | Cheever et al. |
| 5,840,839 | A | 11/1998 | Wang et al. |
| 5,961,978 | A | 10/1999 | Gaudernack et al. |
| 6,759,046 | B1 | 7/2004 | Gaudernack et al. |
| 6,861,057 | B2 | 3/2005 | Gaudernack et al. |
| 7,078,416 | B2 | 7/2006 | Gaudernack et al. |
| 7,192,927 | B2 | 3/2007 | Gaudernack et al. |
| 7,375,117 | B2 | 5/2008 | Gaudernack et al. |
| 7,794,723 | B2 | 9/2010 | Gaudernack et al. |
| 7,863,244 | B2 | 1/2011 | Gaudernack et al. |
| 8,053,552 | B2 | 11/2011 | Von et al. |
| 8,193,326 | B2 | 6/2012 | Gaudernack et al. |
| 8,614,177 | B2 | 12/2013 | Gaudernack et al. |
| 8,796,414 | B2 | 8/2014 | Johnston |
| 8,821,864 | B2 | 9/2014 | Knebel-Doeberitz et al. |
| 9,115,402 | B2 | 8/2015 | Hacohen et al. |
| 9,205,140 | B2 * | 12/2015 | Kloor ................. A61K 39/0011 |
| 9,254,311 | B2 | 2/2016 | Bancel et al. |
| 9,265,816 | B2 | 2/2016 | Scheinberg et al. |
| 9,284,349 | B2 | 3/2016 | Tsunoda et al. |
| 9,340,830 | B2 | 5/2016 | Lipson et al. |
| 9,732,131 | B2 | 8/2017 | Johnston |
| 2002/0052308 | A1 | 5/2002 | Rosen et al. |
| 2004/0265803 | A1 | 12/2004 | Doeberitz |
| 2005/0239070 | A1 | 10/2005 | Von et al. |
| 2005/0244421 | A1 | 11/2005 | Strittmatter et al. |
| 2006/0194731 | A1 | 8/2006 | Gaudernack et al. |

(Continued)

FOREIGN PATENT DOCUMENTS

| AU | 2007220042 A1 | 9/2007 |
| CA | 2486738 A1 | 12/2003 |

(Continued)

OTHER PUBLICATIONS

Schiffman et al. Philos Trans R Soc Lond B Biol Sci. Jul. 19, 2015; 370 (1673) , p. 1-13.*
Vannelli et al., "Development of an autologous canine cancer vaccine system for resectable malignant tumors in dogs", Veterinary Immunology and Immunopathology, vol. 182, Dec. 31, 2016 (Dec. 31, 2016), pp. 95-100, XP029810135.
Zhang et al., "Frameshift Antigens for Cancer Vaccine Development", May 31, 2018 (May 31, 2018), XP055767123, Retrieved from the Internet: URL:https://core.ac.uk/download/pdf/157755541. pdf [retrieved on Jan. 20, 2021] * the whole document*.

(Continued)

*Primary Examiner* — Bao Q Li
(74) *Attorney, Agent, or Firm* — Knobbe, Martens, Olson & Bear, LLP

(57) ABSTRACT

Provided herein, are methods of treating cancer in dogs using personalized cancer vaccines comprising peptides having frameshift mutations caused by errors in transcription and splicing of an mRNA.

18 Claims, 17 Drawing Sheets

Specification includes a Sequence Listing.

(56) References Cited

U.S. PATENT DOCUMENTS

| | | | |
|---|---|---|---|
| 2008/0207483 | A1 | 8/2008 | Volinia |
| 2009/0186042 | A1 | 7/2009 | Johnston et al. |
| 2010/0111993 | A1 | 5/2010 | Tuereci et al. |
| 2011/0105721 | A1 | 5/2011 | Gaudernack et al. |
| 2012/0269858 | A1 | 10/2012 | Gaudernack et al. |
| 2013/0072660 | A1 | 3/2013 | Johnston et al. |
| 2013/0129760 | A1 | 5/2013 | Gaudernack et al. |
| 2013/0236490 | A1 | 9/2013 | Kalyanasundaram |
| 2013/0273002 | A1 | 10/2013 | Tuohy |
| 2014/0087963 | A1 | 3/2014 | Johnston et al. |
| 2014/0113286 | A1 | 4/2014 | Chan et al. |
| 2014/0170178 | A1 | 6/2014 | Kloor et al. |
| 2015/0079119 | A1 | 3/2015 | Johnston et al. |
| 2015/0241420 | A1* | 8/2015 | Johnston ............ G01N 33/6845 506/9 |
| 2016/0038579 | A1 | 2/2016 | Kloor et al. |
| 2016/0051654 | A1 | 2/2016 | Singh et al. |
| 2016/0051657 | A1 | 2/2016 | Varga et al. |
| 2016/0069895 | A1 | 3/2016 | Delamarre et al. |
| 2016/0101170 | A1 | 4/2016 | Hacohen et al. |
| 2017/0334963 | A1 | 11/2017 | Johnston |

FOREIGN PATENT DOCUMENTS

| | | | |
|---|---|---|---|
| CA | 2651796 | A1 | 9/2007 |
| EP | 1354895 | A1 | 10/2003 |
| EP | 1369126 | A1 | 12/2003 |
| EP | 1994181 | A2 | 11/2008 |
| EP | 2572725 | A1 | 3/2013 |
| JP | 2009532664 | A | 9/2009 |
| WO | WO-9532731 | A2 | 12/1995 |
| WO | WO-9958552 | A2 | 11/1999 |
| WO | WO-02051994 | A2 | 7/2002 |
| WO | WO-03084467 | A2 | 10/2003 |
| WO | WO-2004111075 | A2 | 12/2004 |
| WO | WO-2005076009 | A2 | 8/2005 |
| WO | WO-2005076099 | A1 | 8/2005 |
| WO | WO 2007/101227 | A2 | 9/2007 |
| WO | WO-2007101227 | A2 | 9/2007 |
| WO | WO-2010037395 | A2 | 4/2010 |
| WO | WO 2014/154905 | A1 | 10/2014 |
| WO | WO-2015103037 | A2 | 7/2015 |
| WO | WO-2015171747 | A1 | 11/2015 |
| WO | WO-2018222917 | A1 | 12/2018 |
| WO | WO-2018223092 | A1 | 12/2018 |
| WO | WO-2018223093 | A1 | 12/2018 |
| WO | WO-2018223094 | A1 | 12/2018 |

OTHER PUBLICATIONS

Extended Search Report issued in EP application No. EP 18810474, dated Jan. 21, 2021.
Yannelli et al., "Development of an autologous canine cancer vaccine system for resectable malignant tumors in dogs", Veterinary Immunology and Immunopathology, vol. 182, Dec. 31, 2016 (Dec. 31, 2016), pp. 95-100, XP029810135.
Bellone et al., Relevance of the Tumor Antigen in the Validation of Three Vaccination Strategies for Melanoma. J Immunol , 165 (5), 2651-6 (2000).
Berzofsky, J., et al. Progress on new vaccine strategies for the immunotherapy and prevention of cancer. J. Clin. Invest. 113(11):1515-1525 (Jun. 2004).
Cancer Facts and Figures 2016 Special Section: Cancer in Asian Americans, Native Hawaiians, and Pacific Islanders. American Cancer Society pp. 1-72.
Chan, TA et al. 5-day dosing schedule of temozolomide in relapsed sensitive or refractory small cell lung cancer (SCLC) and methyl-guanine-DNA methyltransferase (MGMT) analysis in a phase II trial. Journal of Clinical Oncology, 2012 ASCO Annual Meeting Abstracts. 30(15 Suppl) (May 20, 2012) Abstract No. 7052.
Chan, TA et al. Phase II Trial of Temozolomide in Patients with Relapsed Sensitive or Refractory Small Cell Lung Cancer, with Assessment of Methyl-guanine-DNA Methyltransferase as a Potential Biomarker. Clinical Cancer Research, 18(4):1138-1145 (Feb. 15, 2012).
Chang et al., Identifying recurrent mutations in cancer reveals widespread lineage diversity and mutational specificity. Nature Biotechnology 34(2): 155-163 (2016).
Chen, W. et al. Modification of Cysteine Residues In Vitro and In Vivo Affects the Immunogenicity and Antigenicity of Major Histocompatibility Complex Class I restricted Viral Determinants. The Journal of Experimental Medicine, 189(11):1757-1764 (Jun. 7, 1999).
Combination Vaccines and Multiple Vaccinations—Vaccine Knowledge Project University of Oxford. (http://vk.ovg.ox.ac.uk/combination-vaccines-and-multiple-vaccinations) Website Accessed Oct. 4, 2013.
Co-pending U.S. Appl. No. 16/617,805, filed Nov. 27, 2019.
Co-pending U.S. Appl. No. 16/617,830, filed Nov. 27, 2019.
Disis et al., HER-2/neu Oncogenic Protein: Issues in Vaccine Development. Critical Reviews in Immunology. 18(1-2): 37-45 (1998).
Donnelly et al., Technical and Regulatory Hurdles for DNA Vaccines. Int J Parasitol , 33 (5-6), 457-67 (2003).
Emens et al., Toward a Breast Cancer Vaccine: Work in Progress. Oncology (Williston Park) , 17 (9), 1200-11; discussion 1214, 1217-8 (2003).
Englehard, VH, Structure of peptides associated with class I and class II MHC molecules. Annu Rev Immunol. 12:181-207 (1994).
European Application No. 07757589 Supplementary Search Report dated Apr. 20, 2010.
Fidler, Selection of Successive Tumor Lines for Metastasis. Nature New Biology 242:148-149 (1973).
Finn, Cancer Vaccines: Between the Idea and the Reality. Nat Rev Immunol , 3 (8), 630-41 (2003).
Finn, Premalignant Lesions as Targets for Cancer Vaccines. J Exp Med 198 (11): 1623-1626 (2003).
Gite, S. et al. A high-throughput nonisotopic protein truncation test. Nature Biotechnology, 21(2):194-197 (2003) [Abstract Only].
Guo, C. et al. Past, Present and Future. Advances in Cancer Research, 119:421-475 (2013).
Hellmann, M. et al. Genomic profile, smoking, and response to anti-PD-1 therapy in non-small cell lung carcinoma, Molecular & Cellular Oncology, 3(1):e1048929 (3 pages) (2016).
International Application No. PCT/US18/35741 International Search Report and Written Opinion dated Sep. 7, 2018.
International Application No. PCT/US18/35744, International Search Report and Written Opinion dated Aug. 31, 2018.
International Application No. PCT/US2007/062920 International Search Report and Written Opinion dated May 16, 2008.
Jaffe, Vax Facts. The Scientist (2004).
"Kerr, C. Huntington's disease provides cancer clues. The Lancet, Oncology, 3(9):518 (2002)".
Kirovski, D. et al. Combinatorics of the Vaccine Design Problem: Definition and an Algorithm. Technical Report MSR-TR-2007-148. Microsoft Research (http://research.microsoft.com) (Nov. 2007).
Kloor, M. et al. The Immune Biology of Microsatellite-Unstable Cancer. CellPress Trends in Cancer 2(3):121-133 (Mar. 2016).
Konig, Interactions Between MHC Molecules and Co-Receptors of the TCR. Curr Opin Immunol , 14 (1), 75-83 (2002).
Korber, B. et al. Immunoinformatics Comes of Age. PLoS Computation Biology, 2(6):e71(9pages) (Jun. 2006).
Krieg, CpG Motifs: The Active Ingredient in Bacterial Extracts? Nat Med , 9 (7), 831-5 (2003).
Leaf, C. Why we're losing the war on cancer. Fortune, 149(6):76-82 (2004).
Lee, HoJoon. Identification of Neo-antigens for a Cancer Vaccine by Transcriptome Analysis. A Dissertation Presented in Partial Fulfillment of the Requirements for the Degree Doctor of Philosophy, Arizona State University. p. 1-168 (May 2012).
Lennerz et al. The response of autologous T cells to a human melanoma is dominated by mutated neoantigens. PNAS USA 102(44):16013-16018 (2005).
Lewis, J. Therapeutic cancer vaccines: using unique antigens. PNAS: 101 Supplement 2:14653-14656 (2004).

(56) References Cited

OTHER PUBLICATIONS

Leyssen et al., Prospects for Antiviral Therapy. Adv Virus Res , 61, 511-53 (2003).
Lin, Hong Huang et al. Evaluation of MHC class I peptide binding prediction servers: Application for vaccine research. BMC Immunology 9(8):1-13 (Mar. 16, 2008).
Lindahl, DNA Repair. DNA Surveillance Defect in Cancer Cells. Curr Biol , 4 (3), 249-51 (1994).
Linnebacher, M. et al. Frameshift Peptide-Derived T-Cell Epitopes: A Source of Novel Tumor-Specific Antigens, International Journal of Cancer, 93; 6-11 (2001).
Minev, Melanoma Vaccines. Semin Oncol , 29 (5), 479-93 (2002).
Nestle et al., Vaccines and melanoma. Clinical and Experimental Dermatology 27: 597-601 (2002).
No Author, Misguided cancer goal. Nature 491: 637 (2012).
Pawlik et al., Malignant Melanoma: Current State of Primary and Adjuvant Treatment. Crit Rev Oncol Hematol, 45 (3), 245-64 (2003).
PCT/US2018/03573 International Preliminary Report on Patentability dated Dec. 3, 2019.
PCT/US2018/035741 International Preliminary Report on Patentability dated Dec. 3, 2019.
PCT/US2018/035744 International Preliminary Report on Patentability dated Dec. 3, 2019.
Rammensee, H.G. et al. Peptides naturally presented by MHC class I molecules, Annu. Rev. Immunol. 11:213-244 (1993).
Rammensee et al., Towards patient-specific tumor antigen selection for vaccination. Immunological Reviews. 188:164-176 (2002).
Rappuoli, Rino et al. New Approaches to Vaccine Design, from Vaccine Design Innovative Approaches and Novel Strategies Eds: Rino Rappuoli and Fabio Bagnoli (2011) Caister Academic Press.
Renno et al., What's new in the field of cancer vaccines? Cellular and Molecular Life Sciences CMLS 60(7): 1296-1310 (2003).
Saeterdal et al., Frameshift-mutation-derived Peptides as Tumor-Specific Antigens in Inherited and Spontaneous Colorectal Cancer. Proc Natl Acad Sci U S A , 98 (23), 13255-60 (2001).
Saeterdal, I., et al. Frameshift-mutation-derived peptides as tumor-specific antigens in inherited and spontaneous colorectal cancer. PNAS 98(23):13255-13260 (2001).
Schultze JL et al. From cancer genomics to cancer immunotherapy: toward second-generation tumor antigens. Trends Immunol. 22(9):516-23 (Sep. 1, 2001).
Sette et al. The relationship between class I binding affinity and immunogenicity of potential cytotoxic T cell epitopes. J Immunol 153:5586-5592 (1994).
Shen, Luhui. Investigation of Tumor Frame Shift Antigens for Prophylactic Cancer Vaccine, Cancer Detection and Tumorigenicity. A Thesis Presented in Partial Fulfillment of the Requirements for the Degree of Doctor of Philosophy. Arizona State University. pp. 1-256 (Dec. 2012).
Snyder, Alexandra et al. Genetics and Immunology: reinvigorated, OncoImmunology, 4(10);e1029705 (2 pages) Oct. 2015.
Sorensen, S.A., et al. Significantly lower incidence of cancer among patients with Huntington disease. Cancer, 86(7):355-359 (1999) [Abstract Only].
Sussman, Personalized Cancer Vaccine Promises Remission. Drug Discov Today , 8 (15), 657-8 (2003).
Sykes et al., Genetic Live Vaccines Mimic the Antigenicity but not Pathogenicity of Live Viruses. DNA and Cell Biology 18(7): 521-531 (1999).
Sykes, K.F. et al., Linear expression elements: a rapid, in vivo, method to screen for gene functions. Nat. Biotechnology, 17(4):355-359 (1999).
Tang et al., Genetic Immunization Is a Simple Method for Eliciting an Immune Response. Nature , 356 (6365), 152-4 (1992).
Timares et al., Quantitative analysis of the immunopotency of genetically transfected dendritic cells. PNAS 95(22): 13147-13152 (1998).
U.S. Appl. No. 14/451,374 Final Office Action dated Dec. 27, 2016.
U.S. Appl. No. 15/669,666 Final Office Action dated Jan. 24, 2020.
U.S. Appl. No. 15/669,666 Office Action dated Sep. 30, 2019.
Usmani, Genomic Instability and Metastatic Progression. Pathobiology 61: 109-116 (1993).
Vogelstein, et al. Cancer genome landscapes. Science. Mar. 29, 2013;339(6127):1546-58. doi: 10.1126/science.1235122.
Wang, R. et al. Utilization of an alternative open reading frame of a normal gene in generation a novel human cancer antigen. The Journal of Experimental Medicine 183:1131-1140 (1996).
Weinschenk, Toni et al. Integrated Functional Genomics Approach for the Design of Patient-Individual Antitumor Vaccines, Cancer Research 62(20):5818-5827 (2002).
Woerner, SM et al. Systematic Identification of Genes with Coding Microsatellites Mutated in DNA Mismatch Repair-Deficient Cancer Cells, International Journal of Cancer, 93(1); 12-19 (2001).
Wolchok et al., Phase I Trial of High Dose Paracetamol and Carmustine in Patients With Metastatic Melanoma. Melanoma Res, 13 (2), 189-96 (2003).

* cited by examiner

Sec62 XM_846664.4 (11A)
WT: AAA GAA AAA AAA AAA GAT GGG GAA AAG GAA GAG CCT AAA
    K    E    K    K    K    D    G    E    K    E    E    P    K
                                1A Insertion 1A Ins: AAA GAA AAA AAA AAA AGA TGG GGA AAA GGA AGA GCC TAA
       K    E    K    K    K    <u>R    W    G    K    G    R    A    *</u>
                      1A Deletion
                          Insertion Frameshift Sequence 1A Del: AAA GAA AAA AAA AAG ATG GGA AAA AGG AAG AGC CTA AAA
      K    E    K    K    K    <u>M    G    K    R    K    S    L    K...</u>
                                Deletion Frameshift Sequence

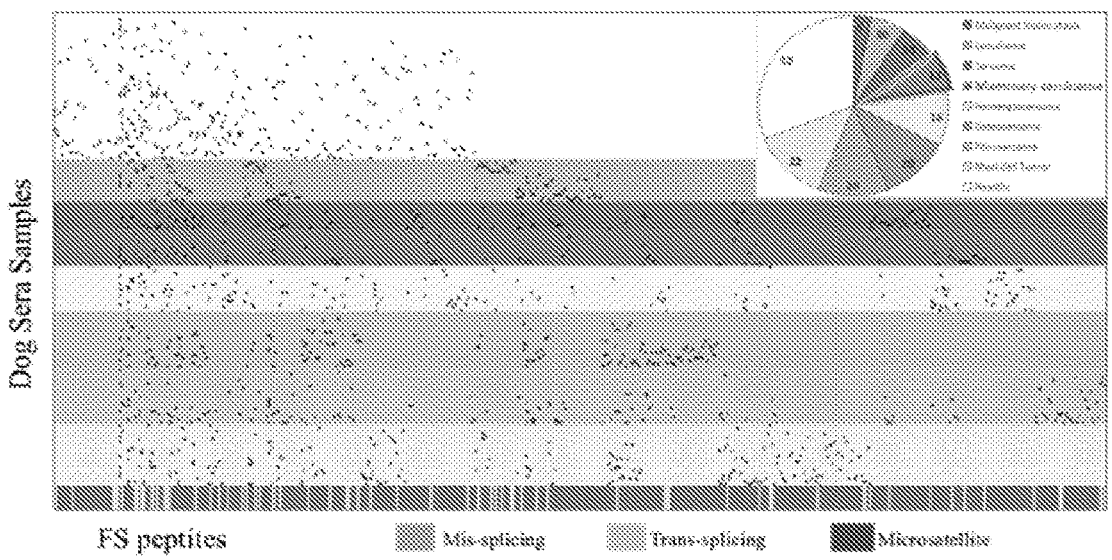
FIG. 9
A
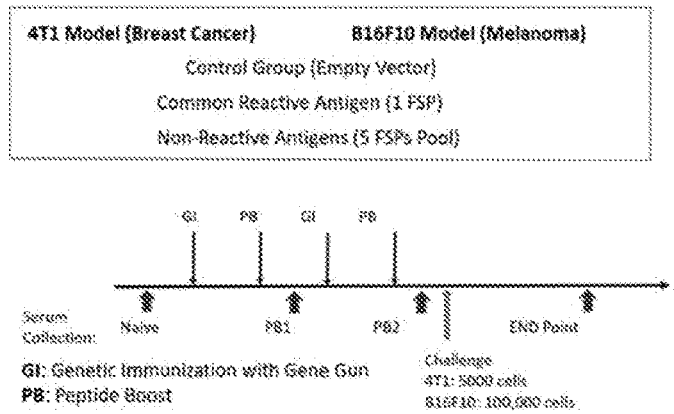
FIG. 10A
B
FIG. 10B

C

D

METHOD TO CREATE PERSONALIZED CANINE CANCER VACCINES

CROSS-REFERENCE

This application is a U.S. National Phase of International Application No. PCT/US2018/035744, filed on Jun. 1, 2018, which claims the benefit of U.S. Provisional Application No. 62/514,689, filed Jun. 2, 2017, and U.S. Provisional Application No. 62/514,679, filed Jun. 2, 2017, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 16, 2018, is named 42206-717_831_SL.txt and is 3,114,193 bytes in size.

BACKGROUND

There is a resurgence of enthusiasm to use the immune system to treat canine cancer. This is most notable with respect to using checkpoint inhibitors (as antibodies) to release the existing immune response in the patient to their own tumor. Yet, only a small proportion of the patients treated have a positive response. The evidence to date is that whether a patient has an effective response to the treatment depends on the nature of the immune response they have established against the tumor. More specifically, the level and quality of the immune response to neopeptides in the cancer seems to be most important. This has led to the concept of personal cancer vaccines to bolster the response of the inhibitors and therefore, to increase the response rate.

SUMMARY

Provided herein are methods of treating an individual in need of treatment for a cancer. Some such methods comprising, a) identifying peptides that are immunoreactive with a biological sample from the individual in a first population of peptides; b) preparing a vaccine composition comprising a second population of peptides comprising one or more peptides identified in step a) or a nucleic acid sequence encoding the second population of peptides; and c) administering an effective amount of the vaccine composition to the individual, thereby treating the cancer. In some cases, the method comprises obtaining the biological sample from the individual. Often, treating the cancer comprises reducing tumor size, inhibiting tumor growth, reducing tumor burden, increasing survival, or increasing cancer-free survival. In some cases, administering the vaccine composition elicits an immune response in the individual against the cancer. Sometimes, the second population of peptides is a subpopulation of the first population. Often, the identified peptide elicits a positive response in an antibody assay or a T cell assay performed on the biological sample from the individual. In some cases, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. Often, the biological sample comprises cells selected from B cells, T cells, CD4+ T cells, CD8+ T cells, Th17 cells, and combinations thereof. Alternatively and in combination, the biological sample comprises an antibody. Often, identifying comprises determining immunoreactivity of the first population of peptides to the biological sample using antibody reactivity. In some cases, antibody reactivity is detected using an antibody assay selected from the group consisting of ELISA, radio-immunoassay, western blot, surface plasmon resonance, immunostaining, immunoprecipitation, mass spectrometry, phage display, ELISPOT, flow cytometry, cytometric bead array, immunohistochemistry, high density array, microarray, delayed-type hypersensitivity (DTH), and combinations thereof. Alternately, or in combination, identifying comprises determining immunoreactivity of the first population of peptides to the biological sample using a T cell response. Often, the T cell response is detected using an assay selected from the group consisting of proliferation assay, 3H-thymidine assay, BrdU assay, CFSE assay, cytokine secretion assay, ELISA assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. In some cases, the first population of peptides comprises peptides encoded by a frameshifted mRNA expressed by a cancer cell. Sometimes, a frameshifted mRNA is created in a splicing error or a transcription insertion or deletion error. Often, the first population of peptides comprises peptides having a sequence selected from SEQ ID NO: 1-10665. In some cases, each of the first population of peptides binds to at least one MHC subtype. Sometimes, each of the first population of peptides comprises at least one T cell epitope. In some cases, each of the first population of peptides comprises at least on B cell epitope. Often, the first population of peptides is bound to a substrate. In some cases, the first population of peptides is part of an array or a phage display library. Often, the vaccine composition comprises a pharmaceutically acceptable adjuvant or excipient. Often, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+ TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan. In some cases, the vaccine composition comprises an immune checkpoint inhibitor. Often, the immune checkpoint inhibitor is selected from one or more of the group consisting of a PD-1 inhibitor, a PD-L1 inhibitor, and a CTLA-4 inhibitor. Often, the immune checkpoint inhibitor is selected from one or more of the group consisting of Pembrolizumab, Nivolumab, and Atezolizumab. Sometimes, the vaccine is administered via a route selected from the group consisting of subcutaneous, intradermal, intramuscular, intranasal, intravenous, and sublingual. In some cases, the individual is a mammal. In some cases, the individual is a dog. Often, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

Also provided herein are methods of eliciting an immune response in an individual having cancer. Some such methods comprising, a) identifying peptides that are immunoreactive with a biological sample in a first population of peptides; b) preparing a vaccine composition comprising a second population of peptides comprising one or more peptides identified in step a) or a nucleic acid sequence encoding the second population of peptides; and c) administering the vaccine composition to the individual, wherein administering the vaccine composition elicits an immune response in the individual against the cancer. In some cases, the method comprises obtaining the biological sample from the individual. Often, the method comprises treating the cancer. In some cases, treating the cancer comprises reducing tumor size, inhibiting tumor growth, reducing tumor burden, increasing survival, or increasing cancer-free survival. Often, the second population of peptides is a subpopulation of the first population. In some cases, the identified peptide elicits a positive response in an antibody assay or a T cell assay performed on the biological sample from the individual. In some cases, the immune response is a T cell response. Alternately, or in combination, the immune response is an antibody response. Often, the immune response is directed to a cancer. In some cases, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor. Often, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. In some cases, the biological sample comprises cells selected from B cells, T cells, CD4+ T cells, CD8+ T cells, Th17 cells, and combinations thereof. Alternately, or in combination, the biological sample comprises an antibody. Often, identifying comprises determining immunoreactivity of the first population of peptides to the biological sample using antibody reactivity. In some cases, antibody reactivity is detected using an antibody assay selected from the group consisting of ELISA, radio-immunoassay, western blot, surface plasmon resonance, immunostaining, immunoprecipitation, mass spectrometry, phage display, flow cytometry, cytometric bead array, immunohistochemistry, high density array, microarray and combinations thereof. In some cases, identifying comprises determining immunoreactivity of the first population of peptides to the biological sample using a T cell response. In some cases, the T cell response is detected using an assay selected from the group consisting of proliferation assay, 3H-thymidine assay, BrdU assay, CFSE assay, cytokine secretion assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. Often, the first population of peptides comprises peptides encoded by a frameshifted mRNA expressed by a cancer cell. In some cases, a frameshifted mRNA is created in a splicing error or a transcription insertion or deletion error in a microsatellite. Often, the first population of peptides comprises peptides having a sequence selected from SEQ ID NO: in 1-10665. In some cases, each of the first population of peptides binds to at least one MHC subtype. Often, each of the first population of peptides comprises at least one T cell epitope. In some cases, each of the first population of peptides comprises at least on B cell epitope. Often, the first population of peptides is bound to a substrate. In some cases, the first population of peptides is part of an array or a phage display library. Often, the vaccine composition comprises a pharmaceutically acceptable adjuvant or excipient. Sometimes, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan. Often, the vaccine composition comprises an immune checkpoint inhibitor. In some cases, the immune checkpoint inhibitor is selected from one or more of the group consisting of a PD-1 inhibitor, a PD-L1 inhibitor, and a CTLA-4 inhibitor. In some cases, the immune checkpoint inhibitor is selected from one or more of the group consisting of Pembrolizumab, Nivolumab, and Atezolizumab. Often, the vaccine is administered via a route selected from the group consisting of subcutaneous, intradermal, intramuscular, intranasal, intravenous, orally, intradermal and sublingual. In some cases, the individual is a mammal. Often, the individual is a dog.

Also provided herein are methods of reducing risk of developing cancer in an individual. Some such methods comprising, a) identifying peptides that are immunoreactive with a biological sample in a first population of peptides; b) preparing a vaccine composition comprising a second population of peptides comprising one or more peptides identified in step a) or a nucleic acid sequence encoding the second population of peptides; and c) administering the vaccine composition to the individual, wherein administering the vaccine composition elicits an immune response in the individual against the cancer and wherein the risk of developing cancer in the individual is reduced compared to an individual who did not receive the vaccine. In some cases, the method comprises obtaining the biological sample from the individual. Often, administering the vaccine composition elicits an immune response in the individual against the cancer. In some cases, the second population of peptides is a subpopulation of the first population. Often, the identified peptide elicits a positive response in an antibody assay or a T cell assay performed on the biological sample from the individual. Sometimes, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. Often, the biological sample comprises cells selected from B cells, T cells, CD4+ T cells, CD8+ T cells, Th17 cells, and combinations thereof. In some cases, the biological sample comprises an antibody. Often, identifying comprises determining immunoreactivity of the first population of peptides to the biological sample using antibody reactivity. In some cases, antibody reactivity is detected using an antibody assay selected from the group consisting of ELISA, radio-immuno assay, western blot, surface plasmon resonance, immunostaining, immunoprecipitation, mass spectrometry, phage display, ELISPOT, flow cytometry, cytometric bead array, immunohistochemistry, high density array, microarray, delayed-type hypersensitivity (DTH), and combinations thereof. Often, identifying comprises determining immunoreactivity of the first population of peptides to the biological sample using a T cell response. In some cases, the T cell response detected using an assay selected from the group consisting of proliferation assay, 3H-thymidine assay, BrdU assay, CFSE assay, cytokine secretion assay, ELISA assay, ELISPOT assay, intracellular staining assay, quantitative rtPCR assay, cytometric bead array assay, Cytotoxicity assay, 51-chromium assay, degranulation assay, granulysin assay, granzyme A assay, granzyme B assay, and perforin assay. In some cases, the first population of peptides comprises peptides encoded by a frameshifted mRNA expressed by a cancer cell. Often, a frameshifted mRNA is created in a splicing error or a transcription insertion or deletion error in a microsatellite. In some cases, the first population of peptides comprises peptides having a sequence selected from SEQ ID NO: 1-10665. Often, each of the first population of peptides binds to at least one MHC subtype. In some cases, each of the first population of peptides comprises at least one T cell epitope. Alternately, or in combination, each of the first population of peptides comprises at least on B cell epitope. In some cases, the first population of peptides is bound to a substrate. Often, the first population of peptides is part of an array or a phage display library. Often, the vaccine composition comprises a pharmaceutically acceptable adjuvant or excipient. In some cases, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan. Often, the vaccine composition comprises an immune checkpoint inhibitor. In some cases, the immune checkpoint inhibitor is selected from one or more of the group consisting of a PD-1 inhibitor, a PD-L1 inhibitor, and a CTLA-4 inhibitor. Often, the immune checkpoint inhibitor is selected from one or more of the group consisting of Pembrolizumab, Nivolumab, and Atezolizumab. In some cases, the vaccine is administered via a route selected from the group consisting of subcutaneous, intradermal, intramuscular, intranasal, intravenous, and sublingual. Often, the individual is a mammal. In some cases, the individual is a dog. In some cases, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

Also provided herein are methods of designing a personalized vaccine for an individual. Some such methods comprise a) identifying peptides that are immunoreactive with a biological sample in a first population of peptides; b) preparing a vaccine composition comprising a second population of peptides comprising one or more peptides identified in step a) or a nucleic acid sequence encoding the second population of peptides. In some cases, the method comprises obtaining the biological sample from the individual. Often, administration of an effective amount of the vaccine treats the cancer in the individual. In some cases, the cancer comprises reducing tumor size, inhibiting tumor growth, reducing tumor burden, increasing survival, or increasing cancer-free survival. Often, administering the vaccine composition elicits an immune response in the individual against the cancer. Sometimes, the second population of peptides is a subpopulation of the first population. Often, the identified peptide elicits a positive response in an antibody assay or a T cell assay performed on the biological sample from the individual. In some cases, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. Often, the biological sample comprises cells selected from B cells, T cells, CD4+ T cells, CD8+ T cells, Th17 cells, and combinations thereof. Alternately or in combination, the biological sample comprises an antibody. Often, identifying comprises determining immunoreactivity of the first population of peptides to the biological sample using antibody reactivity. In some cases, antibody reactivity is detected using an antibody assay selected from the group consisting of ELISA, radio-immuno assay, western blot, surface plasmon resonance, immunostaining, immunoprecipitation, mass spectrometry, phage display, flow cytometry, cytometric bead array, immunohistochemistry, high density array, microarray, and combinations thereof. Often, identifying comprises determining immunoreactivity of the first population of peptides to the biological sample using a T cell response. In some cases, the T cell response is detected using an assay selected from the group consisting of proliferation assay, 3H-thymidine assay, BrdU assay, CFSE assay, cytokine secretion assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. In some cases, the first population of peptides comprises peptides encoded by a frameshifted mRNA expressed by a cancer cell. Often, a frameshifted mRNA is created in by a transcription insertion or deletion error in a microsatellite in a coding region. In some cases, the first population of peptides comprises peptides having a sequence selected from SEQ ID NO: 1-10665. In some cases, each of the first population of peptides binds to at least one MHC subtype. Often, each of the first population of peptides comprises at least one T cell epitope. In some cases, each of the first population of peptides comprises at least on B cell epitope. In some cases, the first population of peptides is bound to a substrate. Often, the first population of peptides is part of an array or a phage display library. In some cases, the vaccine composition comprises a pharmaceutically acceptable adjuvant or excipient. Often, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan. Often, the vaccine composition includes an immune checkpoint inhibitor. In some cases, the immune checkpoint inhibitor is selected from one or more of the group consisting of a PD-1 inhibitor, a PD-L1 inhibitor, and a CTLA-4 inhibitor. Often, the immune checkpoint inhibitor is selected from one or more of the group consisting of Pembrolizumab, Nivolumab, and Atezolizumab. In some cases, the method further comprises administration of the personalized vaccine to the individual. Often, the vaccine is administered via a route selected from the group consisting of subcutaneous, intradermal, intramuscular, intranasal, intravenous, and sublingual. In some cases, the individual is a mammal. Often, the individual is a dog. In some cases, the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

BRIEF DESCRIPTION OF THE DRAWINGS

Certain novel features herein are set forth with particularity in the appended claims. A better understanding of the features and advantages of the present disclosure will be obtained by reference to the following detailed description that sets forth non-limiting and non-exhaustive illustrative embodiments, in which the principles of the invention are utilized, and the accompanying drawings of which:

FIG. 1A shows 1,259 10-aa peptides were generated using the same method for MHC I prediction, y axis was the best prediction percentile rank for each peptide, reference to human HLA types is used. FIG. 1B shows 1,242-point mutation peptides were somatic cancer genome missense point mutations, 20 aa peptides were generated from the point mutation site, same number of 20-aa MS FS peptides and paired WT peptides were used for comparison, y axis was number of hits with percentile rank <10 in MHC II prediction.

FIG. 8A shows an example of 500 most common positive FSPs and 500 negative FSPs form 8 different dog cancers (BC: breast cancer, n=12; FSA: fibrosarcoma, n=5; HSA: hemangiosarcoma, n=12; LC: lung cancer, n=12; MCT: master cell tumor, n=14; MEL: melanoma, n=12; OSA: osteosarcoma, n=17, STS: soft tissue sarcoma, n=12) and 81 non-cancer normal controls. Each red spot indicates the serum sample (Y axis) has positive antibody reactivity to the FSP (X axis). The positive cut off value of each peptide was calculated by the average plus two fold of standard deviation of the normal controls' signal of that peptide. FIG. 8B shows an example of personalize FS antigens selection for 4 OSA patients. 20 FS positive antigens were selected from the highest IgG activity fold change to the cut-off value in each patient. FIG. 8C shows an example of personalized FS antigen selection for 4 MCT patients.

FIG. 9 shows an FSP array analysis of dog serum. 8 types of 116 dog cancer serum and 52 non-cancer serum were analyzed by the small FSP array. Each red spot indicates the serum has positive antibody reactive with this peptide.

FIG. 10A, FIG. 10B, FIG. 10C, and FIG. 10D show reactive FSPs showed protection in the mouse melanoma and breast cancer models. FIG. 10A shows reactive and non-reactive FSPs from the same microsatellite frameshift antigen of CIS (SEQ ID NO: 1524). FIG. 10B shows 3 groups of mice were used: the control group was immunized with control plasmid, non-reactive FSPs pool and reactive FSP. All 3 groups received 2 rounds of genetic immunization with gene gun and peptide boost via subcutaneous injection. The B16F10 cell line was used for the melanoma model and the 4T1 cell line was used for breast cancer model. Each group had 10 mice. FIG. 10C shows reactive FSPs slowed tumor growth significantly compared to the non-reactive FSPs pool and the control group in the melanoma model (student's t-test, p-value <0.01), error bar represented mean±SEM. FIG. 10D shows the Reactive FSPs offered tumor protection in mouse breast cancer model as well. The tumor volume was significantly lower than control group and non-reactive FSPs pool group (student's t-test, p-value <0.05).

FIG. 13A shows a corner of the scanned FS array of each cancer dog analysis. FIG. 13B shows normalized antibody active to each peptide of each dog with cancer. Both FIG. 13A and FIG. 13B showed each dog has personal highly reactive FS peptides.

FIG. 15A shows a trial schedule. FIG. 15B shows ELISA analysis of the IgG reactive to the vaccine. FIG. 15C shows IFN-r ELISPOT analysis of the T cell response to the vaccine.

FIG. 16A shows tumor growth curve by three MS FS antigens immunization with 4T1-BALB/c tumor model. Mice (n=10 per group) were genetically immunized at 8 weeks of age, boosted twice genetically 3 weeks later with two days apart and another peptide boost 2 weeks later. Mice were challenged 2 week later by subcutaneous injection of $5 \times 10^3$ 4T1 cells. All vaccine groups significantly delayed tumor growth. FIG. 16B shows ELISPOT analysis of the three MS FS antigen immunization. Three mice were genetically immunized with pool of the three MS FA antigens and genetically boosted 6 weeks later. Immunized mice were challenged by $5 \times 10^3$ 4T1 cells 3 weeks later. Splenocytes were collected at 19 days after tumor challenge and pool three splenocytes for the assay.

Error Bars Represent SD.

Figure 17A:
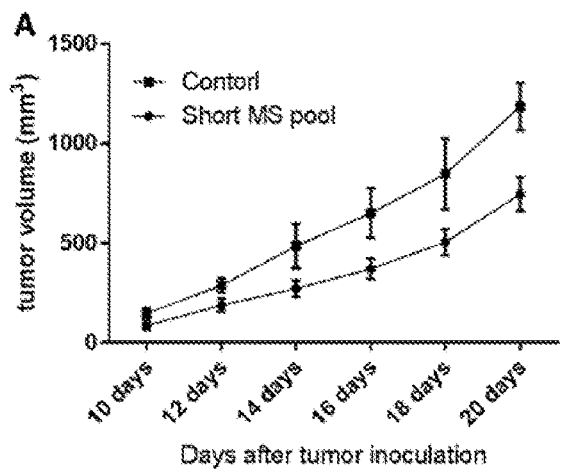
Figure 17B:
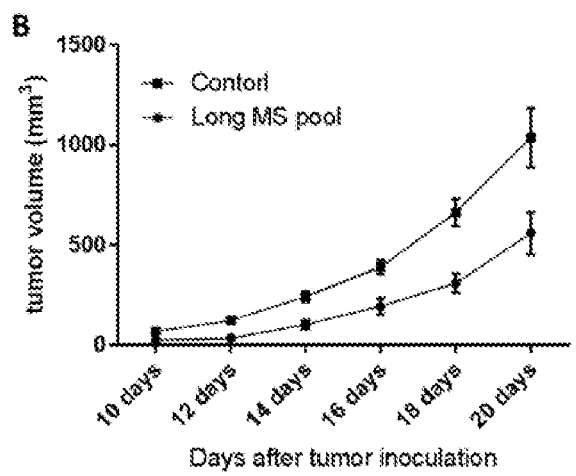

FIG. 17A and FIG. 17B show that FSPs have significant protection as vaccine candidates in different mouse tumor model. Tumor growth of curve the vaccine test of the two FSPs pool from short and long MS in 4T1-BALB/c tumor model. FIG. 17A shows tumor growth curve with short MS FSPs vaccine group. FIG. 17B shows tumor growth curve with long MS FSPs vaccine group.

Figure 18A:
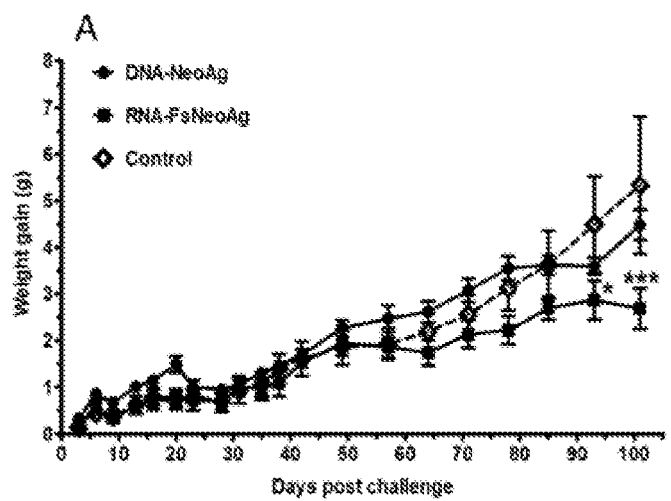
Figure 18B:
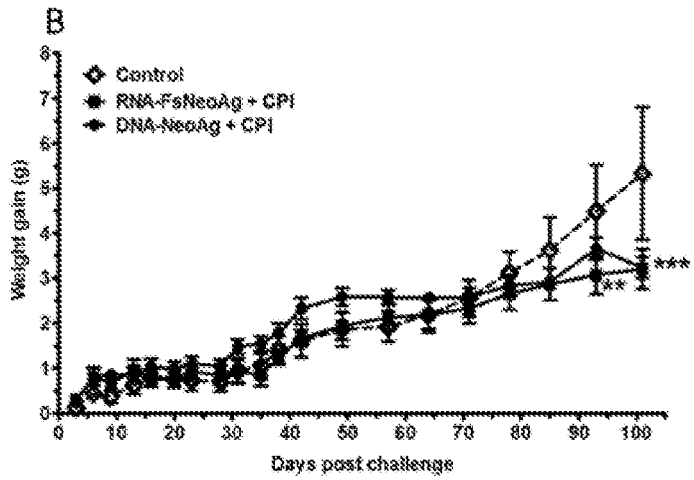

FIG. 18A and FIG. 18B show that FSPs have significant protection as vaccine candidates in different mouse tumor model. Therapeutic immunization with FS antigens against ovarian cancer in mouse model. FIG. 18A shows female C57BL/6 mice (n=10) were challenged intraperitoneally with 1D8 ($5 \times 10^5$ cells/mice) at day 0 and then, immunized subcutaneously 3 times with pool of FSPs (RNA-FsNeoAg) (10 FS from MS INDEL and 3 FS from mis-splicing) or neo antigens from DNA mutations (DNA-NeoAg) at days 3, 6 and 78. Control group mice were injected PBS buffer. FIG. 18B shows the vaccine group received additionally a checkpoint inhibitor treatment (CPI) composed by antibody anti-PD-L1 and CTLA-4, six times divided in two sets. Mice were weighing once a week until reach endpoint.

Figure 19:
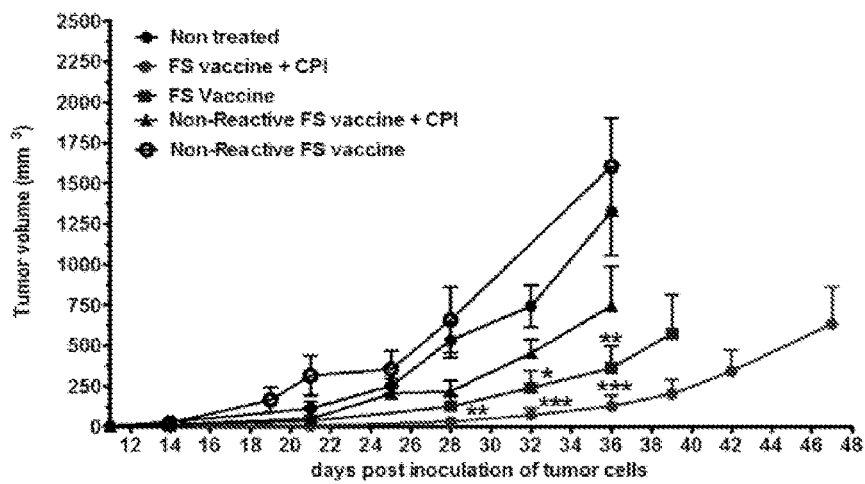

FIG. 19 shows the SPCV system successfully identified protective personalized cancer vaccines in two mouse tumor models. Protection by personalized pool FS neoantigens in 4T1 BALB/c tumor model. Serum from BALB/c mice (n=10/group) were collected two days previous and 7-days post subcutaneous injection of 4T1 tumor cells (500 cells/mouse). Both sera were run on microarray slides containing peptides for human FS neoantigens and the 10 mouse homologs neoantigens with higher median normalized signal on the array were selected as targets for the vaccines formulations for each mice. Mice were vaccinated subcutaneously on days 12 and 19. For the immunization group with the combined immunotherapy, the antibody treatment, anti-PD-L1 and CTLA-4, were administrated intraperitoneally on days 12, 15, 19, 22. Control group (non-treated) was immunized with PBS at the same schedule as the vaccine groups. Non-reactive groups were immunized with FS antigens without signal in the microarray before and after tumor challenge, and followed the same vaccine regimen as the other groups. *$p<0.05$; $p<0.01$; *$p<0.001$, analyzed by two-way ANOVA with Bonferroni multiple comparisons post-test.

Figure 20:
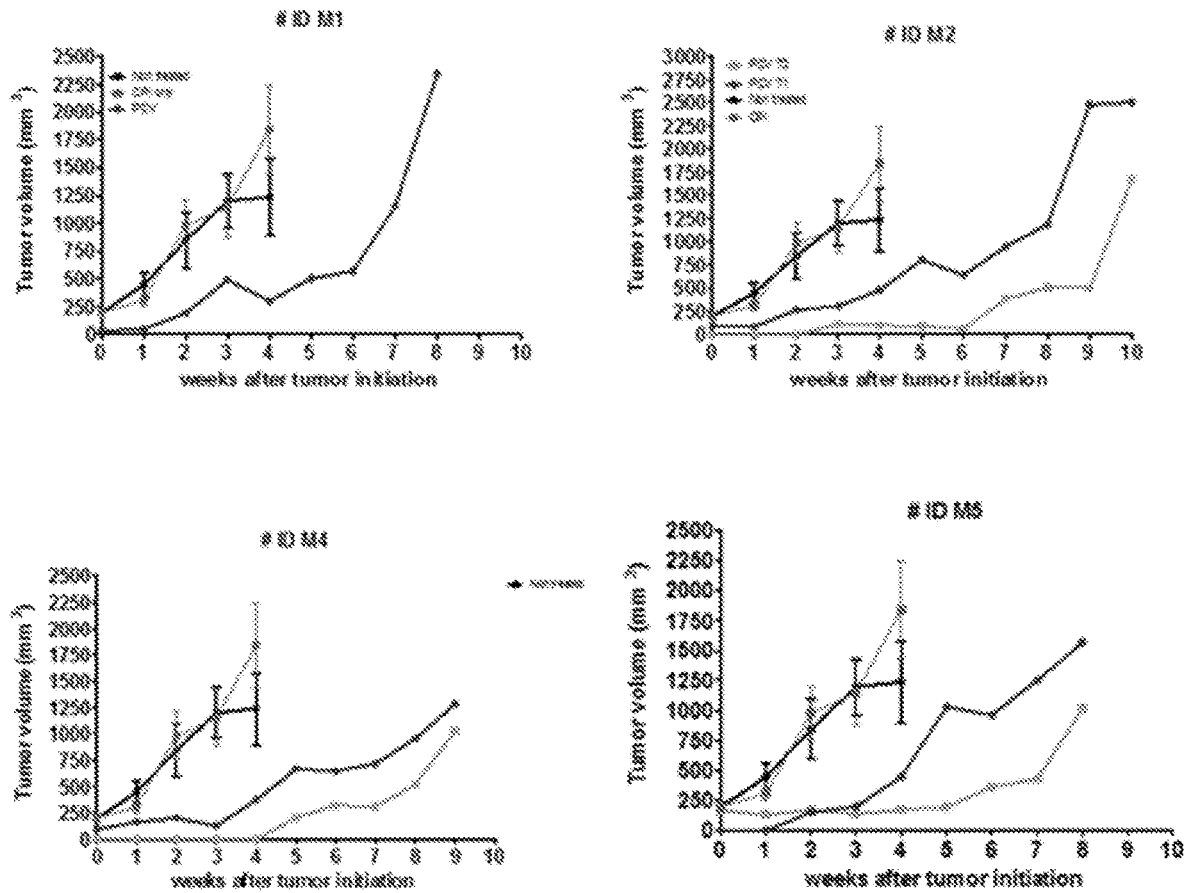
Figure 20:
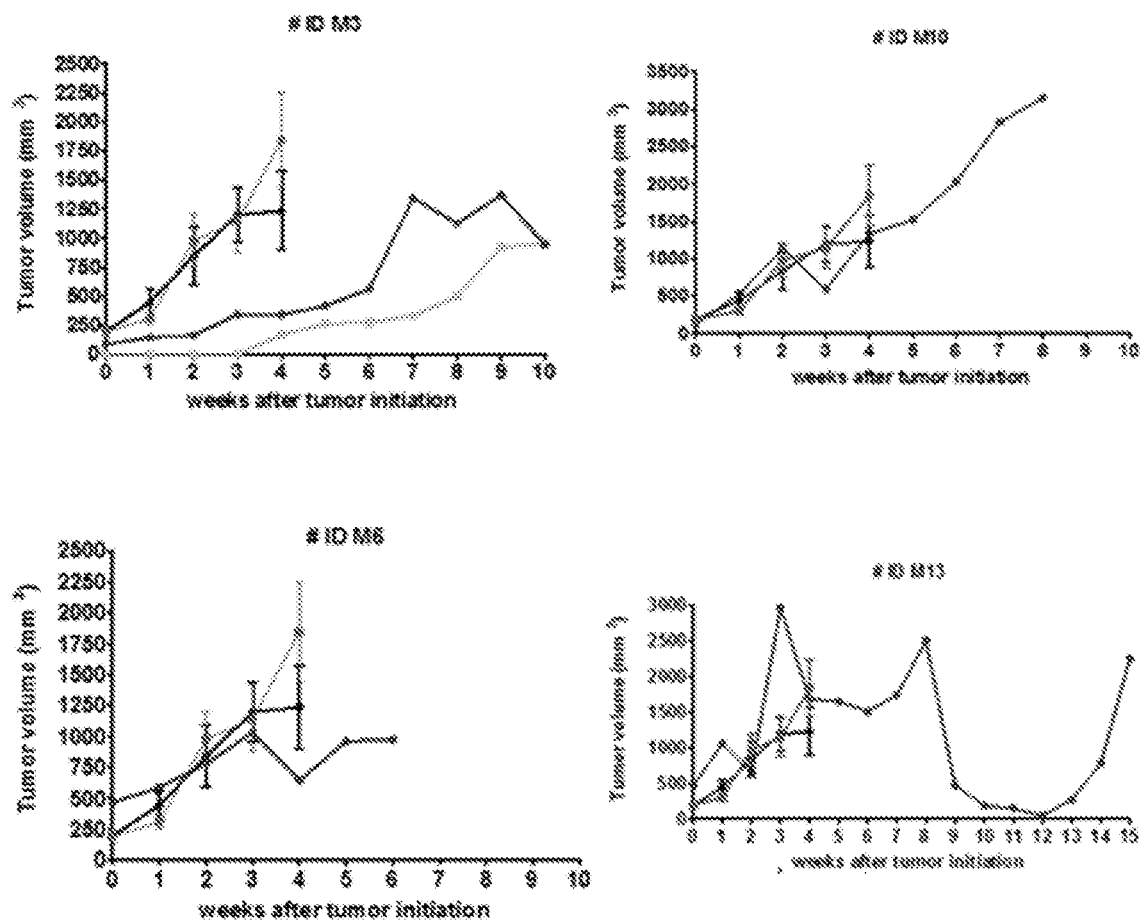
Figure 20:
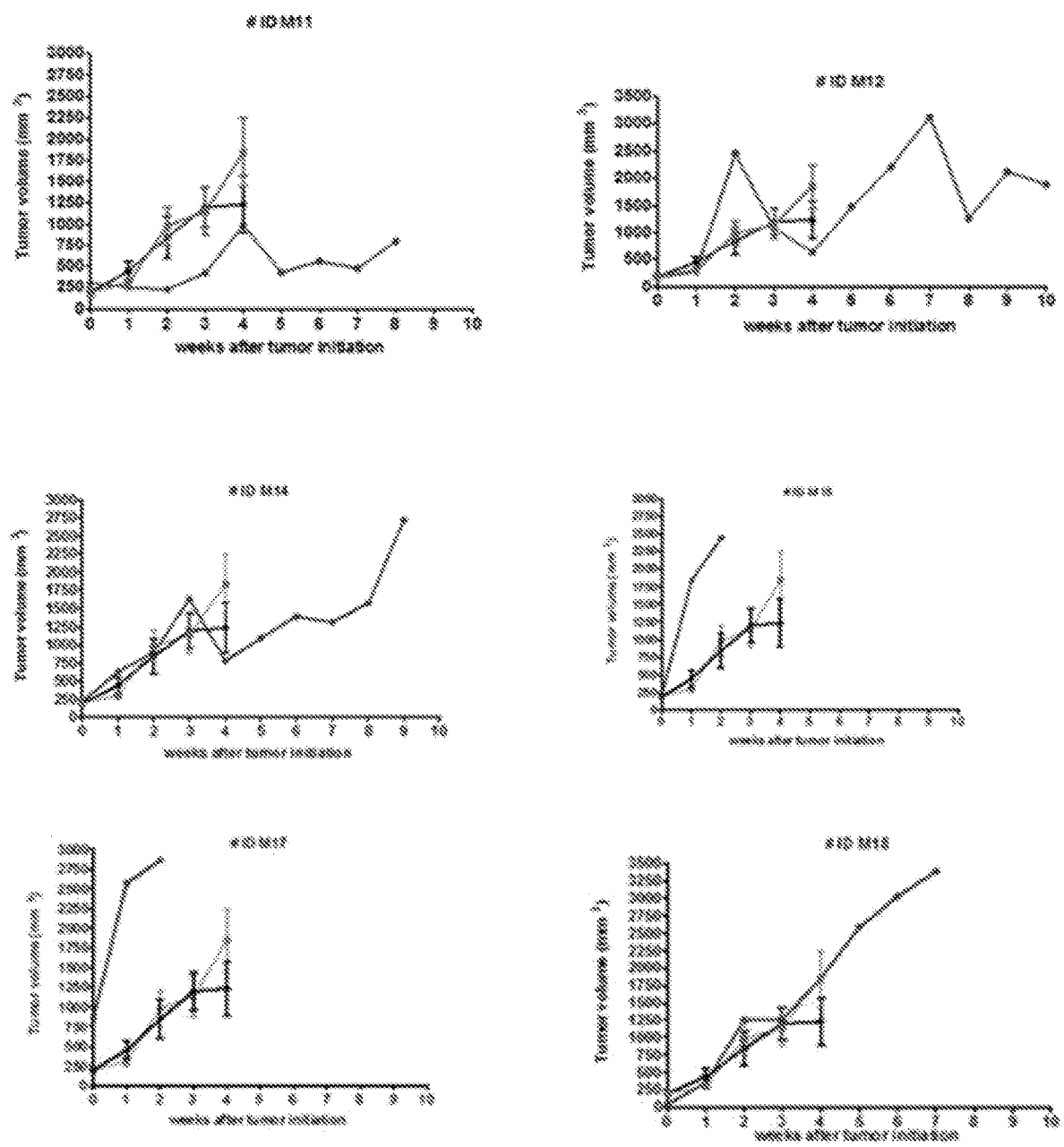
Figure 20:
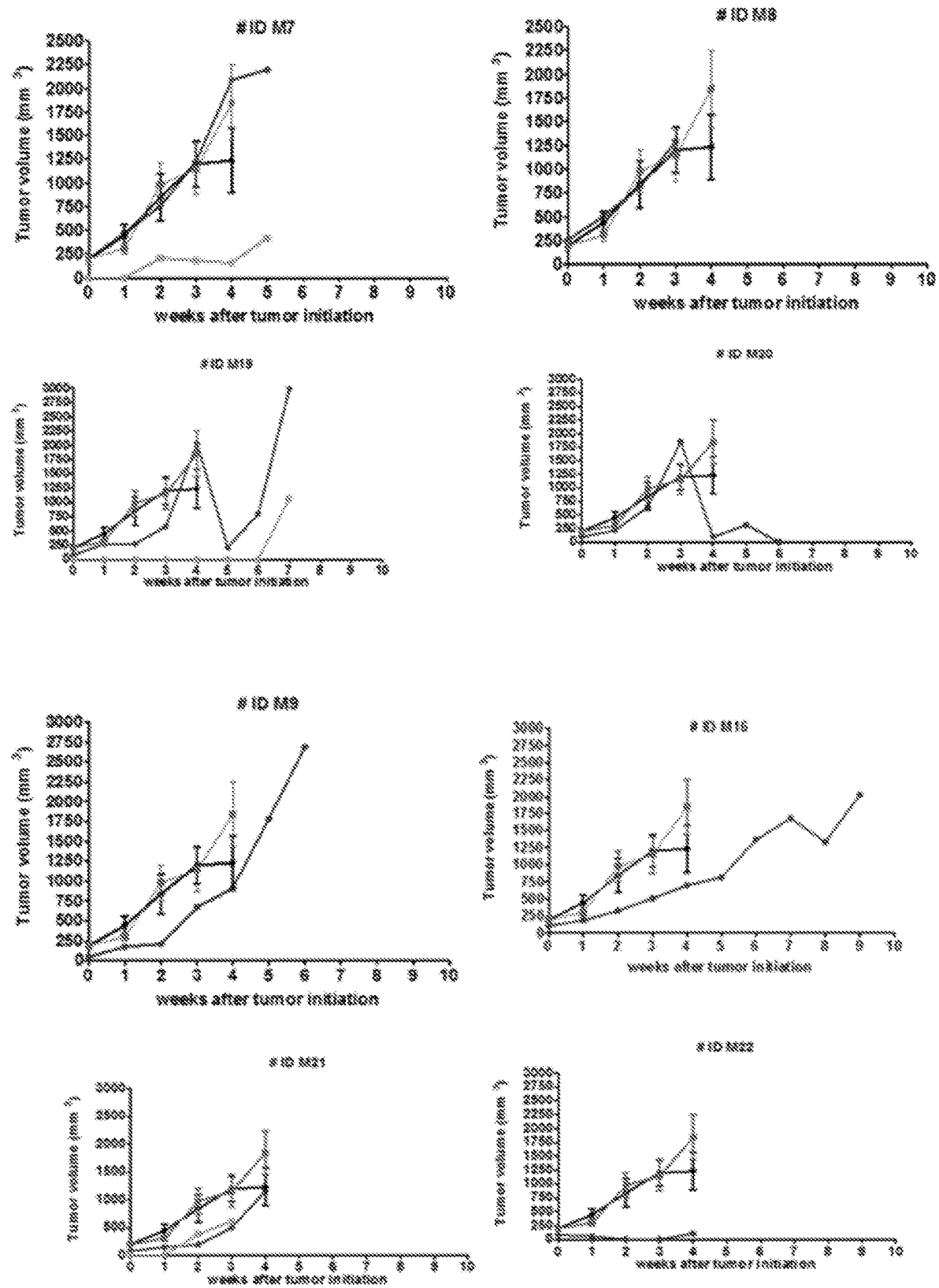

FIG. 20 shows the SPCV system successfully identified protective personalized cancer vaccines in two mouse tumor models. Female FVB/N mice (n=22) were evaluated weekly for the presence of palpable tumor, when tumor was detected sample blood was collected and run on microarray slides containing peptides for human FS neoantigens. The 10 mouse homologs neoantigens with higher median normalized signal compared to age matched FVB/NJ samples on the array were selected as targets for the vaccines formulations for each mice. Mice were vaccinated subcutaneously with pool of FS peptide with minimum two doses and maximum seven doses, as needed to maintain tumor control, with intervals 1-2 weeks between doses. Each vaccine dose was followed by checkpoint inhibitor treatment (antibody anti-PD-L1 and anti-CTLA-4) (CPI), two doses, three days a part. As a control group, we immunized animals with PBS (non-treated) at the same schedule as the vaccine groups or only with CPI treatment (CPI only), twice per animal. Personalized FS vaccine conferred 68.2% of protection.

DETAILED DESCRIPTION

Figure 1A:
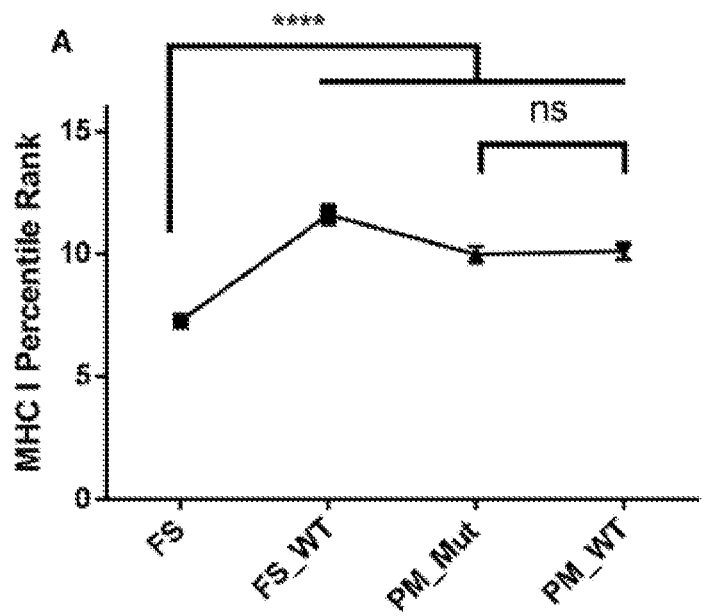
FIG. 1A and FIG. 1B show a bioinformatics comparison demonstrating that FS are superior neo-antigens to point mutations. MHC Class I and II prediction for MS FS peptides and point mutation peptides. FS: MS FS peptide, FS_WT: FS peptide paired WT peptide, PM_Mut: point mutated peptide, PM_WT: point mutation paired WT peptide. Reference to human HLA types is used.
Figure 1B:
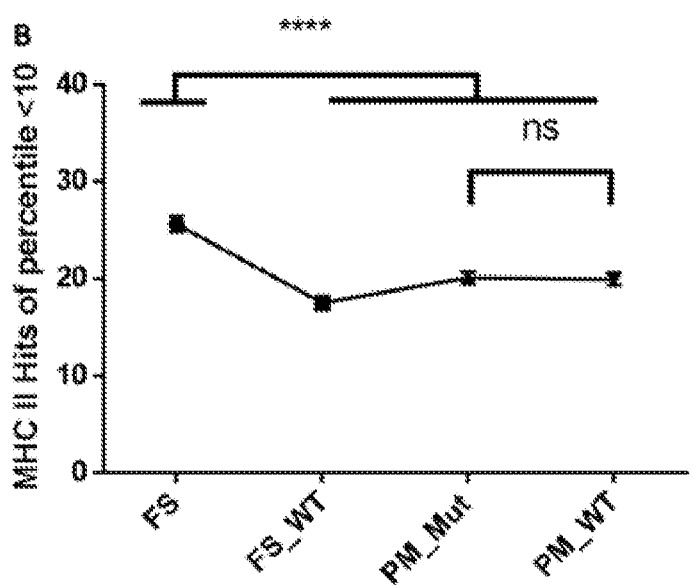

Provided herein is a novel approach to personalized cancer vaccines that overcome the limitations of conventional methods. The advent of the use of immunotherapeutics has resulted in emphasis on the importance of neo-epitopes in the immune response to cancer. Neo-epitopes are peptides that are normally not produced to an immunologically recognized level in healthy cells, but are so in tumors. They are essentially foreign epitopes. Of the neo-epitopes, frameshifts peptides (FS) are the best antigens as shown in FIG. 1. FS neo-antigens were the basis for the first tumor agnostic approval of a checkpoint inhibitor. It has been established based on sequencing the DNA of ~100,000 tumors that millions of neo-antigens are produced by tumors, with very few of them repeated in different tumors, even among tumors the same type and FS at the DNA level are very rare. Therefore, conventionally, it has been thought that to develop a personalized cancer vaccine, each tumor would need to be sequenced as well as the non-tumor cells (germline) for each person. Further, it is not feasible to create a library of all the possible neo-antigens to create a personal vaccine. Therefore, each set of neoantigens would have to be customized and manufactured for each patient after the determination of the appropriated vaccine components. Since most neo-antigens are the product of point mutations, and only a small portion of these are immunogenic (~3%) in patients, current methods involve application of a complicated informatics approach to predict the best vaccine components. The current basic concept as described in the art is that personal neoantigens in one's tumor are developed by sequencing the patient's tumor. The germline sequence of the patient would also be analyzed for comparison purposes. The developed neoantigens Would then be informatically screened to predict which are likely to be immunogenic, and a vaccine manufactured for these particular antigens and delivered in a timely fashion to the patient. In some instances, it is envisioned that this personal vaccine would be delivered with a checkpoint inhibitor. However, personal cancer vaccine development and the checkpoint inhibitor are both expensive. We have developed a system to create a personal vaccine that is much faster and less expensive than existing methods, yielding more immunogenic antigens for a personal cancer vaccine.

Figure 2:
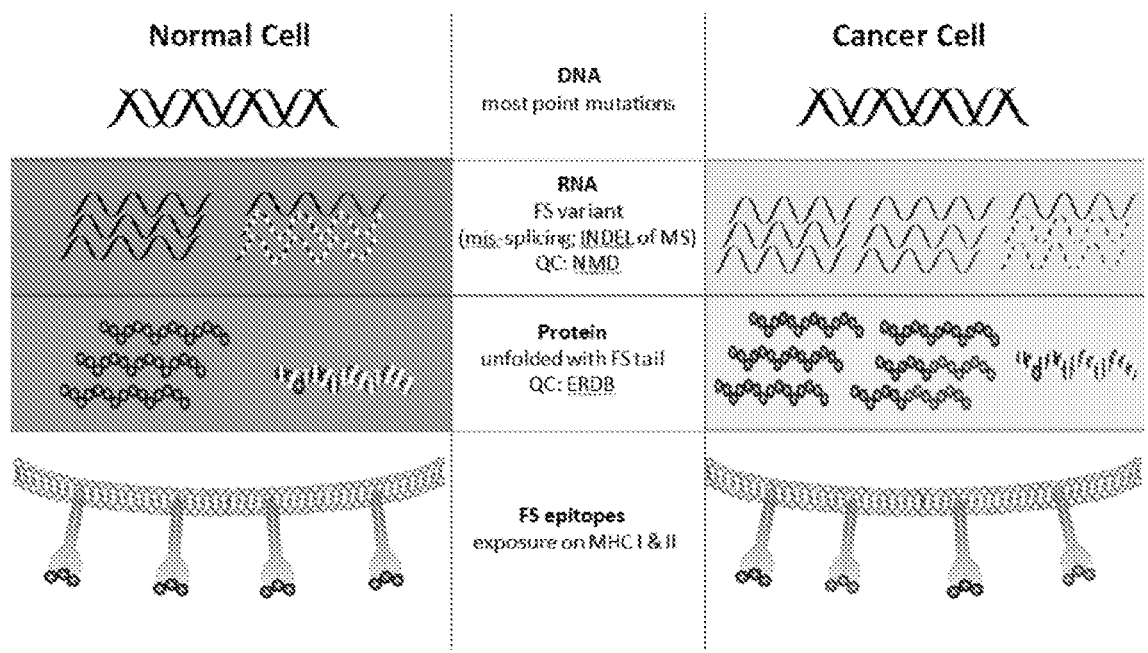
FIG. 2 shows a model of the FS antigens from the FS RNA variants and illustrates the basic theory behind the importance of RNA generated FS peptides from mis translation through microsatellites. Normal Cell: Errors in DNA replication are very low and repaired. Transcription error rates are higher but also rare as are mis-splicing in intron excision. Any frameshift (FS) transcript with premature stop is the degraded target of nonsense-mediated decay (NMD). Aberrant proteins, including those with frame-shifts are largely eliminated by the protein quality control system. The net result is that very few FS peptides are presented on MHC I/II or escape the cell to be presented to the immune system. Cancer Cell: In general more RNA is produced and increased error rates are observed at the DNA, RNA, and protein levels. More errors are made in DNA replication, but only in dividing cells. Most DNA mutations are single nucleotide changes and encode low or non-immunogenic peptides. Transcription is generally less accurate, especially through microsatellites (MS), producing insertions and deletions (Indels). Most transcribed genes with MSs in the coding region will have more FS transcripts. RNA splicing is also far less accurate in cancer cells, creating more FS transcripts from each out of frame splicing between exons form the same gene and different genes. The large increase of the FS transcripts from Indels of MS and mis-splicing overwhelms RNA quality control systems, such as NMD. Consequently, more truncated proteins with the FS peptide will be translated. These un-folded proteins, combining with aberrant proteins from other variants, overwhelms the protein quality control system leading to more FS peptides being presented on MHC II and mis-secreted or released from the cancer cell and elicit an immune response.
Figure 3:
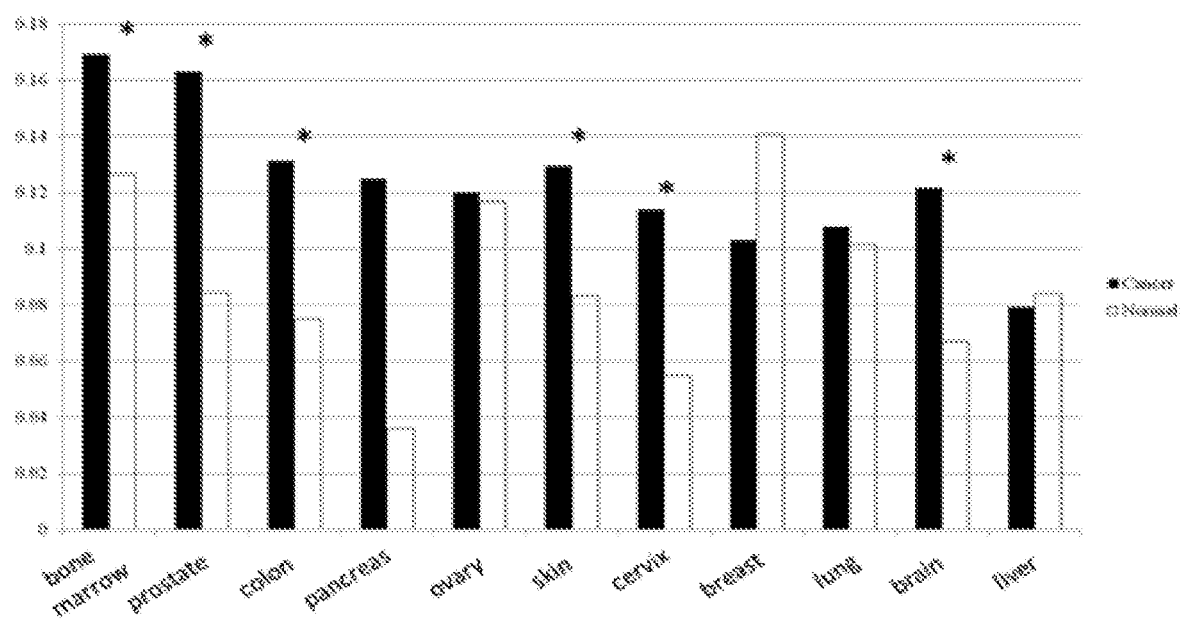
FIG. 3 shows cancer ESTs have more MS INDELs than normal ESTs. Analysis of homopolymer (repeat bp>6) MS INDEL rate in EST database between different cancer and normal libraries.* indicate P<0.0001.
Figure 4:
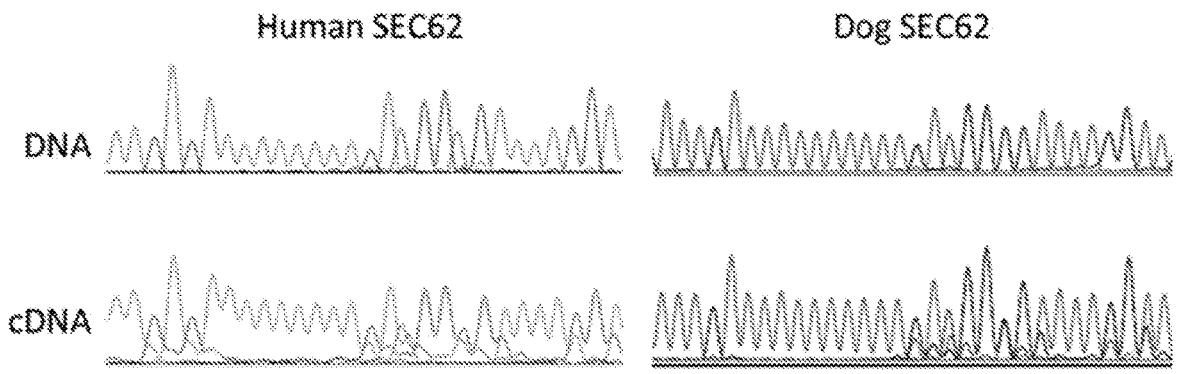
FIG. 4 shows MS INDELs only exist in RNA not DNA. Examples of the sequence traces of MS region in SEC62 homolog genes in paired DNA/cDNA samples. Four human breast cancer cell lines were sequenced: HTB26, CRL2315, CRL1504, CRL2326; 5 dog mast cell tumors and 3 dog carcinomas. They all showed similar pattern, where the A MSs have an A insertion in RNA not in DNA.
Figure 5:
FIG. 5 shows how an insertion or deletion in transcription of a MS would each produce a different FS peptide. This figure shows an example of frameshift peptides produced by either an insertion or deletion in the A MS in the Sec62 gene. Figure discloses SEQ ID NOS 10669-10674, respectively, in order of appearance.
Figure 5:

We have discovered that a smaller subset of neo-antigens ("frameshift neo-antigens") can be utilized to develop a personalized cancer vaccine. This is an important advance because the number of frameshift (FS) neo-antigens is much smaller than the total of all possible neo-antigens. We have discovered that FS peptides are frequently and recurrently produced in tumor cells. These FS peptides are produced by insertion and deletion variants (INDELS) occurring in microsatellite regions or by mis-splicing of RNA (FIG. 2). The microsatellite generated FS are predictable and will be made in each tumor that expresses the gene containing them. The mis-splicing events are also predictable and the ones that actually occur are detectable by the FS peptide arrays described. Our discovery that FS antigens occur more frequently and more recurrently in different tumors in the RNA by transcription or mis-splicing is surprising (FIG. 3). These INDEL variants only exist in the RNA, not in the DNA (FIG. 4). There are approximately 14,000 potential FS peptides transcribed from microsatellites in exons and approximately 200,000 potential FS from mis-splicing. We have also discovered that tumors make INDEL variants (FIG. 5) in most microsatellites and that mis-splicing is also recurrent at the same genes in tumors. We can also further limit the number of candidate FS peptides by restricting them to ones that are at least 8 amino acids long and/or in oncogenes, essential genes and or highly expressed genes. These genes would be more difficult for a tumor to evolve away from. Therefore, it is only necessary to screen a limited number of approximately 1000 to 200,000 FS peptides to determine the components of a personal vaccine. This screen can be done in a day or less, rather than a month or more by current practice, and at much lower cost.

Most importantly, there is no dog personal cancer vaccine available and even in the trial. With the matured DNA sequence and analysis pipeline, the human personal cancer vaccine as currently envisioned would cost>$50,000. Dog DNA sequence and analysis is much more difficult, and the cost of such vaccine should not be affordable to most owners. Disclosed herein are several methods and systems for such non-sequencing based screens. All approaches to date described in the art begin with sequencing the DNA and RNA of the patient. An important aspect of our approach is that our immunological screens indicate that the FS peptides are produced by the tumor and are reactive with the immune system, which is not the case with current protocols which only sequence the RNA to determine if the gene is transcribed. Further, the number of candidate FS antigens could be restricted to a low enough number to allow the vaccine components, i.e. frameshift neo-antigens, to be pre-synthesized and the personal vaccine readily formulated for each patient. This potentially simplifies regulatory approval of the personal vaccine approach by making uniform certain constituents of the personal vaccine across patient populations.

Figure 6:
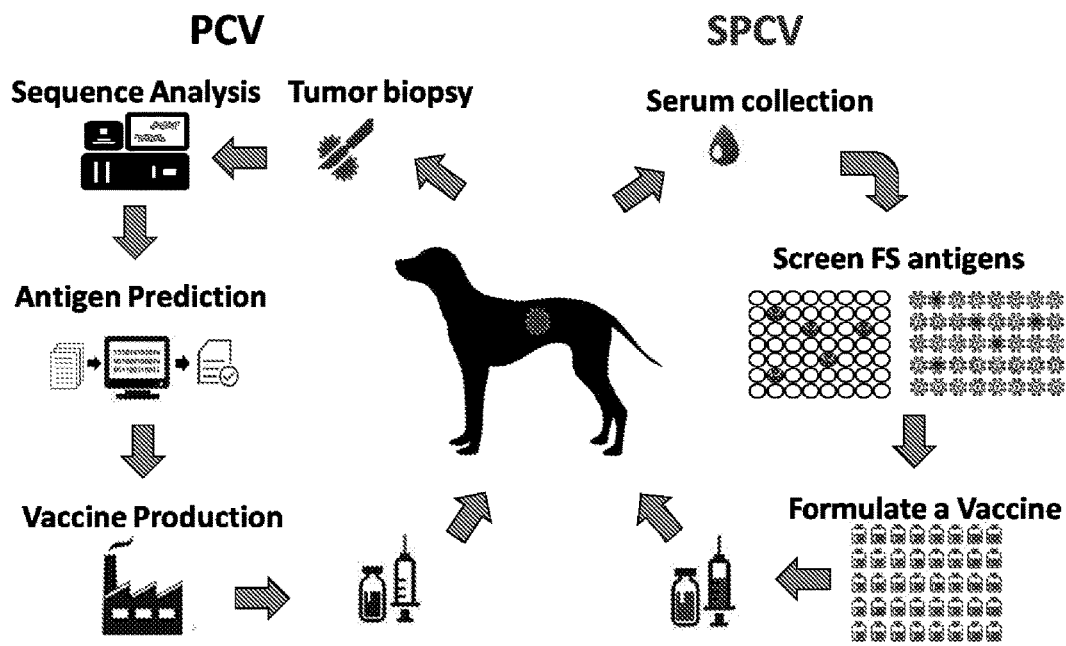
FIG. 6 shows a comparison of the current approach to making personal cancer vaccines (PCV) versus a much simpler and faster system (SPCV).

A comparison of the current approach to making personal cancer vaccines (PCV) (as described in patents, for example US 2016101170) to our method of making simple personal cancer vaccines (SPCV) disclosed herein is illustrated in FIG. 6. The two systems vary fundamentally at almost every step:

Step 1. The PCV requires taking a biopsy of the patient's tumor. In contrast, the SPCV only requires a small amount of blood. Because blood can readily be obtained, unlike tumor biopsies, the patient can be continuously monitored relative to the vaccine response and tumor status.

Step 2. In the PCV the tumor DNA and RNA are sequenced, as well as the patient's germline, to find to determine candidate tumor mutations. In the SPCV, blood samples are assayed to directly determine which tumor variants are both expressed and have an immune response in the patient.

Step 3. The PCV system requires applying an algorithm to estimate which of the mutations might be expressed as peptides and the immune system would respond to. This is not required by SPCV, since any expressed FS of 8aa or longer would be highly likely to elicit an immune response. Moreover, since the screen is for immune reactivity, the results directly indicate that the neo-antigen is expressed and immune reactive.

Step 4. In several embodiments of the peptide arrays in SPCV, the numbers are small enough that the peptides could be pre-made. This would allow, for example, screening candidate peptides directly in T-cell assays to determine specific immunogenicity in patients. This is not practical for the PCV approach as it would take too long to get the information.

Step 5. In the PCV system it is expected it will take at least 2 weeks or more to manufacture the vaccine for the patient. Currently it takes months. Because the domain of possible mutations in PCV assays is so large, the manufacturing will need to be specific for each person. In contrast, in several embodiments of the SPCV arrays, the number of variants are small enough such that the collection of possible vaccines can be pre-made, greatly reducing the time to get back to the patient. This would also allow the vaccine components to be pre-validated by the FDA, which currently cannot be done for the PCV system and thus poses a potential regulatory problem. These comparisons are summarized in Tables 1 and 2. In the PCV system even if the manufacture of the vaccine as peptide or nucleic acid can be improved to take less time, the SPCV system is inherently still better as the FS antigens will be much more broadly immunogenic.

Figure 7:
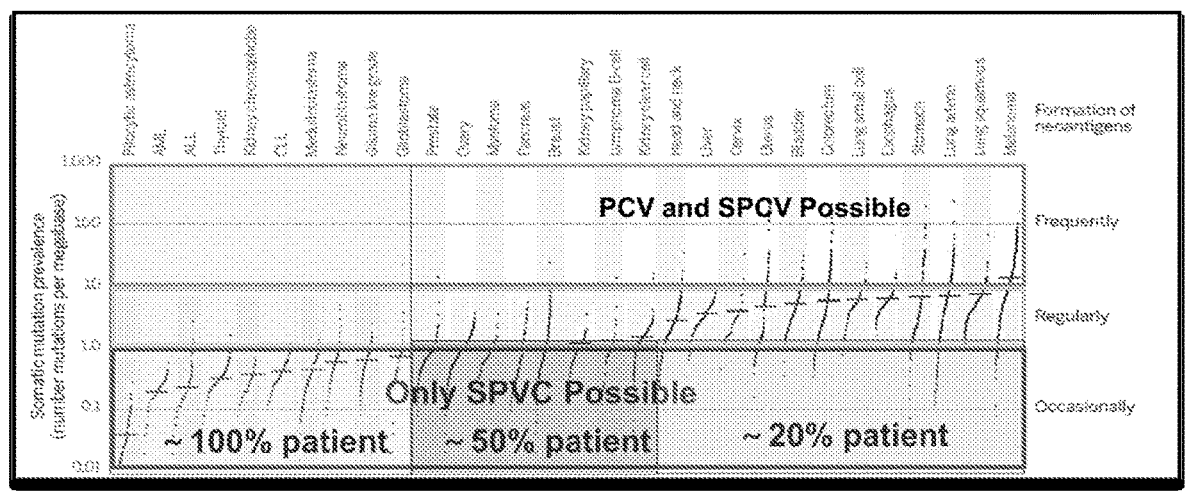
FIG. 7 shows an exemplary embodiment of SPCV in low mutation burden cancers.

Step 6. The current PCV cannot find enough neo-antigens from low mutation burden cancer patients, which is about 30% of total cancers and almost 100% of certain types of cancer. The SPCV potentially works all types of cancers (FIG. 7).

TABLE 1

Comparison of PCV versus SPCV

|  | Traditional PCV | SPCV |
|---|---|---|
| Ag Identification | ≥2 weeks | 1~5 days |
| Ag Immunogenicity | Algorithm Predicted (3%) | confirmed |
| Vaccine Production | ≥2 weeks | 1 days |
| Cost | $$$ | $ |

TABLE 2

Peptide Numbers

| FS mutation category | peptide number | methods for screening |
|---|---|---|
| All Possible FS mutations | ~2*10$^6$ | Phage or RNA display |
| All possible splice variants FS | ~6*10$^5$ | In situ synthesized arrays |
| All MS FS | ~2*10$^4$ | Spotted arrays |
| All MS FS in Driver genes | ~2*10$^3$ | Spotted arrays or micro titer plates |
| All MS FS in Essential genes | ~1.6*10$^3$ | Spotted arrays or micro titer plates |

Disclosed herein are streamlined, cost effective, and efficacious methods to design and produce personal vaccines for dogs, such as personal canine cancer vaccines. Methods herein include methods of determining the optimal components of a vaccine to be given to an individual to treat the cancer in that individual. Such methods include determining whether a candidate vaccine peptide is both expressed in the tumor of the individual and elicits an immune response in the individual. In some embodiments, the methods herein disclosed comprise obtaining a blood sample from an individual diagnosed with a cancer or a pre-cancer, diluting the blood sample in a buffer, contacting the diluted blood sample to a collection of peptides, wherein the collection of peptides comprises predicted frame-shift peptides that may be produced by a cancer cell from the individual. In some embodiments, the collection of peptides is an array, a high density array, a phage library, a plate-based assay, or other means of assembling a pre-determined collection of frame-shift peptides for testing against patient samples, including blood, serum, plasma, saliva, cerebrospinal fluid, and others. The results of the assay determine which peptides have strong (e.g. $K_D>10^{-8}$) binding to antibodies in the patient's blood compared to an average binding in blood from people without cancer or compared to a sample taken from the individual before they had cancer. In additional embodiments, variant peptides could be used in assays for T-cell reactivity using cells from the same patient. Peptides eliciting a strong response in T-cell activity assays are more likely to be good vaccine components, an assay which can be personalized with an individual's T-cell samples. Those peptides with high reactivity can form the basis of a personal vaccine to treat the individual's cancer. Variants or FS antigens herein are the products of alterations at the RNA level, such as errors in transcription of RNA processing. This is in contrast to germline "mutations" which occur in the DNA and are heritable.

Vaccines designed using methods herein could comprise the personalized set of peptides in a number of forms, including as a DNA vaccine, a peptide vaccine, an RNA vaccine, a viral vaccine, a bacterial vaccine or combinations thereof. Vaccines herein can also be loaded or incorporated into antigen presenting cells, such as dendritic cells or macrophages and the loaded cells administered to the individual. Alternatively, genes encoding the vaccine antigens can be used to transform antigen presenting cells through techniques known by those of skill in the art such as CRISPR transfection, viral or vector transduction, or other gene transfer or incorporation technology.

Vaccines designed using methods herein could also be given to an individual to prevent reoccurrence of a cancer. Collections of peptides herein developed in individual patients could also be used, for example, to diagnose cancer in other patients.

Figure 10C:
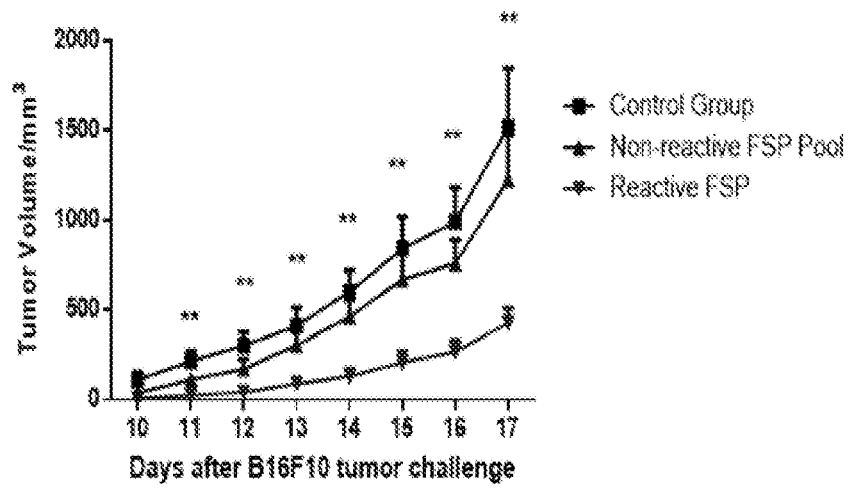
Figure 10D:
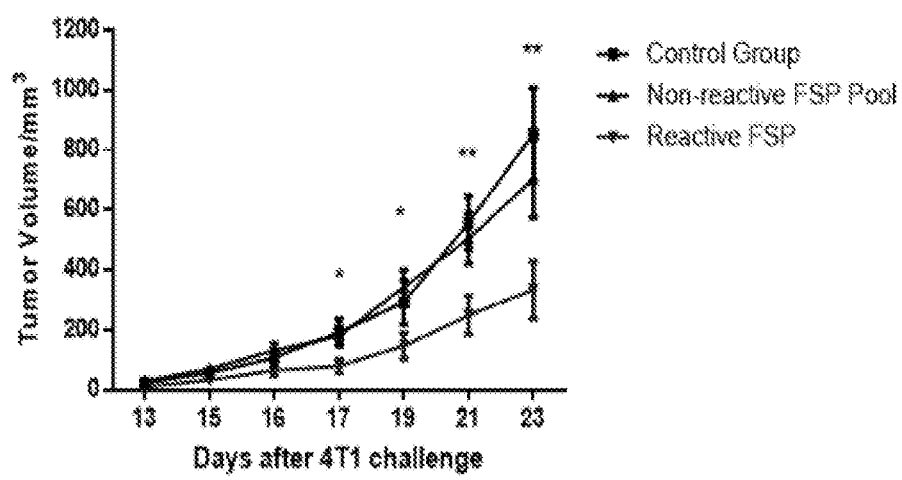
Figure 11:
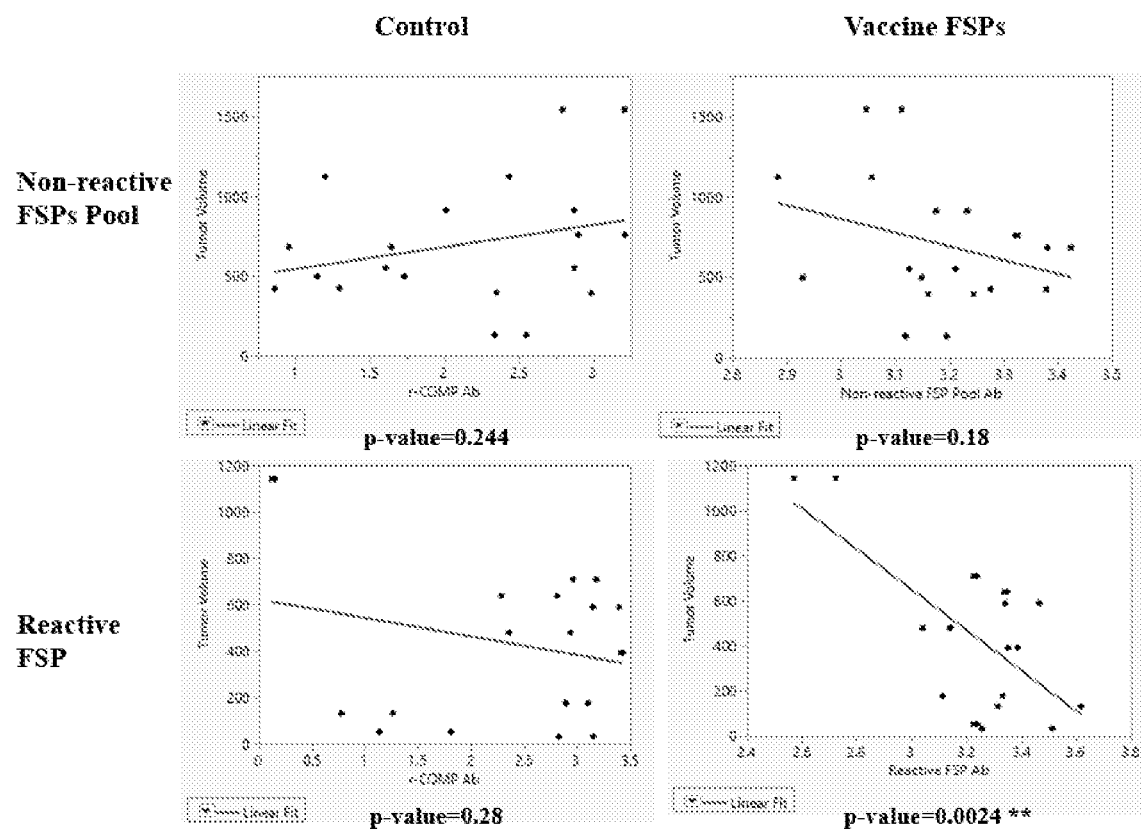
FIG. 11 shows screen dog cancer serum with a small FSP array. The reactive FSPs have protection and correlated with vaccine elicited antibody reactive. Tumor volume was linearly correlated to antibody response against vaccinated reactive FSPs in the 4T1 breast cancer model. Tumor volume at the end point was used for analysis. The antibody response was measured by ELISA after PB2 and at the end point. R-COMP peptide was encoded in a plasmid and used as an internal control for genetic immunization. The p-value was calculated for linear fit of antibody response against tumor volume.

The variant peptides comprising the collection for screening could be from several sources. They could be peptides known to result from point mutations, frameshifts, deletions/insertions or translocation in tumor DNA. Because these types of mutations are personal and occur infrequently, it would take a large number of peptides to represent all of them. Conventional practice is to determine neo-antigens encoded at the DNA level and then confirm expression at the RNA level. We have unexpectedly discovered that mutations occur much more frequently at the RNA processing level. Since microsatellites in coding regions are predicted and limited in number, one can predict a small set of FS peptides resulting from insertion or deletions during transcription that will produce FS neo-antigens. Therefore, methods herein, in some embodiments, comprise screening frameshift variants formed from 1) insertions or deletions in microsatellites in coding regions or 2) from mis-splicing events either in or between genes that create an out-of-frame fusion. These variants have several attractive features as sources for a personal vaccine component. First, frameshift variants generally have variant peptide sequences of over more than 8 amino acids. In contrast with point mutations that often only alters one amino acid, a FS variant is completely foreign sequence and therefore is much more likely to be immunogenic. Our work indicates that there are only a few thousand frameshifts from microsatellite insertion/deletions that are more than 8 amino acids long. Frameshifts of 8-60 amino acids long are very likely to include MHCI and MHCII epitopes. Further, because of their increased immunogenicity, FS variants are much more likely to create both T- and B-cell responses. Therefore, fewer peptides are required to be screened to determine vaccine components. Point mutation neo-epitopes are unlikely to produce both B and T-cell responses. Even though the arrays we developed (FIG. 8A, FIG. 9) record B-cell responses to the FS peptides, the antibody response level on the arrays correlates with the tumor protection (FIG. 10, FIG. 11). This may be because the antibody response requires CD4 help and it has been discovered that CD4 responses are important for protection. Further, the realm of FS space is much more restricted than that of all possible point mutations. This is particularly true for INDELS in microsatellites in coding regions. There are 2 possible FS that can be predicted from each of the ~7000 microsatellites in coding regions. These numbers become smaller as putative peptides are filtered for restrictions for minimal length (e.g. >7aa) and the probability of eliciting immune responses. This makes it feasible to have a pre-existing set of FS peptides made that can be used to screen the T-cells of a patient for reactivity.

Peptides to be screened by the methods herein are produced and displayed in a number of ways. For example, in some embodiments the peptide candidates are synthesized and spotted on arrays. In some embodiments, arrays have about 100 selected FS peptides. In some embodiments, arrays have about 200 selected FS peptides. In some embodiments, arrays have about 300 selected FS peptides. In some embodiments, arrays have about 400 selected FS peptides. In some embodiments, arrays have about 500 selected FS peptides. In some embodiments, arrays have about 600 selected FS peptides. In some embodiments, arrays have about 700 selected FS peptides. In some embodiments, arrays have about 800 selected FS peptides. In some embodiments, arrays have about 900 selected FS peptides. In some embodiments, arrays have about 1000 selected FS peptides. In some embodiments, arrays have about 10,000 selected FS peptides. In some embodiments, arrays have about 20,000 selected FS peptides. In some embodiments, in-situ synthesis could produce an array having 1,000,000 or more peptides per array, or at least 1000, 10,000 or 100,000 or 400,000 (FIG. 8A, FIG. 8B, FIG. 9) peptides per array.

Figure 12:
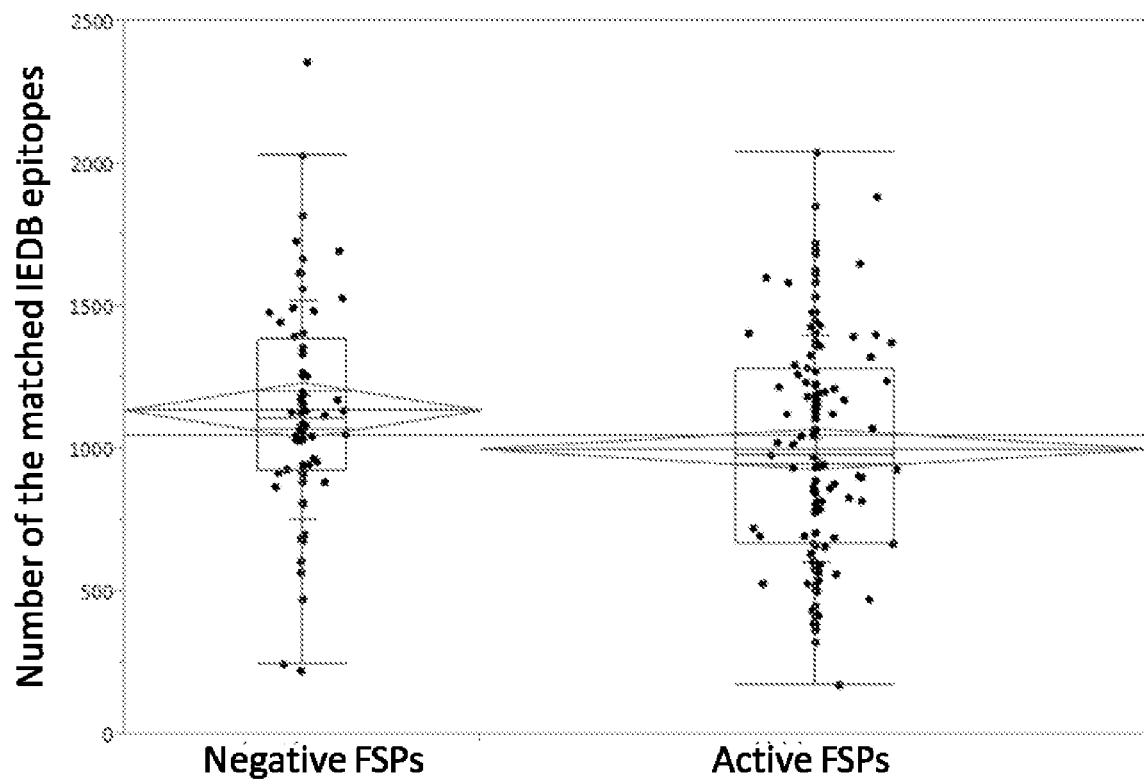
FIG. 12 shows that the negative FSPs have more pathogen epitopes than the highly active FSPs. This figure compares the negative FSPs with active FSPs in cancers. All negative FSPs and the FSPs with >10% positive rate in cancers from FIG. 9 were selected for analysis. A BLAST search against the Immune Epitope Database (IEDB) shows differential similarity with pathogen of peptides from these two sets of FSPs. Each peptide was searched using BLAST against epitopes in the IEDB and all the epitopes having an e value less than 10,000 were recorded as the matches. The number of the matched epitopes of each peptide was put into boxplot and represented the pathogen similarity of that peptide. The difference in similarity was statistically calculated with T-test P<0.05.

In an exemplary method of developing a personalized cancer vaccine, the blood from a cancer patient is diluted and applied to the array. After incubation the array is washed and the bound patient's antibodies are detected with a labeled secondary antibody, for example a fluorescently labeled secondary antibody. The secondary antibody can be to any combination of one or more isotypes, including but not limited to IgG1, IgG2, IgG3, IgG4, IgA1, IgA2, IgD, IgM, and IgE. The level of fluorescence indicates the amount and/or affinity of the antibody to the FS peptide. We have shown that the relative binding correlates to protection (FIG. 11). The assay may be optimized to selectively detect high affinity binding of antibodies to their cognate FS antigen. The reactivity can be compared to the reactivity seen in healthy people without cancer or to a previous baseline blood sample of that same patient. The readout is the antibody response to particular FS peptides. A positive response indicates that the peptide must be made in that tumor and that the immune system has reacted to it. Sequencing the DNA or RNA from the tumor does not convey either of these important pieces of information. Sequence analysis of the negative IgG reactive FSPs showed that these FSPs contain more pathogen epitopes (FIG. 12). So it is also contemplated that the frequently contacting different pathogen in regular life induces the tolerance to these epitopes and consequently, decreases the effective immune responses to the FPSs containing these epitopes. The approach disclosed herein gives a direct readout of the antibody response to the FS peptides, which is important information in designing a vaccine. Antibody binding to a FS peptide could also be detected by any number of label-free methods.

Accordingly, in some embodiments, selecting candidate FSPs for a personalized cancer vaccine herein, comprises determining the sequence similarity to known pathogen epitopes and selecting FSPs that do not show sequence similarity to known pathogen epitopes. Known pathogen epitopes comprise peptides catalogued in the Immune Epitope Database (IEDB, available on the internet at iedb.org). In some cases, candidate FSPs are searched via a BLAST algorithm against pathogen epitopes in the IEDB. In some embodiments, a candidate FSP is selected for having a BLAST e value less than 10,000.

A T-cell response, in some embodiments, is important for killing cancer cells. Since the FS peptides are generally 8 aa or longer, it is very likely that a FS peptide will have a region that would bind to the patient's MHC to initiate an immune response. JMHC binding can be predicted from commonly available algorithms. Alternatively, the blood sample from the patient could be screened for T-cell activity to the peptide candidates using a T cell assay, such as a proliferation assay, a cytokine assay, a cytotoxicity assay, a degranulation assay, flow cytometry, or combination thereof.

Methods of designing personalized cancer vaccines disclosed herein would not only provide much more relevant information for making a vaccine, but it would have benefits over the existing methods such as simplicity and cost efficacy. It would not require a biopsy of the tumor with the inherent cost, discomfort and danger. The assay itself would be simpler, less expensive and faster than deep sequencing the tumor DNA. The mutations identified in the DNA are most likely to be the result of point mutations which have a low probability of being produced by a patient, or at least immunogenic. Current sequencing protocols are very poor at identifying insertions/deletions in microsatellites or mis-splicing events. The best source of peptides (FS) would be missed by current sequencing protocols. Sequencing a biopsy will only identify mutations in that part of the tumor and mutations in other parts will be missed. By methods disclosed herein, all immune reactive parts of the tumor will be identified. The identification of vaccine components by sequencing will require the application of proprietary algorithms and other assays to identify potentially produced and immunogenic peptides. In contrast, this information is directly readout from our assay. While the broadest application may be for cancer, the same procedure would apply for a vaccine against other chronic diseases. Vaccines based on the MS FS herein also could eliminate cells that are not tumors but are aberrant for other reasons. Such aberrant, dysfunctional cells play a role in diseases such as diabetes, Alzheimer's disease, aging, autoimmune disease, chronic infections, and other diseases.

Microsatellite and Splicing FS Variants

Methods herein, in some embodiments, comprise methods of frameshift variant development for inclusion in personal cancer vaccine development. Frameshift variants, as referred to herein, are alterations in an mRNA caused by errors in transcription, causing an insertion or deletion (INDEL) of one or two nucleotides in the mRNA or by mis-splicing of RNA resulting in a change in the amino acids of the resulting protein that are encoded after the frameshift variant. Methods of frameshift variant development herein include but are not limited to mRNA sequencing and array based hybridization. In some embodiments, frameshift peptides are developed by bioinformatics analysis of already available sequence data. FS variants peptides due to INDELs in MS can be directly inferred from the genome sequence data. Any INDEL in a coding sequence will produce FS if expressed. On the other hand a specific exon mis-splicing may or may not be produced. Therefore, this application focuses on the MS FS, all of which will be produced.

In some embodiments, mRNA sequencing for development of frameshift variants herein includes a method where mRNA from a tumor or cancer tissue is sequenced. In some embodiments, mRNA is purified from a tumor or cancer tissue from a patient. In some embodiments, mRNA is isolated from total mRNA from the tumor or cancer tissue. In some embodiments, mRNA is isolated using oligo-dT purification of total RNA In some embodiments, mRNA is targeted for sequencing using an oligo-dT to prime the RNA sample. In some embodiments, the mRNA is amplified before sequencing. In some embodiments, the mRNA is amplified by PCR before sequencing. In an embodiment the mRNA is sequenced by random priming of the cDNA to detect FS sequences. In some embodiments the mRNA is amplified by RT-PCR before sequencing. In some embodiments, mRNA sequencing comprises targeted sequencing of an mRNA having a microsatellite in the transcript. In some embodiments, mRNA is sequenced using at least one technique selected from Sanger sequencing, pyro-sequencing, ion semiconductor sequencing, polony sequencing, sequencing by ligation, nanoball sequencing, and single molecule sequencing.

Variants identified from mRNA sequencing are classified by type of variant. Variants may arise from mutations in DNA or alterations in the RNA during transcription or splicing herein, which include but are not limited to point mutations, silent mutations, insertions, deletions, cis-splicing errors, and trans-splicing errors. Of these, only insertions, deletions, cis-splicing errors, and trans-splicing errors are expected to lead to a frameshift in a protein produced from the mutant mRNA. Confirmed frameshift variants are those that when translated produce a protein with a different amino acid sequence at more than one residue at residues C-terminal to the alteration. Frameshifted polypeptide sequences resulting from frameshift variants are assembled for further analysis.

In some cases frameshift mutations are predicted based on microsatellite location in the genome. As transcripts having a microsatellite are more prone to transcription errors, frameshift polypeptides can be predicted to be resulting from an insertion or a deletion of one or two basepairs. Alternatively, frameshift polypeptides can be predicted by bioinformatics prediction of cis and/or trans splicing errors. A selection of all possible frameshift peptides can be assembled for further analysis.

Peptides from Frameshifts from MS Indels and Mis-Splicing

Frameshifted polypeptide sequences, determined by mRNA sequencing or prediction, are further analyzed to determine immunoreactivity. In some embodiments, immunoreactivity is measured by MHC or HLA binding. In some embodiments, immunoreactivity is measured by antibody binding. In some embodiments, immunoreactivity is measured by T cell activity. In some embodiments, immunoreactivity is measured by antibody binding and T cell activity.

Binding to MHC is required for T cell activity and can be determined by binding assays. Alternatively, in silico methods of MHC binding are used to predict binding of a peptide to a MHC subtype. Data of peptides binding to MHC subtype molecules are used to develop binding prediction algorithms. These algorithms calculate scoring matrices that quantify the contribution of each residue in a fixed-length peptide to binding to an MHC molecule. Algorithms predict binding of a peptide to class I MHC or class II MHC. Algorithms to predict class I MHC binding include but are not limited to Artificial neural network (ANN), Stabilized matrix method (SMM), SMM with a Peptide:MHC Binding Energy Covariance matrix (SMMPMBEC), Scoring Matrices derived from Combinatorial Peptide Libraries (Comblib_Sidney 2008), Consensus, NetMHCpan, NetMHCcons and PickPocket. Algorithms to predict class II MHC binding, include but are not limited to Consensus method, Combinatorial library, NN-align (netMHCII-2.2), SMM-align (netMHCII-1.1), SturniO10, and NetMHCIIpan. The entire population of frameshift polypeptides is then scanned using one or more of the above algorithms for peptides binding to an MHC subtype molecule with a predicted affinity of IC50<500 nM.

Identifying Frameshift Peptide Antibody Response

Candidate frameshift peptides for personalized cancer vaccines, in some embodiments, are screened for antibody reactivity in an individual needing treatment using a personalized cancer vaccine. Antibody reactivity is determined using an assay for antibody binding to a peptide. In some embodiments, peptides for antibody screening are bound to a substrate, such as a plate, a glass slide, a bead, or other substrate. Assays for antibody binding include but are not limited to ELISA, radio-immuno assay, western blot, surface plasmon resonance, immunostaining, immunoprecipitation, mass spectrometry, phage display, flow cytometry, cytometric bead array, immunohistochemistry, high density array, microarray, and combinations thereof.

In an exemplary embodiment, a blood sample is obtained from an individual needing treatment for breast cancer. The blood sample is diluted in an appropriate buffer and applied to a peptide microarray spotted with vaccine candidate frameshift peptides. The diluted blood sample is incubated with the peptide microarray overnight and the peptide microarray is then washed and exposed to a secondary antibody that binds to canine IgG bound to the microarray. The secondary antibody is conjugated with Alexa Fluor 488 and the microarray is analyzed for fluorescence at each peptide spot. The peptides bound to the individual's antibodies are deemed immunoreactive and selected for the individual's personalized cancer vaccine.

In another exemplary embodiment, an individual is given an intradermal injection of each candidate peptide in a pre-determined pattern on the patient's back to measure delayed-type hypersensitivity (DTH) response. Erythema and induration are measured at 24, 48, and 72 hours. The peptides which elicit a DTH response are deemed immunoreactive and selected for the individual's personalized cancer vaccine.

Identifying Frameshift Peptide T Cell Response

In some embodiments, candidate frameshift peptides are screened for T cell activity in cells obtained from an individual needing treatment using a personalized cancer vaccine. T cell activity is determined using a T cell assay measuring proliferation, cytokine secretion, cytotoxicity, or degranulation in response to a frameshift peptide bound to an antigen presenting cell. T cell assays include but are not limited to proliferation assay, 3H-thymidine assay, BrdU assay, CFSE assay, cytokine secretion assay, ELISA assay, ELISPOT assay, intracellular staining assay, quantitative rtPCR assay, cytometric bead array assay, MHC-tetramer binding assay, cytotoxicity assay, 51-chromium assay, degranulation assay, granulysin assay, granzyme A assay, granzyme B assay, and perforin assay.

In an exemplary embodiment, a blood sample is obtained from an individual needing treatment for breast cancer. PBMCs are isolated from the blood sample and the PBMCs are cultured to expand T cells in the sample and the T cells are incubated in culture media containing one or more candidate peptides for a cytokine release assay. The production of IFN-γ is analyzed in ELISPOT assays. Flat-bottom 96-well nitrocellulose plates are prepared and coated with either anti-canine IFN-γ. Cells were then incubated at a density of $1 \times 10^5$/well either with peptide pools or individual peptides (10 μg/ml), PHA (10 μg/ml), or medium (containing 1% DMSO corresponding to the percentage of DMSO in the pools/peptides) as a control. After 24 hours, cells are removed, and plates are incubated with HRP-conjugated anti-canine IFN-γ Ab (Clone 7-B6-1, Mabtech) at 37° C. After 2 hours, spots corresponding to the HRP-conjugated Ab (IFN-7) are developed with 3-amino-9-ethylcarvazole solution (Sigma-Aldrich, St. Louis, Mo.). Spots are counted by computer-assisted image analysis (Zeiss, KS-ELISPOT reader, Munich, Germany). Each assay is performed in triplicate. The level of statistical significance is determined with a Student's t-test using the mean of triplicate values of the response against relevant pools or individual peptides versus the response against the DMSO control. Criteria for peptide pool positivity are 100 spot-forming cells (SFCs)/ $10^6$ PBMC, p≤0.05 and a stimulation index (SI)≥2, while criteria for individual peptide positivity are ≥20 SFC/$10^6$ PBMC, p≤0.05, and a SI≤2.

Platforms for Screening Peptides for Personalized Cancer Vaccines

In some embodiments, disclosed herein are array platforms that allow for development of peptides suitable for personalized cancer vaccines. The array platforms comprise a plurality of individual features on the surface of the array. Each feature typically comprises a plurality of individual peptides synthesized in situ on the surface of the array or spotted on the surface, wherein the molecules are identical within a feature, but the sequence or identity of the molecules differ between features. Such array molecules include the synthesis of large synthetic peptide arrays.

The peptide arrays can include control sequences that match epitopes of well characterized monoclonal antibodies (mAbs). Binding patterns to control sequences and to library peptides can be measured to qualify the arrays and the assay process. Additionally, inter wafer signal precision can be determined by testing sample replicates e.g. plasma samples, on arrays from different wafers and calculating the coefficients of variation (CV) for all library peptides. Precision of the measurements of binding signals can be determined as an aggregate of the inter-array, inter-slide, inter-wafer and inter-day variations made on arrays synthesized on wafers of the same batch (within wafer batches). Additionally, precision of measurements can be determined for arrays on wafers of different batches (between wafer batches). In some embodiments, measurements of binding signals can be made within and/or between wafer batches with a precision varying less than 5%, less than 10%, less than 15%, less than 20%, less than 25%, or less than 30%.

The technologies disclosed herein include a photolithographic array synthesis platform that merges semiconductor manufacturing processes and combinatorial chemical synthesis to produce array-based libraries on silicon wafers. By utilizing the tremendous advancements in photolithographic feature patterning, the array synthesis platform is highly-scalable and capable of producing combinatorial peptide libraries with 40 million features on an 8-inch wafer. Photolithographic array synthesis is performed using semiconductor wafer production equipment in a class 10,000 cleanroom to achieve high reproducibility. When the wafer is diced into standard microscope slide dimensions, each slide contains more than 3 million distinct chemical entities. Maskless photolithography can also be used to create peptides arrays.

In some embodiments, arrays with peptide libraries produced by photolithographic technologies disclosed herein are used for immune-based assays. Using a patient's antibody repertoire from a biological sample bound to the arrays, a fluorescence binding profile image of the bound array provides sufficient information to classify which peptides are reactive with an antibody from the patient.

Platforms disclosed herein comprise a selection of frameshift peptides disclosed herein, such as peptides resulting from an insertion or deletion error in transcription of an mRNA or peptides resulting from a splicing error such as a trans-splicing error or a cis-splicing error. In some embodiments, platforms herein comprise frameshift peptides comprise peptides having a sequence selected from all MS FS or MS FS from oncogenes, essential genes, highly expressed genes, such as the peptides provided in SEQ ID NO: 1-10665.

In some embodiments, the array is a wafer-based, photolithographic, in situ peptide array produced using reusable masks and automation to obtain arrays of scalable numbers of combinatorial sequence peptides. In some embodiments, the peptide array comprises about 100, about 500, about 1000, about 2000, about 3000, about 4000, about 5,000, about 6000, about 7000, about 8000, about 9000, about 10,000, about 15,000, about 20,000, about 30,000, about 40,000, about 50,000, about 100,000, about 200,000, about 300,000, about 400,000, about 500,000, or more peptides having different sequences. Multiple copies of each of the different sequence peptides can be situated on the wafer at addressable locations known as features.

In some embodiments, the array is a glass slide or nitrocellulose membrane having in vitro synthesized peptides spotted in a predetermined pattern and screened for binding of antibodies in a biological sample from a patient.

In some embodiments, detection of antibody binding on a peptide array poses some challenges that can be addressed by the technologies disclosed herein. Accordingly, in some embodiments, the arrays and methods disclosed herein utilize specific coatings and functional group densities on the surface of the array that can tmle the desired properties necessary for performing assays. For example, non-specific antibody binding on a peptide array may be minimized by coating the silicon surface with a moderately hydrophilic monolayer polyethylene glycol (PEG), polyvinyl alcoHO1, carboxymethyl dextran, and combinations thereof. In some embodiments, the hydrophilic monolayer is homogeneous. Second, synthesized peptides are linked to the silicon surface using a spacer that moves the peptide away from the surface so that the peptide is presented to the antibody in an unhindered orientation.

Platforms herein are also contemplated to include peptides in microtiter plates for determining T cell activity in response to frameshift peptides herein. In some embodiments, microtiter plates include but are not limited to 96 well, 384 well, 1536 well, 3456 well, and 9600 well plates. In some embodiments, more than one peptide is present in each well of a microtiter plate, i.e., the peptides are pooled and individual peptides eliciting T cell activity are determined by deconvolution of the positive and negative wells in the T cell assay.

Screening for Immunogenic Peptides

Optionally, it is useful to determine immunogenicity of a candidate frameshift peptide for use in a personalized cancer vaccine. Immunogenicity, as used herein, refers to the ability of a substance, such as a peptide, to elicit an immune response, such as an antibody response or a T cell response, when administered to an individual, for example, in a vaccine formulation. For individuals, such as dogs, with cancer it is the immune response to the tumor. In some embodiments, a peptide that reacts with an antibody or elicits T cell activity in a biological sample from an individual is not immunogenic when administered in a vaccine formulation. In some embodiments, a peptide that reacts with an antibody or elicits T cell activity in a biological sample from an individual is immunogenic when administered in a vaccine formulation. Immunogenicity is determined by methods of those of skill in the art including in animal model testing and using in silico prediction of immunogenicity. In silico immunogenicity prediction tools are available for free to the public, for example at the Immune Epitope Database and Analysis Resource (www.iedb.org).

Alternatively, mice, such as mice transgenic for canine HLA genes are used to determine the immunogenicity of a candidate frameshift peptide. The candidate frameshift peptide is administered to the transgenic mouse in a vaccine formulation. Response to the vaccine is determined using antibody assays and/or T cell assays described elsewhere herein. In the case of mice that are injected with a tumor or are transgenic to develop tumors, the protection of the frameshift peptide as a vaccine can be determined.

Methods of Designing a Personalized Vaccine

Provided herein are methods of designing a personalized vaccine for an individual, the method comprising, a) obtaining a biological sample from the individual; b) determining immunoreactivity of the biological sample to a first population of peptides; c) preparing a vaccine composition comprising a second population of peptides that have immunoreactivity with the biological sample from the individual, wherein the second population of peptides is a sub-population of the first population. In some embodiments, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. In some embodiments, the biological sample is blood, serum, plasma, or saliva. In some embodiments, the biological sample comprises cells selected from B cells, T cells, CD4+ T cells, CD8+ T cells, Th17 cells, and combinations thereof. In some embodiments, the biological sample comprises an antibody.

Methods herein comprise administration of one or more immunoreactive polypeptides reactive to immune cells and antibodies, for example from an individual with cancer. In some embodiments, immunoreactivity comprises antibody reactivity. In some embodiments, immunoreactivity comprises a T cell response. A T cell response herein includes but is not limited to one or more of proliferation assay, 3H-thymidine assay, BrdU assay, CFSE assay, cytokine secretion assay, ELISA assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. Methods herein, in some embodiments, screen a first population for peptides binding to antibodies or eliciting a T cell reaction in a biological sample from an individual, wherein the first population of peptides comprises peptides encoded by a frameshifted mRNA expressed by a cancer cell. In some embodiments, the first population of peptides comprises peptides having a sequence selected from the peptides provided in SEQ ID NO: 1-10665. In some embodiments, each of the first population of peptides binds to at least one MHC subtype. In some embodiments, a portion of the first population of peptides binds to more than one MHC subtype. In some embodiments, each of the first population of peptides binds to at least on HLA subtype. In some embodiments, each of the first population of peptides comprises at least one T cell epitope. In some embodiments, at least one of the first population of peptides comprises at least one T cell epitope. In some embodiments, each of the first population of peptides comprises at least on B cell epitope. In some embodiments, at least one of the first population of peptides comprises at least on B cell epitope. In some embodiments, first population of peptides is bound to a substrate.

Vaccine Compositions and Formulations

Personalized cancer vaccines herein comprise one or more peptides determined to have immunoreactivity with a biological sample from an individual in need of treatment for cancer. For example, personalized cancer vaccines, in some embodiments, comprise 1, 2, 3, 4, 5, 6, 7, 8, 9, 10, 11, 12, 13, 14, 15, 16, 17, 18, 19, 20, or more frameshift peptides determined to have immunoreactivity with a sample from an individual in need of treatment for cancer. In some embodiments, peptides for personalized cancer vaccines are selected from the peptides provided in SEQ ID NO: 1-10665.

In some embodiments, the vaccine can consist of plasmids encoding the MS FS variants. DNA or Gene Vaccines consist of a plasmid with a promoter and appropriate transcription and translation control elements. The plasmids may also sequences that encode peptide or protein fusions to the FS peptide to enhance, for example, expression levels, intracellular targeting or proteasomal processing. For example the LAMP sequence when fused to a FS peptide sequence will enhance MHCII responses. In additional aspects, personalized cancer vaccines herein comprise one or more nucleic acids encoding peptides determined to have immunoreactivity with a biological sample. For example, in some embodiments, personalized cancer vaccines comprise one or more nucleotides encoding 1, 2, 3, 4, 5, 6, 7, 8, 9, 10, 11, 12, 13, 14, 15, 16, 17, 18, 19, 20, or more FS peptides determined to have immunoreactivity with a sample. In some embodiments, nucleotides encode peptides for personalized cancer vaccines selected from the peptides provided in SEQ IDNO: 1-10665. These plasmids can be introduced by a needle, a gene gun, an aerosol injector, with patches, via microneedles, by abrasion among many forms. In some forms the DNA vaccine is incorporated into liposomes or other forms of nanobodies. They may also be administered by inhalation or ingestion. The plasmid can be introduced into the blood, the thymus, the pancreas, the skin, the muscle, a tumor or other sites.

Alternatively or in combination, the peptides can be encoded in RNA that is directly introduced into the individual, such as a dog. The RNA can be chemically synthesized or more commonly in vitro transcribed. The RNA will encode one or more FS peptides and will include signals to enhance stability and translation. The RNA may also include unnatural nucleotides to increase the half-life. These RNAs can be introduced by a needle, a gene gun, an aerosol injector, with patches, via microneedles, by abrasion among many forms. In some forms the RNA is incorporated into liposomes or other forms of nanobodies. They may also be administered by inhalation or ingestion. The RNA can be introduced into the blood, the thymus, the pancreas, the skin, the muscle, a tumor or other sites Alternatively or in combination, the peptides coding sequences can be introduced into a virus as a vector. The peptide encoding sequences can be fused to other sequences that enhance transcription, translation or presentation to the immune system. These viral vectors include pox viruses, adenovirus, lentiviruses, retroviruses, alpha viruses and others using a needle, a gene gun, an aerosol injector, with patches, via microneedles, by abrasion among many forms. They may also be administered by inhalation or ingestion.

Alternatively or in combination, the peptides can be administered via a bacterial vector. The FS coding sequences are introduced into the bacteria, usually in the form of plasmid or lysogenic phage, and the bacteria administered to the patient. Listeria is commonly used in this way, but other bacteria could be used or developed. The bacteria can be administered by needle to the blood or intraperitoneal injection.

Bacteria can Also be Administered Orally.

The peptides can also be delivered as peptides. Usually the peptides are 10aa long or longer, preferably 25aa or longer. 25-40aa long may be ideal. Usually the peptides are fused to a carrier such as albumin, keyhole limpet protein etc. In some forms the peptides are incorporated into liposomes or other forms of nanobodies.

Personalized vaccine formulations herein comprise a personalized vaccine composition in a biologically acceptable formulation, gaseous, liquid or solid, or mixture thereof, which are suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacteRIA1, antiviral and antifungal agents) can also be incorporated into the compositions.

To increase an immune response and efficacy in treating cancer, peptides herein are optionally coupled to another protein such as ovalbumin or keyhole limpet hemocyanin (KLH), thyroglobulin or a toxin such as tetanus or cholera toxin. Peptides herein are also mixed with adjuvants or checkpoint inhibitors.

Adjuvants include, for example: ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS- 1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan.

Checkpoint inhibitors are inhibitors of proteins known to potentiate or inhibit an immune response and accordingly a checkpoint inhibitor increases the immune response. In some instances, tumors are known to upregulate checkpoint inhibitors to evade the immune response in a patient and checkpoint inhibitors allow the immune system of the patient to recognize and eliminate the tumor. Checkpoint inhibitors herein include but are not limited to a PD-1 inhibitor, a PD-L1 inhibitor, a CTLA-4 inhibitor, Pembrolizumab, Nivolumab, or Atezolizumab. They may be administered systemically or locally as an adjuvant.

Cosolvents may be added to a frameshift peptide composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, ophthalmic, optical, intravenous (i.v.), intramuscular, intraglandular, intraorgan, or intralymphatic.

Formulations suitable for parenteral administration include aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Methods of Eliciting an Immune Response

Also provided herein, are methods of eliciting an immune response in an individual having cancer, the methods comprising, a) obtaining a biological sample from the individual; b) determining immunoreactivity of the biological sample to a first population of peptides; c) preparing a vaccine composition comprising a second population of peptides that have immunoreactivity with the biological sample from the individual, wherein the second population of peptides is a sub-population of the first population; and d) administering the vaccine composition to the individual, wherein administering the vaccine composition elicits an immune response in the individual against the cancer.

Methods herein comprise administration of one or more immunoreactive polypeptides reactive to immune cells and antibodies, for example from an individual with cancer. In some embodiments, immunoreactivity comprises antibody reactivity. In some embodiments, immunoreactivity comprises a T cell response. A T cell response herein includes but is not limited to one or more of proliferation assay, 3H-thymidine assay, BrdU assay, CFSE assay, cytokine secretion assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. Methods herein, in some embodiments, screen a first population for peptides binding to antibodies or eliciting a T cell reaction in a biological sample from an individual, wherein the first population of peptides comprises peptides encoded by a frameshifted mRNA expressed by a cancer cell. In some embodiments, the first population of peptides comprises peptides having a sequence selected from the peptides provided in SEQ ID NO: 1-10665. In some embodiments, each of the first population of peptides binds to at least one MHC subtype. In some embodiments, a portion of the first population of peptides binds to more than one MHC subtype. In some embodiments, each of the first population of peptides binds to at least on HLA subtype. In some embodiments, each of the first population of peptides comprises at least one T cell epitope. In some embodiments, at least one of the first population of peptides comprises at least one T cell epitope. In some embodiments, each of the first population of peptides comprises at least on B cell epitope. In some embodiments, at least one of the first population of peptides comprises at least on B cell epitope. In some embodiments, first population of peptides is bound to a substrate.

Methods of Treatment

Provided herein, in some aspects, are methods of treating an individual in need of treatment for a cancer using a personalized cancer vaccine. An "individual" or "patient", used interchangeably herein, refers to a canine, for example a dog. Some such methods comprise, a) obtaining a biological sample from the individual; b) determining immunoreactivity of the biological sample to a first population of peptides; c) preparing a vaccine composition comprising a second population of peptides that have immunoreactivity with the biological sample from the individual, wherein the second population of peptides is a sub-population of the first population; and d) administering the vaccine composition to the individual, wherein administering the vaccine composition elicits an immune response in the individual against the cancer and wherein the cancer in the individual is reduced. In some embodiments, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. In some embodiments, the biological sample comprises cells selected from B cells, T cells, CD4+ T cells, CD8+ T cells, Th17 cells, and combinations thereof. In some embodiments, the biological sample comprises an antibody.

Also provided herein, in some aspects, are methods of reducing risk of reoccurrence of cancer in an individual, the methods comprising, a) obtaining a biological sample from the individual; b) determining immunoreactivity of the biological sample to a first population of peptides; c) preparing a vaccine composition comprising a second population of peptides that have immunoreactivity with the biological sample from the individual, wherein the second population of peptides is a sub-population of the first population; and d) administering the vaccine composition to the individual, wherein administering the vaccine composition elicits an immune response in the individual against the cancer and wherein the risk of developing cancer again in the individual is reduced compared to an individual who did not receive the vaccine.

Methods herein comprise administration of one or more polypeptides reactive to immune cells and antibodies, for example in a biological sample from an individual with cancer. In some embodiments, immunoreactivity comprises antibody reactivity. In some embodiments, immunoreactivity comprises a T cell response. A T cell response herein includes but is not limited to one or more of proliferation assay, 3H-thymidine assay, BrdU assay, CFSE assay, cytokine secretion assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. Methods herein, in some embodiments, screen a first population for peptides binding to antibodies or eliciting a T cell reaction in a biological sample from an individual, wherein the first population of peptides comprises peptides encoded by a frameshifted mRNA expressed by a cancer cell. In some embodiments, the first population of peptides comprises peptides having a sequence selected from SEQ ID NO: 1-10665. In some embodiments, each of the first population of peptides binds to at least one MHC subtype. In some embodiments, a portion of the first population of peptides binds to more than one MHC subtype. In some embodiments, each of the first population of peptides binds to at least on HLA subtype. In some embodiments, each of the first population of peptides comprises at least one T cell epitope. In some embodiments, at least one of the first population of peptides comprises at least one T cell epitope. In some embodiments, each of the first population of peptides comprises at least on B cell epitope. In some embodiments, at least one of the first population of peptides comprises at least on B cell epitope. In some embodiments, first population of peptides is bound to a substrate.

Methods herein comprise administration of a vaccine composition to an individual. Vaccine compositions herein, in some embodiments, comprise a pharmaceutically acceptable adjuvant or excipient. In some embodiments, the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, Interferon-Gamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, P1005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan. Vaccine compositions herein, in some embodiments, are administered via a route selected from the group consisting of subcutaneous, intradermal, intramuscular, intranasal, intravenous, and sublingual. Individuals in need of administration of a personalized vaccine, in some embodiments are mammals. In some embodiments, the individual is a dog.

Methods herein comprise administration of a personalized vaccine in an individual with cancer. In some embodiments, the cancer comprises Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal gem1 cell tumor, Mediastinal tumor, Medullary thyroid cancer, Medulloblastoma, Medulloepithelioma, Melanoma, Meningioma, Merkel Cell Carcinoma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple myeloma, Mycosis Fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neurofibroma, Neuroma, Nodular melanoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral cancer, Oropharyngeal Cancer, Osteosarcoma, Ovarian cancer, Ovarian Epithelial Cancer, Ovarian Germ Cell Tumor, Ovarian Low Malignant Potential Tumor, Paget's disease of the breast, Pancoast tumor, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma InvoMng the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal PeMs and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, or Wilms' tumor.

Provided herein, in some aspects, are methods of monitoring treatment of an individual receiving a personalized cancer vaccine. Some such methods comprise, a) obtaining a biological sample from the individual; b) determining immunoreactivity of the biological sample to a first population of peptides; c) comparing immunoreactivity of the biological sample to a previous immunoreactivity in the individual, wherein successful treatment is indicated by reduced immunoreactivity to the first population of peptides. In some embodiments, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. In some embodiments, the biological sample comprises cells selected from B cells, T cells, CD4+ T cells, CD8+ T cells, Th17 cells, and combinations thereof. In some embodiments, the biological sample comprises an antibody.

Methods of Diagnosing Cancer

Provided herein, in some aspects, are methods of determining whether an individual has cancer. Some such methods comprise, a) obtaining a biological sample from the individual and b) determining immunoreactivity of the biological sample to a first population of peptides, wherein the individual is determined to have cancer if the sample from the individual is immunoreactive with one or more of the peptides. In some embodiments, the method further comprises treating the individual using a method comprising, a) preparing a vaccine composition comprising a second population of peptides that have immunoreactivity with the biological sample from the individual, wherein the second population of peptides is a sub-population of the first population and b) administering the vaccine composition to the individual, wherein administering the vaccine composition elicits an immune response in the individual against the cancer and wherein the cancer in the individual is reduced. In some embodiments, the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor. In some embodiments, the biological sample comprises cells selected from B cells, T cells, CD4+ T cells, CD8+ T cells, Th17 cells, and combinations thereof. In some embodiments, the biological sample comprises an antibody.

Methods herein comprise determining whether an individual has cancer by determining whether one or more polypeptides reactive to immune cells and antibodies, for example in a biological sample from the individual. In some embodiments, immunoreactivity comprises antibody reactivity. In some embodiments, immunoreactivity comprises a T cell response. A T cell response herein includes but is not limited to one or more of proliferation assay, 3H-thymidine assay, BrdU assay, CFSE assay, cytokine secretion assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay. Methods herein, in some embodiments, screen a first population for peptides binding to antibodies or eliciting a T cell reaction in a biological sample from an individual, wherein the first population of peptides comprises peptides encoded by a frameshifted mRNA expressed by a cancer cell. In some embodiments, the first population of peptides comprises peptides having a sequence selected from SEQ ID NO: 1-10665. In some embodiments, each of the first population of peptides binds to at least one MHC subtype. In some embodiments, a portion of the first population of peptides binds to more than one MHC subtype. In some embodiments, each of the first population of peptides binds to at least on HLA subtype. In some embodiments, each of the first population of peptides comprises at least one T cell epitope. In some embodiments, at least one of the first population of peptides comprises at least one T cell epitope. In some embodiments, each of the first population of peptides comprises at least on B cell epitope. In some embodiments, at least one of the first population of peptides comprises at least on B cell epitope. In some embodiments, first population of peptides is bound to a substrate.

Methods herein comprise determining whether an individual has cancer. In some embodiments, the cancer comprises Acanthoina, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degas disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloepithelioma, Melanoma, Meningioma, Merkel Cell Carcinoma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple myeloma, Mycosis Fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neurofibroma, Neuroma, Nodular melanoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral cancer, Oropharyngeal Cancer, Osteosarcoma, Ovarian cancer, Ovarian Epithelial Cancer, Ovarian Germ Cell Tumor, Ovarian Low Malignant Potential Tumor, Paget's disease of the breast, Pancoast tumor, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma InvoMng the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezaiy Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart. Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyle leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal PeMs and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, or Wilms' tumor.

The following peptides are for use in a personalized cancer vaccine for dogs. NM_001171544.1, SPAG11B, Ins, A_10, ICLLFASERVGI, (SEQIDNO:1); XM_005623762.2, DDX24, Ins, A_10, IGAFPGYCSKGAQKSKDMDA, (SEQIDNO:2); XM_014117090.1, MORN5, Ins, A_10, KCFKRASA, (SEQIDNO:3); XM_014109016.1, ENO4, Del, A_10, KDKSKEGMILSQRNLFCLQNLLNPYSVAAWP, (SEQIDNO:4); XM_005617440.2, SREK1IP1, Ins, A_10, KEKVLFIQFH, (SEQIDNO:5); XM_014116982.1, TTF1, Del, A_10, KERISSIFFLPL, (SEQIDNO:6); XM_014122648.1, SYTL2, Del, A_10, KFWQERKQRN, (SEQIDNO:9); XM_005617440.2, SREK1IP1, Del, A_10, KGKGLIHPVPLKRTLPSKRNKNTRRKKRRKKKRISQKEGNIIKRKKRREKRRSIHPLLI LLRSPKS, (SEQIDNO:10); XM_005627009.1, SMAP1, Ins, A_10, KGREKERKGARKACETSYN, (SEQIDNO:11); XM_014118197.1, AK9, Ins, A_10, KGTKFALSTAQ, (SEQIDNO:12); XM_005638510.2, KIAA0101, Del, A_10, KHVLCHLITQMTKKN, (SEQIDNO:13); XM_014119761.1, LRRIQ1, Del, A_10, KIRHTDTQRDLQVFQLREYLLQ, (SEQIDNO:14); XM_014119762.1, LRRIQ1, Del, A_10, KIRHTDTQRDLQVSCGFLQS, (SEQIDNO:15); XM_014117913.1, ROR2, Del, A_10, KKERKPACSQTVSSPETTTMRTASASLTGGSRVHASLGTPSMWTPSRCRGRLKTESQRPSP, (SEQIDNO:16); XM_014116982.1, TTF1, Ins, A_10, KKGFPASSFFPFEKIRNM, (SEQIDNO:17); XM_014106280.1, LOC100686575, Ins, A_10, KKRIWSHQQE, (SEQIDNO:18); XM_014120850.1, NME8, Del, A_10, KLSRQGTSWKLRTRECSQNNKQGSSIVAKRRSLTFKILSFL, (SEQIDNO:19); XM_005630994.2, TMEM60, Del, A_10, KPGTSLQCYLN, (SEQIDNO:20); XM_014118680.1, PRR27, Del, A_10, KPPITLGILTLIQGHHPIPGFSLLLEPPSTAFLVFP, (SEQIDNO:21); XM_005625148.1, STKLD1, Ins, A_10, KQSKARDKAGGMY, (SEQIDNO:22); XM_014119593.1, EIF2B3, Del, A_10, KQWSSVTSLEWTAQERGCSSWLMKRTWMKSWSLRDPSCRSTQEYISTQALWTPIST A, (SEQIDNO:23); XM_005627009.1, SMAP1, Del, A_10, KRKRKRKKRSQKSL, (SEQIDNO:24); XM_014118197.1, AK9, Del, A_10, KRNKVCLIHCTIAHRL, (SEQIDNO:25); XM_005620751.2, LOC479667, Del, A_10, KRNWPRKQGKRLLTIWLLGKMNELGSEWSTLSEKITLWRPWRSWSYIVICCWLGLA SSS1, (SEQIDNO:26); XM_014117603.1, ZNF207, Del, A_10, KRSNKMILMNTMMTLQLQLHFSHSLFSLNKVISPRWCNQDCHQFQEHQECLQAYLH (SEQIDNO:27); XM_005634282.1, ULK4, Del, A_10, KRTLENAGLFPWLRTQC, (SEQIDNO:28); XM_014119762.1, LRRIQ1, Ins, A_10, KSGTQTLSGIFK, (SEQIDNO:29); XM_014119761.1, LRRIQ1, Ins, A_10, KSGTQTLSGIFKFFN, (SEQIDNO:30); XM_536376.4, HK1, Del, A_10, KSRTRNYQWDSHFLSLVGSPR, (SEQIDNO:31); XM_005623082.2, ANKRD12, Del, A_10, KTKQQTVVTTLSQKKVKIKKRTGK, (SEQIDNO:32); XM_014110095.1, PHACTR4, Del, A_10, KVVINSKRPQKF, (SEQIDNO:33); XM_014110582.1, C35H6orf201, Del, A_10, KWRSLQCQP, (SEQIDNO:34); XM_014106934.1, MACROD2, Ins, A_10, NERVFPCR, (SEQIDNO:35); XM_005615627.2, ECHDC1, Del, A_10, NFNSFLVDPLTFRRKTVALVFLP, (SEQIDNO:36); XM_014110582.1, C35H6orf201, Ins, A_10, NGGASNVNHSCQMVEKIHATHRRPSVSNPEAVRVWAN, (SEQIDNO:37); XM_005620751.2, LOC479667, Ins, A_10, NGTGPESKERDC, (SEQIDNO:38); XM_005632046.2, THUMPD3, Ins, A_10, NKTQKDKSEFK, (SEQIDNO:39); XM_532252.6, SEC63, Del, A_10, NLHLCPYHSQSNRNKSRQMELLGVKLR, (SEQIDNO:40); NM_001171544.1, SPAG11B, Del, A_10, NMPAVCIRTCWY, (SEQIDNO:41); XM_536376.4, HK1, Ins, A_10, NQGQEITSGIHIFFPLSAVQDRRGHPDHLDKEI, (SEQIDNO:43); XM_014122648.1, SYTL2, Ins, A_10, NSGKRGNREIKFKVHTPGVTR, (SEQIDNO:44); XM_014119437.1, CEP290, Ins, A_10, NSPNGSRKRKKSCNFRINHGGLEPN, (SEQIDNO:45); XM_014110220.1, KIAA1524, Del, A_10, NVKGWSRPLKFC, (SEQIDNO:46); XM_005623762.2, DDX24, Del, A_10, NWSLPRVLLQRCPKKQRHGCLKCMTIRQM, (SEQIDNO:47); XM_014120850.1, NME8, Ins, A_10, NYRGRVRLGN, (SEQIDNO:48); XM_014117913.1, ROR2, Ins, A_10, RKKENQHAHRPYLPQRRLP, (SEQIDNO:49); XM_005630994.2, TMEM60, Ins, A_10, SLVPHCNVT, (SEQIDNO:50); XM_005632220.2, RAD18, Ins, A_10, SNKRRRWIYRKAVTCICGTR, (SEQIDNO:51); XM_014118680.1, PRR27, Ins, A_10, SPQLPWES, (SEQIDNO:52); XM_005634064.2, CCDC168, Ins, A_10, TGDIKSNSTAQPTLQISFRPKEGA, (SEQIDNO:53); XM_005624758.2, BCAS3, Ins, A_10, TMPTAQRP, (SEQIDNO:54); XM_848628.4, ISL1, Ins, A_10, TSDFPMCWLRQSNSRSVYSEGFSGFGMACGMFEMCGV, (SEQIDNO:55); XM_005615627.2, ECHDC1, Ins, A_10, TSTVSWWIR, (SEQIDNO:56); XM_532252.6, SEC63, Ins, A_10, TYTCALTTVKATETKAGKWNCWE, (SEQIDNO:57); XM_536179.5, CHD2, Ins, A_11, ILLNLSSESCTF, (SEQIDNO:58); XM_014119273.1, LOC106559736, Ins, A_11, KARGGNVPAERKGRGREPRTERARQRAEL- RAPPPPPRRA, (SEQIDNO:59); XM_014118903.1, LOC102156909, Del, A_11, KDSASTLS, (SEQIDNO:60); XM_014118224.1, MARCKS, Ins, A_11, KEALLLQEVLQAERLLLQEEQEGGGRGGGRGGG-GRARRRPQGRGRRAGRAGAGAA AGAGAGAGAGAGAGGRGRGGRGGGRGGRRAPGG, (SEQIDNO:61); XM_005632295.2, LOC610950, Del, A_11, KEERTLYSMHLFQVPGNILMGTT, (SEQIDNO:62); XM_005636122.2, SBNO1, Ins, A_11, KEKYRSRFYSKCLISIRSWIKTT, (SEQIDNO:63); XM_005640067.2, E2F3, Del, A_11, KHGMTHHLVCSPRSSFSC, (SEQIDNO:65); XM_014115818.1, G2E3, Del, A_11, KLKDYGLIKPIS-GIVP, (SEQIDNO:66); XM_846664.4, SEC62, Del, A_11, KMGKRKSLKRRKLQELPKRRKLRKNSNLSHM-MIKFFWMEMRYLCGSMTQFTLKHL SWD, (SEQIDNO:67); XM_005632295.2, LOC610950, Ins, A_11, KRREPSTQCTYFKSQGTSSWVQPDSHNQPTANCCG, (SEQIDNO:68); XM_014118224.1, MARCKS, Del, A_11, KRSASPSRSPSS, (SEQIDNO:69); XM_005632360.2, LOC102156781, Ins, A_11, KSDEESEDCFGKDAVLQM, (SEQIDNO:70); XM_014112072.1, LOC100688285, Del, A_11, KSFESREPIRFIFTRLKRSGFF, (SEQIDNO:71); XM_014118903.1, LOC102156909, Ins, A_11, KTLPQP-SAEQLCRSS1, (SEQIDNO:72); XM_014118275.1, ENPP3, Ins, A_11, KVNSEEIVRNLSE, (SEQIDNO:73); XM_014111381.1, EFHC2, Del, A_11, KYYPAKT-SEGCASPSGYLCLMIFWDPYCPGLKTAKNK, (SEQIDNO:74); XM_014106804.1, TOPAZ1, Ins, A_11, NKCQIIRERSM, (SEQIDNO:75); XM_005615796.1, ZCCHC6, Ins, A_11, NNTRELWEYPQKR-TICCFQQSLCV, (SEQIDNO:76); XM_014112072.1, LOC100688285, Ins, A_11, SHSSPANQFDLFLHV, (SEQIDNO:77); XM_014111381.1, EFHC2, Ins, A_11, SITQQRHQKA VQVLQVTFV, (SEQIDNO:78); XM_005637891.1, FANK1, Del, A_12, KEVWESHHPQS-LIHLLWAK, (SEQIDNO:79); XM_014106746.1, XRN1, Del, A_12, KGKWITYF, (SEQIDNO:80); XM_014106745.1, XRN1, Ins, A_12, KGNGSLTFENPYI-ATFQ, (SEQIDNO:81); XM_014106746.1, XRN1, Ins, A_12, KGNGSLTFENPYIATFQWL, (SEQIDNO:82); XM_005637891.1, FANK1, Ins, A_12, KKSGNHTILKASSTCCGQSDSSQH, (SEQIDNO:83); XM_014106803.1, ERICH6, Del, A_12, KPKALKLN, (SEQIDNO:84); XM_014116352.1, EFCAB13, Ins, A_12, RIHRCTEISNN, (SEQIDNO:85); XM_014111397.1, ARL13A, Del, A_13, KEEGTISP, (SEQIDNO:86); XM_005638321.2, UBR1, Del, A_13, KEHSGGGISK, (SEQIDNO:87); XM_014117915.1, SVEP1, Del, A_13, KEMHLKEGISELCPLLLLQMQL-SANQAPTHQMGLKRVNRVLWAVISQHLVPRAASC VQKTLHL, (SEQIDNO:88); XM_014109361.1, LTK, Del, A_13, KGTLCAVWG, (SEQIDNO:89); XM_014111397.1, ARL13A, Ins, A-13, KKKEPSAHN, (SEQIDNO:90); XM_014111037.1, HSPE1, Ins, A_13, KPVPEGRAGV, (SEQIDNO:92); XM_014110403.1, LOC102151755, Del, A_13, KTLKVQKD, (SEQIDNO:93); XM_014107150.1, SYCP2, Del, A_13, NLCYLVFCTISVEIKCPPNG-HAGHL, (SEQIDNO:94); XM_014109537.1, KIAA0lOl, Del, A_13, NVRVPTWT, (SEQIDNO:95); XM_014107150.1, SYCP2, Ins, A_13, TCVTWCFVQYLWK, (SEQIDNO:96); XM_014106529.1, LOC102151520, Del, A_14, KKKKAK-STPPVRGTPTSCSRGEAPQH, (SEQIDNO:97); XM_014112055.1, LOC100684352, Del, A_14, KSFES-REPIRFIFTRLKRSGYF, (SEQIDNO:100); XM_014119387.1, LOC102152631, Del, A_14, KSTLGS-WRIPTTL, (SEQIDNO:101); XM_014109494.1, LOC106558056, Del, A_14, KTNTTGFRLLLF-SPCPSVSLLGKQVLRQARPPRPGATSL, (SEQIDNO:102); XM_005641614.1, LOC492038, Del, A_14, KTRRVSTSTSPGF, (SEQIDNO:103); XM_014119387.1, LOC102152631, Ins, A_14, KVLLGPGESQLHFDRV, (SEQIDNO:104); XM_014106529.1, LOC102151520, Ins, A_14, RRKKQRAPHLSEAHPPPAAEEKPRSTDQR, (SEQIDNO:106); XM_014119729.1, MAP9, Ins, A_14, TLICFLYISDPVRV, (SEQIDNO:107); XM_014110590.1, LOC106558261, Ins, A_15, KELQIR-GGSAAAAAAAAATCRLRAVPGGEAETR-GIPGCGCGCGCDSGSGSGHRRLP PSPAPQRT, (SEQIDNO:108); XM_005631118.2, EHF, Ins, A_15, KERKEKKKKEKKKKSWLLARIA1, (SEQIDNO:109); XM_005631118.2, EHF, Del, A_15, KRKKRKEKERKEK-KIVAAGQTRPVSRS, (SEQIDNO:110); XM_014110590.1, LOC106558261, Del, A_15, KRVANTRWVRCGCGCGRRYMSP-PRSSRRRSGDPRDSGLRLRLRLRLRLRLRPPPAP AQPCPAAHLGL, (SEQIDNO:111); XM_014111331.1, VMA21, Del, A_16, KEFHKYSSKKGI, (SEQIDNO:113); XM_005617128.2, BEND7, Del, A_16, KEKEKGGGSFKHQKAAH, (SEQIDNO:114); XM_005617128.2, BEND7, Ins, A_16, KKKKKVVVLSSTRKQLIRLSP, (SEQIDNO:116); XM_014119733.1, LOC102156511, Del, A_16, KLT-NIRKRQVS, (SEQIDNO:117); XM_014111331.1, VMA21, Ins, A_16, KNSTSTPPRRVYKGG, (SEQIDNO:118); XM_014118792.1, ATP10D, Del, A_16, KRKARR-GAGRQSGSSPWMSIWKEELLFSIPSARGFARRWTPR-TRTPVAGASPDYLHT PDLSAFWT, (SEQIDNO:119); XM_005615677.1, LOC102154410, Ins, A_16, SDGKPRF1, (SEQIDNO:120); XM_014106767.1, VEPH1, Ins, A_17, KHCRELTLGIMAPVGRWQHCS, (SEQIDNO:121); XM_005631271.2, LRP4, Del, A_17, KRLKRIPTKPERRLSPSALGKVELEGSGLR-LAKRILLLQSCQNCVHSSALRMEASPAA LSVLVV-GATSRVR, (SEQIDNO:122); XM_014106767.1, VEPH1, Del, A_17, KTLQGTHPWDYGSSGSVAALL-MMKRTPKGVRLMWGAWQRWHRKQMTLPGGSQQ TLHRGGAEILGL, (SEQIDNO:123); NM_001346046.1, KRT73, Ins, A_18, KEKEAHFPAVHLALLFLR-SPFPGKTPVSHLSCSPPCFSSP1, (SEQIDNO:125); XM_005635589.2, LOC102153838, Del, A_19, KRSPT-PASSPPTRW, (SEQIDNO:127); XM_005628326.1, LOC102152757, Del, A_28, KRPTHYLVSPKTLLWKA, (SEQIDNO:128); XM_544109.5, VCPIP1, Ins, A_7, IAG-NGFFHPSFDGQAFAGSKYRAVTI, (SEQIDNO:129); XM_014119817.1, GALNTL5, Ins, A_7, IATANYPRT-PANPKTAYEI, (SEQIDNO:130); XM_534296.5, PCOLCE2, Ins, A_7, IAYNYSTTCYHHVPCNYRFK-THRFPVSTKV, (SEQIDNO:131); XM_005623751.2, BTBD7, Ins, A_7, ICESYITLYVY, (SEQIDNO:132); XM_546553.6, TRPC6, Ins, A_7, ICSSSKLSAAASVHMV, (SEQIDNO:133); XM_005629273.2, SCYL2, Ins, A_7, IDKTGSSCFC1, (SEQIDNO:134); XM_533782.4, DENND6A, Ins, A_7, IEELKDTGF, (SEQIDNO:135); XM_005639100.2, FRAS1, Ins, A_7, IEFGGQSQQ-FARWNRSL, (SEQIDNO:136); XM_005623155.1, CAT-SPERB, Ins, A_7, IEKLLRITS, (SEQIDNO:137); XM_005641884.1, CXHXorf66, Ins, A_7, IEVILPRKVI, (SEQIDNO:138); XM_539103.4, FBXO43, Ins, A_7, IFAAQKVGHIFLSSKWGL, (SEQIDNO:139); XM_005624758.2, BCAS3, Ins, A_7, IFCHKLLSVSRAQHESYCSWEPLACL-CRKQVDSMPSVPWWSLWRQHSVLHCHGH, (SE- QIDNO:140); XM_014114812.1, LOC100684252, Ins, A_7, IFIGGKVVPSRNPFP, (SEQIDNO:141); XM_005623827.1, ZNF839, Ins, A_7, IFKSENTFRTDISTSQV, (SEQIDNO:142); XM_539156.5, FAM91A1, Ins, A_7, IFQKENSS, (SEQIDNO:143); XM_014120092.1, TEX15, Ins, A_7, IFSDGARREHR, (SEQIDNO:144); XM_005638869.2, DNAJC28, Ins, A_7, IFWLFIYRSHDSQPEQNIDR, (SEQIDNO:145); XM_848169.4, KIAA2026, Ins, A_7, IGQMVSSEASCKRIAWYIDTPFK, (SEQIDNO:146); XM_014117490.1, VWA3B, Ins, A_7, IGSSQRSESYCKM, (SEQIDNO:147); XM_005636896.2, CCNT1, Ins, A_7, IGTCHQSSTCLSPSAGITS, (SEQIDNO:148); XM_532882.5, SMC6, Ins, A_7, IGVNSGQRN, (SEQIDNO:149); XM_005618961.2, DDX50, Ins, A_7, IHEIQIRTG, (SEQIDNO:150); XM_848173.4, ZFHX4, Ins, A_7, IHFCLSPFFYYKPHRT, (SEQIDNO:151); XM_003639638.3, POGZ, Ins, A_7, IHPKSLEPEGGFLSPAGRRALHGSLSAVSPSPRPLPCSHPLLPAPGARSL, (SEQIDNO:152); XM_014107422.1, LOC606856, Ins, A_7, IHYLFNSWCWKRQWK, (SEQIDNO:154); XM_014109628.1, UNC13C, Ins, A_7, IIQTQRNRNWNLNRYSYS, (SEQIDNO:156); XM_005634064.2, CCDC168, Ins, A_7, IIRSQKATQPQVCN, (SEQIDNO:157); XM_014107447.1, LOC486036, Ins, A_7, IKSVTLCPHRVLRI, (SEQIDNO:158); XM_005636673.2, SLCO1B3, Ins, A_7, ILYLCTGASLELFFLFIGKHPNYHAGF, (SEQIDNO:159); XM_014110874.1, ERICH2, Ins, A_7, IMSDDPN1, (SEQIDNO:160); XM_005622326.2, LOC609365, Ins, A_7, IMSTSRRTQQWPGSPRR, (SEQIDNO:161); XM_014110545.1, LOC100686395, Ins, A_7, INEYLWISSHCCVHLLWNYNLHVPTTR, (SEQIDNO:162); XM_014117985.1, CNTLN, Ins, A_7, INFSKEEW, (SEQIDNO:163); XM_543280.4, SLC16A14, Ins, A_7, IPGWCPR1, (SEQIDNO:164); XM_532445.5, WAS1, Ins, A_7, IPKSSYRLVGPATKEI, (SEQIDNO:165); XM_005626541.2, CDKL3, Ins, A_7, IPKTKWIVGRYS, (SEQIDNO:166); XM_014120611.1, AP4B1, Ins, A_7, IPPCTNRCACASQGTFAGCLFFREP, (SEQIDNO:167); XM_848523.3, ZNF804A, Ins, A_7, IQAHQEPGGTGHSGREIHHHKVEGYPRTLVP, (SEQIDNO:168); XM_005619526.2, TVP23B, Ins, A_7, IQDQTSSGIIFPFILSSQCNCSLSS1, (SEQIDNO:169); XM_014115688.1, FERMT2, Ins, A_7, IQEQADNSKNLGGPSECSSDESN, (SEQIDNO:170); XM_843555.3, TRIML1, Ins, A_7, IQHGHNSGPSYSQCLPCLV, (SEQIDNO:171); XM_005641806.2, RBMX2, Ins, A_7, IQKRQKGEKEKKERQREH, (SEQIDNO:172); XM_014106331.1, BORA, Ins, A_7, IQLGKYNQPFTSFFTHFLTDRISNRKDSTPGTKEVYFSFS, (SEQIDNO:173); XM_014107769.1, ZNF26, Ins, A_7, IQSEHELDSFKEIKQ, (SEQIDNO:174); XM_003434814.3, ZNF75A, Ins, A_7, IQSELPPY, (SEQIDNO:175); XM_005619062.2, ADK, Ins, A_7, IQSRISCWWLYPEFN, (SEQIDNO:176); XM_532364.5, IREB2, Ins, A_7, IRFRELQRLGCQRTVSAGRESCFG, (SEQIDNO:177); XM_535304.5, CHD9, Ins, A_7, IRRRCRRETI, (SEQIDNO:178); XM_005623020.2, ESCO1, Ins, A_7, IRSKGNCKITG, (SEQIDNO:179); XM_538971.3, FAM83B, Ins, A_7, IRTKNGFIS, (SEQIDNO:180); XM_005630347.2, CEBPZ, Ins, A_7, IRVCFLGAL, (SEQIDNO:181); XM_005636978.2, KIF21A, Ins, A_7, ISEERIDWPSNF, (SEQIDNO:182); XM_005615521.2, CCDC170, Ins, A_7, ISGRSRKERKAAGGLQRGDFQDAGLEHDQSCTS, (SEQIDNO:183); XM_014116465.1, NOS2, Ins, A_7, ISLHAERAYQQVQVCRVWPRLQHVPSVLCLCS, (SEQIDNO:184); XM_005637743.2, PLEKHS1, Ins, A_7, ISRTQTSSFTTRLLVRNY, (SEQIDNO:185); XM_014119368.1, LRBA, Ins, A_7, ISSLTFYTYYKSTYKCCQCGFFSRFNPNLRWRRRITWW, (SEQIDNO:186); XM_846123.4, POLE2, Ins, A_7, ISSSINDQPPCTKFIWNSKG, (SEQIDNO:187); XM_005638907.2, TTC3, Ins, A_7, ISTRKNGRGPKGK, (SEQIDNO:188); XM_014110841.1, CCDC148, Ins, A_7, ISVCLYRA, (SEQIDNO:189); XM_539419.4, RBM48, Ins, A_7, ITGEEGLYSKNY, (SEQIDNO:190); XM_014110823.1, ZNF385B, Ins, A_7, ITVLFTMQSGCELPVTARGTQHRI, (SEQIDNO:191); XM_005629985.2, CFAP97, Ins, A_7, IVGCYNRA, (SEQIDNO:192); XM_014112496.1, KIAA0232, Ins, A_7, IWHGEECSDVPGFSGGISWDSAGGEAESVFGM, (SEQIDNO:193); XM_849077.4, PPAT, Ins, A_7, IWSIVGQL, (SEQIDNO:194); XM_014120510.1, TPRKB, Ins, A_7, IWYLSKRHFSSNCIH, (SEQIDNO:195); XM_014114179.1, DTX2, Ins, A_7, IYGRAENGLR, (SEQIDNO:196); XM_005618061.2, GIN1, Ins, A_7, IYLQRKKAVLCWKRQKTKSFGNCFRRRKKESPKRVP, (SEQIDNO:197); XM_014120145.1, PCMI, Ins, A_7, NPSCYFNPSC, (SEQIDNO:198); XM_014119418.1, CHD8, Ins, A_7, IYRGSGYKDHR, (SEQIDNO:199); XM_014114967.1, ASPM, Ins, A_7, NSCSTSTSAWLVSKKKNFRTKNQNQTSSLHSSCILSPVCS, (SEQIDNO:200); XM_005618961.2, DDX50, Del, A_7, KAAHQRFLFWLLQGNWQTK, (SEQIDNO:201); XM_014118822.1, REST, Del, A_7, KAASLLRKRLLRRSLLRRGL1, (SEQIDNO:203); XM_014121623.1, TRNT1, Del, A_7, KAATKWRKMNSSVTSRRVKI, (SEQIDNO:204); NM_001024633.1, HTR2B, Ins, A_7, KAAVCYQLFSNVPSSG, (SEQIDNO:205); XM_005621312.2, AG1, Ins, A_7, KAAWSPRHENFGSRRYGLLWNL, (SEQIDNO:206); XM_014106867.1, MYBL2, Ins, A_7, KACCPVPCHREQRQPVLPRLL, (SEQIDNO:207); XM_014119192.1, VWDE, Ins, A_7, KACEPKQTGITFTKTSWK, (SEQIDNO:208); XM_005629416.2, STIL, Del, A_7, KACHAFYLVLS, (SEQIDNO:209); XM_532156.6, CDC5L, Ins, A_7, KACTWFLRYF, (SEQIDNO:210); XM_005642075.2, LOC100683955, Del, A_7, KADKAKPGSGTTSRFLKQGAVWICGNGGPVTWPSLLKWMCRNTPEGRGRPDATSP LQGSGQPPR, (SEQIDNO:211); XM_014110764.1, KCNH7, Del, A_7, KADLHLSSPPLMMNKSLSSQE, (SEQIDNO:212); XM_005623023.2, ROCK1, Ins, A_7, KAEGRERSSREG, (SEQIDNO:213); XM_005616873.2, CD3EAP, Ins, A_7, KAEKATAGSCV, (SEQIDNO:214); XM_014115181.1, LOC106559028, Ins, A_7, KAEKNSLHRYIW, (SEQIDNO:215); XM_537461.5, ARID4A, Ins, A_7, KAETENTGTVITREKNKN, (SEQIDNO:216); XM_014108264.1, PPFIBP1, Ins, A_7, KAEVNQIFNGQTF, (SEQIDNO:217); XM_003640002.3, EDRF1, Del, A_7, KAFHVLKKEFTILSQLMMPQMLPFCCVTRGDS, (SEQIDNO:218); XM_014114842.1, KIAA1107, Del, A_7, KAFKKKLI, (SEQIDNO:219); XM_014122448.1, C2CD3, Del, A_7, KAFLGDHLS, (SEQIDNO:220); XM_014114451.1, ZNF471, Del, A_7, KAFPKILW, (SEQIDNO:221); XM_005627613.2, RARS2, Ins, A_7, KAFSASVPNASDHGI, (SEQIDNO:222); XM_014106856.1, PLCB1, Ins, A_7, KAGEDNRS, (SEQIDNO:223); XM_005628737.1, LOC102153873, Ins, A_7, KAGGWSQVLEIWGCCHC, (SEQIDNO:224); XM_535304.5, CHD9, Ins, A_7, KAGKEEECRRC, (SEQIDNO:225); XM_014108788.1, MK167, Ins, A_7, KAGLLWWSSETGVI, (SEQIDNO:226);

XM_005617306.2, DIAPH1, Ins, A_7, KAGLRVNSPT, (SEQIDNO:227); XM_014109172.1, PRKDC, Ins, A_7, KAGPSRGQSR, (SEQIDNO:228); XM_005616994.2, ARHGAP21, Ins, A_7, KAHCYRNVRCQTG, (SEQIDNO:229); XM_014106956.1, ADNP, Ins, A_7, KAHLQMHPLPWCIHQQHDRLDYHSASSSLQRCWKDPEWPG, (SEQIDNO:230); XM_005640932.2, KCTD3, Del, A_7, KAILQVKSTVC, (SEQIDNO:231); XM_534297.5, U2SURP, Del, A_7, KAIWNSSKKN, (SEQIDNO:232); XM_014110541.1, PGBD1, Ins, A_7, KAKAVKCAREELDQKRH, (SEQIDNO:233); XM_536302.5, RASA1, Del, A_7, KAKENGGKIYILS, (SEQIDNO:234); XM_014111707.1, LOC102153942, Del, A_7, KAKKVKQVRILTS, (SEQIDNO:235); XM_005623486.2, SYNE2, Ins, A_7, KALFGYPANKKESG, (SEQIDNO:236); XM_005615387.2, C1H18orf54, Del, A_7, KALHPYFVEERLLMT, (SEQIDNO:237); XM_542589.4, OLFM4, Ins, A_7, KALQPNHPHRDHGKGYHFLHGTGL, (SEQIDNO:238); XM_014122806.1, ZNF214, Ins, A_7, KALQRGHVGELHKCHVSRKLERELQIPRRKIQIFRT, (SEQIDNO:239); XM_005626549.2, JADE2, Ins, A_7, KALRGFPDRPNHSHEDPRLLPTQPG, (SEQIDNO:240); XM_005631042.2, RTN3, Del, A_7, KALRQHKFSLIFLKGVQLVRPHVHKYLT, (SEQIDNO:241); XM_005622426.1, RGL1, Ins, A_7, KALRVFLVVFLYPFHGHHFLRDVVLNQPPLLPSVLQQQPQNPQALRLCDIHYLDSAA SRLQPTERRHLHNPHQCRGQQRQHVQEHRADEPR, (SEQIDNO:242); XM_548044.5, NSF, Del, A_7, KALTPTLTILTRWQQNSFSSSTIRHSQWDSSLCLASMKNFLACW, (SEQIDNO:243); XM_005620768.2, NFAT5, Del, A_7, KALVPDWFLELTSQGKMAP1, (SEQIDNO:244); XM_844360.4, C16H4orf47, Ins, A_7, KAMWFRKLLWNNRWSSAILQCTVKTQRKI, (SEQIDNO:247); XM_844191.4, KCNT2, Del, A_7, KAMYQGHFIMDLLDYLYIA, (SEQIDNO:248); XM_537580.5, CEP112, Ins, A_7, KAPQCCRRNGKGKV, (SEQIDNO:249); XM_545800.5, OCA2, Ins, A_7, KAQDIRQDSAHQMPDGVGICYLHVLSQFICPWCSS, (SEQIDNO:250); XM_014113223.1, DYNC2H1, Del, A_7, KAQLISIF, (SEQIDNO:251); XM_005628249.2, STAP1, Del, A_7, KAQNMLTS, (SEQIDNO:252); XM_014115681.1, RALGAPA1, Ins, A_7, KAQRERSWT, (SEQIDNO:253); XM_533351.4, KIF5C, Ins, A_7, KAQWEALSS, (SEQIDNO:254); XM_860109.5, RBM39, Del, A_7, KARAEVVVMNEKEAKVRNGNEVEIEKGKRAKVAKGSEVGAKKGDGAAQEVEIAD SEAATEVLTDDAPEAKVHSEKTRAP, (SEQIDNO:255); XM_005629880.1, NRG1, Ins, A_7, KAREVRTSH, (SEQIDNO:257); XM_535474.5, USP8, Ins, A_7, KARFQATAGLLSFNTWTRKHQKSY, (SEQIDNO:258); XM_537686.5, COIL, Del, A_7, KARGKTEPRVV, (SEQIDNO:259); XM_546967.5, LOC489848, Ins, A_7, KARHRRERPKGEGQRFGKKLQPEFKL, (SEQIDNO:260); XM_003639390.3, TLN1, Del, A_7, KARIILGWRETRSLLCWRTQFPPKSRQSSSSSITGWGRWSTALWPCLLSCALEPPVLK ISRWAACHQPSSRLPVARCTEDTCPL, (SEQIDNO:261); XM_005628720.1, KIAA0895, Ins, A_7, KASFTKTVFLHLLQKM, (SEQIDNO:262); XM_005626529.2, AFF4, Del, A_7, KASMDQNTPNHALPALENPRLFLH, (SEQIDNO:263); XM_845921.4, ECM1, Ins, A_7, KASSSHGLELS, (SEQIDNO:264); XM_014121388.1, IWS1, Ins, A_7, KASTEKINIITYCGYAP, (SEQIDNO:265); XM_014121139.1, APIP, Del, A_7, KASVLLF1, (SEQIDNO:266); XM_003639956.1, PZP, Ins, A_7, KASVPLCSGFPGLVPIWNTHIHQDWESCTGNHSEFHGICYKFPSG, (SEQIDNO:267); XM_014119282.1, ANKS1B, Del, A_7, KATNLKTIPLLAQEQLGVDPGMGTNG1, (SEQIDNO:268); XM_845166.4, CACNG3, Del, A_7, KATPMAGPFISGPSLSSSQKLWESLPCTSI, (SEQIDNO:269); XM_014120026.1, WHSC1L1, Del, A_7, KATSMTHVDLKSASHTKSPN, (SEQIDNO:270); XM_005618261.2, ZNF518B, Del, A_7, KAVCTHTDRLFLLSP, (SEQIDNO:271); XM_005618061.2, GIN1, Ins, A_7, KAVLCWKRQKTKSFGNCFRRRKKESPKRVP, (SEQIDNO:272); XM_537619.5, GPATCH8, Del, A_7, KAVLPSLRAVSRWQ, (SEQIDNO:273); XM_014110273.1, KIAA1407, Del, A_7, KAWSLGRD, (SEQIDNO:275); XM_014107753.1, LOC106557817, Del, A_7, KCACTLIGRQGICC, (SEQIDNO:276); XM_005626240.1, EML6, Ins, A_7, KCCFQHPDRWAHGRGDLGPGHSPHQGHLHLCQQ, (SEQIDNO:277); XM_005629547.2, AGK, Ins, A_7, KCCPDFTLIWHGCDCC, (SEQIDNO:278); XM_005615542.2, SERAC1, Del, A_7, KCCWKPPRSQK, (SEQIDNO:279); XM_547651.5, THOC1, Ins, A_7, KCCYLEIKYILFCWEKLFTTYVQ, (SEQIDNO:280); XM_847556.4, BRIP1, Ins, A_7, KCDFQIHKPNLQQTNKAS, (SEQIDNO:281); XM_535195.5, ITIH2, Ins, A_7, KCEAAHTRQHLLVQLGDRI, (SEQIDNO:282); XM_014112095.1, LOC102156264, Ins, A_7, KCELIYRLEKQRESSKTSD, (SEQIDNO:283); XM_014119642.1, ZMYM6, Del, A_7, KCFIKGKLHIIRPDLLSSFAPRGASLDILHGSAYHLLPRKPAQTVQKTF, (SEQIDNO:285); XM_014118277.1, ENPP3, Del, A_7, KCGITSTVFF1, (SEQIDNO:286); XM_005622209.2, KDM5B, Del, A_7, KCGPPKRRKSN, (SEQIDNO:287); XM_005619751.1, NXPE4, Ins, A_7, KCHQCLQMQQKNCSSEKEMQVWNDIHNPWWTCLERDMESCLL, (SEQIDNO:289); XM_014121779.1, NISCH, Ins, A_7, KCHSPSGPRNSYLPGPCRPGWATTLVGVPLCREAGK1, (SEQIDNO:290); XM_003640144.3, EIF2B5, Ins, A_7, KCICHDNDLQRVIP, (SEQIDNO:291); XM_849749.4, ST3GAL5, Del, A_7, KCINIWTQTV, (SEQIDNO:292); XM_014117196.1, LOC106559354, Ins, A_7, KCISYKRKAVRF, (SEQIDNO:294); XM_014109138.1, CFAP43, Ins, A_7, KCKDSRNYFRSGLGRSGLATRI, (SEQIDNO:295); XM_005630416.1, BUB1, Ins, A_7, KCKFFWGLGSQ, (SEQIDNO:296); XM_003434003.1, DSPP, Ins, A_7, KCKPGGRSNTRGKWSWQWRRCWPG, (SEQIDNO:298); XM_005623486.2, SYNE2, Ins, A_7, KCLARSLF, (SEQIDNO:299); XM_005633861.2, CAB39L, Del, A_7, KCLCLVNHPKIQQKL, (SEQIDNO:300); XM_005630011.2, WWC2, Del, A_7, KCLEARVAMNLVKPKPF, (SEQIDNO:301); XM_005616987.1, ENKUR, Del, A_7, KCLIGMSPENLLCH, (SEQIDNO:302); XM_005638071.2, ZNF704, Del, A_7, KCLINTCFPWPWRKM, (SEQIDNO:303); XM_534555.5, CEP44, Del, A_7, KCLKKLQSY, (SEQIDNO:304); XM_005619368.2, CARD6, Del, A_7, KCLKMSCHV, (SEQIDNO:305); XM_844363.3, C33H3orf17, Del, A_7, KCLQLLQLKE, (SEQIDNO:306); XM_014109639.1, LONP2, Del, A_7, KCLSQCQNML, (SEQIDNO:307); XM_014110870.1, FSIP2, Del, A_7, KCLTNGKRNQMTWKMKSIS, (SEQIDNO:308); XM_005631810.2, LARP1B, Del, A_7, KCMRNLDNLLGKMQKKITGMD, (SEQIDNO:309); XM_014118978.1, AKAP9, Del, A_7, KCMSSSPK, (SEQIDNO:310); XM_014108087.1, CCDC62, Ins, A_7, KCNCYLICIYKRLTGEAKVLVSGRKNASRT, (SEQIDNO:311); XM_544601.6, ARHGAP11A, Ins, A_7, KCPAFHITHNSYTKC, (SEQIDNO:314); XM_857524.4, TAOK3, Del, A_7, KCPIVGNRHMRNGKIFSRKSSFYNN, (SEQIDNO:315); XM_534136.5, WBP4, Ins, A_7, KCPRAKFIRSK, (SEQIDNO:316); XM_863207.4, SNW1, Del, A_7, KCQMHWPFRWMLKEKLNMMQLLGKDSQKTRSFIASILTWFPRKS, (SEQIDNO:318); XM_014116784.1, SUPT6H, Del, A_7, KCQMTRMTTRRNMAKRNMKKRLLQRKSSRMGKGKKGRKLWRPPWLLQRRRRKM MKNQTSMTLLWMMTDSP, (SEQIDNO:319); XM_003434930.3, SLC30A1, Del, A_7, KCQTNNLNHLC, (SEQIDNO:320); XM_005618730.2, WHAMM, Ins, A_7, KCRCCRRIRNTVL, (SEQIDNO:321); XM_014106804.1, TOPAZ1, Ins, A_7, KCRGVPEAPRVDATP, (SEQIDNO:322); XM_014111503.1, LOC102153069, Del, A_7, KCRGWHCCQ, (SEQIDNO:323); XM_005633661.2, ZNF143, Del, A_7, KCRLSYKDMQQE, (SEQIDNO:324); XM_005640594.2, PIKFYVE, Ins, A_7, KCRPFCSFKGSTCYGKQQTRKQN, (SEQIDNO:325); XM_536013.5, GTF3C3, Ins, A_7, KCRRRNFRRE, (SEQIDNO:326); XM_014122578.1, CEP295, Ins, A_7, KCSFPAFCRKCAEFSLQFL, (SEQIDNO:327); XM_014121376.1, TNIP3, Ins, A_7, KCSHKQEEGTLRM, (SEQIDNO:328); XM_014120929.1, AP2A2, Del, A_7, KCSIPTLRTPCSLRRSA, (SEQIDNO:329); XM_014114455.1, TRMT13, Ins, A_7, KCSREVDPCGWHCYCTLLSPQV, (SEQIDNO:330); XM_544733.5, DENND4A, Del, A_7, KCSRKRWIHLMKCATAFSCSSVGSTISPCLQFECFLKCRKLVLIPMPLLMVIIIRLFWK APGPQEVVVAIFFGQK, (SEQIDNO:331); XM_005640584.2, ZDBF2, Ins, A_7, KCSSGRQKQ, (SEQIDNO:332); XM_535180.5, HSPA14, Ins, A_7, KCSWGSSQSCWV, (SEQIDNO:333); XM_005623470.2, C8H14orf39, Del, A_7, KCTMVIYVSIKMF, (SEQIDNO:334); XM_005628374.2, COPG2, Del, A_7, KCTPSSTLLQSVKEI, (SEQIDNO:335); XM_005632905.2, DNMT1, Del, A_7, KCTRGRKRNRTRIGSLGLEMLSRLMGRRITIRRFASIQKPWKWETVSLLFQMTLQNR CI, (SEQIDNO:336); XM_014111638.1, ZFX, Del, A_7, KCTSVDIVTLRLQIHLF, (SEQIDNO:337); XM_014109263.1, ST18, Ins, A_7, KCVCSDHK, (SEQIDNO:338); XM_014108953.1, ZNF518A, Ins, A_7, KCVIFVSIRIGYSISKFDHKS, (SEQIDNO:339); XM_005628611.2, DNAH11, Del, A_7, KCWKPLVNVLKV, (SEQIDNO:340); XM_005623751.2, BTBD7, Ins, A_7, KCWNICSSSTILSLCGGSKVSAGRDDG, (SEQIDNO:341); XM_014109476.1, STARD9, Del, A_7, KCYTLTPVTSIPTSSPPIQRGLCRLAGSSMCLAVH, (SEQIDNO:342); XM_005616244.2, VSIG10L, Ins, A_7, KDAEHNPSADPTASALQSAAGGP, (SEQIDNO:343); XM_014119604.1, TMPO, Del, A_7, KDAPFPCG, (SEQIDNO:344); XM_005623416.2, SAMD4A, Del, A_7, KDCCHGNSRCRSSFGLSLGKPF, (SEQIDNO:345); XM_855384.3, USP15, Del, A_7, KDC1HSSSTI, (SEQIDNO:346); XM_005639666.2, DNAH5, Del, A_7, KDCPNLITFWIN, (SEQIDNO:347); XM_537432.5, MDGA2, Del, A_7, KDDFGSHQILITKMTTSRLGVR, (SEQIDNO:348); XM_014113138.1, C4H5orf42, Del, A_7, KDEDDELRKSCKKKDQKN, (SEQIDNO:349); XM_005632115.2, CCDC174, Ins, A_7, KDEKVKRRWSRGRK, (SEQIDNO:350); XM_531770.5, GCC2, Ins, A_7, KDEVPSRRECSSV, (SEQIDNO:351); XM_014114846.1, ZNF644, Ins, A_7, KDFHERLCCRIIQKISHLYM, (SEQIDNO:352); XM_014106427.1, EPSTI1, Del, A_7, KDFKKTSEEKHLESTTNTKLLSS, (SEQIDNO:353); XM_539598.4, CLSPN, Ins, A_7, KDGKNQAAKKEGNEK, (SEQIDNO:354); XM_844509.3, NPM2, Ins, A_7, KDGKRRGGSETQA, (SEQIDNO:355); XM_542243.5, ANKRD49, Ins, A_7, KDGKRSKQIASLGC, (SEQIDNO:356); XM_539736.5, IKBIP, Ins, A_7, KDGRLNYSDVQYGRRYAESSI, (SEQIDNO:357); XM_005629238.2, METAP2, Del, A_7, KDGRRRRVKGLPQGNKNLIKNQEPQLMR, (SEQIDNO:358); XM_861061.4, METAP2, Del, A_7, KDGRRRRVKGLPQQGNKNLIKNQEPQLMR, (SEQIDNO:360); XM_005619587.1, PATE2, Del, A_7, KDGVCIFIPNCHV, (SEQIDNO:361); XM_005629420.2, LOC102153096, Ins, A_7, KDHLLYWMFRPILFLFLFGNF, (SEQIDNO:362); XM_005624764.2, PIGW, Del, A_7, KDHMSKTG, (SEQIDNO:363); XM_855384.3, USP15, Del, A_7, KDILMKMPQRILKNMKVWNINLLKNPL, (SEQIDNO:364); XM_005635616.2, CLCN3, Del, A_7, KDILRHMAQTANQDPASIMFN, (SEQIDNO:365); XM_546818.5, CDYL2, Del, A_7, KDIQASPLQEVTGPPRRCLTGLPPVVCRSCR, (SEQIDNO:366); XM_014118170.1, PNISR, Del, A_7, KDIVGVDLQQLKLDGVEVEVTHAE, (SEQIDNO:367); XM_014113670.1, PTPRK, Del, A_7, KDIYVGEDTSALETLGGATILTPTTSSLLKNAKMPWGTPGRR, (SEQIDNO:368); XM_003639701.3, NIFK, Del, A_7, KDKEKAIS, (SEQIDNO:369); XM_005632477.1, LOC484748, Ins, A_7, KDKERERDEERRASTSNSTPSN, (SEQIDNO:370); XM_005626023.2, EIF5B, Del, A_7, KDKKSVSK, (SEQIDNO:371); XM_014108034.1, MYO1H, Del, A_7, KDKQPSDLKPTGVGPWLGRWPKGESGLCGP, (SEQIDNO:372); XM_003432496.2, C1H18orf63, Del, A_7, KDLIITFR, (SEQIDNO:373); XM_544630.4, RTF1, Del, A_7, KDLKSGKN, (SEQIDNO:374); XM_014111172.1, LOC102152583, Del, A_7, KDLRLRIMCTCGRYITQIWDGCALMPPIQRRGTGCDM, (SEQIDNO:375); XM_014109094.1, KIF20B, Del, A_7, KDLYMLVQLSLKMKRKAKKCQRTFQKMKTLEFYKKIIKS, (SEQIDNO:376); XM_849225.4, C5H11orf65, Del, A_7, KDMTMQICQRRKWEHQKILYMEIFLKNQIMLD, (SEQIDNO:377); XM_014113966.1, LOC102156567, Ins, A_7, KDNDSKAVSTGPGTRQAVNL, (SEQIDNO:378); XM_005629009.2, RNF11, Ins, A_7, KDPGVCYLYDGLCLWGPNSISAVHAHLSPGLYR, (SEQIDNO:379); XM_005620334.1, DOCK7, Ins, A_7, KDPGVGICNTPGSCRPQNASDGTPGVCRYNSESGAFGGCPSFSV, (SEQIDNO:380); XM_547161.5, MEFV, Ins, A_7, KDPVVLPEIRVCREEHEVPLRNAAFRNRYLQCSRTHLCSGTCR, (SEQIDNO:381); XM_846278.4, MAP4K5, Del, A_7, KDQLLKDF, (SEQIDNO:382); XM_534762.5, MRPL40, Ins, A_7, KDQTTGES, (SEQIDNO:384); XM_005634064.2, CCDC168, Ins, A_7, KDRKKERENCIKCGPKIYV, (SEQIDNO:386); XM_531828.5, RTN4, Ins, A_7, KDRRKTGPNCNREEF, (SEQIDNO:387); XM_005625106.2, SEC16A, Ins, A_7, KDRSLFARRQEQIDRLG, (SEQIDNO:388); XM_003434330.2, LEMD1, Del, A_7, KDSRLPTLTQKP, (SEQIDNO:390); XM_014121497.1, LOC476151, Ins, A_7, KDSRTGETRDH, (SEQIDNO:391); XM_005615576.2, DSE, Ins, A_7, KDSTESSDLGTERTAHR, (SEQIDNO:392); XM_014108622.1, DYRK4, Del, A_7, KDTRIPRISRWC, (SEQIDNO:393); XM_014118118.1, PHIP, Ins, A_7, KDVKTPAKIRYLYLSILYTYTNSSTKA, (SEQIDNO:394); XM_014120722.1, SYCP1, Ins, A_7, KDVRRKSFARG, (SEQIDNO:396); XM_005623743.2, RPS6KA5, Del, A_7, KDWDVVHVMRMKSKNISFFRK, (SEQIDNO:397); XM_543400.5, NAA25, Del, A_7, KDWRPQRN, (SEQIDNO:398); XM_014122300.1, GTPBP4, Ins, A_7, KEAENSAVQGEEHTGPQDASDG, (SEQIDNO:400); XM_846524.3, ACSL3, Del, A_7, KEAKGIQLC, (SEQIDNO:402); XM_005636136.2, C26H12orf65, Ins, A_7, KEAPERTPGIK, (SEQIDNO:403); XM_536179.5, CHD2, Del, A_7, KEAQQSKYRGFRLT, (SEQIDNO:404); XM_014111405.1, LUZP4, Del, A_7, KECDFKTPIKWS, (SEQIDNO:405); XM_005639728.2, MFN1, Ins, A_7, KECEDSQSAGPCPSYGQRLESWLPCTCILAKGKMCPLER, (SEQIDNO:406); XM_014110764.1, KCNH7, Ins, A_7, KECIPSFFR, (SEQIDNO:407); XM_535547.4, SCAPER, Ins, A_7, KECSRSDCISSCWWINSP, (SEQIDNO:408); XM_005618341.2, AGBL1, Ins, A_7, KECVPLWL, (SEQIDNO:409); XM_005617217.2, SMN, Ins, A_7, KECYHSPEAVESW, (SEQIDNO:410); XM_014108062.1, DENR, Ins, A_7, KEDCTTKSYDSQNS, (SEQIDNO:411); XM_014109172.1, PRKDC, Del, A_7, KEDHGFKK, (SEQIDNO:412); XM_005636081.1, SFSWAP, Ins, A_7, KEEEALTVTDRVQGRVPVGVPKQASHTSAHGPLSQHLSRGESGLQSGALQGSFSGK RRPDLLSNCLLCAEQNNSGPHGQSEGDARCFQEHADQCLL, (SEQIDNO:413); XM_005641516.2, ATRX, Ins, A_7, KEEEGYSHAAKGHHTCRTSSNT, (SEQIDNO:414); XM_535608.5, SDAD1, Ins, A_7, KEEEETRGV, (SEQIDNO:415); XM_005633448.2, RSF1, Del, A_7, KEEEKEKMR, (SEQIDNO:416); XM_535884.5, PAK11P1, Ins, A_7, KEEKKEENI, (SEQIDNO:417); XM_005617440.2, SREK1IP1, Ins, A_7, KEEKKGEAFIHS, (SEQIDNO:418); XM_014113675.1, PTPRK, Ins, A_7, KEELLFLLLLPQAC, (SEQIDNO:419); XM_545078.5, ZBTB11, Del, A_7, KEEQSRTWNGCVNNVEGNSLS, (SEQIDNO:420); XM_014110285.1, PARP9, Ins, A_7, KEESDGRENTWETCELQVVSASSLPV1, (SEQIDNO:421); XM_542610.5, DIS3, Del, A_7, KEESKKGL, (SEQIDNO:422); XM_014119891.1, UBN2, Ins, A_7, KEETLQRFSFSGCHDTKISEREGCIKEGA, (SEQIDNO:423); XM_014115182.1, SUCO, Ins, A_7, KEETLQVQN, (SEQIDNO:424); NM_001038648.1, TMEM57, Ins, A_7, KEEVGRSYCCPGRCICCCI, (SEQIDNO:425); NM_001005869.1, HTR2A, Ins, A_7, KEFKERCQEHR, (SEQIDNO:426); XM_005615489.2, SHPRH, Del, A_7, KEFPSFPSINMSVLYIDMMFSGTGVF, (SEQIDNO:427); XM_005641516.2, ATRX, Del, A_7, KEFQIKKTMILLKMKNTEKKEWIIKGRKI, (SEQIDNO:428); XM_005621999.2, SSX2IP, Ins, A_7, KEFREGKTKLYRSSHSPRIGEKGV, (SEQIDNO:429); XM_005621312.2, AG1, Del, A_7, KEFSLIMKSE, (SEQIDNO:430); XM_541861.5, PARP3, Ins, A_7, KEGAAGCRGGGQLPHCRGPQSCTHREARSPSGPSMPAQPQPSDPGA, (SEQIDNO:431); XM_005626522.2, KIF3A, Del, A_7, KEGAVAAAVVQTPHVLS, (SEQIDNO:432); XM_014117357.1, FAM227A, Ins, A_7, KEGKPHVHPTFKLP, (SEQIDNO:435); XM_005615620.2, RSPO3, Del, A_7, KEGRGKGKNPIRKRVRTQYLTTKVWNPAEKPRNHEKTKTNSSRRSERSKINNRNRL WISFGD, (SEQIDNO:436); XM_005626521.2, KIF3A, Del, A_7, KEGVKRKCPQIRWLKCKQKLMRREKHLKQSLIWKKKKETRLELN, (SEQIDNO:437); XM_014118152.1, CASP8AP2, Ins, A_7, KEHFVFVSIC, (SEQIDNO:438); XM_014119762.1, LRRIQ1, Ins, A_7, KEHHEKRKRATAKQRNIKIKRRCKQTGNNK, (SEQIDNO:439); XM_014117920.1, C11H9orf84, Del, A_7, KEHMPLTF1, (SEQIDNO:440); XM_544889.6, BRWD1, Ins, A_7, KEHQSNQLC, (SEQIDNO:441); XM_014118968.1, ZNF800, Ins, A_7, KEHTGSTEK, (SEQIDNO:442); XM_534564.5, PBK, Ins, A_7, KEICIMFNSMYKYSCLSNAEAWLWYWGKCVPYEKISKRLVSFSLGCEKD, (SEQIDNO:443); XM_014122577.1, CEP295, Ins, A_7, KEICQNYKSATTTSKSF, (SEQIDNO:444); XM_003431866.2, ISPD, Del, A_7, KEIFYYVVFLYITHRRSRTYRQV, (SEQIDNO:445); XM_536312.4, CMYA5, Del, A_7, KEILLNLKMFQQTQKIIL, (SEQIDNO:446); XM_005638550.2, LRRC49, Ins, A_7, KEILQDVYGGPCEGSHGNQYEK, (SEQIDNO:447); XM_014110128.1, STX19, Del, A_7, KEILVRYCAVGVVHAVVQN, (SEQIDNO:448); XM 014110659.1, SYCP2L, Ins, A_7, KEIPKTVF, (SEQIDNO:449); XM_005634066.2, KDELC1, Ins, A_7, KEIQLTNPSNLFLVWLHRFQGYRDAYLRPD, (SEQIDNO:450); XM_532920.5, WDR43, Ins, A_7, KEIRSYRNE, (SEQIDNO:451); XM_014120231.1, ROCK2, Del, A_7, KEIRTLKYPPRK, (SEQIDNO:452); NM_001003222.1, CNGA1, Ins, A_7, KEKEKRKEEQIRR, (SEQIDNO:454); XM_005618268.2, TRPM1, Del, A_7, KEKGIKMSRIVV, (SEQIDNO:455); XM_014114536.1, TNRC6A, Ins, A_7, KEKGKGNHERWKQTRRSMDKSIR, (SEQIDNO:456); XM_536845.5, BAZ1B, Del, A_7, KEKGNGLHQNFCLTNMM, (SEQIDNO:457); XM_014110443.1, ZNF639, Del, A_7, KEKGRHYTLLVTQIPLE, (SEQIDNO:458); XM_005639570.2, PARP14, Del, A_7, KEKHLRLLPNSLWSLN, (SEQIDNO:459); XM_014120361.1, MYT1L, Del, A_7, KEKHRISSPKNLLPSGNRLP, (SEQIDNO:460); XM_005631271.2, LRP4, Ins, A_7, KEKKKKKG, (SEQIDNO:461); XM_005631005.2, ABCA13, Del, A_7, KEKQLTTLLTLRN, (SEQIDNO:462); XM_005633942.2, DIAPH3, Del, A_7, KEKQRKGKNVPK, (SEQIDNO:463); XM_014109202.1, CCNE2, Del, A_7, KEKRRPPGNSSMRLGIVGHLYYPGGSVHVLSLKHPTKKWEQVTSLDLQITDLKIFLLI LHLCLI, (SEQIDNO:464); XM_014115188.1, PRRC2C, Del, A_7, KEKTPNQALKNPKRK, (SEQIDNO: 466); XM_544645.5, UBR1, Ins, A_7, KEKTRKQR, (SEQIDNO:467); XM_003434948.2, DSC3, Del, A_7, KEKVFLKI, (SEQIDNO:468); XM_534311.5, DHX36, Del, A_7, KEKWSRFTQKLMD, (SEQIDNO:470); XM_005641516.2, ATRX, Del, A_7, KELENTVKKTQEMKEQKIKSIMNQIQILKNLRSQDTDIGF, (SEQIDNO:471); XM_859741.4, WAP1, Del, A_7, KELKQLHPPPCSLLLKALIIPRTVSLVLTMQKT, (SEQIDNO:472); XM_859725.4, WAP1, Del, A_7, KELKQLHPPPCSLLLKALIIPRTVSLVLTMQRTCLVCLKV, (SEQIDNO:473); XM_532130.5, DNAH8, Del, A_7, KELMISVSHVLC, (SEQIDNO:474); XM_005633366.2, CCDC67, Del, A_7, KELNPLIHLLLKN, (SEQIDNO:475); XM_005627496.2, COL21A1, Del, A_7, KELRGFLV, (SEQIDNO:476); XM_014116439.1, ABCA6, Del, A_7, KELSPSYGSQASILLPTGLGRHWWILASLFFFSFQCFYFCM, (SEQIDNO:478); XM_005627784.2, LOC102155928, Del, A_7, KELTGFPL, (SEQIDNO:479); XM_014118080.1, DST, Ins, A_7, KEMSFLLYHCVLCFQGHSWK, (SEQIDNO:482); XM_005633847.2, KPNA3, Del, A_7, KEMSPKKKV, (SEQIDNO:483); XM_014110232.1, GOLGB1, Del, A_7, KEMWKPSNKLSWRRISK, (SEQIDNO:484); XM_005626867.1, TEX10, Del, A_7, KENAKMIFKK, (SEQIDNO:485); XM_005636161.2, RSRC2, Ins, A_7, KENALARQKRRG, (SEQIDNO:486); XM_535027.5, FAM204A, Del, A_7, KENAPGKVN, (SEQIDNO:487); XM_014115747.1, LOC102156002, Ins, A_7, KENFNRNQPKMEFRSRKRR, (SEQIDNO:488); XM_003639068.2, ATMIN, Ins, A_7, KENGELPAQPKVVQ, (SEQIDNO:489); XM_005619382.2, NIPBL, Del, A_7, KENKILTHRRLGVLQEVIDQLLRRRVLREMGQGQH, (SEQIDNO:490); XM_549626.5, TMCO1, Ins, A_7, KENREARRETEK, (SEQIDNO:491); XM_536590.4, GUCY1A2, Ins, A_7, KENSGSSVFYFPW, (SEQIDNO:493); XM_014112357.1, LCOR1, Del, A_7, KENTLKMIISK, (SEQIDNO:494); XM_005641136.2, BMX, Ins, A_7, KENVAKQLREAFCFNQNKSLL1, (SEQIDNO:495); XM_536371.4, TET1, Del, A_7, KENVLLSPYLVLERRGQQ, (SEQIDNO:496); XM_005635695.2, DOCKS, Del, A_7, KEPHFMRTSLKQ, (SEQIDNO:497); XM_014111407.1, DOCK11, Del, A_7, KEPHPKSPGLPSSGGRKRPKLLSPWTMRMLSPKGKPRFTATPSETSLCFQWKNLSQ, (SEQIDNO:498); XM_014116869.1, CAMSAP1, Ins, A-7, KEQACVSASTLRPASCCQL, (SEQIDNO:499); XM_005630347.2, CEBPZ, Del, A_7, KEQLMTFNKVNWKHLFRILVWPSMQKLS, (SEQIDNO:500); XM_003638844.3, KIAA0355, Ins, A_7, KEQQWRQLIWHEPHT, (SEQIDNO:501); XM_014119939.1, ZNF786, Del, A_7, KEQRKANCPTSYL, (SEQIDNO:502); XM_850237.2, CLCA2, Del, A_7, KEQTRKRMEQN, (SEQIDNO:503); XM_014119186.1, FAM133B, Del, A_7, KERCILKINHYHLSPYQNQIILRRYEQKRRKAVKNEKK, (SEQIDNO:504); XM_005632477.1, LOC484748, Ins, A_7, KERERQRQKERKDRKKDKERERDEERRASTSNSTPSN, (SEQIDNO:505); XM_005624905.2, NSRP1, Del, A_7, KERKIILNCFWEKTESPSIFTTY, (SEQIDNO:506); XM_014111124.1, SGOL2, Ins, A-7, KERKIKETI, (SEQIDNO:507); XM_014112349.1, BOD1L1, Del, A_7, KERKIQGMLKRILKRNCNLKKIPKKLSRQVSIVKRKRYLLQRI, (SEQIDNO:508); XM_014114042.1, PMFBP1, Ins, A_7, KERKNDKRKFEDVGGGK, (SEQIDNO:509); XM_547771.4, CFL2, Del, A_7, KERKQFSSV, (SEQIDNO:510); XM_014120446.1, EML4, Ins, A_7, KERKITRTEGKKRGISF, (SEQIDNO:511); NM_001287118.1, CFDP1, Del, A_7, KERLRAFRPGRENKVASH, (SEQIDNO:512); XM_005617350.2, RBM27, Del, A_7, KERMASGETMTGTMSGMNCTVRNMTGEEAGVRVGVRAEA, (SEQIDNO:513); XM_014119702.1, CFAP54, Del, A_7, KERPTYHQMLKNFPHLLIPE, (SEQIDNO:514); XM_014117407.1, LOC102155766, Del, A_7, KERRDHFPNTCVQNTNGHL, (SEQIDNO:515); XM_014113223.1, DYNC2H1, Ins, A_7, KERRKEKKLS, (SEQIDNO:516); XM_014111364.1, FAM133A, Del, A_7, KERRLILKINLCLQNPHQNQIMKRKCKQKRREDMKSEKKQQKKQRRRRRGRRNSTRNIVRRRKRSRVQVTSQD, (SEQIDNO:517); XM_014118978.1, AKAP9, Ins, A_7, KERRLQNAN, (SEQIDNO:518); XM_535878.4, RIOK1, Del, A_7, KERRRQPG, (SEQIDNO:519); XM_014122593.1, MCM10, Ins, A_7, KERTTYLPGI, (SEQIDNO:521); XM_014117413.1, TLE1, Del, A_7, KERWMIRTPATMTAMVTKAMTT, (SEQIDNO:522); XM_014112204.1, CAST, Del, A-7, KERWRRTQ, (SEQIDNO:523); XM_014112203.1, CAST, Del, A_7, KERWRSRTQ, (SEQIDNO:524); XM_014115197.1, GORAB, Ins, A_7, KESGIARKISLGSPPTRATANGREK, (SEQIDNO:525); XM_849701.4, FGD6, Del, A_7, KESHSVLVGVLMRLTQKIKRKLVLLDQRLPSGSLIPEPQCV, (SEQIDNO:526); XM_014112483.1, ZFAND6, Ins, A_7, KESLFHVQEESGTYWV, (SEQIDNO:527); XM_014121706.1, CNTN6, Del, A_7, KESLILKGLEGRNLLGI, (SEQIDNO:528); XM_014115025.1, LUC100683727, Ins, A_7, KESMEEDGH, (SEQIDNO:529); XM_005618061.2, GIN1, Ins, A_7, KESPKRVP, (SEQIDNO:530); XM_849201.4, ATG5, Ins, A_7, KESSDDSWN, (SEQIDNO:531); XM_005624831.2, TEFM, Del, A_7, KESSRTTGS, (SEQIDNO:532); XM_536224.5, WHSC1, Del, A_7, KESTQRGHRSLLKTLTAKMHPGRDSGPTSTVFGRERRSMTRQPEQAPARPSRQPPHS RARQQRNICQMHANH, (SEQIDNO:533); XM_534539.6, IFT88, Del, A_7, KESTRMILLMKN, (SEQIDNO:534); XM_533861.5, KIAA1143, Del, A_7, KETCQLKKS, (SEQIDNO:536); XM_014106852.1, KIZ, Ins, A_7, KETGPGKETL, (SEQIDNO:537); XM_535949.5, KLHL41, Del, A_7, KETGRIWLQ, (SEQIDNO:538); XM_005629203.2, MGAT4C, Del, A_7, KETIYLRQSSQFLSNPATKS, (SEQIDNO:539); XM_544163.4, CPNE3, Ins, A_7, KETKEEKLQEFRCYQCETV, (SEQIDNO:540); XM_014116764.1, ATAD5, Ins, A_7, KETKEKDGNSR, (SEQIDNO:541); XM_014107297.1, PSMA7, Ins, A_7, KETKESIM, (SEQIDNO:542); XM_005626618.2, KDM4C, Ins, A_7, KETKNAELQV, (SEQIDNO:543); XM_014112822.1, ANK3, Ins, A_7, KETPQTVPGSEEKV, (SEQIDNO:545); XM_532056.6, ABCF1, Ins, A_7, KETRHPKRPKEEGCG, (SEQIDNO:546); XM_003639968.3, PDZRN4, Del, A_7, KETRKSWTTG, (SEQIDNO:547); XM_005636681.2, PTHLH, Ins, A_7, KETSNSVCLAKLWRG, (SEQIDNO:548); XM_005615345.2, VPS4B, Ins, A_7, KETTESTSRCHCYRATKCEMERCCWS, (SEQIDNO:549); XM_536846.5, NSUN5, Ins, A_7, KETTPDCGPSHTAPYRAGRKAV, (SEQIDNO:550); XM_014114292.1, KLK8, Ins, A_7, KEVHSTPGGSQPEE, (SEQIDNO:551); XM_014113160.1, CDH18, Ins, A_7, KEVIYSHHRRSKHTS, (SEQIDNO:552); XM_005640039.2, HIVEP1, Ins, A_7, KEVPSGARDHV, (SEQIDNO:553); XM_005622350.2, TMEM206, Del, A_7, KEVRQQTT, (SEQIDNO:554); XM_014110716.1, SCN1A, Ins, A_7, KEVWRSRHLHDRRTEEIL, (SEQIDNO:555); XM_005641516.2, ATRX, Del, A_7, KEWIIKGRKI, (SEQIDNO:556); XM_014119796.1, KDM7A, Del, A_7, KEWQPPNSVLGRFLS, (SEQIDNO:557); XM_005634410.2, COL6A5, Del, A_7, KEWSVKSARAVGKRIALWT, (SEQIDNO:558); XM_014120373.1, ALMS1, Ins, A_7, KEWVTIRSF, (SEQIDNO:559); XM_005616987.1, ENKUR, Ins, A_7, KFCKHKCSRCHYGSG, (SEQIDNO:560); XM_014115682.1, TTC6, Del, A_7, KFCKTTPLLPFMICVPLSQPRSCLLTCTWLLECTIQLTRKVTILCLRYWEPiS, (SEQIDNO:561); XM_538192.4, FMR1NB, Ins, A_7, KFCMGNSVEFFPSNNLHSKGE, (SEQIDNO:562); XM_005622295.2, ZBTB41, Del, A_7, KFCNVLNVIRHLTA, (SEQIDNO:563); XM_005623023.2, ROCK1, Del, A_7, KFCSIMMNKIRNNPIHPWYWT, (SEQIDNO:564); XM_014115665.1, ZBTB1, Ins, A_7, KFCVQIIYSKRTCVTALWTEFYL, (SEQIDNO:565); XM_005640330.2, GPR155, Ins, A_7, KFCWTNSGVCSIVQLPL, (SEQIDNO:566); XM_537272.5, HAUS1, Ins, A_7, KFDCNVSVRKMSTRGSKEGRAASLYRKGQS, (SEQIDNO:567); XM_005628611.2, DNAH11, Ins, A_7, KFDTEADYFESSAP, (SEQIDNO:568);

XM_005638799.2, USP16, Ins, A_7, KFEKDNGG, (SEQIDNO:569); XM_014109056.1, SMC3, Del, A_7, KFENLDHFPRKHLKSTRH, (SEQIDNO:570); XM_014118548.1, RGS22, Del, A_7, KFFETSNLEIPSMML, (SEQIDNO:571); XM_005628254.2, CENPC, Ins, A_7, KFFNNFRNCKTKK, (SEQIDNO:572); XM_543416.5, FBXO21, Del, A_7, KFFTTYANRKF, (SEQIDNO:573); XM_003433570.1, SLC15A5, Del, A_7, KFGLESACFWWRCVRGSLSLKLSAI, (SEQIDNO:574); XM_014116163.1, LOC100688895, Del, A_7, KFGLSRTARAQTGACRAAY, (SEQIDNO:575); XM_535238.5, DHX29, Ins, A_7, KFGSKYERMDLAVC, (SEQIDNO:576); XM_539002.5, COL12A1, Del, A_7, KFHTKVATQ, (SEQIDNO:577); XM_532397.5, CABS1, Ins, A_7, KFHYSRHNCLYRRENN, (SEQIDNO:578); XM_005618917.2, RTKN2, Del, A_7, KFIISLSSTLLPDSL, (SEQIDNO:579); XM_014112848.1, RUFY2, Del, A_7, KFMNRSKLFKNLATNLANQNLK, (SEQIDNO:580); XM_014116492.1, NF1, Ins, A_7, KFISLSVDYIGYTGKMSCWATKGHDEIR, (SEQIDNO:581); XM_846170.4, CAPN7, Del, A_7, KFITQVTRLHTLMAFELTALII, (SEQIDNO:583); XM_005641236.2, CFAP47, Del, A_7, KFITSKMK, (SEQIDNO:584); XM_005619358.2, ZNF131, Del, A_7, KFIYVNTVRNSLTTLDILKSIFGNIQVKNLLNVQIVMNDLLEIAPSNVT, (SEQIDNO:585); XM_014112357.1, LCOR1, Ins, A_7, KFKEVDTQ, (SEQIDNO:586); XM_014111598.1, MBTPS2, Ins, A_7, KFKFKFLYNTFFGNSHSLNKSETSTSN, (SEQIDNO:587); XM_014107055.1, LOC106557703, Del, A_7, KFKKQHLT, (SEQIDNO:588); XM_014115771.1, NGDN, Del, A_7, KFKLEPILQRRVSASWK, (SEQIDNO:589); XM_847666.4, PPM1D, Ins, A_7, KFKNVNSRSNESPRS, (SEQIDNO:590); XM_005637264.2, RAD51AP1, Del, A_7, KFLFQRSLGNHHKYAALQLKAENLSGSHQ, (SEQIDNO:591); XM_532881.5, RAD51AP2, Del, A_7, KFLFQWILMTGMKFL, (SEQIDNO:592); XM_843857.4, HNRNPD, Del, A_7, KFLLVAFLQIHLKKK, (SEQIDNO:593); XM_014117399.1, CCDC138, Del, A_7, KFLLYVSYTVS, (SEQIDNO:594); XM_849254.4, RPL26L1, Del, A_7, KFLNAKPNLDRSEKRKANIRKNLLRKCRS, (SEQIDNO:595); XM_005619238.2, ZBED8, Del, A_7, KFLVSQTSLNRSYSYSRSHC, (SEQIDNO:596); XM_014106493.1, TTC21A, Del, A-7, KFLWLAGCVGGTRRFYS, (SEQIDNO:597); XM_014115270.1, DNAH14, Del, A_7, KFMILQTSQKNQS, (SEQIDNO:598); XM_005622923.1, CCDC178, Del, A_7, KFMINLLGREKVMKRSIWMYLIIIMPQKHHGILSFLMLQKTFQISQLQMLS, (SEQIDNO:599); XM_014115932.1, KIAA0586, Del, A_7, KFMQMQFLLFLLKKTRTLWFHRKQPTIQRTWKTVQVSLVKDKGLG, (SEQIDNO:600); XM_848323.4, EYS, Del, A_7, KFMWIIADPRILLC1HCPLLLLLV, (SEQIDNO:601); XM_005618201.2, LOC479005, Ins, A_7, KFPAHRQRSGRTCKSWIPSSSLLCLCLLTQGLAVRGGCRSLQRAVAGVPGCLESSA, (SEQIDNO:602); XM_014111937.1, CFAP47, Del, A_7, KFPDRTTFQNIIRPFMM, (SEQIDNO:603); XM_005623657.2, CCDC176, Ins, A_7, KFPEVARDSDFPFTSKGDQ, (SEQIDNO:604); XM_014108601.1, SLC4A8, Del, A_7, KFPLGQRPQMSWLERWIVWTAPLLPL, (SEQIDNO:605); XM_536590.4, GUCY1A2, Del, A_7, KFPTTLAPCSSGRQAS, (SEQIDNO:607); XM_005633789.2, LOC100856360, Del, A_7, KFPVMSTS, (SEQIDNO:608); XM_005628995.2, ZCCHC11, Del, A_7, KFQALLLLWTK, (SEQIDNO:609); XM_535625.5, GK2, Del, A_7, KFQEIITLSSPRQAFHLALTSVQ, (SEQIDNO:610); XM_005636067.2, GOLGA3, Ins, A_7, KFQIKQNSVSG, (SEQIDNO:611); XM_003833885.2, SPESP1, Del, A_7, KFQILSHRYNRYLLLKASSQNTERIFEPLESI, (SEQIDNO:612); XM_532047.5, CNTR1, Del, A_7, KFQKRRKTFFSSS, (SEQIDNO:613); NM_001003294.1, DLD, Del, A_7, KFQKRWLSLVQE, (SEQIDNO:614); XM_014110462.1, ZBBX, Ins, A_7, KFQLPWLLPSSIKKCSCSIII, (SEQIDNO:615); XM_005625995.2, IL1RL1, Ins, A_7, KFQNILSYN, (SEQIDNO:616); XM_005640594.2, PIKFYVE, Del, A_7, KFQVERSLILWLSMDLFVPKILHIKR, (SEQIDNO:617); XM_014120087.1, LOC607729, Ins, A_7, KFRCAIEKSFENTSRYG, (SEQIDNO:618); XM_534816.5, CCDC65, Del, A_7, KFRDYRTP, (SEQIDNO:619); XM_005627018.2, TFAP2B, Del, A_7, KFRFLPN1, (SEQIDNO:620); XM_014113689.1, SGIP1, Del, A_7, KFRRKAMGHQMDFMRKLIGKDITPLSWMKKATASDLRNPALPKESTFILQANRKRK KNHTRNLTSRLSHCNLKTFLRMLQP, (SEQIDNO:622); XM_005640670.2, CCDC108, Ins, A_7, KFRSPHLLLPQPQREDPARHNCSGLVDLLTY, (SEQIDNO:623); XM_014112960.1, FAM35A, Del, A_7, KFSCHTINTLYI, (SEQIDNO:624); XM_539084.5, REV3L, Ins, A_7, KFSEETSGNSQTE, (SEQIDNO:625); XM_005627714.2, SLC16A10, Del, A_7, KFSILPSSR, (SEQIDNO:626); XM_846103.4, LMTK2, Del, A_7, KFSLCDGPLQN, (SEQIDNO:627); XM_014114597.1, LOC102156157, Del, A_7, KFSLERKGMNLRP, (SEQIDNO:628); XM_859534.4, WNK3, Del, A_7, KFSNKVTTSHLSAQLMKLMYLQ, (SEQIDNO:629); XM_005620779.2, PRMT7, Del, A_7, KFSRLTTWKIKLI, (SEQIDNO:630); XM_005638476.2, VPS13C, Ins, A_7, KFSSAESDCIL, (SEQIDNO:631); XM_005621931.2, GLMN, Ins, A_7, KFSYASAVY, (SEQIDNO:632); XM_014121650.1, MYO3A, Ins, A_7, KFSYFLLHLCWIS, (SEQIDNO:633); XM_843944.4, NSUN3, Ins, A_7, KFTFKGLSHPLSGVFALPP, (SEQIDNO:634); NM_001003144.2, CHRNA1, Del, A_7, KFTFPRKRSGAQTSFSITMQMVTLPLSSSPKCSWTTRATSHGHLRPSSKATVRSLSPT FPLMNRTA A, (SEQIDNO:635); XM_014108414.1, PLEKHA5, Del, A_7, KFTILERDLIQLKGILMHLWSDEVGFINRTVLA, (SEQIDNO:636); XM_535836.5, KNG1, Del, A_7, KFTLLSTVSHWERSY, (SEQIDNO:637); XM_014121550.1, ZNF660, Del, A_7, KFTNVRSVGKHVFLIQRL, (SEQIDNO:638); XM_005634030.1, IPOS, Del, A_7, KFVILLQSWPGI, (SEQIDNO:639); XM_005638131.2, FSBP, Ins, A_7, KFWIVCSGEEGWIEKKAAARGRAAKSKN, (SEQIDNO:640); XM_014119209.1, CFAP69, Del, A_7, KFWKLLQQHQKILARWLLLFKAR, (SEQIDNO:641); XM_014107673.1, TRAF3IP1, Del, A_7, KFWRPRKIMRSYSGHPDLERRAATGTNLV, (SEQIDNO:642); XM_014107674.1, TRAF3IP1, Del, A_7, KFWRPRKIMRSYSGHPDLERRRNCLSLSQHGRRRRT, (SEQIDNO:643); XM_005637236.2, CHD4, Ins, A_7, KGAGGQLWGGAGVCGGGGRGGSSLRQ, (SEQIDNO:644); XM_005622874.2, GALNT1, Ins, A_7, KGARTSCWGCSRASTKAS, (SEQIDNO:645); XM_542654.5, NALCN, Ins, A_7, KGASRNEKESAGRGAERESPILRQATVHSWTGAQVQKLLPGGGPGTLQCI, (SEQIDNO:647); XM_005637237.2, CHD4, Ins, A_7, KGAYALMPAAGGQLWGGAGVCGGGGRGGSSLRQ, (SEQIDNO:648); XM_536846.5, NSUN5, Del, A_7, KGDHAGLWPLAHCPLQSRKESG, (SEQIDNO:650); XM_538328.5, SMC1B, Del, A_7, KGDMTFSASVLSTFQSLLMKSTRS-

SAETSVPRHFLAQRTQKSLT, (SEQIDNO:651); XM_005632616.2, SETD2, Del, A_7, KGDRNWR-VILKVMVNFRTERKFEWRWSRGKRQCP, (SEQIDNO: 652); XM_014118575.1, OXR1, Del, A_7, KGEDINQLI-INIL, (SEQIDNO:653); XM_003639443.3, OXR1, Del, A_7, KGEDINQLIINILW, (SEQIDNO:654); XM_014117985.1, CNTLN, Ins, A_7, KGEDTNRRMFQQEGIN, (SEQIDNO:655); XM_014113564.1, CHD3, Ins, A_7, KGEEDKAAEKRG-GRWGTKAGRTEVVSHSASDLGPGGRGTCVL, (SEQIDNO:656); XM_014113549.1, CHD3, Ins, A_7, KGEEDKAAEKRGGRWGTKGRTEVVSHSASDLGP-GRGTCVL, (SEQIDNO:657); XM_537657.5, CWC25, Ins, A_7, KGEEEKEGKEKEAQET, (SEQIDNO:658); XM_014114536.1, TNRC6A, Del, A_7, KGEGKGEP, (SEQIDNO:659); XM_844090.4, INO80, Del, A_7, KGEGMKNSPLKNLLVAITTRPKSLPSSLMMHLLLAP-RRSTYPSSSLMLVAEKYG1A1, (SEQIDNO:660); XM_014106851.1, CTCFL, Ins, A_7, KGEGSKTNLPL, (SEQIDNO:661); XM_014120175.1, WDR17, Ins, A_7, KGENCIWSY, (SEQIDNO:662); XM_544645.5, UBR1, Del, A_7, KGENKKTKMKHYHHHHLLNSALL-SAKWLTFSIVIS, (SEQIDNO:663); XM_014122593.1, MCM10, Del, A_7, KGENNLPTWNLKNFRKF, (SEQIDNO:664); XM_014121595.1, LOC106560076, Ins, A_7, KGETWEKSVHDCS, (SEQIDNO:665); XM_014109094.1, KIF20B, Ins, A_7, KGFHTSII, (SEQIDNO:666); XM_850643.4, SH3RF1, Ins, A_7, KGFIEVAFWRLH, (SEQIDNO:667); XM_005616337.2, IZUMO1, Ins, A_7, KGFLSQQMWSDVADSDLVP, (SEQIDNO:668); XM_860876.4, SPAG9, Ins, A_7, KGFTDPSGIFRISNKTT, (SEQIDNO:669); XM_005635616.2, CLCN3, Ins, A_7, KGGAIS-CLSCRGFCSFWCTNWRSSF, (SEQIDNO:670); XM_014113675.1, PTPRK, Del, A_7, KGGATIL-TPTTSSLLKNAKMPWGTPGRR, (SEQIDNO:671); XM_014108010.1, MYO18B, Ins, A_7, KGGDSRDSS-WPPGQH, (SEQIDNO:672); XM_535304.5, CHD9, Del, A_7, KGGEGGRMSKVLTSSFLTEINHLIMLL, (SEQIDNO:673); XM_545270.2, LOC488146, Ins, A_7, KGGGGEGRRMF, (SEQIDNO:675); XM_005617790.2, SRRM1, Ins, A_7, KGGHEQSKFGGYKALDNKTSNG-NPWV, (SEQIDNO:676); NM_001003060.2, FMO3, Ins, A_7, KGGKAQMVWHQRDSTDGLY, (SEQIDNO:677); XM_005616571.2, LOC100684414, Del, A_7, KGGKTFHHGLRFAQQHSIPTG, (SEQIDNO:678); XM_014107827.1, CLIP1, Ins, A_7, KGGNEPQPVPGS-ESQV, (SEQIDNO:680); XM_005640523.2, NIF3L1, Ins, A_7, KGGPHSLLPSTYFSTLKTHNLENLE-GAPGDPGSGKQSWYLLSSHRL, (SEQIDNO:681); XM_014108788.1, MK167, Del, A_7, KGGSPLVVV, (SEQIDNO:682); XM_005620292.2, ACAD8, Ins, A_7, KGGVELTANPRGDL, (SEQIDNO:683); XM_014121542.1, LOC106560070, Ins, A_7, KGHCDHSLTHEFLCGHVLFGLHCLLFFKNVVEQ, (SEQIDNO:684); XM_545798.5, NIPA1, Ins, A_7, KGHRARQAARYLL-FNRHCVVGRHNCNGCWPDWKLPGLHSGPHSPGD-STGCPWSAI WVHFSFLSSEGKAQYLGQIGVSAKL-CRFCCADYPLPKI, (SEQIDNO:685); XM_005624373.2, NMT1, Ins, A_7, KGHSSSAPAPHQVPEAVPPHASHEP-GGGGALVLSPGEYH, (SEQIDNO:686); NM_001286231.1, TAF9, Ins, A_7, KGINFCGKNNSSTVKCWFCY, (SEQIDNO:687); XM_005617803.2, STPG1, Ins, A_7, KGIQQSSQEIL1, (SEQIDNO:689); XM_005620109.2, SPECC1, Del, A_7, KGISCWHLKQPKV, (SEQIDNO:690); XM_005642451.2, TDRD3, Del, A-7, KGITLCK-ADQAKVHPMQRQRKIHLLKNP-LIIITRNVGKEKTKQQILIIFMTGNHEQVT KLSVV, (SEQIDNO:691); XM_005635696.1, ADAM7, Del, A_7, KGITLIMFYYSVGSGSTHMHKELLFQRAY-VCPITPPVLLRIFCLT, (SEQIDNO:692); XM_847163.4, LOC491346, Del, A_7, KGITLRKADQAKVHPMQRQRKIHLLKNP-LIIITRNVGKEKTKQQILIIFMTGNHKQVT KLSVV, (SEQIDNO:693); XM_532236.6, UFL1, Ins, A_7, KGKADTVPASTSTG, (SEQIDNO:694); XM_005636161.2, RSRC2, Del, A_7, KGKCFGKAKKKGINPNLLKYGKN, (SEQIDNO:695); NM_001003057.1, TCOF1, Ins, A_7, KGKEEEGKKGLNQRP, (SEQIDNO:696); XM_535126.4, LOC477937, Del, A_7, KGKEMKKIKKFLQPNQQE, (SEQIDNO:697); XM_846752.4, ZNF318, Ins, A_7, KGKGHEGNKRG, (SEQIDNO:699); XM_532236.6, UFL1, Del, A_7, KGKGRYCSSIDKHWLSS, (SEQIDNO:700); XM_005641869.2, MAP7D3, Ins, A_7, KGKHQTDTL, (SEQIDNO:701); XM_014113223.1, DYNC2H1, Del, A_7, KGKKKRKKAQLISIF, (SEQIDNO:702); XM_537751.5, NUFIP2, Del, A_7, KGKL-GAIVPRVVKTL1, (SEQIDNO:703); XM_014116492.1, NF1, Ins, A_7, KGKQKISG, (SEQIDNO:704); XM_014113123.1, FYB, Del, A_7, KGKRRKRRD, (SEQIDNO:707); XM_538677.5, MLLT3, Del, A_7, KGKR-VAQRLYLKVFLAHHH, (SEQIDNO:708); XM_005626022.2, EIF5B, Del, A_7, KGKTLMKMIS, (SEQIDNO:709); XM_005641869.2, MAP7D3, Del, A-7, KGKTSDRHL, (SEQIDNO:710); XM_005625969.2, 43353, Ins, A_7, KGKYSFFNYVWPCWL, (SEQIDNO:712); XM_014115269.1, DNAH14, Del, A_7, KGLCHMIE, (SEQIDNO:713); XM_546502.5, MPZL2, Ins, A_7, KGLCLFRRHRL, (SEQIDNO:714); XM_005637210.2, C1S, Ins, A_7, KGLETSLPWRSNPLFQRSHCQFCLGA, (SEQIDNO:715); XM_014110401.1, PHC3, Del, A_7, KGLFWIIR, (SEQIDNO:716); XM_005628768.2, AASS, Ins, A-7, KGLGSWIWLCI, (SEQIDNO:717); XM_005625404.2, RBM18, Del, A_7, KGLLLILEQLGN-LED, (SEQIDNO:718); XM_536010.5, TMEFF2, Ins, A_7, KGLQCIVRCSRPRAISVCLNRSCDWNHSDCRHLCGG-PLHHQEMPQKQQNSQTEAKY RALQFRQHNKSI-HEVNL, (SEQIDNO:719); XM_005634010.2, SLITRK1, Ins, A_7, KGLYKSAAFHRPDFPVLPSISAW, (SEQIDNO:721); XM_005629212.2, C15H12orf50, Del, A_7, KGNGFMMNRRIFLAQECGEQYSPQIPKIK, (SEQIDNO:722); XM_005629213.1, C15H12orf50, Del, A_7, KGNGFMMNRRIFLAQECGEYSPQIPKIK, (SEQIDNO:723); XM_014112822.1, ANK3, Del, A_7, KGNTANGP-GIGRKSLMPMQVT, (SEQIDNO:725); XM_014117291.1, GOLM1, Ins, A_7, KGPKPAAPSPQ, (SEQIDNO:728); XM_014116352.1, EFCAB13, Ins, A_7, KGQEKEKFTSTIAY, (SEQIDNO:729); XM_005625106.2, SEC16A, Del, A_7, KGQKLICQT-TRTNRSSGMKRRTGGWM, (SEQIDNO:730); XM_003639492.3, TFEC, Ins, A-7, KGQPQPHRKKKKV, (SEQIDNO:732); NM_001204095.1, ANKHD1, Ins, A_7, KGQRGDNPQHQSEK, (SEQIDNO:733); XM_537467.4, PPM1A, Del, A_7, KGQRGLRKNRRKGEK, (SEQIDNO:734); XM_005621609.2, CORO7, Ins, A_7, KGRAAKCYGGKAGEPGGSAPPG11, (SEQIDNO:735); XM_005635616.2, CLCN3, Del, A_7, KGRCYQLPQLQGFL, (SEQIDNO:736); NM_001003060.2, FMO3, Del, A_7, KGRESSNGLAPAR-QYRRIIMWMNLPPSLGQSPIS-RGCSSQIPNWLWRFSLALAAHTN LG, (SEQIDNO:

737); XM_005618461.2, AFAP1, Ins, A_7, KGRFHSRCEANIFKC, (SEQIDNO:738); XM_005634496.2, CEP70, Ins, A_7, KGRGPRETR, (SEQIDNO:740); XM_005627752.1, LOC100856021, Ins, A_7, KGRKQSQRTA, (SEQIDNO:741); XM_014121376.1, TNIP3, Ins, A_7, KGRRAENETGRGRKIPRRAGEGEGTDSEGQRQAARPDPPAAAAPGEGKGEPK, (SEQIDNO:742); XM_005627838.2, UBR5, Ins, A_7, KGRRRTECGARRS, (SEQIDNO:743); NM_001038648.1, TMEM57, Del, A_7, KGRSWKKLLLPGPLHLLLHLGGSAPKPYGIGSEN, (SEQIDNO:744); XM_534762.5, MRPL40, Del, A_7, KGSDDWRKLARS, (SEQIDNO:745); XM_005636842.2, FAM186A, Ins, A_7, KGSLNATIVFSEAN, (SEQIDNO:747); XM_014118910.1, AVL9, Ins, A_7, KGSLLYFSSE, (SEQIDNO:748); XM_536459.3, GEMIN5, Del, A_7, KGSLNLSQSPKRRKSPPQELL, (SEQIDNO:749); XM_844507.4, AIDA, Del, A_7, KGSPAPSALLSWRWMKLKPGR1, (SEQIDNO:750); XM_005630829.2, FLG, Del, A_7, KGSPNPQNEIQYLPVQRDKVATIS-SHRTPPDTRKLDMDPVTANTGNPVSVRPATVKD NH, (SEQIDNO:751); XM_005632455.2, GNL3, Ins, A_7, KGSRAPSKIEEGGQKARSQKA, (SEQIDNO:752); XM_014107556.1, FDFTI, Ins, A_7, KGSTATQLSLLPL, (SEQIDNO:753); XM_014114292.1, KLK8, Del, A_7, KGSTQYAWGITA, (SEQIDNO:754); XM_014110067.1, STPG2, Ins, A_7, KGSTRAWKI, (SEQIDNO:755); XM_005628768.2, AASS, Del, A_7, KGSWFLDLVM-YLNPFWNTCQEITG, (SEQIDNO:756); XM_014111664.1, DACH2, Ins, A_7, KGTANGAL, (SEQIDNO:757); XM_014106867.1, MYBL2, Del, A_7, KGVLPCPLSQRTAPACPS, (SEQIDNO:758); XM_005629765.2, SH2D4A, Ins, A_7, KGVPASDIQAEEREWQICSLETGSR, (SEQIDNO:760); XM_014111832.1, PIGA, Del, A_7, KGVRIMRCLKPG, (SEQIDNO:761); XM_844509.3, NPM2, Del, A_7, KGWKKKRRQ, (SEQIDNO:762); XM_014115441.1, SLC14A1, Del, A_7, KGWLKALC, (SEQIDNO:763); XM_005636978.2, KIF21A, Del, A_7, KGYRNLRKAIEKKEV-WPVKRIIQTLTKRRKKKRVLQKEKTMN, (SEQIDNO:764); XM_014113043.1, TTC1, Ins, A_7, KHARRGETEKKRREH, (SEQIDNO:765); XM_005619751.1, NXPE4, Ins, A_7, KHCHCYFSGPAFQALPH, (SEQIDNO:766); XM_532378.4, PDCL2, Ins, A_7, KHCRCDGIFN, (SEQIDNO:767); XM_005620651.1, HSBPI, Ins, A_7, KHCRPHDPGWGGRAGGGEQDPCHTEEL, (SEQIDNO:768); XM_005620592.1, MTHFSD, Del, A_7, KHCWSQHHD, (SEQIDNO:769); NM_001313804.1, ALCAM, Ins, A_7, KHDCFNSYHSSLFGFVLKPKWRSDQADWRCLACVMHNIC, (SEQIDNO:770); XM_005628489.1, GTPBP10, Ins, A_7, KHDSKEDHGVPTYHPHLCNYRRRNR, (SEQIDNO:771); XM_844824.2, LOC607953, Ins, A_7, KHELWWMCGPALCGYGVGIL, (SEQIDNO:772); XM_005629406.2, SFPQ, Ins, A_7, KHERCERQIGK, (SEQIDNO:773); XM_014121388.1, IWS1, Ins, A_7, KHEWQAQA, (SEQIDNO:774); XM_014110870.1, FSIP2, Ins, A_7, KHGNNETNFHIKSKPFVCNI, (SEQIDNO:775); XM_014114190.1, ZAN, Ins, A_7, KHGPHRKTHLPK, (SEQIDNO:776); XM_005633672.2, USP47, Del, A_7, KHGRILALSFWIIIFMKKILIFPATGRFSLKFLMG, (SEQIDNO:777); XM_014115878.1, FAM179B, Ins, A_7, KHGSRIRYYSKSSVAQG-WRIKYNKRRC, (SEQIDNO:778); XM_005618160.2, SSBP2, Ins, A_7, KHHIGGTTRILT-FLVVCILGSLLCSSRKTGNM, (SEQIDNO:779); XM_014113244.1, SSBP3, Ins, A_7, KHHIGRTAWV-FALVVVCILGPLLCSS, (SEQIDNO:780); XM_014106743.1, XRN1, Del, A_7, KHKG-YAHQKKPHFTSYTCL, (SEQIDNO:781); XM_005624533.2, TOP2A, Del, A_7, KHKWLKFCLL-LAEKESSPE, (SEQIDNO:782); XM_005615469.2, PHACTR2, Del, A_7, KHLCLQKGLLLGQAPRLTKCLLLKKLPRLL-VSRPPSLHPSQQAETRPERLLVPLIQKK QLGPNHQL HHLLPPPHLVPELRRRHSLAKQGQ, (SEQIDNO:783); XM_014113470.1, CEP126, Del, A_7, KHLKRNEKNKK-NENNKSESKSFSKGKRSLKKSRKSSSVPIFPFHSGG-GQFFKNQFLP WKKPSSKFRNPTYNQK, (SEQIDNO:784); XM_014112460.1, AP3B2, Del, A_7, KHL-PAAKVPPWPRRSPCLT, (SEQIDNO:785); XM_005635475.2, PDS5B, Del, A_7, KHLSQIQKRN, (SEQIDNO:787); XM_005634064.2, CCDC168, Del, A_7, KHLTCIFQSRRHL, (SEQIDNO:789); XM_005638404.2, TRPM7, Del, A_7, KHLTLARVKQFNFKH, (SEQIDNO:790); XM_014114271.1, ZNF789, Del, A_7, KHLVRIQPLFDIS, (SEQIDNO:791); XM_014106295.1, MYCBP2, Del, A_7, KHLYNKSK, (SEQIDNO:792); XM_538101.4, TNMD, Del, A_7, KHMTWSTL-STAMERRRRFTWKLIL, (SEQIDNO:793); XM_014114838.1, RPAP2, Ins, A_7, KHNEKESWSES, (SEQIDNO:794); XM_014112334.1, PRC1, Del, A_7, KHPRLAGTEPTRRTWSSMAAS, (SEQIDNO:795); XM_531753.4, BPIFC, Ins, A_7, KHPRPKRF, (SEQIDNO:796); XM_531770.5, GCC2, Ins, A_7, KHQNQAAACENQKRTGRFKASRN, (SEQIDNO:797); XM_537623.5, LSM12, Ins, A_7, KHRSHGRSCYYTPIS-SGK1, (SEQIDNO:799); XM_005620768.2, NFAT5, Ins, A_7, KHSCQIGF, (SEQIDNO:800); XM_844295.4, TNKS, Del, A_7, KHSLWKSLIS-NNHSLMKLRCTVLWPPCIPNESK, (SEQIDNO:801); XM_014116355.1, BPTF, Del, A_7, KHSYRRIMTPLFLL-PRALHFHQYLKVLMIEIPHLCQKQ, (SEQIDNO:802); XM_005630591.1, DCDC2C, Ins, A_7, KHTCTTRTR-SKNRRPKRTTHGTRTTRIIIKTIRRRI, (SEQIDNO:803); XM_014112960.1, FAM35A, Ins, A_7, KHTLL-CEDLRFGNTPGR, (SEQIDNO:804); XM_535482.5, SCG3, Del, A_7, KHTLQKISQVKAIIPLLIT, (SEQIDNO:805); XM_005640714.2, EPHA4, Ins, A_7, KHTNPNLPSVQRDGTQPE, (SEQIDNO:806); XM_014117987.1, SECISBP2, Del, A_7, KHTSKSL-TARRRPTDLCHRI, (SEQIDNO:807); XM_014107377.1, NBEA, Ins, A_7, KHVFWRFNETVPKASLLCCCEKL-FRMSAEAERQGEQIFPWQQ, (SEQIDNO:808); XM_014109413.1, SLTM, Del, A_7, KHVLLQEEKIQVLKGIPKISVTPEEMSLHHQEMN-LEKRTGEKSEENETRGEL, (SEQIDNO:809); XM_534172.5, TM9SF2, Ins, A_7, KHVTELSTSLDC, (SEQIDNO:810); XM_005641783.2, LOC102151581, Del, A_7, KHWISSTRSLPQDAVQ, (SEQIDNO:811); XM_532397.5, CABS1, Ins, A_7, KHYFGRRPHYSSK, (SEQIDNO:812); XM_539259.4, TEC, Del, A_7, KHYLQHQKQRSEGLPHQFHLKKRIIVKKSL, (SEQIDNO:813); XM_014108547.1, LRRK2, Ins, A_7, KHYVGRMWYKTFLIF, (SEQIDNO:814); XM_535026.4, RAB11FIP2, Del, A_7, KIAEDLINLTMGDLIALVT, (SEQIDNO:815); XM_857278.5, HELZ, Del, A_7, KIAQLFITMQRYSKWWNE, (SEQIDNO:816); XM_005636026.2, OAS2, Del, A_7, KIASNIQLQR-FRRPSREGRPAKAQL, (SEQIDNO:817);

XM_014120087.1, LOC607729, Del, A_7, KIAVDMGFAMIGLIVTVMLDILLQFVSHHHHHQEEVIMMDFGIHKRKATPYSESDML LLKKMAS, (SEQIDNO:818); XM_532457.5, CYP51A1, Del, A_7, KICLKLFRSS, (SEQIDNO:819); XM_014119368.1, LRBA, Del, A_7, KICLLVEFCDSVSD, (SEQIDNO:820); XM_005641161.2, CDKL5, Del, A_7, KICLNCWKKCQMGFHLKRLKVISIS, (SEQIDNO:821); XM_532881.5, RAD51AP2, Del, A_7, KICQRLQSTKYVSLLCSVILLRDTKVHLNGKEHRITENRKFQMNIAVQEHWTKNCFIP FPRKTARNLHLKGLLFSPMNLRKNLIIC, (SEQIDNO:822); XM_545603.5, NBEAL1, Del, A_7, KICSFCSKCISNFLTSVFGTVEIFPFELVNSIFPPSSKTAGEFSERSMVCNFS, (SEQIDNO:823); XM_014108317.1, LOC106557878, Del, A_7, KICSILKKLMELRTQKVEIQKLCHASILPFTI, (SEQIDNO:824); XM_014108877.1, HELLS, Del, A_7, KICTASTQIQMYLSS, (SEQIDNO:825); XM_005639041.1, PPP3CA, Del, A_7, KICWILMHRSQFVGTSMDNSLI, (SEQIDNO:826); XM_855010.4, WDR48, Del, A_7, KIDSLLVTCSKSGK, (SEQIDNO:828); XM_014115152.1, AXDND1, Del, A_7, KIESYWLKDFTSMKKLGINLLSISSYCCQPRTLQTLHYCTS, (SEQIDNO:829); XM_014112063.1, TMEM232, Del, A_7, KIFCSLINQKNHQN, (SEQIDNO:830); XM_005634466.2, SLC35G2, Del, A_7, KIFFNPEKCG, (SEQIDNO:831); XM_014109293.1, LRRCC1, Del, A_7, KIFIAWLYLPQIG, (SEQIDNO:832); XM_014121650.1, MYO3A, Del, A_7, KIFIFFTTSMLD, (SEQIDNO:833); XM_845734.4, NAPG, Del, A_7, KIFIRRLKITQMRKQLLKS, (SEQIDNO:834); XM_014110169.1, ACAP2, Del, A_7, KIFLKWLRLWLMARM, (SEQIDNO:835); XM_539103.4, FBXO43, Del, A_7, KIFQVVLQVFQGKRVLVL, (SEQIDNO:836); XM_005633957.2, LOC485485, Del, A_7, KIFRETIRCPGMRTRLLEKKTNPSGEKIKLFDEKTKPSEWTS, (SEQIDNO:837); XM_539084.5, REV3L, Del, A_7, KIFRRDFRKFSNRMISL, (SEQIDNO:839); XM_014118218.1, REV3L, Del, A_7, KIFRRDFRKFSNRMISLSEHYQDWTTAMDLRSSLLS, (SEQIDNO:840); XM_014116402.1, DDX42, Del, A_7, KIFTMSMKR, (SEQIDNO:841); XM_014118865.1, UTRN, Del, A_7, KIGCLKVRKKQ, (SEQIDNO:842); XM_844759.4, ADAM23, Del, A_7, KIGEPWQMKTTHHNRIAVISVTAMHCRKKSHCLQDSYTTSTKTRKALTMFLTQRQD TSKNTTRLSIWPRQASRLKPLAPNSFLTSH, (SEQIDNO:843); XM_014109172.1, PRKDC, Del, A_7, KIGIPGKKYITLRES, (SEQIDNO:844); XM_014115688.1, FERMT2, Del, A_7, KIGLIMLSGGKRRELGFLKHIGPWISMAFRQMLSFSSPPSTNCFAYSFPT, (SEQIDNO:845); XM_542243.5, ANKRD49, Del, A_7, KIGLLQCGGYCLKRLLM, (SEQIDNO:846); XM_014108105.1, FGF1, Del, A_7, KIGLLVSRRMEAANAVLGLTMVKKQFCFSPCQCPLI, (SEQIDNO:847); XM_005641603.2, BHLHB9, Del, A_7, KIGLRTGLR, (SEQIDNO:848); XM_532888.5, ATAD2B, Del, A_7, KIGWRTRRKIL, (SEQIDNO:849); XM_005630596.1, APOB, Del, A_7, KIHWSLVMVCSSR, (SEQIDNO:850); XM_005638363.2, SPG11, Del, A_7, KIIFLKMKKEL, (SEQIDNO:851); XM_014110829.1, METTL8, Del, A_7, KIIIRKGVVHQMVKGKRDHIFPT, (SEQIDNO:852); XM_014110062.1, ZGRF1, Del, A_7, KIIKYLLVRMTRCV, (SEQIDNO:853); XM_855243.4, BCLAF1, Del, A_7, KIINLKRLAT, (SEQIDNO:854); XM_539571.5, LOC482454, Del, A_7, KIIQEKNPLNA VTVGKPIAGRLTLQLIRKSIMERDPLCATIVGKRLRIKHNW, (SEQIDNO:855); XM_845588.3, BRE, Del, A_7, KIIRTAPDGMEMKWPKEQRLISKPLSLSSRRQRLPMESS, (SEQIDNO:856); XM_014107422.1, LOC606856, Del, A_7, KIITELWIP1, (SEQIDNO:857); XM_532793.5, IDO1, Del, A_7, KIKELEALMPWIS, (SEQIDNO:858); XM_014106387.1, NAA16, Del, A_7, KIKRKKEMKKKKKPVVSKKNLYLKN, (SEQIDNO:859); XM_539006.5, IMPG1, Del, A_7, KIKRKKYSNMFHLQNFGGYYQALILTSTQCC1HFLLITQRM11, (SEQIDNO:860); XM_014118898.1, LOC102152714, Del, A_7, KIKRRVRDEHLLNC, (SEQIDNO:861); XM_005623486.2, SYNE2, Del, A_7, KIKSCAHGWCRWKTKFCRRQILVLKK, (SEQIDNO:862); XM_005642331.2, LOC102153385, Del, A_7, KIKTEFSVIT1, (SEQIDNO:863); XM_005638131.2, FSBP, Del, A_7, KILDCMFRRRGMD, (SEQIDNO:865); XM_005618153.2, XRCC4, Del, A_7, KILEQNRKWFLRYTSLKKRKT, (SEQIDNO:866); XM_014112240.1, XRCC4, Del, A_7, KILEQNRKWFLRYTSLKKRSLILHYLRRQKRSTAQLKTCL, (SEQIDNO:867); XM_014122800.1, BBOX1, Del, A_7, KILERSRFCPPLLWTLQTLEWITVISPYSPNTR, (SEQIDNO:868); XM_538192.4, FMR1NB, Del, A_7, KILHGKLC, (SEQIDNO:870); XM_014118978.1, AKAP9, Del, A_7, KILKLTIRSYRRTMLAFSR, (SEQIDNO:873); XM_014120092.1, TEX15, Del, A_7, KILLLRGQRCVRVEDMAENLKNISAF, (SEQIDNO:876); XM_014115152.1, AXDND1, Del, A_7, KILLRNFMSWMR, (SEQIDNO:877); XM_014120154.1, FAT1, Del, A_7, KILMLKHERRSGCKCWIQMT, (SEQIDNO:878); XM_858916.4, MED1, Del, A_7, KILMNFLSTLRVLLIFITFQGTTN, (SEQIDNO:879); XM_014107325.1, BRCA2, Del, A_7, KILMTVESISLRKITPIKQQL, (SEQIDNO:880); XM_005641566.1, BTK, Del, A_7, KILPLKDRFQEGVKSPVKWSRFQSLKGSLTPSRLYMMKGLFMSSPQLKN, (SEQIDNO:881); XM_005641567.1, BTK, Del, A_7, KILPLKDRFQLYMMKGLFMSSPQLKN, (SEQIDNO:882); XM 534297.5, U2SURP, Del, A_7, KILQISHPMKDHRLF1, (SEQIDNO:883); XM_531679.5, ZFC3H1, Del, A_7, KILRTQRFFIICANSSSYKIKEIIFFHFWGNLSHPSLNLGLRSIITWICFGIF, (SEQIDNO:884); XM_005638791.2, LTNI, Del, A_7, KILRYSFYIRN, (SEQIDNO:885); XM_014119437.1, CEP290, Del, A_7, KILSLSKI, (SEQIDNO:886); XM_534301.5, CP, Del, A_7, KILTKSLW, (SEQIDNO:887); XM_005622462.2, TDRD5, Del, A_7, KILVQQGVKSSQT, (SEQIDNO:888); XM_014119665.1, ZMYM1, Del, A_7, KILVVEENHLQAKEFLIGKRL, (SEQIDNO:889); XM_005627548.1, MYO6, Del, A_7, KIMMLYICLLNP, (SEQIDNO:890); XM_014120276.1, TDRD15, Del, A_7, KIMWTLMNFAW, (SEQIDNO:891); XM_014106380.1, AKAP11, Del, A_7, KINLKIHP, (SEQIDNO:892); XM_014109907.1, ANK2, Del, A_7, KINRMSRNGSRRGWHILLITLASAGQN, (SEQIDNO:893); XM_005623470.2, C8H14orf39, Del, A_7, KINTWKRERN, (SEQIDNO:894); XM_005619203.2, CREBRF, Del, A_7, KINWLPGLVD, (SEQIDNO:895); XM_014108622.1, DYRK4, Ins, A_7, KIPGFQGSHDGAENL, (SEQIDNO:896); XM_005623657.2, CCDC176, Del, A_7, KIPRSCKRLRLSFYIKRRSMIF, (SEQIDNO:898); XM_014111704.1, REPS2, Del, A_7, KIPSKEWTMRINRKHSLPRCHPSPPLLLPRLITRGCP, (SEQIDNO:899); XM_014111703.1, REPS2, Del, A_7, KIPSKEWTMRINSRKHSLPRCHPSPPLLLPRLITRGCP, (SEQIDNO:900); NM_001194952.1, PLAU, Del, A_7, KIPTLLQKKQSFNVARRL, (SEQIDNO:901);

XM_014114463.1, LOC106558915, Del, A_7, KIQAST-TAGFLAVVPACPWERLRVFLLQQRWGFAGIRYLVR-GLTGLL, (SEQIDNO:902); XM_536310.6, ZFYVE16, Del, A_7, KIQFWLNKGYLTVNLRLQMNYQSLILTI-SLFMLEGPDQSNCLTFHQDQEVQRNQINQ MFQI-CLKVSPA, (SEQIDNO:904); XM_014117552.1, KIAA1841, Del, A_7, KIQGLKAVLVQGVLH, (SEQIDNO:905); XM_544755.5, MYO9A, Del, A_7, KIQII-CALTL, (SEQIDNO:906); XM_014111106.1, ALS2CR11, Del, A_7, KIQIKKENQ, (SEQIDNO:907); XM_005629294.2, CCDC53, Del, A_7, KIQKKVQTVNLLLVT, (SEQIDNO:908); XM_014110816.1, USP48, Del, A_7, KIQMCGTLSNSSS-VENMLT, (SEQIDNO:909); XM_532552.5, UTP11L, Del, A_7, KIQMNSTIK, (SEQIDNO:910); XM_014116115.1, SPATA7, Del, A_7, KIQVSQTA, (SEQIDNO:912); XM_014108625.1, RECQL, Del, A_7, KIQVTSGSLQIRFSNLRIQGLRKEKLMMH, (SEQIDNO:913); XM_005640342.2, KIAA1715, Del, A_7, KIRDYKNYGLED, (SEQIDNO:914); XM_014111472.1, CYLCI, Del, A_7, KIRESQRIPRRQIMISYVQRRIL-RIHRTILMPNLRLVQKIVQIWI, (SEQIDNO:915); XM_014116428.1, NOL11, Del, A_7, KIREWLDHCC, (SEQIDNO:916); XM_544672.5, SECISBP2L, Del, A_7, KIRHFLEVEGRLNKEIIHRLDSDAEDIVLPQKEDRIC-RRDKIIISS, (SEQIDNO:917); XM_014113360.1, CEP85L, Del, A_7, KIRICKRLS, (SEQIDNO:918); XM_014118151.1, ANKRD6, Del, A_7, KIRKPREERL-GRTLEDQREKKRLETQHFMLLLP, (SEQIDNO:919); XM_005631802.2, SCLT1, Del, A_7, KIRLFFRR-SKKKKM, (SEQIDNO:920); XM_005638404.2, TRPM7, Del, A_7, KIRLQMDQNFF, (SEQIDNO:921); XM_003638878.3, KIF5B, Del, A_7, KIRPCGTPFSGLKMNSTGGVMERQCLL-MNSLTKRKPTWKLLQ, (SEQIDNO:922); XM_005638009.2, CHD7, Del, A_7, KIRRNRKNPRRKK-SPRNPRPRKPLRFPKSQRKRKQKLPRQNPNPAKSQ-VIRNLIQKQ VL, (SEQIDNO:924); XM_014115916.1, ATG14, Del, A_7, KIRSFILEHSGIKRKRRRFRG-TIANLVTW, (SEQIDNO:925); XM_014113440.1, EXPH5, Del, A_7, KIRVILGVEELAQQLPFLSFR-KAEQHLFPAQSKVVTRK, (SEQIDNO:926); XM_005616994.2. ARHGAP21, Del, A_7, KIRWNQET, (SEQIDNO:927); XM_536459.3, GEMIN5, Del, A_7, KISHFLCLN, (SEQIDNO:928); XM_005623084.2, TXNDC2, Del, A_7, KISHSSRLTSLISQQNP-SHPKRVTPPVF, (SEQIDNO:929); NM_001025397.1, SPINK5, Del, A_7, KISILATDQMRLNQHQKR-TRVMSLEAK, (SEQIDNO:930); XM_005640670.2, CCDC108, Del, A_7, KISITPSSAASTPT-GRSSQAQLLRSCGSSHLLRPRPTRWMCPY-TSWDGTQPSSASREW AMTPMSWGTQPHSTT-SPLGMTTPYILG, (SEQIDNO:931); XM_005639099.2, MRPL1, Ins, A_7, KISKTNSKFYWP, (SEQIDNO:932); XM_005639497.2, KIAA2018, Del, A_7, KIS-LFIPMGVSLVETAREQLFRG, (SEQIDNO:933); XM_014112381.1, LINS1, Del, A_7, KIS-LNTLKMRRWYIASGPLL1, (SEQIDNO:934); XM_005635238.2, NELFCD, Del, A_7, KISLSLLRW-CATGSTRTCLPRP, (SEQIDNO:935); XM_014111626.1, THOC2, Del, A_7, KISQNLQAKKKVVIRLNLKRWIK-SPPVAKRSPGMIKKR, (SEQIDNO:936); XM_005626023.2, EIF5B, Del, A_7, KISQVLMWRVGMKMMIPPSK-LRRWPKRRQKRKSVKEKREMKKKQNYGS, (SEQIDNO:937); XM_014106427.1, EPSTI1, Ins, A_7, KIS-RKPQKRSI, (SEQIDNO:938); XM_003639986.2, CEP55, Del, A_7, KISRLNDRP, (SEQIDNO:939); XM_014117962.1, LOC102153482, Del, A_7, KISSSGCC, (SEQIDNO:940); XM_534518.5, POMP, Del, A_7, KISSSTKIK, (SEQIDNO:941); XM_005635615.2, CLCN3, Del, A_7, KISSVIWPRRQTKTPLQ, (SEQIDNO:942); XM_849319.3, LOC611632, Del, A_7, KISTDLMLCCFL, (SEQIDNO:943); XM_014106605.1, GOLGA4, Del, A_7, KISTIKKLQSWLKNTKQN, (SEQIDNO:944); XM_014108806.1, SORBS1, Del, A_7, KISTSAQQS, (SEQIDNO:945); XM_534306.5, EIF2A, Del, A_7, KISWRKFKKRKPFSRSWKIWNWVF, (SEQIDNO:946); XM_014108253.1, MRPS35, Del, A_7, KISYKHFSK, (SEQIDNO:947); XM_014119765.1, ZNF112, Del, A_7, KITAAMTVERTS, (SEQIDNO:948); XM_014115454.1, TPGS2, Del, A_7, KITACYLRM, (SEQIDNO:949); XM_005624764.2, PIGW, Ins, A_7, KITCQRLDKSNILYSADSN, (SEQIDNO:950); XM_014116357.1, LOC102152996, Del, A_7, KITCVSRLIMVVGVEKEWLDY, (SEQIDNO:951); XM_547258.5, OLFM3, Del, A_7, KITESGTWT-VILTTKLFVSTNQLQTLSVGLNQGHTTSL-SNGQELTMLSTMAHSILTSIR VTSSSNTALIWGECSP-NEASSMLVFTTCTPIHGVDSLTST, (SEQIDNO:952); XM_014107338.1, NEK3, Del, A_7, KITPAESR, (SEQIDNO:953); XM_005630978.2, NAPEPLD, Del, A_7, KITVVFQAPKRNWTRSSRCCGPTSSTAPRPRG, (SEQIDNO:954); XM_014118218.1, REV3L, Del, A_7, KIVEQERRLRNRKLNLLIP1, (SEQIDNO:955); XM_014115234.1, PLD5, Del, A_7, KIVKINVELPWWKI-FLKALTIQKMHHFTYHFSKAG, (SEQIDNO:956); XM_538969.5, TINAG, Del, A_7, KIVLHHGHFLLQVWQLTE, (SEQIDNO:957); XM_846233.4, PPFIA1, Del, A_7, KIVNFKKSMNCSRKPGDKVC1IHSGMGRPLLFG, (SEQIDNO:958); XM_014122184.1, SMARCC1, Del, A_7, KIVRRSRTVKLVRILNQKKRKLRRTRNSLIL-VKKEKAISGRRK, (SEQIDNO:959); XM_014122183.1, SMARCC1, Del, A_7, KIVRRSRTVKLVRILNQKRKLRRTRNSLILVKKEKAI-SGRRK, (SEQIDNO:960); XM_014116359.1, LOC611199, Del, A_7, KIVSGAGGMKNWVAWRLH-CAGRPLSYWMTGCFSG, (SEQIDNO:961); XM_855384.3, USP15, Ins, A_7, KIVYIPVQQFRQY, (SEQIDNO:962); XM_014107158.1, BCAS1, Del, A_7, KIWKTRHPKQKVSVMAKRDRRPVRTKLKAPRK-STCTAPG, (SEQIDNO:963); XM_014117553.1, USP34, Del, A_7, KIWLILMVKNLGVKRN, (SEQIDNO:964); XM_846064.4, LOC608913, Del, A_7, KIWNVISMRR-PLVMVYTTLNIRKLILERNLMKIGKGISGTH-NLPPNIIRVFMVGRNIM CMKEP, (SEQIDNO:965); XM_014112852.1, CCAR1, Del, A_7, KIWPF-LIHQMLTNTVQR, (SEQIDNO:966); XM_005628224.2, PAICS, Del, A_7, KNENNFMEH, (SEQIDNO:967); XM_005625993.2, IL18R1, Del, A_7, KIYFFHIIALW-PAREAQTPSTLSC, (SEQIDNO:968); XM_014115915.1, DLGAP5, Del, A_7, KNHHKITSYRKRKPKFLSQYLILE-ASRLNAIFLIRRT, (SEQIDNO:969); XM_005626930.2, ZFP37, Del, A_7, KNLGLLKSNRK, (SEQIDNO:970); XM_014118218.1, REV3L, Del, A_7, KNLIFPTTCLR, (SEQIDNO:971); XM_544601.6, ARHGAP11A, Del, A_7, KNLKLMI, (SEQIDNO:972); XM_014113670.1, PTPRK, Ins, A_7, KNMLEKTHLH, (SEQIDNO:973); XM_005622326.2, LOC609365, Del, A_7, KIYTVKFLVLTVIEWFGVMIPHCVQRYCVSHLEK, (SEQIDNO:974); XM_531794.5, TMEM131, Del, A_7, KIYYPKSLLSSPG11, (SEQIDNO:975); XM_005622023.2, TTLL7, Ins, A_7, KKAENFYSKTS, (SEQIDNO:976); XM_005633847.2, KPNA3, Ins, A_7, KKCPPRRKFRRFRC, (SEQIDNO:977); XM_014121409.1, INPP4B, Ins, A_7, KKECRNHVAGCNDLSQTKRYSFHLLQKCQRQDVDVSDS, (SEQIDNO:978); XM_014112349.1, BOD1L1, Ins, A_7, KKERFKEC, (SEQIDNO:979); XM_547771.4, CFL2, Ins, A_7, KKESSSLLFKR, (SEQIDNO:980); XM_536762.5, ATP2C2, Del, A_7, KKFHSVQSRSGWQ, (SEQIDNO:981); XM_005624835.2, SUZ12, Ins, A_7, KKGCKLSNKASSYR, (SEQIDNO:982); XM_535878.4, RIOK1, Ins, A_7, KKGEDSQDEKGQI, (SEQIDNO:983); XM_014112203.1, CAST, Ins, A_7, KKGGGAGRNE, (SEQIDNO:984); XM_014112204.1, CAST, Ins, A_7, KKGGGGRNE, (SEQIDNO:985); XM_844383.3, ERMN, Del, A_7, KKGLPNNL, (SEQIDNO:986); XM_014119702.1, CFAP54, Ins, A_7, KKGQLTIRC, (SEQIDNO:987); NM_001287118.1, CFDP1, Ins, A_7, KKGSEHSGQEEKTRWLLIRRRGRGGCQ, (SEQIDNO:989); XM_014119150.1, DNAH11, Ins, A_7, KKHYFKVHWKS, (SEQIDNO:990); XM_544889.6, BRWD1, Del, A_7, KKISLKKRTCGG, (SEQIDNO:991); XM_005631143.2, QSER1, Del, A_7, KKKAWLVQ, (SEQIDNO:992); XM_535898.5, NUP153, Del, A_7, KKKCLPPKEGSLSVV, (SEQIDNO:993); XM_014110443.1, ZNF639, Ins, A_7, KKKEDITPFSLLRFLWNKQDCRWIQWNFF, (SEQIDNO:994); XM_014110273.1, KIAA1407, Del, A_7, KKKGERNSAGR, (SEQIDNO:995); XM_844375.4, EPRS, Del, A_7, KKKILQIGILRSSQSQK, (SEQIDNO:996); XM_014117069.1, GOLGA1, Del, A_7, KKKLWGKRSKSWRHEPEN, (SEQIDNO:999); XM_846664.4, SEC62, Del, A_7, KKKRKERPKVEKKKIKRAGKKI, (SEQIDNO:1000); XM_532159.4, TDRD6, Del, A_7, KKLKHSSLSLKPLR, (SEQIDNO:1002); XM_843366.4, CHD1, Del, A_7, KKLRDFLVQEGQRGEKQELRRIKQ, (SEQIDNO:1003); XM_005639750.2, FXR1, Del, A_7, KKLVKEMK, (SEQIDNO:1004); XM_014119437.1, CEP290, Del, A_7, KKMIITGSKCRSLQIF, (SEQIDNO:1005); XM_005630347.2, CEBPZ, Del, A_7, KKMPAKKKQYLK, (SEQIDNO:1006); XM_014109541.1, NUSAP1, Del, A_7, KKMRVRMELKLLHPPGMRLRCR, (SEQIDNO:1007); XM_005627829.2, RNF19A, Ins, A_7, KKNFNRLSVSEEKG, (SEQIDNO:1008); XM_534311.5, DHX36, Ins, A_7, KKNGQGLHKN, (SEQIDNO:1009); XM_014110756.1, BAZ2B, Ins, A_7, KKNGRKHFC, (SEQIDNO:1010); XM_863229.4, TAOK1, Del, A_7, KKNKSGFQSRRRIYSISKQRKRLIFFDDKGNT, (SEQIDNO:1011); XM_014115688.1, FERMT2, Del, A_7, KKNLLELHTTD, (SEQIDNO:1012); XM_542610.5, DIS3, Ins, A_7, KKNRKRGFDSFFSRSSIPHGQ, (SEQIDNO:1014); XM_003434954.4, RCOR3, Del, A_7, KKPRKRVILNNLSKLARLDLEGENIRVYNIAIILSDLSAVHLRACT, (SEQIDNO:1015); XM_005639717.2, ABCC5, Del, A_7, KKPVVHRRRNHKTRVLKQDQ, (SEQIDNO:1016); XM_003639968.3, PDZRN4, Ins, A_7, KKQENLGQLDDNPRTDDPRGQVSGWHTSS, (SEQIDNO:1017); XM_843679.5, SON, Del, A_7, KKQIVFMESGFL, (SEQIDNO:1018); XM_544621.5, RMDN3, Del, A_7, KKQRLPWRRGMRMLNVTSGMQCFVVSWLSMRASRGASRVALASRSI, (SEQIDNO:1019); XM_014115954.1, SNAPC1, Ins, A_7, KKQRNIEIRRKEDAFQKQR, (SEQIDNO:1020); XM_014112750.1, C4H1orf131, Ins, A_7, KKREARSK, (SEQIDNO:1021); XM_005630473.2, IMMT, Del, A_7, KKRFLGPNLI, (SEQIDNO:1022); XM_014109202.1, CCNE2, Ins, A_7, KKRGGRQETAV, (SEQIDNO:1023); XM_533102.5, KMT2E, Del, A_7, KKRIFQKKKIHRIRILLWIVKEQPTK, (SEQIDNO:1024); XM_533359.5, PRPF40A, Del, A_7, KKRRKANQQKKPILGIQRRKQSKHLKNY, (SEQIDNO:1026); XM_533359.5, PRPF40A, Del, A_7, KKRSKQSSYEREIGKP, (SEQIDNO:1027); XM_014120231.1, ROCK2, Ins, A_7, KKSELSNIHRESESAPETTG, (SEQIDNO:1028); NM_001003075.1, IL13RA2, Del, A_7, KKSFLIKTHSV, (SEQIDNO:1029); XM_014106344.1, PHF11, Del, A_7, KKSTEGGS, (SEQIDNO:1030); XM_847045.4, ADAMTS20, Del, A_7, KKSTYKELFLNTVVQTAQLKELIVLIGWKKKLFCRFYVWVIYTTLMYDIPSISPWKRRTT, (SEQIDNO:1031); XM_005628564.1, LOC102157031, Del, A_7, KKSYSHHNVKWKSTHGK, (SEQIDNO:1032); XM_536371.4, TET1, Ins, A_7, KKTFYSARTSFWKEEGSNDDRSSRT, (SEQIDNO:1033); XM_014110025.1, FAM175A, Ins, A_7, KKTGTNPSSTREHRKRPSGEHFSLSSFTDLFSRSRISSFMCYLLEKQAYL, (SEQIDNO:1034); XM_005619382.2, NIPBL, Ins, A_7, KKTRFLPTGGWGCYRR, (SEQIDNO:1035); XM_014122663.1, UPF2, Del, A_7, KKTRNGRKKKKKR, (SEQIDNO:1036); XM_005624831.2, TEFM, Ins, A_7, KKVPGQPALEKAHQTRNRKREA, (SEQIDNO:1037); XM_014112204.1, CAST, Del, A_7, KKVSQCLLQTLRNPWGPMMP, (SEQIDNO:1038); XM_005618261.2, ZNF518B, Del, A_7, KLAPCTVSKEAVN, (SEQIDNO:1041); XM_014106660.1 PIK3CB, Del, A_7, KLASSSTLTLDIFLEISSLNLALKGNGCLLFLPMISFM, (SEQIDNO:1042); XM_538283.5, PTPRB, Del, A_7, KLAWEQKFQ, (SEQIDNO:1043); XM_005633939.2, SUGT1, Ins, A_7, KLCCCFRNFYRRTEIR, (SEQIDNO:1044); XM_538969.5, TINAG, Ins, A_7, KLCCIMGIFYCKCGS, (SEQIDNO:1045); XM_538778.5, RAD23B, Ins, A_7, KLCGGYGDKTQSSDNTSTSYNPAVESCHHYYS, (SEQIDNO:1046); XM_014114371.1, ZNF629, Ins, A_7, KLCPQLRAAAAPESPCGWENSEESGAGEELFCPPGAPQEPPGGQALQLLRLWGLLS, (SEQIDNO:1047); XM_014115171.1, RFWD2, Ins, A_7, KLCRPRFQWRLYSLWK, (SEQIDNO:1048); XM_005626595.2, FAM13B, Del, A_7, KLDNLRNSLKGKEIASPPTVILQPIQRY, (SEQIDNO:1049); NM_001033996.2, CTSK, Ins, A_7, KLEAYFYP, (SEQIDNO:1050); XM_532881.5, RAD51AP2, Del, A_7, KLEKNRIFYNY, (SEQIDNO:1051); XM_005638171.2, UACA, Del, A_7, KLERQKESMKNHLLKSDS, (SEQIDNO:1052); XM_533429.5, TXLNB, Del, A_7, KLETQKCLKGMTKVSTPPTKSPSLLCLGGQGLMPRKSVVFTM1, (SEQIDNO:1053); XM_014118910.1, AVL9, Del, A_7, KLETSWSQPAEMLSKQEKLLASQLEELFPVQRQLC1HGFLLSPVPAPRVSLSHLTGS1, (SEQIDNO:1054); XM_005621408.2, RBBP6, Del, A_7, KLEVQKMYLIQKNPLKN, (SEQIDNO:1055); XM_537096.5, RPF1, Del, A_7, KLFHSAFQEISQI, (SEQIDNO:1056); XM_014114451.1, ZNF471, Ins, A_7, KLFPKFCGSKTQESLFRKETF, (SEQIDNO:1058); XM_014115086.1, NSL1, Del, A_7, KLFQQTHSVRFVLATMS, (SEQIDNO:1059); XM_544308.5, TAF7, Del, A_7, KLFTRQLIYVRCLSPQLMVISILLWRNQLLLLIPKQARKRIRTKRRSLYGTMELLCL, (SEQIDNO:1060); XM_014118218.1, REV3L, Ins, A_7, KLFVIYRKVK, (SEQIDNO:1061); XM_005628809.2, PTPRZ1, Ins, A_7, KLGKEVPNV, (SEQIDNO:1062); XM_005633836.2, DZIP1, Del, A_7, KLGKNRRNLYL, (SEQIDNO:1063); XM_005639425.2, TRMT10C, Del, A_7, KLGKQKRN, (SEQIDNO:1064);

XM_014108478.1, KIF21A, Del, A_7, KLGLNMKRNSKP, (SEQIDNO:1065); XM_014110047.1, BANK1, Del, A_7, KLGVDLL1, (SEQIDNO:1066); XM_005619375.2, OSMR, Ins, A_7, KLHELLRRNPSWRK, (SEQIDNO: 1067); XM_005617173.2, FBXO18, Del, A_7, KLHGIVCPCHAQDPGKPGKKRGTLCHGVLQSLENPANKWRTLV, (SEQIDNO:1068); XM_014111818.1, LOC100683280, Del, A_7, KLHLSYTN, (SEQIDNO:1069); XM_005636930.1, RPAP3, Del, A_7, KLHMYCSIT, (SEQIDNO:1070); XM_005622945.2, PSMA8, Ins, A_7, KLHRRCYSKRQ, (SEQIDNO:1071); XM_014120092.1, TEX15, Del, A_7, KLIGEFTHLCN1, (SEQIDNO:1072); XM_005628331.2, LOC611685, Del, A_7, KLIGHGKPACK, (SEQIDNO:1073); XM_014119574.1, OSBPL8, Del, A_7, KLIIQRFSGTQHQTLSSGD, (SEQIDNO:1074); XM_847173.4, LOC609830, Del, A_7, KLILLFLN, (SEQIDNO:1075); XM_535304.5, CHD9, Del, A_7, KLINPGTIKMAINSGNINWKDSTGSYSIGTIDETAF, (SEQIDNO:1076); XM_014114985.1, LOC484341, Del, A_7, KLIQGKNLMDAVNVEKPSRDLSSLDTRELTLERNHIIAVNVGKALV, (SEQIDNO:1077); XM_014113312.1, CHEK1, Del, A_7, KLIQLLLLCCIKS, (SEQIDNO:1078); XM_848169.4, KIAA2026, Del, A_7, KLIVIKKI, (SEQIDNO:1079); XM_843319.4, TMEM236, Del, A_7, KLKDGDLLW, (SEQIDNO:1080); XM_005628256.2, TMPRSS11F, Del, A_7, KLKGFYLKV, (SEQIDNO:1083); XM_005626663.2, PLIN2, Del, A_7, KLKGLIQFRNQVITLDWAPCLPSSAHVPTNRLSAGLKKPSKKAKRPFLSSIPLLI, (SEQIDNO:1084); XM_532929.5, FAM98A, Del, A_7, KLKKEAVVRSFKS, (SEQIDNO:1085); XM_005619544.1, SPATA19, Del, A_7, KLKKRLPRT, (SEQIDNO:1086); XM_005623082.2, ANKRD12, Del, A_7, KLKKSANCCVVLFLKHLSIMMNM, (SEQIDNO:1087); XM_014120026.1, WHSC1L1, Ins, A_7, KLKKTSSLQTHQS, (SEQIDNO:1088); XM_005627518.2, PHF3, Del, A_7, KLKLLLEYLVNIQIMKQKV, (SEQIDNO:1089); XM_005639568.2, PARP15, Del, A_7, KLKLSSFYLIC, (SEQIDNO:1090); XM_005638100.1, CNBD1, Del, A_7, KLKNLFVWVNLRKRSPLVRLVFFFKFLSHVL, (SEQIDNO:1091); XM_005628611.2, DNAH11, Ins, A_7, KLKQKPLCSCLLPRM, (SEQIDNO:1092); XM_531681.5, TBC1D15, Del, A_7, KLKRILIQQLW, (SEQIDNO:1093); XM_014119477.1, UTP20, Del, A_7, KLKRNSQYP, (SEQIDNO:1094); XM_005640622.2, SMARCAL1, Del, A_7, KLKRTGKRLWPVELRNY, (SEQIDNO:1095); XM_005639816.2, MASP1, Del, A_7, KLKWMRRTNPGQSNRQN, (SEQIDNO:1096); XM_014110037.1, CDK12, Del, A_7, KLLCEKSSY, (SEQIDNO:1097); XM_014120622.1, SPAG17, Del, A_7, KLLDLHLALRFGRVLTLGPNS, (SEQIDNO:1098); XM_014120363.1, PTCD3, Ins, A_7, KLLFLLHNDPRNGEAPSSCAGIKLVC, (SEQIDNO:1099); XM_014118520.1, LRP12, Ins, A_7, KLLFLPARKFSL, (SEQIDNO:1100); XM_014119702.1, CFAP54, Del, A_7, KLLFMILV, (SEQIDNO:1101); XM_014121504.1, MGAT5, Del, A_7, KLLGHPGFTTSACSESWIHLVPSQNLTMLTMPSLKATRRPGANGI, (SEQIDNO:1102); XM_537175.5, FAM20B, Del, A_7, KLLKLTWVIKGHS, (SEQIDNO:1103); XM_005637578.2, LOC486817, Del, A_7, KLLKPLTGA, (SEQIDNO:1104); XM_005634135.2, TMCO3, Ins, A_7, KLLLDVASTASFDSRCCRTRRGSKTCHQVTPRQRSGHRSEEAVGPGQLQKALWASSPKGCGS, (SEQIDNO:1105); XM_014115836.1, AKAP6, Ins, A_7, KLLLLPKSRHQEWSGCGGLVWL, (SEQIDNO:1106); XM_534311.5, DHX36, Del, A_7, KLLLVFGK, (SEQIDNO:1107); XM_845166.4, CACNG3, Ins, A_7, KLLLWLVLLFRGL1FHHRRNCGSRCRAHLYRKTSAVTCQIPLGAPEEIYLCSPSTLQV (SEQIDNO:1108); XM_005615672.2, LOC483960, Del, A_7, KLLMLKLKYWTFIILINFLKVWMGLT, (SEQIDNO:1109); XM_005636026.2, OAS2, Ins, A_7, KLLPTFSYKGSEDRQGRVDRQRHSSEDWLRCRPRRVPR1A, (SEQIDNO:1110); XM_005634563.2, ANKUB1, Del, A_7, KLLQQLGKKKSS, (SEQIDNO:1111); XM_005627518.2, PHF3, Del, A_7, KLLQQSMN, (SEQIDNO:1112); XM_532318.5, TAF2, Del, A_7, KLLVLMNTAIGLKRS, (SEQIDNO:1113); XM_542300.5, PRKRIR, Del, A_7, KLMKLLNRNPNIKK, (SEQIDNO:1116); XM_005618133.2, MEF2C, Del, A_7, KLMKNLII, (SEQIDNO:1117); XM_535769.5, UMPS, Del, A_7, KLMLRWSRE, (SEQIDNO:1118); XM_005637317.2, LOC102156193, Del, A_7, KLMNILTSGLSLLPG, (SEQIDNO:1119); NM_001287138.1, MMP12, Del, A_7, KLMQLFLTHFSIRPTSL, (SEQIDNO:1120); XM_014112389.1, MEF2A, Del, A_7, KLMRNLII, (SEQIDNO:1121); XM_532130.5, DNAH8, Del, A_7, KLMTQVHSLNWSTGNACQPNSITSSNRLKGQLVRLS, (SEQIDNO:1122); NM_001003154.2, TRDN, Del, A_7, KLNIKKKNLQL, (SEQIDNO:1123); XM_845904.4, FBXO33, Del, A_7, KLNKFSNCLKKY, (SEQIDNO:1124); XM_014113223.1, DYNC2H1, Del, A_7, KLNLMILKS, (SEQIDNO:1125); XM_536371.4, TET1, Del, A_7, KLNPNHLCQSEAF, (SEQIDNO:1126); XM_847246.3, FAM111B, Del, A_7, KLNRRVKVPLMRSVPLNSYSLRS, (SEQIDNO:1127); XM_014119762.1, LRRIQ1, Del, A_7, KLNWKTQI, (SEQIDNO:1128); XM_537144.4, NEK2, Ins, A_7, KLPAEKQTDSGHAL, (SEQIDNO:1129); NM_001005870.1, RXFP2, Del, A_7, KLPCRLQK, (SEQIDNO:1130); XM_014110285.1, PARP9, Del, A_7, KLPGYIKVLSWYWSQKDLNCPVNVYTMCCGTQDVSKSLRC, (SEQIDNO:1131); XM_005630954.2, GPR22, Del, A_7, KLPLKIVK, (SEQIDNO:1132); XM_014110821.1, DYNC1I2, Del, A_7, KLPQNMCFTAS1L, (SEQIDNO:1133); XM_014112279.1, ANKRD31, Del, A_7, KLPRKSKTIKTLHLCLVLV, (SEQIDNO:1134); XM_005615469.2, PHACTR2, Del, A_7, KLPRLLVSRPPSLHPSQQAETRPERLLVPLIQKKQLGPNHQLHHLLPPPHLVPELRRR HSLAKQGQ, (SEQIDNO:1135); XM_005620337.1, USP24, Del, A_7, KLPSLKTMNLSVSLSTVGRHMQVTTIPSLRTGGAVEKESGTSLMTQS, (SEQIDNO:1136); XM_536972.4, RSL1D1, Del, A_7, KLPTPPNSGPKSAKYPSQP, (SEQIDNO:1137); XM_005617972.2, FHADI, Del, A_7, KLQAKPRNFRSRSTALRKPSSLLCKRSCRSIWQRRRS, (SEQIDNO:1138); XM_014120239.1, SOS1, Del, A_7, KLQETMDQVIILHFRVHLPQSSGI, (SEQIDNO:1140); XM_014113297.1, GPRC6A, Del, A_7, KLQEVNISAAMNVWTVLKITTVTRQIWITASYATMKLTGPLSGAQGALKRKWNIST GMIPWLYCSWPSPY, (SEQIDNO:1141); XM_847828.4, C9H17orf78, Del, A_7, KLQGSLSSTTHTS, (SEQIDNO:1142); XM_539934.4, LMBR1, Del, A_7, KLQHGKEIWCILLLWFSSLLRHPSRSSWWMFFACWLMKQPCQREQGVLE, (SEQIDNO:1143); XM_005627580.2, DOPEY1, Del, A_7, KLQMKNSNKPVCSSATV, (SEQIDNO:1145); XM_005621271.2, RNF40, Del, A_7, KLQMRMPCGAFGRRRSRSNICSASWVLPSRKRKLCCQRWM, (SEQIDNO:1146); XM_003433767.3, DIMT1, Ins, A_7, KLQNPLFAP, (SEQIDNO:1147); XM_014115338.1, ASHIL, Del, A_7, KLQRETMDN, (SEQIDNO:1149);

XM_014117442.1, LOC102156332, Del, A_7, KLQRIIVPRR, (SEQIDNO:1150); XM_005638476.2, VPS13C, Del, A_7, KLQRPQMRSSLIFY, (SEQIDNO:1151); XM_014106605.1, GOLGA4, Del, A_7, KLQRRK-MIYKEQPKDMKKSLMLVKKK, (SEQIDNO:1152); XM_005615672.2, LOC483960, Del, A_7, KLQRYL-VLELTM, (SEQIDNO:1153); XM_005616781.2, ZNF507, Ins, A_7, KLQSGPSQYGVLCFTLLLLYLWLRIYQQRK-SPGSYERA, (SEQIDNO:1154); XM_014119322.1, MACF1, Del, A_7, KLQTDNPGSRTVCKKLRNIS-GMFKTSCHG, (SEQIDNO:1155); XM_014107150.1, SYCP2, Ins, A_7, KLQTIEDYFC, (SEQIDNO:1156); XM_005622441.2, SWT1, Del, A_7, KLQVLVQFAV, (SEQIDNO:1157); XM_014120087.1, LOC607729, Ins, A_7, KLQWTWDLQ, (SEQIDNO:1158); XM_005623940.2, TDRD9, Ins, A_7, KLRDSEKAYC, (SEQIDNO:1159); XM_005615947.1, LOC102155374, Ins, A_7, KLRGSLVQEIGTDQ, (SEQIDNO:1160); XM_014121223.1, CCDC73, Del, A_7, KLRKFQYM, (SEQIDNO:1161); XM_003638871.2, PTCHI, Ins, A_7, KLRQVLGCGPPHIWGLRCGIKGS, (SEQIDNO:1162); XM_005615403.2, RNMT, Ins, A_7, KLRRRTQFSSGCPL, (SEQIDNO:1163); XM_005630615.2, PIP5K1A, Ins, A_7, KLRRSGTRFYQFGDPKKPAM1, (SEQIDNO:1164); XM_005622349.2, PPP2R5A, Del, A_7, KLRSLFLSRYPSVYPVLIFRLQKGHCTSGIMSIFLV, (SEQIDNO:1165); XM_845578.4, PALB2, Del, A_7, KLRSLKITQV, (SEQIDNO:1166); XM_014108413.1, PLEKHA5, Del, A_7, KLRTFFPKRSSNLNQME, (SEQIDNO:1167); XM_014107378.1, NBEA, Del, A_7, KLSIACLGLE, (SEQIDNO:1169); XM_003435003.3, LAMA3, Del, A_7, KLSISTQLK, (SEQIDNO:1170); XM_005619370.2, C9, Del, A_7, KLSKRRHQILKQI, (SEQIDNO:1171); XM_539474.5, IGF2BP3, Del, A_7, KLSKTLTLKSQFLHCRN, (SEQIDNO:1172); XM_851151.4, NFASC, Del, A_7, KLSLLRARSSPYS, (SEQIDNO:1173); XM_534417.5, BPI, Del, A_7, KLSLRSERP, (SEQIDNO:1174); XM_005638943.2, NDUFV3, Del, A_7, KLSLTPQSQDC1-HSQMSAQQLGNRQKEPKRQDSCKHLLIPEKDILK-SKYWKVTGRW HFPYPTRKMQGSR, (SEQIDNO:1175); XM_014111818.1, LOC100683280, Del, A_7, KLSPPVLHTCLLFPLHTAAVFSSISSLRPKKR-WISIKGYPCSLHLLLLC, (SEQIDNO:1176); XM_005627395.2, XPO5, Del, A_7, KLSQCWRQRCWTIRRAAWPPSLNP, (SEQIDNO:1177); XM_535945.5, NOSTRIN, Ins, A_7, KLSRQCLGLGLR-GHEVSGGPTSKTWQSN, (SEQIDNO:1178); XM_545261.4, NMD3, Del, A_7, KLSTIWNS, (SEQIDNO:1181); XM_845588.3, BRE, Ins, A_7, KLSVQPQMGWK, (SEQIDNO:1182); XM_005624045.1, DNAH17, Del, A_7, KLSVSWER, (SEQIDNO:1183); XM_014115969.1, PPPIR36, Ins, A_7, KLTGKTIQK-LYGGPCREKRDGIGYK, (SEQIDNO:1184); XM_005623485.2, SYNE2, Del, A_7, KLTM-NYTDYKHFSSICSVITEIRIS, (SEQIDNO:1185); XM_005628611.2, DNAH11, Del, A_7, KLTPSINS1, (SEQIDNO:1186); XM_005623378.2, KLHDC2, Del, A_7, KLTQKEMFLLPCQEAVLCV, (SEQIDNO:1187); XM_005621408.2, RBBP6, Del, A_7, KLTTITESTQVPN-VEMKGMN, (SEQIDNO:1189); XM_014108105.1, FGFI, Ins, A_7, KLVCWSQEEWKLQTRSSDSLWSKSNFVSP-PASVL, (SEQIDNO:1190); XM_535783.4, ATP13A3, Del, A_7, KLVFSVLVPKG, (SEQIDNO:1191); NM_001005869.1, HTR2A, Ins, A_7, KLVGSVDS-GRDYSDHCWKHTRHHGSVPREKAAER-HQLFPDVTCHS, (SEQIDNO:1192); XM_547945.4, PTPN21, Del, A_7, KLVLSSWLP, (SEQIDNO:1193); XM_014121598.1, MKRN2, Del, A_7, KLVNTL-SKARGPAHLEANAFTATLTLTGGWQSLRSPGSSSVL-RAP, (SEQIDNO:1194); XM_014108855.1, CC2D2B, Del, A_7, KLVRRCFPTEESQLLSLIVKGYRS, (SEQIDNO:1195); XM_014118218.1, REV3L, Del, A_7, KLVSNKGQIVKILKELCLLGENDHMLSCLLPHHLT-TLKPKTVT, (SEQIDNO:1196); XM_014109172.1, PRKDC, Ins, A_7, KLVSPAKNTLR, (SEQIDNO:1197); XM_005637209.2, CIR, Del, A_7, KLWGGSVGSWVLHWATPQKQGNSCLKGTRCS, (SEQIDNO:1198); XM_005627781.1, AIM1, Ins, A_7, KLWIQRFQY, (SEQIDNO:1199); XM_014121650.1, MYO3A, Del, A_7, KLWNLVLAKSQFIKTQIARKRRHL, (SEQIDNO:1200); XM_005628783.1, LOC100856700, Del, A_7, KLWPPALPI, (SEQIDNO:1201); XM_014109144.1, LOC607941, Ins, A_7, KLWTSEGDG-GAGPAPGGQ, (SEQIDNO:1203); XM_014113138.1, C4H5orf42, Del, A_7, KLYGIKHN, (SEQIDNO:1204); XM_014114250.1, ZKSCAN5, Del, A_7, KMAFVRKH-IVGT, (SEQIDNO:1205); XM_005641533.2, HDX, Del, A_7, KMAKHKLF, (SEQIDNO:1206); XM_014108953.1, ZNF518A, Del, A_7, KMCHLCQHQNWLQHQ, (SEQIDNO:1207); XM_005617406.2, GPBP1, Del, A_7, KMDGGCMEEMVLKT, (SEQIDNO:1208); XM_014109460.1, ZNF280D, Del, A_7, KMD-VIQIHLKAH, (SEQIDNO:1210); XM_014115228.1, RGS7, Del, A_7, KMEFLFVLSKAFFPRY-LASSLGQTLFSG, (SEQIDNO:1211); XM_539311.4, ADAMTS3, Del, A_7, KMEGFMLSTRDQP, (SEQIDNO:1212); XM_014122056.1, FBXO15, Del, A_7, KME-KNTSCSTLTF, (SEQIDNO:1213); XM_005619169.2, NSD1, Del, A_7, KMEMALRNQYVLALVGVTLHCLE-NYLYLYLA, (SEQIDNO:1214); XM_014109744.1, SCAF4, Del, A_7, KMEYSK-LKLSSPFWTWLQEPVMLPQ, (SEQIDNO:1215); XM_005640584.2, ZDBF2, Del, A_7, KMFIWKTKTVNMVK, (SEQIDNO:1216); XM_014114455.1, TRMT13, Del, A_7, KMFQRSG-PLWLALLLHSVVTTGVIGDIMWAKSISGL, (SEQIDNO:1217); XM_014120493.1, SPDYA, Del, A_7, KMHIIPTSLNAPKDPV, (SEQIDNO:1219); XM_005637882.2, FAM160B1, Del, A_7, KMIGHLHLL-FLYKKILFITGRQLPITT, (SEQIDNO:1220); XM_014112349.1, BOD1L1, Del, A_7, KMILKPHI, (SEQIDNO:1221); XM_546816.3, PKD1L2, Del, A_7, KMIS-CRKKERLLICY, (SEQIDNO:1222); NM_001003379.1, CD3E, Del, A_7, KMITLWKVLVTESYLRRSFQKWTTV-VIMPAMQIP, (SEQIDNO:1223); XM_014106549.1, ZBTB38, Del, A_7, KMKKGMKNLQSPMGQGSQMHFPSSKQKIV-ITCFLHWT, (SEQIDNO:1224); XM_014109295.1, LRRCC1, Del, A_7, KMKKITLSVVYQGTE-QLCSRHCHSLES, (SEQIDNO:1225); XM_532888.5, ATAD2B, Del, A_7, KMKKTPNLQTMRTIRRTGSC, (SEQIDNO:1226); XM_850315.4, IL7R, Del, A_7, KMKMT-GRV, (SEQIDNO:1227); XM_014108110.1, SPECC1L, Del, A_7, KMKNSQKNWRK, (SEQIDNO:1228); XM_014112182.1, AHI1, Del, A_7, KMKQNSSQRHLLLPPPSASMG, (SEQIDNO:1229); XM_005627935.2, KIAA0196, Del, A_7, KMKTYKLGS-ERSQNKSCL, (SEQIDNO:1231); XM_003433082.3, NUDT15, Del, A_7, KMKVGSGFPGKN-FLPWTSFSGYCDV, (SEQIDNO:1233); XM_014109687.1, SYNJ1, Del, A_7, KMLDRFLEDF, (SEQIDNO:1235); XM_014112214.1, KIAA0825, Del, A_7, KMLKNYWKKYLYH, (SEQIDNO:1237);

XM_535180.5, HSPA14, Del, A_7, KMLLGKQPELLGLMFCG, (SEQIDNO:1238); XM_547651.5, THOC1, Del, A_7, KMLLLGNQIHSILLG-KIIYYVCAM15, (SEQIDNO:1239); XM_005629547.2, AGK, Del, A_7, KMLPRFYTYLAWM, (SEQIDNO:1241); XM_014111866.1, CXHXorf58, Del, A_7, KMLPWGLNHKRTNQAQSNNSQSSSLPHLLTL, (SEQIDNO:1242); XM_014113467.1, CEP126, Del, A_7, KMLQIVLC, (SEQIDNO:1243); XM_003639701.3, NIFK, Del, A_7, KMLQTLVLRSLQIARSCRKRRRRRRRVHVLLPLLRRP-WIARAPHQFVHQHFWRNEN LKQLK, (SEQIDNO: 1244); XM_532014.5, LOC612942, Del, A_7, KMMDYSIDQM, (SEQIDNO:1245); XM_014109909.1, ANK2, Del, A_7, KMMRQSLQKHLS, (SEQIDNO:1246); XM_535747.5, GAP43, Del, A_7, KMMRTKRLNK-MASNQKIKLIRPRPKFRLASVDT, (SEQIDNO:1247); XM_005638097.2, RMDN1, Del, A_7, KMNPVLQLIS-GMQSVLVMLEIMKASRLKLQMPTLSRSILRKQLN, (SEQIDNO:1248); XM_545669.5, SCG2, Del, A_7, KMNRSTTK, (SEQIDNO:1249); XM_014113355.1, LOC106558787, Del, A_7, KMNRVTLMVWGGML-SPSLLGSGLFLWCMIPTGR1, (SEQIDNO:1250); XM_014113356.1, LOC106558787, Del, A_7, KMNRVTLMVWGGMLSPSLLGSGLFLWCMIPT-GRYFLH, (SEQIDNO:1251); XM_014113357.1, LOC106558787, Del, A_7, KMNRVTLMVWGGML-SPSLLGSGLFLWCMIPTGSATRHLLMNLAQLCS-LYTSMQPN AILTYF, (SEQIDNO:1252); XM_014119696.1, MRPL42, Del, A_7, KMNTLSKDS, (SEQIDNO:1253); XM_544601.6, ARHGAP11A, Del, A_7, KMPSFPYHPQFLHQMLSVNCQWILL-MVSQVRRGSPSSTILTLNSCQLIFSVAVLRQY QFPLI-QAQKGHLRIHSLLSPSMETI, (SEQIDNO:1254); XM_536013.5, GTF3C3, Del, A_7, KMQKKELQKRIKLVRMLPAVYLMVCQ, (SEQIDNO: 1255); XM_014111854.1, ATP7A, Del, A_7, KMQLLFMTLNYRLQRPYWKLLMTWALMLFSTILILSLF, (SEQIDNO:1256); XM_005640594.2, PIKFYVE, Del, A_7, KMQTLLLIQRKHLLWQAADQEAKLRVMKRKG, (SEQIDNO:1257); XM_003434003.1, DSPP, Del, A_7, KMQTRRQE, (SEQIDNO:1258); XM_005630416.1, BUB1, Del, A_7, KMQVLLGLGESIRSSPLCHLLFLCLK-METKKIMDYHSLKINPQEPGPLENAL, (SEQIDNO: 1259); XM_005617569.2, CYLD, Del, A_7, KMRKLE-FLQFSSY, (SEQIDNO:1260); NM_001168012.1, CCDC66, Del, A_7, KMRLFHLSWMKINPL, (SEQIDNO: 1262); XM_531828.5, RTN4, Del, A_7, KMRLLMSRMKLDHYLAQSYPMTFLSR1, (SEQIDNO:1263); XM_014117467.1, VPS13A, Del, A_7, KMRLNFFIKI, (SEQIDNO:1264); XM_014116764.1, ATAD5, Del, A_7, KMRNRKICWIA, (SEQIDNO:1265); XM_535474.5, USP8, Del, A_7, KMRPQRKGQSQQRSCIQ, (SEQIDNO:1267); XM_005615794.2, ZCCHC6, Del, A_7, KMRQIALWV, (SEQIDNO:1268); XM_014111472.1, CYLC1, Del, A_7, KMRRKRMPRRMKCPLM-LILNLNGIQKRVNKMKKRIREFQKKTKINLQ, (SEQIDNO:1269); XM_005633939.2, SUGT1, Del, A_7, KMRSWREMQL, (SEQIDNO:1270); XM_539955.5, PLAT, Del, A_7, KMRTATLEKG, (SEQIDNO:1271); XM_014120778.1, CACNA2D1, Del, A_7, KMRVSQAARG, (SEQIDNO:1272); XM_014113435.1, RDX, Del, A_7, KMSALRSNSRH, (SEQIDNO:1273); NM_001048021.1, ABCG2, Del, A_7, KMSELTRSFSN, (SEQIDNO:1274); XM_005621835.2, WDR47, Del, A_7, KMSFEIQQNSFKNIIGKDYAINSI, (SEQIDNO:1275); XM_014117434.1, IL1R1, Del, A_7, KMSFPKYSGIR-IANLCFLTI, (SEQIDNO:1276); XM_014116249.1, LOC609770, Del, A_7, KMSQIFRKLETTLKLL, (SEQIDNO:1278); XM_014121779.1, NISCH, Del, A_7, KMSQPFRPEK, (SEQIDNO:1279); XM_014111702.1, TAF7L, Del, A_7, KMSSSFPYGNN, (SEQIDNO:1280); XM_014107151.1, SYCP2, Del, A_7, KMSST-TLITRTLFFDLRCVQ, (SEQIDNO:1281); XM_005619749.1, NXPE4, Del, A_7, KMSSVSPNATH, (SEQIDNO:1283); XM_005638190.2, CHRM5, Del, A_7, KMTMTPKNTSCPQVLLIDPRVRNVWPISSNWW, (SEQIDNO:1284); XM_532129.4, GLO1, Del, A_7, KMTSQKIKMKK, (SEQIDNO:1285); XM_005636950.2, SCAF11, Del, A_7, KMTSVQMLLMIQILPTNI-EMTVPVG, (SEQIDNO:1286); XM_846278.4, MAP4K5, Del, A_7, KMVATTSSVISGQWE, (SEQIDNO:1287); XM_005640267.2, XIRP2, Del, A_7, KMVFLHHCPQR, (SEQIDNO:1288); XM_545075.4, ADGRG7, Del, A_7, KMVITPFRWTLMLMKCSRKIFMTSGIPRALWLLPCC-TISFW, (SEQIDNO:1289); XM_005633870.2, SETDB2, Del, A_7, KMVMQKLSGWIWKMMEKWT-SYLNKCKMCCNH, (SEQIDNO:1290); XM_847551.4, SLC25A13, Del, A_7, KMVSFLCLPMTSSHDI, (SEQIDNO:1291); XM_014119574.1, OSBPL8, Del, A_7, KMVSGLEQFF, (SEQIDNO:1292); XM_003640020.3, MRPL15, Del, A-7, KMVVLLLLQLSMIQEV, (SEQIDNO: 1293); XM_532130.5, DNAH8, Ins, A_7, KNICFK-PIWTKTIRRCYFLYKN, (SEQIDNO:1295); XM_014113470.1, CEP126, Del, A_7, KNLNMNIIV, (SEQIDNO:1296); XM_014119939.1, ZNF786, Ins, A_7, KNNERRIALPATSDF, (SEQIDNO:1298); XM_536224.5, WHSC1, Ins, A_7, KNPHKEDTGAY, (SEQIDNO:1299); XM_014111407.1, DOCK11, Ins, A_7, KNPTQKAPGSQARAGGKDQNC, (SEQIDNO:1301); XM_005624991.1, MED13, Ins, A_7, KNSKALGSSRSSH-LATVS, (SEQIDNO:1302); XM_014110851.1, EIF4G3, Del, A_7, KNSLLKSYISDSRNSLLRTRRMMNRSLTG, (SEQIDNO:1303); XM_542340.5, AKIRIN2, Del, A_7, KNSPYLLYDRLG, (SEQIDNO:1304); XM_014111650.1, GPRASP1, Del, A_7, KNTGFGLEKRLITCQGPN-PRKRPGPE, (SEQIDNO:1305); XM 005624024.1, CCDC40, Del, A_7, KPAKSSRRKSSLWGHNTTFD, (SEQIDNO:1306); XM_014119962.1, RNF32, Del, A_7, KPALSVEGTSIKPE, (SEQIDNO:1307); XM_005629416.2, STIL, Ins, A_7, KPAMLFTWFSHSR, (SEQIDNO:1308); XM_859168.4, SLTM, Del, A_7, KPARLLKRKEAIQIILN, (SEQIDNO:1309); XM_005615470.1, PHACTR2, Del, A_7, KPASSQPL-DRPQMQPPLARLT, (SEQIDNO:1310); XM_005626529.2, AFF4, Ins, A_7, KPAWIRTLQITLFQPWKTPGCFFIEL, (SEQIDNO:1311); XM_854588.4, CNOT4, Ins, A_7, KPCLC-CRTVSAPSRSRGFETTRIFWEVW, (SEQIDNO:1312); XM_005618098.2, TTC37, Ins, A_7, KPCTKDHSESSSFSR, (SEQIDNO:1313); XM_003639778.2, CCDC105, Ins, A_7, KPEGAAR-HAQEPHREPQLQEDRV, (SEQIDNO:1314); XM_005632154.2, ATG7, Ins, A_7, KPERRHGTEDGEPQ, (SEQIDNO:1315); XM_843302.3, COR6C33, Del, A_7, KPFLHAPLI, (SEQIDNO:1316); XM_844234.4, TAF1, Del, A_7, KPFLLTQKVASARG, (SEQIDNO:1317); XM_014118021.1, MCHR2, Del, A_7, KPFLT-FISATWLWLIWSTSLECHFLFISGPGEESGCLGGPSAP-LSHPWIPATSLPVVPS, (SEQIDNO:1318); XM_014111411.1, LOC611589, Del, A_7, KPFQRSE-QLIFWIFLLGSSCLLSQEATMYSILRI, (SEQIDNO: 1319); XM_005619571.2, KIRREL3, Del, A_7, KPGLDCPGEQISKGLCQPRMTSEWRSSTRSQPLVER- LRNTPPSSS, (SEQIDNO:1320); XM_005631628.2, ASRGL1, Ins, A_7, KPGNCGCRCLGLQRKRGLCNLDGWHR, (SEQIDNO:1321); XM_546237.5, SH3PXD2B, Del, A_7, KPHLPGPSRRSEGHSGKQVKAKQLLLQAGPYWSLLKPNLFFPTPQAATMTCEAKVV WDRGWWAK, (SEQIDNO:1322); XM_014112906.1, USP54, Ins, A_7, KPHPFASTLEPRHRAGDFRIGVSLPSQSSDFSSWLFWMGAARCGLALIKPNRIHQMR GKSLWKPG TVVPAPLPSLSSM, (SEQIDNO:1323); XM_014112904.1, USP54, Ins, A_7, KPHPFASTLEPRHRAGDFRIGVSLPSQSSDFSSWLFWMGAARCGLALIKPNRNFEECP AVSGYV, (SEQIDNO:1325); XM_534366.4, PTPRA, Ins, A_7, KPICKH1A1, (SEQIDNO:1326); XM_005628165.2, CORIN, Del, A_7, KPILNLTGVSLWSPMVKSQCLRLFLQIQSVTRAPQHRLHIPVNTFQPGPRMLLSQGTK ITGTQVPV, (SEQIDNO:1327); XM_014119437.1, CEP290, Del, A_7, KPKALLILNSLYDKQQRGNKKLRNTRKTSSNRLRFSNMFLKVLRQSKAFNESFKF, (SEQIDNO:1328); XM_545071.5, DCBLD2, Del, A_7, KPKAPMTYLTGTGQVGGKE, (SEQIDNO:1329); XM_005636930.1, RPAP3, Del, A_7, KPKMKTQKTG, (SEQIDNO:1330); XM_005623780.2, AK7, Del, A_7, KPKNSRLMWLLLDFNME, (SEQIDNO:1331); XM_005626210.1, PKDREJ, Del, A_7, KPKPVTRTQKTIKIKMPNLSL, (SEQIDNO:1332); XM_014122498.1, NUMA1, Ins, A_7, KPKTSLFSGMPSVRAEGNRGVRAGIGQDDYAALIPLHHELQKSQGLGTIRI, (SEQIDNO:1333); XM_005622017.2, PRKACB, Del, A_7, KPLEQVHLEESCW, (SEQIDNO:1334); XM_003639939.3, COPS7A, Del, A_7, KPLKLQQPQLPRLHLRTLSST, (SEQIDNO:1335); XM_850195.4, C4H5orf34, Del, A_7, KPLKSFRILTIFYQILKS, (SEQIDNO:1336); XM_531828.5, RTN4, Del, A_7, KPLLIQNKRTDHHLLYFQQS, (SEQIDNO:1337); XM_014117890.1, SMC2, Del, A_7, KPLRKVRRP, (SEQIDNO:1338); XM_548321.5, TSR1, Ins, A_7, KPLSRPVQFGEW, (SEQIDNO:1339); XM_014117962.1, LOC102153482, Ins, A_7, KPLSYFERNVATV, (SEQIDNO:1340); XM_005618961.2, DDX50, Ins, A_7, KPLTKGSCFGSYKGTGKPSSQRLQRYH, (SEQIDNO:1341); XM_014118588.1, CSMD3, Ins, A_7, KPLVESSTSNL, (SEQIDNO:1342); XM_850281.4, POLE3, Del, A_7, KPMQRSKTRAEMRTTMKTKNGWKKKNRTKRRK, (SEQIDNO:1343); XM_014118452.1, GLTSCR1L, Del, A_7, KPNASAEH, (SEQIDNO:1344); XM_014121964.1, ARHGAP12, Ins, A_7, KPNDLSEYSNCFWSHSVKARERDW, (SEQIDNO:1345); XM_014109318.1, TRIQK, Del, A_7, KPNLFYEQPN, (SEQIDNO:1346); XM_539422.5, SAMD9L, Ins, A_7, KPNSKPSLSKSV, (SEQIDNO:1347); XM_535063.5, MCM4, Del, A_7, KPPLKISSCLTRYYQGLI, (SEQIDNO:1348); XM_005622209.2, KDM5B, Del, A_7, KPPMLWICMSASCVAVATMKTGFSCVMGVTTVTTPFA, (SEQIDNO:1349); XM_005637095.1, PLCZ1, Ins, A_7, KPPRIFETRTVCT, (SEQIDNO:1350); XM_014119556.1, EEA1, Ins, A_7, KPQLTGTSNSTNREAEESVRKP, (SEQIDNO:1351); XM_014119166.1, LRGUK, Del, A_7, KPQWKEILWRDNMRQPGRP, (SEQIDNO:1352); XM_005615889.2, DOCK8, Ins, A_7, KPRKFGD1R1, (SEQIDNO:1354); XM_005637524.2, SLC16A12, Del, A_7, KPSCGSLPKNLIRSCSSGPMDRWLIL, (SEQIDNO:1355); XM_014107870.1, GLT1D1, Ins, A_7, KPSDGESPRGSQIRCRFHRINEGDGANAVAACQG, (SEQIDNO:1356); XM_014110190.1, SENP5, Del, A_7, KPSEAGCRSLGTIKRPLGKTVRVA-IAAHSLPQNLKTLLVSINRTFQIWTAMLW, (SEQIDNO:1357); NM_001168012.1, CCDC66, Del, A_7, KPSGRKSLMNRLL, (SEQIDNO:1358); XM_014111292.1, RGS2, Del, A_7, KPSHPKSCPPKQGKYILIS, (SEQIDNO:1359); XM_547384.2, IL19, Del, A_7, KPSKLRTPSKMSPSCPHRRPCIALSPQTYAA, (SEQIDNO:1360); XM_005642434.2, LOC100686288, Del, A_7, KPSLCIEILFDIRVFILVGNFLDVRNVRRPIVLAQTLFSIRKFILVGSPMTVGNVGRPLV GLQTLFNMREFILN, (SEQIDNO:1361); XM_014111020.1, INO80D, Del, A_7, KPSLLHLPKNIRKREGVDLVDPKNPFPLQCPKETSACPPASHCQWRLPRSGARPRQS, (SEQIDNO:1362); XM_014121789.1, UNC13A, Del, A_7, KPSLMVPKRNSTHT, (SEQIDNO:1363); XM_003431606.1, LOC100685645, Del, A_7, KPSPLLDVLFRCLPPTLWGPQSVCS, (SEQIDNO:1364); XM_014109144.1, LOC607941, Del, A_7, KPSRRIASGRSGLSW, (SEQIDNO:1367); XM_014119477.1, UTP20, Ins, A_7, KPSSPYSGPTPSTPELSSAAPNSSARWAESCCEQENQHAHIY, (SEQIDNO:1369); XM_014114304.1, LOC479758, Del, A_7, KPSSRSPTSLNTREHTLGRSPMNVTNVGNHSVISQP, (SEQIDNO:1370); XM_014119418.1, CHD8, Ins, A_7, KPSTQTGNYH, (SEQIDNO:1371); XM_005630719.2, POLR3C, Del, A_7, KPSVCLSNITW, (SEQIDNO:1372); XM_005640279.2, NOSTRIN, Ins, A_7, KPSWLCCQTEVGKYPGKLLPEYPGAGEGKN, (SEQIDNO:1373); XM_014118492.1, TDRD6, Del, A_7, KPTLILHSFLTGISQR, (SEQIDNO:1374); XM_014110645.1, ELOVL2, Del, A_7, KPVRLLFFTCTTMPLCLTSGGVF, (SEQIDNO:1375); XM_005634561.2, RNF13, Del, A_7, KPVRSASKKWFLPKATQTPTQTAVKKKMRCPNTPLFLDLWLLSAPSHLGLCRNLAH IRI, (SEQIDNO:1376); XM_005626337.2, SEMA6A, Del, A_7, KPVSPPETHTVGG, (SEQIDNO:1377); XM_005629247.2, USP44, Del, A_7, KPVTPQVNEGQ, (SEQIDNO:1378); XM_014121139.1, APIP, Ins, A_7, KPVYSSFYECIHNERSRCSDSYSL, (SEQIDNO:1379); XM_014112831.1, CTNNA3, Del, A_7, KPWKCTSIHGRIISMSSLKL, (SEQIDNO:1380); XM_005640528.2, FAM126B, Del, A_7, KPWYQLSIKSFRIRIMSFWNLSATSCLSSIVALKFDLRGSHCSSCQN, (SEQIDNO:1381); XM_014112420.1, TICRR, Ins, A_7, KPYRSDPWQTGHF, (SEQIDNO:1382); XM_005627271.2, PNPLA1, Del, A_7, KQAAKCSLLPVPSTSLCSPLPRQFGSPTGLIPARSRNTAVLRKL, (SEQIDNO:1383); XM_005619653.2, C5H11orf63, Ins, A_7, KQADFGITYS, (SEQIDNO:1384); XM_005639155.2, PTPN13, Del, A_7, KQAFLMQQITLTVEIQTWMKLLIPAVRIIKHQKREV, (SEQIDNO:1385); XM_014109969.1, PTPN13, Del, A_7, KQAFLMQQITLTVEIQTWMKLLIPAVRIIKHQKRNLPPQ, (SEQIDNO:1386); XM_531673.4, YEATS4, Del, A_7, KQALKLQSLRRD, (SEQIDNO:1387); XM_005634418.2, ATP2Cl, Del, A_7, KQANYQSVKLQAFSKLIFRMV, (SEQIDNO:1388); XM_535238.5, DHX29, Ins, A_7, KQARPKRGSRKNKEISKRNGNFRRPSSIQSSHKDFTSTE, (SEQIDNO:1389); NM_001002968.1, SLC10A2, Ins, A_7, KQCGISREQRQRNGL, (SEQIDNO:1390); XM_844191.4, KCNT2, Ins, A_7, KQCIKVILSWTFSITCT, (SEQIDNO:1391); XM_005621555.2, ATF7IP2, Del, A_7, KQCLQVAGSK, (SEQIDNO:1392); XM_014115116.1, CACNA1E, Ins, A_7, KQDGGERPGMEAP, (SEQIDNO:1393); XM_014109954.1, CCDC158, Ins, A_7, KQDGWRTRSPEITGTPFERKGC, (SEQIDNO:1394); XM_005633481.2, WNT11, Del, A_7, KQDPKPIN, (SEQIDNO:1396); XM_005619375.2, OSMR Del, A_7, KQDTPRSWLLRTTLEWS, (SEQIDNO:1397); XM_003639330.3, CCT4, Del, A_7, KQDVMSSSYRSLS, (SEQIDNO:1398); XM_537686.5, COIL, Ins, A_7, KQEEKQSHV, (SEQIDNO:1399); XM_014112131.1, LOC100688660, Ins, A_7, KQEENRGRKCCQKGR-GASGF, (SEQIDNO:1401); XM_005620337.1, USP24, Ins, A_7, KQEGWIQVISA, (SEQIDNO:1402); XM_003435066.3, TRAF3, Ins, A_7, KQEHTKFAQSDM, (SEQIDNO:1403); XM_850902.4, G3BP2, Del, A_7, KQELQESEKPEVVVMIAGILGAMIEVLVVHVA, (SEQIDNO:1404); XM_534297.5, U2SURP, Ins, A-7, KQFGTLQRRIETNSGRA, (SEQIDNO:1405); XM_005627588.2, CEP162, Ins, A_7, KQFIGRHQKTEAR (SEQIDNO:1406); XM_014114222.1, ZCWPW1, Del, A_7, KQFRLILRSETSKEEKEVILANVLFGSSAP-LQTVRSGGGFVETLTLQCFQMIGPVIRIQ T, (SEQIDNO:1407); XM_535242.6, PLK2, Del, A_7, KQFTIMQSLASALFSQQQMLLNNSLVK, (SEQIDNO:1408); XM_003639390.3, TLN1, Ins, A_7, KQGSFWAG-GRRGVYY AGGLSFPQKVDSPPAAV, (SEQIDNO:1409); XM_005640790.1, LEMD1, Ins, A_7, KQGTQKKPSF, (SEQIDNO:1410); XM_003434330.2, LEMD1, Ins, A_7, KQGTQKKTRGFQH, (SEQIDNO:1411); XM_014108953.1, ZNF518A, Del, A_7, KQHYIESVKKSLNLKMPVNHLD-LTDQGFQKIQSELCGFSLLVPNS1, (SEQIDNO:1412); XM_014109172.1, PRKDC, Ins, A_7, KQHYSK-VAPGFQSFS, (SEQIDNO:1413); XM_014111106.1, ALS2CR11, Del, A_7, KQICQIIVRGLIEKKMI, (SEQIDNO:1414); XM_014121388.1, IWS1, Ins, A_7, KQIC-TRSENQHRGQ, (SEQIDNO:1415); XM_014110764.1, KCNH7, Ins, A_7, KQIFIFHLLH, (SEQIDNO:1416); XM_014118880.1, LOC482344, Del, A_7, KQIHVKGI, (SEQIDNO:1417); XM_014119627.1, ANO4, Ins, A_7, KQIKWTLLQRWKVSD, (SEQIDNO:1418); XM_861118.4, PTPRE, Ins, A_7, KQISQHPSQ, (SEQIDNO:1419); XM_005628464.2, DBF4, Ins, A_7, KQNEIYEN, (SEQIDNO:1420); XM_005620331.2, C5H11orf141, Del, A_7, KQKDISASKMSLNLERVILES, (SEQIDNO:1421); XM 005640597.2, MAP2, Del, A_7, KQKFRPTLPPGNSF, (SEQIDNO:1422); XM_533539.4, KIAA0020, Ins, A_7, KQKHQQRNRNAT, (SEQIDNO:1423); XM_014115681.1, RALGAPA1, Ins, A_7, KQKHRIDHTIFCYLYSRSDISCINKNAF, (SEQIDNO:1424); XM_014112733.1, ARID4B, Del, A_7, KQKKMKI-WRIKMRRQLVWMNPSA, (SEQIDNO:1426); XM_014118258.1, OGFRL1, Del, A_7, KQKKQLKDSS-WPIR, (SEQIDNO:1427); XM_531833.5, PPP4R3B, Del, A_7, KQKKVKTRKTFLKGHHLVASNLHSPTLPVLL-MEQIVQTVSL, (SEQIDNO:1428); XM_014115508.1, CEP192, Del, A_7, KQKLVDJMKVDWKTFQELVRLIFGNLCPKNRLHKT-SIQWT, (SEQIDNO:1429); XM_014110297.1, POLQ, Del, A_7, KQKMFVWNILSHDPKVKK, (SEQIDNO:1430); XM_541863.4, IQCF2, Del, A_7, KQKQPQRFRPGGV APSYAGHCCTQLSVPGSFSAGGG, (SEQIDNO:1432); XM_005641869.2, MAP7D3, Del, A_7, KQKRREAR1, (SEQIDNO:1433); XM_858323.4, EIF2S2, Del, A_7, KQKRYLILMKLKKV, (SEQIDNO:1434); XM_542579.5, CCDC122, Ins, A_7, KQKSSITFAE, (SEQIDNO:1435); XM_005623784.2, PAPOLA, Del, A_7, KQKTLKISVLIS-PMIFSLSQIQFIGKQ, (SEQIDNO:1436); XM_844661.3, RGS21, Del, A_7, KQKVQKKLLLKPR, (SEQIDNO:1437); XM_005615470.1, PHACTR2, Del, A_7, KQLGPNHQLHHLLPPPHLVPELRRRHSLAKQGQ, (SEQIDNO:1439); XM_005620305.1, KMT2A, Ins, A_7, KQLGPRPNCPIPGEGENPLPFHSFI, (SEQIDNO:1440); XM_014115880.1, MIS18BP1, Del, A_7, KQLKLIFQLQHQEKKPCLTKN, (SEQIDNO:1442); NM_001003222.1, CNGA1, Del, A_7, KQLMRKKSSSIY-LIS, (SEQIDNO:1443); XM_862810.4, NUMB, Del, A_7, KQLRQSCGYQQMDSELWMKKLRTS, (SEQIDNO: 1444); XM_014117096.1, ZNF510, Del, A_7, KQLSLTVKELG, (SEQIDNO:1445); XM_014113138.1, C4H5orf42, Del, A_7, KQLSRRNGQKL, (SEQIDNO: 1446); XM_539701.5, TMTC2, Del, A_7, KQLSWTAR-SLMWSSVLPTCSDRLASTKPPRSIMIWQPD, (SEQIDNO:1447); XM_014111218.1, ZC3H11A, Del, A_7, KQLWQLFHSFLRTSQSLCPRWKNLETVMC-CLQPSLLQTPLHRKSLALLHPK, (SEQIDNO:1448); XM_014115168.1, LOC480059, Del, A_7, KQMNLLISS-WLKSWR, (SEQIDNO:1450); XM_534832.5, PUS7L, Del, A_7, KQNLIFKIYPVKRAATKKSILSPSALMMTKI-ISLVQKRKILSMMELPKVKKKKFMF, (SEQIDNO: 1452); XM_005618005.1, EXOSC10, Del, A_7, KQNLKLFGCFMQKTSSGLSLNSEKRSTTPTLRFF-PRSSSSPMLRNPSLRHSRKKGESA RRIVRRTWMSPLPWLISSINREPSRWSRTCIHILTSMN, (SEQIDNO:1453); NM_001197076.1, ASPM, Del, A_7, KQNLLLLWHS1L, (SEQIDNO:1454); XM_852177.4, SMARCB1, Del, A_7, KQNLTLRIMDTQPWPPA, (SEQIDNO:1455); XM_005625951.2, POLR3B, Ins, A_7, KQNQYGCETGAILFET, (SEQIDNO:1457); XM_005639977.2, MYLK4, Ins, A_7, KQNRCSESR, (SEQIDNO:1458); XM_005618072.2, ERAP2, Ins, A_7, KQNSVCIVNQQTSGKVNKIN, (SEQIDNO:1459); XM_014118543.1, RGS22, Del, A_7, KQNTGVMFLKNIGTLILMT-CLTTNWSLNISVSFLRLILQVWTLCAGQTLNS-SEESFME TESRGKQNLYILKTNTLIKN-ISLAPKVQLLNISRTR, (SEQIDNO:1460); XM_005620578.2, ZC3H18, Del, A_7, KQPFEKNRSLILKKKGLR, (SEQIDNO:1461); XM_844527.4, DMTF1, Ins, A_7, KQPNAFGE, (SEQIDNO:1462); XM_014115181.1, LOC106559028, Del, A-7, KQPPQIHLVMTWKISPSMTLIKYSAGWWPQHQ, (SEQIDNO:1463); XM_014120448.1, EML4, Ins, A_7, KQPRRRIC, (SEQIDNO:1464); XM_014120704.1, SYT6, Del, A_7, KQPSRRTLLIL-STMKPSSLIFPQRTWIKSACSSPSWIMIEWATTRS, (SEQIDNO:1465); XM_005626304.2, RUFY1, Ins, A_7, KQPSYVQHETDGRKVTALRKGTARGRGAE-PQGAAGAGRPDVRTAAAALAAA, (SEQIDNO:1466); XM_014110870.1, FSIP2, Del, A_7, KQQIQLVCQMYKLMILDKRKRK, (SEQIDNO:1467); XM_014113218.1, LOC102152874, Ins, A_7, KQQQASGPSNL, (SEQIDNO:1468); XM_533512.5, C1H9orf64, Ins, A_7, KQQRDQFHSSGLLPVGLRP, (SEQIDNO:1469); XM_014119438.1, C15H12orf29, Ins, A_7, KQQTVLLAFLSS, (SEQIDNO:1470); XM_014117106.1, LOC100685665, Del, A_7, KQRCYQLESQRQF, (SEQIDNO:1471); XM_014122749.1, ARHGAP42, Ins, A_7, KQRDAGHLNKAPRKSITTQPTKSHD-CLKPWCHIWPNSNESTRRNCGCHDEY, (SEQIDNO: 1472); XM_003434478.3, CCDC152, Ins, A_7, KQRDCSSP, (SEQIDNO:1473); XM_003434415.3, SLF1, Ins, A_7, KQRFLERYGIS, (SEQIDNO:1474); XM_014121880.C MAP4, Del, A_7, KQRHLLR-LESLNLTQSLKQLVPLRVHRNHLLGKFRFRIRRWT-SLRSPPNVGPRLTSST NLVEETSRLKVRS, (SEQIDNO:1475); XM_014121888.1, MAP4, Del, A_7, KQRHLLRLESLNLTQSLKQLVPLRVHRNHLLGKSR, (SEQIDNO:1476); XM_531825.4, C10H2orf73, Del, A_7, KQRKETQRKAK, (SEQIDNO:1477); XM_005623023.2, ROCK1, Ins, A_7, KQRKFKENTRATK, (SEQIDNO: 1478); XM_005628611.2, DNAH11, Del, A_7, KQRKIMAILHGKGLISTGSSWKVPDGTHSREPLLKPASRRSP1, (SEQIDNO:1479); XM_859339.4, CTCF, Del, A_7, KQRKPKRANCVTQRKAKMWMCLSMILRKNSRRACCQRLMQRK, (SEQIDNO:1480); XM_005635796.1, SPHKAP, Del, A_7, KQRKPLRKNGITTRKSYFMLWKTNILANIIRR, (SEQIDNO:1481); XM_005615806.2, NAA35, Del, A_7, KQRKRRKFAH, (SEQIDNO:1482); XM_005641359.2, GSPT2, Ins, A_7, KQRNLVFVLGLRYKPGRTRQG, (SEQIDNO:1483); NM_001313825.1, MEPE, Ins, A_7, KQRQYCSSKFW, (SEQIDNO:1485); XM_005633448.2, RSF1, Del, A_7, KQRRIRILK, (SEQIDNO:1486); XM_846653.4, DDX21, Del, A_7, KQRSPLKRKLFLLKQKK, (SEQIDNO:1487); XM_014110420.1, GOLIM4, Ins, A_7, KQRWRRTRSSR, (SEQIDNO:1488); XM_547403.4, BATF3, Ins, A_7, KQSCCSEKSEEADPEG, (SEQIDNO:1490); XM_860109.5, RBM39, Ins, A_7, KQSCSNGKQSTKGKCWTYEALCGLIT1, (SEQIDNO: 1491); XM_014106519.1, EPB41, Del, A_7, KQSFLKHRRKQ, (SEQIDNO:1492); XM_014109132.1, TDRD1, Del, A_7, KQSFSEINM, (SEQIDNO:1493); XM_545702.4, RGS1, Del, A_7, KQSLIFCIAKRRKYIKLLCIQMLLNKSTLTFTLENLQPRRLKHQPLRVLMKPKKLYILL WKRIPIPDFSNQIYI, (SEQIDNO:1494); XM_005623935.2, HSP90AA1, Del, A_7, KQSLKICARS, (SEQIDNO:1495); XM_014120175.1, WDR17, Del, A_7, KQSQLSLGVHITLICLQVAVPII, (SEQIDNO:1496); XM_005617376.1, C2H5orf46, Del, A_7, KQSQNSPNS, (SEQIDNO:1497); XM_533254.6, HRASLS5, Del, A_7, KQSQTQPQSLRVEGN, (SEQIDNO:1498); XM_014110795.1, CCDC173, Ins, A_7, KQSRIKSNCRI, (SEQIDNO:1499); XM_532130.5, DNAH8, Del, A_7, KQSRTGCINCPLPQT, (SEQIDNO:1500); XM_014120092.1, TEX15, Ins, A_7, KQSRTLPSNFTSRFTSENH, (SEQIDNO:1501); XM_845513.2, SSMEM1, Del, A_7, KQSRTNLLL, (SEQIDNO:1502); XM_005631781.2, MGARP, Ins, A_7, KQSRVTSTAR, (SEQIDNO:1503); XM_014122324.1, ERC2, Del, A_7, KQSSCRTSRKRRGHWPERFET, (SEQIDNO:1504); XM_532840.5, CCDC110, Ins, A_7, KQSTFFGEA TNDRNIRSTKK, (SEQIDNO:1505); XM_541240.4, SAMD3, Del, A_7, KQSTFWNPIQKRY, (SEQIDNO:1506); XM_540739.5, FNBP4, Del, A_7, KQSYEPWRKEMVVCQGLVHVLTSASQHLRMECVDLCLKGGNGRCLFELQVQNLR AGVLAKLDGRLQKMEKL, (SEQIDNO:1507); XM_014113182.1, JAK1, Ins, A_7, KQTETEKTGK, (SEQIDNO:1508); XM_014109153.1, KNDC1, Del, A_7, KQTGPQKGNKVRKVSAFPHLTWVYTFFNLNFFSSEL, (SEQIDNO:1509); XM_014107325.1, BRCA2, Ins, A_7, KQTKLQRHR, (SEQIDNO:1510); XM_005642075.2, LOC100683955, Ins, A_7, KQTKPSRAAVRPQDF, (SEQIDNO:1511); XM_014116087.1, TTLL5, Ins, A-7, KQVCKCLLGDSLKKF, (SEQIDNO:1512); XM_014113324.1, CCDC15, Del, A_7, KQVFFQTT, (SEQIDNO:1513); XM_005620894.2, DYNC1LI2, Del, A_7, KQVLLEVLVLVVCRAQPRSDKRLC, (SEQIDNO: 1514); XM_005632616.2, SETD2, Del, A_7, KQVLRRNPHNLKAPFLLQNLMKILYGLPQVKDHMI, (SEQIDNO:1515); XM_014111910.1, NKRF, Del, A_7, KQVNTQLLMRR, (SEQIDNO:1516); XM_005623862.2, RD3L, Del, A_7, KQVWIITG, (SEQIDNO:1517); XM_533327.6, DDX18, Del, A_7, KQWKLYKLERKKRNLP, (SEQIDNO:1518); XM_014109265.1, NDUFAF6, Del, A_7, KQWTTYTVITHPSSLWPWSCGR1, (SEQIDNO:1519); XM_005617866.2, HP1BP3, Del, A_7, KQYLPGLPFLPAS, (SEQIDNO:1520); XM_014111056.1, DNAH7, Del, A_7, KQYMIINLSLRE, (SEQIDNO:1521); XM_005618261.2, ZNF518B, Ins, A_7, KQYVPTQTGFSFSLLKRSFSSISSKKQYFPQSWSCIKSLSI, (SEQIDNO:1522); XM_014109202.1, CCNE2, Del, A_7, KRADMFTTNILKFCILTWSHR, (SEQIDNO:1523); XM_005637210.2, C1S, Del, A_7, KRAGNFVTVEIQSLVPKKSLPILFGSLRKQYMYSKM, (SEQIDNO:1524); XM_014118152.1, CASP8AP2, Del, A_7, KRALCIC1HLLKNTAPMAFGHVPIIRLVRVSQMRIVEEGEKILDIANIAEERIEYGKT, (SEQIDNO:1525); XM_005634010.2, SLITRK1, Del, A_7, KRALQVCSVSPPRLPSFTIYFCMVIPSLDFSLMSLLTFIMRLVCTWKTMACMKSFLGL FWGCSW, (SEQIDNO:1526); XM_545798.5, NIPA1, Del, A_7, KRASCAPSGEVPPI, (SEQIDNO:1527); XM_014110232.1, GOLGB1, Ins, A_7, KRCGNPPTNYPGEGSASDRNQ1, (SEQIDNO:1528); XM_014120722.1, SYCP1, Del, A_7, KRCQKKIFCKRLRKQKQ, (SEQIDNO:1529); XM_846379.3, ANKRD13A, Del, A_7, KRDIKRTGTHWNLCWELWNTSLEPKGTSPQNVPLPTTPQPSRLTSILMKSLI, (SEQIDNO:1530); XM_005624542.1, MED24, Del, A_7, KRDIVKTSRIMSVSSPWMTCSPQS, (SEQIDNO:1531); XM_544163.4, CPNE3, Del, A_7, KRDKRRKATRIQVLSV, (SEQIDNO:1532); XM_014122577.1, CEP295, Del, A_7, KRDLPKLQVCHHHLQVFLRTLI, (SEQIDNO:1533); XM_539103.4, FBXO43, Del, A_7, KRDLSFLGRNMIKPQNSVKPLKSVEKNFCCAEGWTYLSLF, (SEQIDNO:1534); XM_843366.4, CHD1, Del, A_7, KRDRLIHLRRKMMKKIMIMIKEVLVAKQLSMLAIKKMKK, (SEQIDNO:1535); XM_005617803.2, STPG1, Del, A_7, KRDSTVKPRDFIIKRMVSQVPGSMTSFTNLQCSTMSHCLRKGHALFPLWPLSLAASR ETTSLPEPGLCPKPREDFSLSLKQDLPQGITISMNPL, (SEQIDNO:1536); XM_014118080.1, DST, Del, A_7, KRDVIPSVPLCPLLPRTQLEMRYLISMLLESRRICLLRRDCYCGHSRQQRVTLEYGVK ISLPAGEMENYLMPSFINTGRT, (SEQIDNO:1537); XM_005640326.2, ZAK, Ins, A_7, KREINHSKQLPQKFC, (SEQIDNO:1539); XM_542038.5, RAD23A, Ins, A_7, KRELGCQLPPESEL, (SEQIDNO: 1541); XM_005636026.2, OAS2, Ins, A_7, KREMPYHQGNP, (SEQIDNO:1542); XM_005621959.2, LOC490172, Del, A_7, KREMSFVNRTCKHQQIVAQIYLRKFSVL, (SEQIDNO:1543); XM_014114846.1, ZNF644, Del, A_7, KRESEKWM, (SEQIDNO:1544); XM_005619490.2, LEPR, Ins, A_7, KREWCVFD, (SEQIDNO:1545); XM_014110067.1, STPG2, Del, A_7, KREYQGLENMTLKANFGRLKVYQV, (SEQIDNO: 1546); XM_005615576.2, DSE, Del, A_7, KRFDRKLRSWHRKNCP, (SEQIDNO:1547); XM_005632455.2, GNL3, Del, A_7, KRFESTIEN, (SEQIDNO:1548); XM_005640932.2, KCTD3, Ins, A_7, KRFFRSRVQFV, (SEQIDNO:1549); XM_014107556.1, FDFT1, Del, A_7, KRFHCYTTFTLTFMNQTGGIWRARRRIDKC, (SEQIDNO:1550); XM_547475.5, BLZF1, Del, A_7, KRFHQWLNSAAPQQKKWLKRFYAFWIQLPVQKAHLIIHFLSLHQLPYLRQRKILDDF IPILDMKI, (SEQIDNO:1551); XM_014109094.1, KIF20B, Del, A_7, KRFPHVHHLRKHTLYGVRHPQLVQTWPLR, (SEQIDNO:1552); XM_014118910.1, AVL9, Del, A_7, KRFSFIFLQ, (SEQIDNO:1553); XM_014121497.1, LOC476151, Del, A_7, KRFTNWRNKG- PLKFRRKGMGTLPYCQWWL-LAHCPRGQKRQWVTLWDR, (SEQIDNO:1554); XM_545270.2, LOC488146, Del, A_7, KRGG-GRGQKNVLDSLIRLCLVSRGQKKIAESANFLIS-LKKM, (SEQIDNO:1555); XM_014108010.1, MYO18B, Del, A_7, KRGGLQGLLVAPRPALRTQPQRPR-SPGLRVLGTQAWCY, (SEQIDNO:1556); XM_014117407.1, LOC102155766, Ins, A_7, KRGGTIFQTHVFRIPMDIFREFFAAT, (SEQIDNO:1557); XM_005636809.2, SLC4A8, Del, A_7, KRGITSFPL-FAPLLRLARSSLIHTQWIKMVKLYLLSLFLLQVLK, (SEQIDNO:1558); XM_014120175.1, WDR17, Del, A_7, KRGKLYMLMEVYQFFNQVIKVRSMF, (SEQIDNO:1559); XM_532888.5, ATAD2B, Del, A_7, KRGKTRCLI-FIDLQQEEVISGERSMPFIVVTQLLLMKNALKEG-NQRAWQEQEIDVCL, (SEQIDNO:1560); XM_005617350.2, RBM27, Ins, A_7, KRGWQVER1, (SEQIDNO:1561); XM_014113761.1, DAB1, Del, A_7, KRHKRISSVNKLCIRQFWKRMLKILYT-STLCLRLDTSQSVIPKQKKTFIRFPPAKRRK VFMMCQKVNL, (SEQIDNO:1562); XM_005628697.2, PDE1C, Del, A_7, KRHLEKLRIKLTEHAQTKVTTL-VERIPNLRSPQEKNNRMVT, (SEQIDNO:1563); XM_005615829.2, CEP78, Del, A_7, KRHLKK-KNQNQSRTP, (SEQIDNO:1564); NM_001286231.1, TAF9, Del, A_7, KRHQLLREE, (SEQIDNO:1565); XM_003639075.3, NAE1, Del, A_7, KRIIAILHGL, (SEQIDNO:1567); XM_005620886.2, ADAMTS18, Ins, A_7, KRIPHLTVTSAAGPGA, (SEQIDNO:1568); NM_001005869.1, HTR2A, Del, A_7, KRIQRKM-PRAQIMTTAWLL, (SEQIDNO:1569); XM_014111472.1, CYLC1, Del, A_7, KRIREFQKKTKINLQ, (SEQIDNO:1570); XM_005617440.2, SREK1IP1, Del, A_7, KRIS-QKEGNIIKRKKKRREKRRSIHPLLILLRSPKS, (SEQIDNO:1571); XM_005621999.2, SSX2IP, Del, A_7, KRISRRKDEALQKQPFA, (SEQIDNO:1572); XM_860876.4, SPAG9, Del, A_7, KRIYRPEWNL, (SEQIDNO:1573); XM_005641136.2, BMX, Del, A_7, KRKCRQAITKRGFLF, (SEQIDNO:1575); XM_005621851.2, RNPC3, Del, A_7, KRKDLMTLWK-MIKKRKNLVV, (SEQIDNO:1576); XM_005627838.2, UBR5, Del, A_7, KRKEKNRMWCQKKLKVQNQGHLL-MILLHN, (SEQIDNO:1577); XM_014115025.1, LOC100683727, Del, A_7, KRKHGRGWSLKSALLET-ALQENHLNRKDSLGQWAYVSKRPM, (SEQIDNO:1578); XM_014110866.1, NR4A2, Ins, A_7, KRKIRVFSK, (SEQIDNO:1579); XM_005627752.1, LOC100856021, Del, A_7, KRKKAKPKNCLKKSLSKGSNCINKT-GEKQNYMLTGERNNKKKIFFLQLLLLWIQTA LIPIS-SYLRIENKFL, (SEQIDNO:1580); XM_005631271.2, LRP4, Del, A_7, KRKKKKKRLKRIPTKPERRLSPSAL-GKVELEGSGLRLAKRILLLQSCQNCVHSSALR MEASPAALSVLVVGATSRVR, (SEQIDNO:1581); XM_014115156.1, RASA12, Del, A_7, KRKKKTRIIM, (SEQIDNO:1582); XM_005638100.1, CNBD1, Del, A_7, KRKKLKNLFVWVNLRKRSPLVRLVFFFKFLSHVL, (SEQIDNO:1583); XM_014120446.1, EML4, Del, A_7, KRKKNHKDRGKKKRNLILM-IKVHKFEHHLLPSPLHSLSKYTDKLKKARILLPPKA, (SEQIDNO:1584); XM_847054.5, TRIM24, Del, A_7, KRKLKALLN, (SEQIDNO:1586); XM_014114906.1, LRRC7, Del, A_7, KRKMTKMLGKLRITPAKPPGK-GASVGLLSNLPDCLAIAAHHGPGVISRSKICPSPRM THSWHGVV, (SEQIDNO:1587); XM_014114904.1, LRRC7, Del, A_7, KRKMTKMLGKLRLK, (SEQIDNO:1588); XM_533405.4, FAM210A, Del, A_7, KRKN-LILYKTNLLIYINDLRKHLDNMGKF, (SEQIDNO:1589); XM_536590.4, GUCY1A2, Del, A_7, KRKQWIFCILF-SLVM, (SEQIDNO:1590); NM_001003222.1, CNGA1, Del, A_7, KRKRKKKRRANQEIKM-KIKRTQRRKRRKKRKKRRKIKRRKAKIRKKRRRKR-SWLLI LQETC-TITGCFASLYLLCTTGLWLLQEHVLMNFSLIT, (SEQIDNO:1591); XM_005632477.1, LOC484748, Del, A_7, KRKRKTKTKRKKRQKKRQRKRKRRRKKSLYFQLHPL, (SEQIDNO:1592); XM_005627803.2, ANGPT1, Del, A_7, KRKRNHLETVQMYIKLVLIKVESTLFIL-IICQNPKRYFAIWILLGEVGL, (SEQIDNO:1593); NM_001005754.2, ANGPT1, Del, A_7, KRKRNHLETVQMYIKLVLIKVESTLFIL-IICQNPKRYFAIWMSMGEVGL, (SEQIDNO:1594); NM_001003057.1, TCOF1, Del, A_7, KRKRRRQKRPQPKTLTHYSRRKRRKRRRQQSKLS, (SEQIDNO:1595); XM_005636842.2, FAM186A, Del, A_7, KRKSHLCHDCIFRSQLVQSLKLAPYSHLRAW-THY, (SEQIDNO:1596); XM_014106893.1, MAST4, Del, A_7, KRKSRGKSQSPFLPVPCPS, (SEQIDNO:1597); XM_014116492.1, NF1, Del, A_7, KRKT-KNQWLASVSLRTASVQWEVPCSSDLSIL-PLSHRTKQGF, (SEQIDNO:1598); XM_014115197.1, GORAB, Del, A_7, KRKWNCKKNLIGKSSNKSNG, (SEQIDNO:1600); XM_005618382.2, PDE8A, Del, A_7, KRLICSIL, (SEQIDNO:1601); XM_014120337.1, BIRC6, Del, A_7, KRLIFLLLDTW, (SEQIDNO:1602); XM_005625193.2, GTF3C4, Del, A_7, KRLKAVEP-PIFGVSNFSS, (SEQIDNO:1603); XM_014108224.1, PCDH15, Del, A_7, KRLKILQRFWIAMFR-SKSLVPRWWWSPLVLAGMGMPF1, (SEQIDNO:1604); XM_848166.4, FAM135A, Del, A_7, KRLKKPLKK, (SEQIDNO:1605); XM_003432210.3, TAF1B, Del, A_7, KRLKLANS, (SEQIDNO:1607); XM_014108373.1, CECR2, Del, A_7, KRLKTSLSWMMISLPCIKF, (SEQIDNO:1608); XM_014107327.1, PARP4, Ins, A_7, KRLLLDRSTTR1, (SEQIDNO:1609); XM_014108433.1, ATF7, Del, A_7, KRLLLGPLTCLC11HQTSKSKKKSQWR, (SEQIDNO:1610); XM_014111409.1, SMARCA1, Del, A_7, KRLMELNLLHQKRLKKKKNFSHKDLQTGLSEILT-SLLKLMRSMEEMTLII, (SEQIDNO:1611); XM_014113657.1, SOGA3, Del, A_7, KRLNRLPQRRTTKTSSAICSS, (SEQIDNO:1612); XM_014121623.1, TRNT1, Ins, A_7, KRLPNGER, (SEQIDNO:1613); XM_005634369.2, EFHB, Del, A_7, KRLQRYYVTLVLSFLMKNLKMYGILHQKNT-TEEKFVLKPSEMFWMSYNMQTESSV KQAC, (SEQIDNO:1614); XM_014112884.1, MICU1, Del, A_7, KRLQVFVLSLIRKRKRRNVLDSETEK, (SEQIDNO:1615); XM_005640290.2, PPIG, Del, A_7, KRL-REIKVHSQK, (SEQIDNO:1616); XM_005620795.2, SLC7A6, Del, A_7, KRLRGKLT, (SEQIDNO:1617); XM_538880.5, FKBP5, Del, A_7, KRLRSTMSETAG-YMPTCLRSLQNRMQRKRPVKPWARRL, (SEQIDNO:1618); XM_546165.5, DNAJC9, Del, A_7, KRLSRKKRN, (SEQIDNO:1619); XM_532408.5, AFM, Ins, A_7, KRLWGTYEIWPASLRIHKCCYT, (SEQIDNO:1620); XM_005618341.2, AGBL1, Del, A_7, KRMCSFMAVAS-RRLCGKQSLLWAHQLSQKTSPTGLFPKSLIS, (SEQIDNO:1622); XM_014110764.1, KCNH7, Del, A_7, KRMHPLLLQIKPLLHPRLKIEHTM, (SEQIDNO:1623); XM_014111664.1, DACH2, Del, A_7, KRNCEWSSIER-EKLEKTLKDNLQLSFKAELPCKNV, (SEQIDNO:1626); XM_535698.4, LARP7, Del, A_7, KRNGHELNKCWQILLSKWTSGLEMQIYTKIDFFESK, (SEQIDNO:1628); XM_014107297.1, PSMA7, Del, A_7, KRNKRKHH, (SEQIDNO:1629); XM_014116764.1, ATAD5, Del, A_7, KRNKRKRWKF, (SEQIDNO:1630); XM_534564.5, PBK, Del, A_7, KRNLHYVQLHV, (SEQIDNO:1631); XM_005622441.2, SWT1, Del, A_7, KRNLRGKAPLHHPTLT, (SEQIDNO:1632); XM_014122663.1, UPF2, Del, A_7, KRNMKRKRKRSKKSRQNVSKKKKLPS, (SEQIDNO:1633); XM_005619653.2, C5H11orf63, Del, A_7, KRNMRNKLRSIT, (SEQIDNO:1634); XM_014109424.1, MGA, Del, A_7, KRNRDNRPHHCPHHFSSRAHVSLILRTVV, (SEQIDNO:1636); XM_005638550.2, LRRC49, Del, A_7, KRNSARCIWRT1, (SEQIDNO:1637); XM_014122790.1, NUCB2, Del, A_7, KRNSWSRIAGRQWISNSSSQRKN, (SEQIDNO:1638); XM_005636681.2, PTHLH, Del, A_7, KRNVELGLPG, (SEQIDNO:1639); XM_005615345.2, VPS4B, Del, A_7, KRNYRINFKVP1L, (SEQIDNO:1640); XM_005626595.2, FAM13B, Del, A_7, KRNYVKHYGNLKKHFINRMEGMPRKRIVFQCLKSIGSTRKLKPNLGFLKFLSANKIL QNPY, (SEQIDNO: 1641); XM_014109405.1, LPCAT2, Ins, A_7, KRPHPFCW, (SEQIDNO:1642); XM_014118865.1, UTRN, Del, A_7, KRPLMKSLRIRDLHYIHLQKKQRLWRKLFLQM, (SEQIDNO:1643); XM_014121542.1, LOC106560070, Del, A_7, KRPLRPFSYS, (SEQIDNO:1644); XM_536179.5, CHD2, Ins, A_7, KRPNNQNIGGSG, (SEQIDNO:1645); XM_005620334.1, DOCK7, Del, A_7, KRPRSWHLQHTRILQTPKCFRWYSRG1, (SEQIDNO:1646); XM_005629420.2, LOC102153096, Del, A_7, KRPSPLLDVSSNFISFSLWELLNVCSWPSWPLIGTLLSAVPCTTLIS, (SEQIDNO:1647); XM_005616743.2, LOC484590, Del, A_7, KRQKIGNQDGKTRNY, (SEQIDNO:1648); XM_005623593.2, MED6, Del, A_7, KRQNLYQKR, (SEQIDNO:1649); XM_005632477.1, LOC484748, Del, A_7, KRQRKRKRRRKKSLYFQLHPL, (SEQIDNO:1650); XM_014108798.1, SORBS1, Del, A_7, KRQRMTAGGWLRALRT, (SEQIDNO:1651); XM_005634496.2, CEP70, Del, A_7, KRQRTQRNQMNPTEITSSRP, (SEQIDNO:1652); XM_014106506.1, EPB41, Del, A_7, KRQRVVKNMLHQESHLESKMDHFLTLILPW, (SEQIDNO:1653); XM_014106519.1, EPB41, Del, A_7, KRQRVVKNMLHQESHLESKMDHFLTLMWVTSSPPSFEVSSLPW, (SEQIDNO:1654); XM_005626399.1, HSPA4, Ins, A_7, KRRAEWTSGRTRRQPRPPGC, (SEQIDNO:1655); XM_014112377.1, LRRK1, Ins, A_7, KRRDKNHLPVGNEGLLRDGFYHRPCQFPDRSVVSRPDSHRK, (SEQIDNO:1656); XM_535884.5, PAK1IP1, Del, A_7, KRREKRRKH, (SEQIDNO:1657); XM_005617440.2, SREK1IP1, Del, A_7, KRREKRRSIHPLLILLRSPKS, (SEQIDNO:1658); XM_005622787.2, ATP8B2, Ins, A_7, KRRGAVLQGSVPGRGGPGHRSQELRFCIPLSHPQNHHCPRDGHSRHLSAAGHPGLQ, (SEQIDNO:1659); XM_541861.5, PARP3, Del, A_7, KRRGGRVQRRRTASAPLPRPSELHPQRST, (SEQIDNO: 1660); XM_005638175.2, FGF7, Del, A_7, KRRKNKKQPTFFLWQ, (SEQIDNO:1661); XM_005624373.2, NMT1, Del, A_7, KRRKRKAMRQIQPRISL, (SEQIDNO:1662); XM_014108062.1, DENR, Del, A_7, KRRLYHKKLR, (SEQIDNO:1663); XM_005630156.2, NT5C1B, Del, A_7, KRRMRLDRRTQKTA, (SEQIDNO:1664); XM_014115182.1, SUCO, Del, A_7, KRRNAASTKLKKLKP, (SEQIDNO:1665); XM_014121595.1, LOC106560076, Del, A_7, KRRNMGKKCP, (SEQIDNO:1666); XM_014119891.1, UBN2, Del, A_7, KRRNVTKILFLWLP, (SEQIDNO:1667); XM_014115188.1, PRRC2C, Ins, A_7, KRRPQIRP, (SEQIDNO:1668); XM_014117357.1, FAM227A, Del, A_7, KRRQTTCSSNLQASLRNPLTRNVEEVMRGRLRFFQGLGSSCRRPGALIFLPERTPRSQ NQRRN, (SEQIDNO:1669); XM_005636081.1, SFSWAP, Del, A_7, KRRRGAHGHGPSPRPGPSRRPQASKPHVGTRPTQPASLPWRVGAPVRSAPGEFLRKK TARSPQQLSPLCRAK, (SEQIDNO:1670); XM_847542.4, CPLX4, Del, A_7, KRRRGHASEFISEKNTDSQRVKWTRTKSRWPETMWTCPKISGKW, (SEQIDNO:1671); XM_005641516.2, ATRX, Del, A_7, KRRRGILPCCQRTPYLQNFFKYIKNT1, (SEQIDNO:1672); XM_535608.5, SDAD1, Del, A_7, KRRRNQRCLTFQLFI, (SEQIDNO:1673); XM_537657.5, CWC25, Del, A_7, KRRRRKRRRKRKRSTRNISTEAQVVMVAVARMSAVGGDLKRSWQILPLCCPKPLDM AYRSGTPVIAREYRV1, (SEQIDNO:1674); XM_014113549.1, CHD3, Del, A_7, KRRRRQSGGKKGREMGDKR, (SEQIDNO:1675); XM_014113564.1, CHD3, Del, A_7, KRRRRQSGGKKGREMGDKSR, (SEQIDNO:1676); XM_005640523.2, NIF3L1, Del, A_7, KRRTSFSPTIHLFFDP, (SEQIDNO:1677); XM_003434147.2, GPR160, Del, A_7, KRSCPSSLSVFSALGYHLYYFK, (SEQIDNO:1678); XM_005622874.2, GALNT1, Del, A_7, KRSEDFLLGMF, (SEQIDNO:1679); XM_014116352.1, EFCAB13, Del, A_7, KRSGERKIYKYNCILKELSLPLPQ, (SEQIDNO:1680); XM_005622350.2, TMEM206, Ins, A_7, KRSGSKPHKL, (SEQIDNO:1681); XM_005629009.2, RNF11, Del, A_7, KRSGSVLSV, (SEQIDNO:1682); XM_014113160.1, CDH18, Del, A_7, KRSHILSP, (SEQIDNO:1683); XM_005639570.2, PARP14, Ins, A_7, KRSISGFSPTVSGV, (SEQIDNO: 1684); XM_014110716.1, SCN1A, Del, A_7, KRSLEVKTSS, (SEQIDNO:1685); NM_001197076.1, ASPM, Del, A_7, KRSLQSSHLTEGWWQRRSCRRCTGLRFSSRPLTECTEHMLHFRPGNMPPF, (SEQIDNO:1687); XM_014119381.1, ARHGAP10, Del, A_7, KRSLTKRQKRTIV, (SEQIDNO:1688); XM_005640039.2, HIVEP1, Del, A_7, KRSPIRGEGPCLSVKPVETGIENWRILKTIRNFTAQSYTDQKQR, (SEQIDNO:1689); XM_537556.5, DYNC1H1, Del, A_7, KRSQNLKWGSFTCSKILKFQRSACQFIPLLQMLQNNVMNVEKSQKLQTLEIRLKTQL FSISYNQELTVGYEKFKK, (SEQIDNO:1690); XM_005633942.2, DIAPH3, Ins, A_7, KRSRGKGKTCPNSQRIGRERKT, (SEQIDNO:1691); XM_005636081.1, SFSWAP, Del, A_7, KRSRGSALMMMMMKKMEVTCTRLFLLPRSVIAWRS, (SEQIDNO:1692); XM_541885.4, BSN, Del, A_7, KRSRIPWRLDTRPSCPRNPCHSS, (SEQIDNO:1693); XM_547161.5, MEFV, Del, A_7, KRSSCSTGNQSL, (SEQIDNO:1694); XM_005631005.2, ABCA13, Ins, A_7, KRSSLQLF11, (SEQIDNO:1695); XM_538557.5, FEM1C, Ins, A_7, KRSTWGLKILEKGNEHEVQR, (SEQIDNO:1696); XM_005637237.2, CHD4, Del, A_7, KRSVCSYAGSWGTALGRGRSLWRRRKRWLFAQTVRAATIPLARRRRRSLDLRKKR RANPSGRK RKKRMTTTMIQRSLNHLLSS, (SEQIDNO:1697); XM_005637236.2, CHD4, Del, A_7, KRSWGTALGRGRSLWRRRKRWLFAQTVRAATIPLARRRRRSLDLRKKRRANPSGR KRKKRMTTTMIQRSLNHLLSS, (SEQIDNO:1698); XM_003638844.3, KIAA0355, Del, A_7, KRTAVAAYLA, (SEQIDNO:1699); XM_003432274.3, LOC100683958, Ins, A_7, KRTELPRPHREIPHIQGYC1HLGQPAAEI, (SEQIDNO:

1700); XM_014116869.1, CAMSAP1, Del, A_7, KRTGLCLSQHPSPCIMLPAVTWTLALVTASAW-PAPSARIVWPLMSLT, (SEQIDNO:1701); XM_014118968.1, ZNF800, Del, A_7, KRTHRQHRKIKLNKTRKAL-NQLVRLLQVASKKPGNQNFQLALTL-SNFTVNFVNVSL LPNRT, (SEQIDNO:1702); XM_014117291.1, GOLM1, Del, A_7, KRTKASSSEPPVSLSPGHRKQTCLRQRYHK, (SEQIDNO:1703); XM_005623645.2, FAM161B, Del, A-7, KRTKQMRVLSG, (SEQIDNO:1704); XM_014115695.1, PLEKHD1, Del, A_7, KRTLKPINTSIYILRVSSP-WEAAWWRPRKNPACPMP, (SEQIDNO:1705); XM_005616957.2, LOC480753, Del, A_7, KRTMVLILLKVLHKSKQLMTI, (SEQIDNO:1706); XM_014118915.1, CTTNBP2, Ins, A_7, KRTSRKTKPTGLPTTVSRLPCV, (SEQIDNO:1707); XM_536010.5, TMEFF2, Del, A_7, KRTTVYC-TLFPAPCDFSMS, (SEQIDNO:1709); XM_014120322.1, KIDINS220, Del, A_7, KRVAYHLLSSSFLSLAALL-RELPSWLSLELTQNI, (SEQIDNO:1710); XM_548229.6, EPX, Del, A_7, KRVFSPRDSARPCARFPCLELCVTI-RASPPFRGTSSGPTFSHGAL, (SEQIDNO:1711); XM_005616337.2, IZUMO1, Del, A_7, KRVFVPTNVVRCCR1, (SEQIDNO:1712); XM_014120373.1, ALMS1, Del, A_7, KRVGHYQKL-LISPHVERSTVFSTNRSF, (SEQIDNO:1713); XM_005640584.2, ZDBF2, Del, A_7, KRVIHIVVLE, (SEQIDNO:1714); XM_534457.5, ATP9A, Ins, A_7, KRVLF-PADGSAGRGDRLEAAAPRGLHAEAPHCCRSPSDSII-CLCRRAKYRHSQLCGN FYQRGQRPSDQREFEH, (SEQIDNO:1715); XM_536972.4, RSL1D1, Del, A_7, KRVLVPTDPVEKRERPVQVWRPRRLQR-PRLQVTAQRRSQESKKRQRKKETLHWGK KTQDRRPKSQEPGSLLLLINLQKKLPTPPNSGPK-SAKYPSQP, (SEQIDNO:1716); XM_539460.4, MACC1, Del, A_7, KRVTTYLNISKGTQ, (SEQIDNO:1717); XM_005620292.2, ACAD8, Del, A_7, KRWGGTHSQPAR, (SEQIDNO:1718); XM_014106605.1, GOLGA4, Del, A_7, KRWKKLSRKQKRCKKR, (SEQIDNO:1720); XM_539598.4, CLSPN, Del, A_7, KRWKKSGG, (SEQIDNO:1721); XM_014108060.1, STX2, Ins, A_7, KRYERHRLRRAC, (SEQIDNO:1723); XM_014109449.1, ZNF106, Ins, A_7, KRYRSVLRPSSA, (SEQIDNO:1724); XM_005641356.2, SHROOM4, Del, A_7, KRYSLLKA-LAENSLS, (SEQIDNO:1725); XM_014113138.1, C4H5orf42, Del, A_7, KRYVIRKKILKE-KIMKSYYKMRF1, (SEQIDNO:1726); XM_003433297.3, ATP8A2, Del, A_7, KRYWRRYKSWRRSPE, (SEQIDNO:1727); XM_005623717.2, CEP128, Ins, A_7, KSAAPAD-AMQTAAAEEYDGKQGI, (SEQIDNO:1728); XM_005620663.2, C5H16orf46, Ins, A_7, KSANKGI-CLVQGRLGHH, (SEQIDNO:1730); XM_005629927.2, KLKB1, Del, A_7, KSAPIAFTANFSHMPLKHFTT, (SEQIDNO:1732); NM_001003040.2, RPI, Del, A_7, KSAS-TRAETHSLAGSRWWSTRVPSRHLMLCSITYQGR-CLYLSG, (SEQIDNO:1733); XM_005625479.2, CDK2, Del, A_7, KSAWTLRRRVYPVLLYERSPCLRSLT-TRTLSSYWMSSTQKTNSTWFLNFCTRI, (SEQIDNO:1734); XM_005641542.2, ZNF711, Ins, A_7, KSAY-YEAPQGGSYV, (SEQIDNO:1735); XM_542243.5, ANKRD49, Ins, A_7, KSAYYSAEATV, (SEQIDNO:1736); XM_005618061.2, GIN1, Del, A_7, KSCFMLEKTEN-KIVW, (SEQIDNO:1737); XM_005638791.2, LTN1, Ins, A_7, KSCGTVFISETDRLAK, (SEQIDNO:1738); XM_005639666.2, DNAH5, Del, A_7, KSCRKPISLFWSY, (SEQIDNO:1739); NM_001024633.1, HTR2B, Del, A_7, KSCSMLPIIF, (SEQIDNO:1740); XM_532888.5, ATAD2B, Ins, A_7, KSDGGPGGKYFKRVA-VVSQGCNQEAGHR, (SEQIDNO:1741); XM_546022.5, FAM81B, Del, A_7, KSDQQKIKPGNQAS, (SEQIDNO:1742); XM_014115916.1, ATG14, Ins, A_7, KSEALYSSTAASREKGEDSEAQSQTW, (SEQIDNO:1743); XM_014111056.1, DNAH7, Del, A_7, KSEQR-WRISSSTFLSFK, (SEQIDNO:1745); XM_540029.5, TRAPPC11, Del, A_7, KSEVQSCLLSMLHGCLNNSR-PLEIYLMKLLS, (SEQIDNO:1746); XM_014119220.1, LOC482280, Ins, A_7, KSEWGETL, (SEQIDNO:1747); XM_014106804.1, TOPAZ1, Ins, A_7, KSFKGFEKNKP, (SEQIDNO:1748); XM_014109263.1, ST18, Del, A_7, KSFLERPPYQVLNPSSMQEISKKN, (SEQIDNO:1749); XM_014119514.1, ZMYM4, Del, A_7, KSFRRGKLLIR-GKGLLSFSAPRCASLDIQFHLPAHRLLP-PRKLVQAAQKIF, (SEQIDNO:1750); XM_014119662.1, ZMYM1, Del, A_7, KSFRRGKLPIRGKGLLSFSAPR-CASMSTFHLPIHQLFPRELVQTAQKTS, (SEQIDNO:1751); XM_005638519.2, SPG21, Del, A_7, KSF-SETFHLAQWTL, (SEQIDNO:1752); XM_857524.4, TAOK3, Del, A_7, KSFSKRHEMDP, (SEQIDNO:1753); XM_005631802.2, SCLT1, Ins, A_7, KSGCSSGEAKRRR-CRENERNCLSACARCCHDNQEGSCKHKKTV, (SEQIDNO:1754); XM_005620231.2, INAD1, Del, A_7, KSGKDMQTFLENCTLLSLKRIRMDLDSALMKTDHA, (SEQIDNO:1755); XM_005616873.2, CD3EAP, Del, A_7, KSGKSYSRILC, (SEQIDNO:1756); XM_005638256.1, CASC5, Del, A_7, KSGKVRLGVVILH-KIRRFLITMLKGI, (SEQIDNO:1757); XM_014110145.1, SLC9Cl, Del, A_7, KSGNIYLMRIGTTRCN, (SEQIDNO:1758); XM_535303.4, RBL2, Del, A_7, KSGPVLNSP, (SEQIDNO:1759); XM_014110756.1, BAZ2B, Del, A_7, KSGQIFSK, (SEQIDNO:1760); XM_014119283.1, ANKS1B, Del, A_7, KSGRLNLLTF, (SEQIDNO:1761); XM_005639728.2, MFN1, Del, A_7, KSGRLQKRWQTRFHVQ, (SEQIDNO:1762); XM_014117699.1, RAPGEF6, Ins, A_7, KSGRYENEWS-SPVIEYCLCCKGQVETGGAAKGFPGVPSAFQP, (SEQIDNO:1763); XM_540380.5, SLC26A3, Del, A_7, KSGSCRRKACCK, (SEQIDNO:1764); XM_014120481.1, SELV, Ins, A_7, KSGTAISKLSTL, (SEQIDNO:1765); XM_003639255.2, LOC100856208, Del, A_7, KSHCLRQPMLRPRKPRPAVPEIPAHLRHSPRPTSWA, (SEQIDNO:1766); XM_014108894.1, CCDC125, Ins, A_7, KSHERQFCIKVLGEIFRIPCTA, (SEQIDNO:1767); XM_014114271.1, ZNF789, Del, A_7, KSH-ISVMTVENFSARWHILLNIRGSIPKKNPINVV-SAKKHLVRIQPLFDIS, (SEQIDNO:1768); NM_001003018.2, ASB17, Ins, A_7, KSHQHCDNNI-ALPFKSENNG, (SEQIDNO:1770); NM_001003212.1, F8, Del, A_7, KSHRRTQLLKGKTPFCPWALVKIMIQQQQ, (SEQIDNO:1771); XM_014110685.1, LOC102155713, Del, A_7, KSHSLRPRRDKGLPCRHNITREPPLTHPELN-TEEQGRKTSAFVSAVLPTPTQWSHQH, (SEQIDNO:1772); XM_003639317.1, LOC100856706, Del, A_7, KSHSYQRC, (SEQIDNO:1773); XM_005627613.2, RARS2, Del, A_7, KSIFSKCSKCFRSWDMTQK-GASTCPLEWCRE, (SEQIDNO:1774); XM_005628720.1, KIAA0895, Del, A_7, KSIIHKNSLPPPTPKDVEN-PANLLVLLVVKIFAR, (SEQIDNO:1775); XM_843679.5, SON, Del, A_7, KSIKDSQKNLSQR, (SEQIDNO:1776); XM_863061.4, PNISR, Del, A_7, KSIKRKRNKEG-VDQEVLVVVVPVAIAELVVLVVLSLALHIV-LAQVVVALLLDLLLLK GKKDI-VGVDLQQLKLDGVEVEVTHAE, (SEQIDNO:1777); XM_014118132.1, ZNF484, Del, A_7, KSILERN- TLNVLNVEKPSQGNQ1, (SEQIDNO:1778); XM_005634064.2, CCDC168, Del, A_7, KSILLIKAVILDTH, (SEQIDNO:1779); XM_541074.4, SERPINB3, Del, A_7, KSINFFKNTWITLRNFT, (SEQIDNO:1780); XM_005639981.2, RIPK1, Del, A_7, KSIQTQPKIQL, (SEQIDNO:1781); XM_535027.5, FAM204A, Del, A_7, KSISRALKRA, (SEQIDNO:1782); XM_005642460.1, LOC100686962, Del, A_7, KSISVITQGDFISALLSWVLGDLVLAGITGK, (SEQIDNO:1783); XM_005639173.2, NAP1L5, Del, A_7, KSITTSISPYLPRSKSSPVRWRGVHGP, (SEQIDNO:1784); NM_001287155.1, SLC39A6, Del, A_7, KSNTMTMTITPTMITTLTVIMLLPIKIIGKLFVQTMNLIVWVRIPETARGKDLTDQSMP MVKGMF, (SEQIDNO:1785); XM_005620937.2, LOC102154551, Del, A_7, KSKAKQRMKNQE, (SEQIDNO:1786); XM_014116115.1, SPATA7, Ins, A_7, KSKCLRQLNRPRDLCERH, (SEQIDNO:1787); XM_014108938.1, PCGF6, Del, A_7, KSKCMISIKKEV, (SEQIDNO:1788); XM_014119970.1, GIMAP4, Del, A_7, KSKCYKNFTEQS, (SEQIDNO:1789); XM_535949.5, KLHL41, Del, A_7, KSKFSKTPSQANSQNLAKMQRRLGPVR, (SEQIDNO:1790); XM_005630608.2, CTSS, Ins, A_7, KSKICDASQSGTLNGNAFI, (SEQIDNO:1791); XM_005635396.2, CKAP2, Del, A_7, KSKMTKQSI, (SEQIDNO:1792); XM_536278.5, NCAPG, Del, A-7, KSKPFKVKMQK, (SEQIDNO:1793); XM_014118171.1, USP45, Del, A_7, KSKRMEEKV, (SEQIDNO:1794); XM_014113144.1, SPEF2, Del, A_7, KSKSALKKMLLHESKGRKDGGDY, (SEQIDNO:1795); XM_014115252.1, EFCAB2, Del, A_7, KSKTLLKCLTTRRIIQWM, (SEQIDNO:1796); XM_005641935.2, MTM1, Del, A_7, KSKTSFILMWKSLTGCPVWSLPIG, (SEQIDNO:1797); NM_001313774.1, CLGN, Del, A_7, KSKVMVKLLKKKRKLNLRKRVKKKLKS, (SEQIDNO:1798); XM_005627636.2, MDN1, Ins, A_7, KSLAGLGIGPQS, (SEQIDNO:1799); XM_014117631.1, CCDC112, Del, A_7, KSLFRTGKPKSSKRRRKFSS, (SEQIDNO:1800); XM_014110411.1, B3GALNT1, Del, A_7, KSLGGDMKFLHFSY, (SEQIDNO:1801); XM_532156.6, CDC5L, Del, A_7, KSLHLVSTILLRKTTRLLMQISEN, (SEQIDNO:1802); XM_014116402.1, DDX42, Del, A_7, KSLILFLQLIIQRLTIHHLKKIFTMSMKR, (SEQIDNO:1803); XM_005633718.2, NCR3LG1, Ins, A_7, KSLILYLKSFSSEHPK, (SEQIDNO:1804); XM_014113360.1, CEP85L, Del, A_7, KSLKRSKNSVKKRRHS, (SEQIDNO:1805); XM_533945.4, SAFB2, Del, A_7, KSLKTLRRKKKMRMSRNQDLQIGPESPNPEAEEWNGRS, (SEQIDNO:1806); XM_005629178.2, NAV3, Del, A_7, KSLLGFQVPLGCQLQAAAARSKEPLI, (SEQIDNO:1807); XM_014113193.1, ATM, Del, A_7, KSLLKRNMKLSWISAKNFSQFSVTSAWKSSWTQLFGLRSDWLILAVWPLPRLLVTY LDMDMC RIS, (SEQIDNO:1808); XM_003431655.3, PNRC1, Del, A_7, KSLLKTLRILKICI, (SEQIDNO:1809); XM_005639514.2, ZBTB20, Del, A_7, KSLMSALSATRLSPPNRTTSSTCSYTQVRSPTNAASVGAPSP, (SEQIDNO:1810); XM_003639998.2, CFAP58, Del, A_7, KSLNQRLS, (SEQIDNO:1811); XM_543244.5, LOXL2, Del, A_7, KSLNTSVDS, (SEQIDNO:1812); XM_005615711.2, HDDC2, Del, A_7, KSLPTWPCVPLRPNHPEAWHPCPTLESCTKLTTPRPGLYYHCGPSPSISSGTGESPGR AGYTEASRGRRVYRITCTEWQLWLW, (SEQIDNO:1813); XM_014110775.1, FASTKD1, Del, A_7, KSLQFCINIWMTINHSSY, (SEQIDNO:1814); XM_536509.5, TARS, Del, A_7, KSLRKNRLLKDWK, (SEQIDNO:1815); XM_014117390.1, MTERF2, Del, A_7, KSLRLTLAKFRPKKEGRYLTLWHH, (SEQIDNO:1816); XM_005637371.2, ADIPOR2, Del, A_7, KSLRNMSAMMKLLRKMRGLWVCPLFYKPIMLWKEWKNLFVRYGKVDGE, (SEQIDNO:1817); XM_005630127.1, E2F6, Del, A_7, KSLRTIFDG, (SEQIDNO:1818); XM_014112221.1, FAM172A, Del, A_7, KSLSQKDME, (SEQIDNO:1819); XM_003434864.3, CREBBP, Del, A_7, KSLSQRSYARL, (SEQIDNO:1820); XM_843829.4, PANK1, Del, A_7, KSLTALITHTLCCW, (SEQIDNO:1821); XM_005630596.1, APOB, Del, A_7, KSLTDSLWTFRTRKSLRSLSLAT, (SEQIDNO:1822); XM_005637776.2, FAM45A, Del, A_7, KSLTQRLPGEWGPSEKKRTQMEKFCGCGVILPRQLL, (SEQIDNO:1823); XM_014107044.1, PLCB4, Del, A_7, KSMETKLII, (SEQIDNO:1824); XM_546107.5, TFAM, Del, A_7, KSMKMLIGQTGRHTKKR, (SEQIDNO:1825); XM_853581.4, SEC31A, Del, A_7, KSMLLRLNLKNMCGPF, (SEQIDNO:1827); XM_003432357.3, DNAJC24, Del, A_7, KSMTCSGMKTI, (SEQIDNO:1830); XM_005631157.2, DNAJC24, Del, A_7, KSMTCSGMMITLF1, (SEQIDNO:1831); XM_005633892.2, LRRC63, Del, A_7, KSNLRILTLILFFGKKIH, (SEQIDNO:1832); XM_014116842.1, SMG6, Del, A_7, KSNMRNWN, (SEQIDNO:1833); XM_005634227.2, EPM2AIP1, Ins, A_7, KSNTLCSLQRSC, (SEQIDNO:1834); XM_014109094.1, KIF20B, Ins, A_7, KSPDPGTGTTN, (SEQIDNO:1835); XM_549024.5, LOC491904, Ins, A_7, KSPDVHISPHLHHG, (SEQIDNO:1836); XM_005623486.2, SYNE2, Del, A_7, KSPFWISCQ, (SEQIDNO:1837); XM_844339.5, PAK2, Del, A_7, KSPGIKSSLYSPAQRKEVRRKKRNGQKFLLHLILSIPSMLALMRLRENLLACQNSGLD YRRPPISPN, (SEQIDNO:1838); XM_014117059.1, MAPKAP1, Del, A_7, KSPLKRNRQVLESSQYYLYDWSSALCS, (SEQIDNO:1839); XM_005616994.2, ARHGAP21, Del, A_7, KSPLLQERSVSDWMIVHQHIPIGIFH, (SEQIDNO:1840); XM_014114325.1, GNA12, Del, A_7, KSPLRWWTWVARGLSARSGSSASTESHRSCSWCPPVSTTRCSWRTGAPTGWWSP, (SEQIDNO:1841); NM_001194952.1, PLAU, Ins, A_7, KSPLSSRKSRVSMWPEGSEAS1, (SEQIDNO:1842); XM_546967.5, LOC489848, Del, A_7, KSPPQEREAQGRRAKVWEEASA, (SEQIDNO:1843); XM_005626549.2, JADE2, Del, A_7, KSPQRFSGQT, (SEQIDNO:1844); NM_001313825.1, MEPE, Del, A_7, KSPVILKAVVTQIFKRGGTMISLLSAEMVNLLRTFLVRENLLVLT, (SEQIDNO:1845); XM_005640898.1, PEA15, Del, A_7, KSPWRTWSSSSRPARRTSPARRARRSRPAAPGSASWRATTSWTKITSRTSSTSLRSPA APTSSPWWWTTEPAS, (SEQIDNO:1846); XM_014111645.1, RPS6KA3, Del, A_7, KSQALMLDSFMP, (SEQIDNO:1848); XM_014114831.1, CCDC18, Del, A_7, KSQEIRCLFHLPPWIRRSEVFERNLTNSDNRMLVWSHRIIL, (SEQIDNO:1849); XM_533808.5, IQCF1, Del, A_7, KSQETKMSPLPVIRKS, (SEQIDNO:1850); XM_005629880.1, NRG1, Del, A_7, KSQGSQNFALAKHHWLILENICAK, (SEQIDNO:1852); XM_003431985.3, PLXNC1, Del, A_7, KSQILMSYIFGKQTAFLFASG, (SEQIDNO:1853); XM_005637042.2, ITPR2, Del, A_7, KSQKNSSKFSMTE, (SEQIDNO:1854); XM_005638154.2, E2F5, Del, A_7, KSQKTVYNGKV, (SEQIDNO:1855); XM_849701.4, FGD6, Del, A_7, KSQLLSKKYQQTQKILP, (SEQIDNO 1856); XM_014107587.1, NC1, Del, A_7, KSQLPHQPRKQLSPLAKRQQLHQPKRRLHQPKQ, (SEQIDNO:1857); XM_536323.5, HMGCR, Del, A_7, KSQMIVVDVNLCWSGIATKSMQQRRRQG, (SEQIDNO:1858); XM_845208.4, HECTD1, Del, A_7, KSQQKFCSRLRNHWPWQVELYQTGVNS, (SEQIDNO:1859); XM_005634020.2, UGGT2, Del, A_7, KSQTKLRRISLPIKMKRKKECGIPLKVSQEGCTKKKTKTKQIF, (SEQIDNO:1861); XM_014116333.1, C9H17orf80, Del, A_7, KSQTSRILKRES, (SEQIDNO:1862); XM_014120571.1, LOC607974, Del, A_7, KSRASGSKLASIGLSLSMTYSL, (SEQIDNO:1864); XM_014110816.1, USP48, Ins, A_7, KSRCAEHCPTAVLWRICLRNRLQSMWQRV, (SEQIDNO:1865); XM_534241.4, TOP2B, Ins, A_7, KSRFWESLLISFILSEVRR, (SEQIDNO:1866); XM_005627906.2, ATAD2, Ins, A_7, KSRIQYFSVGKFICSNQPVYLSASHGL, (SEQIDNO:1867); XM_859377.4, UPF3B, Del, A_7, KSRKVVLAIEKKEERS, (SEQIDNO:1868); XM_005631997.2, PRPF40A, Del, A_7, KSRLLMLTKSRQRKKKKKRQDQNTKRPRNHFNVFLKIMRK, (SEQIDNO:1869); XM_005627765.2, CAPN11, Del, A_7, KSRNGRTSSESVTRTTRAA, (SEQIDNO:1870); XM_850237.2, CLCA2, Ins, A_7, KSRQEREWNKINM, (SEQIDNO:1872); XM_014112822.1, ANK3, Del, A_7, KSRRASCLCTRSLLEKSSRRP, (SEQIDNO:1873); XM_014114127.1, CCT6A, Ins, A_7, KSRRCIHPHMQCVLRV, (SEQIDNO:1874); XM_014115168.1, LOC480059, Ins, A_7, KSRRCIHPHMQCVVRV, (SEQIDNO:1875); XM_532236.6, UFL1, Del, A_7, KSRRKEEKKRIVMMSHLTLERRSQRSLSCSRMRLKTF, (SEQIDNO:1876); XM_014116489.1, HEATR9, Ins, A_7, KSRRNINSGGFN, (SEQIDNO:1877); XM_861964.4, CLK3, Del, A_7, KSRRRTKRTNSCVS, (SEQIDNO:1878); XM_014112077.1, MAN2A1, Ins, A_7, KSRSETSVRLGY, (SEQIDNO:1879); NM_001205203.1, MEF2B, Del, A_7, KSRSRAFWTKGIGR, (SEQIDNO:1880); XM_003433570.1, SLC15A5, Del, A_7, KSRTGCFT, (SEQIDNO:1881); XM_014117962.1, LOC102153482, Ins, A_7, KSRVQGVADFGQGSQPPRLLILCSP, (SEQIDNO:1882); XM_532843.5, SNX25, Del, A_7, KSSCLLLASCLSNL, (SEQIDNO:1883); XM_531679.5, ZFC3H1, Ins, A_7, KSSERRGFLSYVQILHLTKSRR, (SEQIDNO:1884); XM_014116966.1, RALGDS, Del, A_7, KSSGSPPPSHPRRPPASAQPPAAPPPPQPPPRPCPPHAPTSAPSQGSAATAPHCRSTTSR WATAASSSASAWTWTTATCTRASW, (SEQIDNO:1885); XM_532840.5, CCDC110, Ins, A_7, KSSIRHTH, (SEQIDNO:1886); XM_005634448.1, TOPBP1, Del, A_7, KSSKDKNQALLRGHLVGGRLSYMLTSPEKQDSNAFFSQEEQRYYMLYLYLKKLHIS FLTSIN, (SEQIDNO:1887); XM_534297.5, U2SURP, Ins, A_7, KSSKSVIQ, (SEQIDNO:1888); XM_005639335.1, CYP2U1, Del, A_7, KSSKTIKSL, (SEQIDNO:1889); XM_847262.4, MRPS23, Del, A_7, KSSLCKKFHRTRIRRLLKNSRKVSHLP, (SEQIDNO:1890); XM_014108490.1, GPR19, Del, A_7, KSSLGPLIQIHQILLC, (SEQIDNO:1891); XM_535303.4, RBL2, Del, A_7, KSSLKEKKKILQGF, (SEQIDNO:1892); XM_014116985.1, SETX, Del, A_7, KSSLNLKKNVKTRRILWETVEI, (SEQIDNO:1893); XM_005632646.2, ZDHHC3, Del, A_7, KSSPLKSVPQSAAPSRHLPQ, (SEQIDNO:1895); XM_005622426.1, RGL1, Del, A_7, KSSPSLPRRVPLSIPWTPLPQGCRP, (SEQIDNO:1896); XM_014106956.1, ADNP, Del, A_7, KSSPTNASIALVYTPAT, (SEQIDNO:1897); XM_845288.4, ENTPD7, Del, A_7, KSSQESLQWQTPRNMPVITFVLC, (SEQIDNO:1898); XM_014114569.1, LOC489979, Del, A_7, KSSRNILLFTDLFLSCSHLLSSITGVLYMKLHMIYLLTVMWQKIL1R1, (SEQIDNO:1899); XM_005621408.2, RBBP6, Del, A_7, KSSSTEKLVKKLEVQKMYLIQKNPLKN, (SEQIDNO:1900); XM_014122800.1, BBOX1, Ins, A_7, KSSSVPDFVLHFCGLYRHWSGLL, (SEQIDNO:1901); XM_014122806.1, ZNF214, Del, A_7, KSSTERSCGRTTQMSCQ, (SEQIDNO:1902); XM_537580.5, CEP112, Del, A_7, KSSTMLSQKWKRKSLIFKSGTRKIFKNCSRTQTCV, (SEQIDNO:1903); XM_533351.4, KIF5C, Del, A_7, KSSVGSFI, (SEQIDNO:1904); XM_003434950.3, C4BPA, Del, A_7, KSSVLGQRLEMEK, (SEQIDNO:1905); XM_005630991.2, CCDC146, Del, A_7, KSSWNMNSKN, (SEQIDNO:1906); XM_014115665.1, ZBTB1, Del, A_7, KSSYLNILPVLFDVLIVASGLKPKI, (SEQIDNO:1907); XM_014112259.1, WDR41, Ins, A_7, KSTDLDSLF, (SEQIDNO:1908); XM_848248.5, KCTD8, Del, A_7, KSTFQIISQSANASGNRNCCRSMGY, (SEQIDNO:1909); XM_005620921.2, SUMF2, Del, A_7, KSTGQRLRCSGGVLSLRSLSPMSLETK, (SEQIDNO:1910); XM_545800.5, OCA2, Del, A_7, KSTGYQTRFCSPNA, (SEQIDNO:1911); XM_535814.5, TTC14, Del, A_7, KSTIGGGSQVLRGVPLHQQAQTTLVSQLKNLKNTLILDHVISVDMSKDIS, (SEQIDNO:1912); XM_014115681.1, RALGAPA1, Del, A_7, KSTKGKELDMNFRKFQLTSHFLEDGVVISLAKPQ, (SEQIDNO:1913); XM_014108499.1, KRAS, Del, A_7, KSTKKKRLLAV, (SEQIDNO:1914); XM_005634045.1, GPR183, Del, A_7, KSTLPLYIQQIW, (SEQIDNO:1915); XM_005615655.2, AKAP7, Del, A_7, KSTPNSMKNLSVIHLEKKWYIA, (SEQIDNO:1916); XM_005628257.2, LOC482176, Del, A_7, KSTRQKQTTL, (SEQIDNO:1917); XM_545105.5, QTRTD1, Del, A_7, KSTRRTLIH1, (SEQIDNO:1918); XM_005641214.2, POLA1, Ins, A_7, KSTSCTCCPLDEFSRRQKNESWRYCVICHLSGWVKPHCESEGLCT, (SEQIDNO:1919); XM_014112808.1, SYNE1, Del, A_7, KSTVVISSW, (SEQIDNO:1920); XM_005640463.2, GLS, Del, A_7, KSVFQKAQTWLVY, (SEQIDNO:1922); XM_532130.5, DNAH8, Del, A_7, KSVGMWLVCCLGHLLWQHFMVSIEKCCP, (SEQIDNO:1924); XM_014114457.1, OPYD, Del, A_7, KSVNSCLSCPHGRLN, (SEQIDNO:1925); XM_014115338.1, ASHIL, Del, A_7, KSVQTSTWMSNPFLVTRPPPVTVRSQRMTPGRAVWMTASIE, (SEQIDNO:1926); XM_005641551.2, PCDH19, Del, A_7, KSVRMTSVWYPGMWRRQTR, (SEQIDNO:1927); XM_014109172.1, PRKDC, Del, A_7, KSWAFQGTK, (SEQIDNO:1928); XM_014110675.1, LUZP1, Del, A_7, KSWEDLELRPQRRSRNPPPSQGQTR, (SEQIDNO:1929); XM_005630442.2, ZC3H6, Ins, A_7, KSWFLQGL, (SEQIDNO:1930); XM_533729.5, MRPS25, Del, A_7, KSWGRTRKPWKRRSRRKSSFLTQPTSGPESTACGSVSARWRGRSPARACCHYPRS, (SEQIDNO:1931); XM_014116764.1, ATAD5, Del, A_7, KSWKILIFKWFQIHSHILIKEVFLRRKVKS, (SEQIDNO:1932); XM_005638207.2, ZNF770, Del, A_7, KSWLNLNVLGVRN, (SEQIDNO:1933); XM_014113086.1, C1H6orf118, Del, A_7, KSWNRSSRKCVYATLSNSTDCTSSEKSLKTFAIVL, (SEQIDNO:1934); XM_014112240.1, XRCC4, Ins, A_7, KSWNRTENGFSGTPASRKEA, (SEQIDNO:1935); XM_005618153.2, XRCC4, Ins, A_7, KSWNRTENGFSGTPASRKEKLELSPN, (SEQIDNO:1936); XM_005628737.1, LOC102153873, Del, A_7, KSWRMVPSS, (SEQIDNO:1937); XM_014118119.1, PHIP, Ins, A_7, KSWRQKTKKEDEDTKTRFRSHSSYKC, (SEQIDNO:1938); XM_014115723.1, ADSSL1, Del, A_7, KSWWKGPKQPSLILTSGGGRTPL, (SEQIDNO:1939); XM_005618243.2, TLR10, Ins, A_7, KSYFREFQDNFIT, (SEQIDNO:1940); NM_001253787.1, OAS1, Del, A_7, KSYGVAVICWRLGLRTWRSSRE-SPTLLSSPSRPGGPQRSSLSPSCLPTGPWGLLLPTLS HILRSMRV, (SEQIDNO:1941); XM_539571.5, LOC482454, Ins, A_7, KSYKKKTL, (SEQIDNO:1943); XM_014111941.1, PPEF1, Del, A_7, KSYKSWKM-SIPGSQLVQSLTVKSWSSMVVYQSPQT, (SEQIDNO:1944); XM_014118548.1, RGS22, Del, A_7, KSYLQPHHLLQTSSLLLPLCL, (SEQIDNO:1945); XM_014120076.1, BAG4, Del, A_7, KSYMCWRRSSIS-SKK, (SEQIDNO:1946); XM_532831.5, FGL1, Del, A_7, KTAAMHNINFSKLEMKRIPMS, (SEQIDNO:1947); XM_003638871.2, PTCH1, Del, A_7, KTAASSWLWAS-SYLGPSLWD, (SEQIDNO:1948); XM_533512.5, C1H9orf64, Del, A_7, KTAER-SIPFFWIITCGTTPVITGKT, (SEQIDNO:1949); XM_014118520.1, LRP12, Del, A_7, KTAFFASQEI-FIVKTIGVCLKAGCVILRMTAVMAAMRRI-AQLLCLPES, (SEQIDNO:1950); XM_005631997.2, PRPF40A, Ins, A_7, KTAIRVSVCLRTFF, (SEQIDNO:1951); XM_005618779.2, RYR2, Del, A_7, KTAPCRLY, (SEQIDNO:1952); XM_014113043.1, TTC1, Del, A_7, KTCQKRRNRKEEKRALD, (SEQIDNO:1954); XM_014120242.1, DNAH6, Del, A_7, KTCSL-LIIICDQLFLK, (SEQIDNO:1955); XM_005618915.2, RTKN2, Ins, A_7, KTCSPSSF, (SEQIDNO:1956); XM_014114037.1, RYDIN, Del, A_7, KTCWSNLTLPTEVI, (SEQIDNO:1957); XM_861118.4, PTPRE, Del, A_7, KTDIPTSFPMIIPG, (SEQIDNO:1958); XM_005634774.2, ESF1, Ins, A_7, KTEEETEGSC, (SEQIDNO:1959); XM_014119186.1, FAM133B, Ins, A_7, KTEKEKRKEEIW, (SEQIDNO:1960); XM_005641359.2, GSPT2, Del, A_7, KTEKLGICPGP, (SEQIDNO:1961); XM_547403.4, BATF3, Del, A_7, KTELLLREVGRSR-PRRLTNSTRSMSAWSKRTPCCGERLGS, (SEQIDNO:1962); XM_860109.5, RBM39, Del, A_7, KTELQQWQTIYKREVID1, (SEQIDNO:1963); XM_014122498.1, NUMA1, Del, A_7, KTENIPLLRNA, (SEQIDNO:1964); XM_014122749.1, ARHGAP42, Del, A_7, KTERCWTS, (SEQIDNO:1965); XM_005633338.2, CWC15, Del, A_7, KTETVQQENIQPPRRCQRSLG, (SEQIDNO:1966); XM_014106902.1, LOC106557681, Del, A_7, KTFHIITV, (SEQIDNO:1967); XM_005625641.2, CAPS2, Del, A_7, KTFIVISVDEEKGSSTNSVIFMSVET, (SEQIDNO:1968); XM_005618176.2, PAPD4, Del, A_7, KTFLLTVNGNVSIHPTKNQ1, (SEQIDNO:1969); XM_014119514.1, ZMYM4, Del, A_7, KTFLNS-LIRFLSLNQYGKILV, (SEQIDNO:1970); XM_014115463.1, ZNF420, Del, A-7, KTFMKQNYPNGK, (SEQIDNO:1971); XM_005623362.2, PRPF39, Del, A_7, KTFPNQER-CFWKQSKETKKIQSYTSIYLKWNIVVTSNKMKKIS, (SEQIDNO:1972); XM_543400.5, NAA25, Ins, A_7, KTGDHKETKNL, (SEQIDNO:1973); XM_005628809.2, PTPRZ1, Del, A_7, KTGERSTQRVVAPNSLPSILMKIL-PKST, (SEQIDNO:1974); XM_544956.5, THAP9, Ins, A_7, KTGLCKKL, (SEQIDNO:1975); XM_534457.5, ATP9A, Del, A_7, KTGLVSCGRISWTGRQIGSCGSPW-PARRGSPLLPISFRFDHMSMQKSQISTFTTLWEL LPERTATLRSARV, (SEQIDNO:1976); XM_014112420.1, TICRR, Del, A_7, KTGQLNLPSLHGFQFCHLMPL, (SEQIDNO:1978); XM_005627482.2, KLHL31, Del, A_7, KTHLPKGWISMISRRQAWLLLSPMPTLES, (SEQIDNO:1979); XM_005640714.2, EPHA4, Del, A_7, KTHQSEPTKCAT, (SEQIDNO:1980); XM_014118696.1, LOC484323, Del, A_7, KTHTDVINMRTCLVKNQD, (SEQIDNO:1981); XM_014115969.1, PPP1R36, Del, A_7, KTHWKNNPKAIWWAL, (SEQIDNO:1982); XM_014118218.1, REV3L, Del, A_7, KTICHLSES, (SEQIDNO:1983); XM_014115880.1, MIS18BP1, Del, A_7, KTIKVKVALSGAISRKKQLKLIFQLQHQEKKPCLTKN, (SEQIDNO:1984); XM_539574.5, ZFP69B, Del, A_7, KTINIRYLEREIDTI, (SEQIDNO:1985); XM_005615889.2, DOCK8, Del, A_7, KTKEVRR-FAALKRLDPEEIFTRHFRNRRLSQSPWRAMNQAHR-CAPAT, (SEQIDNO:1986); XM_537881.5, OSBPL1A, Del, A_7, KTKFCQKHWRLWPPSIMN, (SEQIDNO:1988); XM_003434415.3, SLF1, Del, A_7, KTKISG-KIWDFLK, (SEQIDNO:1989); XM_542579.5, CCDC122, Del, A_7, KTKKFYYICRVNSVSLKTK, (SEQIDNO:1990); XM_003639701.3, NIFK, Ins, A_7, KTKKKQSV, (SEQIDNO:1991); XM_014120092.1, TEX15, Del, A_7, KTKQNSAIQFYFQIYK (SEQIDNO:1993); XM_014114898.1, LRRIQ3, Del, A_7, KTKRLKTVC, (SEQIDNO:1995); XM_003434478.3, CCDC152, Del, A_7, KTKRLQFSVIPFTI, (SEQIDNO:1996); XM_014120532.1, ZC3H8, Del, A_7, KTKTLKL-FRKMVNRRK, (SEQIDNO:1998); XM_533539.4, KIAA0020, Del, A_7, KTKTPAKE, (SEQIDNO:1999); XM_014107179.1, AURKA, Del, A_7, KTKTQLANS1, (SEQIDNO:2000); XM_014120520.1, BCL2L11, Del, A_7, KTKWQSNLQM, (SEQIDNO:2001); XM_014108547.1, LRRK2, Del, A_7, KTLCGEDVVQNFSHFLMISPFRN-SLRQRQISCFLMQHSVIPTS, (SEQIDNO:2002); XM_005627781.1, AIM1, Del, A_7, KTLDPKVPVLMC, (SEQIDNO:2003); XM_003432496.2, C1H18orf63, Del, A_7, KTLGPVKI, (SEQIDNO:2004); XM_005617102.2, PTER, Del, A_7, KTLIPIKRIFS, (SEQIDNO:2005); XM_014108953.1, ZNF518A, Del, A_7, KTLKCLKK, (SEQIDNO:2006); XM_536371.4, TET1, Del, A_7, KTLKIIYRVWLHD, (SEQIDNO:2007); XM_005618919.2, RTKN2, Del, A_7, KTLKRQMDSFLL-VSMKNPHHLFGPASLMVIIKWLSRKRSEFWMGSS, (SEQIDNO:2008); XM_005618918.2, RTKN2, Del, A_7, KTLKRQMDSFLL-VSMKNPHHLFGPASLMVIIKWLSRKRSEFWMGSSGL-SA, (SEQIDNO:2009); XM_005618915.2, RTKN2, Del, A_7, KTLKRQMDSFLLVSMKNPHHLFGPA-SLMVIIKWLSRKRYYLLQASSYMMGKGKKD VLP-FLLLIKLHSA, (SEQIDNO:2010); XM_005638410.2, DMXL2, Del, A_7, KTLLIKLIL, (SEQIDNO:2011); XM_014109094.1, KIF20B, Del, A_7, KTLLLMFKYNT, (SEQIDNO:2012); XM_532397.5, CABS1, Del, A_7, KTLLRKETTLLQ, (SEQIDNO:2013); XM_544755.5, MYO9A, Del, A_7, KTLMDQSIMVVCSHGYG, (SEQIDNO:2014); XM_005633353.2, MRE11A, Del, A_7, KTLMKKMMKFERL, (SEQIDNO:2015); XM_005619751.1, NXPE4, Del, A_7, KTLSLLFLWASIS-GPSPLMFLSEGPSMSTKLFSVFF, (SEQIDNO:2016); XM_005623067.2, ARHGAP28, Del, A_7, KTLYQKLKSCPLKYLIQKWLQKFQKEINLR-SQILRKKTTL, (SEQIDNO:2018); XM_014109144.1, LOC607941, Del, A_7, KTMDKRRRWWSRPSAW-GAVRTSGTAQP, (SEQIDNO:2019); XM_014108034.1, MYO1H, Del, A_7, KTMISSTDI, (SEQIDNO:2020); XM_014114822.1, BCAR3, Del, A_7, KTMKAVRLC, (SEQIDNO:2021); XM_014121157.1, SUV420H1, Del, A_7, KTMQLLTENLQLV, (SEQIDNO:2022); NM_001002968.1, SLC10A2, Del, A_7, KTMRNFQRAKTTKRSLSHRSIR, (SEQIDNO:2023); XM_005639890.1, LOC102151275, Del, A_7, KTNGKHGYKKTGRTARI, (SEQIDNO:2024); XM_014116355.1, BPTF, Del, A_7, KTNHIFDMNLL-DMTGVGGNTGS, (SEQIDNO:2025); XM_544755.5, MYO9A, Del, A_7, KTNKIHLILDGMEEL-GFVRADFQVAPPCLIKTGYLLIQLVANCWREPMEF1, (SEQIDNO:2026); XM_014118915.1, CTTNBP2, Del, A_7, KTNKSQNQTNRPAYNSLTLTLC, (SEQIDNO: 2027); XM_014107325.1, BRCA2, Del, A_7, KTNKTPKT, (SEQIDNO:2028); XM_014119627.1, ANO4, Del, A_7, KTNQMDFTSEMESVGLTIFLCTENLTHRPKREKCL-NEILEQKDYKWRKSP1, (SEQIDNO:2029); XM_014112349.1, BOD1L1, Del, A_7, KTNQQTKVKR-SQRAMTKEKERKKRRKRLKRNLITQKGVRNYKK, (SEQIDNO:2030); XM_014116543.1, EZH1, Del, A_7, KTNSFLNTVVSLFLRMRLIDGGRSMTNTCPASSSTST-MIL, (SEQIDNO:2032); XM_014120363.1, PTCD3, Del, A_7, KTPIPTAQ, (SEQIDNO:2035); XM_531770.5, GCC2, Del, A_7, KTPKSSSCL, (SEQIDNO:2036); XM_536098.5, MDM4, Del, A_7, KTPSFLIPATQWN-SWIWPTVLKAKKPYQAWENHQITFLNREQIQKT-WRIARIS, (SEQIDNO:2037); XM_005616781.2, ZNF507, Del, A_7, KTPVWPLPVWSIVFYSSVVVFVASNLPAK-KISWII, (SEQIDNO:2038); XM_014120026.1, WHSC1L1, Del, A_7, KTQENLLLTNTSKLTK, (SEQIDNO:2039); XM_005630615.2, PIP5K1A, Del, A_7, KTQKIWNQILPVW, (SEQIDNO:2040); XM_005628611.2, DNAH11, Del, A_7, KTQTEAPMFL-FASKNVKG, (SEQIDNO:2045); XM_003435066.3, TRAF3, Del, A_7, KTRAYKVCTIRY-VALKLKLRDKKKCFEIMNPKYFICSE, (SEQIDNO: 2046); XM_005636026.2, OAS2, Del, A_7, KTR-DAVSSRKSINS, (SEQIDNO:2047); XM_003434330.2, LEMD1, Del, A_7, KTRHSKKDSRLPTLTQKP, (SEQIDNO:2048); XM_005640790.1, LEMD1, Del, A_7, KTRHSKKTQFLKYKSSRKR, (SEQIDNO:2049); XM_005632154.2, ATG7, Del, A_7, KTRKAAWDRGW, (SEQIDNO:2050); XM_534611.5, IQCA1, Del, A_7, KTRKKMRDGKCHRVCSFP, (SEQIDNO:2051); XM_544123.3, TRPA1, Del, A_7, KTRLKVLNFFLAKE-LTQTSETAT, (SEQIDNO:2052); XM_014121682.1, KBTBD12, Del, A_7, KTRMLKSIGIM-IEETSFGKSYAQLNFESYMLWAVSIMTSML, (SEQIDNO:2053); XM_535344.5, IFI6, Del, A_7, KTRN-MARKAEAPGS, (SEQIDNO:2054); XM_014115652.1, MTHFD1L, Del, A_7, KTRPLSRCLLLFRQVMIT, (SEQIDNO:2055); XM_014112131.1, LOC100688660, Del, A_7, KTRRKQRKKMLPERERR-FRLLNDGKRKRWNILERKIKR-RENMKEQRSRKRRKQLLR KGKIT, (SEQIDNO:2057); XM_005620337.1, USP24, Del, A_7, KTRRMDSSHLS-LIIPSLCGWCQLCVSSTRSPARL, (SEQIDNO:2058); XM_003640140.3, LRRIQ4, Del, A_7, KTRSRRSRRIFST, (SEQIDNO:2059); XM_542038.5, RAD23A, Del, A_7, KTRTWLPTSS, (SEQIDNO:2060); XM_005623084.2, TXNDC2, Del, A_7, KTSCASRVTPPNHQQNPSCLN-RAVALSS, (SEQIDNO:2061); XM_005626701.2, DDX58, Del, A_7, KTSEIVKKK, (SEQIDNO:2062); XM_014113244.1, SSBP3, Del, A_7, KTSHWENRLGFC-TRGGVYFGTFTVQLLKGETLVNIRVKQKPFMITVQQP-PRALCLAT FPPTMGCREAPSLRVSFRVLRGH-SPRRTHSLHLTIPAA, (SEQIDNO:2063); XM_005618160.2, SSBP2, Del, A_7, KTSH-WGNHQDSYILGGVYFGISTVQLQKDGKHV-NIQVKQKPSMIILLCHLGTLEVQG PH, (SEQIDNO: 2064); XM_536304.5, SSBP2, Del, A_7, KTSHWGNHQDSYILGGVYFGISTVQLQKDGKHV-NIQVKQKPSMIIVLQQLPAQC, (SEQIDNO:2065); XM_005626121.2, VRK2, Del, A_7, KTSIVREVLSPA, (SEQIDNO:2066); XM_535238.5, DHX29, Del, A_7, KTSKAKKRLKKK, (SEQIDNO:2067); XM_005624902.2, EFCAB5, Del, A_7, KTSLGIIWPKSGLMLKA, (SEQIDNO:2068); XM_014116087.1, TTLL5, Del, A_7, KTSLQVSS-WGLTQKVLKTATIILIVGQRVTTMQRWKK, (SEQIDNO:2069); NM_001286960.1, PLG, Del, A_7, KTTAVILMVMSMVLGATQ, (SEQIDNO:2071); XM_003433767.3, DIMT1, Del, A_7, KTTESTVRSIIL, (SEQIDNO:2072); XM_014118588.1, CSMD3, Del, A_7, KTTGGVIHFQPVMHYVEEMLEGLVEQSYHLVTRN-FIQIL, (SEQIDNO:2073); XM_547299.4, CLCA1, Del, A_7, KTTIKMPQTHKTEDAISEAHGK, (SEQIDNO: 2074); XM_005630975.2, RELN, Del, A_7, KTTKGITGMSGLSIFSTSYLFSLLRCLT, (SEQIDNO: 2075); XM_014120448.1, EML4, Del, A_7, KTTKKENMLKCLCEVGQLRCSFLLMLKTMMTSE-QNCLLRN, (SEQIDNO:2076); XM_005626304.2, RUFY1, Del, A_7, KTTKLCPA, (SEQIDNO:2077); XM_005638156.1, NECAB1, Del, A_7, KTTKRP-PIWNNL, (SEQIDNO:2078); XM_014109172.1, PRKDC, Del, A_7, KTTLLKSCSRISVIFLTPLSLSFHLL-SPVFRKSVANTQTC, (SEQIDNO:2079); XM_014110420.1, GOLIM4, Del, A_7, KTT-MAKNKKFEMTTAP-KAERNPMRRRRRKKKMGLGLQRNHSEERKC, (SEQIDNO:2080); XM_540382.5, SLC26A4, Del, A_7, KTTMLALLNPSRGGFCLLYFHL, (SEQIDNO:2081); XM_014119438.1, C15H12orf29, Del, A_7, KTTNSIA-GIPQ, (SEQIDNO:2082); XM_014109405.1, LPCAT2, Del, A_7, KTTPSFLLVESEI, (SEQIDNO:2083); XM_844527.4, DMTF1, Del, A_7, KTTQRF-WRINQDLEFQTVIPIPVYSMFRSESPAWKTIQPSLQAP, (SEQIDNO:2084); XM_005634135.2, TMCO3, Del, A_7, KTTSGCCFHCFV, (SEQIDNO:2086); XM_014119556.1, EEA1, Del, A_7, KTTTYRNK, (SEQIDNO:2087); XM_014112996.1, UIMC1, Del, A_7, KTTVKADSSVSWSSLNTRLQMQK, (SEQIDNO:2088); XM_547275.5, DNTTIP2, Del, A_7, KTTVSHHIANQSIN-FRKNAEKNDRKQQVMAGLA, (SEQIDNO:2089); XM_014116355.1, BPTF, Del, A_7, KTTWKQNHVY, (SEQIDNO:2090); XM_005620305.1, KMT2A, Del, A_7, KTTWTSAQLPHPWRRRKPSAFPLLHLALLNIPLPP, (SEQIDNO:2091); XM_014120351.1, CLIP4, Del, A_7, KTVLLNQHFHCLLVMNRNL, (SEQIDNO:2092); XM_003639039.3, L1TD1, Del, A_7, KTVMTWRLF, (SEQIDNO:2093); XM_532840.5, CCDC110, Del, A_7, KTVNFLWRSNK, (SEQIDNO:2094); XM_014114460.1, ZNF326, Del, A_7, KTVRNTEMDTE-WHLRVHFVNSEHLKKKILNYIWKVLHTKKH, (SEQIDNO:2095); XM_535945.5, NOSTRIN, Del, A_7, KTVSSVPGPGSQRA, (SEQIDNO:2096); XM_005627588.2, CEP162, Del, A_7, KTVYWKTSKD, (SEQIDNO:2097); XM_005631628.2, ASRGL1, Del, A_7, KTWELWVPLPWTAKETWPMQPRRVAS-LIRWLAVLGTPHA, (SEQIDNO:2098); XM_532030.5, SVEP1, Del, A_7, KTWMSVSVNHAKMELPVKMV-PIASGANVQQASQGHIVK, (SEQIDNO:2099); XM_014114190.1, ZAN, Del, A_7, KTWPPQKNTPSQVK, (SEQIDNO:2100); XM_005617457.2, CENPH, Del, A_7, KTWRKLTPRLVCSWIT, (SEQIDNO:2101); XM_537131.4, DYRK3, Ins, A_7, KTWSDRWSQ, (SEQIDNO:2102); XM_014111411.1, LOC611589, Del, A_7, KTYLTERLIQISQNILLKSCSIKVIIKKNFNCKY, (SE- QIDNO:2103); NM_001076794.1, MYH4, Del, A_7, KVARRRVLLSRQCQPFSGRI, (SEQIDNO:2104); XM_005624952.2, PAFAH1B1, Del, A_7, KVASLGHSY-CLDPETRLLRCGTSVLACAL, (SEQIDNO:2105); XM_014112347.1, GRK4, Del, A_7, KVAVVKDGGKC, (SEQIDNO:2106); XM_014108830.1, FAM21C, Del, A_7, KVDLHHLLMSWQLESKGKLQARWKRSE-QPCPQEKQNLGRH, (SEQIDNO:2107); XM_014110756.1, BAZ2B, Ins, A_7, KVDRYFQSEL, (SEQIDNO:2108); XM_005638394.2, CEP152, Del, A_7, KVEYLEKNWKRRFILFRESLS, (SEQIDNO:2111); XM_014122578.1, CEP295, Del, A_7, KVFISSFL, (SEQIDNO:2112); XM_005640463.2, GLS, Ins, A_7, KVFSR-RHRHGWYIRLLFPAMLH, (SEQIDNO:2113); XM_533102.5, KMT2E, Del, A_7, KVGK-KNKTFQNVKKPFVKDLGSHQELRVQLQRLILHLM-VQILDGRQKSKHGWIDM KRQIVTNIVRVFRGRHKE, (SEQIDNO:2114); XM_540027.5, STOX2, Del, A_7, KVGLIGSPMESLGHTARHECLKETLRMVLI-WISQVTESMTFVTLLPGHPGRAASSLN TREITSSCI-ATRT, (SEQIDNO:2115); XM_014121431.1, INTU, Del, A_7, KVGNRALERDLWSMACYQEDL1, (SEQIDNO:2116); XM_005616571.2, LOC100684414, Ins, A_7, KVGRPFIMDSDLLNSTVFLLV, (SEQIDNO:2117); XM_014113086.1, C1H6orf118, Ins, A_7, KVGT-GAPESVCMRPSAIQQTAHLQRSL, (SEQIDNO:2118); XM_014114869.1, SPATA1, Del, A_7, KVHFFGKMK-MIELISLEQRTIR, (SEQIDNO:2119); XM_844507.4, AIDA, Ins, A_7, KVHQHQVLCFHGDG, (SEQIDNO:2120); XM_005628565.2, LOC102157031, Del, A_7, KVIFQKQCFTCPT, (SEQIDNO:2121); XM_003433299.3, NUP58, Del, A_7, KVIKQEQDQRIVKH, (SEQIDNO:2122); XM_005620385.2, CCNL2, Del, A_7, KVITIE-ISEGSVLGLTSEQVIATSGITLVTAGIGG, (SEQIDNO:2124); XM_014118548.1, RGS22, Ins, A_7, KVIYSHTIFYKLQVYCFHYVFEKDRIFPQHPDFLH, (SEQIDNO:2125); XM_014118537.1, RGS22, Ins, A_7, KVIYSHTIFYKLQVYCFHYVFEKDRIFPQHPELDHSC-GAS, (SEQIDNO:2126); XM_014118539.1, RGS22, Ins, A_7, KVIYSHTI-FYKLQVYCFHYVFEKDRIFPQHPENF1, (SEQIDNO:2127); XM_005635475.2, PDS5B, Del, A_7, KVKEADHLNLLVEVHQRKSQQ, (SEQIDNO:2128); XM_005628746.2, PPP1R3A, Del, A_7, KVKEELRKWKQKAWKV, (SEQIDNO:2129); XM_014111411.1, LOC611589, Del, A_7, KVKIER-LKVNLVNQTIHEKLTVGFFLLTF, (SEQIDNO:2130); XM_534241.4, TOP2B, Del, A_7, KVKILGISSHFLHTLR-SQKMIQLNLIAMKKILPLFFHRHLV, (SEQIDNO:2131); XM_014110062.1, ZGRF1, Del, A_7, KVKKINLKIN-HIHKKIWY, (SEQIDNO:2132); XM_014118874.1, ABCB1, Del, A_7, KVKKMRRKKRNQLSARLQCFAIQI-GLIGCICWWGQWLPSSMELHSLS, (SEQIDNO:2134); XM_005627906.2, ATAD2, Del, A_7, KVKNTIFFSW-KIYMQ, (SEQIDNO:2136); XM_014119398.1, RAPGEF2, Del, A_7, KVKPILLEEGTS, (SEQIDNO:2137); XM_014112126.1, LOC607401, Del, A_7, KVKSSERKTHSRID, (SEQIDNO:2138); XM_549075.3, ERCC6L, Ins, A_7, KVKYPRGDQI, (SEQIDNO:2139); XM_014115665.1, ZBTB1, Del, A_7, KVLCP-NYLLQKNVCHGALDGVLPVTVVDLALA-VKNYWMSMC, (SEQIDNO:2140); NM_001313780.1, GMPS, Del, A_7, KVLEKMESSVLVWT-TLAHCSGAFRRKKLFCLPMEIV, (SEQIDNO:2141); XM_005635410.2, MRPS31, Del, A_7, KVLG-KICSKGRDLIFLTLRQLLKRHLKQRLHLHSGI, (SEQIDNO:2142); XM_014120784.1, PC10, Del, A_7, KVLIQVSKLMMKIRNINGICLLERGGKLE, (SEQIDNO:2144); XM_005626673.2, FOCAD, Del, A_7, KVLNLCSRHFSKL, (SEQIDNO:2145); XM_005630596.1, APOB, Ins, A_7, KVLQTHFGHSE-QENH, (SEQIDNO:2146); XM_014110473.1, ECT2, Del, A_7, KVLSKSSLIFVKN, (SEQIDNO:2147); XM_014118152.1, CASP8AP2, Del, A_7, KVLTLAL-ITLRTLNLKNTPWNQTVPTPQSQGKLKAAP, (SEQIDNO:2148); XM_540159.5, THUMPD2, Del, A_7, KVNFLKEMLTH, (SEQIDNO:2149); XM_014107431.1, ZNIYM5, Ins, A_7, KVNKSRCI, (SEQIDNO:2150); XM_005627564.1, TTK, Del, A_7, KVNNFFIK1, (SEQIDNO:2151); XM_014110462.1, ZBBX, Del, A_7, KVPAALAPPILDQKVQLLDHYLELLLKFQKLNILI-LLTITSLS, (SEQIDNO:2152); XM_005627009.1, SMAP1, Del, A_7, KVPALKKLQSPLLIF, (SEQIDNO:2153); XM_005618201.2, LOC479005, Del, A_7, KVPGPQAKEWKDLQELDPEQLSPLPLPSY-AGPGGQGRMQISAASCCRSPWMP, (SEQIDNO:2154); XM_005636067.2, GOLGA3, Del, A_7, KVPNQAKFGLWLIIKLKTSVLGVL-VETLQLWTLPGS1, (SEQIDNO:2155); XM_005625871.2, GTPBP1, Del, A_7, KVPRPSEKKEAHLEGQQ, (SEQIDNO:2156); XM_014113440.1, EXPH5, Del, A_7, KVQKRNP-KIVNSPLNQVTAVLLIFWLIRKRMLEIPKP, (SEQIDNO:2157); XM_014111598.1, MBTPS2, Del, A_7, KVQVQVSV, (SEQIDNO:2158); XM_005622377.2, CEP350, Ins, A_7, KVRATARKSLFTDRQFTNSLCEGH-SQSTTRNQKI, (SEQIDNO:2159); XM_014120373.1, ALMS1, Del, A_7, KVRCFLLIKLENPIRLKLNRLSLISIS, (SEQIDNO:2160); XM_860879.4, VPS54, Ins, A_7, KVR-GYRRKETS, (SEQIDNO:2161); XM_005637042.2, ITPR2, Ins, A_7, KVRKILQSS1, (SEQIDNO:2162); XM_846025.3, ADAMTS5, Del, A_7, KVRVTLTW, (SEQIDNO:2163); XM_014121223.1, CCDC73, Del, A_7, KVSAAYCHLSKLQFFNKSVMILQRNLN, (SEQIDNO:2164); XM_003434330.2, LEMD1, Ins, A_7, KVSAIVGLASLCINCDEWTLRAGQSSG, (SEQIDNO:2165); XM_005623486.2, SYNE2, Del, A_7, KVSCKIT-FLSY, (SEQIDNO:2166); XM_005627636.2, MDN1, Del, A_7, KVSCRPGDWSSELIFWKMPIQMS, (SEQIDNO:2167); XM_541074.4, SERPINB3, Ins, A_7, KVSIS-SRIHG, (SEQIDNO:2168); XM_005630977.2, DNAJC2, Del, A_7, KVSLNM, (SEQIDNO:2169); XM_536878.5, CCZ1, Del, A_7, KVSLSPPLSNKKHLRQKPTQNEPSPD-LAKRGCWAAGSLSGSAATTSGAAASEAEVRS PQGGCLWAGRGRLPRLGAGPGWRQRRPGPGPGR-PRRSSSRRRC, (SEQIDNO:2170); XM_005621835.2, WDR47, Ins, A_7, KVSLYYPEAEVFRSSMC, (SEQIDNO:2171); XM_005634713.2, RALGAPA2, Ins, A_7, KVSNYNTKH, (SEQIDNO:2172); XM_005615711.2, HDDC2, Ins, A_7, KVSQLGHVFP, (SEQIDNO:2173); XM_014109263.1, ST18, Ins, A_7, KVSWRGLHTKS, (SEQIDNO:2174); XM_003639255.2, LOC100856208, Ins, A_7, KVTASGNQCSGHGSPGQRFPRYQRT, (SEQIDNO:2175); NM_001003212.1, F8, Ins, A_7, KVTDE-HSF, (SEQIDNO:2176); XM_014116676.1, WDR87, Del, A_7, KVTFCLRT, (SEQIDNO:2177); XM_005631968.2, ORC4, Del, A_7, KVTGLVAAQ, (SEQIDNO:2178); XM_535886.5, MAK, Del, A_7, KVTGQKGTSLHPL, (SEQIDNO:2179); XM_005623743.2, RPS6KA5, Del, A_7, KVTKHSQSK, (SEQIDNO:2180); XM_014115836.1, AKAP6, Del, A_7, KVTPPPQVTSPGMVRLWRPG-MALMNT, (SEQIDNO:2181); XM_014109094.1, KIF20B, Del, A_7, KVTRSRNWNNKLKNYRQN, (SEQIDNO:2182); XM_532494.5, C14H7orf31, Del, A_7, KVTS- MEMIL, (SEQIDNO:2183); XM_005624741.2, TEX14, Del, A_7, KVTVAGNLSPKSLKKALGISQRRAIS-CQLFVDLENRALVNNHSPLKEPSTVWKETGA QIPAAMEGLKSPVPEPG, (SEQIDNO:2184); XM_014118119.1, PHIP, Del, A_7, KVVEAENQKGR, (SEQIDNO:2185); XM_537573.5, ABCA5, Del, A_7, KVVFRKFFFHYFFYFG, (SEQIDNO:2186); XM_005622125.1, SYDE2, Del, A_7, KVVQLTGLSQIK, (SEQIDNO:2187); XM_005639188.2, MMRN1, Del, A_7, KVVWLQMRETRLFKCRY, (SEQIDNO:2188); XM_014120481.1, SELV, Del, A_7, KVWNSNFQTVYS-LRRRELPRLQGSLKCLWMENW-SIQRRKVMVLWMRPGCRRL, (SEQIDNO:2189); XM_014108479.1, KIF21A, Del, A_7, KVWPVKRHQTLTKRRKKKRVLQKEKTMN, (SEQIDNO:2190); XM_005621519.2, KIAA0430, Ins, A_7, KVWTQVECVGFI, (SEQIDNO:2191); XM_005641214.2, POLA1, Del, A_7, KVYLMYMLPSG, (SEQIDNO:2192); XM_005638229.2, EIF2AK4, Del, A_7, KWAR-SLPVKRRRRLISAKSRFKGQKRNSTHW, (SEQIDNO:2193); XM_014109944.1, WDFY3, Del, A_7, KWCE-MICFITITPMCQKRSKRQMWRLRSQVNSLRHLMISF-LKRNPLDTEEP, (SEQIDNO:2194); XM_014109945.1, WDFY3, Del, A_7, KWCEMICFITITPMCQKR-SKRQMWRNPLDTEEP, (SEQIDNO:2195); XM_846266.3, PHAX, Del, A_7, KWDQRKRKMGKVIS-NGNDLSKTD, (SEQIDNO:2196); XM_005616957.2, LOC480753, Del, A_7, KWDVRLMDYKRSYQKQKK, (SEQIDNO:2197); XM_014121431.1, INTU, Ins, A_7, KWETGHWRETCGPWPATRRICYEEWSDINW, (SEQIDNO:2198); XM_003431865.4, THSD7A, Del, A_7, KWFSRKPAPSLAQVTVI, (SEQIDNO:2199); XM_005640267.2, XIRP2, Ins, A_7, KWFS-SITVPRDDKG, (SEQIDNO:2200); NM_001287021.1, IL6ST, Del, A_7, KWGKMKLS, (SEQIDNO:2201); XM_533102.5, KMT2E, Ins, A_7, KWGKRTKHFKM, (SEQIDNO:2202); XM_539311.4, ADAMTS3, Ins, A_7, KWKDSCCLQEISRRTGSHKHVPRLPIQRVESGRP, (SEQIDNO:2203); XM_005623031.2, SMCHD1, Del, A_7, KWKIFKSWGIIH, (SEQIDNO:2205); XM_003638878.3, KIF5B, Del, A_7, KWKKMKRS, (SEQIDNO:2206); XM_014122056.1, FBX015, Ins, A_7, KWKRIHHAAH, (SEQIDNO:2208); XM_535180.5, HSPA14, Ins, A_7, KWKVKIRSRYW, (SEQIDNO:2209); XM_539276.4, CEP135, Del, A_7, KWKVLQLQKENLLWKLKG, (SEQIDNO:2210); XM_540152.4, RMDN2, Del, A_7, KWLLLCLEKYHPQQWKKLCKISLRLKNYTLVFL-SPITCTWPSVTLILNKQIT1, (SEQIDNO:2211); NM_001010944.1, PPT1, Del, A_7, KWLRRKYLEFT-SYL, (SEQIDNO:2212); XM_014110870.1, FSIP2, Del, A_7, KWLTIYKKCKKMALKEKI, (SEQIDNO:2213); XM_005617406.2, GPBP1, Ins, A_7, KWMADAWKKWY, (SEQIDNO:2214); XM_005638410.2, DMXL2, Del, A_7, KWMIYLQNQRF, (SEQIDNO:2215); XM_014115228.1, RGS7, Ins, A_7, KWNSYSYCQKLSFQDT, (SEQIDNO:2218); XM_005638394.2, CEP152, his, A_7, KWN-TWKRIGREDSFSSERA, (SEQIDNO:2219); XM_005624952.2, PAFAH1B1, Ins, A_7, KWQAWAIL-TVWIQRQDY, (SEQIDNO:2220); XM_014111411.1, LOC611589, Del, A_7, KWQLQLRQLLLMRHLLWLT-YHQVIKGWSTRLFTPLYAIFCGNIDLKTPFTRT, (SEQIDNO:2221); XM_005641533.2, HDX, Ins, A_7, KWQNTNYSKGRNQVLSHKYM, (SEQIDNO:2222); XM_850059.4, PARK2, Ins, A_7, KWRNIHA-HEVPTAPVPAGVVLDLQL, (SEQIDNO:2224); XM_014109472.1, RPGRIP1L, Ins, A_7, KWRPFLL-RESRQ, (SEQIDNO:2225); XM_005624391.1, C9H17orf104, Del, A_7, KWRRQYLTSRISHFQKPHHI, (SEQIDNO:2226); XM_005619169.2, NSD1, Ins, A_7, KWRWHSEISTS, (SEQIDNO:2227); XM_014107474.1, LOC477353, Del, A_7, KWSGYCILV, (SEQIDNO:2228); XM_014119574.1, OSBPL8, Ins, A_7, KWSVGWNSSSEC1, (SEQIDNO:2230); XM_005624530.2, KRT222, Del, A_7, KWTKTKRL, (SEQIDNO:2231); XM_014108788.1, MK167, Del, A_7, KWTLMKTFQG, (SEQIDNO:2232); XM_014109323.1, EFCAB1, Del, A_7, KWTMTMMGSCLSQTMNRL, (SEQIDNO:2233); XM_535817.5, MCCCI, Del, A_7, KWVYGPQLCIVRPTGIPCM, (SEQIDNO:2234); XM_003640020.3, MRPL15, Ins, A_7, KWWCCYYSFL, (SEQIDNO:2235); XM_846278.4, MAP4K5, Ins, A_7, KWWLQPA1, (SEQIDNO:2236); XM_545603.5, NBEAL1, Ins, A_7, KYAASAANVSVFTF, (SEQIDNO:2237); XM_014108877.1, HELLS, Ins, A_7, KYAQLQHRSRCIYLLSEYTSWWPGH, (SEQIDNO:2238); XM_543182.3, RNF17, Ins, A_7, KYDSTLSP-TYFA, (SEQIDNO:2239); XM_014116352.1, EFCAB13, Del, A_7, KYESNFELSMKRQYSSVVKKN-PLIFQEKKRSGERKIYKYNCILKELSLPLPQ, (SEQIDNO:2240); XM_014119437.1, CEP290, Ins, A_7, KYFHYRRFEK, (SEQIDNO:2241); XM_014122439.1, DDIAS, Del, A_7, KYFLQKFLDSK, (SEQIDNO:2242); XM_005634466.2, SLC35G2, Ins, A_7, KYFSIQKNVD-SAVWICFGSWMCSSYH, (SEQIDNO:2243); NM_001017533.1, cOR9K3, Del, A_7, KYFYLILS, (SEQIDNO:2244); XM_531939.5, PSIP1, Del, A_7, KYGD-SKLVRLSWKSLQCCITSLRICFWLVKEIL, (SEQIDNO:2245); XM_014111472.1, CYLC1, Del, A_7, KYGIKIIFL, (SEQIDNO:2246); XM_014117777.1, CCDC171, Ins, A_7, KYGKIESY, (SEQIDNO:2247); XM_005639497.2, KIAA2018, Ins, A_7, KYHCLFQWESAWWKQPGN-SCSGDNL, (SEQIDNO:2249); XM_005619458.1, EMB, Ins, A_7, KYHFRTTF, (SEQIDNO:2250); XM_003639447.3, SNX31, Del, A_7, KYHIQQSQKD-SCFLPRNKI, (SEQIDNO:2251); XM_005641549.2, DIAPH2, Del, A_7, KYINLRCP, (SEQIDNO:2252); XM_005622295.2, ZBTB41, Del, A_7, KYIQVRRP-ISVKNVENVLVVGIISLFITKVYTWEKKCGKNTKQPF-INVMFVRKFLKAN QV, (SEQIDNO:2253); XM_014118822.1, REST, Ins, A_7, KYKEEKSEK, (SEQIDNO:2254); XM_539407.5, ZNF804B, Ins, A_7, KYKHHTKPSGKRLTQYLLHKLSNLARQK, (SEQIDNO:2255); XM_014114888.1, FUBP1, Del, A_7, KYKMMLVFEFSLSQMMEQHLIE, (SEQIDNO:2256); XM_014114463.1, LOC106558915, Ins, A_7, KYKPP-PRLDS, (SEQIDNO:2257); XM_005621312.2, AG1, Del, A_7, KYKTTLKSYFMCQKTLQILMKSILTWFTNVAYT-KIVMELPALGVTISSGLILP, (SEQIDNO:2258); XM_005640342.2, KIAA1715, Del, A_7, KYLKKSWKKKLIKRLN, (SEQIDNO:2259); XM_535836.5, KNG1, Del, A_7, KYLLTAQSWRC1, (SEQIDNO:2260); XM_014111704.1, REPS2, Ins, A_7, KYLQKNGR, (SEQIDNO:2261); XM_014106956.1, ADNP, Del, A_7, KYLVTLGWNTVKNT, (SEQIDNO:2262); XM_005627588.2, CEP162, Del, A-7, KYLVVLHY-CLRRTK, (SEQIDNO:2263); XM_014109018.1, HECTD2, Del, A_7, KYPRRGSNNW, (SEQIDNO:2264); XM_014108253.1, MRPS35, Ins, A_7, KYPTNTSPNESC, (SEQIDNO:2265); XM_005624391.1, C9H17orf104, Del, A_7, KYPVLTTLQFQG, (SEQIDNO:2266); XM_014114844.1, HFM1, Del, A_7, KYQIL-HILLRKWISLLETMNVKRKLISACQFLAAA, (SEQIDNO:2267); XM_005621939.2, HFM1, Del, A_7, KYQILHILLRKWISL- LETMNVKRKLISVGIILMMKLMK, (SEQIDNO:2268); XM_005629477.2, LUC7L2, Del, A_7, KYREHRRE-WEILLVNESNSAMTEYARVTF-STVAPMMSSLELEWILENV, (SEQIDNO:2270); XM_535814.5, TTC14, Ins, A_7, KYRGKKRAP, (SEQIDNO:2271); XM_014115182.1, SUCO, Del, A_7, KYRKIEIIMPQ, (SEQIDNO:2272); XM_014110037.1, CDK12, Del, A_7, KYRKMPEIFLYLKNPKTERRKRKRMIP, (SEQIDNO:2273); XM_849319.3, LOC611632, Ins, A_7, KYRQILCFAVFYN, (SEQIDNO:2274); XM_005629294.2, CCDC53, Ins, A_7, KYRRKFRQ, (SEQIDNO:2275); XM_531794.5, TMEM131, Ins, A_7, KYTIQNHC, (SEQIDNO:2276); XM_005628224.2, PAICS, Ins, A_7, KYTKTTLWNTKK, (SEQIDNO:2277); XM_014109133.1, TDRD1, Del, A_7, KYTSWLRIPCP, (SEQIDNO:2278); XM_014119368.1, LRBA, Ins, A_7, KYVFWWNFA TVSPTSVCSGSKELFRVSTAFTAES, (SEQIDNO:2279); XM_014117695.1, FBN2, Del, A_7, KYVLMAQDIPPMEEILMNVR, (SEQIDNO:2280); XM_005617177.2, ASB13, Del, A_7, KYVPMLFFSTLMNPLNVLNLEACYPSRSRGPL, (SEQIDNO:2281); XM_005621538.2, ZC3H7A, Del, A_7, KYVQDQQKQIMRDLIIYVKMLLLRRNVDTQATARSLIAKKR, (SEQIDNO:2282); XM_005622271.2, CAMSAP2, Del, A_7, KYWRKWRSQMPTTF, (SEQIDNO:2283); XM_005622462.2, TDRD5, Ins, A_7, KYWYNKESKAAKLRKFFGFSHIAQVGGVLHFSGRVTAVSRRESV, (SEQIDNO:2284); XM_005627518.2, PHF3, Ins, A_7, MAASSSSKDGTTSFTSEILRRKK, (SEQIDNO:2285); XM_005639761.2, B3GNT5, Ins, A_7, MAVCSALCHLFCTKPHVFLGPNR, (SEQIDNO:2286); XM_005630442.2, ZC3H6, Ins, A_7, MEGYDSGIH, (SEQIDNO:2287); XM_014115009.1, FMN2, Ins, A_7, MFRCCSAGRF, (SEQIDNO:2288); XM_005619006.2, P4HA1, Ins, A_7, MGREVRSTNQHSNKRSRRICWAPCKCIQINETSEH, (SEQIDNO:2289); XM_014112822.1, ANK3, Ins, A_7, MGYQRRKKCYN, (SEQIDNO:2290); NM_001284489.1, DEFB118, Ins, A_7, MLAQIWILQENLQS, (SEQIDNO:2291); XM_854556.3, NRD1, Ins, A_7, MLGSCAIWWKW, (SEQIDNO:2292); NM_001287076.1, LTF, Ins, A_7, MLQIPSEYEKSRWPHCLLYKESLP-PRMYPGYQGKQGRCCDPGWWFGV, (SEQIDNO:2293); XM_003435003.3, LAMA3, Ins, A_7, MLRGLEARAICLILQGWTVEVHRFGSPFAQ, (SEQIDNO:2294); XM_014115649.1, GALC, Ins, A_7, MVYAHVNY, (SEQIDNO:2295); XM_014120092.1, TEX15, Ins, A_7, MYGKDRHSGQNNVEN, (SEQIDNO:2296); NM_001003300.2, KCNMA1, Del, A_7, NAAANGLKMSSHRRCPQKKSSGTEACGTHPAPRPS, (SEQIDNO:2297); XM_014108599.1, RHNO1, Del, A_7, NAANLPGKPSCYSNKNHWRAPNTTMALPSVPSPTLDRCPASPLTTTPSLPGYHLSLI, (SEQIDNO:2298); XM_005633661.2, ZNF143, Ins, A_7, NADCLTRTCNKSNC, (SEQIDNO:2299); XM_005622209.2, KDM5B, Ins, A_7, NADPQKEENQTEPLQGHEQFQVREGA, (SEQIDNO:2300); XM_005618617.2, UGDH, Ins, A_7, NAEASLYL, (SEQIDNO:2301); XM_014111503.1, LOC102153069, Ins, A_7, NAEDGTAVSERGRRGSIPPRRLSHILGR, (SEQIDNO:2302); XM_005634656.1, ARHGEF26, Ins, A_7, NAERTRNI, (SEQIDNO:2303); XM_014117473.1, VPS13A, Ins, A_7, NAFKTIEE, (SEQIDNO:2304); XM_854556.3, NRD1, Del, A_7, NAGLLRYLVEMVRQDLSKILLTQYSAFQLH, (SEQIDNO:2305); NM_001284489.1, DEFB118, Del, A_7, NAGTNLDTAGKPAKLTK, (SEQIDNO:2306); XM_005616483.2, ZNF235, Del, A_7, NAIGVMSVGRVSVRAQTCKLIRESTQGRSPIRALSVVRALTRPHIFMLICLFTQERNPT DVKVVGRASVVAQI, (SEQIDNO:2307); XM_005628918.2, MACF1, Ins, A_7, NAKFRIKTRV, (SEQIDNO:2308); XM_005619413.2, RAIZ14, Del, A_7, NAKLHHLLSVLLS, (SEQIDNO:2309); XM_534306.5, EIF2A, Ins, A_7, NAKLVSILVRR, (SEQIDNO:2310); XM_003434147.2, GPR160, Ins, A_7, NALAQVHYLFSRHLVTICTTSSNYPFT, (SEQIDNO:2311); XM_849749.4, ST3GAL5, Ins, A_7, NALCGPRPCKESSEICSASLAKGVPTQVCEEVDGAVVRAQVQHGLATFREGDPQNE, (SEQIDNO:2312); XM_005639168.2, HERC6, Del, A_7, NALNVKWLRVKLQ, (SEQIDNO:2313); XM_005632905.2, DNMT1, Ins, A_7, NAPGEEKETEQESDLLGWRCCQD, (SEQIDNO:2314); XM_003435003.3, LAMA3, Del, A_7, NAQRTGSSCDLPHSPGMDS, (SEQIDNO:2315); XM_005635030.2, MROH8, Del, A_7, NARGKLTS, (SEQIDNO:2316); XM_546165.5, DNAJC9, Ins, A_7, NASQERKEI, (SEQIDNO:2317); XM_014110776.1, ATF2, Ins, A_7, NASRFIPSCNTYHKKQN, (SEQIDNO:2319); XM_014109639.1, LONP2, Ins, A_7, NASVNARICSD, (SEQIDNO:2320); XM_544733.5, DENND4A, Ins, A_7, NAVEKDGST, (SEQIDNO:2322); XM_005615542.2, SERAC1, Ins, A_7, NAVGSLQEARNECCYKQYQRNYFL, (SEQIDNO:2323); XM_005628719.2, ANLN, Del, A-7, NAVLTTLK, (SEQIDNO:2324); XM_014109133.1, TDRD1, Ins, A_7, NCAEQNNHGESGRQAGKQLPGGARR, (SEQIDNO:2325); XM_005638791.2, LTN1, Del, A_7, NCFASYLKMSLILWRRNLSLFYHRISFGSMENTVYLRSAQLILS, (SEQIDNO:2327); XM_014115086.1, NSL1, Ins, A_7, NCFNKPTVSDLF, (SEQIDNO:2328); XM_005626092.1, LHCGR, Del, A_7, NCHRGKNLPASWMPH, (SEQIDNO:2329); XM_539598.4, CLSPN, Del, A_7, NCIVRLNALFESLRLIFHIICLRIKPFMISSNVNPDPLARGMPWHY, (SEQIDNO:2330); XM_014111818.1, LOC100683280, Ins, A_7, NCNLTQI, (SEQIDNO:2331); XM_014120239.1, SOS1, Ins, A_7, NCKRQWTRS, (SEQIDNO:2332); NM_001005870.1, RXFP2, Ins, A_7, NCLADFRSEESHWKRGGCCKSFLFYSVL, (SEQIDNO:2333); XM_014120276.1, TDRD15, Ins, A_7, NCLEQSNFASSYSKKR, (SEQIDNO:2334); XM_534296.5, PCOLCE2, Del, A_7, NCLQLQYHLLPPRSL, (SEQIDNO:2336); XM_014110770.1, UBR3, Del, A_7, NCLSLKRSRFTLGIHVQQFMM, (SEQIDNO:2337); XM_014119817.1, GALNTL5, Del, A_7, NCNSKLPTDPSKSQDCI, (SEQIDNO:2338); XM_005616720.2, FAM187B, Del, A_7, NCPGAAFN, (SEQIDNO:2339); XM_005619370.2, C9, Ins, A_7, NCPREDIKF, (SEQIDNO:2340); XM_014109455.1, TLN2, Ins, A_7, NCQPLGGGS, (SEQIDNO:2341); XM_005620755.2, PMFBP1, Del, A_7, NCRASNSRAS, (SEQIDNO:2342); XM_544109.5, VCPIP1, Del, A_7, NCRKWFLPSKLRWTSICGIKVQSSHHLIFLKEK, (SEQIDNO:2343); XM_014119322.1, MACF1, Ins, A_7, NCRQTIQAQGLYAKSSEISVACSRPRAMDRRL, (SEQIDNO:2344); XM_005641575.2, ARMCX2, Del, A_7, NCSAPKCHHHLVPFIILMWNQKFLLMPLLYLRSSMTISEQRYSTTENLIKVLFFNVPH LECALRKFEP, (SEQIDNO:2345); XM_014119173.1, AOAH, Ins, A_7, NCSQQENELRSFLRGF, (SEQIDNO:2346); XM_003639982.3, TNKS2, Del, A_7, NCVLFRVSTAETLKGVSLRHSILQLAII-GYLWWSICCNMELTCMLKIKEALYLCTML VLTDIMKLQNFLLSMEQ, (SEQIDNO:2348); XM_014110037.1, CDK12, Ins, A_7, NCYA- RNQVTKATEA, (SEQ ID NO:2349); XM_005639910.2, SKIL, Ins, A_7, NDDRHSRKRENDDQQQDANREEGTLG, (SEQ ID NO:2350); XM_534400.5, EDEM2, Ins, A_7, NDELGAMATSNRGRHVLLT, (SEQ ID NO: 2351); XM_005615498.2, STXBP5, Del, A_7, NDGLSPCPRPLLRKSVKTSMQ, (SEQ ID NO:2352); XM_003639377.3, FAM13B, Ins, A_7, NDKRSFDRRENFSPKKSS1L, (SEQ ID NO:2353); XM_014117407.1, LOC102155766, Ins, A_7, NDRAGKSPAKSQVHVSLRAAPRPS, (SEQ ID NO:2354); XM_014109171.1, PRKDC, Del, A_7, NDVGHEDFHLRHHCVYWIWSSGC, (SEQ ID NO:2356); XM_014120338.1, GEN1, Ins, A_7, NDWNSHEAPPQEFIFSYLIFNTNGRKTGIRYGRGTPEAES, (SEQ ID NO:2357); XM_014112723.1, RYR2, Ins, A_7, NEAAQELPADKWV, (SEQ ID NO:2358); XM_014115128.1, SMG7, Ins, A_7, NEAFSHGAI, (SEQ ID NO:2359); XM_003432681.3, KMT2B, Ins, A_7, NEDGTVVLGT, (SEQ ID NO:2360); XM_005639172.2, HERC5, Ins, A_7, NEDTFRGPRSRAHADSILRWKTIRVQL, (SEQ ID NO:2361); XM_014112808.1, SYNE1, Ins, A_7, NEDVGGFAKRHGKRP, (SEQ ID NO:2362); XM_014117599.1, IFGGB2, Ins, A_7, NEEEFLLCPI, (SEQ ID NO:2363); XM_005638429.2, WDR72, Ins, A_7, NEEFQEDAP, (SEQ ID NO:2364); XM_014110187.1, KALRN, Ins, A_7, NEEKRASCPRGCPASAPAAPPVHHSP, (SEQ ID NO:2365); XM_014119188.1, ABCB4, Ins, A_7, NEENEADWIINFG, (SEQ ID NO:2366); XM_539403.5, ABCB4, Ins, A_7, NEENEADWIINFV, (SEQ ID NO:2367); XM_005638175.2, FGF7, Ins, A_7, NEERTKNSPLSSYGNNI, (SEQ ID NO:2368); XM_531814.5, MSH6, Del, A_7, NEGSYQTLRVTLVALMWNLSQMLRRKEAVMK, (SEQ ID NO:2369); XM_003639581.3, LOC100855940, Ins, A_7, NEICGVKSRATSSRYEF, (SEQ ID NO:2370); XM_005632220.2, RAD18, Ins, A_7, NEILRYFPHNKPLLSIKAGIPRENGA, (SEQ ID NO:2371); XM_014116764.1, ATAD5, Ins, A_7, NEKKEAQRYNRSI, (SEQ ID NO:2372); XM_538964.5, ICK, Ins, A_7, NEKKVLFLGGMHEPSGG, (SEQ ID NO:2373); XM_014116333.1, C9H17orf80, Ins, A_7, NEKNRRHQEY, (SEQ ID NO:2374); XM_014121650.1, MYO3A, Ins, A_7, NELHHWGRG, (SEQ ID NO:2375); XM_005622971.2, WDR64, Ins, A_7, NELNVFAFQTYTSQGL, (SEQ ID NO:2376); XM_014110675.1, LUZP1, Ins, A_7, NEPRLYKECF, (SEQ ID NO:2377); XM_005617055.2, KIAA1462, Ins, A_7, NERDDILFGFHPS, (SEQ ID NO:2378); XM_005624998.1, LOC100687222, Ins, A_7, NERLSAAKKAE, (SEQ ID NO:2379); XM_014109854.1, SAMSN1, Ins, A_7, NESYFLDNEEKSE, (SEQ ID NO:2380); XM_014116764.1, ATAD5, Del, A_7, NEVSTKYFLNVIVNKKVHN, (SEQ ID NO:2381); XM_005615397.2, ME2, Ins, A_7, NEWPFGKVHLYNGNTRKK, (SEQ ID NO:2382); XM_014115682.1, TTC6, Ins, A_7, NFARLPHSYPS, (SEQ ID NO:2383); XM_539103.4, FBXO43, Del, A_7, NFCCAEGWTYLSLF, (SEQ ID NO:2384); XM_014112813.1, BICC1, Ins, A_7, NFCFFKWTCTVSKYKIWCNTHLITWRKSAEWESW, (SEQ ID NO:2385); XM_014112357.1, LCOR1, Del, A_7, NFCKITRRIQNWRILKRL, (SEQ ID NO:2386); XM_843857.4, HNRNPD, Ins, A_7, NFCWWPFSRYT, (SEQ ID NO:2387); XM_535483.5, LYSMD2, Ins, A_7, NFEHPSYIREAFVV, (SEQ ID NO:2388); XM_014116442.1, ABCA5, Ins, A_7, NFEYQRVMYLFCDSIGLHCDH, (SEQ ID NO:2389); XM_014119209.1, CFAP69, Ins, A_7, NFGSYYNSIRKYWQDGCFSSKRDD, (SEQ ID NO:2390); XM_003640173.3, SCN9A, Ins, A_7, NFHSIEQRESNLPFQCHPCFVHAVSIQSSKKNIY, (SEQ ID NO:2391); XM_005636673.2, SLCO1B3, Del, A_7, NFIFMHWCKS, (SEQ ID NO:2392); XM_005638869.2, DNAJC28, Del, A_7, NFLAVHISIP, (SEQ ID NO:2393); XM_545261.4, NMD3, Ins, A_7, NFLLSGTVDFEIWNASEYTSYQRDS, (SEQ ID NO:2394); XM_005636722.1, LOC100687255, Del, A_7, NFLRRKIQLF, (SEQ ID NO:2395); XM_005624758.2, BCAS3, Del, A_7, NFLSQAAIRVQGPT, (SEQ ID NO:2396); XM_014119270.1, LOC102151283, Del, A_7, NFMKQCLLREKIGKD, (SEQ ID NO:2397); XM_014113138.1, C4H5orf42, Ins, A_7, NFMVSNTIKSKTS, (SEQ ID NO:2398); XM_846103.4, LMTK2, Ins, A_7, NFPSAMDRSRISNQLSRQTTNCRSN, (SEQ ID NO:2399); XM_005624045.1, DNAH17, Ins, A_7, NFQFPGRDDKSHPHCGALHHHEPWVRGTHRVARKPKGLVQALRHGRPRL, (SEQ ID NO:2400); XM_014111937.1, CFAP47, Ins, A_7, NFQTERLFKI, (SEQ ID NO:2401); XM_532047.5, CNTR1, Ins, A_7, NFRSGERPSFQAVEW, (SEQ ID NO:2402); XM_539156.5, FAM91A1, Del, A_7, NFSEGKQMFYQ, (SEQ ID NO:2403); XM_005617569.2, CYLD, Ins, A_7, NFSFFGVKYNRFT, (SEQ ID NO:2404); XM_014106569.1, EFHB, Del, A_7, NFSTIETHQLEPKEYFMAEQMILRLLLI, (SEQ ID NO:2406); XM_854584.4, ATF4, Ins, A_7, NGAEQDSSH, (SEQ ID NO:2407); XM_014117118.1, MYRF1, Del, A_7, NGCVLTGFSRPWL, (SEQ ID NO:2408); XM_540152.4, RMDN2, Ins, A_7, NGCYSVWKNTILNSGRSFAKFP, (SEQ ID NO:2409); XM_005626991.2, CCDC180, Ins, A_7, NGDHRRHPWLRPDLEGKTWPEDSVPQLQARHSVRDSSGLY, (SEQ ID NO:2410); XM_005626727.1, DNAI1, Ins, A_7, NGEDGHEEDDIYGVPE, (SEQ ID NO:2411); XM_014114575.1, DNAH3, Del, A_7, NGEMKLHQCTLPCLWPCSALTP, (SEQ ID NO:2412); XM_014119270.1, LOC102151283, Ins, A_7, NGERKASAPWEVQILGLTISHPSHQSSLAITTHDLLFHGASERI, (SEQ ID NO:2413); XM_014114037.1, HYDIN, Ins, A_7, NGFHHEQQPHPAHL, (SEQ ID NO:2414); XM_846266.3, PHAX, Ins, A_7, NGIKGRGKWARSSQTETTCQRQTRGQTRNEL, (SEQ ID NO:2415); XM_539276.4, CEP135, Ins, A_7, NGKFCSYRKRTYSGS, (SEQ ID NO:2416); XM_005631276.2, CKAP5, Del, A_7, NGKRGKKLWRL, (SEQ ID NO:2417); XM_005623031.2, SMCHD1, Ins, A_7, NGKYSKVGELYIEITSCIE, (SEQ ID NO:2418); XM_548222.4, DGKE, Ins, A_7, NGLCSAS1, (SEQ ID NO:2419); XM_014107325.1, BRCA2, Del, A_7, NGLEKENGMINQKE, (SEQ ID NO:2420); XM_014112822.1, ANK3, Del, A_7, NGLPETEKMLQLMP, (SEQ ID NO:2421); XM_014110870.1, FSIP2, Ins, A_7, NGLPFTKNARKWL, (SEQ ID NO:2422); XM_005636851.2, LIMA1, Ins, A-7, NGNVCRRTQA, (SEQ ID NO:2423); XM_005638229.2, EIF2AK4, Ins, A_7, NGPVPYQSREGED, (SEQ ID NO:2424); XM_014116206.1, PCSK5, Del, A_7, NGQRGIMTSVVPSRLTSTIPSGQACGICTAATTRIPANQT, (SEQ ID NO:2425); XM_014117435.1, MAP4K4, Del, A_7, NGQRNFLVL, (SEQ ID NO:2426); XM_005624530.2, KRT222, Ins, A_7, NGQRRRGFKGSASRTQRSSAPVAAPASGN, (SEQ ID NO:2427); XM_547651.5, THOCC Ins, A_7, NGRIKNRRRTCIFCKIFNK, (SEQ ID NO:2428); XM_863511.5, CDC42BPB, Ins, A_7, NGRKIQSRYWTQTSRFSGFNI, (SEQ ID NO:2429); XM_005639761.2, B3GNT5, Del, A_7, NGSLF- SSLPLVLY, (SEQIDNO:2430); XM_005632905.2, DNMT1, Ins, A_7, NGSNQNSSVLQDPSSTVCAVWTVPG, (SEQIDNO:2431); XM_003431865.4, THSD7A, Ins, A_7, NGSRGNLHQALPR, (SEQIDNO:2432); XM_014113182.1, JAK1, Ins, A_7, NGTEALIP, (SEQIDNO:2433); XM_003431657.2, LOC100684448, Del, A_7, NGTSMTDTAKKD, (SEQIDNO:2434); XM_014107908.1, PRR14L, Del, A_7, NGTSPVTCLPCRGSS, (SEQIDNO:2435); XM_537313.5, NDC80, Ins, A_7, NGVRRYFRTVKYNDNRKQERCKNSERRSSKAG, (SEQIDNO:2436); XM_535817.5, MCCC1, Ins, A_7, NGYTVRSCV, (SEQIDNO:2437); XM_005616822.2, ERMP1, Ins, A_7, NHADFNCSVYGHLLPGLQWRILPV, (SEQIDNO:2438); XM_005639666.2, DNAH5, Ins, A_7, NHAENQSVFSGAIEHIDRHHNKRSEFHGTGQI, (SEQIDNO:2439); XM_014111056.1, DNAH7, Ins, A_7, NHEPGLIPICHRTHQQDFQDPEAAPQPRSSGRGRREWKAVCHPVSCPHG, (SEQIDNO:2440); XM_014112831.1, CTNNA3, Ins, A_7, NHGNVQAYMGESYPCPH, (SEQIDNO:2441); XM_005619841.2, GUCY1A2, Del, A_7, NHGTSQVGIRVMSWEA, (SEQIDNO:2442); XM_005618201.2, LOC479005, Del, A_7, NHLNRVLQDK, (SEQIDNO:2444); XM_003639824.3, ACAD11, Del, A_7, NHLVHYFLKHIRLIENSKSRKLCFQLDSPFPNLYCTAVILLSLEQNFT, (SEQIDNO:2445); XM_845208.4, HECTD1, Ins, A_7, NHNKNFAAD, (SEQIDNO:2446); XM_005640898.1, PEA15, Ins, A_7, NHPGGPGAAQVGLQGGHPQREERGDHDRQRLVQLPGEPQQAGQR, (SEQIDNO:2447); XM_005622209.2, KDM5B, Ins, A_7, NHQCCGSVCLPLVWQWQR, (SEQIDNO:2448); XM_535952.5, SSB, Ins, A_7, NHRRSTRISKQMEIKRSQI, (SEQIDNO:2449); XM_014114919.1, LOC100855888, Del, A_7, NHSGVINLGTCFVKHQG, (SEQIDNO:2450); XM_861131.4, PATZ1, Del, A_7, NHSQPSKTWAQHTPAALSSAQPRRDI, (SEQIDNO:2451); XM_014111411.1, LOC611589, Ins, A_7, NHSRGRSS, (SEQIDNO:2452); XM_014120076.1, BAG4, Ins, A_7, NHTCAGEGPVSRARSRRVRREKDRQSVLASGRNANQGAFGTGFS, (SEQIDNO:2453); XM_014109628.1, UNC13C, Del, A_7, NHTNSKEQELESQQIFLLMT, (SEQIDNO:2454); XM_005622326.2, LOC609365, Del, A_7, NHVYIQENPAMAR, (SEQIDNO:2455); XM_547829.5, TMEM260, Ins, A_7, NIC1HRNS, (SEQIDNO:2456); XM_005642422.1, OVCH1, Del, A_7, NIEGHLWAFSPRCIS, (SEQIDNO:2457); XM_005619814.2, DDX10, Ins, A_7, NIERFARSPVPFGN, (SEQIDNO:2458); XM_014122447.1, PCF11, Del, A_7, NIFRIRLIAKMMM, (SEQIDNO:2459); XM_014120092.1, TEX15, Del, A_7, NIFRWCKKRT, (SEQIDNO:2460); XM_014106295.1, MYCBP2, Ins, A_7, NIFTTRASEKTSKDPWQPCSSSCTF, (SEQIDNO:2461); XM_003640018.2, SLC26A7, Del, A_7, NIGTWIKSTGASGSVRTYLQYALLPMWGCCSVWSVP, (SEQIDNO:2462); XM_005631165.2, DCDC1, Del, A_7, NIIHRVKWPKLSLEDSKLLR, (SEQIDNO:2463); XM_014112357.1, LCOR1, Del, A_7, NILKKIQGS, (SEQIDNO:2465); XM_005632452.1, PBRM1, Ins, A_7, NILYEKGRN, (SEQIDNO:2466); XM_544715.5, USP3, Del, A_7, NIMKMHKYP, (SEQIDNO:2467); XM_005638363.2, SPG11, Del, A_7, NINNISRQTR1, (SEQIDNO:2468); XM_532840.5, CCDC110, Ins, A_7, NIPASKGKKLS, (SEQIDNO:2469); XM_014109018.1, HECTD2, Ins, A_7, NIPEEVQTIGREIAAVYFFAPVSCKA, (SEQIDNO:2470); XM_005618024.2, AP3B1, Ins, A_7, NIPSAKTCTTA, (SEQIDNO:2471); XM_014106605.1, GOLGA4, Del, A_7, NISKRSLMHL, (SEQIDNO:2472); XM_014120145.1, PCM1, Del, A_7, NISQLLLQPQLLMGMKPVQANLLLSLQILQEWIMSCGQKCEDMRC, (SEQIDNO:2473); XM_003640060.3, MAP2K5, Ins, A_7, NISQWSDE, (SEQIDNO:2474); XM_005628771.2, IQUB, Del, A_7, NITQKQLLR, (SEQIDNO:2475); XM_005627518.2, PHF3, Ins, A_7, NITRSKFSAGFQTLNSFFE, (SEQIDNO:2476); XM_005620592.1, MTHFSD, Ins, A_7, NIVGPNTTTENRVIQ, (SEQIDNO:2477); XM_542763.5, NR1D2, Del, A_7, NIVSMIYTQWEQGIC, (SEQIDNO:2478); XM_014120276.1, TDRD15, Del, A_7, NIVTKHTVWKRVLK, (SEQIDNO:2479); XM_005627588.2, CEP162, Ins, A_7, NIWWFFIIASGGQNK, (SEQIDNO:2480); XM_014122324.1, ERC2, Ins, A_7, NKAAAGPHGREGDTGRRDSRHEGYVRSEGKKNQCSSEED, (SEQIDNO:2481); XM_845513.2, SSMEM1, Ins, A_7, NKAEPTYSCN, (SEQIDNO:2482); XM_005617106.2, RPP38, Del, A_7, NKAQTNVAQKLIRARI, (SEQIDNO:2484); XM_005624391.1, C9H17orf104, Ins, A_7, NKATKWIL, (SEQIDNO:2485); XM_014113324.1, CCDC15, Ins, A_7, NKCFFKQLECCYWKC, (SEQIDNO:2486); XM_005628711.2, KBTBD2, Ins, A_7, NKCRELCAIVEFC, (SEQIDNO:2487); XM_005615806.2, NAA35, Ins, A_7, NKEKEESSPIEPRDHNEPGISEHVCWNV, (SEQIDNO:2489); XM_005615442.2, AHI1, Ins, A_7, NKEKKESSNFI, (SEQIDNO:2490); XM_014116541.1, LOC102151568, Ins, A_7, NKENLDAGC1HHWARQHlvlALPLPVSSERRRQLYPDVLLHAPLVRDPPLVHGDDHG ALAAYGQHPGLEAARPLAGRHRIR, (SEQIDNO:2491); XM_859339.4, CTCF, Ins, A_7, NKENQKEQTALHRGRQRCGCVCL, (SEQIDNO:2492); XM_014111673.1, LOC492092, Ins, A_7, NKERRGRGCKKKKGGGEESPGEEEEGQGGQETGPEGKRQAPPQETEGQSHSPRCPGA LLFRGVGGEEVPAGSEEGGGSPVATGTLEENCRIHTV, (SEQIDNO:2493); XM_005631123.2, NAT10, Ins, A_7, NKEWDVEHKAG, (SEQIDNO:2494); XM_014115573.1, EPB41L3, Del, A_7, NKFEVVLGTFHLM, (SEQIDNO:2495); XM_005630385.2, NCAPH, Ins, A_7, NKGCYYSDQVHFGEPELESHHSSYRFPL, (SEQIDNO:2496); XM_005619458.1, EMB, Del, A_7, NKGKGNET, (SEQIDNO:2497); XM_005628611.2, DNAH11, Ins, A_7, NKGRLWPSSTGRGLSPRVPPGRCQMGHTVGNHC, (SEQIDNO:2498); XM_005635796.1, SPHKAP, Ins, A_7, NKGSHSGRMELQQGKVTLCFGRQIYWQISSDVDESRRISGKSRRHHFAEPGHIS, (SEQIDNO:2499); XM_014108478.1, KIF21A, Ins, A_7, NKGSTNETNERRTRKSQIDRVQEKQRDCSIEKRST, (SEQIDNO:2500); XM_540152.4, RMDN2, Ins, A_7, NKHFLEEV, (SEQIDNO:2501); XM_014117449.1, LOC102154536, Del, A_7, NKILVCTMKAVLKR, (SEQIDNO:2502); XM_014114967.1, ASPM, Ins, A_7, NKKDDNTHLKTF, (SEQIDNO:2503); XM_005620331.2, C5H1orf141, Ins, A_7, NKKIYLLQK, (SEQIDNO:2504); XM_005639424.2, SENP7, Del, A_7, NKKMTQQYLLNLKSQVKTIKTQKCLKKLHLN1, (SEQIDNO:2505); XM_005623792.2, SETD3, Del, A_7, NKKVCLLLLMEKEKITFLT, (SEQIDNO:2506); XM_005635616.2, CLCN3, Del, A_7, NKKVLWAVLVCVLHSTPRLFQQKVHGH, (SEQIDNO:2507); XM_005627518.2, PHF3, Del, A_7, NKLRKIQKFRVAILVLN1, (SEQIDNO:2508); XM_533859.5, ZDHHC3, Ins, A_7, NKMDEHESRFWPPLLSRLGQPLCHARPREGRPVPVCGL, (SEQIDNO:2509); XM_014115783.1, ZNF793, Del, A_7, NKMNAVDVGNCYSIQTTIEDLMEKDSGNAVIARKL- SATTQHLCINQQ, (SEQIDNO:2510); XM_005619310.2, CSNK1A1, Del, A_7, NKNMKRLVKRRCPLLLKFYVRGFLQNLPCT, (SEQIDNO:2511); XM_014109043.1, CCDC186, Ins, A_7, NKNNSELYFTGRIRHTFFRGI, (SEQIDNO:2512); XM_005627246.2, TAF11, Ins, A_7, NKNRYQRKEREEAKSG, (SEQIDNO:2513); XM_005639205.2, PDLIM5, Ins, A_7, NKPHPGDFSAVGTISSFSTEHA, (SEQIDNO:2514); XM_534105.5, MS4A14, Del, A_7, NKPNCSSPKLCHPKFLHPI1, (SEQIDNO:2515); XM_014109153.1, KNDC1, Ins, A_7, NKQAPRRETR, (SEQIDNO:2516); XM_005629837.1, LOC482849, Ins, A_7, NKRAVLQRGN, (SEQIDNO:2517); XM_014108511.1, PHC1, Ins, A_7, NKRFPRIQLCSCSSAWASPQLLRHRPCQDPGQAPPENL, (SEQIDNO:2518); XM_014108509.1, PHC1, Ins, A_7, NKRFPRIQLCSCSSAWASPQLLRHRPCQDPGQAPPGSRG1, (SEQIDNO:2519); XM_537429.4, FANCM, Ins, A_7, NKRKCFRIP, (SEQIDNO:2520); XM_014108746.1, PIK3C2G, Ins, A_7, NKRNVSCS, (SEQIDNO:2521); XM_850902.4, G3BP2, Ins, A_7, NKSCKRARNQRWW, (SEQIDNO:2522); XM_014107008.1, DIDO1, Del, A_7, NKSCRLLRRKSQNPSMRPLPLSQFLAPLMK, (SEQIDNO:2523); XM_536334.4, HEATR1, Del, A_7, NKSFFISLFLFLQVEGSISF, (SEQIDNO:2524); XM_546398.5, NFRKB, Ins, A_7, NKTDQIRGRGFGRTIKQCRRDPTSLTGPFSAGYTCYQGGAS, (SEQIDNO:2525); XM_014117412.1, LOC100683777, Ins, A_7, NKTPAPTASNKRQPRAPAI, (SEQIDNO:2526); NM_001197076.1, ASPM, Ins, A_7, NKTYCCCGTVYFNLHKTTKNRYS, (SEQIDNO:2527); XM_005624435.2, PSME3, Ins, A_7, NKVFTVWGSLSFSLQLQG, (SEQIDNO:2528); XM_539558.4, C15H1orf50, Del, A_7, NLATFTTFINGRVVNSIFLLFLQRNGVQVVHMTSLVPTSYNMTCLGLHMRTLRSMM LKST, (SEQIDNO:2529); XM_014112496.1, KIAA0232, Del, A_7, NLAWRRVLRRPWILRRNQLGFCRWGSRISVWNVA, (SEQIDNO:2530); XM_014116163.1, LOC100688895, Ins, A_7, NLDYQEQLGHRLGHAGLHTDSQKPGQPLGKHH, (SEQIDNO:2531); XM_849077.4, PPAT, Del, A_7, NLEYCRTTLKAKELF1, (SEQIDNO:2532); XM_003433570.1, SLC15A5, Ins, A_7, NLGWNLLASGGDV, (SEQIDNO:2534); XM_546237.5, SH3PXD2B, Ins, A_7, NLIFQAPPGGQRATAGSK, (SEQIDNO:2535); XM_545570.5, GLS, Del, A_7, NLILEEKVVIKG, (SEQIDNO:2536); XM_005640463.2, GLS, Del, A_7, NLILEEKVVIKGIPLDHWTMKVSNKNL1, (SEQIDNO:2537); XM_534852.5, ERGIC2, Ins, A_7, NLKFGERVGCLSKGS, (SEQIDNO:2539); XM_014109749.1, ITSN1, Del, A_7, NLKLRRLSPATQLLVPSSSPWPLVS, (SEQIDNO:2540); XM_014122251.1, IP6K2, Del, A_7, NLKSCTTV, (SEQIDNO:2541); XM_014107055.1, LOC106557703, Ins, A_7, NLKSNTSLNLPQAGLDPNLHGAGSKRVGVAVFKKYEI, (SEQIDNO:2542); XM_005635468.2, NBEA, Del, A_7, NLKTLYGSTGWPWKVNLFLANCISGLTLYLATNSEDKQSVL, (SEQIDNO:2543); XM_014109621.1, ICE2, Del, A_7, NLLNEYIKNLIQLEKF, (SEQIDNO:2545); XM_014114304.1, LOC479758, Ins, A_7, NLLPEVPPH, (SEQIDNO:2546); XM_005626899.2, FKTN, Del, A_7, NLNTCFPSLHCAGLSL, (SEQIDNO:2547); XM_005617406.2, GPBP1, Ins, A_7, NLPSSSLRVSSES, (SEQIDNO:2548); XM_535836.5, KNG1, Ins, A_7, NLPYCQLSVTGKGHIDEKASRFFTFPILIH-GENRKRNN, (SEQIDNO:2549); XM_005637743.2, PLEKHS1, Del, A_7, NLQDSDKLNHTTSCQKLLKIQKKRVIISVLKVFFRSWILLLLPVILVNLLNLVVQINSL RELSIITCQ, (SEQIDNO:2551); XM_856735.5, DNM3, Del, A_7, NLQILMKFAMRLKQKQIE, (SEQIDNO:2552); XM_014114967.1, ASPM, Del, A_7, NLQLFYKH, (SEQIDNO:2553); XM_540240.5, PTPN22, Del, A_7, NLQTLFSQITPAPF, (SEQIDNO:2554); XM_536845.5, BAZ1B, Del, A_7, NLRQTTL1, (SEQIDNO:2555); XM_005634561.2, RNF13, Ins, A_7, NLSGLQAKSGSFPRRLRLRHRQQSRRK, (SEQIDNO:2556); XM_005618061.2, GIN1, Del, A_7, NLSSKKKSCFMLEKTENKIVW, (SEQIDNO:2557); XM_537353.5, CPSF2, Del, A_7, NLSSQKRQT, (SEQIDNO:2558); XM_005622961.2, PRG4, Del, A_7, NLTCSPGPLC, (SEQIDNO:2559); XM_014111941.1, PPEF1, Ins, A_7, NLTNLGRCLYLAPNWYNH, (SEQIDNO:2560); XM_014115877.1, FAM179B, Del, A_7, NLVQQDFLLQRIKTLK, (SEQIDNO:2561); XM_014120510.1, TPRKB, Del, A_7, NLVSQQKTLQF, (SEQIDNO:2562); XM_005620331.2, C5H1orf141, Del, A_7, NLWASLIKLLFKK, (SEQIDNO:2563); XM_014116360.1, LOC100685630, Ins, A_7, NLWVQRIWRSL, (SEQIDNO:2564); XM_014112221.1, FAM172A, Ins, A_7, NLYPRRIWSNSTESQ, (SEQIDNO:2565); XM_014112218.1, FAM172A, Ins, A_7, NLYPSRCH, (SEQIDNO:2566); XM_005626337.2, SEMA6A, Ins, A_7, NLYRLQRPILWVGKGSRFLCPSVTQQQIDI, (SEQIDNO:2567); XM_005627811.2, MATN2, Ins, A_7, NMCKDRLLC1A, (SEQIDNO:2568); XM_005638063.2, ZC2HC1A, Del, A_7, NMDPFARKLPLKNVRLLIQADKELKELISQQ, (SEQIDNO:2569); XM_005633672.2, USP47, Ins, A_7, NMEESWHCLFGLSYL, (SEQIDNO:2570); XM_014111472.1, CYLC1, Ins, A_7, NMESRLFSFDISQTTPAR, (SEQIDNO:2571); XM_014111164.1, MIA3, Del, A_7, NMFKKPRNKI, (SEQIDNO:2572); XM_005639118.2, RASGEF1B, Ins, A_7, NMGQSEDCKV, (SEQIDNO:2573); NM_001048138.1, IL7, Del, A_7, NMHVMIIRKVCFYIVLLTS, (SEQIDNO:2574); XM_005615937.2, CD274, Del, A_7, NMIYNLKRH, (SEQIDNO:2575); XM_005616951.1, CCDC7, Del, A_7, NMLTLQIICFL, (SEQIDNO:2576); XM_536300.5, CCNH, Del, A_7, NMSHPDLKKLL1, (SEQIDNO:2578); XM_014116352.1, EFCAB13, Ins, A_7, NMSQTLNLV, (SEQIDNO:2579); XM_005617177.2, ASB13, Ins, A_7, NMSRCFSFQH, (SEQIDNO:2580); XM_537080.5, CDC7, Del, A_7, NMSRILNYQVLKKISRSFMKLYHSMCLRLRTKLEKALLALFIWPQHSYE, (SEQIDNO:2581); XM_014109708.1, TRPM2, Del, A_7, NMSRRCQQTPLVTLFSRAWARRESTSASPRTHPPA, (SEQIDNO:2582); XM_014117695.1, FBN2, Ins, A_7, NMSSWPRIYHRWKRY, (SEQIDNO:2583); XM_005621555.2, ATF7IP2, Ins, A_7, NNACKLPEASRDPE, (SEQIDNO:2584); XM_014121817.1, LOC106560102, Ins, A_7, NNFSFASHRFP, (SEQIDNO:2587); XM_014120704.1, SYT6, Ins, A_7, NNHQEEHS, (SEQIDNO:2588); XM_014120175.1, WDR17, Ins, A_7, NNHSYLLVST, (SEQIDNO:2589); XM_014110825.1, LOC478773, Del, A_7, NNKKKLRQQLQPHLQNQESSVVLVG, (SEQIDNO:2590); XM_014120084.1, UBXN8, Del, A_7, NNKRHRVKRPADT, (SEQIDNO:2591); XM_003431743.3, DEFB112, Del, A_7, NNPEVKNTILSLIGGMHA, (SEQIDNO:2593); NM_001109813.1, ANGPTL1, Ins, A_7, NNPKEIPSCHGC, (SEQIDNO:2594); XM_005642422.1, OVCH1, Ins, A_7, NNRDNSRKQYWKTAT- PRHMWNSSC, (SEQIDNO:2595); XM_543821.5, OLR1, Ins, A_7, NNRNPYPEA, (SEQIDNO:2597); XM_014115168.1, LOC480059, Ins, A_7, NNRTEKESLW, (SEQIDNO:2598); XM_014115881.1, MIS18BP1, Ins, A_7, NNRTEMHAV, (SEQIDNO:2599); XM_005617866.2, HP1BP3, Ins, A_7, NNTFLGYPFCQPASQGPETNTDGFLPTSQDGCNPN, (SEQIDNO:2601); XM_539698.4, PTPRQ, Del, A_7, NNTYLNLEPQMLWDNLLILIILIL1R1, (SEQIDNO:2602); XM_005623466.2, LOC490717, Ins, A_7, NNVLQYAYKNCSEAS, (SEQIDNO:2603); XM_005637524.2, SLC16A12, Ins, A_7, NPAAVPCQRI, (SEQIDNO:2604); XM_005634448.1, TOPBP1, Ins, A_7, NPAKTRIRHC, (SEQIDNO:2605); NM_001205203.1, MEF2B, Ins, A_7, NPDLAHSGPKESAGDVYQAEVRADEEGL, (SEQIDNO:2606); XM_540380.5, SLC26A3, Ins, A-7, NPEAAEERPAANDTKRTHMYP, (SEQIDNO:2607); XM_014120571.1, LOC607974, Ins, A_7, NPEPVEASWHRSAFHSR, (SEQIDNO:2608); XM_014110690.1, EPHB2, Ins, A_7, NPEQYPGDAGTDEPDPVCGGL, (SEQIDNO:2609); XM_014115338.1, ASHIL, Ins, A_7, NPFKRLRGCQTPFWLRGHH1, (SEQIDNO:2610); XM_857524.4, TAOK3, Ins, A_7, NPFPRDTKWTLK, (SEQIDNO:2611); XM_014112822.1, ANK3, Ins, A_7, NPGEQAACVPGLC, (SEQIDNO:2612); XM_014115723.1, ADSSL1, Ins, A_7, NPGGRGQSSPP, (SEQIDNO:2613); XM_844262.4, DGAT2L6, Ins, A-7, NPGIKFLYLPWSGPHSRLLGLPSFQSAHYHCCWGAPANPQD, (SEQIDNO:2614); XM_547682.5, AFG3L2, Ins, A_7, NPGSAARGEEDRGIP, (SEQIDNO:2615); XM_003431543.3, ZNF354A, Ins, A_7, NPHCRKKP, (SEQIDNO:2616); XM_843509.4, TTC17, Del, A_7, NPKGIIRKLLGKR, (SEQIDNO:2618); XM_014109908.1, ANK2, Del, A_7, NPKSRTAMQASSVLPEQATWTK, (SEQIDNO:2619); XM_848173.4, ZFHX4, Del, A_7, NPLLFIPIFLLQTS, (SEQIDNO:2620); XM_014117114.1, LEMD3, Del, A_7, NPLMKHLEKYKKVRKIL, (SEQIDNO:2621); XM_539571.5, LOC482454, Del, A_7, NPLNAVTVGKPIAGRLTLQLIRKSIMERDPLCATIVGKRLRIKHNW, (SEQIDNO:2622); XM_005616128.1, LOC611492, Del, A_7, NPPDSSLLLRSPAFPFCSSSSPSSSSTYAPSMVHHHMKKPPKD, (SEQIDNO:2623); XM_542164.5, CREB3L3, Ins, A_7, NPPENQKQAVGPRKPEKEEGIY, (SEQIDNO:2625); XM_014108780.1, LOC106557931, Del, A_7, NPPERAGERASAEKARGRTLERARLDPGRRGRRRQPKMAG1, (SEQIDNO:2626); XM_005630908.2, DDC, Ins, A_7, NPPGSLSPQRQVRAALCHLRPHRGICPRAAGLEARRSAGHQPPGHPQGL, (SEQIDNO:2627); XM_014112831.1, CTNNA3, Ins, A_7, NPPSASYE, (SEQIDNO:2628); XM_014114850.1, LOC106558969, Ins, A_7, NPRFAEPPGVE, (SEQIDNO:2629); XM_014111056.1, DNAH7, Ins, A_7, NPRQFEPLPSP1, (SEQIDNO:2630); XM_014112442.1, BLM, Del, A_7, NPRRWHLIA, (SEQIDNO:2631); XM_005619526.2, TVP23B, Del, A_7, NPRSDIQWHHFSNSFESVQL, (SEQIDNO:2632); XM_849701.4, FGD6, Ins, A_7, NPSCSQRSISKHRRFFHEWLLVQIKRQ, (SEQIDNO:2633); XM_014119662.1, ZMYM1, Ins, A_7, NPSEGANCLSEERVYSAFLLHAVHQ, (SEQIDNO:2634); XM_014119514.1, ZMYM4, Ins, A_7, NPSEGANCLSEERVYSAFLLHAVPHWNSSTCPPTASSHQENLFKLLKRYFKSKGCDQ CPV, (SEQIDNO:2635); XM_014119166.1, LRGUK, Ins, A_7, NPSGKRFSGETI, (SEQIDNO:2636); XM_003640104.2, TIGD2, Del, A_7, NPVHSKELTFQTFLSLISVKKVHG, (SEQIDNO:2637); XM_005622017.2, PRKACB, Ins, A_7, NPWNRFIWKSHVGET, (SEQIDNO:2638); XM_014114190.1, ZAN, Del, A_7, NPWPPQKNTLSPVK, (SEQIDNO:2639); XM_848169.4, KIAA2026, Del, A_7, NPYLKKQSQRRGKLSQSHLLYQNFSLFALILMNSGN, (SEQIDNO:2640); XM_014118132.1, ZNF484, Ins, A_7, NPYWRETL, (SEQIDNO:2641); XM_005620231.2, INAD1, Ins, A_7, NQAKICRPSWRIAHY, (SEQIDNO:2642); XM_005621408.2, RBBP6, Ins, A_7, NQAQQRNW, (SEQIDNO:2643); XM_845288.4, ENTPD7, Ins, A_7, NQARNLCNGRHPGTCQ, (SEQIDNO:2644); XM_014111020.1, INO80D, Ins, A_7, NQASCTYQKT, (SEQIDNO:2645); XM_014113201.1, MLLT4, Del, A_7, NQASTSPATRKDQTLTWDLPGQLLAPTMPIGTREKDCLKATRQNLGALEPLKT, (SEQIDNO:2646); XM_005635161.2, STAU1, Del, A_7, NQCISLSTLTLGCSPPITTT, (SEQIDNO:2647); XM_532236.6, UFL1, Ins, A_7, NQEERKKRRG, (SEQIDNO:2648); XM_005617034.2, ARHGAP12, Ins, A_7, NQEKLKEVSYTAPHFASCS, (SEQIDNO:2649); XM_005627765.2, CAPN11, Ins, A_7, NQEMDGHLPRV, (SEQIDNO:2650); XM_534306.5, EIF2A, Ins, A_7, NQEPKEETESYRATERTSSSWKTARKKSVGENSKRESPSPGAGRFGIGYL, (SEQIDNO:2651); XM_005641892.2, SLITRK4, Ins, A_7, NQEVPDRRQPQ, (SEQIDNO:2652); XM_005629808.2, KAT6A, Del, A_7, NQFFTEEGGSENANTTIAVWSQKLFQRLQRC, (SEQIDNO:2653); XM_005639728.2, MFN1, Ins, A_7, NQGGYRRGGKQGFMCNDR, (SEQIDNO:2655); XM_535898.5, NUP153, Del, A_7, NQHSTCLPLERFPLHLGILQSLKQVSLEILLFILEKQRMVGQQLL, (SEQIDNO:2656); XM_005633958.2, DACH1, Ins, A_7, NQIGSHEQLSCQ, (SEQIDNO:2657); XM_014109582.1, RFX7, Del, A_7, NQKALQPME, (SEQIDNO:2658); XM_014117985.1, CNTLN, Del, A_7, NQLFKRRMVIYKRAHIQQFLPELTEKSGKI, (SEQIDNO:2659); NM_001003040.2, RPI, Ins, A_7, NQLLQERRPTVWRGQGGGQPAFLQDI, (SEQIDNO:2660); XM_546652.5, EPN2, Del, A_7, NQLRQWPLHHPKTMELRARTPLSASPCPLPQASPAAPGKHPSPSWAPTQPW, (SEQIDNO:2661); XM_005634045.1, GPR183, Ins, A_7, NQLYHSIFNKFGDF, (SEQIDNO:2662); XM_844389.4, DNAJC1, Del, A_7, NQNLNFLYIRL, (SEQIDNO:2663); XM_538971.3, FAM83B, Del, A_7, NQNQKWIHLLEESVLPHQILKAVFTRVRKM, (SEQIDNO:2664); XM_005637963.2, SNTG1, Ins, A_7, NQPKLSCKPADSLYGLV, (SEQIDNO:2665); XM_014110108.1, ABBBP, Del, A_7, NQPQSQARAAHPCHLDLCPHEENLYHQIMSLGSQEVQESFHQAK, (SEQIDNO:2667); XM_005628257.2, LOC482176, Ins, A_7, NQQDRNRQLYKQLLWDTKE, (SEQIDNO:2669); XM_014108499.1, KRAS, Ins, A_7, NQQRRKDSWLCEN, (SEQIDNO:2670); XM_014119368.1, LRBA, Del, A_7, NQQSYLLHLLQVYLQMLSVWFLQ, (SEQIDNO:2671); XM_005622961.2, PRG4, Del, A_7, NQRLHQLPQR, (SEQIDNO:2672); XM_005624024.1, CCDC40, Ins, A_7, NQRRAPAGSLPSGGITPPSTEPGEQQYL1R1, (SEQIDNO:2673); XM_014120511.1, KRCC1, Del, A_7, NQRRNSPSIREKKVVRNQI, (SEQIDNO:2674); XM_014120231.1, ROCK2, Ins, A_7, NQRSTDEGRRL, (SEQIDNO:2675); XM_014110645.1, ELOVL2, Ins, A_7, NQSDYFSSRVPPCLYV, (SEQIDNO:2676); XM_848511.4, ZNF653, Del, A_7, NQSGRKGGDAT, (SEQIDNO:2677); XM_005630347.2, CEBPZ, Del, A_7, NQSLLLGCTLII, (SEQIDNO:2678); XM_014106798.1, SCN11A, Ins, A_7, NQSPVSPGSVPPGFLHCYNS, (SEQIDNO:2679); XM_535949.5, KLHL41, Ins, A_7, NQSSQRRLRRQTPRT, (SEQIDNO:2680); XM_014109318.1, TRIQK, Ins, A_7, NQTYFTSNQIKSRSKENSNRHKEFAITITKHCLLFTPDC, (SEQIDNO: 2681); XM_014109320.1, TRIQK, Ins, A_7, NQTYFTSNQIKSRSKENSNRHKGSWPRTCSYIGPPTGFLCFLLSQTVHRC, (SEQIDNO:2682); XM_014111292.1, RGS2, Ins, A_7, NQVTPKAVLQSKENN, (SEQIDNO:2683); XM_848169.4, KIAA2026, Del, A_7, NRANGIIGGK1, (SEQIDNO:2684); XM_005617376.1, C2H5orf46, Ins, A_7, NRARIPQIPKPFGHRDH, (SEQIDNO:2685); XM_005626438.2, SRFBP1, Ins, A_7, NRCAKSCCQSL, (SEQIDNO:2686); XM_850281.4, POLE3, Ins, A_7, NRCRGARQGQR, (SEQIDNO:2687); XM_005633308.2, ZBED5, Ins, A_7, NRCSITIK, (SEQIDNO:2688); XM_014115260.1, AHCTF1, Ins, A_7, NRDSSPAARISFRFIFSVCLLTSCFKDQAENHI, (SEQIDNO:2689); XM_005635927.2, PER2, Ins, A_7, NREEQKTEVQTGQASRFVREHRVWGARTPPAPAAGPERHGLVTV, (SEQIDNO:2690); XM_844360.4, C16H4orf47, Ins, A_7, NREERITYTPL, (SEQIDNO:2691); XM_531825.4, C16H2orf73, Ins, A_7, NRERKLSGKQNDLTRSLPTKFPRAARD, (SEQIDNO:2692); XM_005620894.2, DYNC1LI2, Ins, A_7, NRFSWKSWCWWCAEHSQEVRTKDCVDKCSGRTG, (SEQIDNO:2693); XM_005626169.2, ETAA1, Del, A_7, NRFTPQNMRSHISLIVLLLRMKNHQQTPC, (SEQIDNO:2694); XM_014111218.1, ZC3H11A, Ins, A_7, NRGFATYSYQQRTIRGAHR, (SEQIDNO:2695); XM_014111056.1, DNAH7, Ins, A_7, NRGFLGSS, (SEQIDNO:2696); XM_014121880.1, MAP4, Ins, A_7, NRGICSGSKA, (SEQIDNO:2697); XM_005618123.2, POLR3G, Ins, A_7, NRGIGKER, (SEQIDNO:2698); XM_005616290.2, MED25, Ins, A_7, NRICVERIQPETSLRIKAQ, (SEQIDNO:2699); XM_005619375.2, OSMR, Ins, A_7, NRILPGAGSFGQPSSGHE, (SEQIDNO:2700); XM_003639317.1, LOC100856706, Ins, A_7, NRIPIKDV, (SEQIDNO:2701); XM_844590.3, DAPL1, Ins, A_7, NRIRENKYHCKCCQTPGHGYSE, (SEQIDNO:2702); XM_005623486.2, SYNE2, Del, A_7, NRISPILTIMKILSYLKKKNQLLIFQQICP, (SEQIDNO:2703); XM_540029.5, TRAPPC11, Ins, A_7, NRKCRAVF, (SEQIDNO:2704); XM_844661.3, RGS21, Ins, A_7, NRKCRKNCF, (SEQIDNO:2705); XM_005641869.2, MAP7D3, Ins, A_7, NRKEEKLVFD, (SEQIDNO:2706); XM_014112279.1, ANKRD31, Del, A_7, NRKKLPRKSKTIKTLHLCLVLV, (SEQIDNO:2707); XM_003434394.3, UBE2K, Ins, A_7, NRKPMCYGL, (SEQIDNO:2708); XM_849763.4, LOC612035, Ins, A_7, NRKTSGQGPAQEPSPPCATSFQLRQLSCPTARTVCI, (SEQIDNO:2710); XM_014118452.1, GLTSCR1L, Ins, A_7, NRMPRQSTEI, (SEQIDNO:2712); XM_014119811.1, LOC106559806, Ins, A_7, NRMYNEGWTGRAPHSGGRLRSQRSEWI, (SEQIDNO:2713); XM_014107325.1, BRCA2, Ins, A_7, NRNYKGIFGQSKKSF, (SEQIDNO:2715); XM_545545.5, PRKRA, Del, A_7, NRPRGTLLRNFLPNSVIFLQRTTF1, (SEQIDNO:2716); XM_846013.4, ERI2, Del, A_7, NRPSLFMKKNLHHLMAPQ, (SEQIDNO:2717); XM_005615470.1, PHACTR2, Ins, A_7, NRQAANLSIVLRCNHLWHV, (SEQIDNO:2718); XM_014118286.1, DHX16, Ins, A_7, NRQDTGRARI, (SEQIDNO:2719); XM_005615442.2, AHI1, Ins, A_7, NRQIWRKNCT, (SEQIDNO:2720); XM_014119347.1, NAV3, Ins, A_7, NRRCNCHF, (SEQIDNO:2721); XM_014114844.1, HFM1, Ins, A_7, NRRNRCKGT, (SEQIDNO:2722); XM_532882.5, SMC6, Del, A-7, NRRQFWTKKLID, (SEQIDNO:2723); XM_005627271.2, PNPLA1, Ins, A_7, NRRQSAVCSLSPRLHSALHFRDSLGHLQASSQPDPGTQLS, (SEQIDNO:2724); XM_005617973.2, FHAD1, Ins, A_7, NRRRDCNLEGQ, (SEQIDNO:2725); XM_005638009.2, CHD7, Del, A_7, NRRTLEKR, (SEQIDNO:2726); XM_005638435.2, DYX1C1, Ins, A_7, NRRYERKGTNKSN, (SEQIDNO:2727); XM_014107325.1, BRCA2, Ins, A_7, NRSCSCGLFVR, (SEQIDNO:2728); XM_542898.4, FERMT1, Del, A_7, NRSLSSWQPGF, (SEQIDNO:2729); XM_014112357.1, LCOR1, Ins, A_7, NRSPGCEAN, (SEQIDNO:2730); XM_005638519.2, SPG21, Ins, A_7, NRSRKLFIWPSGPYDG, (SEQIDNO:2731); XM_005640597.2, MAP2, Ins, A_7, NRSSGPLSLQEIHFKTCYQN, (SEQIDNO:2732); XM_014119970.1, GIMAP4, Ins, A_7, NRSVTRILQSRARETESADKRGVWRENQNAGG, (SEQIDNO:2733); XM_014115509.1, ACAA2, Ins, A_7, NRTESQGHGFGRGE, (SEQIDNO:2734); XM_844126.3, CD2, Del, A_7, NRTVGEMMRSWGHEHTE, (SEQIDNO:2735); XM_533254.6, HRASLS5, Ins, A_7, NRVKLNPKA, (SEQIDNO:2736); XM_543821.5, OLR1, Del, A_7, NRWNFITRT, (SEQIDNO:2737); NM_001012995.2, CAPZA2, Ins, A_7, NRWTANHYCMHREPSVPSKKLLEWSLEVRVEVYNHSFNHSSGWHLENSGS1L, (SEQIDNO:2738); XM_014107388.1, PAN3, Ins, A_7, NSALQYCNPA, (SEQIDNO:2739); XM_014112960.1, FAM35A, Ins, A_7, NSAVIQSTLFTSEG, (SEQIDNO:2740); XM_014111218.1, ZC3H11A, Ins, A_7, NSCGSCSTPF, (SEQIDNO:2741); XM_005625753.2, ATXN10, Ins, A_7, NSCLLINDFVHIPEF, (SEQIDNO:2743); XM_014117890.1, SMC2, Ins, A_7, NSCPENYRKKRG, (SEQIDNO:2744); XM_014115932.1, KIAA0586, Ins, A_7, NSCRCNSFSSC, (SEQIDNO:2745); XM_546437.4, COR8C4, Ins, A_7, NSEKNFQY, (SEQIDNO:2747); XM_532445.5, WAS1, Del, A_7, NSEKQLQTCWAGDKGNLRRGETPQMVLNPWQQLTSKIQKSQPIDFMVHKSITSPIPK KRKKEKLKRRD, (SEQIDNO:2748); XM_534816.5, CCDC65, Ins, A_7, NSETTGRHNYFKK, (SEQIDNO:2749); XM_014112808.1, SYNE1, Del, A_7, NSFMKTRVNAVDLLT, (SEQIDNO: 2750); XM_005635642.2, CEP44, Del, A_7, NSFSNVDLQNGKSKLFVIF, (SEQIDNO:2751); XM_003639706.3, RIF1, Ins, A_7, NSFYCLEESNR, (SEQIDNO:2752); XM_014107674.1, TRAF3IP1, Ins, A_7, NSGDQERL, (SEQIDNO:2753); XM_005637209.2, CIR, Ins, A_7, NSGEVLWAAGFSTGQPPRSKGIRVSREQDAADLPHRLLQRGEWHHYVPQGLPGLLP GCGPR, (SEQIDNO:2754); XM_005628783.1, LOC100856700, Ins, A_7, NSGHLLFPSNCGESLLWPKHIYLYVFHFLPQCGAGPSSFCIQQYSNTHVEPSHLQPEE QRGGGSSQEAYGEMCDIL, (SEQIDNO:2755); XM_005627588.2, CEP162, Ins, A_7, NSGSRATS, (SEQIDNO:2756); XM_014114524.1, ZNF274, Ins, A_7, NSHRREALCVSGLWESICSELLPHTASESSHWRETI, (SEQIDNO:2757); XM_003435418.3, LOC100688087, Ins, A_7, NSHRSKAI, (SEQIDNO:2758); NM_001003144.2, CHRNA1, Ins, A_7, NSHSLGKDLAPRPRSL, (SEQIDNO:2759); XM_014108601.1, SLC4A8, Ins, A_7, NSHWGRGLKCPGWRGG, (SEQIDNO:2760); XM_014113618.1, ZNF624, Ins, A_7, NSHWRKTL, (SEQIDNO:2761); XM_532318.5, TAF2, Ins, A_7, NSIDEWRRS, (SEQIDNO:2762); XM_005622341.2, RCOR3, Ins, A_7, NSIQDQLDGSPGS, (SEQIDNO:2763); XM_539002.5, COL12A1, Ins, A_7, NSIQRWQHNDGGCH, (SEQIDNO:2764); XM_005622049.2, USP33, Del, A_7, NSIRNTEVLFQT-FLMEQLLVQCSV, (SEQIDNO:2765); XM_538266.5, TBK1, Del, A_7, NSITKILSNYLLLKRRQQQDIKYLL-WNFVHVEVYILF, (SEQIDNO:2766); XM_003434950.3, C4BPA, Del, A_7, NSKCLVLERH, (SEQIDNO:2767); XM_005622027.2, IFI44, Ins, A_7, NSKGVDKVWYN-TCGVAHSCG, (SEQIDNO:2768); XM_005628995.2, ZCCHC11, Ins, A_7, NSKLFYFSGQSEY, (SEQIDNO:2769); XM_014112716.1, ZNF25, Del, A_7, NSK-LMPERKSINAMNVGSPSVRSLSS, (SEQIDNO:2770); XM_005630592.1, MBOAT2, Ins, A_7, NSKRKDYT, (SEQIDNO:2771); XM_005619062.2, ADK, Del, A_7, NSKSNIMLVALPRIQLKWHSG, (SEQIDNO:2772); XM_005629940.2, MTMR7, Ins, A_7, NSKSPVKSH, (SEQIDNO:2773); XM_014110870.1, FSIP2, Ins, A_7, NSKSSWSVRCTS, (SEQIDNO:2774); XM_014106549.1, ZBTB38, Ins, A_7, NSKWRPEA, (SEQIDNO:2775); NM_001002963.1, MET, Ins, A_7, NSLCCEIPE, (SEQIDNO:2776); XM_014107422.1, LOC606856, Del, A_7, NSLFIQFMVLEKAMEMI, (SEQIDNO:2777); XM_014115181.1, LOC106559028, Ins, A_7, NSLHRYIW, (SEQIDNO:2778); XM_543416.5, FBXO21, Ins, A_7, NSLLPTPTENFK, (SEQIDNO:2779); XM_542564.5, RCBTB2, Ins, A_7, NSLPQLWEWPPYCPCDHRRRS-LYLGS, (SEQIDNO:2780); XM_535769.5, UMPS, Del, A_7, NSMKVESSK, (SEQIDNO:2781); XM_005633789.2, LOC100856360, Ins, A_7, NSPLCPHP-SCQSLCGLPTCPQSYYLWCEDKADS, (SEQIDNO:2782); XM_014109416.1, KATNBL1, Del, A_7, NSPLEV-GAVTWQIKKMN, (SEQIDNO:2783); XM_014120611.1, AP4B1, Del, A_7, NSPMYKPMCLCK-SRDLCWLPVLQRAVSSVLLLYVMCVRSCIVCPVT-LAATTKNFFA PTRSPTISSCRRWRCCVSW, (SEQIDNO:2784); XM_003434574.3, ATP5L, Ins, A_7, NSQECSNW, (SEQIDNO:2785); XM_014115143.1, HMCN1, Ins, A_7, NSQQTSARNTYLRAAEYFWNFCPSQSRSSRASEY-LRQFS, (SEQIDNO:2786); XM_544656.5, EIF3J, Ins, A_7, NSRENKRERTATEEKARRN, (SEQIDNO:2787); XM_548436.5, ODF2, Del, A_7, NSRNHQQPTARNLI-SAE, (SEQIDNO:2788); XM_014118132.1, ZNF484, Del, A_7, NSRTMTHLEGV, (SEQIDNO:2789); XM_014109056.1, SMC3, Ins, A_7, NSRTWITSPGSI, (SEQIDNO:2790); XM_532130.5, DNAH8, Del, A_7, NSSFFLMVIVLI, (SEQIDNO:2791); XM_014121788.1, CRLF1, Del, A_7, NSSFGGLPGDLEVLAWCGGG-GAQGHSISGLTGTPL, (SEQIDNO:2792); XM_014118548.1, RGS22, Ins, A_7, NSSKPATSKSHI1, (SEQIDNO:2793); XM_535242.6, PLK2, Ins, A_7, NSSLLCRAWPVLCFPSNRCS, (SEQIDNO:2794); XM_005626026.1, LYG2, Ins, A_7, NSSPCWYLGQQRTPSAGCWDSHRQN, (SEQIDNO:2795); XM_005621631.2, TIGD7, Del, A_7, NSSRIE-SILELVVF, (SEQIDNO:2796); XM_005618818.2, SPRTN, Ins, A_7, NSSSVPYSYCQSPKCLKQLLS, (SEQIDNO:2797); XM_014121199.1, EXT2, Del, A_7, NSSVL-SAQPLMGFHLTRRTWWRGLSAST-SLLQSLEQCLLRWWSTEQTLSCTKMTFL RN, (SEQIDNO:2798); XM_534311.5, DHX36, Ins, A_7, NSS-WCSENSNCY, (SEQIDNO:2799); XM_005626267.2, ZFP62, Ins, A_7, NSSWGEAL, (SEQIDNO:2800); XM_005617173.2, FBXO18, Ins, A_7, NSTASFVPVMHKTQGSQARSG-GLSVTVFCRVWRTQPTNGGHWSRSHS, (SEQIDNO:2801); XM_005639497.2, KIAA2018, Del, A_7, NSTERK-TERHTMQWRGIERRKSMLE, (SEQIDNO:2802); XM_003434814.3, ZNF75A, Del, A_7, NSVRTPTLLNI-GEPTQVSNHILVACAEETSAGDQAFLDTRNSTA, (SEQIDNO:2803); XM_014121504.1, MGAT5, Ins, A_7, NSWAILGSLPVHAPSPGFIWYRARI, (SEQIDNO:2804); XM_014120622.1, SPAG17, Ins, A_7, NSWTSIWHSDLEGS, (SEQIDNO:2805); XM_005621999.2, SSX2IP, Ins, A_7, NSYGSFKLCGESRWKKRLLEDG, (SEQIDNO:2806); XM_014114985.1, LOC484341, Ins, A_7, NSYRGKTLWMQ, (SEQIDNO:2807); XM_014117920.1, C11H9orf84, Ins, A_7, NSYRNDDRD, (SEQIDNO:2808); XM_005635068.2, ZHX3, Ins, A_7, NSYTQGEPPQSACG, (SEQIDNO:2809); XM_014107150.1, SYCP2, Ins, A_7, NTAKQN-RESRSGSLQKRHSTATK, (SEQIDNO:2810); XM_005639670.2, CMBL, Del, A_7, NTAKWNIKLKHFLGKPMASCIGREKIVQQKTSPI, (SEQIDNO:2811); XM_005615469.2, PHACTR2, Ins, A_7, NTCASKRGCCWGKPQG, (SEQIDNO:2812); XM_005635475.2, PDS5B, Ins, A_7, NTCHRFRREIRYG, (SEQIDNO:2813); XM_014112733.1, ARID4B, Ins, A_7, NTEGAFFRL, (SEQIDNO:2814); XM_005622271.2, CAMSAP2, Ins, A_7, NTGGNGEVRCQQLFNLVPG-FRLPIQVFVYLLPRN, (SEQIDNO:2815); XM_843373.4, AGAP1, Del, A_7, NTGGRKAPA-TSKPTGSPAPLKNKKKTLSLSLCPSLARRGTLKP-PHMKSGMRGSKPSR ARS, (SEQIDNO:2816); XM_005635912.2, AGAP1, Del, A_7, NTG-GRKAPATSKPTGSPAPLKPNARLGN, (SEQIDNO:2817); XM_005619334.2, ITGA2, Ins, A_7, NTGGVNS-VCQQTKSCI, (SEQIDNO:2818); XM_536875.4, TRRAP, Ins, A_7, NTGRYLLSPLCRRAA, (SEQIDNO:2819); XM_005638476.2, VPS13C, Del, A_7, NTGSCSR-VIKVPIRSS, (SEQIDNO:2820); XM_005629477.2, LUC7L2, Ins, A_7, NTGSIGENGRYYSSTNQIQR, (SEQIDNO:2821); XM_014111169.1, LOC610561, Del, A_7, NTGVKLKSFFIRPRTSS, (SEQIDNO:2822); XM_005621522.2, NTAN1, Del, A_7, NTH-LQPVHCFLETKLCSTRRMKVAYGKRSLVQEA, (SEQIDNO:2823); XM_005639188.2, MMRN1, Del, A_7, NTNLGMKFRVVVMPWTDVSMNMP, (SEQIDNO:2824); XM_014114277.1, KPNA7, Del, A_7, NTKAPRLLNKGPNP, (SEQIDNO:2825); XM_845305.4, CCNB1, Ins, A_7, NTKASGEGT, (SEQIDNO:2826); XM_014114844.1, HFM1, Ins, A_7, NTKFFTFC, (SEQIDNO:2827); XM_014106743.1, XRN1, Ins, A_7, NTKGMRTRRNHISPPTLVFNERVY, (SEQIDNO:2828); XM_005640040.2, HIVEP1, Ins, A_7, NTKIP-TEESSSGKT, (SEQIDNO:2829); XM_534086.4, SPTY2D1, Del, A_7, NTKMKAIMPY-VTWRVVGKSSRRKKQRV, (SEQIDNO:2830); XM_005618730.2, WHAMM, Ins, A_7, NTPAVESI, (SEQIDNO:2832); XM_005623453.2, DACT1, Ins, A_7, NTPCKDQQTKNQREC, (SEQIDNO:2833); XM_014112334.1, PRC1, Ins, A_7, NTPGWQER-SQQGEPGAQWQHPERWVPRLGSPPAQLQH, (SEQIDNO:2834); XM_535304.5, CHD9, Del, A_7, NTQKMQKGNNLKKRFKVL, (SEQIDNO:2835); XM_850014.3, SLC26A2, Ins, A_7, NTQPSLSKGS-SEEGRKEKDHKGNSDSQWSPG, (SEQIDNO:2836); XM_003433632.3, TACC2, Ins, A_7, NTRETRQH-SCLAYQIPR, (SEQIDNO:2837); XM_003433617.3, USMG5, Ins, A_7, NTSCESNI, (SEQIDNO:2839); XM_014114507.1, LOC611144, Del, A_7, NTSKSME-KRNF, (SEQIDNO:2840); XM_005621538.2, ZC3H7A, Ins, A_7, NTSKTNKNK1, (SEQIDNO:2841); XM_014112460.1, AP3B2, Ins, A_7, NTSQQQKCPRGQGDLPA, (SEQIDNO:2842); XM_005641542.2, ZNF711, Del, A_7, NTSVQIVTLQL-TRK, (SEQIDNO:2843); XM_014109413.1, SLTM, Ins, A_7, NTSYCKKRRSRF, (SEQIDNO:2844); XM_003639447.3, SNX31, Ins, A_7, NTTFNKARKTLVFYQETR1, (SEQIDNO:2846); XM_532364.5, IREB2, Del, A_7, NTVPGTPETGLPKDRICWA, (SEQIDNO:2847); XM_005640003.2, PRPF4B, Del, A_7, NTVRMLVFILKL, (SEQIDNO:2848); XM_848173.4, ZFHX4, Del, A_7, NTWKQATPS, (SEQIDNO:2849); XM_543280.4, SLC16A14, Del, A_7, NTIVMVPTF, (SEQIDNO:2850); XM_014114846.1, ZNF644, Del, A_7, NTIVNTCIHHHV-LIHLVVLLDLINEKVTFSKNL, (SEQIDNO:2851); XM_014111106.1, ALS2CR11, Ins, A_7, NTYSFCK-RRWNL, (SEQIDNO:2852); XM_005637424.1, LOC102156279, Del, A_7, NVAIHVRLIVDLHS, (SEQIDNO:2853); XM_539362.3, LOC482243, Ins, A_7, NVECGICLTGTYKI, (SEQIDNO:2854); XM_535893.4, RANBP9, Ins, A_7, NVEGCIQFTRLFGSLEQPSWKSA, (SEQIDNO:2855); XM_850162.3, HCN1, Ins, A_7, NVFHSTWCCWCHHKIQ, (SEQIDNO:2856); XM_539060.3, LOC481939, Ins, A_7, NVFVVYHENHL, (SEQIDNO:2857); XM_863207.4, SNW1, Ins, A_7, NVKCIGHSGGC, (SEQIDNO:2859); XM_014115709.1, CCNK, Del, A_7, NVKISSKQLVVY, (SEQIDNO:2860); XM_005616743.2, LOC484590, Ins, A_7, NVKRLGIKMGKQGITNEGGYL, (SEQIDNO:2861); XM_538136.5, ATG4A, Ins, A_7, NVLCPPLECRHNW, (SEQIDNO:2862); XM_005639326.1, FAM47E, Del, A_7, NVLPRSTRAVIPRRLQWHIQVNGLMKKR-SQVKQICSMKMVLFFMKMEVQTSMKSS F, (SEQIDNO:2864); XM_014120322.1, KIDINS220, Ins, A_7, NVLPTIFCHLPFYLWLHYCGNYPPGYL, (SEQIDNO:2865); XM_014111009.1, TYW5, Del, A_7, NVLYYSVLEMPSNNQVLSQKSWI, (SEQIDNO:2866); XM_005628374.2, COPG2, Ins, A_7, NVPPAQLCFSL, (SEQIDNO:2867); XM_005623470.2, C8H14orf39, Ins, A_7, NVPWLYMSV, (SEQIDNO:2868); XM_014115009.1, FMN2, Del, A_7, NVQMLFSGKILR, (SEQIDNO:2869); XM_014116985.1, SETX, Del, A_7, NVRENDLRNLWLKILYGLHHLREMRTSLIFLMGEV, (SEQIDNO:2870); XM_014121449.1, RALB, Ins, A_7, NVREQRQEWQEKQQEEKF, (SEQIDNO:2871); XM_005638071.2, ZNF704, Ins, A_7, NVSSTLVFLGHG-GRCENSRHQKSPSP, (SEQIDNO:2873); XM_005618169.2, ANKRD34B, Ins, A_7, NVVKETI-IANRTN, (SEQIDNO:2875); XM_014115866.1, CTAGE5, Del, A_7, NVVTWNVKL, (SEQIDNO:2876); XM_014120092.1, TEX15, Del, A_7, NVWQRQTFRPEQCGKLNKQKKQKIHFIEKA, (SEQIDNO:2877); XM_005630011.2, WWC2, Ins, A_7, NVWRPEWL, (SEQIDNO:2878); XM_005633836.2, DZIP1, Ins, A_7, NWARTEGTSTCEE, (SEQIDNO:2879); XM_014109139.1, CFAP43, Del, A_7, NWEGTAIKKI, (SEQIDNO:2880); XM_014110047.1, BANK1, Ins, A_7, NWESIFYYKQTSCPYT-STHKYPSKRRNHTLHSSSVSTKDS, (SEQIDNO:2881); XM_005634924.1, ASXL1, Ins, A_7, NWGDAAASCPDSSEGKRGPRGIGVRSDEAQQR-GRDRF, (SEQIDNO:2882); XM_005618541.2, FAM184B, Del, A_7, NWGRSWLLPKTD, (SEQIDNO:2884); XM_014117490.1, VWA3B, Del, A_7, NWIL-SKVRKLLQDVMKMAFIFQGL, (SEQIDNO:2885); XM_846354.4, BLOC1S2, Del, A_7, NWKPSTRSWRSD, (SEQIDNO:2886); XM_005621408.2, RBBP6, Ins, A_7, NWKYRKCI, (SEQIDNO:2888); XM_005618261.2, ZNF518B, Ins, A_7, NWPPAQSARKQ, (SEQIDNO:2889); XM_005638171.2, UACA, Ins, A_7, NWRDRKRV, (SEQIDNO:2890); XM_532881.5, RAD51AP2, Ins, A_7, NWRKIEFSTIIRNRSFKQRRLSPCRCHKYM, (SEQIDNO:2891); XM_005625616.2, CCT2, Ins, A_7, NWSKSTKAN, (SEQIDNO:2892); XM_547945.4, PTPN21, Ins, A_7, NWSSQVGCPKWTLPLSTASAR, (SEQIDNO:2893); XM_014110860.1, DPP4, Del, A_7, NWTPLFCMKQNFGIR, (SEQIDNO:2894); XM_540963.4, KIAA1109, Del, A_7, NWVLHY-RMKRKRKEKTKKNT, (SEQIDNO:2895); XM_542845.5, C23H3orf33, Ins, A_7, NWVRFQFEKRKL1, (SEQIDNO:2896); XM_014110823.1, ZNF385B, Del, A_7, NYCIVHYAKWL, (SEQIDNO:2897); XM_014115338.1, ASHIL, Ins, A_7, NYKEKQWTINENNYPQNK, (SEQIDNO:2898); XM_014113297.1, GPRC6A, Ins, A_7, NYKKSTYLL1, (SEQIDNO:2899); XM_005617972.2, FHAD1, Ins, A_7, NYKPNPGTSDQDPQLSGNPAVF-YAREVAGASGREGEAE, (SEQIDNO:2900); XM_014110285.1, PARP9, Ins, A_7, NYLDTSRFSVGTGHKRI, (SEQIDNO:2901); XM_005627265.2, SRPK1, Ins, A_7, NYPASVTGS, (SEQIDNO:2902); XM_014110821.1, DYNC112, Ins, A_7, NYPRICVSLPVCCDVCYICKISSKSGCWWYIFRPN-CAVG, (SEQIDNO:2903); XM_005634064.2, CCDC168, Del, A_7, NYQEPKGYSAPSL, (SEQIDNO:2904); XM_545492.6, TBR1, Ins, A_7, NYQGDDESVRYRQFS, (SEQIDNO:2905); XM_014112279.1, ANKRD31, Ins, A_7, NYRENPK1, (SEQIDNO:2906); XM_539419.4, RBM48, Del, A_7, NYRRGRLI, (SEQIDNO:2907); XM_005615602.2, TBC1D32, Del, A_7, NYRSAG-IKSLAMEFW, (SEQIDNO:2908); XM_014111407.1, DOCK11, Del, A_7, NYSLMDVQPSRKLLPT, (SEQIDNO:2909); XM_014117827.1, C11H9orf131, Del, A_7, NYSRAPLPDPLTQVNHLAAPLP, (SEQIDNO:2910); XM_537096.5, RPF1, Ins, A_7, NYSTVHFKRFHRSDSY, (SEQIDNO:2911); XM_014111592.1, GPRASP2, Del, A_7, NYSVPKLYRYLWVSLT, (SEQIDNO:2912); XM_005615937.2, CD274, Ins, A_7, NYTICEWKGRPES-SAQQLQPEGSAIEGPALLGEGCASDHRCEIAGCR-GLLLLDRLWR C, (SEQIDNO:2913); XM_014108595.1, TULP3, Del, A_7, NYVIHHIQWQRDPILL-LARNQPQIQELLVLHPNKLITSWEKWRI, (SEQIDNO:2914); XM_003433570.1, SLC15A5, Ins, A_7, RAEQAVLHSAISHLPWHRRNESHRLPTE-CLQPSGVWIPETDVFF, (SEQIDNO:2915); XM_005639762.2, MCF2L2, Ins, A_7, RAETKGQTIRDRLFSKIGQQSVL, (SEQIDNO:2916); XM_005615473.2, ZC2HC1B, Ins, A_7, RANCNQCRGSPAAKQGSGDPKYGPS, (SEQIDNO:2917); XM_005627636.2, MDN1, Ins, A_7, RAVSCLKKPVYRNMVPTKHKS, (SEQIDNO:2918); XM_005639442.1, EPHA3, Ins, A_7, RDFGGHKNPKSGLHRKAEERLPRRSKYHGTI, (SEQIDNO:2919); XM_005635468.2, NBEA, Ins, A_7, RECEHHLWSFITDYRSKRWIGNSRDRRPFTKPEPRK, (SEQIDNO:2920); XM_005635519.2, MTIF3, Ins, A_7, REECRGART, (SEQIDNO:2921); XM_005622441.2, SWT1, Ins, A_7, REISEERHHCITQL, (SEQIDNO:2922); XM_014109202.1, CCNE2, Ins, A_7, REQICSRQTF, (SEQIDNO:2923); XM_014120723.1, SYCP1, Ins, A_7, RETNEDLRKQV, (SEQIDNO:2924); XM_855716.4, CWC27, Ins, A_7, RETRGRSKEIETQRHKKF, (SEQIDNO:2925); XM_532881.5, RAD51AP2, Ins, A_7, RFANGYSPQNM, (SEQIDNO:2926); XM_853101.4, RBM26, Ins, A_7, RGDNKGGRAREEVFQKAKS, (SE- QIDNO:2927); XM_014106573.1, MYRIP, Ins, A_7, RGRTAERDEAEAG, (SEQIDNO:2928); XM_005623593.2, MED6, Ins, A_7, RGRTYTRNGKI, (SEQIDNO:2929); XM_014109424.1, MGA, Ins, A_7, RGTETTVPITVPIISAAGLMSV, (SEQIDNO:2930); XM_546818.5, CDYL2, Ins, A_7, RIFRQAPCRR, (SEQIDNO:2931); XM_014111650.1, GPRASP1, Ins, A_7, RILDLAWRKGS, (SEQIDNO:2932); XM_014119574.1, OSBPL8, Ins, A_7, RISQGAKEKLPRRKEKSHKGVTQYNHRSFCYCYG, (SEQIDNO:2933); XM_005630347.2, CEBPZ, Ins, A_7, RKCQQKRSNI, (SEQIDNO:2934); XM_844383.3, ERMN, Ins, A_7, RKDCRTTSRRERRGGWEEQS, (SEQIDNO:2935); XM_535304.5, CHD9, Ins, A_7, RKDRESKFREWGRKLCVKFSFHILYCCIKYSCSCQPISS, (SEQIDNO:2936); XM_005622378.2, CEP350, Ins, A_7, RKDRMAGFTHWKCSELTS, (SEQIDNO:2937); XM_005615620.2, RSPO3, Ins, A_7, RKGEEKEKTQ, (SEQIDNO:2939); XM_005621973.2, CLCA4, Ins, A_7, RKGIRTIR, (SEQIDNO:2940); XM_005619255.1, FAM71B, Ins, A_7, RKKRKEGQNFQQEKFPSPQDR, (SEQIDNO:2943); XM_846524.3, ACSL3, Ins, A_7, RKQRGYNYVETNTDGSCSGNHGSDLQKCHE, (SEQIDNO:2945); XM_846664.4, SEC62, Ins, A_7, RKRERKGRKWKRRR, (SEQIDNO:2946); XM_545078.5, ZBTB11, Ins, A_7, RKSKAEPGTGV, (SEQIDNO:2947); NM_001048129.1, FGF5, Ins, A_7, RKTPCKCQVYR, (SEQIDNO:2948); XM_863229.4, TAOK1, Ins, A_7, RKTRVAFKAEGEYTAFPSRGRG, (SEQIDNO:2949); XM_005638156.1, NECAB1, Ins, A_7, RLPRGLQFGTICNSIFIEGDLESAAVSPEFSGMCHGNY, (SEQIDNO:2950); XM_014116359.1, LOC611199, Ins, A_7, RLSLEQGV, (SEQIDNO:2951); XM_005626121.2, VRK2, Ins, A_7, RLYQKLDKTQKT, (SEQIDNO:2952); XM_535743.5, CFAP44, Ins, A_7, RMGRTVQE, (SEQIDNO:2953); XM_014119796.1, KDM7A, Ins, A_7, RNGNRQTASWEDS, (SEQIDNO:2954); XM_014106344.1, PHF11, Ins, A_7, RNPQREEVDMCFL, (SEQIDNO:2955); XM_847045.4, ADAMTS20, Ins, A_7, RNQHTRSYF, (SEQIDNO:2956); XM_005639717.2, ABCC5, Ins, A_7, RNQWFTEEITRQGS, (SEQIDNO:2957); XM_535737.5, ABHDIO, Ins, A_7, RNRDERHVGHAIKVQ, (SEQIDNO:2958); XM_005624798.2, LOC491140, Ins, A_7, RNRKLCRKVANIPLL1, (SEQIDNO:2959); XM_536762.5, ATP2C2, Ins, A_7, RNSIQFRAEVDGSEMQPQE, (SEQIDNO:2960); XM_014110273.1, KIAA1407, Ins, A_7, RPGALEEIENAKQAKHPGG, (SEQIDNO:2961); XM_005627482.2, KLHL31, Ins, A_7, RPIYPKGGSQ, (SEQIDNO:2962); XM_014120520.1, BCL2L11, Ins, A_7, RPNGKATFRCKF, (SEQIDNO:2963); XM_005618779.2, RYR2, Ins, A_7, RQLPVGCTELYRREVSDVETRSRLH, (SEQIDNO:2965); XM_536302.5, RASA1, Ins, A_7, RQRKTVEKFIFYLRRQ, (SEQIDNO:2966); XM_005630977.2, DNAJC2, Ins, A_7, RRDEQNKNIS, (SEQIDNO:2967); XM_533359.5, PRPF40A, Ins, A_7, RRGGKPTSKKNLYLEYKGGSKASI, (SEQIDNO:2968); XM_005630473.2, IMMT, Ins, A_7, RRGSWGQISYNCCRGETSQHDS, (SEQIDNO:2969); XM_014109172.1, PRKDC, Ins, A_7, RRIMDSRNKRN, (SEQIDNO:2970); XM_536845.5, BAZ1B, Ins, A_7, RRKEMGSTKISASQI, (SEQIDNO:2972); XM_005631143.2, QSER1, Ins, A_7, RRKHGWFSDTTYPTNWPSQYSNP, (SEQIDNO:2973); XM_844375.4, EPRS, Ins, A_7, RRKSCRLVFSGHHKVRND, (SEQIDNO:2974); XM_535949.5, KLHL41, Ins, A_7, RRLEGSGSNENPSFHVWSGGA, (SEQIDNO:2975); XM_535898.5, NUP153, Ins, A_7, RRNACRQRRVHFRWYRTCPSAICLIVCFGKDRRETAGASHFYFSGVWEES, (SEQIDNO:2976); XM_014117069.1, GOLGA1, Ins, A_7, RRNSGENGARVGGTNQRTESHPGGVDDLQSDVIRLEPEVGRIAETLLSAGRAERSRD SFKNRCRK, (SEQIDNO:2977); XM_014122663.1, UPF2, Ins, A_7, RRQGTEEKRRRKGEGGGRIKEKRGRRKKET, (SEQIDNO:2978); XM_005620224.2, USP1, Ins, A_7, RRSKKCGRIIY, (SEQIDNO:2979); XM_014110474.1, ECT2, Ins, A_7, RRTSQIGDIGSSHGWSYSKRL, (SEQIDNO:2980); XM_014115688.1, FERMT2, Ins, A_7, RRTYWNCIQQTD, (SEQIDNO:2981); XM_014112204.1, CAST, Ins, A_7, RRYHSASSRLFETHGAQ, (SEQIDNO:2982); XM_005638009.2, CHD7, Ins, A_7, RSEGTERTQGEKRAQGTQDPESP, (SEQIDNO:2983); XM_005615489.2, SHPRH, Ins, A_7, RSFHPFHL, (SEQIDNO:2984); XM_014122295.1, LOC612320, Ins, A_7, RSFPKRSDTLPR, (SEQIDNO:2985); XM_014107158.1, BCAS1, Ins, A_7, RSGRHGIQSRKCL, (SEQIDNO:2986); NM_001003075.1, IL13RA2, Ins, A_7, RSLFSSRHIL1, (SEQIDNO:2987); XM_014120782.1, DUS4L, Ins, A_7, RSNRNASFWAAGKSLCPNGSIFKVGF, (SEQIDNO:2988); XM_014119379.1, PPFIA2, Ins, A_7, RSPCPFKNGG, (SEQIDNO:2989); XM_531734.5, GTPBP1, Ins, A_7, RSPDQARRRRPIWRASSRGAPSWRRSLLSRGCAANLVQQSPATAQAQQRGPATGGP ASQSEVPGGLRDSCQRLL, (SEQIDNO:2990); XM_005625871.2, GTPBP1, Ins, A_7, RSPDQARRRRPIWRASSRGAPSWRRSLLSRGCAANLVQQSPATAQVQGTNVQFPRW SPVPY, (SEQIDNO:2991); XM_005628564.1, LOC102157031, Ins, A_7, RSPTATTM, (SEQIDNO:2992); XM_844495.4, OCIAD1, Ins, A_7, RSQSKQIWRYLG, (SEQIDNO:2993); XM_544621.5, RMDN3, Ins, A_7, RSRDCPGEGG, (SEQIDNO:2994); XM_014108806.1, SORBS1, Ins, A_7, RSRPLPSRVRGTFRKHGDT, (SEQIDNO:2995); XM_014110297.1, POLQ, Ins, A_7, RSSEFQFRKDQYCLWILET, (SEQIDNO:2996); XM_005632611.2, KIF9, Ins, A_7, RSSERSCQ, (SEQIDNO:2997); XM_843366.4, CHD1, Ins, A_7, RSSETFWCRRVKEEKSKS, (SEQIDNO:2998); XM_005627496.2, COL21A1, Ins, A_7, RSSGDSWFNGT, (SEQIDNO:2999); XM_547299.4, CLCA1, Ins, A_7, RSSKMFSRY, (SEQIDNO:3000); XM_005635984.2, ING5, Ins, A_7, RSSSERKKGLPGSWQEDLRGRYSKEKEA, (SEQIDNO:3001); XM_014114967.1, ASPM, Ins, A_7, RSYTDHSKVLQSVSERKDGAHQLFAETGCSHSTADCFQEDESSQFIQTKQSCLCSSV LLEDETRQISISKP, (SEQIDNO:3002); XM_542340.5, AKIRIN2, Ins, A_7, RTALIYSTTGWDD1, (SEQIDNO:3003); XM_005621532.2, GSPT1, Ins, A_7, RTCKCGIHWACRCWQVNHWRTNNVFDRNG, (SEQIDNO:3004); XM_005619587.1, PATE2, Ins, A_7, RTEYVFLFQTVMCDQLRRHQLLEF, (SEQIDNO:3005); XM_537432.5, MDGA2, Ins, A_7, RTILDHTRSLSQR, (SEQIDNO:3006); XM_014119604.1, TMPO, Ins, A_7, RTLHSHVDKNFAVCCCGHFFVFGLSSYGNQPRKSVQ, (SEQIDNO:3007); XM_005626023.2, EIF5B, Ins, A_7, RTRSLCQNRTYPW, (SEQIDNO:3008); NM_001171748.1, RBM12, Ins, A_7, RVKDTCAR, (SEQIDNO:3009); XM_014114569.1, LOC489979, Ins, A_7, RVPECYYLQISFCLVPTSFPL, (SEQIDNO:3010); XM_005639981.2, RIPK1, Ins, A_7, RVSRPSPKFSCEENAVSPD, (SEQIDNO:3011); XM_014117631.1, CCDC112, Ins, A_7, RVYSELENQKAAKEGGNFQVKGKSREPISTLS, (SEQIDNO:3012); XM_014110062.1, ZGRFI, Ins, A_7, RWFDISLFRSFRKHQKQSTDISSSKVQIN, (SEQIDNO:3013); NM_001076794.1, MYH4, Ins, A_7, RWQEEGFFFPDSVSPFQGEFK, (SEQIDNO:3014); XM_014116721.1, PRR11, Ins, A_7, RWTHADNS, (SEQIDNO:3015); XM_543181.4, CENPJ, Ins, A_7, RWVHEFISSITEESDFFRNSGRKIQEKSFADTRQSISKIQAYTSS, (SEQIDNO:3016); XM_005635615.2, CLCN3, Ins, A_7, RYPPSYGPDGKPRPRFNNVQL, (SEQIDNO:3017); XM_014121014.1, AHNAK, Ins, A_7, RYQPRGSQNGHREPKNQCGRCRRKLKRSQTQDA, (SEQIDNO:3018); XM_014113440.1, EXPH5, Ins, A_7, RYRREIRKLSTVH, (SEQIDNO:3019); XM_005630575.2, ZNF638, Ins, A_7, RYRRFQRC, (SEQIDNO:3020); XM_847828.4, C9H17of78, Ins, A_7, SCRDHYHPRHIL1, (SEQIDNO:3021); XM_005615672.2, LOC483960, Ins, A_7, SCSDTWYWN, (SEQIDNO:3022); XM_005622027.2, IFI44, Ins, A_7, SDYEIRYN, (SEQIDNO:3023); XM_536747.5, HIBADH, Ins, A_7, SEERLTINRLQYY, (SEQIDNO:3024); XM_014106330.1, PIBFI, Ins, A_7, SEHLQFSGI, (SEQIDNO:3025); XM_536121.3, IARS2, Ins, A_7, SEIYSWISTECHGRNDGQTAILVYIKAKSLGCSNPCISSQDKR, (SEQIDNO:3026); XM_014113689.1, SGIP1, Ins, A_7, SFEEKQWGTKWILCGN, (SEQIDNO:3027); XM_549109.5, RPS6KA6, Ins, A_7, SFFKSSRQSSDKNGKGYTGGSKSSIYC, (SEQIDNO:3028); XM_014111818.1, LOC100683280, Ins, A_7, SFLHLFFTHACCFHYIRQLYFHLYQAFGQRRGGYQ, (SEQIDNO:3029); XM_536590.4, GUCY1A2, Ins, A_7, SFLQHWHHVPPGDKPL, (SEQIDNO:3030); XM_005627714.2, SLC16A10, Ins, A_7, SFQFCHLQGDSLCSLGSWNTTCTFWIFCALCSLDETRE, (SEQIDNO:3031); XM_005637264.2, RAD51AP1, Ins, A_7, SFSFFRGH, (SEQIDNO:3032); XM_539934.4, LMBR1, Ins, A_7, SFSMGKKFGVSCCYGSPPY, (SEQIDNO:3033); XM_014107474.1, LOC477353, Ins, A-7, SGAGTVFWFKRLK, (SEQIDNO:3034); XM_532445.5, WAS1, Ins, A_7, SGTKQSTGILLWKGCTFRPDTIGYSAEICI, (SEQIDNO:3036); XM_005641783.2, LOC102151581, Ins, A_7, SIGFPAPEACLRMQSSELGLPMV, (SEQIDNO:3037); XM_014106746.1, XRN1, Ins, A_7, SIRKRRNSSYRGQI, (SEQIDNO:3038); XM_005630575.2, ZNF638, Ins, A_7, SIRRCSTIIWACFRIQ, (SEQIDNO:3039); XM_014122439.1, DDIAS, Ins, A_7, SISFRNSWIPSDGSKEMLCCL, (SEQIDNO:3040); XM_014117106.1, LOC100685665, Ins, A_7, SKDVISWSHRGSFEIP, (SEQIDNO:3041); XM_005619838.2, CWF19L2, Ins, A_7, SKEREEKKE, (SEQIDNO:3042); XM_014115025.1, LOC100683727, Ins, A_7, SKKDDWSES, (SEQIDNO:3043); XM_005623023.2, ROCK1, Ins, A_7, SKSEFTAC, (SEQIDNO:3044); XM_843302.3, COR6C33, Ins, A_7, SLFYMLLSYDCGLTFLWKLYLYVHKSFC, (SEQIDNO:3045); XM_532655.4, NTN4, Ins, A_7, SLKIYQIENFTRKKNIVSRIMD, (SEQIDNO:3046); XM_003434058.3, LOC100684793, Ins, A_7, SLLHLWGPSLFCVFILWPPPFHVCAP, (SEQIDNO:3047); XM_844234.4, TAF1, Ins, A_7, SLSFSLRK, (SEQIDNO:3048); XM_532130.5, DNAH8, Ins, A_7, SLWECGWSAVLDTCYGNILWYQ, (SEQIDNO:3049); XM_005620578.2, ZC3H18, Ins, A_7, SNHSKRTGA, (SEQIDNO:3050); XM_005615470.1, PHACTR2, Ins, A_7, SNWVQIISFTIYFLHLISSQSFEGDTL, (SEQIDNO:3051); XM_014110190.1, SENP5, Ins, A_7, SPAKLGAGHWGPSRDP, (SEQIDNO:3052); XM_005630719.2, POLR3C, Ins, A_7, SPLCAYPT, (SEQIDNO:3053); XM_849173.4, ZIC5, Ins, A_7, SPPSEGLWV, (SEQIDNO:3054); XM_005623780.2, AK7, Ins, A_7, SQKTHDLCGCCWTSIWSRRRHLTLFF, (SEQIDNO:3055); XM_014111056.1, DNAH7, Ins, A_7, SQSKGGGFQAAHSSHSSD1, (SEQIDNO:3056); XM_014118171.1, USP45, Ins, A_7, SQSVWKRRCENELHRSDLYW, (SEQIDNO:3057); XM_005615949.1, LOC484191, Ins, A_7, SRGEERMAESTGYSL, (SEQIDNO:3058); XM_005640299.2, METIL8, Ins, A_7, SRGKLSCSSPSGRTS, (SEQIDNO:3059); XM_014110829.1, METIL8, Ins, A_7, SRGKLSCSSPSGRTSYV, (SEQIDNO:3060); XM_014107587.1, NC1, Ins, A_7, SRSCHTSQESSCHPWQKGSSYTSQKGGCTSQSSSNTWQEGNHTRQGIGSNPW, (SEQIDNO:3061); XM_540739.5, FNBP4, Ins, A_7, SRVTSLGGRRW, (SEQIDNO:3062); XM_005627018.2, TFAP2B, Ins, A_7, SSGSSQICDFSDDE, (SEQIDNO:3063); XM_536972.4, RSL1D1, Ins, A_7, SSPHPQTVAQKAQSTPVNL, (SEQIDNO:3064); XM_014108414.1, PLEKHA5, Ins, A_7, SSQFWKEI, (SEQIDNO:3065); NM_001003294.1, DLD, Ins, A_7, SSRKDGCHWCRSNRCRIGFSLAETWCRCDSS, (SEQIDNO:3066); XM_005619238.2, ZBED8, Ins, A_7, SSSFLRHH, (SEQIDNO:3067); XM_014110037.1, CDK12, Ins, A_7, STERCQKYFFI, (SEQIDNO:3068); XM_539259.4, TEC, Ins, A_7, STTSSTRNKEAKASPTNST, (SEQIDNO:3069); XM_005633756.2, HTATIP2, Ins, A_7, SWGGRICSCRSRLCLQVCGAGKSWRVQTF, (SEQIDNO:3070); XM_538283.5, PTPRB, Ins, A_7, SWPGSRSFSKEH, (SEQIDNO:3071); XM_014121223.1, CCDC73, Ins, A_7, SYLRLDKVQGHMST, (SEQIDNO:3072); XM_005620755.2, PMFBP1, Ins, A_7, TAGLPTAERARGARLRQEAGGDEQPSAAVAEAAPERPQDAGS, (SEQIDNO:3073); XM_005626092.1, LHCGR, Ins, A_7, TAIEGKNQPPGCHTDLPQPLLCF, (SEQIDNO:3074); XM_537710.5, USP32, Ins, A_7, TAKRSLWA, (SEQIDNO:3075); XM_014112716.1, ZNF25, Ins, A_7, TANSCQRENP, (SEQIDNO:3076); XM_014121788.1, CRLF1, Ins, A_7, TAPLEDCQETWRSWPGAEEAGLRATPSQA, (SEQIDNO:3077); XM_005641575.2, ARMCX2, Ins, A_7, TAQHPSAIII, (SEQIDNO:3078); XM_014111942.1, AFF2, Ins, A_7, TAQKSREEYQH, (SEQIDNO:3080); XM_014111009.1, TYW5, Ins, A_7, TCCTIQSSRCPVFIFIRY, (SEQIDNO:3082); XM_014109708.1, TRPM2, Ins, A_7, TCPGDANRRLW, (SEQIDNO:3083); XM_540240.5, PTPN22, Ins, A_7, TCRLCSVKSLQLLSEFWFCKSFFKTQRTKETTINLEYL, (SEQIDNO:3084); XM_014111164.1, MIA3, Ins, A_7, TCSRNQETKYNSV, (SEQIDNO:3085); XM_546045.5, SPZ1, Ins, A_7, TDDSGKPEL, (SEQIDNO:3086); XM_543821.5, OLR1, Ins, A_7, TDGTSSPEPESPRSSEESSKLFRSLSPGLALA, (SEQIDNO:3087); XM_014110293.1, IQCG, Ins, A_7, TDKISSKTSNCQKGTAS, (SEQIDNO:3088); XM_005615442.2, AHI1, Ins, A_7, TEEKNRQIWRKNCT, (SEQIDNO:3090); XM_005617072.1, C2H10orf67, Ins, A_7, TEGERRDY, (SEQIDNO:3091); XM_005638009.2, CHD7, Ins, A_7, TEGLWRRGRS, (SEQIDNO:3092); XM_014121289.1, ELP4, Ins, A_7, TEKHFKNRNPESWITFMGR, (SEQIDNO:3093); XM_014112279.1, ANKRD31, Ins, A_7, TEKNYRENPK1, (SEQIDNO:3094); XM_005634655.1, MED12L, Ins, A_7, TEKRTRRQEIRKY, (SEQIDNO:3095); XM_546858.5, CIRH1A, Ins, A_7, TEREPPSLHSTF1, (SEQIDNO:3096); XM_014112442.1, BLM, Ins, A_7, TESCFSGKDVSERRSGKEVSWRTDRSV, (SEQIDNO:3097); XM_014112357.1, LCOR1, Ins, A_7, TFAKSQGESKTGEY, (SEQIDNO:3098); XM_005639326.1, FAM47E, Ins, A_7, TFFPGLPGL, (SEQIDNO:3099); XM_005621512.2, SMG1, Ins, A_7, TFLNYTESPGNIA, (SEQIDNO:3100); XM_014107721.1, LOC478037, Ins, A_7, TFRQGGRFRASLGAQSN, (SEQIDNO:3101); XM_005618541.2, FAM184B, Ins, A_7, TGGEAGYCQRQTDAAGASREPEN, (SEQIDNO:3102); NM_001003154.2, TRDN, Ins, A_7, TGKERKIRGTSKVVKEGTFSSK, (SEQIDNO:3103); XM_014118141.1, PM20D2, Ins, A_7, TGNRNFRRCNVEWLFRN, (SEQIDNO:3105); XM_545951.5, RHOH, Ins, A_7, TGPGSESKGLSGVLGPQQPGGSAGV, (SEQIDNO:3106); XM_005631421.2, SPTBN2, Ins, A_7, TGRFHEHHGCQWRADPRPAGGWTPAGV, (SEQIDNO:3107); XM_846354.4, BLOC1S2, Ins, A_7, TGSQVQEAGEAM, (SEQIDNO:3108); XM_003435518.3, CLCN5, Ins, A_7, TGWGCEYFHHLFHRAFSSDATIHPTHSQASEHPGSQPLHCD, (SEQIDNO:3109); XM_014116024.1, PCNX, Ins, A_7, TGYRIRCFNDHHCWSEVATILF, (SEQIDNO:3110); XM_014114846.1, ZNF644, Ins, A_7, THGILAFIIMC, (SEQIDNO:3111); XM_014114190.1, ZAN, Ins, A_7, THGPHRKTHCPQ, (SEQIDNO:3112); XM_014109297.1, OTUD6B, Ins, A_7, TINTCNETCIRLRRTLQFCYTVGEHSY, (SEQIDNO:3113); XM_014111592.1, GPRASP2, Ins, A_7, TIQCQSSIDICGS1, (SEQIDNO:3114); XM_848511.4, ZNF653, Ins, A_7, TKAEEKEATQRELPEERGDLVRGPQAPLPIRATPGRAGPHLWPVHHSCVAVRSWPPL LPGPALTPEATQ, (SEQIDNO:3115); XM_005622961.2, PRG4, Ins, A_7, TKDYTNSPKDDYIDNAQITPYLFSGSHAPNYHQPQPKT, (SEQIDNO:3116); XM_005619458.1, EMB, Ins, A_7, TKEKGTKLRNAFKKKSMCYHTVEKHQILLLFYVRT, (SEQIDNO:3117); XM_014115747.1, LOC102156002, Ins, A_7, TKKENFNRNQPKMEFRSRKRR, (SEQIDNO:3118); XM_014120175.1, WDR17, Ins, A_7, TKMVFRMFISSRWQ, (SEQIDNO:3119); XM_005616951.1, CCDC7, Ins, A_7, TKNIQKGKKHCS, (SEQIDNO:3120); XM_005638805.2, GRIK1, Ins, A_7, TKPWCREVSLFQCHHGRTGNLTQKSEKAKEKVKN, (SEQIDNO:3121); XM_005623792.2, SETD3, Ins, A_7, TKRSVCYF, (SEQIDNO:3122); XM_014107325.1, BRCA2, Ins, A_7, TKSFRYKRKSLAYSKSPSCATFRSGR, (SEQIDNO:3123); XM_847556.4, BRIP1, Ins, A_7, TKSMSVLHSTRTNRRCSHNILSLQLSSRCTNKGKYGYQSERTGCHFRRSS, (SEQIDNO:3124); XM_848173.4, ZFHX4, Ins, A_7, TLGSRPPRAERGRTSAAVCLLARERRTVGRE, (SEQIDNO:3125); XM_014119282.1, ANKS1B, Ins, A_7, TLLLRNCKGPFSKN, (SEQIDNO:3126); XM_014108599.1, RHNO1, Ins, A_7, TLPTFPESPAAIPTRTTGGPQTPLWLSPASHHPH, (SEQIDNO:3127); XM_005639670.2, CMBL, Ins, A_7, TLQSGISN, (SEQIDNO:3128); XM_014115877.1, FAM179B, Ins, A_7, TLSNKTFFCKE, (SEQIDNO:3129); XM_005619841.2, GUCY1A2, Ins, A_7, TMAHLKSESE, (SEQIDNO:3130); XM_014108595.1, TULP3, Ins, A_7, TMSFTIFSGRETQFCF, (SEQIDNO:3131); XM_005634064.2, CCDC168, Ins, A_7, TMSKDPEITSY, (SEQIDNO:3132); XM_534105.5, MS4A14, Ins, A_7, TNPTAAVPSFAIPSFSILFCKKAPTVIT, (SEQIDNO:3133); XM_014115573.1, EPB41L3, Ins, A_7, TNSKWCLALFI, (SEQIDNO:3134); XM_005629808.2, KAT6A, Ins, A_7, TNSSPKKEGPKTQTPQ, (SEQIDNO:3135); XM_005638661.2, SCAPER, Ins, A_7, TPASCERE, (SEQIDNO:3136); XM_005635912.2, AGAP1, Ins, A_7, TPEEEKHQQLQSRRALRHR, (SEQIDNO:3137); XM_548436.5, ODF2, Ins, A_7, TPETISNQQPEIS, (SEQIDNO:3139); XM_014112646.1, PCDH7, Ins, A_7, TPGRTRSTTSQHICGSRRQHLNWIRSIL, (SEQIDNO:3140); XM_005621522.2, NTAN1, Ins, A_7, TPISNQCTVSWKQSSALQEE, (SEQIDNO:3141); XM_014109066.1, SEC31B, Ins, A_7, TPQMDEKASRCFICFWGEAGYLWPPQHPCPSGATALPPPC1-HQSSYHRI, (SEQIDNO:3142); XM_005634369.2, EFHB, Ins, A_7, TPQRRSLC, (SEQIDNO:3143); XM_005631747.1, SARTI, Ins, A_7, TPWGERGGRDDGGGQHRRRHRAAAAAP-GAQKTQAPERRWREQRWRTSEAESGA WGRARGRAAARDRSRDTQRRARAGARPG, (SEQIDNO:3144); XM_014114507.1, LOC611144, Ins, A_7, TQASLWRKETFEM, (SEQIDNO:3145); XM_005638476.2, VPS13C, Ins, A-7, TQAVAQEL, (SEQIDNO:3146); XM_014114222.1, ZCWPW1, Ins, A_7, TQGKRPSRWTRWDPAKEDTEEISGK, (SEQIDNO:3147); XM_005624991.1, MED13, Ins, A_7, TQGRRWAI, (SEQIDNO:3148); XM_538266.5, TBK1, Ins, A_7, TQSQKYCQIICY, (SEQIDNO:3150); XM_005623020.2, ESCO1, Ins, A_7, TQSRASNSLYL, (SEQIDNO:3151); XM_005619413.2, RAI14, Ins, A_7, TQSSTTSCQSYSVE, (SEQIDNO:3152); XM_536334.4, HEATR1, Ins, A_7, TRAFSSVYFSFYKWREVSVFSRF, (SEQIDNO:3153); XM_014120511.1, KRCC1, Ins, A_7, TRGGTAQA, (SEQIDNO:3155); XM_014113201.1, MLLT4, Ins, A_7, TRLLPAQPLERTKLLPGICRDSCWHPRCLSGPERKTV, (SEQIDNO:3156); XM_014109582.1, RFX7, Ins, A_7, TRRHYNQWSD, (SEQIDNO:3157); XM_005629056.2, NASP, Ins, A_7, TRRPVSGKA, (SEQIDNO:3158); XM_005635616.2, CLCN3, Ins, A_7, TRRYCGQFSCVFCTAHPVSSSRKSTATEASEHS, (SEQIDNO:3159); XM_534035.5, PRKCDBP, Ins, A_7, TRSRGRGELRRGAGGVPGPAAAAHRVAEGTEPAKGLVRPQRPGLADTHAGQAAPP WARPER, (SEQIDNO:3160); XM_014113014.1, RANBP17, Ins, A_7, TSEDRCCENAKKPHE, (SEQIDNO:3162); XM_005623724.2, KCNK10, Ins, A_7, TSEPDQDPGHLNHPVHLGRLYCICDDPRCHFQN, (SEQIDNO:3163); XM_005622961.2, PRG4, Ins, A_7, TSHVPQAPCVNSYIYPRD, (SEQIDNO:3164); XM_535898.5, NUP153, Ins, A-7, TSIQLVCLWNAFPFTIVEFFSP, (SEQIDNO:3165); XM_014110108.1, ABI3BP, Ins, A_7, TSRNPRHAPPTLAT, (SEQIDNO:3166); XM_014111457.1, LOC100686985, Ins, A_7, TSVLLKEVRGKQYLWY, (SEQIDNO:3167); XM_005615498.2, STXBP5, Ins, A_7, TTACLRVPVLFSGNQ, (SEQIDNO:3168); XM_014117827.1, C11H9orf131, Ins, A_7, TTAEPRFQIP, (SEQIDNO:3169); XM_014107475.1, LOC106557767, Ins, A_7, TTEAGPGRRFPPSTAPGPPRPSPQTPLPGSNPESRSARPG, (SEQIDNO:3170); XM_014110825.1, LOC478773, Ins, A_7, TTRRSSGSSCSRICRIKRVQWCWWDRSFLREFFSSIKVELQE, (SEQIDNO:3172); XM_539305.3, ENAM, Ins, A_7, TTTKATFKAATTYPSTARRGRPATSGIPTIWQWAISLSTATMAGSTQGTTRLWTSAS QQ, (SEQIDNO:3173); XM_005635642.2, CEP44, Ins, A_7, TVSPMWICRMENPNYL, (SEQIDNO:3174); XM_003639982.3, TNKS2, Ins, A_7, TVYCSECQLQRH, (SEQIDNO:3175); XM_005615936.2, CD274, Ins, A_7, TWENDGCGKMLHPR, (SEQIDNO:3176); XM_005638869.2, DNAJC28, Ins, A_7, TWESNDTE, (SEQIDNO:3177); XM_005634064.2, CCDC168, Ins, A_7, TWIQFKSQNATDESK, (SEQIDNO:3178); XM_539558.4, C15H1orf50, Ins, A-7, TWQHLLPL, (SEQIDNO:3179); XM_005638063.2, ZC2HC1A, Ins, A_7, TWTHLPENCH, (SEQIDNO:3180); XM_005635807.1, TRIP12, Ins, A_7, TYCEQRGAAETSGVCNAGSR, (SEQIDNO:3181); XM_005617306.2, DIAPH1, Ins, A_8, ICAKEKSKRVKGVGFKDGPESLHLSGFLSHGLSRD, (SEQIDNO:3182); XM_014119671.1, LOC106559776, Ins, A_8, ICIFTSQVKESNNNMDWS, (SEQIDNO:3183); XM_005615312.2, ZNF407, Ins, A_8, ICSGNGFP, (SEQIDNO:3184); XM_005632220.2, RAD18, Ins, A_8, IDPSERSEHFFKDQRDTFYRKDSSAFLRCSCS, (SEQIDNO:3185); NM_001005760.1, LIFR, Ins, A_8, IFNHRSHSFKGTRYLERVEF, (SEQIDNO:3186); XM_005636132.2, MPHOSPH9, Ins, A_8, IFRNSHRHPC, (SEQIDNO:3187); XM_535118.4, ATP6VOD2, Ins, A_8, IGERNSGQVPPIGPFHRNGSCQHCGDTF, (SEQIDNO:3188); XM_014120072.1, WRN, Ins, A_8, IGKNSTAAKTS, (SEQIDNO:3189); XM_005637995.1, LOC102156503, Ins, A_8, IHESKNQQETL1, (SEQIDNO:3190); XM_535949.5, KLHL41, Ins, A_8, IHRLHPKSR, (SEQIDNO:3191); XM_005618961.2, DDX50, Ins, A_8, IKASVILR, (SEQIDNO:3192); XM_014119437.1, CEP290, Ins, A_8, IKEFRRVS, (SEQIDNO:3193); XM_532929.5, FAM98A, Ins, A_8, IKGDISKSST, (SEQIDNO:3195); XM_014119919.1, NUB1, Ins, A_8, IKLGSEML, (SEQIDNO:3196); XM_005623082.2, ANKRD12, Ins, A_8, IKVGKKHKR, (SEQIDNO:3197); XM_005633985.2, MYCBP2, Ins, A_8, ILVRICSGFFII, (SEQIDNO:3198); NM_001110501.1, VEGFA, Ins, A_8, INSRKGEGAKKKAQEIPSLWALLRAEKAFVCTRSADV, (SEQIDNO:3199); NM_001003175.2, VEGFA, Ins, A_8, INSRKGEGAKKKAQEIPV, (SEQIDNO:3200); XM_546767.5, LOC489647, Ins, A_8, IPLCSFPSCCVFNWECCGGYVGDCDHSDRPE, (SEQIDNO:3201); XM_005618620.2, WDR19, Ins, A_8, IRKLPCSNRS, (SEQIDNO:3202); XM_014114844.1, HFM1, Ins, A_8, IRNRDFPF, (SEQIDNO:3203); XM_005628633.1, STK31, Ins, A_8, IRSWSACPQEPQKPHSLMGA, (SEQIDNO:3204); XM_014122790.1, NUCB2, Ins, A_8, IRTRNSSIRAWWWKIEV, (SEQIDNO:3205); XM_014113891.1, CAMTA1, Ins, A_8, ISAEPACCCADPEVLPEL, (SEQIDNO:3206); XM_535150.5, MTPAP, Ins, A_8, ISEIFIPTWTY, (SEQIDNO:3207); NM_001003212.1, F8, Ins, A_8, ISGRDRKKGKINPGECGFASGTYYDWH, (SEQIDNO:3208); XM_003639633.3, HORMAD1, Ins, A_8, ISKDGCSSCVHQSRRPSDNFRMLPV, (SEQIDNO:3209); XM_014117518.1, FOXN2, Ins, A_8, ISNCKAPIL1, (SEQIDNO:3210); XM_534048.5, DENND5A, Ins, A_8, ITFQTPEAASLRP, (SEQIDNO:3211); XM_014120114.1, SORBS2, Ins, A_8, ITNSGTLSTTQKRELL, (SEQIDNO:3213); XM_535848.5, SMC4, Ins, A_8, IWQDSRNIWQIGGFRSN, (SEQIDNO:3214); XM_852167.4, ACVR2A, Ins, A_8, KAACFKRLLAETCWDGNAL, (SEQIDNO:3215); XM_532971.5, RNF103, Ins, A_8, KAAICTTPALVK, (SEQIDNO:3217); XM_014116133.1, UNC79, Ins, A_8, KAALFKTKIS, (SEQIDNO:3218); XM_539948.5, HGSNAT, Ins, A_8, KACRAEDGPGFAAHP, (SEQIDNO:3219); XM_543550.5, LOC486424, Ins, A_8, KAEEWKFCKAQLPILLLCCWQQGPFSLCLAHVSETAFGCHP, (SEQIDNO:3220); XM_535848.5, SMC4, Ins, A_8, KAEITRRKC, (SEQIDNO:3221); XM_005619774.2, C5H11orf57, Ins, A_8, KAEKKVTQKTEEKQKRSHRYNSRFLK, (SEQIDNO:3222); XM_005632059.2, ZXDC, Ins, A_8, KAERNWEQCRSLRSRSEENERWHGQSCSLPHKPNWLVVRELSGAQWRCARTSSSSRCAVRSGPVAAG, (SEQIDNO:3223); XM_005616873.2, CD3EAP, Ins, A_8, KAGAKRTRGFEASSSRSPP, (SEQIDNO:3224); XM_014112788.1, LSM11, Ins, A_8, KAKAQSGLPAGIHSTHKSDIHSR, (SEQIDNO:3225); XM_014119014.1, TULP2, Del, A_8, KAKPPITSSLWTPQTCLGMGTTLWAKSDLMSWALSSPSLTMG, (SEQIDNO:3226); XM_005615655.2, AKAP7, Ins, A_8, KAKRLSTQLFPIHSDHQQRDYERN, (SEQIDNO:3227); XM_014121537.1, ZNF197, Del, A_8, KALFYIRGSILERISMNVKTVVRSLVLTETSLTTRDYTMGKSHMNVESVGKLSS, (SEQIDNO:3228); XM_544717.5, HERC1, Del, A_8, KALWSWLMPWQPAASPPGCPHSIGNGLLNSLCALLLRMTATIKLLPKHSPIWEEISE NAPLSSWRLIRTG, (SEQIDNO:3229); XM_014107179.1, AURKA, Ins, A_8, KAMGFGRF, (SEQIDNO:3230); XM_014112827.1, ZNF365, Ins, A_8, KANSNCEHH1, (SEQIDNO:3231); XM_005620256.1, LEXM, Ins, A_8, KAQGTDEFYELRGRT, (SEQIDNO:3233); XM_014106985.1, ZMYND8, Ins, A_8, KAQTGQPSGD, (SEQIDNO:3234); XM_014106985.1, ZMYND8, Ins, A-8, KARHQGNRKQ, (SEQIDNO:3235); XM_005616415.2, LOC102151906, Ins, A_8, KAVCEAGGVSFEEAYGKMCLEGSQYPIPRSPVRSCESWGCFGVRPRWRSGGPPKEE SHELGLGKEFCPHEKEEEGELGPCFIRPC, (SEQIDNO:3236); XM_014115507.1, PIEZO2, Ins, A_8, KAVVAALG, (SEQIDNO:3237); XM_014109240.1, STAU2, Ins, A_8, KCCGSNAVTAWL, (SEQIDNO:3238); XM_014122842.1, CCDC81, Ins, A_8, KCCLQSRSC, (SEQIDNO:3239); XM_014117230.1, C1H9orf3, Del, A_8, KCGNHFSSN, (SEQIDNO:3240); XM_014114898.1, LRRIQ3, Ins, A_8, KCGTKTNCKR, (SEQIDNO:3241); XM_533784.5, FAM208A, Ins, A_8, KCGWGLRHRRYEKQNCLEEEA, (SEQIDNO:3242); XM_003431635.3, RANBP6, Ins, A_8, KCHCYRELYFSSREDSEV, (SEQIDNO:3243); XM_005628995.2, ZCCHC11, Ins, A_8, KCINRCGI, (SEQIDNO:3244); XM_014113324.1, CCDC15, Ins, A_8, KCINVPRW, (SEQIDNO:3245); XM_014109213.1, CSPP1, Ins, A_8, KCNYGVIRNEKTAS, (SEQIDNO:3246); NM_001003176.1, RPE65, Ins, A_8, KCQKGSAA, (SEQIDNO:3247); XM_543895.5, FRMPD2, Ins, A_8, KCQWFGIQLRADEERELQSSQE, (SEQIDNO:3248); XM_014121374.1, NAA15, Ins, A_8, KCRKRKAAEKSEKEKG, (SEQIDNO:3249); XM_005620224.2, USP1, Ins, A_8, KCRSYWTSWRTKEQSRL, (SEQIDNO:3250); XM_538328.5, SMC1B, Ins, A_8, KCSCRTQTCKIRERRGRTLSESA, (SEQIDNO:3251); XM_547684.5, SPIRE1, Ins, A_8, KCSRNHPGLHQIKTPFKAGCSQKTETHSTTTTEPP, (SEQIDNO:3252); XM_005638791.2, LTN1, Ins, A_8, KCVSKAVSCGA, (SEQIDNO:3253); XM_005627838.2, UBR5, Del, A_8, KCWRKLEQKIKSPNLALVFLQCQTSLLVPRYA, (SEQIDNO:3254); XM_845089.4, CXCL13, Ins, A_8, KCYFNSTSSSAEEKNQ1, (SEQIDNO:3255); XM_005622133.1, ZRANB2, Del, A_8, KDEQDHGHPKGTTGHLLDHPILVPVQVQKRN, (SEQIDNO:3256); XM_003432196.3, MAP4K3, Del, A_8, KDLLLRSYYSILLSHN1, (SEQIDNO:3258); XM_014110862.1, PLA2R1, Del, A_8, KDLYAKWKQVFMQ, (SEQIDNO:3259); XM_014113698.1, SGIP1, Ins, A_8, KDPEDSASPHLLLLAQSPLVNSVSAAQPT, (SEQIDNO:3260); XM_014113688.1, SGIP1, Ins, A_8, KDPEDSASPHLLLLAQSPLVNSVSAQPT, (SEQIDNO:3261); XM_014113703.1, SGIP1, Ins, A_8, KDPEDSASPHLLLLAQSPLVNSVSEEKQWGTKWILCGN, (SEQIDNO:3262); XM_844389.4, DNAJC1, Ins, A_8, KDRQQECGCIKTWCFRKK, (SEQIDNO:3263); XM_005625788.2, ARFGAP3, Ins, A_8, KDRVGETWHGIWKLQKWYFTFRDFRYADHRTGNTHRSKAQKEVQ, (SEQIDNO:3264); XM_005621933.2, KIAA1107, Ins, A_8, KDSGEGSTTKDTRLQFWKVH, (SEQIDNO:3265); XM_005615983.2, PHF2, Ins, A_8, KDSQNREDAQAVQSSQVPQTPQAPEAPQTAEA-QGWRQEKREEVQGGGLAHHPQPG PAGGTH-QGGTDQN, (SEQIDNO:3266); XM_005631775.2, ZNF330, Ins, A_8, KDWCEEEGREPSGT, (SEQIDNO: 3267); XM_844219.5, RPL22, Ins, A_8, KEASSEVYP, (SEQIDNO:3269); NM_001003113.1, KCNC1, Ins, A_8, KEAYSTATAAGISQLL, (SEQIDNO:3270); XM_014114295.1, LOC106558887, Ins, A_8, KEDPHVTYIPTTQDLASTKAAEISSKERPQEKQA, (SEQIDNO:3271); XM_005621118.2, USP42, Ins, A_8, KEEEKEEALQEIRGLC, (SEQIDNO:3272); XM_848505.4, TWISTNB, Ins, A_8, KEEERPRV1, (SEQIDNO:3273); XM_014113982.1, CCDC79, Del, A_8, KEEFVKTLLKKK, (SEQIDNO:3274); XM_546032.4, CETN3, Del, A_8, KEENSLKNRNKKLKMLLN-CLTQTKMKQ, (SEQIDNO:3275); XM_005617279.2, HBEGF, Ins, A_8, KEERQRLREEERPVS-SEIQGLLHPWRMQICEGAPGSILHLPPRLPWREVP-WAEPSSRK SLNLRPYNHLGCGGCGAVICLSACHR-GASHV, (SEQIDNO:3276); XM_005618038.2, TSLP, Del, A_8, KEESQQINAGNKSHT, (SEQIDNO:3277); XM_014121882.1, MAP4, Ins, A_8, KEETKAKEIS-SSPGWGTLG, (SEQIDNO:3278); XM_531629.4, PA2G4, Ins, A_8, KEGLQDCRECHQWGNIRRE, (SEQIDNO: 3279); XM_535515.5, ZNF609, Ins, A_8, KEG-VFQGTRKSSDPWEGVSSRRRQKPIQRIIRRWDEDG-GAPEWLIRPPPKPPG, (SEQIDNO:3280); XM_535463.5, BLOC1S6, Del, A_8, KEHLNYSRR-GRKKSWKGSSNARRNLKEKSS, (SEQIDNO:3281); XM_535194.5, KIN, Ins, A_8, KEICPRRNHGD, (SEQIDNO:3282); XM_014110202.1, ABHD10, Del, A_8, KEIEMKGMWDMPSKYS, (SEQIDNO:3283); XM_848169.4, KIAA2026, Ins, A_8, KEIERCFK, (SEQIDNO:3284); XM_014106856.1, PLCB1, Del, A_8, KEIEVLKCLLSWKPKD, (SEQIDNO:3285); XM_005626884.1, CYLC2, Ins, A_8, KEIKTIPT-TRQYSFRI, (SEQIDNO:3286); XM_844090.4, INO80, Ins, A-8, KEIQGGKET, (SEQIDNO:3287); XM_014120797.1, CBLL1, Del, A_8, KEIRCVQAV-VILCSESSSVHEVLSSCVALFKGAREHTCLSETYRL-ISTTAI, (SEQIDNO:3288); XM_533327.6, DDX18, Ins, A_8, KENHNSQWRSRNTASQFRIKKKEEEKEKNGG, (SEQIDNO:3289); XM_014119005.1, MPP6, Ins, A_8, KEKDDVSHNQKCRI, (SEQIDNO:3290); XM_847157.4, PHF20, Ins, A_8, KEKEKENQT, (SEQIDNO:3291); XM_014118938.1, KRIT1, Ins, A_8, KEKESFVGN, (SEQIDNO:3292); XM_542577.3, NUFIP1, Ins, A_8, KEKKGTSFSLF1, (SEQIDNO:3293); XM_014116982.1, TTF1, Ins, A_8, KEKNFTPPGT, (SEQIDNO:3294); XM_005629478.2, LUC7L2, Del, A_8, KEKQRK-FIGILCQLPVSNNRNFESVKSALPI, (SEQIDNO:3295); XM_014117385.1, HMGXB4, Ins, A_8, KEKRGERQR-ERERRKAKKEEHVSLPG11, (SEQIDNO:3296); XM_844389.4, DNAJC1, Del, A_8, KEKRKKRQAARVWMHQNLVLQKKMKDY, (SEQIDNO:3297); XM_005640290.2, PPIG, Del, A_8, KEKRNIGKIPEN-TRKKRRSERKARKVHLVKVRLKILKHNPSLLSVQKRSL-LYLKIDS, (SEQIDNO:3298); XM_005622195.2, NAV1, Ins, A_8, KELAAKFLQQSLQHKKGTQVSFFVLRHRGD-CHTRLLRPVIPQTTARLHGDRLALHQ VLQLLLCGH, (SEQIDNO:3299); XM_014109383.1, SLC24A1, Del, A_8, KELMKVKVNSKQKTVK, (SEQIDNO:3300); XM_014114461.1, LOC612426, Del, A_8, KELQQIK-KKSVHWVHGSLM, (SEQIDNO:3301); XM_005639390.2, LOC487951, Ins, A_8, KENALHPGL, (SEQIDNO:3302); XM_014108716.1, C27H12orf40, Del, A_8, KENLKVITKRRYHRMKARNIQ, (SEQIDNO: 3303); XM_005623751.2, BTBD7, Ins, A_8, KENLWPCHPQKEVYQASKI, (SEQIDNO:3304); XM_014109043.1, CCDC186, Del, A_8, KEQKQRSSI, (SEQIDNO:3305); XM_005623762.2, DDX24, Ins, A_8, KERKKKIGAFPGYCSKGAQKSKDMDA, (SEQIDNO: 3306); XM_014115338.1, ASHIL, Ins, A_8, KERKKSSVD, (SEQIDNO:3307); XM_005623148.2, NLRP3, Ins, A_8, KERLLQEVQKTREEQIPVY, (SEQIDNO:3308); XM_005619358.2, ZNF131, Del, A_8, KER-LQKLQMLSLSHCHLQNQNLLKLR, (SEQIDNO:3309); XM_014110834.1, CWC22, Ins, A_8, KERREKKFFFRK, (SEQIDNO:3310); XM_534970.5, FRA10AC1, Del, A_8, KERTKPKKMKSHHIKNPDYLLQKRPLRKRIKG1HP-QRNQKVV, (SEQIDNO:3311); XM_005626022.2, EIF5B, Ins, A_8, KERTKRQKTKF, (SEQIDNO:3312); XM_014117434.1, IL1R1, Del, A_8, KERVQSSPCLIF, (SEQIDNO:3313); XM_014109645.1, ZWILCH, Del, A_8, KESIMIHLSMRLMFKCS, (SEQIDNO:3314); NM_001005870.1, RXFP2, Ins, A_8, KESLHIHCVDR, (SEQIDNO:3315); XM_014108751.1, TRIM23, Ins, A_8, KFCFIGAFGTTAEWTYWSMWSCRRSHWNI-WRAFSIGTRS, (SEQIDNO:3317); XM_544360.5, TRIM23, Ins, A_8, KFCFIGAFGT-TAEWTYWSMWSCRRSHWNIWREHHSLR, (SEQIDNO:3318); XM_014120122.1, SORBS2, Ins, A_8, KFDPQKTD, (SEQIDNO:3319); XM_540966.5, QRFPR, Ins, A_8, KFFICSLLLHSKRNLISST, (SEQIDNO:3320); XM_005623926.1, SERPINA14, Del, A_8, KFFPR-WASVMCLLQEQTSQASQRRISQLSLRRCMKPQWR, (SEQIDNO:3321); XM_532674.4, HCFC2, Ins, A_8, KFKTKTKSWTLCCCNWHSIVFLEWKRWLQKSTE, (SEQIDNO:3322); XM_542610.5, DIS3, Del, A_8, KFMKNSQNMPCFENTLLLLHQIMKFLLRQLN-PRIWKLKLIQPNPWLTLWTGRIPRLS HISTLS, (SEQIDNO:3324); XM_014111472.1, CYLC1, Del, A_8, KFPKGHLFT, (SEQIDNO:3325); XM_014118166.1, MMS22L, Del, A_8, KFPVQGCN, (SEQIDNO:3326); XM_541834.1, HESX1, Ins, A_8, KFQLKSPGRDRKL, (SEQIDNO:3327); XM_005635554.2, SKA3, Ins, A_8, KFSGYHENKRVFPEVWI, (SEQIDNO:3328); XM_014116745.1, HEATR6, Del, A_8, KFSMATGQPLY-LIHLSLAALSPCP, (SEQIDNO:3329); XM_535814.5, TTC14, Ins, A_8, KFTSKFTQYI, (SEQIDNO:3330); XM_536004.5, INPP1, Del, A_8, KFWEKNQMSLLTNWGKRLS, (SEQIDNO:3331); XM_014116017.1, ADAM20, Ins, A_8, KFWYKAWSCLRWRNMPSSF, (SEQIDNO:3332); XM_849638.4, LOC611915, Del, A_8, KFYKASMVMEH, (SEQIDNO:3333); XM_005624533.2, TOP2A, Ins, A_8, KGCTKRNQKGSRLKF, (SEQIDNO:3334); XM_014107459.1, CCL20, Ins, A_8, KGCVCRSKEE-MGETDCASPQP, (SEQIDNO:3335); XM_005626884.1, CYLC2, Del, A_8, KGDQNHPNYETIQFSYMMQIN, (SEQIDNO:3336); XM_005618163.2, MSH3, Ins, A_8, KGEHFHWNRGSAACHR, (SEQIDNO:3337); XM_005620248.2, C5H1orf168, Del, A_8, KGEKMLKNQKGISLEQRSKT, (SEQIDNO:3338); XM_005615362.2, LMAN1, Ins, A_8, KGGIPEGPS, (SEQIDNO:3340); XM_546411.5, SRPR, Ins, A_8, KGGQE-GEL, (SEQIDNO:3341); XM_014111745.1, CXHXorf23, Ins, A_8, KGICKHCHNNL, (SEQIDNO:3342); XM 005626849.2, TSTD2, Ins, A_8, KGICPFRQNQRNSSTFF, (SEQIDNO:3343); XM_014112635.1, LIAS, Ins, A_8, KGILTKWTRPSRFCIWRSCRQEQVG, (SEQIDNO:

3344); XM_014115338.1, ASH1L, Del, A_8, KGKEEKLG-GLKWWQEAHAGLQKG, (SEQIDNO:3345); XM_014116142.1, CLMN, Ins, A_8, KGKKEACGPRRKFSNSTRHRPILR, (SEQIDNO:3346); XM_005625956.2, APPL2, Ins, A_8, KGKREGKD, (SEQIDNO:3347); XM_014112733.1, ARID4B, Ins, A_8, KGKRQCPT1, (SEQIDNO:3348); XM_014109628.1, UNC13C, Ins, A_8, KGKSSAEKGSRFSYCWPDQNPQIF, (SEQIDNO:3349); XM_544679.5, TMOD3, Del, A_8, KGKYLSRNRNLYRRSQKKKYVLIQN, (SEQIDNO:3350); XM_005637332.2, KDM5A, Del, A_8, KGLAGRLKK, (SEQIDNO:3351); XM_005624533.2, TOP2A, Del, A_8, KGLHQKEPKRIQA, (SEQIDNO:3352); XM_014110313.1, TRIO, Ins, A_8, KGLLDARIPV, (SEQIDNO:3353); XM_014111557.1, TRPC5, Ins, A_8, KGLPRATSHQNCAKSQWHPREVKI, (SEQIDNO:3354); XM_014107179.1, AURKA, Del, A_8, KGNGLWKILKLV AHWVKESLVMFTWQGKNKASLSWLLKYYLKLNW-RKQELNIS, (SEQIDNO:3355); XM_014120784.1, PC10, Ins, A_8, KGNRYSSGDPNSYSYTAS, (SEQIDNO:3356); NM_001003306.2, ATP1A1, Ins, A_8, KGQERKGYG, (SEQIDNO:3357); XM_014119891.1, UBN2, Ins, A_8, KGRAGKQLGENRAPARAKAEGQNSGDGGATQSSVY, (SEQIDNO:3358); XM_014114461.1, LOC612426, Ins, A_8, KGRFLAAE, (SEQIDNO:3359); XM_014116686.1, LOC100686205, Ins, A_8, KGRGASVGDICGTVLCFAD-VAATICKRQHCLDGTVLPTHGSVPI, (SEQIDNO:3360); XM_005627814.2, POPI, Ins, A_8, KGRMESRSRGHVSGDSQVYHCFYFCSGPSC, (SEQIDNO:3361); XM_014107581.1, NUGGC, Del, A_8, KGRSMSLSPPLFRTTSSPVMKRQLRSLARKHVRE, (SEQIDNO:3362); XM_014107402.1, ZMYM2, Ins, A-8, KGSQEKSCIRIPVS, (SEQIDNO:3363); XM_005626885.1, LOC102156133, Ins, A_8, KGS-REENRRDKVAS, (SEQIDNO:3364); XM_014120722.1, SYCP1, Ins, A_8, KGYSRKQATEC1, (SEQIDNO:3365); XM_014112114.1, LOC102151511, Del, A_8, KHCRI-SETPQKPLNQQKAQLLQK, (SEQIDNO:3366); XM_005640182.2, PDE1A, Del, A_8, KHFAL-NYNVGVLRVSQNHSNIS-SKRKLKMNQKDCWILKMSSVTFRQTQSHQKYGT GWRPPSRGKWG, (SEQIDNO:3367); XM_543143.5, B3GLCT, Ins, A_8, KHLKASNKSHTGTP, (SEQIDNO:3368); XM_003435295.1, SLFN5, Ins, A_8, KHLPGSDLENLHEK, (SEQIDNO:3369); XM_847012.4, PDCD1LG2, Ins, A_8, KHNKKLYHRRKEGSGRSYL, (SEQIDNO:3370); XM_014119900.1, WDR60, Ins, A_8, KHQAGLCSVQ, (SEQIDNO:3371); XM_844731.4, UBE4B, Del, A_8, KHQRCAASQQSASFSATSAHSAYP-ILR, (SEQIDNO:3373); XM_014114059.1, C5AR1, Ins, A_8, KHSLDPKGYGVSPELWTPASGLHEFQH-PRVPRLWHCHPGPQHICG, (SEQIDNO:3374); XM_005628506.2, ANKIB1, Ins, A_8, KHTPTLCC-CLRDENLC, (SEQIDNO:3375); XM_847165.4, CCDC88A, Del, A_8, KHWMVLKTLLFS, (SEQIDNO:3376); XM_014121431.1, INTU, Del, A_8, KIAMTMSQCPF, (SEQIDNO:3377); XM_014110870.1, FSIP2, Del, A_8, KIANHLQRLLLEEAKLNFVRGD, (SEQIDNO:3378); XM_014120778.1, CACNA2D1, Del, A_8, KIERKILHCCGRCLAVPQA, (SEQIDNO:3379); XM_014109263.1, ST18, Del, A_8, KIESWTKLHP, (SEQIDNO:3380); XM_005628484.2, C14H7orf62, Del, A_8, KIFLTIMSKCFSQF, (SEQIDNO:3381); XM_014108759.1, ZFAND4, Del, A_8, KIFQETCH-LIMKMTLFYFQLQKNA, (SEQIDNO:3382); XM_014112381.1, LINS1, Del, A_8, KIFSPIMPQHF, (SEQIDNO:3383); XM_540966.5, QRFPR, Del, A_8, KIFYLQFVIA, (SEQIDNO:3384); XM_005619248.2, CLINT1, Del, A_8, KIGEEFTSHCCF, (SEQIDNO:3385); XM_014121533.1, TAMM41, Del, A_8, KIGTITLS, (SEQIDNO:3386); XM_005628375.2, CEP41, Del, A_8, KIID-TERMSSSRD, (SEQIDNO:3387); XM_014107151.1, SYCP2, Del, A_8, KIIKISQIQNQRMNKNFHFRLKRNC, (SEQIDNO:3388); XM_005626702.1, TOPORS, Del, A_8, KIITVKGSITTMKGTDQEACPVIDQKLHLQGLTG, (SEQIDNO:3389); XM_532307.5, NUDCD1, Del, A_8, KIKIIKNTKLLSVIFSVGSQCHIMLL, (SEQIDNO:3390); XM_005626023.2, EIF5B, Del, A_8, KIK-KISQVLMWRVGMKMMIPPSK-LRRWPKRRQKRKSVKEKREMKKKQNYGS, (SEQIDNO:3391); XM_014117392.1, KIAA1033, Del, A_8, KIKLELLSLMMGLPWVWLTF, (SEQIDNO:3392); XM_014109972.1, C32H4orf36, Del, A_8, KIKPLRMFASLLQNPSNLKGSMK, (SEQIDNO:3393); XM_005637551.2, HELLS, Del, A_8, KIKRRMRK-KAPLLISV, (SEQIDNO:3394); XM_545015.5, TBCK, Del, A_8, KIKSGKKRGLTF11, (SEQIDNO:3395); XM_014115144.1, C7H1orf27, Del, A_8, KILKKSFTSSLTEFLSPFRDL1, (SEQIDNO:3396); XM_014115932.1, KIAA0586, Del, A-8, KILLSLLY-RYCPMWILIAFQMVVLMLNLCLVPKKNLLL, (SEQIDNO:3397); XM_544360.5, TRIM23, Del, A_8, KILLY-WSFWNDCRMDILVNVELQKKPLEYLERASFVAMK-MKLTLRLYIALYVQLIC AQSVLKLLILQRH, (SEQIDNO:3398); XM_014108751.1, TRIM23, Del, A_8, KILLYWSFWNDCRMDILVNVELQKKPLEYLE-SIQYWNQKLTRSEHQF, (SEQIDNO:3399); XM_536500.4, NUP155, Del, A_8, KILRVLGFISIN-MENQKKTSWDCRLSKKD, (SEQIDNO:3400); XM_849421.4, YY1, Del, A_8, KILTMRQWLKSRSLERTPLLIIQST, (SEQIDNO:3401); XM_544974.4, PKD2, Del, A_8, KILWMTFLRV, (SEQIDNO:3402); XM_014122434.1, TMEM236, Del, A_8, KIMVLRLPYLKHYLTCQFLWF, (SEQIDNO:3403); XM_005639749.2, FXR1, Del, A_8, KIPSLNAQWMFLRI, (SEQIDNO:3405); XM_532674.4, HCFC2, Del, A_8, KIQDQDQELDTVLLQLALDCIFGVEEMATKKH, (SEQIDNO:3407); XM_014120122.1, SORBS2, Del, A_8, KIRPPKNRLRRQNVKHPCLRP, (SEQIDNO:3408); XM_005617578.1, HEATR3, Del, A_8, KIRTEILLRT, (SEQIDNO:3409); XM_014118268.1, LAMA4, Del, A_8, KIS-NWSRRKLWELVMDAQKTLLYLAE-HISMDRVSLLQFRKCLSSMALKEVLISERYS QMGCYSIMLQGLTCSPFLWITARWSWT, (SEQIDNO:3410); XM_005628995.2, ZCCHC11, Del, A_8, KISK-MIFV, (SEQIDNO:3411); XM_005637237.2, CHD4, Del, A_8, KISNNVSC-SILQMVVLLSCTPFGRMRSGQPQSLRRLTRF-GIGGTTTGCWLAS, (SEQIDNO:3412); XM_541834.1, HESX1, Del, A_8, KISTQISWKR, (SEQIDNO:3414); XM_005634301.2, NKTR, Del, A_8, KITLQVRGTAAALKRDFTINM, (SEQIDNO:3416); XM_014113449.1, CUL5, Del, A_8, KITVVENYIGIIS-CQMEL, (SEQIDNO:3417); XM_014109514.1, MTFMT, Del, A-8, KIVAMQQCI, (SEQIDNO:3418); XM_014120568.1, CD58, Del, A_8, KIWIKSLNGKNT-MAAELSHL1, (SEQIDNO:3419); XM_005623463.2, LOC490717, Del, A_8, KIWNGNLLSSRDLAKGTMIDPI-TIK, (SEQIDNO:3420); XM_535814.5, TTC14, Del, A_8, KNLKNSIYLIR, (SEQIDNO:3421); XM_005619358.2, ZNF131, Ins, A_8, KKDCRNFKCYH, (SEQIDNO:3422); XM_003639706.3, RIF1, Del, A_8, KKDVRKKKRP-FRKVHCM, (SEQIDNO:3423); XM_014117434.1, IL1R1, Ins, A_8, KKEYNHHHA, (SEQIDNO:3424); XM_546524.5, DLAT, Del, A_8, KKGKKSMRVN, (SE- QIDNO:3425); XM_534970.5, FRA10AC1, Ins, A_8, KKGQNQKR, (SEQIDNO:3426); XM_005638329.2, ADAL, Del, A_8, KKHKYFWICFLTELGMGHFSAP-LRKDPLSW, (SEQIDNO:3427); XM_005620105.2, NCOR1, Del, A_8, KKKKRKMKKKKMKRRTLKRT-PRKRTRRKVQQKKRKRENRPRPGDERPPTVRAAE RAGSPGP, (SEQIDNO:3428); XM_014118133.1, ZNF292, Del, A_8, KKKMKWMS, (SEQIDNO:3429); XM_014118082.1, DST, Del, A_8, KKLCLLVKNRWML-SKSLLSH, (SEQIDNO:3431); XM_014112817.1, FAM13C, Del, A_8, KKLNNQPYPCPIYMR-PLCLYFLTISEKLGLTRRDFGKP, (SEQIDNO:3432); XM_005615829.2, CEP78, Del, A_8, KKMNCLE-IADLLQRK, (SEQIDNO:3433); XM_014115201.1, KIFAP3, Del, A_8, KKNQASLKIHLLLKEWRLMKLLTLMTWMINTL-SYYMKIFLTKFGVLL, (SEQIDNO:3434); XM_005628212.2, LOC475149, Del, A_8, KKPNKNTQITFSLTSFTL, (SEQIDNO:3435); XM_005620231.2, INAD1, Del, A_8, KKRDKELLHLQ, (SEQIDNO:3436); XM_014120622.1, SPAG17, Del, A_8, KKRIILQKM, (SEQIDNO:3437); XM_005623419.2, WDHD1, Del, A_8, KKRKISEKS, (SEQIDNO:3438); XM_005634532.2, TFDP2, Del, A_8, KKSSGLA-CLPILLRNVKILR, (SEQIDNO:3439); XM_014112829.1, JMJD1C, Del, A_8, KKTKNLPLKSKLKKRENKTILILQI-AEHHLLHPRIMNRVQLYEIC, (SEQIDNO:3440); NM_001003212.1, F8, Del, A_8, KKTLCHYVQKIQNHP-PRYRSCQIG, (SEQIDNO:3441); XM_844150.4, FAM155B, Ins, A_8, KLAQRPLSELHSLLLRHLHGLG-LAAGHGPPRQPGLQPGHPAGGPAGCSGQPGLRGL GGL, (SEQIDNO:3443); XM_548323.4, CLUH, Ins, A_8, KLCCATEEKGPAPPIREDCHPVPGVQLDSPPGGACH-GLCACGGCLHLEAG1, (SEQIDNO:3444); XM_005626458.2, CSNKIG3, Del, A_8, KLDVAILENYD, (SEQIDNO:3445); XM_535467.5, SLC12A1, Ins, A_8, KLEESSLDRD, (SEQIDNO:3446); XM_005617468.2, BDP1, Del, A_8, KLEETTLPERRYQK, (SEQIDNO:3447); XM_005619248.2, CLINT1, Ins, A_8, KLEKSLQVI-AASSLPHKEWIRACCYKCQRTHL, (SEQIDNO:3448); XM_014121533.1, TAMM41, Ins, A_8, KLEPLL-FPESFGAQDYHHCPE, (SEQIDNO:3449); XM_545208.5, PIK3CA, Del, A_8, KLEVCCYHLNN, (SEQIDNO:3450); XM_005625593.2, HE1B, Ins, A_8, KLGQERSMEVFFGESSGCG, (SEQIDNO:3451); XM_545493.4, IFIH1, Del, A_8, KLHEKEIEKTVFVQSI, (SEQIDNO:3452); NM_001197076.1, ASPM, Ins, A_8, KLHKLQGFGYHNSKMVSRY, (SEQIDNO:3453); XM_014111710.1, BRWD3, Ins, A_8, KLHPRSSNPQLE, (SEQIDNO:3454); XM_535265.5, RAD17, Del, A_8, KLIRFLKTKKSKLL-VAKMFLSFSSEHWGKYYIVKEHL, (SEQIDNO:3456); XM_005623158.1, TRIPI 1, Del, A_8, KLKNLRIK, (SEQIDNO:3457); XM_005621973.2, CLCA4, Del, A_8, KLKQQDVPQVLLD, (SEQIDNO:3458); XM_005635545.2, SACS, Del, A_8, KLKTYRSV-LAQTRTFF, (SEQIDNO:3459); XM_014111654.1, LOC106558442, Del, A_8, KLLEHPLLP, (SEQIDNO:3460); XM_014109514.1, MTFMT, Ins, A_8, KLLLCN-SAL, (SEQIDNO:3461); XM_532916.5, SLC4A1AP, Del, A_8, KLLVQANFQQHFPP-NIQKMTQTTVCGSHLKAKVEMAGPI, (SEQIDNO:3462); XM_014120253.1, SLC4A1AP, Del, A_8, KLL-VQANFQQHFPPNIQKMTQTTVCGSHLKVGQVGTP-WFF, (SEQIDNO:3463); XM_014120252.1, SLC4A1AP, Del, A_8, KLLVQANFQQHFPP-NIQKMTQTTVCGSHLKVVISAS, (SEQIDNO:3464); XM_005630696.2, LOC608067, Ins, A_8, KLPLHVWLGPSIL, (SEQIDNO:3465); XM_005621465.2, ACSM3, Del, A_8, KLQHLTNIPER, (SEQIDNO:3466); XM_534728.4, THOC5, Del, A_8, KLQIQPISISLIKLAS, (SEQIDNO:3467); XM_541402.3, LOC484287, Del, A_8, KLRKSCIG, (SEQIDNO:3468); XM_014119702.1, CFAP54, Del, A_8, KLRLKWILHGFFYCATIFICKGLII, (SEQIDNO:3469); XM_014114998.1, TOR1AP1, Del, A_8, KLRNGLNQPQE, (SEQIDNO:3470); XM_005630347.2, CEBPZ, Del, A_8, KLRQKKLCLTVPV1, (SEQIDNO:3471); XM_005623463.2, LOC490717, Ins, A_8, KLRRI-SIVPGFEI, (SEQIDNO:3472); XM_014116753.1, LIG3, Del, A_8, KLRTSQSWKAGKSWKIMRRNR, (SEQIDNO:3473); XM_014108490.1, GPR19, Ins, A_8, KLRWHFRN-SSHGQNYNQRID1, (SEQIDNO:3474); XM_849218.4, LOC611538, Ins, A_8, KLSKNRKHN1, (SEQIDNO:3475); XM_543181.4, CENPJ, Del, A_8, KLS-LIIEKMYPSVQNMLVAKSGIRHKVKTNFL-FRQDWSAACLLVAPKMRP, (SEQIDNO:3477); XM_005638394.2, CEP152, Del, A_8, KLSVICFV-IFKRVRKELQKW, (SEQIDNO:3478); XM_005638476.2, VPS13C, Del, A_8, KLVCDALSSVTL, (SEQIDNO:3479); XM_014111157.1, COPA, Ins, A_8, KLVPWCSGVR-RERNNWG, (SEQIDNO:3480); XM_543181.4, CENPJ, Del, A_8, KLVVLQKWLILKKDLLKLQSEKGNRHLKTT, (SEQIDNO:3481); XM_539294.3, LOC482175, Del, A_8, KMANTTAGHL, (SEQIDNO:3482); XM_532580.5, EPS15, Del, A_8, KMCLRKYRSKVKMYPQHCHQR-LELQQDPVHHHLGKDPSTNWILLILLN, (SEQIDNO:3483); XM_005630332.2, FEZ2, Del, A_8, KMDHHLLKIFKY, (SEQIDNO:3484); XM_005636122.2, SBNO1, Del, A_8, KMEDMIWEF, (SEQIDNO:3485); XM_545754.6, ATP1A4, Del, A_8, KMGPTPSPRPPQPRSGSSSVASCSGASPSCCGSGPS-SASWPTASRCTTRRTRPRTTCT WAWSWLLWS, (SEQIDNO:3486); XM_014113324.1, CCDC15, Del, A_8, KMHQCSQMVEGKPFPLKRNLTLRNLHLLR, (SEQIDNO:3487); XM_014113138.1, C4H5orf42, Del, A_8, KMIHCSVVSRREDWNLHLCLTQYMQKIM-SRKQIKPLQNCILSRKISLQHGL, (SEQIDNO:3488); XM_014109179.1, ATP8B1, Del, A_8, KMILFQLTSCYC-PALSLTASAMSKQLNWMEKPI, (SEQIDNO:3489); XM_537881.5, OSBPL1A, Del, A_8, KMIRKILKRRK-TANR, (SEQIDNO:3490); XM_005620587.1, ZCCHC14, Del, A_8, KMKDMLNVPLRSCGLILQ, (SEQIDNO:3491); XM_014113954.1, ZCCHC14, Del, A_8, KMKDMLNVPLSYPSCTLKKIWRSSFIA, (SEQIDNO:3492); XM_535952.5, SSB, Del, A_8, KMKKESKIK, (SEQIDNO:3493); XM_014107377.1, NBEA, Del, A_8, KMKKRIMVH, (SEQIDNO:3494); XM_535743.5, CFAP44, Del, A_8, KMKLPSSRTKKKHSMLV-SKQPLEKTINLLISS, (SEQIDNO:3495); XM_857314.4, PHF20L1, Del, A_8, KMKLTLAVLPTLRNLHCY-PQLCLQGRLAARNANMNLEILLGV, (SEQIDNO:3496); XM_843419.4, MICU3, Del, A_8, KMKREKQKEMK-KNVQCCVFNFMDTILLLIVYLKQMLRNLSPEAIGIH, (SEQIDNO:3497); XM_005625970.1, SH3RF3, Del, A_8, KMKRKRRRVGC, (SEQIDNO:3498); XM_540106.4, UBXN2A, Del, A_8, KMKYVCPRSLCSSPSQGKVTDW-EVPHQKLFLSQRVLKLRIKHCLLFN, (SEQIDNO:3499); XM_536785.5, WDR59, Del, A_8, KMLIAS-PPVTTGMCGYGTSGNPVQQWNISQLTSLKSMAWP-GTQMLSTFLLLPVKTT LSSSGITASLGNTSAFSLAR-CLSGRPDTLLSATAW, (SEQIDNO:3500); XM_014117718.1, VDAC1, Del, A_8, KMLKSRQGIS-GSTSTWAVMWILTLL- VLPSGVLWCWAMRAGWLATR. (SEQIDNO:3501); XM_845089.4, CXCL13, Del, A_8, KMLLQLNQLQC, (SEQIDNO:3502); XM_005637095.1, PLCZ1, Del, A_8, KMLLVQNGMKHSHLLFMCQNWR, (SEQIDNO:3503); XM_014122842.1, CCDC81, Del, A_8, KMLPTISELLKL, (SEQIDNO:3504); XM_014109240.1, STAU2, Del, A_8, KMLRKQCCYSMKHPLVFKINL-TRQGKTKDGVVQRLGFLNQQITLQKEFFICLLMFIK RWKPAATK, (SEQIDNO:3505); XM_005635554.2, SKA3, Del, A_8, KMMPTLQILPWHLHSALLV, (SEQIDNO:3506); NM_001145981.1, MPHOSPH8, Del, A_8, KMNPKRKTRKGMIWTRKKKAV, (SEQIDNO:3507); XM-850195.4, C4H5orf34, Del, A_8, KMNSHL-TIVNQNLQRPCWKKLMKREYQWH, (SEQIDNO:3508); NM_001003176.1, RPE65, Del, A_8, KMPER-LRSLKLGDTCFL, (SEQIDNO:3509); XM_014112356.1, CCDC28A, Del, A_8, KMPFQLVKAQGFQILHHSQLHNDQS, (SEQIDNO:3510); XM_543895.5, FRMPD2, Del, A_8, KMPVVWD-SASCR, (SEQIDNO:3511); XM_014121374.1, NAA15, Del, A_8, KMQKKKSSREIRKRKRMMMMKKSEVQK-KNLSLRNWPRLKLHWKKLLNF, (SEQIDNO:3512); XM_005631921.2, NCKAP5, Del, A_8, KMQKVW-GLETNN, (SEQIDNO:3513); XM_014114898.1, LRRIQ3, Del, A_8, KMRHKNELQKIMRQFRMVYNNVGRTDMII, (SEQIDNO:3514); XM_005619180.2, EIF4E1B, Del, A_8, KMRKKGQRG1, (SEQIDNO:3515); XM_014118874.1, ABCB1, Del, A_8, KMRRKKRNQLSARLQCFAIQI-GLIGCICWWGQWLPSSMELHSLS, (SEQIDNO:3516); XM_005616743.2, LOC484590, Del, A_8, KMRRSVVVKRNF, (SEQIDNO:3517); XM_014106743.1, XRN1, Del, A_8, KMRRYLDI-LRKLEVSGCIHLQQSSFLQST, (SEQIDNO:3518); XM_014112364.1, FAN1, Del, A_8, KMSITPLFLFLTMHHLLNLPALFVVKWCQGMT, (SEQIDNO:3519); XM_003431635.3, RANBP6, Del, A_8, KMSLLQRTVFQQ, (SEQIDNO:3520); XM_005623082.2, ANKRD12, Del, A_8, KMTIERKVEKRWIENMTK-KNLKKTGI, (SEQIDNO:3521); XM_014122254.1, ALAS1, Del, A_8, KMTIPIEFLKL, (SEQIDNO:3522); XM_005638152.1, TMEM70, Del, A_8, KMTLRRIRG, (SEQIDNO:3523); XM_005638777.2, LOC100683655, Del, A_8, KMTRCKRKS, (SEQIDNO:3524); XM_003433969.2, LOC100683655, Del, A_8, KMTSRCK-RKS, (SEQIDNO:3525); XM_005616941.2, CUL2, Del, A_8, KMTWQICMSYFVLCPLVYLI, (SEQIDNO:3526); XM_539781.2, ASIC5, Del, A_8, KMVFTSTIELCWNVT-FLESHVVHRTSHMYSLNMEIVLLLIMVKIFQRKK, (SEQIDNO:3527); XM_005624049.2, TNRC6C, Del, A_8, KMVLDGMLT-VIGQGLVGMMPPGLGPVAGVMAQMQR, (SEQIDNO:3528); XM_003433570.1, SLC15A5, Del, A_8, KMV-VATVSSMWKTQNISSPFFLSSFSSSSTKYALCRFLQDIM-CRP, (SEQIDNO:3529); XM_532052.5, MED23, Del, A_8, KMWRRNIGSGSQ, (SEQIDNO:3530); XM_533784.5, FAM208A, Del, A_8, KMWVGTQTQKI, (SEQIDNO:3531); XM_014110001.1, SMARCAD1, Del, A_8, KMYLILKELLKTLNMIRALMWVVH, (SEQIDNO:3532); XM_547682.5, AFG3L2, Del, A_8, KNQSQLL-PRALLEEELVAVENEVARKM-ILTGGPDSRRVTFHGMTRNSGCTFSGLLYF GVESCFTSCSRALGEKSRGRTLSITIFPKE, (SEQIDNO:3533); XM_531808.5, RHOQ, Ins, A_8, KNRIEMYKLL-FDYV, (SEQIDNO:3534); XM_014109043.1, CCDC186, Ins, A_8, KNRNREAAYEHN, (SEQIDNO:3535); XM_005633300.2, MS4A1, Del, A_8, KNSRLKQQKKWLS, (SEQIDNO:3536); XM_005638363.2, SPG11, Del, A_8, KNYMKLTLGLNFWFSVDRFPVI, (SEQIDNO:3537); XM_005631997.2, PRPF40A, Del, A_8, KPILGIQRRKQSKHLKNY, (SEQIDNO:3538); XM_005624343.2, GJC1, Del, A_8, KPKWGPKLGP-TRAVLVANQEMGRPPSGF, (SEQIDNO:3539); XM_005623009.2, RBBP8, Ins, A_8, KPPEN-STLQQHFYF, (SEQIDNO:3540); XM_005633761.2, MUC15, Del, A_8, KPQHKALQQV, (SEQIDNO:3541); XM_005637544.2, MYOF, Ins, A_8, KPSGSFCRSFLCWKKGLHKYN, (SEQIDNO:3543); NM_001197044.1, CYP2C18, Del, A_8, KPTHLPVILLSF-WAVLPAM, (SEQIDNO:3544); NM_001003252.1, CD4, Ins, A_8, KPVGPRILSSGHQGSRSC, (SEQIDNO:3545); XM_014121537.1, ZNF197, Ins, A_8, KPYFTSEVPYWRESL, (SEQIDNO:3546); XM_845607.3, EAF2, Del, A_8, KQDLKEVVKFSIA, (SEQIDNO:3547); XM_014115839.1, BAZ1A, Del, A_8, KQDRIFRVFQNH, (SEQIDNO:3548); XM_005623463.2, LOC490717, Ins, A_8, KQECRHSDK, (SEQIDNO:3549); XM_535077.4, TGS1, Ins, A_8, KQEQKGNWSAS, (SEQIDNO:3550); XM_014118258.1, OGFRL1, Del, A_8, KQHQEDLERKQTVLAQSPAVKLPSQET-PRTVMLKIQILNWKKQSPIPQRGRRLQLLL KKMKKVKIIRKTVKILELQVPMMMYNYS, (SEQIDNO:3553); XM_538754.4, MURC, Ins, A_8, KQIPCGDLPGGDSVSNIPVYCQGQKPN, (SEQIDNO:3554); XM_014120622.1, SPAG17, Del, A_8, KQKRKVRKLVKRKERKR, (SEQIDNO:3555); XM_014119014.1, TULP2, Ins, A_8, KQNLQL-PHLSGPHRPVSGWEQLCGQSQI, (SEQIDNO:3556); XM_544914.5, TRAPPC10, Ins, A_8, KQNQHPSPNFYCGQNKE, (SEQIDNO:3557); XM_005641832.2, USP26, Del, A_8, KQNSKKQLNGDSSMKQ, (SEQIDNO:3558); XM_014120068.1, RAB11FIP1, Del, A_8, KQQQRAP-LIKWKILARGSRFFRPGSHPQRHSQSQLSQAR-ERGQPSTDFIP, (SEQIDNO:3559); XM_005641516.2, ATRX, Del, A_8, KQRNLQVRDAF, (SEQIDNO:3560); XM_014120308.1, FAM228B, Del, A_8, KQSFTKTKDHPFWKKNLYVFMRERRKRPILKVT-SLTLSRR, (SEQIDNO:3561); XM_014120309.1, FAM228B, Del, A_8, KQSFTSSLP, (SEQIDNO:3562); XM_005635835.2, SP100, Ins, A_8, KQSSKSEKERQT, (SEQIDNO:3563); XM_014118899.1, CASD1, Del, A_8, KQTEIVSGILAYC, (SEQIDNO:3564); XM_005617175.2, FAM208B, Del, A_8, KQVITLRKNFKRLSGFFCLKLKIRQS, (SEQIDNO:3565); XM_853584.4, TGFB2, Ins, A_8, KQWEDPT-SPANVVALLQT, (SEQIDNO:3566); XM_005635698.2, ADAM28, Ins, A_8, KQWSPCSWLHGNTL, (SEQIDNO:3567); XM_005622195.2, NAV1, Del, A_8, KRAGCEVP-STKPSA, (SEQIDNO:3568); XM_014110313.1, TRIO, Del, A_8, KRASRCQDSCLRTVSR, (SEQIDNO:3571); XM_014112562.1, FAM193A, Ins, A_8, KRCKKEMLVQFPRCFYGSEQSCDGHV-ISHLLCVLHSHYGAV, (SEQIDNO:3572); XM_846902.4, ZMYM5, Del, A-8, KRDYQNKKKRLQSYRFWQNVQIPY, (SEQIDNO:3573); XM_005627814.2, POP1, Del, A_8, KREDGKQVPRARLRRFPSISLLLLLLRPELLKSVLC, (SEQIDNO:3574); XM_014110834.1, CWC22, Del, A_8, KREEREEILFPKMSTDSEIRTVKML, (SEQIDNO:3575); XM_014112733.1, ARID4B, Del, A_8, KREKAVPHT, (SEQIDNO:3577); XM_014116982.1, TTF1, Del, A_8, KREKFHTTRNLRHWLGLVVSRMCTPKDGKGSV-KLGPQKNGKGSVKLGLLVE, (SEQIDNO:3578);

XM_005623751.2, BTBD7, Del, A_8, KREPLA-LPPSKRSLSSVENLIGLPIMPSRCENSSLGGM-LEMLML, (SEQIDNO:3579); XM_014107402.1, ZMYM2, Del, A_8, KREPREKLYQDTSLMMIVL-TIQNVPFLSNIRMV, (SEQIDNO:3580); XM_014118938.1, KRIT1, Del, A_8, KRERKFCWKLNFKATVK, (SEQIDNO:3581); XM_005636747.2, CBX5, Del, A_8, KRESRAMISLGAL-REDWNQKRSLGRQIPVVI, (SEQIDNO:3582); XM_005626885.1, LOC102156133, Del, A_8, KRFKRGKQKG, (SEQIDNO:3583); XM_014111411.1, LOC611589, Del, A_8, KRGMKRKRKVQLEKRMRRH, (SEQIDNO:3586); XM_546411.5, SRPR, Del, A_8, KRGPRRRALMALWLRAKQFLPKSQVSQRGQRTG, (SEQIDNO:3587); XM_014118978.1, AKAP9, Del, A_8, KRGRLQAVNMMCQHTM1, (SEQIDNO:3588); XM_005618163.2, MSH3, Del, A-8, KRGTFSLESWECSLSQVRLCLIVSKTLLPVRS, (SEQIDNO:3589); XM_005626849.2, TSTD2, Del, A_8, KRHLPFSSKPKKFQHLLLNVKISGGNAVNSSSETR-SASTDMQQHNMLMRFATRLLL C, (SEQIDNO:3590); XM_014119254.1, DMRTA2, Ins, A_8, KRKAREALEL-LEAGLSRPSHAARRAPAAPLAQL-PAAPSWPPPVPVRGDPSPRWAPG CRRDPHAVPRSSR-SPAGADVGPRGGPEGAAPTRHPSF1, (SEQIDNO: 3591); XM_005639390.2, LOC487951, Del, A_8, KRKCSSSRT, (SEQIDNO:3592); XM_005626022.2, EIF5B, Del, A_8, KRKDKKAKNKVLMIMIVKNG-KIKIQNQKRLQSQKWKCTLGVMMMMMILINFLKKL KGKCRNQIKGGMGQKKMRITVKELKSVPE, (SEQIDNO:3593); XM_844389.4, DNAJC1, Ins, A_8, KRKEKKDRQQECGCIKTWCFRKK, (SEQIDNO:3594); XM_005623762.2, DDX24, Del, A_8, KRKEKKNWSL-PRVLLQRCPKKQRHGCLKCMTIRQM, (SEQIDNO: 3595); XM_848505.4, TWISTNB, Del, A_8, KRKENTVRKLNLPHFWNIHLKRKGES, (SEQIDNO: 3596); XM_542577.3, NUFIP1, Del, A_8, KRK-ERNQFFIVFVIPVIVVLKIKKSMINTCLNT, (SEQIDNO: 3597); XM-014108520.1, ZCRB1, Del, A_8, KRKFLSQKKKLKK, (SEQIDNO:3598); XM_014107724.1, LOC478037, Del, A_8, KRKGTARLTTVTS, (SEQIDNO:3600); XM_533087.4, PNPLA8, Del, A_8, KRKINIS-RKNQNLKIKRLKKRKQALQILAS, (SEQIDNO:3602); XM_014114461.1, LOC612426, Del, A_8, KRKISC-CRVKMHLSIIPRQRISNFQSP, (SEQIDNO:3603); XM_005623148.2, NLRP3, Del, A_8, KRKITARSTKNT, (SEQIDNO:3604); XM_014116142.1, CLMN, Del, A_8, KRKKGSMWTT, (SEQIDNO:3606); XM_014117385.1, HMGXB4, Del, A_8, KRKKKRRKTEREREEKSQKRRT-CQPTRSSVKSIG, (SEQIDNO:3607); XM_014116686.1, LOC100686205, Del, A8, KRKRCLSGRHLWHCI-MFCRCCSNDMQKTALLGWNSFTDSWICTNL-SPLKSRGFS, (SEQIDNO:3608); XM_847157.4, PHF20, Del, A_8, KRKRKRKPNLNALAVRRSVIPPRNLLH-PRHLLSTGVGPHISLGSI, (SEQIDNO:3609); XM_005638144.2, MTDH, Del, A_8, KRKRR-SKVKITLLHRTQKN, (SEQIDNO:3611); XM_005621925.2, EVI5, Del, A_8, KRKSK-LRSLFVKGYPTTLEQ, (SEQIDNO:3612); XM_005625956.2, APPL2, Del, A_8, KRKTRRQR1R1, (SEQIDNO:3613); XM_005617083.2, LOC100856304, Del, A_8, KRKWWHFY, (SEQIDNO:3614); XM_014112089.1, LOC608294, Del, A_8, KRKWWYFY, (SEQIDNO:3615); XM_014107459.1, CCL20, Del, A_8, KRLCVQIQRRNG, (SEQIDNO:3616); XM_531814.5, MSH6, Del, A_8, KRLLIFF11, (SEQIDNO:3617); XM_014115260.1, AHCTF1, Del, A_8, KRLLKELKNP, (SEQIDNO:3618); XM_014106956.1, ADNP, Del, A_8, KRLPCKVTESS, (SEQIDNO:3619); XM_546398.5, NFRKB, Del, A_8, KRLRKKRRKRRKK, (SEQIDNO: 3620); XM_005631775.2, ZNF330, Del, A_8, KRLVR-GRRQRAVGNVKNSSEHREAPSIWLNTHAM-HQWNVTSVRGGRRIERFATSA TLYRSYQFVHSVGKRSA, (SEQIDNO:3621); XM_014108948.1, MARVELD2, Del, A_8, KRMIPRFWKKKNAVII, (SEQIDNO:3622); XM_003639706.3, RIF1, Ins, A_8, KRNGFCKI, (SEQIDNO:3623); XM_014111626.1, THOC2, Del, A_8, KRNGTVQEERKRRNSPRTSTD, (SEQIDNO:3626); XM_005632360.2, LOC102156781, Del, A_8, KRN-LAWETSSENQT, (SEQIDNO:3628); XM_014120446.1, EML4, Del, A_8, KRNLILMIKVHKFEHHLLPSPLHSL-SKYTDKLKKARILLPPKA, (SEQIDNO:3629); XM_014111981.1, HBS1L, Del, A_8, KRNLTDLKVKRN, (SEQIDNO:3631); XM_014111745.1, CXHXorf23, Del, A_8, KRNMQTLPQQS, (SEQIDNO:3632); XM_844090.4, INO80, Del, A_8, KRNSRRKRNLKPS, (SEQIDNO:3633); XM_014112635.1, LIAS, Del, A_8, KRNSYKMDQTFKILYLEILQTRASGMNIKET, (SEQIDNO:3634); XM_533976.5, TAF1D, Del, A_8, KRNVKRGNISQKKDQGEDQKEEKPLDAPK, (SEQIDNO:3635); XM_005626240.1, EML6, Del, A_8, KRNWLRSWLSSTCLATGASTVATTCIT, (SEQIDNO: 3636); XM_014111557.1, TRPC5, Del, A_8, KRPATGHLS-SELCQEPVAPKGSQNLSHRANAPSWVLLSRNS-VSCFPSSMVICPNQVQ SQCTPFRMALLN-STTCGKTSDILRWRKGKQGPVLRVK, (SEQIDNO: 3637); NM_001003306.2, ATP1A1, Del, A_8, KRPRKKGIWMN, (SEQIDNO:3639); XM_005627403.2, HSP90AB1, Del, A_8, KRPRRLRKNTLIKKN, (SEQIDNO:3640); XM_014113698.1, SGIP1, Del, A_8, KRPRRLSFSSPLASGSEPSR, (SEQIDNO:3641); XM_003432745.3, ATP2B2, Del, A_8, KRPTCTRRRNL-CYRANSPSWLCRSARRVW, (SEQIDNO:3642); XM_844389.4, DNAJC1, Del, A_8, KRQAARVWMHQNLVLQKKMKDY, (SEQIDNO:3643); NM_001003264.1, SRP72, Del, A_8, KRRENYLKIMTQR, (SEQIDNO:3644); XM_014111841.1, ZC3H12B, Del, A_8, KRRFPLSHTVSSIDHPA, (SEQIDNO:3645); XM_005621668.2, SRRM2, Del, A_8, KRRKIED-AGQRAALLEEKGRRALRRRSTGQSLNPKNE-SIGLPLQRANVNLRTRSGSG LEVQHQP-PRAAGPTVQRLLTLLPLPILLAVGLEVRQQKPIQLP, (SEQIDNO:3646); XM_545754.6, ATP1A4, Del, A_8, KRRLIWRS, (SEQIDNO:3648); XM_014108254.1, LMAN1, Del, A_8, KRRNSRRAILTFSGILQTKYLRV, (SEQIDNO:3650); XM_005615362.2, LMAN1, Del, A_8, KRRNSRRAILTFSGILTKYLRV, (SEQIDNO:3651); XM_531629.4, PA2G4, Del, A_8, KRRPPRLQRM-PPVGKH, (SEQIDNO:3652); XM_005621118.2, USP42, Del, A_8, KRRRKRRGTPGNPRTLLKTQNRTSPRP-PAMRLLTVSGDWTAPSPSPTGCLWKVSGLS VRRENT, (SEQIDNO:3653); XM_848505.4, TWISTNB, Del, A_8, KRRRKTQSPMKWRVITES, (SEQIDNO:3654); XM_014114295.1, LOC106558887, Del, A_8, KRRSAR-HLHSDDPRPCVYEGSRNILERAPPGETSLITMPSSSSP, (SEQIDNO:3655); XM_535515.5, ZNF609, Del, A_8, KRRSLPRNSKVL, (SEQIDNO:3656); NM_001003113.1, KCNCI, Del, A_8, KRSIFHGHRSWDLPIIVNLS, (SEQIDNO:3657); XM_014118174.1, GRIK2, Ins, A_8, KRSIGKESQD, (SEQIDNO:3658); XM_539059.5, GRIK2, Ins, A_8, KRSIGKEVLL, (SEQIDNO:3659);

XM_014118176.1, GRIK2, Ins, A_8, KRSIGKGIFYLVS-ATLPSRHCL, (SEQIDNO:3660); XM_005625840.2, DNAJB7, Del, A_8, KRSIKRYRRSQPKEIV, (SEQIDNO:3661); NM_001003081.1, ABCC2, Del, A_8, KRSLGPQKSFPSPGWSRVSSKLSMSYS, (SEQIDNO:3662); XM_005633326.2, CEP57, Del, A_8, KRSQNHLKRKVLGTILLYNHIIDYAWGICR1, (SEQIDNO:3663); XM_005629478.2, LUC7L2, Ins, A_8, KRSRGSLSEFYASFQFPTTETSSI, (SEQIDNO:3664); XM_535194.5, KIN, Del, A_8, KRSRTLMMRKKQPNLLKNK, (SEQIDNO:3665); XM_005638465.2, RNFLL1, Ins, A_8, KRSVSPKKICIAPQF, (SEQIDNO:3666); XM_014119790.1, IQCAI1, Del, A_8, KRTKRKIRKKKMRKKRGNRRKGRVGRGKQTQC, (SEQIDNO:3667); XM_546107.5, TFAM, Ins, A_8, KRVNNAWKT, (SEQIDNO:3669); XM_014120722.1, SYCPI, Del, A_8, KRVQQKASN, (SEQIDNO:3670); XM_005619838.2, CWF19L2, Del, A_8, KRVRNRSMKKAMSQQTVHQALKMSGLRLSHRRLLAGKRPGK, (SEQIDNO:3671); NM_001005870.1, RXFP2, Del, A_8, KRVSPHPLCGQMTPLHLNLGF, (SEQIDNO:3672); XM_014117985.1, CNTLN, Del, A_8, KSALWVVTTLFSITPSRL, (SEQIDNO:3673); XM_014121947.1, IL17RB, Del, A_8, KSASRQEVCGIQTSLLARRTRRR, (SEQIDNO:3674); XM_005618733.1, HTRA3, Del, A_8, KSCRRCCWDARQTCGPASLWWPSAAPSPYRTR, (SEQIDNO:3676); XM_014112788.1, LSM11, Del, A_8, KSESPKWITSRYSLDT, (SEQIDNO:3677); XM_014116993.1, NUP214, Del, A_8, KSFLAHHFMSQIILSEFWMCCGSVLMSSQLCMLLRMGPWKLLQMW, (SEQIDNO:3678); XM_014107402.1, ZMYM2, Ins, A_8, KSFNNGKQSMSSIPSVFLMWNR, (SEQIDNO:3679); XM_014108759.1, ZFAND4, Ins, A_8, KSFRKM, (SEQIDNO:3680); XM_014122796.1, SWAP70, Ins, A_8, KSHQESPAHYRRRCI, (SEQIDNO:3681); XM_005619774.2, C5H11orf57, Del, A_8, KSHTKNRRKAKKKPQI, (SEQIDNO:3682); XM_534964.5, KIF11, Del, A_8, KSIHRNFAS, (SEQIDNO:3683); XM_005627188.1, C12H6orf10, Del, A_8, KSIKTRWLKRTRI, (SEQIDNO:3685); XM_014116982.1, TTF1, Del, A_8, KSIRKKREKFHTTRNLRHWLGLVVSRMCTPKDGKGSVKLGPQKNGKGSVKLGLLVE, (SEQIDNO:3686); XM_014118114.1, SENP6, Del, A_8, KSIRTLIQQKHL, (SEQIDNO:3687); XM_536616.5, GABARAP, Del, A_8, KSIWCLLISQLVSSTS, (SEQIDNO:3688); XM_005630143.2, NBAS, Del, A-8, KSKIESPSTH, (SEQIDNO:3689); XM_005615655.2, AKAP7, Del, A_8, KSKKVINPTISYPFRSPTKRLREELRSCKMQYSSKMSD, (SEQIDNO:3690); XM_014109018.1, HECTD2, Del, A_8, KSLFKETQNNR, (SEQIDNO:3691); XM_005619382.2, NIPBL, Del, A_8, KSLILSFQRVKQNKMKVDWQNLNQMKTDWWRQNQVKVS, (SEQIDNO:3692); XM_014115507.1, PIEZO2, Del, A_8, KSLQKKNRKEEEKDLGRVLWSGKTERMNQSKRNPMDQIISSRGYLIF, (SEQIDNO:3693); XM_853836.4, TCERG1, Del, A_8, KSLRKILGALSSPPATGKNKESLKNTSETNTSQPKLTSGRF, (SEQIDNO:3694); XM_014117866.1, FBXO10, Del, A_8, KSLTHGAW, (SEQIDNO:3695); XM_014117483.1, LIPT1, Del, A_8, KSMIECRI, (SEQIDNO:3697); XM_545015.5, TBCK, Ins, A_8, KSNLERSED, (SEQIDNO:3698); XM_014109263.1, ST18, Ins, A_8, KSNPGQSCTPNF1, (SEQIDNO:3699); XM_005635021.2, SAMHD1, Del, A_8, KSNTVNTSMWVRLSQREK, (SEQIDNO:3700); XM_014117917.1, ZNF483, Del, A_8, KSPLCVKNVGKF, (SEQIDNO:3701); XM_014106985.1, ZMYND8, Del, A_8, KSPNWPTQWRLRRS, (SEQIDNO:3702); XM_014109477.1, STARD9, Del, A_8, KSPTLCGSESTQSWGPMYKVYLNM, (SEQIDNO:3703); NM_001003154.2, TRDN, Del, A_8, KSQGKLLKPNKGL, (SEQIDNO:3704); XM_014120832.1, YAE1D1, Ins, A_8, KSQLPHILPIRDRSFQRFFSGNKFPLEGEGFPTHTKTHTPTPRSRVARSSSDCARPAP, (SEQIDNO:3705); XM_005618620.2, WDR19, Del, A_8, KSQTVPSTCEQRWSS, (SEQIDNO:3706); XM_005632059.2, ZXDC, Del, A_8, KSREELGAMQEPQVPLRGK, (SEQIDNO:3707); XM_014120778.1, CACNA2D1, Ins, A_8, KSRGRSFIVVAGVWQCHRPSPILSSFSMG, (SEQIDNO:3708); XM_844360.4, C16H4orf47, Ins, A_8, KSRQSLPP, (SEQIDNO:3710); XM_543550.5, LOC486424, Del, A_8, KSRRMEVLQSPAAHIAAVLLAARTVLSLSGSRV, (SEQIDNO:3711); NM_001346066.1, KRT26, Ins, A_8, KSRVGNESPAVCSGRGCECGGERSPRCGPHSPAEQHEGRV, (SEQIDNO:3712); XM_014106438.1, ER1CH6B, Ins, A_8, KSSCCCSS, (SEQIDNO:3713); XM_014115507.1, PIEZO2, Del, A_8, KSSGGGLGLIMLPWSGVEIIICLKRIVKRKKKKN, (SEQIDNO:3714); XM_532971.5, RNF103, Del, A_8, KSSHMHNTSPCQMMSH1, (SEQIDNO:3715); XM_005629390.2, TMA16, Del, A-8, KSSIHIVEKQLKLQERSTNKKKRKN, (SEQIDNO:3716); XM_005640282.2, LRP2, Del, A_8, KSSKLARNQIAVSHQQ, (SEQIDNO:3717); XM_014110629.1, SLC17A1, Del, A_8, KSSKLTPPLKL, (SEQIDNO:3718); XM_005620448.2, CHD5, Del, A_8, KSSRTRRRRKPSGKGRMMTRMIMMMGV, (SEQIDNO:3719); XM_005637015.2, FAR2, Del, A_8, KSSTPWSG, (SEQIDNO:3720); XM_014121223.1, CCDC73, Del, A_8, KSSYIFWLKKIIRSNSMKLRNIMAQ, (SEQIDNO:3722); XM_536037.5, CARF, Del, A_8, KSVNKRAGLVSSTKPLVQPGFILKRYRSFLNMEFLQTPKLTRK, (SEQIDNO:3724); XM_005628540.2, COL28A1, Del, A_8, KSVRILIPTSFKFWVHRHFNLDLGHQGKNLVNPLQSLGRKFQRLSVSLELRTKRMSLQSLPGLAAWPPVLHLRLLPPSSQKMGQRVSNPEFQVLF, (SEQIDNO:3725); XM_014106258.1, OXGR1, Del, A_8, KSVTQTTL, (SEQIDNO:3726); XM_843419.4, MICU3, Del, A_8, KSWGQWTSMMLLTCTVDQGIFWIAVGKFPVGYTGQKFRREICAIAIDWEITKC, (SEQIDNO:3727); XM_545733.5, SPTA1, Del, A_8, KSWQMMKIIRIYRT, (SEQIDNO:3728); XM_014106875.1, ZSWIM6, Del, A_8, KSYPIKASLR, (SEQIDNO:3729); XM_852167.4, ACVR2A, Del, A_8, KTALKCIFVAVRAICVTKGFLIFRRWKSHSLLRTQLHLSHPITTYCFIPWCHLC, (SEQIDNO:3730); XM_005630696.2, LOC608067, Del, A_8, KTATACMAGPLHSVRR, (SEQIDNO:3731); NM_001003252.1, CD4, Del, A_8, KTCGTKDPFLWSSRISKLLTQGFTSVTQTRGKRWNCWCST, (SEQIDNO:3732); XM_014111157.1, COPA, Del, A_8, KTCPLVQWSPT, (SEQIDNO:3733); XM_005628506.2, ANKIB1, Del, A_8, KTHPYTMLLPQG, (SEQIDNO:3736); XM_005618621.2, RFC1, Del, A_8, KTKEKEKLAQLRRNQNLKEVDLLPRRTA1, (SEQIDNO:3737); XM_544914.5, TRAPPC10, Del, A_8, KTKPTSFPELLLWTK, (SEQIDNO:3738); XM_005634774.2, ESF1, Del, A_8, KTLFGIVQTHVPKENSAQETWASLKLQNVPRSSTLRQEDKCNQWFHY, (SEQIDNO:3739); XM_014109172.1, PRKDC, Del, A_8, KTLKRCMKECMQLWEI, (SEQIDNO:3740); XM_005635921.1, RBM44, Del, A_8, KTLMQRWP, (SEQIDNO:3741); XM_014118174.1, GRIK2, Del, A_8, KTLNWKREPRLSYLKTMYSSPFWSQIFPFLQCCH- HHHLHHHYHHVL, (SEQIDNO:3742); XM_539059.5, GRIK2, Del, A_8, KTLNWKRGPSVAPW, (SEQIDNO:3743); XM_014118176.1, GRIK2, Del, A_8, KTLNWKRNLLFG, (SEQIDNO:3744); XM_014112562.1, FAM193A, Del, A_8, KTLQKRNACTISKMLLWKRTKL, (SEQIDNO:3745); XM_014119437.1, CEP290, Del, A_8, KTMNLSNIWMKFRL, (SEQIDNO:3746); XM_005634454.2, CEP63, Del, A_8, KTMTGSLNQHTTEHLSSRIQSSSQPMARTDMME, (SEQIDNO:3747); XM_005635698.2, ADAM28, Del, A_8, KTMVSLLLVTRKHIIIPLERRSPQAHKSWMTAITKDTSLMKRFQMLASAHVGV, (SEQIDNO:3748); XM_005622133.1, ZRANB2, Ins, A_8, KTNKITVTRKAPQVIFWIIPFWFPFKFKKEI, (SEQIDNO:3749); XM_014111710.1, BRWD3, Del, A_8, KTPPQEQQSTVGVIS, (SEQIDNO:3751); XM_014119900.1, WDR60, Del, A_8, KTPSRPMFSTMRIMLTETSRQKRLRPGGCGRSTPERARLCQG-GAGVEMSVRWPQPR RSTRPGWPASFALLAR, (SEQIDNO:3752); XM_014118253.1, CD2AP, Del, A_8, KTPWMNLELRLLNCCAL, (SEQIDNO:3753); XM_005640790.1, LEMD1, Del, A_8, KTQFLKYKSSRKR, (SEQIDNO:3754); XM_005623463.2, LOC490717, Del, A_8, KTQKDQYCPRI, (SEQIDNO:3755); XM_847012.4, PDCD1LG2, Del, A_8, KTQQKTLSPP, (SEQIDNO:3756); XM_014106624.1, TRPC1, Del, A_8, KTQWGQPLKE, (SEQIDNO:3757); XM_014120723.1, SYCP1, Del, A_8, KTRKHRHLY, (SEQIDNO:3758); XM_862709.4, FBXO38, Del, A_8, KTRMFIPAAAAPPPAQWEPPAHTALLLKAPT1, (SEQIDNO:3759); XM_005625593.2, HE1B, Del, A_8, KTRPRTVHGSFLR, (SEQIDNO:3760); XM_537131.4, DYRK3, Del, A_8, KTSFRVLASS, (SEQIDNO:3761); XM_014119301.1, APAF1, Del, A_8, KTSRIFPA, (SEQIDNO:3762); XM_014111529.1, SMC1A, Del, A_8, KTSRLNARKPNRRKKRLTATSA, (SEQIDNO:3763); XM_005616083.2, PEG3, Del, A_8, KTSSIGTMRP1, (SEQIDNO:3764); XM_014116241.1, RNF213, Del, A_8, KTSTTFSTRKALWKAPLRNAFSIS, (SEQIDNO:3765); NM_001197076.1, ASPM, Del, A_8, KTTQTAGLRLS, (SEQIDNO:3767); XM_536025.4, BZW1, Del, A_8, KTTSQNPLSLE, (SEQIDNO:3768); XM_853584.4, TGFB2, Del, A_8, KTVGRPHISC, (SEQIDNO:3769); XM_014117078.1, RABGAP1, Del, A_8, KTVLSLVTTSRFVLN, (SEQIDNO:3770); XM_005638026.2, MYBL1, Del, A_8, KTVVTVQTMRLF1, (SEQIDNO:3771); XM_014107325.1, BRCA2, Del, A_8, KTVYRMTQKNQLCL, (SEQIDNO:3772); XM_005638791.2, LTN1, Del, A_8, KVCFQSCQLWCVKVVGVWPLSYILIFCHLSANCLRPLQIQSWISSEISSPL, (SEQIDNO:3773); XM_014115507.1, PIEZO2, Ins, A_8, KVCKRRTEKKKKRIWGGSCGVGRPRG, (SEQIDNO:3774); XM_843419.4, MICU3, Ins, A_8, KVGGSGHR, (SEQIDNO:3775); XM_014121947.1, IL17RB, Ins, A_8, KVHRGRKSVGSRHHCLQEERDDGRSEFYNQPSWKQIHGSHPK, (SEQIDNO:3776); XM_533539.4, KIAA0020, Ins, A_8, KVHRKRCKDITRKKKIS, (SEQIDNO:3777); XM_014106438.1, ERICH6B, Del, A_8, KVILLLFVLRRKLK, (SEQIDNO:3778); XM_005628374.2, COPG2, Ins, A_8, KVKIWAETNLSCDPVGGSYIPARTVV, (SEQIDNO:3779); XM_014117985.1, CNTLN, Ins, A_8, KVLCGSLPHCSQSLHQGYEQCV, (SEQIDNO:3780); XM_540963.4, KIAA1109, Del, A_8, KVLITQMMKH, (SEQIDNO:3781); XM_014109477.1, STARD9, Ins, A_8, KVLLSAGQRAPRVGALCTRFISTCSYQL, (SEQIDNO:3782); XM_538101.4, TNMD, Del, A_8, KVLNKTSSGWSPK, (SEQIDNO:3783); XM_005630347.2, CEBPZ, Del, A_8, KVLRKTQKMKI, (SEQIDNO:3784); XM_547684.5, SPIRE1, Del, A_8, KVLTKSSWTSSDQDP1, (SEQIDNO:3785); XM_005618927.2, JMJD1C, Del, A_8, KVQTQLHV, (SEQIDNO:3786); NM_001003203.1, SCN10A, Ins, A_8, KVRGPGHLHDRGAKEV1, (SEQIDNO:3787); XM_014120929.1, AP2A2, Ins, A_8, KVRLQVALHLPPGS, (SEQIDNO:3788); XM_005622047.1, NEXN, Del, A_8, KVRPHLLIK, (SEQIDNO:3789); XM_844680.4, TM9SF3, Del, A_8, KVSVITMKLWEKHFKELNWNLVAWILNSKRM, (SEQIDNO:3790); XM_005619774.2, C5H11orf57, Ins, A_8, KVTQKTEEKQKRSHRYNSRFLK, (SEQIDNO:3791); XM_005635475.2, PDS5B, Del, A_8, KVTRETTLIFLNWTNLEAGKKHLSQIQKRN, (SEQIDNO:3792); XM_543139.5, PDSSB, Del, A_8, KVTRETTLIL, (SEQIDNO:3793); NM_001003343.1, DMD, Del, A_8, KWKTAMDLI, (SEQIDNO:3795); XM_005635654.2, MTMR9, Ins, A_8, KWNGNHAKRSATHWHKWEKVQRRREADKCYPQGRKTRLHH, (SEQIDNO:3796); XM_014120087.1, LOC607729, Ins, A_8, KWPLDQFLHFYTCPYFNCHCCP, (SEQIDNO:3797); XM_539294.3, LOC482175, Ins, A_8, KWPTPLRGIFNQ, (SEQIDNO:3798); XM_005634201.2, CLASP2, Del, A_8, KWVLICLGLYRQKFRKPLMLQENLFQMIFSLIF, (SEQIDNO:3800); XM_014115681.1, RALGAPA1, Ins, A_8, KYDLGRSTCRTSFPDSYSCLDQSKSKCIHLSRTMG, (SEQIDNO:3801); XM_005623314.2, ARHGAP5, Ins, A_8, KYDRKFLFI, (SEQIDNO:3802); XM_014110029.1, MRPL1, Ins, A_8, KYERQSIR, (SEQIDNO:3803); XM_849546.1, MMP20, Ins, A_8, KYFDIQNFQIHILHESC, (SEQIDNO:3804); XM_005634064.2, CCDC168, Ins, A_8, KYFTSIEKRRYRRNQYLTRFKRTQVSLY, (SEQIDNO:3805); XM_014120336.1, LOC100685565, Ins, A_8, KYIPCSNL, (SEQIDNO:3806); XM_014115024.1, SETBP1, Del, A_8, KYIRERMSV, (SEQIDNO:3807); XM_540001.4, LONRF1, Del, A_8, KYMMKKLLSSHT, (SEQIDNO:3808); XM_005637237.2, CHD4, Ins, A_8, KYQTTFHVQYCRWWFY, (SEQIDNO:3809); XM_547304.5, BCL10, Del, A_8, KYSVEKTLKKFLAEHQAGKGPENC, (SEQIDNO:3810); XM_005626151.2, UGP2, Del, A-8, KYYRSTIIVV, (SEQIDNO:3811); XM_014116764.1, ATAD5, Ins, A_8, MFCPCFSLFKFSH, (SEQIDNO:3812); XM_005623023.2, ROCK1, Ins, A_8, MGNTFGKEDP, (SEQIDNO:3813); XM_014114827.1, CCDC18, Ins, A_8, NAVRTAFNIRRKPEGSDLYPVRLI, (SEQIDNO:3814); XM_014122375.1, DNAH12, Del, A_8, NDFSSLAFSSYLMMKC, (SEQIDNO:3815); XM_535698.4, LARP7, Ins, A_8, NDIPNEIRVKNGNKWSTYYI, (SEQIDNO:3816); XM_537881.5, OSBPL1A, Del, A_8, NDLRKNKEQPAKTDPSRRRTGRRGGSTKAPTPTMEHRTGSTRAATGTETISICLTFI, (SEQIDNO:3817); XM_014111218.1, ZC3H11A, Ins, A_8, NEGKIQEARRRFFWSFQSFTPTSAHSRS, (SEQIDNO:3818); XM_014120749.1, HGF, Ins, A_8, NEHCRPMCQ, (SEQIDNO:3819); XM_005616957.2, LOC480753, Ins, A_8, NEISIRASKSGMGTRTLQFKIDLKTRKRKKKY, (SEQIDNO:3820); XM_005626020.2, REV1, Ins, A_8, NENRQVYTCCN, (SEQIDNO:3821); XM_547275.5, DNTTIP2, Del, A_8, NEWCKNAVLI, (SEQIDNO:3822); XM_546202.5, DCP2, Del, A_8, NFIHENFRIILKQMLYMTCLAPVKTSC, (SEQIDNO:3823); XM_014111472.1, CYLC1, Ins, A_8, NFPKAICLLNS, (SEQIDNO:3824); XM_014118166.1, MMS22L, Ins, A_8, NFQCRAATDV, (SEQIDNO:3825); XM_014113891.1, CAMTA1, Del, A_8, NFSRAGVLLC, (SEQIDNO:3826); XM_005624952.2, PAFAH1B1, Del, A_8, NGHLLL-DYKRRLWN, (SEQIDNO:3827); NM_001003343.1, DMD, Ins, A_8, NGKQQWILSK, (SEQIDNO:3828); XM_544640.4, VPS39, Del, A_8, NGSIKCSRTSSMQNF, (SEQIDNO:3829); XM_014120762.1, NAMPT, Del, A_8, NGVLKILPLVLVELCYRS, (SEQIDNO:3830); XM_014110770.1, UBR3, Ins, A_8, NHCSREENTGQRR-KATKG, (SEQIDNO:3831); XM_014120784.1, PC10, Del, A_8, NHLLKKKSQALKTKSYLQQQNHQL, (SEQIDNO: 3832); XM_005634505.2, COPB2, Del, A_8, NHLNQILELKVSMEASYWESD1, (SEQIDNO:3833); XM_005633761.2, MUC15, Ins, A_8, NHNTKHCSRFKNNGK, (SEQIDNO:3834); XM_014120114.1, SORBS2, Del, A_8, NHQLRHPFHH-PEKRAFVAP, (SEQIDNO:3835); XM_005637015.2, FAR2, Ins, A_8, NHRLHGVVRRCYY, (SEQIDNO:3836); XM_014119437.1, CEP290, Ins, A_8, NHYAGDEGIK, (SEQIDNO:3837); XM_014109018.1, HECTD2, Ins, A_8, NHYSKRLRTTDDKHRKAKSGG, (SEQIDNO:3838); XM_547250.5, FNDC7, Ins, A_8, NIFSNLL-WKYTWNGDLQGEKKCRM, (SEQIDNO:3839); XM_005634064.2, CCDC168, Ins, A_8, NIKAS-SIPHFKYKRNWFAC, (SEQIDNO:3840); XM_005636132.2, MPHOSPH9, Del, A_8, NIQKQPPTSMLIIALLPNCCQME, (SEQIDNO:3841); XM_005619774.2, C5H11orf57, Ins, A_8, NISSSKIIY-PRVSQTQEVQEIPQKKAEKKVTQKTEEKQKR-SHRYNSRFLK, (SEQIDNO:3842); XM_534832.5, PUS7L, Del, A_8, NISTGRGLFLNAKIKK-LYTQLLPYEKKIWKCLKHLDF, (SEQIDNO:3843); XM_014115143.1, HMCN1, Del, A_8, NITSKSMFLQ, (SEQIDNO:3844); XM_005641516.2, ATRX, Ins, A_8, NKEISRFGMHSSTLHGPW, (SEQIDNO:3845); XM_014114967.1, ASPM, Ins, A-8, NKGVQQSSSHY-TVHI, (SEQIDNO:3846); XM_014119437.1, CEP290, Del, A_8, NKKPIIKCLERKMELIKRMMN, (SEQIDNO:3847); XM_005636842.2, FAM186A, Del, A_8, NKKRLLKIRYH, (SEQIDNO:3848); XM_014110832.1, EIF4G3, Ins, A_8, NKNCGRKWRRS, (SEQIDNO:3849); XM_535848.5, SMC4, Del, A_8, NLAGFQEYMADWGI, (SEQIDNO:3850); XM_014112366.1, MPHOSPH10, Del, A_8, NLGSFKGK, (SEQIDNO:3851); XM_005638791.2, LTN1, Del, A-8, NLGSRILIY, (SEQIDNO:3852); XM_005618561.2, FAM200B, Del, A_8, NLIWQVFLK-MILG, (SEQIDNO:3853); XM_547249.5, STXBP3, Del, A_8, NLKTTTKLMKRAK, (SEQIDNO:3854); XM_005627570.2, IBTK, Del, A_8, NLLLAIVQEIM-SKKFVLKE, (SEQIDNO:3855); XM_005622945.2, PSMA8, Del, A_8, NLLPSFKMKEL, (SEQIDNO:3856); XM_005615312.2, ZNF407, Del, A_8, NLLRKWFP-LIRKENLLSP, (SEQIDNO:3857); XM_542274.5, TMEM126B, Del, A_8, NLNILEEKR1, (SEQIDNO:3858); XM_005618620.2, WDR19, Ins, A_8, NLRLYPVPANRG-GAV, (SEQIDNO:3860); XM_014107482.1, DNAJC18, Del, A_8, NLSMSGIKPGRVRGVPLTLRNSCLGYKGSR-NAEITMKFWEFLEMPVMKSLRKLIENL P, (SEQIDNO:3861); XM_005627467.1, PKHD1, Del, A_8, NLTGQN-REI, (SEQIDNO:3862); XM_538859.5, WDR46, Ins, A_8, NLVKRGGKFLEKGPPVK, (SEQIDNO:3863); XM_532048.4, RAB14, Del, A_8, NLWLIVLTQLVLNLVQE, (SEQIDNO:3864); XM_005631997.2, PRPF40A, Ins, A_8, NLYLEYKGG-SKASI, (SEQIDNO:3865); XM_014119671.1, LOC106559776, Del, A_8, NLYLYFSGQRIK, (SEQIDNO: 3866); XM_544335.4, GZMA, Ins, A_8, NMCWSPDCRRLGIDSSSLCPGQKFPGH-SWSSLNHQEGVGKTDNVC, (SEQIDNO:3867); XM_005630829.2, FLG, Del, A_8, NMHTTHKMKKT-TERKTK, (SEQIDNO:3869); XM_014116498.1, LOC476394, Del, A_8, NMKKTLQPITKISSIENIKNIIN-SIMIFL, (SEQIDNO:3870); XM_003432258.2, TCHHL1, Del, A_8, NMKQRTCLSKVISEMFQKYLMLKL, (SEQIDNO:3871); XM_014118235.1, DPCR1, Del, A_8, NPAIKEKTQISRIDALLILMTLLTHIKDCLVQNIQP, (SEQIDNO:3872); XM_534964.5, KIF11, Ins, A_8, NPFTGTLPVNRSLGRTILCLGGKV, (SEQIDNO:3873); XM_014118865.1, UTRN, Del, A_8, NPRVNGKKS, (SEQIDNO:3874); NM_001012395.1, UTRN, Del, A_8, NPRVNVKKS, (SEQIDNO:3875); XM_014122801.1, LUZP2, Ins, A_8, NPSPAEGASLREERFII, (SEQIDNO:3877); XM_546767.5, LOC489647, Del, A_8, NPTMFF-SFMLCLQLGMLWRIRWRL, (SEQIDNO:3878); NM_001110501.1, VEGFA, Del, A-8, NQFEERGRGKKE-SARNPVPVGLAQSGESICLYKIRRRVNVPAKTQTR-VARRGSLS, (SEQIDNO:3880); XM_005628633.1, STK31, Del, A_8, NQILVSLSSRTSKAPFPHG-GIDQTSQPSPDQRGA, (SEQIDNO:3881); NM_001003327.2, HSP90B1, Del, A_8, NQKPKKLRKLS-GIGS1, (SEQIDNO:3883); XM_014112357.1, LCOR1, Del, A_8, NQKQMRTSQTLTWKIIVLILMTVTLFRED, (SEQIDNO:3884); XM_014114844.1, HFM1, Del, A_8, NQKQRFPILNIQIDL1, (SEQIDNO:3885); XM_014106258.1, OXGR1, Ins, A_8, NQLLKQPL, (SEQIDNO:3886); XM_005635844.2, PSMD1, Del, A_8, NQLTRDWKAL, (SEQIDNO:3887); XM_014117518.1, FOXN2, Del, A_8, NQQLQSPHTPLVFSFTWLSNTLQ-INVCLSKKFIAGFWTASHILLLHQQAGRILFDIICP, (SEQIDNO:3888); XM_005641214.2, POLA1, Del, A_8, NQREGAKKL, (SEQIDNO:3889); XM_532160.5, ADGRF5, Ins, A_8, NRCHAHPNSGN, (SEQIDNO:3890); XM_003431930.3, PPP1R17, Del, A_8, NRGGKIHQHCT-SHLLYQVCFQNI, (SEQIDNO:3891); XM_005635161.2, STAU1, Ins, A-8, NRGWKKSNLF, (SEQIDNO:3892); XM_014118195.1, AK9, Del, A_8, NRKGRLVEKMKTLVKKSLKKMKMILTT-SLKMNFQKMRK, (SEQIDNO:3893); XM_005618393.2, BTBD1, Del, A_8, NRPWDKTILDSVAMELLTHSG, (SEQIDNO:3894); XM_005639600.1, WDR53, Del, A_8, NRRVLQNLPTGRKLKEQLIPSRVETLMFQ, (SEQIDNO:3895); XM_535855.5, PRKCI, Ins, A_8, NRSYL-CNESCEKRAGQ, (SEQIDNO:3896); XM_014111218.1, ZC3H11A, Ins, A_8, NRYKRREETSRRQ, (SEQIDNO:3897); XM_014115049.1, CAMSAP2, Del, A_8, NSAQNLFTEIILSLPKHQ, (SEQIDNO:3898); XM_014121441.1, LARP1B, Del, A_8, NSDKKFLKISKKKPKKTTNLVSCMD, (SEQIDNO:3899); XM_005630447.2, CKAP2L, Ins, A_8, NSGQGHKGYKG, (SEQIDNO:3900); XM_003640176.3, ITGA6, Del, A_8, NSGSQVGMKMKAT1, (SEQIDNO:3901); XM_534716.5, TCHP, Del, A_8, NSKKPLKRKRTNGLKMSMNGPEGKHWSG, (SEQIDNO:3902); XM_005618842.2, RAB4A, Del, A_8, NSKMTQIIQ, (SEQIDNO:3903); XM_534728.4, THOC5, Ins, A_8, NSKSSQSVSV, (SEQIDNO:3904); XM_014119165.1, LRGUK, Del, A_8, NSLFKER-PLKGQGI, (SEQIDNO:3905); XM_014119556.1, EEA1, Del, A_8, NSLNEKLKI, (SEQIDNO:3906); XM_005630261.2, EIF2B4, Del, A_8, NSRRRS-GRRKREQNQKKLPLLYLQPSSK, (SEQIDNO:3908); XM_005630260.2, EIF2B4, Del, A_8, NSRRRS-GRRKREQNQKKLPLLY- LQPSSKAQPKNCQDQAVSWPLLGRKFQLVEVKLN FVLNGGLSRRLSGP, (SEQIDNO:3909); XM_005623926.1, SERPINA14, Ins, A_8, NSSQDGHQ, (SEQIDNO:3910); XM_014111654.1, LOC106558442, Ins, A_8, NSSSIPFFLKNA, (SEQIDNO:3911); XM_005639464.1, BBX, Del, A_8, NSTAFLNIVLLHLTGNA, (SEQIDNO:3912); XM_540699.3, COR4C29, Ins, A_8, NSVCHFFVFLFG-DIAG, (SEQIDNO:3913); XM_014112114.1, LOC102151511, Ins, A_8, NTAEFPKHPRSL, (SEQIDNO: 3914); XM_005618891.2, FAM13C, Del, A_8, NTGLHMVTRLLILKS, (SEQIDNO:3915); XM_532882.5, SMC6, Del, A_8, NTKIFKINWKR, (SEQIDNO:3916); XM_014108478.1, KIF21A, Del, A_8, NTLQLKMGTLLQTLK, (SEQIDNO:3917); XM_005626151.2, UGP2, Ins, A_8, NTTE-VQSLSCENLHF, (SEQIDNO:3918); XM_003431851.2, LOC100686566, Ins, A_8, NVECGICLSGNSKV, (SEQIDNO:3919); XM_014117230.1, C1H9orf3, Ins, A_8, NVEITSAAI, (SEQIDNO:3920); XM_542572.5, ZC3H13, Del, A_8, NVKNPKAILIFLMKKQPCRIKRREVHGLPL, (SEQIDNO:3921); XM_014116764.1, ATAD5, Del, A_8, NVLPLFLTV, (SEQIDNO:3922); XM_014115269.1, DNAH14, Ins, A_8, NVLQLRRNSFRYRNHG, (SEQIDNO:3923); XM_547651.5, THOC1, Del, A_8, NVPLTKLSEVF, (SEQIDNO:3924); XM_014111411.1, LOC611589, Del, A_8, NVSHWMRWDD, (SEQIDNO: 3925); XM_534660.5, VPS33A, Del, A_8, NVSQEKTESL, (SEQIDNO:3926); XM_014120072.1, WRN, Del, A_8, NWKELHSRENFLNGCLCRMRHVLQ, (SEQIDNO: 3927); XM_005617468.2, BDP1, Ins, A_8, NWKRQLSQREDTRNNG, (SEQIDNO:3928); XM_005626458.2, CSNK1G3, Ins, A_8, NWMWQF-WRITIREKFIYK, (SEQIDNO:3929); XM_543181.4, CENPJ, Ins, A_8, NWWFFRSG, (SEQIDNO:3930); XM_544601.6, ARHGAP11A, Del, A_8, NYDYRLQWCRLL-LIMHQILGMFQILSRKRYQLCWVLMVSVLLHH, (SEQIDNO:3931); XM_005624786.2, TADA2A, Ins, A_8, NYKRPWINQP, (SEQIDNO:3932); XM_005630987.1, FBXL13, Del, A_8, NYLQKHYCEYERCATITS, (SEQIDNO:3933); XM_544672.5, SECISBP2L, Del, A_8, NYRKLYQRQLEKRIKPLCS, (SEQIDNO:3934); XM_005621465.2, ACSM3, Ins, A_8, NYSTLQ-ISQKGRIYSRAAKDYQWEDKEK, (SEQIDNO:3935); XM_005618927.2, JMJD1C, Ins, A_8, RCKLSYMSKIL, (SEQIDNO:3936); XM_005631921.2, NCKAP5, Ins, A_8, RCKRFGVWKQTTKIGEKEREKEA, (SEQIDNO:3937); XM_005627049.2, BRD2, Ins, A_8, REKEETEGREAS-RPSWG, (SEQIDNO:3938); XM_545510.4, SPC25, Ins, A_8, RELVKVGC, (SEQIDNO:3939); XM_005617083.2, LOC100856304, Ins, A_8, RENGGIFIRRSKYKCS, (SEQIDNO:3940); XM_544679.5, TMOD3, Ins, A_8, RENN-PETETYTDVHRRKSMS, (SEQIDNO:3942); XM_005641771.2, THOC2, Ins, A_8, RETGQFRRKGREETISFSSYWSF, (SEQIDNO:3943); XM_014111624.1, THOC2, Ins, A_8, RETGQFRRKGREETS, (SEQIDNO:3944); XM_014111626.1, THOC2, Ins, A_8, RETGQFRRKGREETVLGQAQI, (SEQIDNO:3945); XM_005626884.1, CYLC2, Ins, A_8, RFKKGQGVSYRI, (SEQIDNO:3946); XM_014118268.1, LAMA4, Ins, A_8, RFQFIGADGNSGSWLWMPRRLSYISQSIFQW-TEFHCFSSENVFLRWL, (SEQIDNO:3947); XM_544656.5, EIF3J, Ins, A_8, RGSRSKTR-SKSFRKEKNSRENKRERTATEEKARRN, (SEQIDNO: 3948); XM_846902.4, ZMYM5, Ins, A-8, RGTTRTKRKD-FRATGFGRMYRYLTDQTGCNFTFFCVNHS, (SEQIDNO:3949); XM_547682.5, AFG3L2, Ins, A_8, RIKASCYPEPFWRRNWWQWKTRWQER, (SEQIDNO: 3950); XM_014110862.1, PLA2R1, Ins, A_8, RIYMQNG-SRSSCSKGALRKRTKS, (SEQIDNO:3951); XM_005621912.2, MTF2, Ins, A_8, RKEKICRSSTGPNK-KNDSENC, (SEQIDNO:3952); XM_005620231.2, INAD1, Ins, A_8, RKETRNSSTSNETAASLQSSV, (SEQIDNO:3953); XM_537461.5, ARID4A, Ins, A_8, RLR-RINGRGFKSRSRNAFSGSEE, (SEQIDNO:3954); XM_005634532.2, TFDP2, Ins, A_8, RNQVDWLAYQFCSGMSKS, (SEQIDNO:3955); XM_014106274.1, LOC100685903, Ins, A_8, RNSQGLKSSTKQPTM, (SEQIDNO:3956); XM_005638329.2, ADAL, Ins, A_8, RNTSTSGSAS, (SEQIDNO:3957); XM_014120723.1, SYCP1, Ins, A_8, RQENTDTFIENT, (SEQIDNO:3958); XM_014120622.1, SPAG17, Ins, AS8, RRGLFFRRCERRKRGRAES, (SEQIDNO:3959); XM_005623419.2, WDHD1, Ins, A_8, RRGRFQKRAECWLQ, (SEQIDNO:3960); NM_001003212.1, F8, Ins, A_8, RRPCATTCRKSR-SIILQDTVLARLDKDPWQELPKL, (SEQIDNO:3961); XM_014118082.1, DST, Ins, A_8, RSCVFLSRTDGCFPSPC, (SEQIDNO:3962); XM_005638906.2, TTC3, Ins, A-8, RSKKISTRKN-GRGPKGK, (SEQIDNO:3963); XM_005628212.2, LOC475149, Ins, A-8, RSQTKIHRSPSVLRHLLFRTTS, (SEQIDNO:3964); XM_536500.4, NUP155, Ins, A_8, RSSGSWASF1, (SEQIDNO:3965); XM_014115932.1, KIAA0586, Ins, A_8, RSSSAYCTGIAQCGY, (SEQIDNO: 3966); XM_531830.5, MTIF2, Ins, A_8, RTKTFKAKR-ERRKGFTCTSYNY, (SEQIDNO:3967); XM_005634064.2, CCDC168, Ins, A_8, RWRKCSTCER-QNGPPACHFQRTENSF, (SEQIDNO:3968); XM_014117985.1, CNTLN, Ins, A_8, RYQTKFPSIKNK, (SEQIDNO:3969); XM_545493.4, IFIH1, Ins, A_8, SCTRRKSKRPCLCRAFEEVQ, (SEQIDNO:3970); XM_005632697.1, KIAA1683, Ins, A_8, SEHGGGGHPLPCPPAGAVPASWRGQAPSDPACH-GEQRDPVPF1, (SEQIDNO:3971); XM_857314.4, PHF20L1, Ins, A_8, SEIGRKKLNSIW, (SEQIDNO:3972); XM_005618326.2, CHD2, Ins, A_8, SESQKTCPQKN-SAQTSS, (SEQIDNO:3973); XM_014116993.1, NUP214, Ins, A_8, SHSLPTIL, (SEQIDNO:3974); NM_001168012.1, CCDC66, Ins, A_8, SKKADGTA, (SEQIDNO:3975); XM_014118899.1, CASD1, Ins, A_8, SKRKLFLAFWLTVETSLLAVMYMFFGIFSGCI, (SEQIDNO:3976); XM_014115839.1, BAZ1A, Ins, A_8, SKTESSEFSRTTNYSSFILDQPYPSFTLA, (SEQIDNO: 3977); XM_005631802.2, SCLT1, Ins, A-8, SQIKDQYNGT, (SEQIDNO:3978); XM_005624343.2, GJC1, Ins, A_8, SQSGVQSWVQQEQC, (SEQIDNO: 3979); XM_855716.4, CWC27, Ins, A_8, SRKCSKTSRKEK, (SEQIDNO:3980); XM_014120308.1, FAM228B, Ins, A_8, SSHLQKQRIIPSGKRTSMFS, (SEQIDNO:3981); XM_014120309.1, FAM228B, Ins, A_8, SSHLQVLF1, (SEQIDNO:3982); XM_014116745.1, HEATR6, Ins, A_8, SSLWLLVSLCT, (SEQIDNO:3983); XM_535760.5, FAM162A, Ins, A_8, SSPERGSS-CEGQDRV, (SEQIDNO:3984); XM_014118258.1, OGFRL1, Ins, A_8, SSTRRTWRGNRQS, (SEQIDNO: 3985); XM_014120252.1, SLC4A1AP, Ins, A_8, SSWSRQTSSNTFLQISRR, (SEQIDNO:3986); XM_844731.4, UBE4B, Ins, A_8, STKDVQ-PASSQPASQQHPLTVHIPYCVSPTRFPH-TTKVHAAAILPGAVYALQESPIWL HAGTGENHSPG, (SEQIDNO:3987); XM_005630260.2, EIF2B4, Ins, A_8, TAEEEAEGGKGSRTRKNCPCCTCSPAARPSQRTARTRQSVGHCWGESSNWSK, (SEQIDNO:3988); XM_005630261.2, EIF2B4, Ins, A_8, TAEEEAEGGKGSRTRKNCPCCTCSPAASRPSQRTARTRQSVGHCWGESSNWSK, (SEQIDNO:3989); XM_014115049.1, CAMSAP2, Ins, A_8, TAPKIYSQRSY, (SEQIDNO:3990); XM_005618393.2, BTBDI, Ins, A_8, TDPGTKRYWIQLRWNC, (SEQIDNO:3992); XM_014107997.1, KNTCI, Ins, A_8, TEAQAPEVNRS, (SEQIDNO:3993); XM_005617952.1, SZRD1, Ins, A_8, TEDHTKGEEIQISSQSAHCDSGR, (SEQIDNO:3994); XM_846908.3, SZRD1, Ins, A_8, TEDHTKGEQEIQISSQSAHCDSGR, (SEQIDNO:3995); XM_003431930.3, PPP1R17, Ins, A_8, TEEERYTSTAHPTFYTRCAFRTFN, (SEQIDNO:3996); XM_005639600.1, WDR53, Ins, A_8, TEESYKTYPQEEN, (SEQIDNO:3997); XM_003433496.3, HOXC11, Ins, A_8, TEQRPAAVFLGKSSAV, (SEQIDNO:3998); XM_014117181.1, R3HDM2, Ins, A_8, TGGRICKQKQVYF, (SEQIDNO:3999); XM_014121226.1, EIF3M, Ins, A_8, THPFKAP1, (SEQIDNO:4000); XM_014112366.1, MPHOSPHIO, Ins, A_8, TLAASRGSDSSKATREQPSRGDSAL, (SEQIDNO:4001); XM_014112968.1, LOC102154920, Ins, A_8, TLPYKSKQYILPKTQISEGWRGAPE, (SEQIDNO:4002); XM_547275.5, DNTTIP2, Ins, A_8, TNGAKTPF, (SEQIDNO:4003); XM_014119165.1, LRGUK, Ins, A_8, TPYSKRDH, (SEQIDNO:4004); XM_014118235.1, DPCR1, Ins, A_8, TQQSRKKPKYPE, (SEQIDNO:4005); XM_014119796.1, KDM7A, Ins, A_8, TRNNIKLQGGLYCDEELPSEGPEAI, (SEQIDNO:4006); XM_014119545.1, GALNT4, Ins, A_8, TRRDAKLSKRRVPCSSKHRLAF, (SEQIDNO:4007); XM_534660.5, VPS33A, Ins, A_8, TSARRKPSHSDIFPRGCNLC, (SEQIDNO:4008); XM_014111411.1, LOC611589, Ins, A_8, TSIANTRYY, (SEQIDNO:4009); XM_546202.5, DCP2, Ins, A_8, TSSTKTSG, (SEQIDNO:4010); XM_014122375.1, DNAH12, Ins, A-8, TTFLPSLFLLI, (SEQIDNO:4011); XM_544672.5, SECISBP2L, Ins, A_8, TTGSFIKGSWKKE, (SEQIDNO:4012); XM_544601.6, ARHGAP11A, Ins, A_8, TIITGCSGADSY, (SEQIDNO:4013); XM_005630987.1, FBXL13, Ins, A_8, TTYRSTIANTKDVPPLQANNYPD, (SEQIDNO:4014); XM_014118891.1, LOC607634, Ins, A_8, TVPLEACHWPLFLPTTVPSFRCKRRPVCMLGRLSVPVETTTGGLQWYPGPTCW, (SEQIDNO:4015); XM_544640.4, VPS39, Ins, A_8, TVQSSAQEPPPCRISEGPGRADFTPAGEVHHHRGEGVYGV, (SEQIDNO:4016); XM_861706.4, FMR1, Ins, A_8, TYRYKGKQHSFFST, (SEQIDNO:4017); XM_005618911.1, C4H10orf107, Ins, A_9, IEFQKPSHLFKGSHSTRLLCIWIFVG, (SEQIDNO:4018); XM_014108953.1, ZNF518A, Ins, A_9, IFKNKNSCKK, (SEQIDNO:4019); XM_014118548.1, RGS22, Ins, A_9, IGSHRRRKFCKGWNQTISKFFRICNQNSCFSH, (SEQIDNO:4020); XM_005626171.2, ETAA1, Ins, A-9, IKYSASIP, (SEQIDNO:4021); XM_532334.4, KCNQ3, Ins, A_9, IQGDFEALRREGCD, (SEQIDNO:4022); XM_005617803.2, STPG1, Ins, A_9, IQPCQQITERFYCRISNTILHSF, (SEQIDNO:4023); XM_014116147.1, ATG2B, Ins, A_9, IRLSEQELTEFSLCSSEYQSWINGSVYRCQAR, (SEQIDNO:4024); XM_014114898.1, LRRIQ3, Ins, A_9, ISSYHHATRCPRKS, (SEQIDNO:4025); XM_005622971.2, WDR64, Ins, A_9, ITKPSFRLKEL, (SEQIDNO:4026); XM_014106333.1, ERCC5, Ins, A_9, ITQAAAHTWLSQSSCCGCLPQTCGG, (SEQIDNO:4027); XM_014119213.1, TMEM196, Ins, A_9, IWTCHDPFFC11HLWTHWGHPEFSVSSGSDKEDLFSLPSASRLHVPCMHWDRWLHPVFLAHLSTSQLRTEEDVLRKGAFAAP1S, (SEQIDNO:4028); XM_005635476.2, PDS5B, Ins, A_9, IWTFSTRRRGRRRKTKWKHRTEVKEQTAPNIKESTTEPCRTLQTSSY, (SEQIDNO:4029); XM_005635474.2, PDS5B, Ins, A_9, IWTFSTRRRGRRRKTKWKHRTEVKEQTAPNIKESTTEQSRIS, (SEQIDNO:4030); XM_005635475.2, PDS5B, Ins, A_9, IWTFSTRRRGRRRKTKWKHRTEVKEQTAPNIKESTTESRIS, (SEQIDNO:4031); NM_001003300.2, KCNMA1, Ins, A_9, KAAERRHAELTQLLAQADEA, (SEQIDNO:4032); XM_003432210.3, TAF1B, Ins, A_9, KAFKFSVQLD, (SEQIDNO:4033); XM_536223.4, NOP14, Del, A_9, KASTTSMRMKN, (SEQIDNO:4034); XM_005623486.2, SYNE2, Ins, A_9, KCGTKATKTF, (SEQIDNO:4035); XM_005633326.2, CEP57, Del, A_9, KCKSWKQNSGKNNRKGNVCKLRQPSCRLG, (SEQIDNO:4036); XM_005635475.2, PDS5B, Ins, A_9, KCPCRTLQTSSY, (SEQIDNO:4037); XM_005627611.2, C12H6orf165, Ins, A_9, KCRINSVTGTSSTVRNPHSIFSNEGC, (SEQIDNO:4038); XM_005617981.2, PRDM2, Del, A_9, KCRLHPRKVDTRHLPAVTKTAAATGAGLQTRRLRCRACRLLWARPERAAPALRQA RCRPRPSGPSRMSNLQLR, (SEQIDNO:4039); XM_005617468.2, BDP1, Ins, A_9, KCSFRSWTIRKCWRKNWKR, (SEQIDNO:4040); XM_005620331.2, C5H1orf141, Ins, A_9, KDFGYTPDI, (SEQIDNO:4041); XM_533539.4, KIAA0020, Del, A_9, KDFIKTVILVRQRHSQGKLSRKVDLKSHLRTLRNVP, (SEQIDNO:4042); XM_005628464.2, DBF4, Del, A_9, KDIVNVACRNMKILKLIF, (SEQIDNO:4043); XM_005623289.2, SCFD1, Del, A_9, KDLLISIQMLPLLF, (SEQIDNO:4044); XM_532252.6, SEC63, Ins, A_9, KEAFKKKTYTCALTTVKATETKAGKWNCWE, (SEQIDNO:4045); XM_014114026.1, FUK, Ins, A_9, KECVLVGGGLVAELQQAWGWGQFLYLYSLRP, (SEQIDNO:4046); XM_533327.6, DDX18, Ins, A_9, KEEEKEKNGG, (SEQIDNO:4047); XM_005623020.2, ESCO1, Ins, A_9, KEEITSEKFSAWNF, (SEQIDNO:4048); XM_014110821.1, DYNCII2, Del, A_9, KEEKQKHCFKAWG, (SEQIDNO:4049); XM_535246.4, NDUFAF2, Del, A_9, KEKILKLKVNIFMKKKNSLAKGARKNSWLNQFKLRSKGMPRLHTLERKNLPWLPPALVKSFNRDPGCHKAARTQIN, (SEQIDNO:4050); XM_005624758.2, BCAS3, Del, A_9, KEKKNNANSPASVSNPTVTKQVFGMEEELQREGSIETLS, (SEQIDNO:4052); XM_005618622.2, RFC1, Del, A_9, KERVLIKKQSL, (SEQIDNO:4053); XM_014122469.1, LOC100686348, Del, A_9, KFPLIFPSYLMSYTM, (SEQIDNO:4054); XM_848407.3, LOC610853, Del, A_9, KFPLRFPSYLMSYTM, (SEQIDNO:4055); XM_014113182.1, JAK1, Del, A_9, KFQMLPLFLMPVLWSISLLRDSMIWSNAWLPFETPRLSRMGTILRMSVWEWLSWPS PTMP, (SEQIDNO:4056); XM_014113418.1, TBC1D32, Del, A_9, KFRRRKATTVTAQIIALNIHHSIRVTNFVKENYN, (SEQIDNO:4057); XM_014109094.1, KIF20B, Ins, A_9, KFYFKYRGPANSVEL, (SEQIDNO:4058); XM_014119810.1, KMT2C, Ins, A_9, KGARGQNYGSS, (SEQIDNO:4059); XM_014121826.1, LOC106560105, Ins, A_9, KGGGGCIISSPRWPSGSARSRCADDVSSTWASLGLFVLFSYAPALFSGGLLRSRS, (SEQIDNO:4060); XM_005627570.2, IBTK, Del, A_9, KGILKRKRFYQIFIIPHQMCLVSLI, (SEQIDNO:4062); XM_014114974.1, RNASEL, Del, A_9, KGISMRILRVIC, (SEQIDNO:4063); XM_005619174.2, UIMCI, Del, A_9, KGLGNQCYLDLL1, (SEQIDNO:4064); XM_003432210.3, TAF1B, Del, A_9, KGLQVFSSTGLKETLQEPVSTDMASRGF, (SEQIDNO: 4065); XM_003639290.3, SPAG9, Del, A_9, KGQAFGNFSADFSAPQVIQLRSLNHLLI, (SEQIDNO: 4066); XM_005616957.2, LOC480753, Del, A_9, KGRSRRVVKWKEQKTYMLLLLLD, (SEQIDNO:4067); NM_001006950.1, IL5, Del, A_9, KGVQEKDGE, (SEQIDNO:4068); XM_005635025.2, RBL1, Del, A_9, KHHLHLLPH, (SEQIDNO:4069); XM_014113145.1, SPEF2, Del, A_9, KHKYPHWLLMLAPPKKCLFPLLHLTLSCY, (SEQIDNO:4070); XM_014113312.1, CHEK1, Del, A_9, KHTLTLGKKLIQLLLLCCIKS, (SEQIDNO:4071); XM_005634176.2, GINS1, Del, A_9, KIASISYPDGSVSSWLDREFWSTCCP, (SEQIDNO:4072); XM_014111881.1, ZNF711, Del, A_9, KIIIQGTVVKEMKEEFPGGMKIVKHQEIPWTQH, (SEQIDNO:4073); XM_005640445.2, PMSI, Del, A_9, KILKNINLT, (SEQIDNO:4074); XM_005619458.1, EMB, Del, A_9, KINVLSHRGETSDLTALLR, (SEQIDNO:4075); XM_014110679.1, SP3, Del, A_9, KIPGPLRPCPPPLPASSPAAAAFAPHHVTLSRHRSPCWPLPAAR, (SEQIDNO:4076); XM_535304.5, CHD9, Del, A_9, KIQLLYLVNSLYNYLWRIQVKKMLQL, (SEQIDNO:4077); XM_005631118.2, EHF, Del, A_9, KIVAAGQTRPVSRS, (SEQIDNO:4078); XM_536037.5, CARF, Del, A_9, KIWTVRNYLPH, (SEQIDNO:4079); XM_014118792.1, ATP10D, Ins, A_9, KKKRKKKKKEKQGGGRGGRAVPAPGCPFGRRSCFSRFRARGGSRGGGLRARALPW RERAQITCIPRISAHFGHDRVSAMGQVSLAATNGRHKQG, (SEQIDNO:4080); XM_014116149.1, LOC100856221, Del, A_9, KKLDVIRSPLNF, (SEQIDNO:4081); XM_014116721.1, PRR11, Del, A_9, KKPLTLSPS, (SEQIDNO:4082); NM_001114605.1, ZC3H15, Del, A_9, KKRKKMKFH, (SEQIDNO:4083); XM_014110977.1, NBEAL1, Del, A_9, KKRNWQIRHLLKNL, (SEQIDNO: 4084); XM_014110821.1, DYNC1I2, Ins, A_9, KKRSRSIASKHGADSRIPHC, (SEQIDNO:4085); XM_005640306.2, DYNC1I2, Ins, A_9, KKRSRSIASKHGADSRIPHCFF, (SEQIDNO:4086); XM_014110819.1, DYNC1I2, Ins, A_9, KKRSRSIASKHGADSRIPHCPSSYVSILQICEHTK, (SEQIDNO: 4087); XM_850174.2, LOC612447, Del, A_9, KLERNRMERVKK, (SEQIDNO:4088); XM_005637010.2, FAM60A, Ins, A_9, KLESCGRCKGRTQSEDYFETKESENSIWKQDKKQPDQ, (SEQIDNO:4089); XM_014118898.1, LOC102152714, Del, A_9, KLKCNIKTLKNISSSS, (SEQIDNO:4090); XM_544621.5, RMDN3, Del, A_9, KLLQPCLKALSVPL, (SEQIDNO:4091); XM_014117774.1, RFX3, Del, A_9, KLLSWNS1, (SEQIDNO:4092); XM_005639177.2, HERC3, Del, A_9, KLMNILKQVPKSLGLT, (SEQIDNO:4093); XM_005623826.2, MOK, Del, A_9, KLRTICTSYVNPLIICTEMEYFTEM, (SEQIDNO:4094); XM_014115615.1, LOC100682643, Del, A-9, KLSPPVPPISLWSLSIMAPLSLPMFTLQRSTTSPLVK, (SEQIDNO:4095); XM_003431923.4, HOXA11, Del, A_9, KLTETVYSTTQPTRSS, (SEQIDNO:4096); XM_848625.3, ABCA9, Del, A_9, KLTHSYGFQASTLLLIGLARHWWIFHSTS, (SEQIDNO:4097); XM_014111056.1, DNAH7, Del, A_9, KLVMTLTLSG, (SEQIDNO:4098); XM_005638791.2, LTN1, Del, A_9, KLVRLDLLMSCLKVIKRMKNVSPQKARTVKALNQWLKLLLFLIVQTLYHH, (SEQIDNO:4099); XM_014107060.1, TCEB3, Del, A_9, KMIRKALIKTRIQFRNYLK, (SEQIDNO:4100); XM_005617468.2, BDPI, Del, A_9, KMLIQKLDHQEVLEKKLEEIILCL, (SEQIDNO:4101); XM_005616776.2, TDRD12, Del, A_9, KMLMLKKGNPHLIRLLPLEFIGADT, (SEQIDNO: 4102); XM_005623486.2, SYNE2, Del, A_9, KMWNKSYKNFLIS, (SEQIDNO:4103); XM_014112649.1, RBPJ, Del, A_9, KNKWNGMVVLNKSLNHVHLLE, (SEQIDNO:4104); XM_014111562.1, GLRA4, Del, A_9, KPCGNSMWTKPSRLTPSPGLSSLSLSSSSTPSTGLSIKCYGQKIFTRHC, (SEQIDNO:4105); XM_005639444.1, CRYBG3, Del, A_9, KPKSLVERVLEKWRKIPLKERKA, (SEQIDNO:4106); XM_005617337.2, KCTD16, Del, A_9, KPLRKSSQLRRSWRNASRIS, (SEQIDNO:4107); XM_005628367.2, MKLN1, Del, A_9, KPRLPWNIPC, (SEQIDNO:4108); XM_014111547.1, AP3B1, Del, A_9, KQRKIEILPKMFHF, (SEQIDNO: 4109); XM_014121826.1, LOC106560105, Del, A_9, KRGGGMYYFISQVAFRLSSIQMCRRCF, (SEQIDNO: 4110); XM_005630347.2, CEBPZ, Del, A_9, KRKEISVTPVYLYLLKSLATYWMKIWDPSLITLA, (SEQIDNO:4111); XM_014118195.1, AK9, Del, A_9, KRKKQQEKPLKRH, (SEQIDNO:4112); XM_014119443.1, BENDS, Del, A_9, KRKMRSLSHPSRLTN, (SEQIDNO:4113); XM_014112182.1, AHI1, Del, A_9, KRKRRLNQFLIIMKTLMVMVFMK, (SEQIDNO:4114); XM_014114026.1, FUK, Del, A_9, KRMCSGGRWPGGRAATSMGLGSVLVSLQLTSLMAATAT, (SEQIDNO: 4115); XM_533327.6, DDX18, Del, A_9, KRRREREKWWMMLGLIPKNQKLKTKGTLKKGPRLLKRQKTMGRSQMMRKRTVK CPAYPWD, (SEQIDNO:4117); XM_014119810.1, KMT2C, Del, A_9, KRSKRTKLWFLLINILHGKNLWVLVR, (SEQIDNO:4118); XM 005637736.2, TCF7L2, Del, A_9, KSAFATYKVKAAASVHPLQMEAY, (SEQIDNO:4119); XM_539422.5, SAMD9L, Del, A_9, KSKTSCVV, (SEQIDNO:4120); XM_014108379.1, BCL2L13, Ins, A-9, KSLQASDISGISGMYSGDHSSCQRLE, (SEQIDNO:4121); XM_005619458.1, EMB, Ins, A_9, KSMCYHTVEKHQILLLFYVRT, (SEQIDNO:4122); XM_014110679.1, SP3, Ins, A_9, KSPDRSGRVRRRFPHPLPPPPPSLLTM, (SEQIDNO:4123); XM_014119579.1, UHRF1BP1L, Del, A_9, KSQVIQCCLPVKSMI, (SEQIDNO:4124); XM_545992.5, WDR36, Del, A_9, KSSGKDFRMPCQ, (SEQIDNO:4125); NM_001003300.2, KCNMA1, Del, A_9, KSSGTEACGTHPAPRPS, (SEQIDNO:4126); XM_014118880.1, LOC482344, Del, A_9, KSTQFLCVL, (SEQIDNO:4127); NM_001286956.1, HGS, Del, A_9, KSTTRIPMWPCTPWRSWSLW, (SEQIDNO:4128); NM_001197174.1, ABCC4, Del, A_9, KSVRNLPTALC, (SEQIDNO:4129); XM_005631118.2, EHF, Ins, A_9, KSWLLAR1A1, (SEQIDNO:4130); XM_542898.4, FERMT1, Del, A_9, KTKVTRSP, (SEQIDNO:4131); NM_001003057.1, TCOF1, Del, A_9, KTRKKRKRRRQKRPQPKTLTHYSRRKRRKRRRQQSKLS, (SEQIDNO:4132); XM_532542.5, EXO5, Del, A_9, KTVFKSAYTNISLMPWFKGK, (SEQIDNO:4133); NM_001006950.1, IL5, Ins, A_9, KVCRRKMESDKVPRLPASISWCNKHRVDTGK1, (SEQIDNO: 4134); XM_014112285.1, NIPA2, Del, A_9, KVFCDLPRRAP, (SEQIDNO:4135); XM_014111124.1, SGOL2, Del, A_9, KVFMTQKKVTSFL, (SEQIDNO:4136); XM_014117699.1, RAPGEF6, Del, A_9, KVIAIQSRMYREILNTHHRRKEIRK, (SEQIDNO:4137); XM_003639290.3, SPAG9, Ins, A_9, KVKHLAIFQPTFQLLK, (SEQIDNO:4138); XM_014118133.1, ZNF292, Del, A_9, KVLKKQKAPCK, (SEQIDNO:4139); XM_005637736.2, TCF7L2, Ins, A_9, KVRSLHTR, (SEQIDNO:4140); XM_014115152.1, AXDND1, Ins, A_9, KVTDKGRKRTPTWRRGFC, (SEQIDNO:4141); XM_005633512.2, POLD3, Del, A_9, KVTGGSEWSYLMMKQKKLKI, (SEQIDNO:4142); XM_535048.6, ACADSB, Del, A_9, KWESEPLPPVH, (SEQIDNO:4143); XM_850840.5, VPS13B, Del, A_9, KWIHLMEAWLKPHLGTVVPRIVELAVTVLKSE, (SEQIDNO:4144); XM_014112849.1, RUFY2, Del, A_9, KWLITCVA, (SEQIDNO:4145); XM_014110905.1, LOC106558304, Ins, A_9, KWWWRRVYGKTPRGLDETLQIWPPGGRS, (SEQIDNO:4146); XM_014119214.1, FAM221A, Del, A_9, KYYRCAYRTGYL, (SEQIDNO:4147); XM_014111124.1, SGOL2, Ins, A_9, MYFTVTRFFTDICLLRIRFKIYY, (SEQIDNO:4148); XM_005615403.2, RNMT, Del, A_9, NAISLFWTWDVVKVEICSNGKREELTS, (SEQIDNO:4149); XM_005636978.2, KIF21A, Ins, A_9, NARAFPYNQEKSI, (SEQIDNO:4150); XM_005633326.2, CEP57, Ins, A_9, NARVGSKTPGRTTGKETYAS, (SEQIDNO:4151); XM_014107150.1, SYCP2, Ins, A_9, NERKVKRERIY, (SEQIDNO:4152); XM_014115615.1, LOC100682643, Ins, A_9, NFLHLCLPSHCGLYLLWHHYLCLCSPSSEAQLHHW, (SEQIDNO:4153); XM_005619222.2, SPDL1, Ins, A_9, NGGRCNCRSSMQTQRG, (SEQIDNO:4154); XM_535048.6, ACADSB, Ins, A_9, NGNPSLFHLCINI, (SEQIDNO:4155); XM_014111562.1, GLRA4, Ins, A_9, NHAETLCGPSQAD, (SEQIDNO:4156); XM_005622315.2, CD55, Del, A_9, NHVLILEI, (SEQIDNO:4157); XM_535332.5, ZCCHC17, Del, A_9, NIETGSHLTLTAQTLRVTQARGQGTHQKTARQQRRRRRRRSIRRNTRS, (SEQIDNO:4158); XM_014116983.1, TTF1, Del, A_9, NIGGKRLPVMLSRRAHLLGSPCPSRVRIRRSWKACFLWAQRAESHNYQ, (SEQIDNO:4159); XM_005635025.2, RBL1, Ins, A_9, NIICTFYPTDRTAIFTRKRSSHYSCCFSYSKCEPITEYCGWTEKCTK, (SEQIDNO:4160); XM_532882.5, SMC6, Ins, A_9, NILVKRESKGLAGSRKLNQSRD, (SEQIDNO:4162); XM_014112539.1, RGS12, Del, A_9, NIRKLIWTKQRSFLSSFPKLRATEQTTSAGC, (SEQIDNO:4163); XM_532047.5, CNTR1, Ins, A_9, NKCSTNSTIRTT, (SEQIDNO:4164); XM_014114329.1, IQCE, Ins, A_9, NKFDGKPQITCFRSGQGKRCGALCVQLHCVQAATR, (SEQIDNO:4165); XM_005635474.2, PDSSB, Del, A_9, NLDLQHQKKRKKKKDKVETQNRSQRANSTEHQGEHNRAEQNLLKLVQLNPHNPHHRKDEEDHQKRHHHHNQKKMSV, (SEQIDNO:4166); XM_005635476.2, PDS5B, Del, A_9, NLDLQHQKKRKKKKDKVETQNRSQRANSTEHQGEHNRAV, (SEQIDNO:4167); XM_005635475.2, PDS5B, Del, A_9, NLDLQHQKKRKKKKDKVETQNRSQRANSTEHQGEHNREQNLLKLVQLNPHNPHHRKDEEDHQKRHHHHNQKKMSV, (SEQIDNO:4168); XM_005629758.2, PSD3, Del, A_9, NLHQKVLMRRLMEHIQRPSVVSGALPIHS, (SEQIDNO:4169); XM_005639368.1, LOC100856070, Del, A_9, NLMKVGNK, (SEQIDNO:4170); XM_005641429.2, OPHN1, Del, A_9, NLRRMVRGFIPCWIGTYNLPKRKNLSYKRQTSRWTRKGTISLSPLLIMFIKFRKFRSP RSSTLWSQCWPFFIASSFPTV, (SEQIDNO:4171); XM_014120849.1, NME8, Del, A_9, NLTFKILSFL, (SEQIDNO:4172); XM_014113911.1, RERE, Del, A_9, NLVMKGQTLGR, (SEQIDNO:4173); XM_005617803.2, STPG1, Del, A_9, NPAMPTNYREVLLPHIQHNPPFLLKARLQQF, (SEQIDNO:4175); XM_005639444.1, CRYBG3, Ins, A_9, NPRAWWRGCWRNGERSP, (SEQIDNO:4176); XM_014112201.1, CAST, Ins, A_9, NPRSKAKGTQRAKKPTQACIRYGKQACS, (SEQIDNO:4177); XM_005628367.2, MKLN1, Ins, A_9, NQDCPGTSHVNRST, (SEQIDNO:4178); XM_014118880.1, LOC482344, Ins, A_9, NQLSSSVFYE, (SEQIDNO:4179); XM_545547.4, PLEKHA3, Del, A_9, NQTLKILFHPSLP, (SEQIDNO:4180); XM_005640421.1, AOX4, Ins, A_9, NRARKCRAS1, (SEQIDNO:4181); XM_005629522.2, TPK1, Ins, A_9, NRRKRPTGRRNCDLGRSCRAF, (SEQIDNO:4182); XM_014113418.1, TBC1D32, Ins, A_9, NSEGEKQQQLLHR, (SEQIDNO:4183); XM_005626122.2, PAPOLG, Del, A_9, NSFITTFQQRFFKRRKSKVFLMLVEVQVDLNPKDH1, (SEQIDNO:4184); XM_014116072.1, MLH3, Del, A_9, NSMVEEQTFLVMDKLNYVP1A1, (SEQIDNO:4185); XM_005627548.1, MYO6, Del, A_9, NSRKRKQKG, (SEQIDNO:4186); XM_003432384.3, LOC100686139, Ins, A_9, NSRSKSHFDDGIYSFGIF, (SEQIDNO:4187); XM_532047.5, CNTR1, Ins, A_9, NSTCTHKAGN, (SEQIDNO:4188); XM_848625.3, ABCA9, Ins, A_9, NSVDHIIAFWH, (SEQIDNO:4189); XM_014117774.1, RFX3, Ins, A_9, NSYHGTLYKQTSEFW, (SEQIDNO:4190); XM_014110705.1, GRB14, Del, A_9, NTEHRLTMDSALSLTKREGPET, (SEQIDNO:4191); XM_014113145.1, SPEF2, Ins, A_9, NTNTHIGC, (SEQIDNO:4192); XM_014111124.1, SGOL2, Del, A_9, NVFHSYQILYRHLSP, (SEQIDNO:4193); XM_014112778.1, LOC106558676, Ins, A-9, NVFVLFSEHLWSSSARHCSKLWGRGQKSELPARGSGPSRKK, (SEQIDNO:4194); XM_549109.5, RPS6KA6, Del, A_9, NVSQNKKLVMY, (SEQIDNO:4195); XM_850174.2, LOC612447, Ins, A_9, NWKETEWKE, (SEQIDNO:4196); XM_847826.3, SGOL1, Del, A_9, NWMNLSLPMMLTILIW, (SEQIDNO:4197); XM_005623826.2, MOK, Ins, A_9, NYALYVPVM, (SEQIDNO:4198); XM_014106333.1, ERCC5, Del, A_9, NYASCSSHLAFPIQLLRMLTSNLWWMIPGDRFCGGNQIWTKLENFVSVILAGTGRRQ MSLCFQY, (SEQIDNO:4199); XM_005634067.2, ERCC5, Del, A_9, NYASCSSHLAFPIQLLRMLTSNLWWMIPGDRFCGGNQIWTKLETLFWLEQDEDR (SEQIDNO:4200); XM_014119410.1, SYCP3, Ins, A_9, NYDGDCKSLHFKLEK, (SEQIDNO:4201); XM_014120966.1, ZNF236, Ins, A_9, NYKEEVTISAWFNP, (SEQIDNO:4202); XM_005624937.2, SMYD4, Del, A_9, NYKKRGHFS, (SEQIDNO:4203); XM_014118195.1, AK9, Ins, A_9, RGRSSKKSH, (SEQIDNO:4204); XM_014110977.1, NBEAL1, Ins, A_9, RKGIGRSDIY, (SEQIDNO:4205); XM_005624758.2, BCAS3, Ins, A_9, RKKKTMPTAQRP, (SEQIDNO:4206); XM_005617448.2, NLN, Ins, A_9, RNNESRGWNEIQKPNPETWGISGRHGHAPEFLET, (SEQIDNO:4207); XM_014108747.1, NLN, Ins, A_9, RNNESRGWNEIQKPNPETWGISGRHGHAPEFLETSEHRVLV, (SEQIDNO:4208); XM_532542.5, EXO5, Ins, A_9, RPFSSQPIQNL, (SEQIDNO:4209); NM_001003057.1, TCOF1, Ins, A_9, RQGKKGKEEEGKKGLNQRP, (SEQIDNO:4210); XM_863127.3, ZFR Ins, A_9, RSRIESFTKYQQQQQFYSWDSKSATI, (SEQIDNO:4211); XM_014112285.1, NIPA2, Ins, A_9, RSSATCQEGLHESRSRWPCIS, (SEQIDNO:4212); XM_536157.5, NIPA2, Ins, A_9, RSSATCQEGLHESSGSR, (SEQIDNO:4213); XM_014112649.1, RBPJ, Ins, A_9, RTNGTGWLF, (SEQIDNO:4214); XM_005619174.2, UIMC1, Ins, A_9, RVWGTSVT, (SEQIDNO:4215); XM_014119214.1, FAM221A, Ins, A_9, SITDALTEQVICELAITDWNGL, (SEQIDNO:4216); XM_863127.3, ZFR Ins, A_9, SKSR- FASRSKAQYSSQKDSRRENEEADAERRV-LAKTRRRRTLENGNEAL, (SEQIDNO:4217); XM_545992.5, WDR36, Ins, A_9, SQAERTSECHVSE-ASTHHKVCS, (SEQIDNO:4218); XM_005638661.2, SCAPER Ins, A_9, SQKDKSPDELQSQGI, (SEQIDNO: 4219); XM_539422.5, SAMD9L, Ins, A_9, SQRPPVSSNWSG, (SEQIDNO:4220); NM_001286956.1, HGS, Ins, A_9, SQRQESPCGLVRPGGHGVCGEELWPD-GARRGGQQADHGGA, (SEQIDNO:4221); XM_848625.3, ABCA9, Ins, A_9, SSLTATDFRPLPFCLL-VWPGTGGYSTLLLDPPSNANNGLCF, (SEQIDNO: 4222); XM_014113182.1, JAK1, Ins, A_9, SSRCYPSS, (SEQIDNO:4223); XM_005617981.2, PRDM2, Ins, A_9, SVAFIQERWTRVTCRQ, (SEQIDNO:4224); XM_005622165.2, LOC100682872, Ins, A_9, TADHRD-FLSSTSPWQLPLGHPAISLLCFLLI, (SEQIDNO:4225); XM_005627548.1, MYO6, Ins, A_9, TAGRGSRKAEAY-SRRNGKRKKKT, (SEQIDNO:4226); XM_005626122.2, PAPOLG, Ins, A_9, TASSLPSSRDSSKEEKAKSF, (SEQIDNO:4227); XM_014106376.1, RBM26, Ins, A_9, TGGTETSARCKEKETRNFRKAH, (SEQIDNO:4228); XM_014120722.1, SYCP1, Ins, A_9, TKGCRKAICL, (SEQIDNO:4229); XM_005635545.2, SACS, Ins, A_9, TLSFQSIECSCLKCFKRSC, (SEQIDNO:4230); XM_005636132.2, MPHOSPH9, Ins, A_9, TNRDFRYTN-HESFKRT, (SEQIDNO:4231); XM_851972.4, ARV1, Ins, A_9, TQLHFAAESIIIIQLWKALAHSSCHLGA, (SEQIDNO:4233); XM_005615403.2, RNMT, Ins, A_9, TRYHCFGPGMW, (SEQIDNO:4234); XM_014116983.1, TTF1, Ins, A_9, TSEERGFL, (SEQIDNO:4235); XM_005624937.2, SMYD4, Ins, A_9, TTRKEAIFPENFGRKGLDWTSQST, (SEQIDNO:4236); XM_005621019.2, ACTB, Ins, C_10, HRRVPLVATP, (SEQIDNO:4237); XM_003435344.2, DPH7, Del, C_10, PAALTGDFSPHPDRDPRSHRGPQLPHRPYSHRRPQPP-PRPPLSTWPLHPAFAALSPLR LRLTPG, (SEQIDNO: 4238); XM_014116284.1, WNK2, Ins, C_10, PAPSLV-PEPRARRPARPARPGTGQQQQQQEGHLHG, (SEQIDNO:4243); XM_014116598.1, SIX5, Ins, C_10, PCCPPAPPSPPPSSPAGPRPRGAAPGVCGRGRGG, (SEQIDNO:4245); XM_014121371.1, LOC106560024, Ins, C_10, PCGGAPRPAAATGEKRDTDGL-PRAWGLRRPVNTGMGAASAHGARGGRRRGRQGQ PGQRPSAPITAGAASWPRVRPRQEPP, (SEQIDNO: 4246); XM_014114858.1, TRIM28, Ins, C_10, PEPAWCWPECPGAIQWSW, (SEQIDNO:4248); XM_014110311.1, SLC9A3, Del, C_10, PGGPILIGNS-SAKSL, (SEQIDNO:4249); XM_014115712.1, SLC25A29, Ins, C_10, PGPGGPHTRRGCGRRACGTPI, (SEQIDNO:4250); XM_014115712.1, SLC25A29, Del, C_10, PGTGRAPHAA WVWQACLWDTHLTRSRCGCR-CRARRSLSTGGPCTASSPSSSRRACWACTRAWARR SWGSRSSTRWCSACRATPCGRWAATRR, (SEQIDNO: 4251); XM_005620616.2, HSF4, Del, C_I0, PHCPWLWCRPSWKGRGTSAP-RGPGMPNSLNQGVPGRYLTGGLWAWTGGHEAQRI CCLPCCFGP PLKVWSLQGPWMCWAPAIKGENGP, (SEQIDNO:4252); XM_542531.4, DBX1, Del, C_10, PHSPSLHASPLRRAPTPAGVGVGAPPRFPQKKKTR-TRT, (SEQIDNO:4253); XM_014117361.1, LOC106557479, Ins, C_10, PKASWREWLCADPGG-WARCPREECPVAHRSQKTGHVPGPLPQQRPRTP, (SEQIDNO:4254); XM_005640409.1, HOXD8, Del, C_10, PLLGILGLGRRLPPAAGLPVTGSPRSFTDTI-TYRDSRFLRPSKRPSWYNILTVNRPVVI LARTQTT, (SEQIDNO:4255); XM_014116598.1, SIX5, Ins, C_10, PLLPPGPSIPAPLLPCRTPT-PRGCSWGLRQGARRMRGWRPSRRF, (SEQIDNO: 4256); XM_014108684.1, LOC106557920, Ins, C_10, PLPHPAGSNSRGCSESC, (SEQIDNO:4257); XM_014121371.1, LOC106560024, Del, C_10, PLRRRPQARSSDR, (SEQIDNO:4258); XM_014108317.1, LOC106557878, Ins, C_10, PLT-SPPPFSPCSQYFI, (SEQIDNO:4259); XM_014112775.1, PPIF, Ins, C_10, PPAPDSQAEGRCRPKDGREL-QSPVYRGEGLRLQRF, (SEQIDNO:4260); XM_003435344.2, DPH7, Ins, C_10, PPLSPAISAPTRTAT-PALTADPSSHTDPTLTADLSPHPDPRFQPGL-STPPSPPCLRCVCV, (SEQIDNO:4261); XM_014114444.1, BAIAP3, Ins, C_10, PPPAQLEQLAR-RAQRARGHRALPPRRAEQPVCAAAGGAAL-GGEQPSPSDLHAGLRL PAGAAGGHAGTLGGGVLPA-PRAGEEPG, (SEQIDNO:4262); XM_005621019.2, ACTB, Del, C_10, PPQSPPRGHPLKLSPASVSSQAWN-PAASMKLPSTPS, (SEQIDNO:4263); XM_014117361.1, LOC106557479, Del, C_10, PQGFVEGVA1C, (SEQIDNO: 4264); XM_005637736.2, TCF7L2, Del, C_10, PQTP-SHRLSRPSRCRCP, (SEQIDNO:4265); XM_014116284.1, WNK2, Del, C_10, PRPLPGPRAPSQAPSPPCTSRHRPT-TATTRGAPSRMTCTSWWTSGRARRRGPPS, (SEQIDNO:4266); XM_014113226.1, CXCL16, Del, C_10, PRRDPAPVGGSRTFPRFSPGM, (SEQIDNO:4267); XM_014118733.1, GLI4, Del, C_10, PRRPHGPRTTPPGRPAPAAWCPGAAQAGGLP, (SEQIDNO:4268); XM_014122165.1, CBARP, Ins, C_10, PRRRGPQGQPRHIPAPGEGPHRPLRGPQLRPAR, (SEQIDNO:4269); XM_014116598.1, SIX5, Ins, C_10, PRVPPPALPPWTSDPTLLGHISAPPTPTRAPRTQTAR-SPPPPPTPPPCCPPAPPSPPPSSP AGPRPR-GAAPGVCGRGRGG, (SEQIDNO:4270); XM_005637965.1, PXDNL, Del, C_10, PSAR-GRSRAAAAAAAAS, (SEQIDNO:4271); XM_014109368.1, LOC106558038, Del, C_10, PSGLVPWGGPRHAAPLRVWGLLF, (SEQIDNO:4272); XM_014112775.1, PPIF, Del, C_10, PSGSRLTS, (SEQIDNO:4273); XM_005640409.1, HOXD8, Ins, C_10, PSSASSASAAASPLRRDCLSRGAREVLRIR, (SEQIDNO:4274); XM_014108684.1, LOC106557920, Del, C_10, PTAPSRGIQLPRLQRVLLTRPPRP-PRPPGSHSPREQAEPVGAQGRCSLATCRQALG, (SEQIDNO:4275); XM_014116598.1, SIX5, Del, C_10, PTGSPPRAAPLDK, (SEQIDNO:4276); XM_005620616.2, HSF4, Ins, C_10, PTVRGCGAGHPGREGELQPRGAQECPTA, (SEQIDNO: 4277); XM_545337.5, LOC488215, Ins, C_10, RPRGSEKHELLEVLPFRSRPAQRAHPADG-LSQPVAPAAELGEAEWPRPEAREAARLR GRPRREGG FPVGQHLAVARGQRP1, (SEQIDNO:4280); XM_543674.5, SMARCD1, Ins, C_11, PASRAVPLP-DARSGLSETRHAAR-QPNDTSGTFHGTPWLWGEPFSPTWPGPVRDGPVP QETCTSADTAGPAAGGPKSKPQCKEKEDG, (SEQIDNO:4283); XM_014108583.1, ARID2, Ins, C_11, PEPADVAVRNSF, (SEQIDNO:4285); XM_014113969.1, LOC106558847, Del, C_11, PGARSRGRGPLRRARSG-GRSGPAAVSSPHGPRRA-PRAAAQAPAAAGQQPQQLPGAQG YAGARPSLPR-TRAP, (SEQIDNO:4286); XM_005639618.2, LOC102153772, Ins, C_11, PGPPAGGGARPEGGD, (SEQIDNO:4289); XM_850394.4, ST6GALNAC5, Del, C_11, PGPRPRPPPPRRGRWTDTSA, (SEQIDNO:4290); XM_014108583.1, ARID2, Del, C_11, PGTRRRRCPEQFLRRISGEKLLKSSTFPEVVLTLPLL, (SEQIDNO:4291); NM_001205203.1, MEF2B, Del, C_11, PGVLPPGPPN, (SEQIDNO:4292); XM_547695.5, ZBTB7C, Del, C_11, PHHPPSPATSSRTCSPTSLGGR-WAPSRPRVTTVPISTS, (SEQIDNO:4293); XM_014110530.1, LOC106558242, Del, C_11, PHPHLAPSLVPHPYSGPPH, (SEQIDNO:4294); XM_014118871.1, LOC106559658, Ins, C_11, PHTH-TQRLPLPFLLAPKYGLWTQAPGARPQGGIL-GLEKETHTRDSLPPTCPPERGK, (SEQIDNO:4295); XM_005627791.2, TSPYL1, Del, C_11, PLAKAWQRRR-CRCRWQRTAAWKMGVGAPGRAGRVRGALRGRRT-CGRRRRPRSC RPATASLRRRRRRRRRRSPGWRQTR-REGKSWPGGRVPGRPRGPDA, (SEQIDNO:4296); XM_014120240.1, MTA3, Del, C_11, PLRPP-SQLQHRLPELKRSPLGLLRANCPALRSKPREGVP-GAGIILNYYQQFTRHPTPA AQPAPCPPEAKQIMSTL-RIPPVTRT, (SEQIDNO:4297); XM_005634658.1, LOC102156928, Ins, C_11, PQCPTPRCAHRPQSSRPR-SAPPPRSARRPQGPTPRI, (SEQIDNO:4298); XM_543674.5, SMARCD1, Del, C_11, PRLKGCTAPRCPERPIRDQACCQAAE, (SEQIDNO: 4300); XM_005639644.1, LOC102151137, Del, C_11, PRPRPAAGAHSGPGRHTPG, (SEQIDNO:4301); XM_014114924.1, LOC607201, Ins, C-11, PSLELLGQELWGPWSCAGQGAPSVPGSQQAVL-CRAALLATTTLW, (SEQIDNO:4302); XM_014115040.1, SH2D2A, Del, C_11, PSPPIPSTRSPTSPSPSTPWG-GAAPGKPRATSMRRWRWRSRLGPGGP-PASSGTPGPCGN AGPGLSREARIQEPGDHSLRT1, (SEQIDNO:4303); XM_014113855.1, TPRGL1, Del, C_11, PSRVITSLLSSAHWLL, (SEQIDNO:4304); XM_005618215.1, LOC102151979, Del, C11, PTPQVPL-MAPLPLPRRC1, (SEQIDNO:4307); XM_547695.5, ZBTB7C, Ins, C_11, PTTPLPQRLLQGHVPRPPW-GAAGPHQGRE, (SEQIDNO:4308); XM_014115040.1, SH2D2A, Ins, C_11, QALPSHLPGARRAH-RLLRHGAGQPRGSPVQRLCGGGGGGPAWGRGAPLR-PRAPGP AEMPVQACPGKPESRSLATTV, (SEQIDNO:4309); XM_014113969.1, LOC106558847, Ins, C_11, REPGAEGGR, (SEQIDNO:4310); XM_014120240.1, MTA3, Ins, C_11, RSAPRASCSTGSRS, (SEQIDNO:4311); XM_005624453.2, HSD17B1, Ins, C_12, HYGSH-LAGARALAPRYRT-SALQLGGSGPRRLGDWPKVTRRGSPPGWGSDADLPHP HAAAGAGAGRGRGALRAVRRP1, (SEQIDNO:4312); XM_014106269.1, LOC102153036, Del, C_12, PAPSS-ESRLPGHRQAPQNSRGPSQRLRVAAPRP-PHGRCSFGLRWGFPWRPRLRGGHP, (SEQIDNO:4313); XM_014110359.1, LOC106558197, Del, C_12, PGPQVQMEGGGGLRPLHLRPQRGPARLDLGTSPAV-LTGRGWERRREEGKKGLGFR AAGHRKA, (SEQIDNO:4314); XM_845687.4, C1H9orf40, Ins, C_12, PGQQSAGGDRLPWLPPQPVGSQPAPRRGA, (SEQIDNO:4315); XM_005624453.2, HSD17B1, Del, C_12, PLRLTSGGCQGACPSLSHFCPAAGRLRPEEAG, (SEQIDNO:4316); XM_005634658.1, LOC102156928, Del, C_12, PQRPTPAGPDAPH, (SEQIDNO:4318); XM_014117451.1, LOC106559403, Ins, C_12, QNQAASKTFFPLPAASHTRRHPGGPAANGRRGGAR-PRPRRLLGSCTRRPPHGERGA ASSRGGAAS-PHPDRDRRFGIAKD, (SEQIDNO:4319); XM_014110359.1, LOC106558197, Ins, C_12, RGRR-CRWKGAAG, (SEQIDNO:4320); XM_005634658.1, LOC102156928, Ins, C_12, RSARRPQGPTPRI, (SEQIDNO:4321); XM_014106524.1, RBP1, Del, C_13, PGAGFWGPTALGTVLWI-FLPTLCPSVPRHPLQMLMWPCAKLPTC, (SEQIDNO:4323); XM_014111383.1, RBMIO, Ins, C_13, PMAPGRRQSRRPGWVSSRAPSFSLTPT-SAPFIPSLPQH, (SEQIDNO:4325); XM_532513.4, BMPER, Del, C_13, PPLPGARLPPARTVSRLAG, (SEQIDNO:4326); XM_014119800.1, LOC106559804, Del, C_13, PPRGRGVQD, (SEQIDNO:4327); XM_014118514.1, LOC106559608, Del, C_13, PRGCAPPPRSAQPGRAHPRDSPAGLRRAGGGVSSAR-PRARSAACPPGLSE, (SEQIDNO:4328); XM_005642274.1, LOC102152225, Ins, C_13, PRHSPRVCACVPR, (SEQIDNO:4329); XM_014118307.1, LOC100685196, Del, C_13, PRPC-CLRGPWP, (SEQIDNO:4330); XM_005642274.1, LOC102152225, Del, C_13, PTPLTPCVCVCAA-LAAGWLSGPPPAPEPSRRRRWLGGRVWVGPA-PAWGRLPGS, (SEQIDNO:4331); XM_014106524.1, RBPI, Ins, C_13, QELASGAPLP, (SEQIDNO:4332); XM_014119800.1, LOC106559804, Ins, C_13, RPAAGAY-RISCC, (SEQIDNO:4333); XM_014115020.1, INTS3, Ins, C_14, PAMPPWNGHSRCQSVY, (SEQIDNO:4335); XM_014116506.1, SPATA32, Ins, C_14, PGRQGRN-RAGDITGAGAPSISGAPQSPQPKSALEAEGQQP-PARSLPP, (SEQIDNO:4336); XM_014112078.1, LOC102152371, Ins, C_14, PPGEPL-SPHQDPRRLLLLRVRRH-PAQELLRGDGPGHDRYHHVGGRGH, (SEQIDNO:4337); XM_005638993.2, LOC102152474, Del, C_14, PPPGCLRDAEGHSGRPGPGTGNAGLAICTLKPGR-GARGMELARRWSPPRPTLQKAR QARTAWTEG, (SEQIDNO:4338); XM_005637886.1, NSMCE4A, Del, C_14, PPRRGPGDPGLAALLQVITPARTCSRVM-STFPQTLFFVCLVFCFFFFA, (SEQIDNO:4339); XM_014115020.1, INTS3, Del, C_14, PRHAALEWPQSLSECLLSPVWYAKAPHSMRKSA-WASSPSSSLNLPKLKSVTGTWLW (SEQIDNO:4340); XM_014112078.1, LOC102152371, Del, C_14, PSRRTTVAASRSSATVITACPASPSPRTAAWRWAWT, (SEQIDNO:4341); XM_005640730.1, LOC102154007, Ins, C_14, PVVQGRGSHPRHPGP, (SEQIDNO:4342); XM_005637886.1, NSMCE4A, Ins, C_14, RPAGDPGTRAWPRCCR, (SEQIDNO:4343); XM_005638993.2, LOC102152474, Ins, C_14, RPRGVSGMRRVTPGGLGLGLATRASQSAP, (SEQIDNO:4344); XM_014106492.1, VIL1, Ins, C_15, PANT-CALGSPEPEGHSGGIQRPALLGGEGGGRGGAGLG-GRLRAAPAGGAGRGRRAA PGGAGPRVPLFPQLLPPGRPLQERWPELCPQA, (SEQIDNO:4345); XM_847492.2, CCBE1, Ins, C_15, PARGPAPADPAALAPGPPLPRGRPAKWPPRLSS, (SEQIDNO:4346); XM_014116208.1, ITGB4, Ins, C_15, PDSRVCEPVSNHQWHPQYPGGPVVLPD1, (SEQIDNO:4347); XM_005640152.1, IRF4, Ins, C_15, PDTRSRGPSPASPAAPGPRQQRPLAPTRVAPRCPPS-SAPGSAPAGF, (SEQIDNO:4348); XM_005615674.1, LOC102154183, Ins, C_15, PQDPL-HAPPGGQQLQSGAAPPSGPPADGAAGSSAGHPPAR-RAHLRRRGPARP, (SEQIDNO:4349); XM_005640152.1, IRF4, Del, C_15, PRHALPRPEPGLPRGAGSPPAAP-PRPDPGRAALPAQLRPRLRPSGLLSFISSSFPPRHLL GFTS, (SEQIDNO:4350); XM_014106492.1, VIL1, Del, C_15, PRKHLCFRFPGA, (SEQIDNO:4351); XM_847492.2, CCBE1, Del, C_15, PRPGTRARRPRR-PRARPSAPPRPPRQVAAAPVVLGSSARRTR-SPRPGTRV, (SEQIDNO:4352); XM_005639335.1, CYP2U1, Ins, C_15, PVLPAASASRTCKLCALHPRRP-PASGREKGSLPPPHPPLAAGTLGAGVQGESLRGHP GHEEPGSQSVSPAPRPDARAPR-PARRGPQLRGCERRPGPLGRS, (SEQIDNO:4353);

XM_014116368.1, GOSR2, Del, C_16, PAFILIWFILK-TIVMECLVWAGP, (SEQIDNO:4354); XM_014116598.1, SIX5, Del, C_16, PHPPPLLPPGPSIPAPLLPCRTPT-PRGCSWGLRQGARRMRGWRPSRRF, (SEQIDNO: 4355); XM_014116598.1, SIX5, Ins, C_16, PTPPPCCP-PAPPSPPPSSPAGPRPRGAAPGVCGRGRGG, (SEQIDNO:4356); XM_005639009.1, POFUT2, Del, C_17, PGISCTTSTPRRASTSAGMSTSASPPS, (SEQIDNO:4357); XM_014119273.1, LOC106559736, Del, C_17, PLWSIRLRW, (SEQIDNO:4358); XM_014119802.1, LOC482696, Del, C_17, PRTRWQAFGRQLRNIEQRVCSWTLSLLLMGFPT, (SEQIDNO:4359); XM_005639009.1, POFUT2, Ins, C_17, QVSPVRRQPPGGLQPPQGC1HPRRLPPEDAAADRG-VGAGAAP1GPPLSLAEPRHPPG PDSLVRLF, (SEQIDNO:4360); XM_014119802.1, LOC482696, Ins, C_17, REHAGRLLAGS, (SEQIDNO:4361); XM_014106854.1, LOC106557662, Del, C_22, PRQDPGRPR, (SEQIDNO: 4362); XM_014106854.1, LOC106557662, Ins, C_22, RGRTPGARV, (SEQIDNO:4363); XM_014116429.1, SHISA7, Ins, C_7, HAAARAAPTARPARAPPPRPARL-PAAGLDVGRRWGRGHAGAQAALPAPGHAGATA VHPRPPPSATPAHRQQE, (SEQIDNO:4364); XM_014106282.1, STK24, Ins, C_7, HAGRNLQQTPQGIC, (SEQIDNO:4365); XM_014116613.1, SRCIN1, Ins, C_7, HAPP-PADPHLAGTPGPGAPSGLSPGPHMEERWWQRATH-EGGDSRGLSAEGGPGPGR QPRQRQAWQAE-GRVHEDPGPAAGH, (SEQIDNO:4367); XM_014116610.1, SRCIN1, Ins, C_7, HAPP-PADPHLAGTPGPGAPSGLSPGPH-MEGCPKPQGLLRPPDHLDRVYPQPSLTTRG QTRGSWSQDNSHSAPPDPAWQWEGL, (SEQIDNO: 4368); XM_014113911.1, RERE, Ins, C_7, HCGPPPFCFFPPGPEPPGEGETGPGGPPAAA, (SEQIDNO:4370); XM_843373.4, AGAP1, Ins, C_7, HCQHAHTCPEAVQAPLQPFHLSERE, (SEQIDNO: 4371); XM_014121818.1, LOC476718, Ins, C_7, HDCVHIPGLARSGCQPSHLPWPPPGLPPR-SQEPCPGTPSSDTPTHPPAREGWGSHWS RCHLHPPP, (SEQIDNO:4372); XM_014116831.1, ABR, Ins, C_7, HFLRRTEAEHTVLLH, (SEQIDNO:4373); XM_003433467.3, TARBP2, Ins, C_7, HGGAAPRLPSAV, (SEQIDNO:4374); XM_014114672.1, HCFC1R1, Ins, C_7, HGIPPISAPTQEPV1, (SEQIDNO:4375); XM_014121831.1, TLE6, Ins, C_7, HGLPQPPQLPR-GLPGRERRAGHRS, (SEQIDNO:4376); XM_533913.5, RAB3D, Ins, C_7, HGPAGCSRPEL, (SEQIDNO:4377); XM_014116695.1, BZRAP1, Ins, C_7, HGRGDQGLARGWWERAAAPFPEMLPWPGPRI, (SEQIDNO:4379); XM_014117075.1, DENND1A, Ins, C_7, HGRPFSDPNVAPGPLKCQGC, (SEQIDNO:4380); XM_014107665.1, HDAC4, Ins, C_7, HGRRGVLGSLQDRGHAHRERVCPRRGARVIRL, (SEQIDNO:4381); XM_014119061.1, IRF5, Ins, C_7, HGTLFFTQRGCQV AAHPPAACGAGPSC-TRPQPAGPHPWQPCWLWGASP, (SEQIDNO:4382); XM_014118376.1, GRM4, Ins, C_7, HHHQT-GTCGRCHRCFRELCLHHGGQHPSPLQDPPDQLRLH-SPRPE, (SEQIDNO:4383); XM_005630266.2, NRBP1, Ins, C_7, HHPWEPD1, (SEQIDNO:4384); XM_003431507.2, TOM1, Ins, C_7, HHRAR-QGAQPHPVLG, (SEQIDNO:4385); NM_001013847.1, TPP1, Ins, C_7, HIIPEATP, (SEQIDNO:4387); XM_014109477.1, STARD9, Ins, C_7, HKAALWLGKS, (SEQIDNO:4388); XM_546428.4, VSIG2, Ins, C_7, HKRGGHPETD, (SEQIDNO:4389); XM_844789.4, CBX6, Ins, C_7, HLAFLRDGAHHQSQGQASGAQAK-PHHPQPEGDRQGHRRGRPRAGGRSPRSPQSPLQ EPRHWQEQEVQREHPAHPDPPHEVWHLLAVQ, (SEQIDNO:4390); XM_005627318.2, FOXP4, Ins, C_7, HLGCCSCHPPSAPWPQLCLPAQWRPCPPEEQ, (SEQIDNO:4391); XM_014121836.1, LOC106560107, Ins, C_7, HLPEPPLLRPRQQQPGSG, (SEQIDNO:4393); NM_001287125.1, CDH1, Ins, C_7, HLQPNHVPGTGA, (SEQIDNO:4394); XM_843371.3, LOC606890, Ins, C_7, HLRDAQGRARGGGPRGGAPERSSRYHHRDQHPR, (SEQIDNO:4395); XM_014118383.1, UHRF1BP1, Ins, C_7, HLSNISRPYPHHSSHGAYCVEAE, (SEQIDNO: 4396); XM_546572.6, CAMTA2, Ins, C_7, HLSRGFIQR-RHRNPPPDGTGAACGGLDAHQALGSPD, (SEQIDNO: 4397); XM_843636.3, CDSN, Ins, C_7, HNLCRQILWQL, (SEQIDNO:4398); XM_014108022.1, LRRC43, Ins, C_7, HPARAGQWPAGLGA-PAGGGVTCVLRVQLWGDPHPGNRQADVS, (SEQIDNO:4399); XM_544410.5, SALLI, Ins, C_7, HPATSE-QFRPHHRSTQQRLFPQH, (SEQIDNO:4400); XM_005640913.1, LOC488620, Ins, C_7, HPGGRLLP-PAIRRALPGHDGVLPAGRHGSGPPPGHLPPAALPRA-HEQEGAAGAGGG RLGGRLLGGPGASRPHGR-PALLPEAGGPLLL, (SEQIDNO:4401); XM_014112353.1, LOC106558589, Ins, C_7, HPGLSRAPR-GRRLSGAARPEVAPDGPGTLSGRPRRV, (SEQIDNO: 4403); XM_005633500.2, NEU3, Ins, C_7, HPHLPGLC-REALHEQG, (SEQIDNO:4404); XM_538306.5, KLHDC7B, Ins, C_7, HPLPPIPWQGP, (SEQIDNO:4405); XM_005630809.2, POGZ, Ins, C_7, HPLPRGPPAP1GKKIHPKSLEPEGGFLSPAGRRALHG-SLSAVSPSPRPLPCSHPLLPAP GARSL, (SEQIDNO: 4406); XM_544055.4, HMX2, Ins, C_7, HPLSLPGYPQGRRRRGAGELGAHAFPLCFAPGL, (SEQIDNO:4407); XM_014121373.1, LOC106560025, Ins, C_7, HPPAAPGLPP, (SEQIDNO:4408); XM_005618506.2, MFSD10, Ins, C_7, HPPADASGH-PRDHCGLPRPPAGPSGLHSATAPAARTAGEPQSCPRP-PLWLVAARCGL VCSSHQDAS-REEVQQRPVWRSDWLRLLLPAVPPGTTHGGS1, (SEQIDNO:4409); XM_014122263.1, SHC2, Ins, C_7, HPPGAHRPHGGAAAAGTLVPWPDE-PEGGREAAPSRRGLPGARQRH, (SEQIDNO:4410); XM_844754.4, PLEKHO1, Ins, C_7, HPP-SAPPGPAVPDPGPGSQETGKDSGAAGRGSGPGRRE-AEGQGPPLVSP, (SEQIDNO:4412); XM_005619461.2, LOC102153808, Ins, C_7, HPPTAEEAALGSIAYALG, (SEQIDNO:4413); XM_541491.5, SCAF1, Ins, C_7, HPQEVQAGAQAEWWRGQGGCLIVFGCTAR-PASPGLPLGLQEAPLPGPQARLACLVV RPPPFAVPL-SPPPLAQH, (SEQIDNO:4414); XM_005633166.2, LOC102155774, Ins, C_7, HPRQPAGFWGRRHS-GLEPHNRCFCTEVERGTSELME-GRPQGEATWTPVHRPHPPP GQV, (SEQIDNO:4416); XM_005633167.2, LOC102155774, Ins, C_7, HPRQPAGFWGRRHSGLEPHNRL, (SEQIDNO:4417); XM_003639255.2, LOC100856208, Ins, C_7, HPSNRGGL, (SEQIDNO:4418); XM_014110188.1, AHDC1, Ins, C_7, HPTALASHPAPCQPT, (SEQIDNO: 4419); NM_001003008.1, RHPN2, Ins, C_7, HPTDGDLVYLV, (SEQIDNO:4420); XM_014119265.1, C15H12orf74, Ins, C_7, HPTPVLREHSSEPPVLILCTTE-QDTSLGSHITPQARASYDGRWHRKSLPRGYILIRTHW LPSKRVQ, (SEQIDNO:4421); XM_005630123.2, C17H2orf50, Ins, C_7, HPWAPENLVRWVPAALNQAAS-RRFPHCPRWPRGGQGSPSPPGPRSGALGPGNERCA AGPAVEGALGGREEGPAALGSALEFPERLRSPGQ, (SEQIDNO:4422); XM_014119807.1, ATG9B, Ins, C_7, HPWGAQRFFLTSARGLIGQPLGAAPPAPTGPEPHSPLPSCCHSQPPGLHFPPCPGPQL CVSRGHWGPEAGPASRACFC, (SEQIDNO:4423); XM_005635260.2, OSBPL2, Ins, C_7, HQCILFRRPQSGLPVSRLHLPEAEVLGQERGGRAPGDHHAGAAQTQ, (SEQIDNO: 4424); XM_540140.5, GALNT14, Ins, C_7, HQHHHHLPQRGPLHPAQNHPQRIKSHTYESDPGNHISG, (SEQIDNO:4425); XM_014106406.1, LOC102156658, Ins, C_7, HQLRASDMRRAVAAGRSLAPLPPSHASDLLSRACVQRPGSAADVEEPAAGCGDPGP RGGLSADAR, (SEQIDNO:4426); XM_003639777.3, SYDE1, Ins, C_7, HQNLPHEVPRPSQASVHEDEEAARP, (SEQIDNO:4427); XM_853531.4, ARPP21, Ins, C_7, HQPAAPARGNDGAVPAAATATAFSSATAAGATTPATHGRPTGHSERRCGDTVHPDE PEPAILRRDS, (SEQIDNO:4428); XM_014114167.1, GTF2IRD1, Ins, C_7, HRHLLLCGQLPVQHRAP, (SEQIDNO:4431); XM_014107801.1, CCDC92, Ins, C_7, HRLRPQLK, (SEQIDNO:4432); XM_005639690.2, NKD2, Ins, C_7, HRPGPGAPSLQDGG, (SEQIDNO: 4433); XM_014107017.1, CHD6, Ins, C_7, HRPQRLAWGICNRSLLHVRGVSRSHVSFPSERQHP, (SEQIDNO:4434); XM_005624410.2, HDAC5, Ins, C_7, HRRRGVPNGLQDSGDAHCPRVLT, (SEQIDNO:4435); XM_014121827.1, PTPRS, Ins, C_7, HRTVSPPSRR, (SEQIDNO:4436); XM_014106943.1, RIN2, Ins, C_7, HRVADPRRPN, (SEQIDNO:4437); XM_547143.4, ZNF500, Ins, C_7, HSAAPGGPWAKVQPPLVELSASEVPFGISRSEFM, (SEQIDNO:4438); XM_847340.4, UBAP1, Ins, C_7, HSCSKQYQISVLPQT, (SEQIDNO: 4439); XM_014122294.1, LOC100685073, Ins, C_7, HSCSNQYQIPVLPQT, (SEQIDNO:4440); XM_014116490.1, GAS2L2, Ins, C_7, HSRKQLSRYCKWRSYDRIGEWPHSKGCHWGPGWV, (SEQIDNO: 4442); XM_005628998.2, CC2D1B, Ins, C_7, HSWPGARCGHRGRCGGSYFSCCPEAGFLGGSSPSRGGGGGGG, (SEQIDNO:4443); XM_014121888.1, MAP4, Ins, C_7, HTCAQEAHCCQD, (SEQIDNO:4444); XM_014110312.1, AHRR, Ins, C_7, HTLCLPGARAWPS, (SEQIDNO:4445); XM_005627115.2, DDR1, Ins, C_7, HTRLGQTHQHPGLQWGLYGA, (SEQIDNO:4447); XM_014113005.1, FAF2, Ins, C_7, HTSGGRTQPHRSSLCSGPDR, (SEQIDNO:4448); XM_849841.4, APOA1BP, Ins, C_7, HVHVPEPPRGPGHLRTWK, (SEQIDNO:4449); XM_852361.4, TCF20, Ins, C_7, LAEQDSERQPQHRAVGAGV, (SEQIDNO:4450); XM_535696.4, ENPEP, Ins, C_7, LAGPFARDPAARGPGGLSRQRR, (SEQIDNO:4451); XM_014117046.1, GARNL3, Ins, C_7, LAIPTGVYRPPGIQGLFASEVN, (SEQIDNO:4452); XM_005617744.2, ARID1A, Ins, C_7, LARHEEQFGWDPGCLS, (SEQIDNO:4453); XM_005617746.2, ARID1A, Ins, C_7, LARHEQEQFGWDPGCLS, (SEQIDNO:4454); NM_001205203.1, MEF2B, Ins, C_7, LARIPHWERLAPLL, (SEQIDNO:4455); XM_014109253.1, PCMTD1, Ins, C_7, LCCQESTGLGSYLYSTYT, (SEQIDNO:4456); XM_536887.5, RNF216, Ins, C_7, LCLRAPALPPATCPAHVQQLPSQHGPRPSPLRAPSAQCARQLRLCSRPYASGAQPAY ALWPPATASLL, (SEQIDNO: 4457); XM_005628976.2, GJB4, Ins, C_7, LCPLPGRAPPGRELCPHEGRVSLDGRRWVPI, (SEQIDNO:4458); XM_014119660.1, MKNK1, Ins, C_7, LCRSLWDRLWLGPGRSLQGVPEQAI, (SEQIDNO: 4459); XM_014121833.1, LMNB2, Ins, C_7, LDARVEDPEQLGHWRELPDCPGQR, (SEQIDNO:4460); XM_005627762.1, C12H6orf132, Ins, C_7, LDLHPGGPGGGEPRAGWDLCWRQSV, (SEQIDNO: 4461); XM_542953.5, PLAGL2, Ins, C_7, LDSRCKAGGGSGLETSSQASGPGGGESSEVPM, (SEQIDNO: 4462); XM_014118922.1, TEAD2, Ins, C_7, LECSRCEAILTDTVLVTDPPN, (SEQIDNO:4463); XM_014122225.1, TYK2, Ins, C_7, LEIHRAHRPHPGADDGAEAHRAAGTRGEAAPAREMSL, (SEQIDNO: 4464); XM_005631964.2, ZEB2, Ins, C_7, LERLFITQVARKAYGLHNFTIHSRTPQQCNEL, (SEQIDNO:4465); XM_014113085.1, SAL13, Ins, C_7, LGFSGRRNGQSTHWQ, (SEQIDNO:4466); NM_001014375.1, NFKBIL1, Ins, C_7, LGGAGGSEEVLKGPAGPLAP, (SEQIDNO:4467); XM_845370.4, ZNF750, Ins, C_7, LGLRPLQVLPAVPSQPAHSIRVLQTRVCVLLLRSQTPGRRRCFQRSKLTPPGRSCPAL PGPESVQVKSFQHPQKAHRV, (SEQIDNO:4468); XM_542926.4, CPXM1, Ins, C_7, LGPGVPASFG, (SEQIDNO:4469); XM_005642488.1, C1QTNF8, Ins, C_7, LGPQRLRPQEQWGAVGAPALHAAPH, (SEQIDNO: 4470); XM_539044.5, BACH2, Ins, C_7, LGSRWRPPLLLLLLLLLGELHEEAGGQRPGGLPGEGASAGIQEPDGDRGL1PGND, (SEQIDNO:4471); XM_014111337.1, FOXP3, Ins, C_7, LHLRHPDPLGHPGGS, (SEQIDNO:4472); NM_001168461.1, FOXP3, Ins, C_7, LHLRHPHPLGHPGGS, (SEQIDNO:4473); XM_005634969.2, FAM83C, Ins, C_7, LILTLQHQPQQHQTLTSNGPLFLSRSTRW, (SEQIDNO: 4476); XM_014122716.1, PLEKHA7, Ins, C_7, LKQRTPLHLCL, (SEQIDNO:4477); XM_531753.4, BPIFC, Ins, C_7, LLASSFCTARTQ, (SEQIDNO:4478); XM_005619043.2, ZSWIM8, Ins, C_7, LLCCMPGHNLVLFLSVSPSGFCSLPACPSLRVPVSAAEGPAAEVCPVPHQ, (SEQIDNO: 4479); XM_014113364.1, ARHGEF12, Ins, C_7, LLCRLTKPDHGVHS, (SEQIDNO:4480); XM_014116208.1, ITGB4, Ins, C_7, LLLQKCYQPDRKLGGVSE, (SEQIDNO:4481); XM_545640.4, RUFY4, Ins, C_7, LLPEGRGSVPL, (SEQIDNO:4482); XM_014120042.1, MEGF8, Ins, C_7, LLPNASIPRGMSTSPDLQ, (SEQIDNO:4483); XM_854764.4, MAP1A, Ins, C_7, LLSFYIVGRWEALSWCDHKPW, (SEQIDNO:4484); XM_005634296.2, ZBTB47, Ins, C_7, LLSSCLFPARVPGRPP, (SEQIDNO:4485); XM_014109500.1, CILP, Ins, C_7, LPAPCHKHCQRKSVLKETATG, (SEQIDNO:4486); XM_005636541.2, ZDHHC8, Ins, C_7, LPAQHAPLTLLCRPQSCRLHPHGPPPRVATLAGRAKGPPSAEDPPK, (SEQIDNO:4488); XM_848542.4, LURAPIL, Ins, C_7, LPAVLLLVLSNLRLPTSQPLQRPGEAGNQAALPQAGDG, (SEQIDNO:4489); XM_014117280.1, LOC102154639, Ins, C_7, LPGQPVPDESRRQK, (SEQIDNO:4490); XM_005621049.2, PILRA, Ins, C_7, LPKKSPQEETLYSIL, (SEQIDNO:4491); XM_014119801.1, LUZP6, Ins, C_7, LPLAASDWYL, (SEQIDNO:4492); XM_014114806.1, HIAT1, Ins, C_7, LPLWSLFRTAGSACCLVYSRTYQFKLTVQQLEKALWQSQPSS, (SEQIDNO:4493); XM_846788.3, SLC9A5, Ins, C_7, LPNLCREGA TLEEWAGRSGSLRVLGNHQDCARGHAGRLEPEHLVPGEPGIPALYPGPNYDPPASLP TGC, (SEQIDNO:4494); XM_014115086.1, NSL1, Ins, C_7, LPPFRSHSSRPRFKLERWRGLPCRGSLPVRGAWRERRGRTIGRRSPPAPGRTAGCAA RRSGP, (SEQIDNO:4495); XM_014116573.1, DACT3, Ins, C_7, LPQPGPGPWHVRRA, (SEQIDNO:4497); XM_014106807.1, DCLK3, Ins, C_7, LPQPREGPG, (SEQIDNO:4498); XM_014109759.1, NRIP1, Ins, C_7, LPRARGLRGLQAGAGASERLCGRRRQGPH, (SEQIDNO:4499); XM_544370.5, ZNF366, Ins, C_7, LPRLLVLQAQR, (SEQIDNO:4501); XM_845833.4, LDB1, Ins, C_7, LPSRHHARSGCGPNSHVPAYIPGAWDWEAHTIWQPN, (SEQIDNO:4502); XM_014121756.1, LOC106560089, Ins, C_7, LQPRTPGWWFLVTAAAAGKEHSLGALPQVCVQGSQRGKVSPHPEWREHHSQKSLVLAAVVLFKPLLIS1, (SEQIDNO:4503); XM_534025.5, ART1, Ins, C_7, LRDLPGDQCQ, (SEQIDNO:4504); XM_005637736.2, TCF7L2, Ins, C_7, LRLHCQHSSLQGHEKEPLLTQGWGALVFGVEQSARRAAPSPCSPSHAAHHVQQ, (SEQIDNO:4506); XM_005616728.2, GRAMD1A, Ins, C_7, LRLPATAR, (SEQIDNO:4507); XM_846468.4, C7H1orf116, Ins, C_7, LRQRQDLPQRRP, (SEQIDNO:4509); XM_014121534.1, VHL, Ins, C_7, LRRRGPPSSRGAASACWSPPSL, (SEQIDNO:4510); XM_548978.5, CFP, Ins, C_7, LRWRCRPNPHLQYSCALPCEWRVGVLGGVEHLCPSGHKHHV, (SEQIDNO:4511); XM_545122.3, GPR156, Ins, C_7, LSGLCTFLRGASCKSDCVWGAQRAANRAEQGQCQPGPAKC, (SEQIDNO:4512); XM_014113971.1, RLTPR, Ins, C_7, LSLSQPQPTKSQPLPRQPGPPRGPLLGPQE, (SEQIDNO:4513); XM_014116505.1, FMNL1, Ins, C_7, LSPADPCPQQEDPEEFSHC, (SEQIDNO:4514); NM_001003009.2, TPO, Ins, C_7, LSRVGPVQEHQGWFQV, (SEQIDNO:4516); XM_005621867.2, CDC14A, Ins, C_7, LSSVQGCFLWKLHL, (SEQIDNO:4517); XM_014117336.1, MKL1, Ins, C_7, LTHGHLGIALCP, (SEQIDNO:4518); XM_014106880.1, RBBP8NL, Ins, C_7, LTPTAPLPGPSEGRHGEDAGRPRGGRGRPCRKVCGLQDISSGQNLPECQPA, (SEQIDNO:4519); XM_843722.4, MAP3K12, Ins, C_7, LTRTESSWQDSAPEGQRQGQLRRPAWASRGFATP, (SEQIDNO:4520); XM_014120830.1, UPP1, Ins, C_7, LVLALSSSLSQVNKI, (SEQIDNO:4521); XM_005631651.2, LOC612278, Ins, C_7, LVLLTSPSC1HFLPSWAPSLAASLLPVVYFLFCYPAEEVGGLGLDDDLLCSHLPHLRA VFGTERRPGPFLHGQVPGKHLVCMGNTDEPYPHAH, (SEQIDNO:4522); XM_538253.4, 42438, Ins, C_7, LWGHQPPPGCPAHADALASALWLHNPAPPWTAAATRCPFQFPFWPRGCHEGHHGV, (SEQIDNO:4523); XM_548302.6, CORO6, Ins, C_7, LWPPPQPVGQRRLPVAAAHPGDAAGGDQGPARAGAGPGAAHHGPGEHAVRAGGR HRL, (SEQIDNO:4524); XM_005624896.2, CORO6, Ins, C_7, LWPPPQPVGQRRLPVAAAHPGDAAGGDQGPARAGAGPGAAHHGPGEHAVRAGGRH RL, (SEQIDNO:4525); XM_014119957.1, MGAM, Ins, C_7, LYATFGVQG, (SEQIDNO:4526); XM_005631240.2, SPI1, Ins, C_7, PAAAALPPHGAGADARARHPHGSEPRGHRPPGLLSTPDVPPIPLSVPGPA, (SEQIDNO:4527); XM_014114719.1, UNK1, Ins, C_7, PAAAHPQVRARSAGLVGRVLLPGAERRPREHLGLCLRQLLSQPDPDPEPRPCPFVRR EPQRCGAGPGQAAAGRGQEEDPAMGGVLAAGEAGV, (SEQIDNO:4528); XM_014114715.1, UNK1, Ins, C_7, PAAAHPQVRARSAGLVGRVLLPGREPQRCGAGPGQAAAGRGQEEDPAMGGVLAA GEAGV, (SEQIDNO:4529); XM_014108311.1, LOC106557876, Ins, C_7, PAAAPPAGARAHRRPPAPGRPPAARGIPPARRPPALSPAASRSGARAPTNPREQPV, (SEQIDNO:4530); XM_847178.3, PTPRU, Ins, C_7, PAAAPRGAHLPHHPAQHQLHHWRRADRAQGD, (SEQIDNO:4531); XM_545733.5, SPTA1, Ins, C_7, PAAARRTKHHRPAPGRHREPVPLPP, (SEQIDNO:4532); XM_014122224.1, RFX1, Ins, C_7, PAACHRCYPPAPICH, (SEQIDNO:4533); XM_014108558.1, LOC106557908, Del, C_7, PAAFKAPTMQRWRPSSVTMSLRAPANPRGAGGEAAEPRL, (SEQIDNO:4534); XM_014110188.1, AHDC1, Del, C_7, PAAGHPASPSRYTRHPTRRASPTSCTGCRASDGAVGKQAVLVAGAGATQPRQPDAP SVTSLRALARKRKWWRWRLLVLGVPASPNWGTRANGAGGRWTP, (SEQIDNO:4536); XM_850276.3, NCCRP1, Del, C_7, PAAGSRCPTSSASMAPGCASSTSCTRPRTGGSPVGCGGQG, (SEQIDNO:4537); XM_014119392.1, LOC475337, Ins, C_7, PAAGVPGTSPAWHWHCGETNQAPGQLL, (SEQIDNO:4538); XM_850293.5, UCKL1, Ins, C_7, PAAHQQAHHLHGRPAALVQRARHAVQGGLCHWPGRWQRLGEDHRGPDDHRGPG RALGGPAVHGLLLQGAHHAAAGAGRPQQLQL, (SEQIDNO:4539); XM_014117260.1, PPP6R2, Ins, C_7, PAAHVSPQVRARAPRACGNPPRPSCGRAPRGHPRCPGQRPRDDRSGAPGGRHHCGP SHVHSSCSGDRDEG, (SEQIDNO:4540); XM_014115697.1, LOC102152805, Ins, C_7, PAALAAPAHLSGGH, (SEQIDNO:4541); XM_014115611.1, CTIF, Del, C_7, PAALMPPPQGLLKGCPRSSQGVRRLRQSVKTVLFPSASGSGPKLPCSSLPKTGCGEG, (SEQIDNO:4542); XM_005621599.2, UBA1D1, Ins, C_7, PAALPPHRHRQLPRPELACCSLTPGGPTAPPATAAAPVDSGTPLPGVRLATLGPPTGR FRTEGPPCDGG, (SEQIDNO:4543); XM_014108123.1, LZTR1, Ins, C_7, PAALWAHHGGL, (SEQIDNO:4544); XM_003639660.3, B4GALNT4, Ins, C_7, PAAPASRPQDRPPPGRAAADPCPGSGHAGQPGGPGARARPRRGHRGLELVVGSTAR DFLPELVPGVRAAAAWGGRAGGGGGGGRGQGPGRGGQ, (SEQIDNO:4546); XM_014121373.1, LOC106560025, Ins, C_7, PAAPGLPP, (SEQIDNO:4547); XM_005638641.2, CSPG4, Ins, C_7, PAAPGRRALLPCTARPRTAGPRAAPARGPAERGGPSSGDPQRFLLERGRTAADPLCA RRE, (SEQIDNO:4548); XM_014119462.1, SLFNL1, Del, C_7, PAAPRGGPCGGPGARRGARALTAPSRTRRSWARSASSRAPSWAARRAVWSSSAAA VST, (SEQIDNO:4549); XM_014108277.1, LOC106557868, Ins, C_7, PAAPRPQPPLPFTCSRERLRLRAEARPWAGQEGAGVPPGRPRRLAGPAGAPAAREPS RSPRLSLASSRLPRPPAPASLKHSHAGSSAL, (SEQIDNO:4550); XM_014120347.1, ASAP2, Ins, C_7, PAAPTECCQRSLGSHTAPSSSKNAQCDRSLEPAEQACPAWDLTEQSPTPAPAAPAAQ PPPPEEACSRG, (SEQIDNO:4551); XM_005638677.1, CHST14, Del, C_7, PAARPRPGAGPSPGPGRCPWSPGTRTGR, (SEQIDNO:4552); XM_014106264.1, LOC106557546, Del, C_7, PAARTGVWSWPELLGPQAASRLTVQQGQAWAKRVV, (SEQIDNO:4553); XM_003433444.3, HIC2, Del, C_7, PAASGYPQPPSFRRGIQGLWTDAKGPIPPRSSPRPKAQMTSFSSGAPARRVCMAWAG PSVQPVGRPAWAAAAPMGAVGAVSRS, (SEQIDNO:4555); XM_005631072.2, RIC8A, Del, C_7, PAASPGCRASASCPGTEAAWTLSPAARACRPLPAMPASPWRGLARSLWTWTLSSSP, (SEQIDNO:4556); XM_014116213.1, SDK2, Del, C-7, PAASPLAPG11, (SEQIDNO:4557); XM_014121607.1, KBTBD8, Ins, C_7, PAASQNRLQTGVLLW, (SEQIDNO:4558); XM_005635063.2, LPIN3, Del, C_7, PAASSQKGSPHRKPKTSTPTLMASGVPRPASCQVG, (SEQIDNO:4559); XM_014114365.1, SETD1A, Ins, C_7, PAASTPSSSTPSSSSIPGFPAPCLSSPPAGIPLPTAP, (SE- QIDNO:4560); XM_005629808.2, KAT6A, Ins, C_7, PAATAATAARPTATTAPAPAA-TASAPTAAAAPAVTVQYEQQFHSSAHDHGDP, (SEQIDNO:4561); XM_014121835.1, JSRP1, Ins, C_7, PAATATPGPQRRAALGRPVAQQVPGARLLG-GAAGLCLPAVPGCCGRGRSRARTCP, (SEQIDNO:4562); XM_847216.3, RD3, Ins, C_7, PAAVPPEAG, (SEQIDNO:4564); XM_858879.4, EPHX1, Ins, C_7, PAAVQQHPKALADGTRLAWLLLRV1, (SEQIDNO:4565); XM_014118793.1, JRK, Del, C_7, PACCRAATPA-TAPTMPSSTWPAPGVLCQATSSAAPGRSCGPR-SHLPKARLLTRSQMA SR, (SEQIDNO:4567); XM_546894.5, CDH5, Del, C_7, PACCSPTGAR-RETGFGTRCTSMKRKTPRYPIMWARSNRV, (SEQIDNO:4568); XM_844246.4, RBM17, Ins, C-7, PACG-GRPEGSCSQWIFCRRSFDSFS, (SEQIDNO:4569); XM_005642274.1, LOC102152225, Ins, C_7, PACPRPPTARSRARRACRAPN-SALRGPKPASPLLGVLPPPWPPWLGGGVPGRSALGP PRKGRREARGGCWGGASLRVCGRAFSGEPVA, (SEQIDNO:4570); XM_014110256.1, TNK2, Del, C_7, PACPSPRGPPAHGASCLQPPQARRR, (SEQIDNO:4571); XM_005639078.2, SCARB2, Ins, C_7, PACVCPVLFLQCHQSRGDPPRGDPSVRRS-GAIYLQGT, (SEQIDNO:4572); XM_014115407.1, KIR-REL2, Del, C_7, PADCIELGQVISPHPTLEL-SPATSNLHPLDPQIWTPGLYPSPMLPSPHPATRVSRLMY, (SEQIDNO:4573); XM_005633153.2, SBNO2, Ins, C_7, PADPAVRVQCPEHHAALLLVESLLA-HAVPSLLQRKPPVHELHLLHRQPALRRHQLW TLHHHP, (SEQIDNO:4574); XM_014118366.1, PHF1, Ins, C_7, PAE-PLWCPPTLGPSLPCSHLRPQASTLGGSRCAGQVDGW-TAILGDHQESGQFPGGVS GPV, (SEQIDNO:4575); XM_014114725.1, CHTF18, Ins, C_7, PAEPRGPP, (SEQIDNO:4576); XM_014108968.1, PDZD7, Del, C_7, PAESEPPRP-WAASSSSTPPSKPTVMKVTSSMQSGWRRVQQAD, (SEQIDNO:4577); XM_014108967.1, PDZD7, Del, C_7, PAESEPPRPWAASSSSTPPSKSGLACAWGTRSQK, (SEQIDNO:4578); XM_845909.4, AVPI1, Ins, C_7, PAETTG-PLTAPLQPAQNPRALRSTGQPTEW, (SEQIDNO:4579); XM_014109027.1, AVPI1, Ins, C_7, PAETTGPLTA-PLQPAQVGSWNWKAEGRIPEPCAPLANPQSGSTE-TASGDQYL, (SEQIDNO:4580); XM_014112966.1, TULP4, Del, C_7, PAFALTSPPPSSLPSSPQFQIPTT, (SEQIDNO:4581); XM_548250.5, ACACA, Ins, C_7, PAFRHADIYGARVG, (SEQIDNO:4582); XM_005631741.1, KCNQ1, Del, C_7, PAGAGSRWFSPAAPSTPSSSCPATPCPPTNS, (SEQIDNO:4583); XM_005635367.1, LAMA5, Ins, C_7, PAGARAVGLSHAHRGRSLAPALHQAWRSTSHHQ-DAHRPGLQ, (SEQIDNO:4584); XM_005640917.2, SUSD4, Del, C_7, PAGCWPPSCGSSWR-CASGPHSSRAIAASLRSKMRRSVTRPTDVGTR, (SEQIDNO:4585); XM_537262.4, DENND4B, Ins, C_7, PAG-GLLRDSRACRERSSHSRGDTGSRTQWAPAPSPASRA-HHRHGGHCSGTGRGSAP GLHLHPVLRWGPPLGTQC-RALGWNAARHLLPQGP, (SEQIDNO:4586); XM_005616244.2, VSIG10L, Del, C_7, PAGNFQIS-FQVQMPRLLSLIPNGFPRPQILTMCLGPSGQMFLL-RAKS, (SEQIDNO:4587); XM_005638841.1, IFNGR2, Ins, C_7, PAGPGVPAPGQQPSRAGGAPAAPA, (SEQIDNO:4588); NM_001003009.2, TPO, Ins, C_7, PAGPWSGPGRRLWQPGAPPRAAGQDPGRGPHIQ, (SEQIDNO:4591); XM_014111450.1, TNFRSF8, Ins, C_7, PAGQASPDFLSKLQGQDHASWRGCSPHPGR, (SEQIDNO:4592); XM_014109338.1, DUOX1, Ins, C_7, PAGQPHPIWQPRTPGPAAQDPQGV, (SEQIDNO:4593); XM_014109349.1, DUOX2, Ins, C_7, PAGQPH-TVQQPWMPYPATQDPQGV, (SEQIDNO:4594); XM_005630789.1, SEMA6C, Ins, C_7, PAGRAQRQPSPP1, (SEQIDNO:4595); XM_545878.5, TMC3, Ins, C_7, PAGSLSTAE, (SEQIDNO:4596); XM_547741.6, LRRC16B, Del, C_7, PAGSQDSGAASPQPVAPGRICLSCPLTAIN, (SEQIDNO:4597); XM_014109371.1, LOC106558039, Del, C_7, PAGSSPAGVPSRSPRPDPVTALRATRTSALGEKR-CRLFGEARGSCGEGGRRRLSKPVS SGWAAQDQN-WHGCAGKRGTPTAGGLVGGYPPGVVLKGLALPL, (SEQIDNO:4598); XM_005626204.2, SBF1, Del, C_7, PAGSTGASPLPRTRRMRSQCRRSWSPAR, (SEQIDNO:4599); XM_005624000.2, GCGR, Del, C_7, PAGTP-TRAGPQAAPPARSCCFPGAATGRPGTPLQTPAW-WASPLGWPPAPSRARRSPP GPRLGPDSGA, (SEQIDNO:4600); XM_014117947.1, KIF12, Ins, C_7, PAHGDPEHTTSAER, (SEQIDNO:4602); XM_014117945.1, KIF12, Ins, C_7, PAHGDPEHTTSAER-WGCSSKPGPETGGPQRPDWQL-PATRPGPGTPQRGCTEPQPRPP ALL, (SEQIDNO:4603); XM_843488.4, NAV1, Ins, C_7, PAHHQRGLEAAGIL-PRL, (SEQIDNO:4604); XM_014106882.1, COL20A1, Ins, C_7, PAHLGGAQAPWTRRTGQSPPRGQRRAQN-PRSHGQPSAERERASKTPDRNG, (SEQIDNO:4605); XM_014121353.1, RASSF7, Del, C_7, PAHRTFCLRPEK-SPSREPAQNPTLVSSLSPEIAPMRENSWR, (SEQIDNO:4607); XM_014106880.1, RBBP8NL, Del, C_7, PAHSTS-TASPWTASCGPPGPPSRPMSP, (SEQIDNO:4608); XM_014116619.1, SP2, Ins, C_7, PAHTTETRPHQTCPSP-SQSWQE, (SEQIDNO:4609); XM_014116066.1, PGF, Ins, C_7, PAIGLVCWKWLIRGGSGALPASVGTQLLPGTGE-AGGRLVGVPG, (SEQIDNO:4610); XM_005617069.1, PARD3, Del, C_7, PAKASRVPRRTPGTPATKDPGTAT-WAGTASMPG, (SEQIDNO:4611); XM_543139.5, PDSSB, Del, C_7, PAKPNTPFIVSMRYFLVKRPSLHR-YLSLCIRA, (SEQIDNO:4612); XM_854849.4, SGK1, Ins, C_7, PAKSFSANQLGTIIQSSC, (SEQIDNO:4613); XM_005640017.2, RREB1, Ins, C_7, PALAKAPRDGRAAPAGLHRPDHLVRVLGAHLAEG, (SEQIDNO:4615); XM_014108268.1, GRIN2B, Del, C_7, PALALLSSSWALQTRWPSRMPTRKMISTIS-LWFPVWSW, (SEQIDNO:4616); XM_548978.5, CFP, Del, C_7, PALAMPSEPTSAIQLCPA1, (SEQIDNO:4617); XM_005625544.2, MBD6, Ins, C_7, PALCPECPPTWT-TYLQCHHGNY, (SEQIDNO:4618); XM_014109870.1, COL6A2, Ins, C_7, PALGADLAQHLLLLVSVLQ-GELSGDPRAPRPQGLPRTEGRQGQHGRARRTRA-EGSP GRSRHRRPHWLPRTQGCSWLQRREG, (SEQIDNO:4619); XM_014121266.1, LOC106560005, Del, C_7, PALGLLGHPAALLPAPPGPRPGGP-PAATAQCPAAEGVSSGQLTEERLTPPRGSERGRR RRDASGLPQAAEPGRGRSATCWPRRVARPRRPRP-PRELAPHR, (SEQIDNO:4620); XM_014122638.1, ARAP1, Del, C_7, PALGRHACW, (SEQIDNO:4621); XM_846117.4, ST5, Ins, C_7, PALHPSPTSH-SETQEGPAWSPQVPEQKIL, (SEQIDNO:4622); XM_014113910.1, RERE, Ins, C_7, PALICSAP-LCPWGDTHHPSNLLFHLHATCGTRPL-SPAAVLCCCFFGRQHTWGDSLPA PHCPDQGRGSG, (SEQIDNO:4623); XM_014121848.1, ODF3L2, Del, C_7, PALLLLCSSSAGPFTSVPTRTPALGPSTSWTQKSPG-LAEAAPLPTPCRAGASLGVWR, (SEQIDNO:4624); XM_005621146.2, SDK1, Ins, C_7, PALLRQPLHE, (SE- QIDNO:4625); XM_005617128.2, BEND7, Del, C_7, PALLTHAHTPLTKTEAKAKKKKKEKEKGGGSFKHQKAAR (SEQIDNO:4627); XM_014116870.1, COL5A1, Del, C_7, PALPACRVLLGQKVLRAPRVPLAQRVRLATQDPLAHRVPLARSSSPCRSRHPGPGGT LTPASCWMTGPARAMWTTRTAWRKSSARSTP, (SEQIDNO:4628); XM_005640656.2, ZNF142, Ins, C_7, PALPLLRLCVPPPAGARSPREGARGHPALQVYRLRLQHQKPAEDHLAQPHPHGRKA LPLSPLSLCLR, (SEQIDNO:4630); XM_005619085.2, ZMIZ1, Ins, C_7, PALPPSGHAQQHGRPRETPQSPHAGNSPSRTHKSR, (SEQIDNO:4631); XM_005619086.2, ZMIZ1, Ins, C_7, PALPPSGHAQQHGRPRETPQSPHAGNYATRWQF, (SEQIDNO:4632); XM_545531.5, WIPF1, Ins, C_7, PALPWKPRCSFCRRLPPPDILKLLIILLQQASPAPHAQQGLG, (SEQIDNO:4633); XM_014109365.1, CDAN1, Del, C_7, PALQGRSLHVGSTQLR, (SEQIDNO:4634); XM_005621001.2, COL26A1, Del, C_7, PALQVPLGHMVPQDPQVYPDLRAWLESGA, (SEQIDNO:4635); XM_539219.5, FOXH1, Ins, C_7, PALRAASVAALPAHRAQESRWGGFPGGDQQAPTPFP, (SEQIDNO:4636); XM_533664.5, LTBP4, Ins, C_7, PALRLWPV, (SEQIDNO:4637); XM_848478.3, PRDM15, Del, C_7, PALSCACGTRPSMPRRWTSPC, (SEQIDNO:4639); XM_005641877.2, GPR101, Ins, C_7, PALWLGPGCLRPAQCPLLHDLGGQPQLHHPQRRVLHHHSTGCHDCLLLRGVWCRT AAACSAVQRQEPQPGGSSQGPCGE, (SEQIDNO:4640); XM_005628127.1, LOC102154750, Del, C_7, PAMELPPHPPSATRRCRQVAPRHGGL, (SEQIDNO:4641); XM_005634655.1, MED12L, Ins, C_7, PAPADPAAPESDPWSPSDAAAAAFEENIPEIF, (SEQIDNO:4642); XM_014109867.1, LOC611835, Ins, C_7, PAPAPLRGFRVSPVSGRAPGPWGPWSAVVFLNPGPTHVLLFGSLSPRLHPTPAGPHA LRVPPL, (SEQIDNO:4644); XM_005635288.2, CHRNA4, Ins, C_7, PAPAPVSGPDAGGGGRPVHRGPPEGGGHRLLGEGGLEVRGHGHRPNLPLGVHHRLP AGDRGPLPAPLAGRHDL, (SEQIDNO:4645); XM_005631006.1, COBL, Del, C_7, PAPAQETIRPLAGPWRMGPGGSPSTPSPLAPRAGWTPMMAPGRSPWNRRKNRVCRA QDTNPMAPCPPASSGQRRNSAQWSRSQLRKTRRCTAP, (SEQIDNO:4646); XM_005633014.2, ZNRF4, Ins, C_7, PAPARSPAARP ATGPWEALEMPEGLPSAVPSGT, (SEQIDNO:4647); XM_005628317.2, GPT, Del, C_7, PAPCSALRN, (SEQIDNO:4649); XM_005618215.1, LOC102151979, Ins, C_7, PAPGGPRGPGLAPLPAACDPRAQALEPRAPRGRFSHGGLGGWQESGR, (SEQIDNO:4652); XM_003434863.3, VASN, Ins, C_7, PAPGLPGVHLPQRGHLSPGGAGPPGVPVP, (SEQIDNO:4653); XM_546603.2, ALOX15B, Ins, C_7, PAPGPSGQGVQRGRCGGLPGGVPPGRGPAAAAARAQGAPAAARPGRAGGP, (SEQIDNO:4655); XM_014116627.1, TMEM145, Del, C_7, PAPGPSTCGATSAPKRTGCS, (SEQIDNO:4656); XM_014121541.1, IQSEC1, Ins, C_7, PAPGQPPGHQRLSQ, (SEQIDNO:4657); XM_014120658.1, LOC100686114, Del, C_7, PAPHAKGRNWIRWQ, (SEQIDNO:4658); XM_005640394.1, LOC102151535, Del, C_7, PAPHAPPFPARSA, (SEQIDNO:4659); XM_856636.4, BRPF1, Ins, C_7, PAPHHGLPTSAQAG, (SEQIDNO:4660); XM_014121835.1, JSRP1, Ins, C_7, PAPIPSSDPQLRSGPRRLHDHQGAAGAGWRPGQQPGRRGPVHTGGPLPCPAPGRQGS R, (SEQIDNO:4661); XM_014112867.1, COL13A1, Del, C_7, PAPKAPQESLDRQE, (SEQIDNO:4662); XM_014114212.1, LRCH4, Ins, C_7, PAPLAPFWSGGLHFF1, (SEQIDNO:4663); XM_005621001.2, COL26A1, Del, C_7, PAPLAQQAARPSLQTAPRASSTPCSLRRTRATETHSWLLLLWTQCWPASQGPGAPPA LQVPLGHMVPQDPQVYPDLRAWLESGA, (SEQIDNO:4664); XM_014119269.1, LOC106559733, Ins, C_7, PAPLASPWRWL, (SEQIDNO:4665); XM_014118255.1, COL9A1, Del, C_7, PAPLEFQASMASTVTEVPRVPRAPRVLLENRASQELRASRARRAPTD, (SEQIDNO:4666); XM_005630809.2, POGZ, Ins, C_7, PAP1GKKIHPKSLEPEGGFLSPAGRRALHGSLSAVSPSPRPLPCSHPLLPAPGARSL, (SEQIDNO:4667); XM_005631406.2, SSH3, Ins, C_7, PAPLPVGSLHKGTPEPG, (SEQIDNO:4668); XM_014114924.1, LOC607201, Del, C_7, PAPLPWCT, (SEQIDNO:4669); XM_014113968.1, LOC610373, Del, C_7, PAPLRHHPLTSCSVPGPQAVGSLPSTPS, (SEQIDNO:4671); XM_548172.4, HOXB1, Del, C_7, PAPLRLLTVQARPAMVGDCPAPRSSRTQAIPPSSRPRRSGCPSPAPRPRGMPRPPAA PAMGPLSTILWASRKEMEAIIILRAMGPS, (SEQIDNO:4672); XM_014113137.1, RPS6KA2, Del, C_7, PAPMHIICLEDSVLWPQVWSRSPRNKICTKPRSIPSCSSYMETTSTSLMAMRSKRTSG WAPTPCASAVCTKLLRQSMP, (SEQIDNO:4673); XM_014107689.1, LOC100855783, Del, C_7, PAPPAPPAPPPRLLTRRLLSCRTPGPTRTRKRRRPISFPTETPC, (SEQIDNO:4674); XM_536512.5, PDZD2, Del, C_7, PAPPAPPARLPPQPHPPRGASRRAAARSPRPCPAPSCRS, (SEQIDNO:4675); XM_014114446.1, MSLN1, Del, C_7, PAPPAPPPGPPAPHLGCPTQPPPRASPGMTPLPPAAHQPTGCTCHSPWPCPWASCGCC TWAPQAPARIPCGAPAPRPPKMALPQHRMQGNRG, (SEQIDNO:4676); XM_014107689.1, LOC100855783, Del, C_7, PAPPAPPPRLLTRRLLSCRTPGPTRTRKRRRPISFPTETPC, (SEQIDNO:4677); XM_014116569.1, GLTSCR1, Ins, C_7, PAPPIPAPRGAAAPSSPPSSRLHLLWRGLHGYVHQAASPYAS, (SEQIDNO:4680); XM_005633023.2, TICAM1, Ins, C_7, PAPPLLVGPPASRRAAVAGRLARARLPARARLPAAPRLLAAPRAPAEPGAAAPHHPP RADGAAGRQQPHVEPARDPGARGRDARSRV, (SEQIDNO:4681); XM_014108769.1, ARHGAP22, Del, C_7, PAPPPAAGGTAGLPSWAVARTRRAPAAAAASPATQAARPRTTPAAPRLSGAWSRSS GHSCAGRGPSTTRVSKDLKKVVPA, (SEQIDNO:4682); XM_014121829.1, TMIGD2, Del, C_7, PAPPPRDVAPSPRACEASF, (SEQIDNO:4683); XM_014121831.1, TLE6, Del, C_7, PAPPRAPRKGAQSRAPELRACSPAWPRSLLGEPVHS, (SEQIDNO:4684); XM_005635893.1, LOC102152644, Ins, C_7, PAPPRCLLWGSGRNRRHKPLL, (SEQIDNO:4685); XM_014111158.1, LOC106558344, Del, C_7, PAPPRSRPPRSCSSPTPPALPRLRVSGTTCWPGKPRVALDAALGPPA, (SEQIDNO:4686); XM_005626204.2, SBF1, Del, C_7, PAPPRTRGLPSGPCPGIS, (SEQIDNO:4687); XM_003640056.3, RFX7, Del, C_7, PAPPTRGWLCQPWCLGCQGQRPARCNTRSRTPSAKLYNLKWTAF, (SEQIDNO:4689); XM_005615653.2, AKAP7, Del, C_7, PAPQALSAATQQATTAPPGA, (SEQIDNO:4690); XM_014121988.1, WIZ, Ins, C_7, PAPQEEPACPWALGTGGQSAEQQSGCRGSSWQQAGAARSQGPESDHLRGLRCL1, (SEQIDNO:4691); NM_001031818.1, COL4A4, Del, C_7, PAPQGDLEPLVLQVPQEELLKVTFLTQVHPEMWVLLAPMVREERPGPQAPPGALTF, (SEQIDNO:4692); XM_014109393.1, LOC100686862, Ins, C_7, PAPQPGGPPPPPPAARRRTAPLVAPLLRPAD- SLTPQQPGGNLRPGGRAGAPLVRSPPA LPGSPEAAGARRTARPRPARLRLGDPGLAR, (SEQIDNO: 4693); XM_005615881.2, LOC102155525, Ins, C_7, PAPQQDFVVCL, (SEQIDNO:4694); XM_014109869.1, COL18A1, Del, C_7, PAPRATPASR, (SEQIDNO:4695); XM_003433939.2, C30H15orf59, Del, C_7, PAPRPRWAPPSPRPPPASPGALR, (SEQIDNO:4696); XM_545640.4, RUFY4, Del, C_7, PAPRRERLSPT, (SEQIDNO:4697); XM_546635.4, HS3ST3B1, Del, C_7, PAPSPASSVGPGASSCRRPLSSA, (SEQIDNO:4699); XM_014110191.1, PIGZ, Ins, C_7, PAPSPPPRPGLVRGGGGHGWDRGLGPVPCPEQPHQTASLPGGRWAVALPPFCGDPW HHQACHREVPLPSQE, (SEQIDNO:4700); XM_014121412.1, NCKAP5, Ins, C_7, PAPSRQGRLPSHPA, (SEQIDNO:4701); XM_014108893.1, DOCKI, Ins, C_7, PAPSSSPEACSASTAQQDPTSASSEDDAQADVSGLRNRAV, (SEQIDNO: 4702); XM_014112392.1, MEF2A, Del, C_7, PAPTGNGALPCGQSEQLKQLL, (SEQIDNO:4703); XM_844754.4, PLEKHOI, Del, C_7, PAPTRCGPRTPPPSFRPTRPSCPGSRTIV, (SEQIDNO:4704); XM_005615500.2, SASH1, Del, C_7, PAPTRPACRLRRAAPVTVPPLRLLVPPQDRSPAARPAPDHRPGCQSSRRARASRSTAS SWARL, (SEQIDNO:4705); XM_014115764.1, PPP1R3E, Del, C_7, PAPTSPAT, (SEQIDNO:4706); XM_014111713.1, ATP2B3, Ins, C_7, PAPVPQPEQQRHRQRHLPEHARHQVSYLVSAFFQTGEPPPQRGDVPL, (SEQIDNO:4707); XM_014115996.1, PLEKHH1, Ins, C_7, PAPVSILGEPDLCCGHGWHAALRCIFQN, (SEQIDNO: 4708); XM_847792.4, IGFBP5, Del, C_7, PAPWAASWSKSPAAVAA, (SEQIDNO:4709); XM_540976.5, ARHGEF4, Ins, C_7, PAQGFQGCGSSLTCHEECGPAH, (SEQIDNO:4711); NM_001031815.2, HGFAC, Ins, C_7, PAQGSSLQQQPWGPSAHSGWAALQVPLPLWRPHAPRLHFRRKRPQEVVCHHSQL, (SEQIDNO:4713); XM_005627762.1, C12H6orf132, Del, C_7, PAQRTRPPQRLWTGGIPARWKSFGVSSRPISVAPGGRTDPSVTRQAQQRPFRRRRAR TAPACQRRRFLQACQRRRSSQALLRRVPAACQRRGLPPA, (SEQIDNO: 4715); XM_003431483.3, KIAA1644, Ins, C_7, PARAAHPAAPAPARPAATGAPGRAHTAGRRPQPTAHDLPELVRL, (SEQIDNO:4716); XM_014112352.1, LOC102153630, Ins, C_7, PARAGGRQGVRSSREERQQESGRGKARERALTFGGAVLGAADEK, (SEQIDNO: 4718); XM_014121720.1, ARHGAP21, Del, C_7, PARAPGQALPQETQQPRSRRRRLRSRPRVVRRVA, (SEQIDNO:4719); XM_847443.4, GPN2, Del, C_7, PARARPRTAWA, (SEQIDNO:4720); XM_014114191.1, LOC106558877, Del, C_7, PARCPLRPRPVVPQAPARRPLRTLLPGPACQDPARRPQDPPARTCPPGTRPPGPGPPSP RTCPAAACSQHAPHPTWNPTIVGSLVTI, (SEQIDNO:4721); XM_547000.5, TNRC18, Del, C_7, PAREGRAATVAES, (SEQIDNO:4722); XM_005616615.2, RASGRP4, Del, C_7, PARGMAPTAEKS, (SEQIDNO:4723); XM_014107670.1, PER2, Ins, C_7, PARGRPARVWPPALAVRRPPGPGHGTGVTQLSPPRRAPRPAPGLLPRPA, (SEQIDNO:4724); XM_005636883.1, KMT2D, Ins, C_7, PARGTGQSAPCCCPHHFHWQPHNPRRLVYLCGRVPEAASGHSARPRLAR, (SEQIDNO:4 725); XM_014107872.1, VPS37B, Ins, C_7, PARILCTVHVSIPTRSSPETPAPAASTPARLHPPV, (SEQIDNO:4726); XM_014110134.1, ZP1D1, Del, C_7, PARLETPSSLLVPSLLGVTRLQPTIHSLALQMNLLSS, (SEQIDNO: 4727); XM_536512.5, PDZD2, Del, C_7, PARLPPQPHPPRGASRRAAARSPRPCPAPSCRS, (SEQIDNO:4728); XM_547886.5, TTC9, Ins, C_7, PARPPLGGAEQDGGSHRDRLLQQPGSVPAPG, (SEQIDNO: 4730); XM_014107107.1, RAP1GAP, Ins, C_7, PARPRGVQEGA, (SEQIDNO:4731); XM_014108204.1, CABIN1, Del, C_7, PARPSRASCPACQSWSSPRPPPSSPLRSPSRRPPQLCSHPKAASRRRPSRS, (SEQIDNO:4732); XM_014113201.1, MLLT4, Del, C_7, PARRARPPTASFSAPHSGPPWPEPTVLLTKQASPHPLQKNQASTSPATRKDQTLTWD LPGQLLAPTMPIGTREKDCLKATRQIYLGALEPLKT, (SEQIDNO:4733); XM_014116237.1, BAHCC1, Ins, C_7, PARRGRSP, (SEQIDNO:4734); XM_533642.4, CLASRP, Ins, C_7, PARRPRTGT, (SEQIDNO:4735); XM_014111220.1, ELK4, Ins, C_7, PARRQGLQPQRLYTLRLVFFLHSQLFELLQQEAFQTHKD, (SEQIDNO: 4736); XM_014109934.1, ADGRB2, Ins, C_7, PARRQGLRGSRAAD, (SEQIDNO:4737); XM_014117114.1, LEMD3, Del, C_7, PARRRPPPVHSGSITPTIRAPITRT, (SEQIDNO:4738); XM_014122095.1, DDA1, Del, C_7, PARSHGPIARTCMRT1, (SEQIDNO:4739); XM_005622278.1, PTPRC, Ins, C_7, PARTQQLRGASARLQHPGCQLLR, (SEQIDNO:4740); XM_005630838.1, LOC100685649, Ins, C_7, PASAAGETAMPASTPGAMCPQNQGAMPPQGSRALPHQDSRALPHQGSRALPAQGS RAMSLNSDSSTSSAEDQAEV, (SEQIDNO: 4741); XM_014113377.1, PHLDB1, Ins, C_7, PASARQSFPAAAGLPLQDGW, (SEQIDNO:4742); XM_005631006.1, COBL, Ins, C_7, PASATPTPTLPSS, (SEQIDNO:4744); XM_005618001.1, FBXO6, Del, C_7, PASATSSSTEARTRSSGRAGTGPASPTAASSLALR, (SEQIDNO:4745); XM_540770.5, PIDD1, Del, C_7, PASGVAGRWLSGP, (SEQIDNO:4748); XM_014122286.1, MAP1S, Del, C_7, PASGVGRPAPQQRSIVPQLPSWWPHPARRAAWSWG, (SEQIDNO:4749); XM_847877.4, NUTM2F, Ins, C_7, PASLHSRVGLRS, (SEQIDNO:4750); XM_005642137.1, LOC102156225, Ins, C_7, PASLLPPGPGGHRLQQCQDETHPCPD, (SEQIDNO:4751); XM_014107876.1, USP30, Ins, C_7, PASPDALPAPRGS, (SEQIDNO:4753); XM_014114724.1, CACNA1H, Del, C_7, PASPLSPPGRTRVRPGPRRQRAAPPLCGGEPRPARPCRTGTPSSPWRGPGWTLPPRAT GGPRPLAA RNT, (SEQIDNO:4754); XM_861806.4, SF1, Del, C_7, PASPPPFPGPKGASSRGHRLLPGLGRGCWCPGSRRPRPWARWEP, (SEQIDNO:4755); XM_005619870.1, SMTNL2, Ins, C_7, PASPREPLLGAASSACHGHHSDA, (SEQIDNO:4756); XM_014116482.1, SOCS7, Ins, C_7, PASPVSALPARLKQLCSQPSRVGEVWLVLGTNELGRCRDEAEREARWLFPGTR, (SEQIDNO:4757); XM_014108893.1, DOCKI, Ins, C_7, PASQREHGRLWKLDGKPGFDQLAHPPAPSSSPEACSASTAQQDPTSASSEDDAQAD VSGLRNRAV, (SEQIDNO:4758); XM_542121.5, LRRC8E, Del, C_7, PASRSWCTCRSSACSTRLPGCPSRCRSSCGTA, (SEQIDNO:4759); XM_014109357.1, NUTM1, Ins, C_7, PASSILCREPSGALCSP, (SEQIDNO:4761); XM_005636179.2, SETD1B, Ins, C_7, PASSTPTSTPC, (SEQIDNO:4762); XM_014117497.1, FER1L5, Del, C_7, PASSWFGVKKRTSLKSAWCGCTWSEPSTCSPKIPMACATLM, (SEQIDNO:4763); XM_014109643.1, C30H15orf39, Ins, C_7, PASTLTRPQAGAASRSPVPLGLCPPDAELSLRPG, (SEQIDNO:4764); XM_543973.5, SEMA4G, Ins, C_7, PASTTPTPTG, (SEQIDNO:4765); XM_545954.4, KLF3, Ins, C_7, PASTVARESSISHSTTREETFACGVPGHPAETKDTQM, (SEQIDNO:4766); XM_014113666.1, RAI1, Ins, C_7, PATAPARGRGQI, (SEQIDNO:4767); XM_014114530.1, LOC100856086, Del, C_7, PATASPRIQKMGTSVALGCLGRQGKAQFPENQSQISQRLWWVQGLRKLVWVL, (SEQIDNO:4769); XM_014117108.1, LOC106559343, Ins, C_7, PATEGGGAGPRGPGPLGWEGGAGGPRLRAVRTRVTLRAAGPGRATGGAREAPPSPA RLPAPLPA PLRPG, (SEQIDNO:4770); XM_014117262.1, TUBGCP6, Del, C_7, PATERSPTSRRPAGTPSTGSAGSAEGSCRRSAGACCRSRSPCW, (SEQIDNO:4771); XM_014113517.1, DVL2, Ins, C_7, PATGEDQRHRG1, (SEQIDNO:4772); XM_014111179.1, SOX13, Del, C_7, PATGPPRGTCRPARPACP, (SEQIDNO:4773); XM_014112912.1, ARID1B, Ins, C_7, PATPHQKGDHLSSWLSRGVAASLETKAEDYLKRYRYS, (SEQIDNO:4775); XM_014112341.1, ADAMTS7, Del, C_7, PATPLSAMCSAATLTPCSTRASCTRGCLWSTTRTPASCTAGPPMSTLLRSFGTL, (SEQIDNO:4776); XM_543867.5, PRMT8, Ins, C_7, PATPSTRRPNQACAMCPSCVHSTQLPRTG, (SEQIDNO:4777); XM_014108204.1, CABIN1, Ins, C_7, PATQAGGHPQHGLSGPRGRRAGRRGGGHGLPAPGAPAQ, (SEQIDNO:4778); XM_014114743.1, AXIN1, Del, C_7, PATQTWAAWDCGTHTRRTPRASWMSTCSGS, (SEQIDNO:4779); XM_014106880.1, RBBP8NL, Ins, C_7, PATRQEQPPQPTLRAQPPPGQLPAGLPAPRHGL, (SEQIDNO:4780); XM_540754.4, AMBRAC Ins, C_7, PATSALFLPCPCPSPPSWHRRTNAALRPDQQQPPC, (SEQIDNO:4781); NM_001006650.1, PKD1, Del, C_7, PATSTSSFQSRPQA, (SEQIDNO:4782); XM_014106904.1, MMP15, Ins, C_7, PATTPRWEARATPEARPPSPAPSHGTA, (SEQIDNO:4783); XM_014122369.1, FBN3, Del, C_7, PATTSMGTPAPVRTSTNALHTRASVALVPATTPWGTTPVSALQSTCKSTVATTAWT, (SEQIDNO:4784); XM_547926.3, TMEM63C, Ins, C_7, PAVFGDHHRQILLLEGCPGPTP, (SEQIDNO:4785); XM_848382.3, EBNA1BP2, Ins, C_7, PAVGFGLGI, (SEQIDNO:4786); XM_014111404.1, FRMPD3, Del, C_7, PAVGREGWRPAWGGPRSAWEGRKLA, (SEQIDNO:4787); XM_005616615.2, RASGRP4, Del, C_7, PAVLARTCCICSRFPWISSTRRMRSMNFLTLENPAVPRVCHPPPSRHPWWWSGPLA, (SEQIDNO:4788); XM_845641.5, EPN1, Del, C_7, PAVLGHST, (SEQIDNO:4789); NM_001003150.1, MT4, Del, C_7, PAVPSVPRAASAKEARTSAAAVP, (SEQIDNO:4790); XM_014107132.1, PMEPA1, Del, C_7, PAVTRASAPRATGAVGAWRGRPPPTARSSATTRGPRPSSTSRAAGRPPCWRGPGSPT HTSPPWRAQLPGAKKRINRKGTLS, (SEQIDNO:4792); NM_001048091.1, OAS3, Ins, C_7, PAWAGTPDGVRLGAGWAERPVQHGPGLPHRPGAGQPVPSAPCLLDCQLR, (SEQIDNO:4793); XM_547068.4, TBX6, Ins, C_7, PAWDRFQLPACPGRGLPLP, (SEQIDNO:4794); XM_847455.4, CHRNB4, Ins, C_7, PAWPAAAQQDRGRRPPALWEPRVPCEPHACGPQVPSGLGLWRGVHGL, (SEQIDNO:4795); XM_540513.4, NLRP6, Del, C_7, PAWSSLWL, (SEQIDNO:4796); XM_005631651.2, LOC612278, Del, C_7, PCAAHISLLPPFPSQLGPQPCCLSTSSGIFSILLSSGRSGWTWPG, (SEQIDNO:4797); XM_005640656.2, ZNF142, Del, C_7, PCAAPSATLRAATSWCSITT, (SEQIDNO:4798); XM_005618689.2, GAK, Ins, C_7, PCAGQWGSPQHRRPAQPPPGGP, (SEQIDNO:4799); XM_541775.4, PRRT3, Ins, C_7, PCAGVPCGGC, (SEQIDNO:4800); XM_014110586.1, RREB1, Ins, C_7, PCAHPGPRGAPRRGGAARGRAGAGSR, (SEQIDNO:4801); XM_014116569.1, GLTSCR1, Del, C_7, PCAPHPSPQRGRCPQLPTFLPPPPPLARPPRIRPPGCQPLRQLTSSSSFRLARENTSPPRP LRPSTCSLSPLRPPHRLLGPSRW, (SEQIDNO:4802); XM_014120830.1, UPP1, Del, C_7, PCARSLFLSLPSQ, (SEQIDNO:4804); XM_003431951.3, HIVEP3, Ins, C_7, PCASAEKPLNAFCHLHPQYPPPHLPR, (SEQIDNO:4805); XM_850293.5, UCKL1, Del, C_7, PCCAPASAPSTRP AGRPGTTSTARSPRRPLPLAWAVAAPRGRPPWPG, (SEQIDNO:4806); XM_005618371.1, MAN2A2, Del, C_7, PCCVSPKALSSRRWWHTTSIFARWSGYIICQGWRGCLWTCRPWWTSGITSTRSWPC ASTQTLTARVPSSRTSMAFRCSPGAI, (SEQIDNO:4807); XM_541567.5, PPP1R37, Ins, C_7, PCFILPTPLTCPTTS, (SEQIDNO:4808); XM_014117254.1, NCAPH2, Ins, C_7, PCGGGSRTETQEEGCHQAAGLSPVVPGCLR, (SEQIDNO:4809); XM_531841.5, B3GNT2, Ins, C_7, PCGLLEQRTRKAEQAVQSHFEHVGQPDGRSIRVFQHKPSKFL, (SEQIDNO:4810); XM_542327.5, INPP1L, Ins, C_7, PCGRGELIR, (SEQIDNO:4811); XM_540754.4, AMBRA1, Del, C_7, PCHLCPLPPLSLPLSPFLAPKDQRCTAT, (SEQIDNO:4812); XM_005639159.2, AFF1, Del, C_7, PCHLYIPTSKLFPGHKEAARFTAVTVIVKAIAQPNLPKT, (SEQIDNO:4813); XM_014117046.1, GARNL3, Del, C_7, PCHPHRC1QTTRNSGTFC, (SEQIDNO:4814); XM_014113517.1, DVL2, Del, C_7, PCHRRGPAASGTLGLRPSTLTCPAAGRTWSLRRKPSQWCPCGGNGLVGETAGATGL VDPRGWSATWPGMRAPQPL, (SEQIDNO:4815); XM_014113516.1, DVL2, Del, C_7, PCHRRGPAASGTLGLRPSTLTCPAAGRTWSLRRKPSQWCPCGGNGLVGETAVSTVG ATGLVDPRGWSATWPGMRAPQPL, (SEQIDNO:4818); XM_014117542.1, BCL11A, Del, C_7, PCLAHHRDITWTPTA, (SEQIDNO:4821); XM_005639078.2, SCARB2, Del, C_7, PCLCMPSSISSMSPIQRRSSEGRSLG, (SEQIDNO:4822); XM_005630709.2, BCL9, Ins, C_7, PCLGVCCCFACSPQVSITSCPVTWMDLLSKTSPSESRDPSKP, (SEQIDNO:4823); XM_014119889.1, BRAF, Ins, C_7, PCLIAWLTH, (SEQIDNO:4824); XM_544610.5, THBS1, Del, C_7, PCLMTSSKT, (SEQIDNO:4825); XM_014109357.1, NUTM1, Del, C_7, PCLQHSLQGTLWCSLLSLAHCW, (SEQIDNO:4826); XM_014108893.1, DOCK1, Del, C_7, PCLSKGAWQIMET, (SEQIDNO:4828); NM_001284465.1, PSEN2, Del, C_7, PCLVTQGTNWRKRRKGA, (SEQIDNO:4829); XM_005620526.2, UBE4B, Ins, C_7, PCPCGWPDGCALHFPQPAWWHGLWNCHRKPALLSTVSPLHCHPPVGVFDFSYPAIP RHLHSVQLAQPPCPC, (SEQIDNO:4831); XM_844466.4, MAZ, Ins, C_7, PCPGRRPPATAHLL, (SEQIDNO:4832); XM_014112777.1, LOC102154969, Del, C_7, PCPLPPCPPPGAPRARIPSSPAGLQRAHLAPG, (SEQIDNO:4833); XM_014109155.1, ADAM8, Del, C_7, PCPMWSSTRWCGPDVCQRPEPAEPCPPTWTCTQRV, (SEQIDNO:4834); NM_001205203.1, MEF2B, Del, C_7, PCPNSPLGTLGPVI, (SEQIDNO:4835); XM_846117.4, ST5, Del, C_7, PCPPPQPHQSLGDPRRTCVVTASPRAENPLSLRMHPVSSPCTPLLPLRMVLRANPSLD PKAL, (SEQIDNO:4836); XM_547500.5, KIF26B, Del, C_7, PCPPPTARSPRRAGRTAAAAATAATTAAC, (SEQIDNO:4837); XM_014109374.1, PYGO1, Ins, C_7, PCPPSEATNRQLIFLGFKRRHCRTQKK, (SEQIDNO:4838); NM_001204405.1, ARHGAP8, Del, C_7, PCPPSSLASVCSTSRTKIKVNSSLLS, (SEQIDNO:4839); XM_005631472.2, RE1A, Ins, C_7, PCPQDHPSRGR- DADRGPATAAV, (SEQIDNO:4840); XM_005630688.2, NOTCH2, Ins, C_7, PCPSPCSACTVLL, (SEQIDNO: 4841); XM_003431813.2, GLI4, Ins, C_7, PCPVPCQSCITRDTWTPPQRGPASPARSSTRLPWLQP, (SEQIDNO:4842); XM_005628022.2, GLI4, Ins, C_7, PCPVPCQSCITRDTWTPPQRGPASPAR-SSTRVSGCQNHGSSQCLVDAHGLPWLQP, (SEQIDNO: 4843); XM_005628021.2, GLI4, Ins, C_7, PCPVPCQSCITRDTWTPPQRGPASPARSSTRYSP-CAALPPPPPTTGTAGWTRGSSLAT GAPAPLHWGRAAGSSG, (SEQIDNO:4844); XM_014117947.1, KIF12, Del, C_7, PCPWGPRTHHQC, (SEQIDNO:4845); XM_014107670.1, PER2, Del, C_7, PCPWTPGTSLASSPRRSPSPWPRSWHWCYPTIP-SPPCPPACPRPSSPASLTFCRT, (SEQIDNO:4846); NM_001097547.2, PADI6, Ins, C_7, PCQGGRERVP-PRQDPHWQLLLPQQGGPRHEQGPPGLPLRPASPGPG-GALLGLADGG PHG, (SEQIDNO:4847); XM_005642137.1, LOC102156225, Del, C_7, PCQPPAS-WPGRPSPAAMSR, (SEQIDNO:4849); XM_014107876.1, USP30, Del, C_7, PCQPRCPSRSPWFLTTAPPCTSSG, (SEQIDNO:4850); XM_005618215.1, LOC102151979, Del, C_7, PCQRAPPTQSPMHLQARYRGTLHPQPLN-PALPTARLLSRSRHPHLDCPAPPSAWKQV CVPSWWTGVLG, (SEQIDNO:4851); XM_856804.4, PHF21A, Ins, C_7, PCQRRHLYAGPLPLLPELHSELYPG-GRD, (SEQIDNO:4852); XM_014113768.1, ACOTL1, Ins, C_7, PCQSPRQYLWGPDHGLDGERGHHCSQPAVPCP-PYAEGH, (SEQIDNO:4853); XM_014107107.1, RAP1GAP, Del, C_7, PCQTPRCSGRGLSSRNFC, (SEQIDNO:4854); XM_014115692.1, LOC100687926, Del, C_7, PCRAAPALGQRAPLRPQPGPAGELPAPRRR-WASLSALALGRPHPSAASICPLASPHQ ARQWKLCAGGWEMYILQTAAARMSSLHVTSLL, (SEQIDNO:4855); XM_014112423.1, KIF7, Ins, C_7, PCRCRRRRRRPPGRRVRALPGPHRRRLQPPARAAGR-ARAARRRRPQSARLAVRRGG RAQRPELRL-WAGQRHRERFRRGAGHAGARRAEGGQRPG, (SEQIDNO:4856); XM_539044.5, BACH2, Ins, C_7, PCRGHLPGEIQERVLPLLSKVSIQHKK, (SEQIDNO: 4857); XM_005622192.2, ELF3, Ins, C_7, PCRHLWSR, (SEQIDNO:4858); XM_005623751.2, BTBD7, Ins, C_7, PCRNHVYRSGLFCGLPSTLAPTTTSIPPPSHPNP, (SEQIDNO:4859); XM_005620011.2, VAMP2, Ins, C_7, PCRPGWGGRPPGAPSKPHQ, (SEQIDNO:4860); XM_005633153.2, SBNO2, Del, C_7, PCR-PRCAGPVSRTPCCTAPGGVPSRPRRTQPSPAKATSS, (SEQIDNO:4861); XM_539694.5, NAV3, Ins, C_7, PCRQTEAPCLGGGQNNFFRTEIHA, (SEQIDNO:4862); XM_005625430.2, NPDC1, Del, C_7, PCRQYRCTFPPWSPGAGAVTDSSSCSSWRAR, (SEQIDNO:4863); XM_005626845.2, LOC102151424, Del, C_7, PCRSLKSPGSKPEYMSGTLAFSSQAE, (SEQIDNO:4865); XM_852361.4, TCF20, Del, C_7, PCR-TRQRKAASAQSSRSGG, (SEQIDNO:4866); XM_005640017.2, RREB1, Del, C_7, PCSCQSPP, (SEQIDNO:4867); XM_014122286.1, MAP1S, Del, C-7, PCSCRRLRAYASSWSMWQSPWSHHLPLSCLSRRHL-WASSGSPGPAATSSLAASAMQ PSSLSMAS-QCWSMVAPTPSRAFGSWCGTWTGWMLCW, (SEQIDNO:4868); XM_543063.4, FAM210B, Del, C_7, PCSCRRSGAGPTLCCCARSAGTAAAART-PAKSLRQQAGLSAADRRKSKASHSS, (SEQIDNO: 4869); XM_005638086.2, RALYL, Ins, C_7, PCSDS-TEASQSGCHNDSQGKRSLFHERGIENRQWVIFIRL, (SEQIDNO:4870); XM_540605.4, OR10C10, Del, C_7, PCSNWPAQTPP, (SEQIDNO:4871); XM_014107411.1, WASF3, Ins, C_7, PCSRGKAPGDGTATHK, (SEQIDNO: 4873); XM_005618215.1, LOC102151979, Del, C-7, PCSRRSPGPWPCTPSRGL, (SEQIDNO:4874); XM_854764.4, MAP1A, Ins, C_7, PCSYPPEQRPKPPSEW, (SEQIDNO:4875); XM_014115996.1, PLEKHH1, Del, C_7, PCTGFHPGRAGSMLWPWLACGSQMHLPELMSPAV-LQALLPLRPLGLSLALSTRMSP CLSTQP, (SEQIDNO: 4876); XM_014111738.1, MAP7D2, Del, C_7, PCTLSDPVRISAWMTVTKT, (SEQIDNO:4877); XM_014110953.1, STK36, Ins, C_7, PCTSGKPDHPGL, (SEQIDNO:4879); XM_541489.6, MED25, Ins, C_7, PCTTWGPIHGGHGGPRWGEWPCPGAAGGPGPW-GAAVSVQQTPGLERGPRMAGEA QTCLRGRQHQA-DAIAALPGLCESRRELKD, (SEQIDNO:4880); XM_005637917.2, COR12J1, Del, C_7, PCWCSPAPPRS, (SEQIDNO:4881); XM_014111079.1, UBR4, Del, C-7, PCWTSHLMQMTRPWLN, (SEQIDNO:4882); XM_003433475.3, NTF3, Del, C_7, PCWVVAAAGWGGL, (SEQIDNO:4883); XM_005631006.1, COBL, Ins, C_7, PDAAAPDVQPP-GAASHSGQGGKQEERHGCWTAGATKASQRHWP-GAPPASATPTPT LPSS, (SEQIDNO:4884); XM_014117000.1, HMCN2, Ins, C_7, PDAARPAG-PEGAGRRDSGPELHGRGQPGAPAEL-VQGRGGPAGWGA, (SEQIDNO:4885); XM_005633780.1, LOC102154018, Ins, C_7, PDASFPA-SIS, (SEQIDNO:4886); XM_014117415.1, SHANK3, Ins, C_7, PDCAATPTSPLLLRLGAAPRLLASAAPGPRLRH-CALQL, (SEQIDNO:4887); NM_001003291.1, ICAM1, Ins, C_7, PDCGSGHTVVCGLHSGWGVPSFGGPSPPGVSR-REAALHSPVQKGLPLGHGKCQSKP RRRGYPAAMV, (SEQIDNO:4888); XM_005620586.1, ZCCHC14, Ins, C_7, PDDGRSLSPSAHPDAEFGAQVGKRGCGHEAP-PAFRALAAVSRRKE, (SEQIDNO:4889); XM_014106404.1, KIAA0226L, Del, C_7, PDFKSYLM-FIHHSRGISW, (SEQIDNO:4890); XM_542033.5, IER2, Ins, C_7, PDGAAGVRGEAGLPPRGQHAER-ARAGRGGFL, (SEQIDNO:4891); XM_005640052.2, JARID2, Ins, C_7, PDGARPGGEGPAQRAREEGRARAE-PRKEPAEAGHGRQERAGQTSTRQGGQRLL, (SEQIDNO:4892); XM_542234.5, MAML2, Ins, C_7, PDG-LPSSRRHSPTAPARLSPSPPAAPAQQWQ, (SEQIDNO: 4893); XM_005641756.2, LOC102154914, Ins, C_7, PDGSAERGTAAGPRGAGGPAALRAL-GANATLPLGVPSPESEASGSGR, (SEQIDNO:4894); XM_005630474.2, POLR1A, Ins, C_7, PDGVWQITALL, (SEQIDNO:4895); XM_543042.5, KCNB1, Del, C_7, PDHLRNTQQ, (SEQIDNO:4896); XM_005632766.2, WIZ, Ins, C_7, PDITGQVCWQHLHPQVQVL, (SEQIDNO:4897); XM_533117.5, FDXR, Ins, C_7, PDLCGGQWTRWLLYRPTLAKAPPPGPCGHL-REAACAFRPGALWRGA, (SEQIDNO:4898); XM_005620633.2, C5H16orf74, Ins, C_7, PDPHGHDAATGLQADSLAG, (SEQIDNO:4900); XM_014116841.1, DPH1, Ins, C_7, PDPQAA-PAGEGGVHVPLSSRGLRRLQLRRRKGSAAGSV, (SEQIDNO:4901); XM_014106445.1, COL4A2, Del, C_7, PDPQALQDK, (SEQIDNO:4902); XM_003433444.3, HIC2, Ins, C_7, PDPRRPGPVE, (SEQIDNO:4903); XM_014122282.1, TCF3, Ins, C_7, PDPVQPGRGR-GRPSPPRAEG, (SEQIDNO:4904); NM_001170829.2, SMAD3, Ins, C_7, PDREAPAGLEEGRAERAG-GEVVREGGQEFGQEAQEDRAVGRAGEGHHHAER-QHQV HHHPQVPGWPAAGVPSEGAPACHLLPP-VAMARPAQPPRAAGHGAV, (SEQIDNO:4905);

XM_848173.4, ZFHX4, Ins, C_7, PDRLGPRHTARPSGCFPQKETGRQGGHGLQ, (SEQIDNO:4906); XM_014116531.1, LOC106559282, Del, C_7, PDRPPGNPNLRPPPRAPG, (SEQIDNO:4907); XM_847025.3, FADS6, Ins, C_7, PDSHDEPGRAEL-AAAACAGLGLWPLHHQLPRGASLLPPAL, (SEQIDNO:4908); XM_014109943.1, COL16A1, Del, C_7, PDSWDPRASREKQDT-LASQDQRVTVGNRVPQAAVVGPEQRVSLVPWDL-REDPAPQ ATLGLQGL QASQVLPGSLQWA, (SEQIDNO:4909); XM_014110892.1, SH2D5, Ins, C_7, PDTAAPGPCQVRGRAAGPGL, (SEQIDNO:4910); XM_014107733.1, FBRS1L, Ins, C_7, PDTAPAP-GAAGGQQPGHPRTPCRCQPVDLIQPANHVL-PASFGDSD, (SEQIDNO:4911); XM_005638000.2, PLAG1, Ins, C_7, PDTGSSGSCKHPRSQLPALSVSSIHQ, (SEQIDNO:4912); XM_014117336.1, MKL1, Ins, C_7, PDTQPLGSQ, (SEQIDNO:4913); XM_854174.4, BAG6, Ins, C_7, PDTSCGLGAGSLELSNIRSS, (SEQIDNO:4914); XM_014106445.1, COL4A2, Del, C_7, PDWA-CLAPKASVVSPEMPDYLDPQAFPAPPDPQALQDK, (SEQIDNO:4915); XM_014116315.1, LOC102152536, Del, C_7, PDYQGPSAGRLLVSLRPRIGVLGPPSMLSG-GRPGCT, (SEQIDNO:4916); NM_001003016.2, MCLI, Ins, C_7, PEAAAARAPLPRVAA, (SEQIDNO:4917); XM_014113960.1, FOXL1, Ins, C_7, PEAALQLHRAHSHGDPGRARAEGHPERHLPVHHG-PLPLLPRQPARLAEQHPPQPLA QRVLRQGAPRE-GAARQGQLLDAGPPLPGYV, (SEQIDNO:4918); XM_003639850.3, VPS16, Ins, C_7, PEADG-LVQPSSQQREGCRGGMGEASNGGG, (SEQIDNO:4919); XM_005633811.2, LOC102152567, Del, C_7, PEALPPGQNPRVARSTMHPRGPRSARARR-PARWPRPGRGGQAPLRVLLVRSKSGCL MATVSAVPARSSRPFIVSRCRSHRQF, (SEQIDNO:4920); XM_005636589.2, CLDN5, Del, C_7, PEA-PADPRLCQTRRGRGPEAVSRAPGRRGTRARSGR-PAAPPRHRRAPPRGPGAVGRP SRLQPWGRRRWRSSAWCCAWWAGWA, (SEQIDNO:4921); XM_855027.4, ATP2A1, Ins, C_7, PEARGDDS-GRLCQVHGI, (SEQIDNO:4922); XM_005636795.2, LOC486523, Del, C_7, PEASRRSPSTRISSLP, (SEQIDNO:4924); XM_003433503.3, LOC100683813, Del, C_7, PEASRRSRSTRAS, (SEQIDNO:4925); XM_014116790.1, FAM222B, Ins, C_7, PECDRVYLNYPPFNGGHPAAQPAPGPEQHRAP-DQPVLPDEGRHQHYLSV, (SEQIDNO:4926); XM_536304.5, SSBP2, Ins, C_7, PECFRWPR-NAWNEHGSRWW, (SEQIDNO:4927); XM_014116817.1, MYO18A, Ins, C_7, PEDLPGAQG, (SEQIDNO:4929); XM_014110056.1, LOC102151348, Ins, C_7, PEEA-CLLGTLQIPAPRHGRRPQLLLVLLLLL-FPSGQSRRWPFQDG, (SEQIDNO:4930); XM_014115768.1, SYNJ2, Ins, C_7, PEEEEEIGTRSLP-PAGAAEQQPAPPGPHLQHPKQRLAPCTPARPGCT-CAATCQPQCFL CHKPRN, (SEQIDNO:4931); XM_005629703.2, PAXIP1, Del, C_7, PEESHAPSTLF1, (SEQIDNO:4932); XM_005632488.2, VPRBP, Ins, C_7, PEFTSFAWTILCRQFPLDW, (SEQIDNO:4933); XM_005636540.2, ZDHHC8, Del, C_7, PEGL-CAACTQPPPAFSPVSRGLSGTPS, (SEQIDNO:4935); XM_843235.4, LOC607355, Ins, C_7, PEGPAQAPVH-PEPASAGARPFQPGPAHPGGRRAADDRA-HAQGDVPDHG, (SEQIDNO:4936); XM_539768.4, FHDC1, Ins, C_7, PEGPGARGPRLPPPEALGAGRAGQ-DARAPAEV, (SEQIDNO:4937); XM_014122618.1, DCHS1, Ins, C_7, PEGPGPAGCDTTGHQ, (SEQIDNO:4938); XM_014108446.1, PCBP2, Ins, C_7, PEGRDHPVPAQA VQFSSHLCRWSGLYHSRTVCH-STARFDQAAPVGNATVSFSHDAWQHRIQCRFGCIC SDYFS, (SEQIDNO:4939); XM_014108443.1, PCBP2, Ins, C_7, PEGRDHPVPAQA VQFSSHLCRWSG-LYHSRTVCHSTARFDQAAPVG-NATVSFSHDAWQHRIQWH, (SEQIDNO:4940); XM_014108440.1, PCBP2, Ins, C_7, PEGRDHPVPAQAVQFSSHLCRWSGQVQHRQRQCEL-SPHHPVHVPQP, (SEQIDNO:4941); XM_014108448.1, PCBP2, Ins, C_7, PEGRDHPVPAQAVQFSSHL-CRWSVDQAAPVG-NATVSFSHDAWQHRIQCRFGCICSD YFS, (SEQIDNO:4942); XM_014108447.1, PCBP2, Ins, C_7, PEGRDHPVPAQAVQFSSHLCRWSVDQAAPVG-NATVSFSHDAWQHRIQWH, (SEQIDNO:4943); XM_005619422.2, BASP1, Ins, C_7, PEGRGRAG-GRRRPPGRGARAGDPGRGRGGGAGPGARGTRKD, (SEQIDNO:4944); XM_014120647.1, FAM63A, Ins, C_7, PEGSDYIR, (SEQIDNO:4946); XM_541565.4, EXOC3L2, Ins, C_7, PEGSGRAPGPGGPSRK, (SEQIDNO:4947); XM_014112539.1, RGS12, Ins, C_7, PEH-PEKGLVQEGFRDAKHFRSPSTS, (SEQIDNO:4948); XM_005620748.2, ATXNL1, Del, C_7, PEKGLRGQCWDPESNVTVRGRASRQVRAPKW, (SEQIDNO:4950); XM_005618730.2, WHAMM, Ins, C_7, PELGGPALGRRAPRRAPAAGGALAAPGELL-PAVAARAGCARRRGLFSGARALGAR VDRAYGPR, (SEQIDNO:4951); XM_014111821.1, ELK1, Ins, C_7, PELPILPLRYTQPLSSELSALQVPLGWREHSASDG-PLCDAVAVSAAAAERARQWPHH LLDLTGWR, (SEQIDNO:4952); XM_548979.4, ELK1, Ins, C_7, PELPIL-PLRYTQVPLGWREHSASDGPLCDAVAVSAAAAERAR-QWPHHLLDLTGWR, (SEQIDNO:4953); XM_548855.5, WWC3, Ins, C_7, PELPLGHAFPSGLPRLA-LDPTGGHFRGARPGYP, (SEQIDNO:4954); XM_014113658.1, TOP3A, Del, C_7, PELP-SQLASPLTTCKLASPRTERTAPPGCCPCPPPPMGKVIL, (SEQIDNO:4955); XM_014119615.1, TEP1, Ins, C_7, PELRAAAAGDGDGPGRAGVRPAVRTWHRDGR, (SEQIDNO:4956); XM_014119781.1, HIPK2, Ins, C_7, PEN-PGQRSAGGM, (SEQIDNO:4957); XM_014109523.1, PML, Ins, C_7, PEPASCQPAGPEHLLQRPVGG-GRLRSGTRPLHPSHWPQLCKEGMPAEL, (SEQIDNO:4958); XM_014111149.1, SLC30A10, Del, C_7, PEPCLWPTSMA VRSTTAVPLWTRTQV-MASGGEKQQKWLLKYRWTAV, (SEQIDNO:4959); XM_014112349.1, BOD1L1, Del, C_7, PEPGLEAS-RGWKKPLRRRPSG, (SEQIDNO:4960); XM_854614.4, MBD6, Ins, C_7, PEPHLSPGAGACPASPQCLSPTPWFS, (SEQIDNO:4961); XM_853562.3, R3HDM2, Ins, C_7, PEPIHGPVESL, (SEQIDNO:4962); XM_546666.4, MAP2K3, Ins, C_7, PEPRLPDLHHHWR, (SEQIDNO:4963); XM_005620305.1, KMT2A, Ins, C_7, PEPTWLSQG, (SEQIDNO:4964); XM_014114088.1, AKT2, Ins, C_7, PEQLLCRRMPADED, (SEQIDNO:4965); XM_534128.5, TSC22D1, Ins, C_7, PER-CDQWERSSSPPPSPPSHSSRAPPPPRAPP-SIPCRRGQSTHSRRATLQPGIQKTLCPW KRRQRCTSCTDFCCIIGRLTCIRND, (SEQIDNO:4966); XM_005621574.2, RBFOX1, Ins, C_7, PERH-PRGVHGPSPPPRSGVHGPDHRPRAHVKPVPSRPDTL-GAERRGHQRADRVRHR HTDR, (SEQIDNO:4968); XM_005635260.2, OSBPL2, Del, C_7, PERMGFRNT-GRHCPPRCLPEVISVCGVY, (SEQIDNO:4969); XM_014111415.1, LOC612200, Ins, C_7, PERNRGGSRGHWRCHRASTP, (SEQIDNO:4970);

XM_537319.5, ZBTB14, Ins, C_7, PESGGRQVAHD-DAQGSGGNLERAGE, (SEQIDNO:4971); XM_014112876.1, CDH23, Ins, C_7, PESHQQCHSVCE-PLGPQ, (SEQIDNO:4972); XM_014111484.1, LOC100684337, Ins, C_7, PESSEGLPLPQCPGRPSLEPV, (SEQIDNO:4973); XM_014106445.1, COL4A2, Del, C_7, PESSGFLGSQEVGVTRELQGEQAFTAR-WAPQGTLVTVETS, (SEQIDNO:4974); XM_533443.5, UST, Ins, C_7, PETPVLYSNSTGN, (SEQIDNO:4975); XM_014117999.1, COL27A1, Del, C_7, PETSAPKAS-RALGGPLA, (SEQIDNO:4976); XM_014109686.1, SYNJ1, Ins, C_7, PETTSTFRG, (SEQIDNO:4977); XM_014109683.1, SYNJ1, Ins, C_7, PETTSTF-STQKPWNNTERYYRTQSAFTSSRIHRPRT-CWIQCSQTDCSTPCRSDQCPPEP CSGICWKIDS, (SEQIDNO:4978); XM_537502.5, SIPALL1, Del, C_7, PEVKVLTI, (SEQIDNO:4979); XM_848975.4, SLC18B1, Del, C_7, PEVMTLWEIQERHPDSFPENSSLY, (SEQIDNO:4980); XM_005627563.2, LOC102154910, Del, C_7, PEVSASLLLGLDPQREGTTPLRRSMPPAHG, (SEQIDNO:4981); XM_005638369.2, SPATA5L1, Del, C_7, PEWARPSWCGRWPGKPARSCWP, (SEQIDNO:4982); XM_014116906.1, EXD3, Ins, C_7, PFEDGPSRC, (SEQIDNO:4983); XM_843127.2, SH2D4A, Del, C_7, PFHPSRSSCTQRGPLGSLSEPRE, (SEQIDNO:4985); XM_014115375.1, EFNA4, Ins, C_7, PFIFVGASTVPF-HAGPRTCYLQGHSFQASAELGPWDRSEEPR-ARAGRRPL, (SEQIDNO:4986); XM_005638951.2, LOC102156742, Ins, C_7, PFILHLLRTCRGPRPSCSR-PRPSGTARPRPPLPLEVQRVPELPAAS-THRLRLLPNQLGR LPRAASTDSTDPL, (SEQIDNO:4987); XM_005628998.2, CC2D1B, Del, C_7, PFLAWRPLWAPRKMRWQLL, (SEQIDNO:4988); XM_005640394.1, LOC102151535, Ins, C_7, PFLLPLVNLSHPYVFVFL-STLGPGDPRVSRAVPLLGGHGARVPAAASAGGTG-WAQA AARV, (SEQIDNO:4989); XM_846233.4, PPFIA1, Ins, C_7, PFLPKIAPLRQAAQRSTAHSQPR-RHQGCQKLHRLTGWPREQPQQQ, (SEQIDNO:4990); XM_014116949.1, KCNT1, Del, C_7, PFLQRERENGSN-LAFMFRLPFAAGRVFSISMLDTLLYQSFVKDYMISI-TRLLLGLDTT PGSGYLCAMKVT, (SEQIDNO:4991); XM_014118001.1, PHF19, Ins, C_7, PFLSPQSVAS-RVPAAEKASL, (SEQIDNO:4992); XM_861806.4, SF1, Del, C_7, PFPGPKGASSRGHRLLPGL-GRGCWCPGSRRPRPWARWEP, (SEQIDNO:4994); XM_005619930.2, MINK1, Del, C_7, PFPRPPPGL-RAPFPKLRLCRGRWSPRRDRTRAWWHTGSH, (SEQIDNO:4995); XM_005621048.2, PILRA, Del, C_7, PFPRRAPRRRPYTLS, (SEQIDNO:4996); XM_014118308.1, PRRC2A, Ins, C_7, PFPVHPHSRCGSSSHPGEWWWQYQ, (SEQIDNO:4997); XM_005621064.1, LOC100686271, Ins, C_7, PFQDEPPGGDPILYPKGL, (SEQIDNO:4998); XM_014106445.1, COL4A2, Ins, C_7, PFQHVWVTW, (SEQIDNO:4999); XM_532077.5, ABHD16A, Ins, C_7, PFQLLGYVLSTPCLGEAC, (SEQIDNO:5000); XM_014109393.1, LOC100686862, Ins, C-7, PFQLRPAE-PGGSSHAPSPALWEPRPRPPQLRVRRGWAA, (SEQIDNO:5001); XM_844902.3, IL21R, Ins, C_7, PFQRDCDLLGTL, (SEQIDNO:5002); XM_545122.3, GPR156, Del, C_7, PFRALYLPTWGIVQI-GLCLGCAAGG, (SEQIDNO:5003); XM_545710.3, USH2A, Ins, C_7, PFRLPTLTTLPQCVLGGARGECNK-RRSCGV, (SEQIDNO:5004); XM_014106920.1, ZHX3, Ins, C_7, PFRQTPGLAPDPRLHANQVQ-GASPRAAQSPGEQFCAEPSSSRRRAGPPEDGNQDDPE RDRQLVLREAEESGCRGHQEG, (SEQIDNO:5005); XM_005624366.2, FMNL1, Del, C_7, PFRSPRISRS, (SEQIDNO:5006); XM_014118198.1, ZNF581, Ins, C_7, PFS-DRPVSRTWTFLIHRTAPDFLLSEAQPLPAH, (SEQIDNO:5007); XM_014113657.1, SOGA3, Ins, C_7, PFSIRVRGQSRGPRRQEPRKRGSGGRRRRRRGGL-LEGRMPAV, (SEQIDNO:5008); XM_849796.4, TCF7L1, Del, C_7, PFSPGPSPSGPCPQLC, (SEQIDNO:5009); XM_547550.5, FAM189B, Ins, C_7, PGAAASSPGSCAATAAAASVPQ, (SEQIDNO:5011); XM_014120815.1, GRB10, Ins, C_7, PGAAFAARAH-RRRQTPAGRRPAAQNLVSAGHPQPLPRALRPREPA-GADARLPTSRP GSCQAGCENLQ, (SEQIDNO:5012); XM_014110719.1, SCN9A, Ins, C_7, PGAAGEWEDAQCRGLQWCGLPG, (SEQIDNO:5013); XM_014111821.1, ELK1, Del, C_7, PGAANTATALH-TASQL, (SEQIDNO:5014); XM_548979.4, ELK1, Del, C_7, PGAANTATALHTGTPGMA, (SEQIDNO:5015); XM_014117449.1, LOC102154536, Ins, C_7, PGACAVRPILVGPV, (SEQIDNO:5016); XM_005628902.2, PABPC4, Ins, C_7, PGAEADAGRTFVPTHPNHAFKPGW-KNHRHAAGDRQL, (SEQIDNO:5017); XM_014114924.1, LOC607201, Del, C_7, PGAG-MASGCGFTAWGP, (SEQIDNO:5018); XM_846422.2, LOC609208, Del, C_7, PGAGPAAPGAPRSRATC, (SEQIDNO:5019); NM_001131049.1, DNM1, Ins, C_7, PGALAPQPRPARGPQPIGSGKSVPS, (SEQIDNO:5020); XM_005624466.2, KCNH4, Del, C_7, PGALLPGSSPSFSFPHWEPLDLRTSVPG, (SEQIDNO:5021); XM_540897.4, CHRM1, Del, C_7, PGAL-PIQSRGPRGKGASEQARARRPEGRSSWPS-GRPSRWSRKRRRLGP, (SEQIDNO:5022); XM_005621146.2, SDK1, Ins, C_7, PGAPGAPGRSD-CAQPPAPVGPGQRRGLPHSLLHGAGARAAPRR-VADLLLVHQPRGH SLRCRKAEALHFLQAAPESHQ, (SEQIDNO:5023); XM_005637678.2, WBP1L, Del, C_7, PGAPRARRAVPCLGPAEAARDPQASLTLSPPTCP-PAQQPPKPPGWSPVALWLAWGS WTLGPSWT-KIPTVRRSC, (SEQIDNO:5024); XM_537028.5, WDR77, Ins, C_7, PGAPRGPRVEPPP, (SEQIDNO:5025); XM_014122482.1, LOC102152187, Ins, C_7, PGAPSPPGSGSPRVRPSVGPLAAPRDMA-FIWRNRLLSF, (SEQIDNO:5026); XM_003639997.2, CALHM3, Ins, C_7, PGAQRPRRPGWRRWRQGPPAG-GLQPGAGGPPPEHVVLQQTTARPRGIPWAPGGWP QPPSRHGGPGHQAAPAH, (SEQIDNO:5028); XM_014106443.1, MYO16, Ins, C_7, PGARGGR-GRQSNGGGRPRRAQGAAAGLRARGRPGRPPPQG-PLLPREGSQGRALEGQ RRAPQRRF, (SEQIDNO:5029); XM_536262.5, TBC1D1, Ins, C_7, PGARGRPLLGR, (SEQIDNO:5030); XM_003434673.2, C5H1orf233, Ins, C_7, PGARRARRVRGVRSRAGRHAGDRSGHDGG-GRLHLRHAGGHLPARGLHHREPHAPS FRAPR-PAQAAL, (SEQIDNO:5031); XM_536856.5, PLOD3, Ins, C_7, PGASGCVCRTIYPIPAPLPAAAAAPGLPP, (SEQIDNO:5032); XM_546739.5, MEGF6, Del, C_7, PGASGLAVSSHVGVSTGAPVMQPLGPA-SALLGSWGPTAVCPVHRATSAPAVRMCA GVGRP, (SEQIDNO:5033); XM_014118655.1, ZC3H3, Del, C_7, PGATIGLRRGRASPLVGSGNPQSQEESR-GAAVQRTPFWSARRSPASPGW, (SEQIDNO:5034); XM_543528.4, SUSD2, Del, C_7, PGAWTGCAPCK-PAPGSPPASSAATRRPAACS, (SEQIDNO:5035); XM_014107254.1, GMEB2, Ins, C_7, PGCFRQLSSLAPA-RGLHSAGLVGHHLS, (SEQIDNO:5036); XM_536856.5, PLOD3, Del, C_7, PGCFWLCL, (SEQIDNO:5037);

XM_005620448.2, CHD5, Ins, C_7, PGCLQLPLAGAGP-PREEREGV, (SEQIDNO:5038); XM_003639660.3, B4GALNT4, Del, C_7, PGCPGLQATGPAAPRPCSRG-PLPGLRPRRAAGRPRRACPPSPRPPRA, (SEQIDNO:5039); XM_014108770.1, VSTM4, Ins, C_7, PGCQRP-PHQHRLCPDPL, (SEQIDNO:5041); XM_005639502.2, ZDHHC23, Del, C_7, PGCRPGAPPR, (SEQIDNO:5042); XM_005634649.1, CHST2, Del, C_7, PGCSRPRLQPRRA-PCSRRGPGARAVAGPRPRSE, (SEQIDNO:5043); XM_845262.3, ITGA10, Ins, C_7, PGCSVWLCHGCHS, (SEQIDNO:5044); XM_014119834.1, EPHB6, Del, C_7, PGCTATGKASGW, (SEQIDNO:5045); XM_005639039.2, C31H21orf58, Del, C_7, PGDQGGSRRTWWR, (SEQIDNO:5046); XM_545710.3, USH2A, Ins, C_7, PGDSRCFCESPQTAHLLDPARAA, (SEQIDNO:5048); XM_005633456.1, GDPD4, Ins, C_7, PGECETTSAKGK, (SEQIDNO:5049); XM_003640232.3, RAI2, Ins, C_7, PGEGGTEALLSPPAEGVLPAEPPHGHQDGQ, (SEQIDNO:5050); XM_005637802.2, TACC2, Ins, C_7, PGEGSFYLGPR, (SEQIDNO:5051); XM_005628050.2, NRBP2, Ins, C_7, PGEPGEHARG-PEHLPGHGHRGGGGGVERVALRRQEGLRSP, (SEQIDNO:5052); XM_541488.5, PNKP, Del, C_7, PGEPPPSSCPRTGKPLSWAGDP, (SEQIDNO:5053); XM_005620748.2, ATXNL1, Ins, C_7, PGFIPSPLIQQSS-CHFPTWAVATSLKYSATGPCSRPDAHL-LSDVQATCWVHFA, (SEQIDNO:5054); XM_542953.5, PLAGL2, Del, C-7, PGFKMQSRRRKWAGN, (SEQIDNO:5055); XM_005635353.2, LOC102153863, Ins, C_7, PGFPASGPPRRGRGRPLSAGEGRDRGGGARAG-GAARGLRGPGPVAACGAARRSCPA GAAFSESP PEA-AGGRKGSVPCTLPP, (SEQIDNO:5056); XM_014117011.1, PKN3, Del, C_7, PGFRT-SAAWPCWAGDTLGRSSWCNSRARGNTTL-SKRSRSRRC, (SEQIDNO:5057); XM_014116431.1, IL11, Ins, C_7, PGFSLGRHPGSPCHSWGAAPDP, (SEQIDNO:5058); XM_543674.5, SMARCD1, Del, C_7, PGGAGRSGSGSFAACGAAPGCRRPGRAS1L, (SEQIDNO:5059); XM_005622774.1, ZBTB7B, Ins, C_7, PGGAPDLRGL, (SEQIDNO:5060); XM_014115768.1, SYNJ2, Ins, C_7, PGGATSRTPGPPEEEEEIGTRSLPPA-GAAEQQPAPPGPHLQHPKQRLAPCTPARPGCT CAATCQPQCFLCHKPRN, (SEQIDNO:5061); XM_014113186.1, NCAM1, Ins, C_7, PGGCAQPER-PRRRGGGLQGPSSQQAGPRRRGPPR-PAGGGPRHRRPGPRARPARRRREE PGRGSRGPH, (SEQIDNO:5062); XM_847992.3, NCOR2, Ins, C_7, PGGCSSPCSATTTALAARERHPPAAQQQPSRQKQEP-CASCRQGGEACVLPGLCTRGP EAAHGGP MLDVR-PALPCAPS, (SEQIDNO:5063); XM_014107094.1, HSPG2, Ins, C_7, PGGDPSPGVHPGFPGSDSDLHLCGH-WRPHPHHQLEA, (SEQIDNO:5064); XM_005620578.2, ZC3H18, Del, C_7, PGGGPSVAAAAAAATAALAPDPGP, (SEQIDNO:5066); XM_014111170.1, PLEKHM2, Ins, C_7, PGGGRGAQQHSREQRALGARPGGPAYPRDE-GHVHGALGAAPEQGDRPAQRAAGPQ HLALPRP PRPVLSGRLSRGRPGEATMLRL, (SEQIDNO:5067); XM_548447.5, SH2D3C, Ins, C_7, PGGHPSSGTQPFC-NEPHRKA, (SEQIDNO:5070); XM_539847.5, TCAF2, Ins, C_7, PGGLLHQCLQ, (SEQIDNO:5071); XM_014118793.1, JRK, Ins, C_7, PGGLPSALLVHGR-RAL, (SEQIDNO:5072); XM_536660.4, MYO15A, Del, C_7, PGGLQSQSQSQSQSQAWMP-PHWLCSKPSSTNRLSYWPGR, (SEQIDNO:5073); XM_534280.5, PIK3CB, Ins, C_7, PGGLRAS-RFQLSRSVRARICCGLPATDE, (SEQIDNO:5074); XM_544915.6, PWP2, Ins, C_7, PGGPAAESPHGLEGR-PAAGGGGGEGGRRGGGGGDHRPGQSHAGCR-GAAGESQILS AGQVLFQQR-GRFQQADRCGLPQEDPSLGHRLCFRNLPPSRAA, (SEQIDNO:5075); XM_548143.3, PNMT, Ins, C_7, PGG-PEQPRRRRALEAALLGADLRYR, (SEQIDNO:5076); XM_536262.5, TBC1D1, Ins, C_7, PGGPPGARGR-PLLGR, (SEQIDNO:5077); XM_014122618.1, DCHS1, Del, C_7, PGGPRPCWM, (SEQIDNO:5078); XM_005622065.1, LOC102151745, Ins, C_7, PGGPVP-GAVPGSWPRAQLTPRGLWLSCHPRYPLQLPGIA, (SEQIDNO:5079); XM_014110313.1, TRIO, Ins, C_7, PGGQ-PLAEQPGLAAPGKAQAWGHLASELSRGRRITSSNR-QGALSPQQPPAEGGLLLE LHPRL-PRQPARLLHLPGGQ, (SEQIDNO:5080); XM_005635990.1, GAL3ST2, Del, C_7, PGGRLHPLRP, (SEQIDNO:5081); XM_014118179.1, PRDM1, Del, C_7, PGGRTATAPTFHPSPPRGTPTTSEKTGAPRCPSTPGPC-TRVGSLCPRTF, (SEQIDNO:5084); XM_541549.5, FOXA3, Del, C_7, PGGSLPLHCPQD-PWRPQPQRHPWGPPSRAWVPAVVGAAARGMGAR-ERGWCRGRR CPKATGGH-WPTPSRHIPTSRSSPWPSSRRRARC, (SEQIDNO:5085); XM_014114365.1, SETD1A, Ins, C_7, PGGSLWPTLCFVHTRARRPGGILPGSLPPAFACSS, (SEQIDNO:5086); NM_001136500.1, SLC6A3, Del, C_7, PGGSSPPAWCWSSSCSTLACGRE, (SEQIDNO:5087); NM_001287078.1, NCLN, Ins, C_7, PGHAGLHGADAD-PAGAAGLSDGLAHQPAAGR-PAGGQGRHAAQHAGALPEPLPEG GEAAPHQGRQTGPRVCLL, (SEQIDNO:5088); NM_001287079.1, NCLN, Ins, C_7, PGHAGLHGADDPA-GAAAGLSDGLAHQPAAGRPAGGQGRHAAQHAGAL-PEPLPEGGE AAPHQGRQTGPRVCLL, (SEQIDNO:5089); XM_014117262.1, TUBGCP6, Del, C_7, PGHCGGRGTTSCTASTSAGTCPTAATTAQT, (SEQIDNO:5090); XM_014110892.1, SH2D5, Del, C_7, PGHCGPWAMPSPRQSCRAWA, (SEQIDNO:5091); XM_005616509.2, DMRTC2, Ins, C-7, PGHGAY-PQESCQPLSNLCPLPKPR-SHCPPQGPQAPVPLSGLRVSQMCPHLGAPKGHG CPGGLASATGGTAQETSGSGPDKEKDSSSQSS, (SEQIDNO:5092); XM_538465.5, ANKRD23, Del, C_7, PGHLSPWLSHSPRPSGSLWTWRCS, (SEQIDNO:5095); XM_539692.5, E2F7, Ins, C_7, PGHSVHGPA VSHAGPVSRALLSHRAQAGLLCRRRAPRCGACAFR-GAQPGIHGSPPHRPHKRG, (SEQIDNO:5096); XM_014108204.1, CABIN1, Del, C_7, PGHTGRRPPPA WSLWAQREKSWQEGRRAWASRPRSPCTVSR, (SEQIDNO:5097); XM_005616594.2, PLEKHG2, Ins, C_7, PGICGPSRGPGNS, (SEQIDNO:5099); XM_014117665.1, TNC, Ins, C_7, PGICHRLPIGV, (SEQIDNO:5100); XM_546587.5, NEURL4, Ins, C_7, PGI-RAALRLVQVQSQGESPPGSWNDD, (SEQIDNO:5101); XM_003434935.3, LOC100687115, Del, C_7, PGIREDGPGCGEYPTEVC, (SEQIDNO:5102); XM_014118914.1, LOC106559676, Del, C_7, PGLAQGRPPLPREAAPAPLATLG-PEPKTPGYLHPHGRGCRLPGQQPR, (SEQIDNO:5104); XM_005629431.1, LOC102155312, Del, C_7, PGLAR-RAGRRGEQQGSSSSNWRRPAPELTPPIRPHLLQA-FAPRDVWGAGTWGRGRA PSCGPANHTGLGP-GASSRRDWGIRGYFAA, (SEQIDNO:5105); XM_005641552.2, PCDH19, Ins, C_7, PGLCDCAGAGV, (SEQIDNO:5106); XM_862738.4, RBM42, Ins, C_7, PGLHGCSETSPGRASNTSRAGAGPGVGPER-EGRGSGGCSSRAGRG, (SEQIDNO:5107); XM_014116191.1, UNK, Ins, C_7, PGLHQEAPKPGRHCLPWGVWPRPWQL, (SEQIDNO: 5108); XM_846897.3, TBC1D10C, Del, C_7, PGLIEAPHPSWIPDS, (SEQIDNO:5109); XM_541958.3, USHBP1, Del, C_7, PGLKPLTCFRFSSML, (SEQIDNO: 5110); XM_014109098.1, COL17A1, Del, C_7, PGLLEPWDRQDLQVPQVLWAQLVSLDSKA-HAASEDLLANRSWAAAAPSLSSSLPK VLTYGVPQAHLDHQGLQEKAGRARRALRDLC, (SEQIDNO:5111); XM_014109099.1, COL17A1, Del, C_7, PGLLEPWDRQDLQVPQVLWAQLVSLDSKA-HAASEDLLANRSWAAAAPSLSSSLPVL TYGVPQAHLDHQGLQEKAGRARRALRDLC, (SEQIDNO:5112); XM_014110341.1, AIMIL, Ins, C_7, PGLLFSSGDDEETCSRCQGPPPRAGARVASKQ, (SEQIDNO: 5113); XM_541508.4, PLEKHA4, Ins, C_7, PGLNFSPKPGDRYSVDQAVWAGPAPEE-AAGGDRPEAGGKGAARSSLGVN, (SEQIDNO:5114); XM_014108770.1, VSTM4, Del, C_7, PGLPKASP-PAPSMPRSSLRRTRC, (SEQIDNO:5115); XM_541408.4, ZNF579, Ins, C_7, PGLPQRLLFRQPRPFSL, (SEQIDNO: 5116); XM_539044.5, BACH2, Del, C_7, PGLPVAPPPPPPPPPPRRIARGGRRAATRGASRRG-GLRWNPGARR, (SEQIDNO:5117); XM_538386.5, SH3BP1, Ins, C_7, PGLQHALLPSSPPHIPWL, (SEQIDNO:5118); XM_003638871.2, PTCH1, Ins, C_7, PGL-RAPSSWATRPAAPEGTPQRRLAAAPLQTAQRRF, (SEQIDNO:5119); XM_014114192.1, ZNF853, Ins, C_7, PGLRGAAGAHGAACRGRARGGGHSR-PRGQRGSDSGQAAAAAAGAGSADHLRGV WQGLQPQHGPGAPPGHAHGRAAAPLRRVRQGL-LAALQPGDAPAHPHR, (SEQIDNO:5120); XM_005630011.2, WWC2, Del, C_7, PGLRPPSL, (SEQIDNO:5121); XM_014114909.1, VSIG10L, Ins, C_7, PGLWGHCWHRPGFPTGPGPPSIASLQVHPLPVQF, (SEQIDNO:5122); XM_843592.5, CACNA1S, Ins, C_7, PGLWQVLPTPGGLQAAGGHEHALEQRRHRHLQRH-ALRAGPHGPQDQDGR, (SEQIDNO:5123); XM_014110056.1, LOC102151348, Del, C_7, PGMRRLTTSPPTRSS, (SEQIDNO:5124); XM_005619930.2, MINK1, Del, C_7, PGMTTSSGW, (SEQIDNO:5125); XM_014121829.1, TMIGD2, Ins, C_7, PGMWPPPPGHVRPP1, (SEQIDNO:5126); XM_546181.5, ZMIZ1, Del, C_7, PGNSPCSPPSTL, (SEQIDNO:5127); XM_005617936.2, KLHDC7A, Del, C_7, PGNWDPGSRTPPPPTGRPTWKARLT, (SEQIDNO: 5129); XM_542201.5, PCSK4, Del, C_7, PGPAAVWN-LETS, (SEQIDNO:5130); NM_001289435.1, SLC4A3, Ins, C_7, PGPAEPRGRGTSLSPAGGQPWRAAAPSEEAVS-DAGRQGQPRWPGPRPAQEEEEEAA GSEASRGVC-GAE, (SEQIDNO:5131); XM_843844.3, ADAMTS2, Ins, C_7, PGPAPGARS, (SEQIDNO:5132); XM_005639813.1, ST6GAL1, Del, C_7, PGPARPSA VPGAQSRPSPRPPSRCGTRTALPKTSSPGYRRSGEII, (SEQIDNO:5133); XM_005624595.2, ARHGAP23, Del, C_7, PGPAVPPRTG, (SEQIDNO:5134); XM_849794.3, TMEM143, Del, C_7, PGPCRHWRPRWGSTARCGTPR-SPATGPSSTASGSSRSPRSSCSAS, (SEQIDNO:5135); XM_541508.4, PLEKHA4, Ins, C_7, PGPDPGGGGVASASHAAAVQLL, (SEQIDNO:5136); XM_845969.4, C1QL4, Del, C_7, PGPEGL-RESRAGRVPRVLPAQAPAGWRPLPATCLASP-STRVCGGRTRVTRCCASTT W, (SEQIDNO:5137); XM_014119248.1, DLGAP3, Del, C_7, PGPGPSP-PHSSSRPSQAGRSCGAWRASASGGRP, (SEQIDNO: 5140); XM_014112163.1, LOC100856005, Ins, C_7, PGPGQPGAPGGALGEH, (SEQIDNO:5141); XM_014112944.1, LDB3, Del, C_7, PGPKCPPWP-GASCSGRSASRPAAGPRSAATATTSSGAPFW, (SEQIDNO:5142); XM_014119707.1, E2F7, Del, C_7, PGP-PAPRPT, (SEQIDNO:5144); XM_005628933.2, ZC3H12A, Ins, C_7, PGPPGWGHPQGSQP-GALTPGGEQGGQ, (SEQIDNO:5146); XM_014107580.1, NYAP2, Del, C_7, PGPPRPPPPRCPPPRPRRPPCTAR-SPPTATPRATRPRRRP, (SEQIDNO:5148); XM_005624595.2, ARHGAP23, Ins, C_7, PGPQCLPGPVRGSDCPPPMALLHLPGCLEPVGPGR-LAPSSLRRLLEPGHPLS, (SEQIDNO:5149); XM_014106771.1, XIRP1, Ins, C_7, PGPQYGA-GASQRPGGHLPPPTDHGKASASSWGEKARR, (SEQIDNO:5150); XM_543467.4, RHBDD3, Del, C_7, PGPRCGQPWMSKCCRRGSRPHSLRGQPSVL-RAHYGCLSPPSPLCGCSSWSAWASRQ SRQWWHWLPQAEWRVLCHCWLAGRWALRPW, (SEQIDNO:5151); XM_014121783.C PTPN23, Ins, C_7, PGPRPPCCGPGPWSCSLPCPCLHSRVGT-CAPVVPTARCGKQSLWGGRTTPASCRSAL CPSSPVLRTRDGPGGSASHDHCG, (SEQIDNO:5152); XM_543274.5, IRS1, Ins, C_7, PGPRRG-GAEQLHLHGRQRVLHPHRPQRSLHFASGWQWP-PLHPGGWLGHQPGPGCG, (SEQIDNO:5153); XM_003434863.3, VASN, Del, C_7, PGPRTARRPFAST-GAPVTWGCRATWSACALSSSWASTARAG, (SEQIDNO:5154); XM_014110201.1, PHLDB2, Del, C_7, PGPRWAAPGGRGRGTGSRPPAARSTTAT, (SEQIDNO: 5155); XM_846534.4, PRCC, Ins, C_7, PGPSQAKEED-GAREDRGAGAASGGFRFRGR, (SEQIDNO:5156); XM_014115719.1, KIF26A, Ins, C_7, PGPSRAQVQPGTQEQPGSRRAPGRGPDPGRGCRLP-PRGGGGQAGRPG, (SEQIDNO:5157); XM_014106882.1, COL20A1, Del, C_7, PGPSWRRPSSLDEEDRTVPAPRTEASPEPSVPWAAL-GRKGASLQDP, (SEQIDNO:5158); XM_014113507.1, ARRB2, Del, C_7, PGPTHPSPPLACRTGC, (SEQIDNO: 5159); XM_536071.5, RNF25, Del, C_7, PGPVEAPGNSLNGGT, (SEQIDNO:5160); XM_537756.4, CPD, Del, C_7, PGPVVATTAAAVT-STAASPTSSAPASPRPWTRCPRCAPSWTGSAGTSS-CFLEICMVA QW, (SEQIDNO:5161); XM_849794.3, TMEM143, Ins, C_7, PGPVVTGDQDGGVPQDVE-PHGAPRLGPAVPRAVHPVLQGAAAPPPNT-GIPLQPCGE GSFGGFCSPRGLIHLVPLPPHPGPAAGLV, (SEQIDNO:5162); XM_005618689.2, GAK, Ins, C_7, PGQAAPQGLSAAKA, (SEQIDNO:5163); XM_014108452.1, TNS2, Ins, C_7, PGQAVFHLQSHGDVAQC, (SEQIDNO:5164); XM_003431483.3, KIAA1644, Del, C_7, PGQGSPPR-SPSPRQACCHRRPRPCTHCRETPTAHRS, (SEQIDNO: 5165); XM_014110586.1, RREB1, Ins, C_7, PGQQPR-GRHPEPEGEPGRRHQGSQPQGGAGGASDGGRWPG, (SEQIDNO:5167); XM_005631406.2, SSH3, Ins, C_7, PGQRPLHARGAHAGPGIQAEKPAPAKAEL-CSAPWGCPGTAGWRRQWRSS, (SEQIDNO:5169); XM_540820.5, SSH3, Ins, C_7, PGQRPLHAR-GAHGPGIQAEKPAPAKAEL-CSAPWGCPGTAGWRRQWRSS, (SEQIDNO:5170); XM_536071.5, RNF25, Ins, C_7, PGQSRPLETA, (SEQIDNO:5171); XM_014113666.1, RAI1, Ins, C_7, PGQT-GRQAASRLQVWQAGGQAVTQGGVQPQ, (SEQIDNO: 5172); XM_014119248.1, DLGAP3, Ins, C_7, PGRAQAPHTHHQDHPRQGGAAEPGAPAQVAAVHR-GAGGDYLRLGH, (SEQIDNO:5174); XM_014115697.1, LOC102152805, Ins, C_7, PGRARSAVSGALARRLR-MARCGPRPGVYPEQASTSRHSQPHRVL, (SEQIDNO: 5175); XM_544279.5, KLF6, Del, C_7, PGRCAE- GLRGSPVTRAAGTPPRMAGGGCIAATLTAAGKFTP- KAPT, (SEQIDNO:5176); XM_014111403.1, ESX1, Ins, C_7, PGRGGATDRGEKAPPQPHRIHPVAAAGAG- GRFPSHSVP, (SEQIDNO:5178); XM_005619884.2, LOC100688504, Ins, C_7, PGRGLLPRPFPAPLH- LYLRGHRLLDHLLHLHPPAAGL, (SEQIDNO:5179); XM_861784.4, SERTAD1, Ins, C_7, PGRGLQFPLGPF- CAQAPPQPAAE, (SEQIDNO:5180); XM_543059.3, CYP24A1, Del, C_7, PGRGRCPCARPWSRARRR- TRPPCGAPPTGRCWAACWRFSGRGASRNSTTRWP- STTR STARSSA, (SEQIDNO:5182); XM_005619435.1, LOC610073, Del, C_7, PGRGRFSPPLRPRRAEKAAQP- GAGGRGQPGPLSGSGNPMGVR (SEQIDNO:5183); XM_014120942.1, SCYL1, Del, C_7, PGRGSPNLSSMT- PRSWLMA- VAEQLERNGQLTCGAWAASSGKSSMGPYLGRLPCAT LGRSPSRWCPITVN, (SEQIDNO:5184); XM_005640837.2, MIA3, Ins, C_7, PGRLGWHVGRDAATP, (SEQIDNO:5186); XM_014117194.1, B4GALNT1, Del, C_7, PGRN- CRTSRLSPAMHTSPSGSRSKWWGCSLGTTAVVSPAE- GAFTSPSRGRSEPLTSPR PLT- PRSCWLPLPPGSRSSRPSFQGASPPLTSCS, (SEQIDNO: 5188); XM_U14116817.1, MYO18A, Del, C_7, PGRPARGPGMSWMNAAPPSPRPPAAALAGGWRRG- GAQTLTGPPPSLPPPAGPLRPP GVAPGALVRTGPAPP, (SEQIDNO:5189); XM_536920.5, LOC479792, Del, C_7, PGRPCAGGC, (SEQIDNO:5190); XM_014110547.1, GABBR1, Ins, C_7, PGRPDPGHQDIS- LHVTEALHFSLCPLQPGHCPGCGLSVL, (SEQIDNO: 5191); XM_014108804.1, SORBS1, Ins, C_7, PGRPEARPPQPAPSGRDPLWGEAL- GSQTPVFPTHHGEAEPDLGAPSGETRSPRGLPEG LS, (SEQIDNO:5192); XM_014117212.1, TBC1D30, Ins, C_7, PGRPPESAPL, (SEQIDNO:5193); XM_005616836.2, LOC102154596, Ins, C_7, PGRPRSPPLRQPELRPQ, (SEQIDNO:5195); XM_014110527.1, LOC106558240, Ins, C_7, PGRRDDARRELQLAWARH, (SEQIDNO:5196); XM_849440.4, CYP2R1, Del, C_7, PGRRGCHLSAT- STRWRPRASSPTST, (SEQIDNO:5198); XM_005624045.1, DNAH17, Ins, C_7, PGRRGQCHGR- RHDPDRPRGQDPQGQELESRENHDGQSGHLPGL- PEKVRQGAHPRG LPKSV, (SEQIDNO:5199); XM_014108311.1, LOC106557876, Del, C_7, PGRRPPR- GRARAPTPAGSGAPTRAGNPPSPPA- PRFVSGGVALRRSRSHKSP, (SEQIDNO:5200); XM_003640189.3, FZD5, Ins, C_7, PGRRRRLPQAGVP- VARV, (SEQIDNO:5201); XM_014122241.1, AMH, Del, C_7, PGRSAARGRGRPTGPARCAS, (SEQIDNO:5202); XM_538929.4, PTK7, Ins, C_7, PGSARAQCMVGACR- SPATHPWQSLPRGP, (SEQIDNO:5203); XM_005625532.2, STAT6, Ins, C_7, PGSED- SDQVPGWGSILTGPAVGGPRQASAGQGRHGD, (SEQIDNO:5204); XM_014121804.1, CACNA1A, Ins, C_7, PGSGEEVSGQSGLQEAPSHGSACGRRQHR- PLQFYPHGSDPHSPGHQDRQGRSRQTA DGR (SEQIDNO:5205); XM_014109870.1, COL6A2, Del, C_7, PGSGRRPCSAPLASRFSATR, (SEQIDNO:5206); XM_014112130.1, LOC608320, Del, C_7, PGSLIASLDPSLGTKLPSPSQEPSLRMRLLLFT, (SEQIDNO:5207); XM_005616269.2, POLDI, Ins, C_7, PGSPEGAPHLPAVGDRSLCGPSTAPARSTHAIPRL- RAYPASLWSHR (SEQIDNO:5208); XM_005629431.1, LOC102155312, Ins, C_7, PGSPGGLGAAGSSR- GAAVPTGGGLRRS, (SEQIDNO:5209); XM_005637414.1, ANKRD33, Ins, C_7, PGSPWLPGPHPLPEPSGHVECVPSVATTQRQ, (SEQIDNO:5210); XM_546506.4, DSCAM11, Ins, C_7, PGSRPGPCRAPCRPQCCPSGPQHRASEGRGPTHQN- GRFQGLASRDEHIGGGEVSEAG GGGLLQILYPGV, (SEQIDNO:5211); NM_001130437.2, PABPN1, Ins, C_7, PGSSGPWAWLGSPRQPGGGGGAGTGRG, (SEQIDNO: 5212); XM_005622571.1, POGK, Del, C_7, PGSSPVGWKSAATGTGG, (SEQIDNO:5215); XM_005621146.2, SDK1, Del, C_7, PGSSWCPRQK, (SEQIDNO:5216); XM_850107.5, R3HDM4, Ins, C_7, PGSTRHLRRGLQQ, (SEQIDNO:5217); XM_014117262.1, TUBGCP6, Ins, C_7, PGTAAAAGLL- PAQPARRQERALRRLRLLRPER- VRDGCALVDLRGGVLVPGRGPRGA AGDGGGPGRR- PARRGVGALLLRRPLRGQV, (SEQIDNO:5218); XM_005635288.2, CHRNA4, Del, C_7, PGTCPCLRP, (SEQIDNO:5219); XM_014110191.1, PIGZ, Del, C_7, PGTFSTSQAWARPWRWWTWVGPRTGSCAVP, (SEQIDNO:5220); XM_005630260.2, EIF2B4, Ins, C_7, PGTGGSGDHGAGDDSLQFCTGCSTSQE, (SEQIDNO:5221); XM_005621660.2, KREMEN2, Del, C_7, PGTLRLRV, (SEQIDNO:5222); XM_014113787.1, SAMDL1, Ins, C_7, PGTPRPRPPDPSP- GACPPSPSEGGPQPCLSPLQ, (SEQIDNO:5223); XM_005619884.2, LOC100688504, Del, C_7, PGTRAAT- STISRTSPSLSTRPSPSRSPPASSPTSTCSWP, (SEQIDNO:5224); XM_014109643.1, C30H15orf39, Ins, C_7, PGTRALCPGAPGSSAE, (SEQIDNO:5225); XM_005640267.2, XIRP2, Del, C_7, PGTSCPVSLRLT- GRPSPPRQVQPAPRPRPRPRPHPRTRPRPRSPRVARSS- WPSSETPPP G, (SEQIDNO:5226); XM_014107696.1, NEU4, Del, C_7, PGTSPWSAASLP, (SEQIDNO:5227); XM_014114472.1, ZSCAN10, Ins, C_7, PGVPGVRQELQPQL, (SEQIDNO:5229); XM_005631208.2, TNKS1BP1, Del, C_7, PGVPWLSCLLPGR, (SEQIDNO:5230); XM_005630877.1, LOC102151356, Del, C_7, PGWAGRLSFRKAHSQARL- GASGDQQALRGSSGTPSPSPPPCQEY, (SEQIDNO:5232); XM_005637634.2, SFXN3, Ins, C_7, PGWQICAL- CSGGSCQLHQHPPDEAEGTAGGHPSD, (SEQIDNO:5234); XM_005638643.2, LOC102157171, Del, C_7, PGWSHLTRASSWASPAPRAPWDLLARASGLSAL- CGEPSRSPGSVLLCPAPAPPRALT VLQAVWPPPCSHALLLPRALTAFLCLLPSRAPGPCL, (SEQIDNO:5235); XM_847680.4, CHERP, Ins, C_7, PHAATGPSPHQP, (SEQIDNO:5236); NM_001003291.1, ICAM1, Del, C_7, PHALLPPRLWK- WAHSGLWTALWMGCSQLRRPKSTWR, (SEQIDNO:5237); XM_014121720.1, ARHGAP21, Ins, C_7, PHAP- LARPCPRKRSSPEAGGAASDRARASSAASL, (SEQIDNO:5238); XM_014113960.1, FOXL1, Del, C_7, PHAPLPTALPRAPTSPRASA, (SEQIDNO:5239); NM_001007126.2, DIO1, Del, C_7, PHAPWWWTR, (SEQIDNO:5240); XM_845621.5, MLLT6, Del, C_7, PHC- CLPGPW, (SEQIDNO:5241); XM_844150.4, FAM155B, Del, C_7, PHCGPLTPLPVPRPSSPPPKKTCSKATFGTSL- SPFATPTRSGTCCWAWTAPTAWTAA WTPCWGTCWL, (SEQIDNO:5242); XM_014107051.1, ZNF335, Del, C_7, PHCSVLTPLVGPPSSTSKVLRSRQQWPRRRPWICC, (SEQIDNO:5243); XM_532087.5, NELFE, Del, C_7, PHEAAAGTIVVSGTGTETVIENGIET- VIGTGTAIGTGTAIGTGTVIGTGTAIENERALSA GRIHSLNAGPLGRVILSMCMERT, (SEQIDNO:5244); XM_014114351.1, STX1B, Del, C_7, PHEPPEAPSRAP- STPRPRPSGMIGACARGRVSSSPEGA, (SEQIDNO:5245); XM_005616531.1, CIC, Ins, C_7, PHFGGGGTWKGSPSRH, (SEQIDNO:5246);

XM_537251.5, ASH1L, Del, C_7, PHFLLLPICMLAIYF-SIQPNTIRKSISYFARRPF, (SEQIDNO:5247); XM_005616826.1, LOC102153346, Del, C_7, PHFLPSLLHPSPQGQGLPGPQT, (SEQIDNO:5248); XM_014113005.1, FAF2, Del, C_7, PHFRRPD-SATQKFSLFRT, (SEQIDNO:5249); XM_014112760.1, LOC106558669, Del, C_7, PHGLPEEP, (SEQIDNO:5250); XM_014107872.1, VPS37B, Ins, C_7, PHGPAPPA-RILCTVHVSIPTRSSPETPAPAASTPARLHPPV, (SEQIDNO:5251); XM_014116373.1, LOC490917, Del, C_7, PHGRRTGTRAAGAPTTTTQTRA, (SEQIDNO:5252); XM_014116484.1, HOXB4, Del, C_7, PHGS-REPWGGGGL, (SEQIDNO:5253); XM_005622745.2, TRIM46, Del, C_7, PHHFLPPPCLCLPPLCQLRP, (SEQIDNO:5254); XM_005626204.2, SBF1, Ins, C_7, PHHQGQGAFPPDPVPESREERQENHWPAVRD-PEKVQPPQLGAPGPAPSRGPGG, (SEQIDNO:5255); XM_005631742.2, SHANK2, Del, C_7, PHHRQAVPSLPPR, (SEQIDNO:5256); XM_846492.4, XIRP1, Del, C_7, PHHRRVPIPQERGPQLVPSKGPLR-TRRFCREASKSSRAC, (SEQIDNO:5257); XM_014110880.1, MYO3B, Ins, C_7, PHICISRC-CLPMYGYFQQRPVHCHQWRKWLWEDRECPPDCSAFD-FLGKGQ, (SEQIDNO:5258); XM_005641785.2, PRR32, Del, C_7, PHISPQLDQG, (SEQIDNO:5259); XM_849543.1, GPR152, Del, C_7, PHKWTLQPSPSWILWLPHGQILGSSLS, (SEQIDNO:5260); NM_001110767.1, MYH9, Ins, C_7, PHLCH-HRHRLQEYDARPRGPVHFVHG, (SEQIDNO:5261); XM_543989.5, PSD, Del, C_7, PHLHLGWAQGRAL-GWLWGEQPSTPRRTWTRCP, (SEQIDNO:5263); XM_014116032.1, RGS6, Del, C_7, PHLIFCPGVLRRKYPTALGAARLVHLLQQLREKAIE-LYH, (SEQIDNO:5264); XM_014118200.1, WASF1, Del, C_7, PHLLHHLFHLPCQLLH, (SEQIDNO:5265); XM_003639958.3, ATN1, Del, C_7, PHLLPIAGS, (SEQIDNO:5266); XM_014118924.1, TEAD2, Del, C_7, PHLLTSQGTSLPKPCHPLPCPHLPHHPQPGRLGP-WALPGCSWWSSQPLWNRPMQLIL RTSTGARVARR, (SEQIDNO:5267); XM_014115267.1, ENAH, Del, C_7, PHLPLRLPLPPSLHLDFLRHPRPKTIAL, (SEQIDNO:5268); XM_005617572.2, NKD1, Ins, C_7, PHLQPHSVSLP, (SEQIDNO:5269); XM_005636883.1, KMT2D, Del, C_7, PHLRYPACPPCLR-CHACPHHLRNLPCPHHPKSPPHPLHLRLPACSHHLRT-PRLPRRLK THLLLRHRRTYS, (SEQIDNO:5270); XM_546371.5, CDH12, Del, C_7, PHMIHWQHMRMKEMDQ, (SEQIDNO:5271); XM_014117984.1, LOC102154618, Del, C_7, PHMLLQGHSNSPQTAGSAMPV, (SEQIDNO:5272); XM_005624339.1, RARA, Del, C_7, PHPAAVALA-SAPAQTEAARPPTPR, (SEQIDNO:5273); XM_540770.5, PIDD1, Ins, C_7, PHPALPGGGCQDPEW, (SEQIDNO:5274); XM_014119811.1, LOC106559806, Del, C_7, PHPAMLPISTKWIWRRCL, (SEQIDNO:5275); XM_005639705.2, IRX1, Del, C_7, PHPAPRRTPVS, (SEQIDNO:5276); XM_003638834.3, RYR1, Del, C_7, PHPAQLSPPTTSTPCWVTSCESSSTTWALTRPHG, (SEQIDNO:5277); XM_014106880.1, RBBP8NL, Del, C_7, PHPDCSPPRALGRPSRRRRWEATRRPRTTMQKSL-RATGHLQWPKSPRVPTCLRHGP QT, (SEQIDNO:5278); XM_005628972.2, GJA4, Del, C_7, PHP-GAPPQSPMPTRSSSTCPWERDPRPRRAPPTTGSPPAS-RTGPT, (SEQIDNO:5279); XM_005625442.1, PRDM12, Del, C_7, PHPGLQPKSLFWATHGQ, (SEQIDNO:5280); XM_014106943.1, RIN2, Del, C_7, PHPGPRHPL-LIVCTQALSCPGLKPRRACQKQSTITNMGT, (SEQIDNO:5281); XM_849945.3, PGLYRP1, Del, C_7, PHPGPSGRPRVCWLVVWLREN, (SEQIDNO:5282); XM_014111262.1, KIRRE1, Ins, C_7, PHPHLDQKGFKHGAQASWLPTRGCSLCPGPE, (SEQIDNO:5283); XM_005640916.2, KIRRE1, Ins, C_7, PHPHLDQKGFKHGPE, (SEQIDNO:5284); XM_005634969.2, FAM83C, Del, C_7, PHPHP-PASASAASNAH1, (SEQIDNO:5286); XM_014117368.1, TRIOBP, Ins, C_7, PHPHPRVHWAP, (SEQIDNO:5287); XM_848813.4, ACD, Ins, C_7, PHPLGLHPL, (SEQIDNO:5288); XM_005626251.1, ANTXR1, Del, C_7, PHPLHPI-ALPHPPVLPPLRFHPHRPPFPLPLTPHL-PAGRHPPPDLLPGLLS, (SEQIDNO:5289); XM_014118742.1, SCRIB, Del, C_7, PHPLSQPPAPWSL-PALESLGRSGWLLACWLPPWRGRTRWRRSASQEP-GAHWGSASS GALTT-PATRLVSRSLACSSPRCSHGAWPHVVAFELGTAFWQ, (SEQIDNO:5290); XM_541879.3, SEMA3F, Del, C_7, PHPLTRSWPSCWPSQKWASSTSTARAI-GATCPQAPGRHQGRPGLLNPRTRKSPGTAA TTRRTH, (SEQIDNO:5291); XM_541589.4, CIC, Del, C_7, PHP-PAPPQLPQAG, (SEQIDNO:5292); XM_005627115.2, DDR1, Del, C_7, PHPPGPNPPTPR-PAVGTIWSLRSRVPHFCPHLPRTASPINIPRLTL-SPCRASQGATPNIL CPRCPQGLPGMGLPEWISLD-LGSASRRSLARASLGRCTCVR, (SEQIDNO:5293); XM_014114445.1, LOC102155512, Del, C_7, PHPPGWR-GLSGAVSPLRSLGLHARASPHPPWRLRPY, (SEQIDNO:5294); XM_014112562.1, FAM193A, Del, C_7, PHPPPPMAPSALHPAFAATPTVRGTAVRT-ACMTHSRTMGMRVPTRTAALSIALAPQP PPTRR-RASTVTAATVSSSGMVGLQLHQQVEIMQR, (SEQIDNO:5295); XM_545354.5, ATXN1, Del, C_7, PHPPSRTSTCTSPALRRAPGARPLLRPSPSTSTRTRR, (SEQIDNO:5296); XM_014113237.1, LOC106558756, Del, C_7, PHPPTRAGRRPLGLCPLHPGSS-PADPSPLAVPMPNPRLCYCPALRTNGAQARGNPQT RGVGKPSRAGAGRRGPGVGGAGFLPSHL, (SEQIDNO:5297); XM_545695.2, AVPR1B, Ins, C_7, PHPQPQPQWGPRA, (SEQIDNO:5298); XM_005626284.2, FLT4, Ins, C_7, PHPREGGFLPQHLLPPQSPGPHLHCLRGAPPSQCPVA-LAAMDTLQDLHQAQPQPAA AER-PHATVPGLARGDHPGCREPHREPGHLDRVCGGEE, (SEQIDNO:5300); XM_003433968.3, RIPPLY3, Del, C_7, PHPRGRGRRCQAPYLGALPGRPSLPRAPRAPVARA-RGPAARPHLPPGGGVPAKDTA GGSGGIGNRLWQR-PAPHRGDLGS, (SEQIDNO:5301); XM_014121062.1, PHF21A, Del, C_7, PHPVILTPPKMKRQRPHSLSLHLF-SLCPCPAPPPQTVISMRIFAAFAGKVASCLCVTHV PVCIIWTA, (SEQIDNO:5303); XM_014122225.1, TYK2, Del, C_7, PHPVRTLGWSSEWYSRC, (SEQIDNO:5304); XM_005627166.1, EHMT2, Del, C_7, PHPWLRM-PLGEQTLPSPVPGCEGMGSPGAHPATLWPTP-STAQGPP, (SEQIDNO:5305); XM_005630632.1, HIPK1, Del, C_7, PHQCRRVPSAVRRN, (SEQIDNO:5307); XM_843722.4, MAP3K12, Del, C_7, PHQDGVV-VARLGTGRPAPRAAAETCLG-FARLCHPMNPGDQEARGG, (SEQIDNO:5308); XM_005621172.2, MICALL2, Ins, C_7, PHQGQLGPNVSRPSRHPRLGPISSLQDAAGP-GEVLPDSWSCPQPWPSWQGPGSCRCA F, (SEQIDNO:5309); XM_014118653.1, LOC106559635, Del, C_7, PHQMTLMCWLGAPFCSTHPHERTGRPRVLLPP-SALLA, (SEQIDNO:5310); XM_014116993.1, NUP214, Del, C-7, PHQQQLPPPFLPHSPHCPLVAS, (SEQIDNO:5312); XM_005616859.2, BCL2L12, Ins, C_7, PHREGSP-

TAEAGCLAGGRG, (SEQIDNO:5313); XM_545880.5, IL16, Ins, C_7, PHRGAAAARARA TAAGHPHLLQDQRAGSVGVPSPRTAVQSGDPPPRP, (SEQIDNO:5314); XM_014122125.1, KDM4B, Del, C_7, PHRHLSTSCPPRHLARSQR (SEQIDNO:5315); XM_005633018.1, KDM4B, Del, C_7, PHRHLSTSCPPRHLARSQRPLSTLPRGAPPGRNRRPPWS, (SEQIDNO:5316); XM_005633017.1, KDM4B, Del, C_7, PHRHLSTSCPPRHLARSQSRPLSTLPRGAPPGRNRRPPWS, (SEQIDNO:5317); XM_014111179.1, SOX13, Del, C_7, PHRLASCK, (SEQIDNO:5318); XM_845641.5, EPN1, Del, C_7, PHRPHGRHQSHSWGLMQPSLTWTRW, (SEQIDNO:5319); XM_542234.5, MAML2, Del, C_7, PHRPLLPPRRPPKQPPPQPHRPRQTITITTSSTCSAVAIMVAVVGSTGSSRHKLQPLGT RGTQP, (SEQIDNO:5320); XM_850565.3, MGAT1, Del, C_7, PHRRGMAMILAGI, (SEQIDNO:5321); XM_005626805.1, CCIN, Del, C_7, PHRRHWTVLPAV, (SEQIDNO:5322); XM_014107845.1, EP400, Del, C_7, PHRRPRQGPHSPLHKCKCRPRHPRRSRAPSWPRSRPRGPEPCSRAPPWPTSRWPGSCRRKGRCRLRRPSPLRWRLRSLQWCPCLRPWSPRQV, (SEQIDNO:5323); XM_014107852.1, EP400, Del, C_7, PHRRPRQGPHSPLHKCKCRPRHPRRSRAPSWPRSRPRGPEPCSRAPPWPTSRWPGSP GFPLRSCRRKGRCRLRRPSPLRWRLRSLQWCPCLRPWSPRQV, (SEQIDNO:5324); XM_014108566.1, HDAC7, Del, C_7, PHRWAPCSPAWTGSNRTSS, (SEQIDNO:5325); XM_014111758.1, RASGRF2, Del, C_7, PHRWLCPGRPPQ, (SEQIDNO:5326); XM_005619461.2, LOC102153808, Del, C_7, PHSALRTGQPPGEHSTARPRPLPRTAPCGSPFLALSTGC, (SEQIDNO:5327); XM_005621171.2, INTS1, Ins, C_7, PHSGPSEKSKPVPASRAPAVPEPKPRLSPQHHPEAGLLAVHALAGRPGAVQRGFAGR AACAVPV, (SEQIDNO:5330); XM_014121645.1, EFCAB12, Del, C_7, PHSQSPASKPWELGTSKGSQRMRRPGSAKG, (SEQIDNO:5332); XM_532215.5, DOPEY1, Ins, C_7, PHSRQSEIHS, (SEQIDNO:5333); XM_005623133.1, CTIF, Del, C_7, PHSRTAAKTTLWTCWARISGLPTPLIPSVVPPGTCSPKSWTSPSSTGS, (SEQIDNO:5335); XM_005633132.2, DAZAP1, Del, C_7, PHSSALATGLHHHHRISLPPQGSLLHLLLQGQHLWPSLRLRLRPPQT, (SEQIDNO:5336); XM_536901.5, BCL7C, Del, C_7, PHSSASAQMPPTP, (SEQIDNO:5337); XM_847197.3, SCAND1, Del, C_7, PHTLAAPDPARRHSASVSGSSATRTPQVRGRRSGSCGSSPASGCDPTSARRSRSWRC WCRSSCWPSCLRRRGPGGFAAAPMCASRA, (SEQIDNO:5338); XM_005636020.2, TRPV4, Del, C_7, PHTLTAPPWTT, (SEQIDNO:5339); XM_005640917.2, SUSD4, Del, C_7, PHTPAQGTRTRARGRPNPVTAARALPSCSRVRTRLPGATGAHAPAAWTRVLARWE RRRPLARASTSQT, (SEQIDNO:5340); XM_846233.4, PPFIA1, Del, C_7, PHTPHLCSRAPPLRTVGAPPHEGARTAQPGRWTDWGS, (SEQIDNO:5341); XM_534998.5, PPRC1, Del, C_7, PHTRGGEDPVAVPLDVPEDALPLLPPHLLPLLPHLRHPVLEAGPAPHPPDGEVTGGG GTVLIVHMTITKGRGCCRRSVQ, (SEQIDNO:5342); XM_014110312.1, AHRR, Del, C_7, PHTVPAWSTCMALLSRMAPATSVRRLSSPLHCPVTAKPQSPRPSSNESPWTHRHGPV TARVGCLECSPKVPWQH, (SEQIDNO:5343); XM_014122638.1, ARAP1, Ins, C_7, PHWDATPAGEPSLQGREASVTTTVITSPARA, (SEQIDNO:5344); XM_531794.5, TMEM 131, Del, C_7, PHWKVNSAEISLPRFLFQLH, (SEQIDNO:5345); XM_014117000.1, HMCN2, Ins, C_7, PHWLDCQRPASHGGCV, (SEQIDNO:5346); XM_540490.4, SIRT7, Del, C_7, PIAGGRTPSSPWPLPCVRVKKVATVGSRCAEAERTLRLGTGVRP, (SEQIDNO:5348); XM_014119957.1, MGAM, Del, C_7, PICHIWSPGIKA, (SEQIDNO:5349); XM_014116315.1, LOC102152536, Ins, C_7, PIIKARARGACLCP, (SEQIDNO:5351); XM_538150.5, IL13RA1, Del, C_7, PILSVSSSKMVTCMCNGRIHRIFIADAYLTK, (SEQIDNO:5353); XM_014115723.1, ADSSL1, Del, C_7, PILTYLHVGHIPARPWGCWPQRS, (SEQIDNO:5354); XM_014110586.1, RREB1, Ins, C_7, PIPAEAQAAVLQEETQS, (SEQIDNO:5355); XM_014116790.1, FAM222B, Del, C_7, PIPCCMEVGRCQTQMPPRM, (SEQIDNO:5356); XM_005636020.2, TRPV4, Ins, C_7, PIPLPHHRGLPEAGWRDHHALHRGPVLLYQYQRLVHEEMPRSEFSLH, (SEQIDNO:5357); XM_543571.4, LOC486445, Del, C_7, PIPPATPTGPQSPSVDSNPWMLTA, (SEQIDNO:5358); XM_014119811.1, LOC106559806, Ins, C_7, PIPPCSPSPPSGSGGGVL, (SEQIDNO:5359); XM_854308.3, PCOLCE, Del, C_7, PIRSASGQ, (SEQIDNO:5361); XM_014116993.1, NUP214, Ins, C_7, PISNNCHPPSYRIPHIVLW, (SEQIDNO:5362); XM_543989.5, PSD, Ins, C_7, PISTWGGLRAGLWGGCGASSQVLRDGPGHGAPEVLPRDRHR, (SEQIDNO:5363); XM_005630632.1, HIPK1, Ins, C_7, PISVVECLLQCEETENRALWLGCFWTEQQRQILYPQQNPPSHTRASQLLSPGSKFQHP CLRPGPPP PSSCSGAYCCNSC, (SEQIDNO:5364); XM_005624926.2, INPPSK, Del, C_7, PIWPTMTRGWSTLTGSWRCRILKNRISLTSWTMTSFSGLET, (SEQIDNO:5366); XM_014108376.1, CECR2, Del, C_7, PNLALFHR, (SEQIDNO:5367); XM_005624978.1, LRRC3C, Del, C_7, PKAATWQKKLVSGRSVAARQA, (SEQIDNO:5368); XM_014118359.1, COL11A2, Ins, C_7, PKAGRGAVGACVLHGL, (SEQIDNO:5369); XM_849386.2, TMEM119, Del, C_7, PKAPVLAVSPPRS, (SEQIDNO:5371); XM_546575.3, VMO1, Del, C_7, PKASPEMTR1, (SEQIDNO:5372); XM_014122040.1, BRD4, Del, C_7, PKCYCRRTKSHLPRPSPLCRCSSTCSSCRRCSPPHHYSLP, (SEQIDNO:5373); XM_003432681.3, KMT2B, Ins, C_7, PKDSCPETG, (SEQIDNO:5374); XM_005629518.1, EZH2, Ins, C_7, PKEEEEETPVVGGTLQKDTAEKGRL1, (SEQIDNO:5375); XM_005639643.2, CCDC80, Ins, C_7, PKEEGCAGAQGGAPRAPRAAAHQRGPREA, (SEQIDNO:5376); XM_014113940.1, VPS9D1, Del, C_7, PKEGWTAALWGLPHPWRTASRLYRAKTAPLKTSNTSWLLLRGGAGGMGGHLSPKQ QG, (SEQIDNO:5377); XM_005619042.2, ZSWIM8, Del, C_7, PKGPTTWL, (SEQIDNO:5378); XM_014109614.1, ARID3B, Ins, C_7, PKHGRQCQRQQQLSLLPEPYLVPGHPQRRAVHQLVPL, (SEQIDNO:5379); XM_014117011.1, PKN3, Del, C_7, PKHVPRLQPHPGELPSLPRPVMSHPRRAPWEKR, (SEQIDNO:5381); XM_005640903.2, IGSF9, Del, C_7, PKKSQVLSELSLGPQPSTRPGPMTAAAAVPAGCPSPSALQTSALWGPLPQPHLVLCR VQDPCSST, (SEQIDNO:5382); XM_860093.4, EWSR1, Del, C_7, PKLDPTARLQVNIANRAAATGSRVHSDRTTPVAWVFMGRSLEDFPDQERTGA, (SEQIDNO:5383); XM_005625887.2, CSNK1E, Ins, C_7, PKLLACGLDSGAPVL, (SEQIDNO:5384); XM_014110888.1, SPEG, Del, C_7, PKLPHESTGACSLPSKQSPPHPVPRPPRVSPSLPSLTLGPQPQPPPLRGRNQRPPLLPCT W, (SEQIDNO:5385); XM_543052.4, MOCS3, Del, C_7, PKLRGHALVYSSR, (SEQIDNO:5386);

XM_005632193.1, CIDEC, Del, C_7, PKNRVLGTNCPSPISLPRRLMWLK, (SEQIDNO:5388); XM_005616113.2, SSC5D, Del, C_7, PKPHTQPLTLQ, (SEQIDNO:5389); XM_548160.4, GPR179, Ins, C_7, PKPQLTHLHLPLGECRTASQERKCGSGSSLR-PRAKQPVPCPSSGQALESPLCCSRKKG HWREWGGHRGWTCPRGS, (SEQIDNO:5390); XM_844620.4, C5H17orf74, Del, C_7, PKPSPPSCR-SAGPQAAMQATRCMTAWS, (SEQIDNO:5391); XM_547871.5, DCAF5, Ins, C_7, PKQARQYLHWRRQL, (SEQIDNO:5393); XM_005633023.2, TICAM1, Del, C_7, PKRGRWAPTTPWNALKCWQPPALCPCPLEMLALSR-TRPHSHF1, (SEQIDNO:5395); XM_534785.5, ZNF385A, Ins, C_7, PKRGWCSPSSFHGEWTGSSP-GIPRETAWLPISSQHSGDWSRYNQG, (SEQIDNO: 5396); XM_014117075.1, DENND1A, Ins, C_7, PKSGAVPGAPPQCCPSSTHRTAATTQPGPRGCK-HRQRCPAGPPGPSSHSVVRQCSSP RPFSPKCSH-LIHPPV, (SEQIDNO:5398); XM_531943.5, ADAMTSL1, Del, C_7, PKSPRSWKTSGHCFQPLDRTFLQC, (SEQIDNO:5399); XM_543487.4, PLA2G3, Ins, C_7, PKSQP-PEPSPQQASTEAASSEAATTTERV, (SEQIDNO:5400); XM_005640788.1, NUAK2, Del, C_7, PKSRGCP-SIAKASSNTMVLSPFPSFKPGPSLLDSLLGI, (SEQIDNO:5402); XM_005636451.2, OSBP2, Del, C_7, PKSRGVSAFLTNPTTALISGAS, (SEQIDNO:5403); XM_544457.2, RAB42, Ins, C_7, PKTAAPRSLPV1, (SEQIDNO:5404); XM_014110333.1, SLC12A7, Del, C_7, PKTGRAMRTTWSSWRS, (SEQIDNO:5405); XM_548202.5, SPATA20, Ins, C_7, PKTKGGAQRPR-SPPWFRKGQLLPGQGPQCDSQQFST-HAYWREGKPDQLLPIRTPEGP QPPDQ, (SEQIDNO:5406); NM_001048116.1, ARSJ, Del, C_7, PKTPEVTLGSMEESGDHGIRRNTRKRSQA-KIRLRKSRRKVRQRRNSRKQVRFQIAVQ VFA1TVD, (SEQIDNO:5408); XM_005636789.2, EIF4B, Ins, C_7, PKTQTESKASEYS, (SEQIDNO:5409); XM_005625887.2, CSNK1E, Del, C_7, PKTTGLWSGLRGPSS, (SEQIDNO:5410); NM_001204441.1, P2RY11, Ins, C_7, PKTWSPSP1, (SEQIDNO:5411); XM_014106637.1, DLEC1, Ins, C_7, PKY-HYPPSFLHCQEQ, (SEQIDNO:5414); XM_003432562.3, DBP, Del, C_7, PLAGERCLGCGAFCRGPANPKSQPAVS, (SEQIDNO:5415); XM_545660.5, INHA, Del, C_7, PLAGPCC1WPPPPSLC, (SEQIDNO:5416); XM_852173.4, LOC485469, Del, C_7, PLAGTCPQRRKPMKMC, (SEQIDNO:5417); XM_846593.4, KLHL38, Del, C_7, PLAGWTRSCQMGCSSKTMTSPLNC, (SEQIDNO:5418); XM_005641878.2, FGF13, Del, C_7, PLAHRNTL-CYGKIPSNLRN, (SEQIDNO:5419); XM_005623276.2, NFATC4, Del, C_7, PLALTWTSHHPGPLTPPIPMKTLL-MKLLTCQKASAMAHPLCTPRRGPHRPTDLACGC SLRPGVPQ, (SEQIDNO:5420); XM_548302.6, CORO6, Del, C_7, PLAPAAASRPATPPCRSSTPWRRCWRRSRP-CASRCRPRSSASRPWRTCCASWWTAPT, (SEQIDNO:5421); XM_540000.4, LOC482885, Del, C_7, PLAPPLP-PRLPLSPLPPPVPPPRPRPLPPLPLRLLAPLPPSQPASLPA-PRPPPPARQRPGR STCPGSSSATS, (SEQIDNO:5423); XM_014115355.1, TRIM46, Ins, C_7, PLATCLALHHRV-PAYRCACPARPRPLAAAGRGEGHQCPAREP, (SEQIDNO:5425); XM_547396.5, SERTAD4, Del, C_7, PLCLYRVVPTRWILM, (SEQIDNO:5426); XM_535546.6, SIN3A, Del, C_7, PLCMKQCLRPCSQL-REFSTL, (SEQIDNO:5427); XM_014121319.1, CDC42BPG, Del, C_7, PLCVLCCCWQRARPSGSAGCRC-WASCRGCCWTHGQGPVLCTP, (SEQIDNO:5429); XM_005619930.2, MINK1, Del, C_7, PLCVTCTPCEPS-SSSPGPSQREPPSLPGLRSSLTSLTRVLSRPT, (SEQIDNO:5430); XM_541537.5, DHX34, Del, C_7, PLEFG-NASSPPTLLRPLSPLMGSAL, (SEQIDNO:5431); XM_005637886.1, NSMCE4A, Del, C_7, PLESGPRPGR-SPPPPPPRRGPGDPGLAALLQVITPARTCSRVM-STFPQTLFFVCLVFCF FFFA, (SEQIDNO:5432); XM_533751.4, LMCD1, Del, C_7, PLESPRNWVC-STWSSSQKRSSQ, (SEQIDNO:5433); XM_014117067.1, RABEPK, Del, C_7, PLETAPVLGLATAVHIYPQLVM-PREGRSSLLGEQIRTGASQMCTPWIWEHTGGT, (SEQIDNO:5434); XM_544038.5, SLC18A2, Del, C_7, PLGACSMSLWGRQLRSWCWLPWCSWMELF-SSVCSSHPGSSQRARRGHR, (SEQIDNO:5435); XM_014116429.1, SHISA7, Del, C_7, PLGAPRCPQSLP-PAPAWPRPTPTCC, (SEQIDNO:5436); XM_014122069.1, KIAA1462, Del, C_7, PLGEQTPTA, (SEQIDNO:5437); XM_014108793.1, SORBS1, Del, C_7, PLGLLSLKR-TALHGSAPPPVPPRTPST, (SEQIDNO:5438); XM_538253.4, 42438, Del, C_7, PLGPPAAPRLP-GACGRSCLSAVVTQSCTSLDSCGHQMPVPVPI-LAERLS, (SEQIDNO:5439); XM_014107055.1, LOC106557703, Ins, C_7, PLGPR-RHRQPIPRGCQTSSTLRGRQPPDGDLRTPARDWQR-PRWGRRRSRQHGQPPN RA, (SEQIDNO:5440); XM_003431483.3, KIAA1644, Del, C_7, PLGQLAPGMGWWQVAARNI, (SEQIDNO:5443); XM_014117646.1, LOC106559457, Del, C_7, PLGR-GRTSCHFTGHFLVLATHHLRAALPRP-TALPLYLKSQPAHRPRFQAF, (SEQIDNO:5444); XM_014121887.1, MAP4, Del, C_7, PLGR-SQPSPRQRPKLAPPLQPVASVATPPWQGVVTKGR-PRPWTARSRRQAS, (SEQIDNO:5445); XM_014121877.1, MAP4, Del, C_7, PLGR-SQPSPRQRPKLAPPLQPVASVATPPWQGVVTKGR-PRPWTARSRRQI, (SEQIDNO:5446); XM_005625905.2, ELFN2, Del, C_7, PLGRWSGPASSRPRTRRAPTTRS-SAS, (SEQIDNO:5447); XM_005621773.2, RHBDF1, Del, C_7, PLHCMWGRASWACRRS, (SEQIDNO:5448); XM_005628310.2, OPLAH, Ins, C_7, PLHHTAAGGC-CLSVFQTRPGGCLPGGCGD, (SEQIDNO:5449); XM_540889.5, RCOR2, Del, C_7, PLHLPPPCPSRPHC, (SEQIDNO:5452); XM_541489.6, MED25, Del, C_7, PLHNLGPHPWRARWPQVG, (SEQIDNO:5453); XM_544931.6, ADARB1, Ins, C_7, PLHPQQASAQRHQQRGSAAAGEGTQLQRQLDG-GRRGH, (SEQIDNO:5454); XM_005617918.2, KIAA1522, Del, C_7, PLHRGAVG-GAPPVGAALLRPQIQSAFGAVGSCLAGVCPYVS, (SEQIDNO:5455); XM_005638951.2, LOC102156742, Del, C_7, PLHSAPSPDMPRTQALLLAAPSLGD-SPASAASASGGPASPGAACSLHPPPSPSAKPAR PPSSSRIHRLDRPT, (SEQIDNO:5456); XM_540737.4, PTPRJ, Del, C_7, PLIQFLTFE, (SEQIDNO:5458); XM_014112281.1, GCNT4, Del, C_7, PLITLRYS-LAVLILF, (SEQIDNO:5459); XM_532616.4, PARP2, Del, C_7, PLKLPSQVTCLGKESTLLTCLLRAPITASLLA, (SEQIDNO:5460); XM_855886.5, NOVA1, Del, C_7, PLKPAAPRGPIRAKTASIF, (SEQIDNO:5461); XM_533608.5, MYBPC2, Del, C_7, PLKPLLHSPPKKPHLRTSPPLPRSPLGFS, (SEQIDNO:5462); XM_549021.5, FGD1, Del, C_7, PLKPPASVLHH, (SEQIDNO:5463); XM_014121827.1, PTPRS, Del, C_7, PLKTLNVSARAPRPFW, (SEQIDNO:5464); XM_005620616.2, HSF4, Del, C_7, PLKVWSLQGPWMCWAPAIKGENGP, (SEQIDNO:

5465); XM_014113853.1, SKI, Del, C_7, PLLCPP-PLRWQPLQTPRVVGWRQSWSTCDRPWRAAWT-PRKPKRSSCTRW, (SEQIDNO:5466); XM_014110188.1, AHDC1, Ins, C_7, PLLDTQRARVGTPGTRHAEHLPL-PAPGAGLPTARWESRRFWWPGRGPRSQGSPMLL Q, (SEQIDNO:5467); XM_005627280.1, RAB44, Del, C_7, PLLERGHLPWSLPWRGLSLGMEQSLRST-GAAPPPQWS, (SEQIDNO:5468); XM_014118198.1, ZNF581, Del, C_7, PLLGQAGLQNLDLPHPQDCPRLP-PLRSPATTCSLTPRVSPTRCWWTRSLRGSPGQTG LQPRKSVTAAPCAPGSSSTCPTCSDTASPTRR, (SEQIDNO:5469); XM_014110912.1, BARD1, Del, C_7, PLLGWERSLGITLRAKFFGL, (SEQIDNO:5470); XM_005627027.2, MAPK14, Del, C_7, PLLIS-LTGCQAMRQETTFSL, (SEQIDNO:5471); XM_014116271.1, UBE2O, Ins, C_7, PLLLPLPVQWP-PEPQPV, (SEQIDNO:5472); XM_014122593.1, MCM10, Del, C_7, PLLLPVRGKLIKSCKMN, (SEQIDNO:5473); NM_001313776.1, CKM, Ins, C_7, PLLPGRAPGSGETLHRSPQQPDRRVQGEILP-SEEHDRAGAAAAHRRSLPVRQTRVPT AAGLRHGPR-LARRPRHLAQ, (SEQIDNO:5474); XM_005638006.2, TOX, Del, C_7, PLLPSRSAHLFTSISTCSST-SHSPCSSPLGTSSPCRSSLPYTHRPCSRDLLFNPTIRL, (SEQIDNO:5475); XM_005626753.2, PIGO, Del, C_7, PLLRLTWIMWFLKSTDICRRSSGAV, (SEQIDNO:5476); XM_014113971.1, RLTPR, Del, C-7, PLLVPAPA-HEEPAPPQTAWASQRTLAWAPGMKMAN, (SEQIDNO:5477); XM_541071.3, SERPINB10, Del, C_7, PLNLMQTIHSSSSSGTTKLLAFSFMGDSAPP, (SEQIDNO:5479); XM_005620862.2, B3GNT9, Del, C_7, PLPANAAFGPGPVPGCPWDPAPSPGGPGVR-GRAAPKGQACRTPRSDVGARAPAART, (SEQIDNO:5481); XM_532077.5, ABHD16A, Del, C_7, PLPAP-GIRTINPVPWRSMLTASWHWLQSSGPSLITPLPSPSS-TYTGKVT, (SEQIDNO:5482); XM_014116580.1, PNMAL2, Del, C_7, PLPAPGRPPRLTAGLPAPVSPR-LAGGGATRG, (SEQIDNO:5483); XM_003639249.3, ACE, Del, C_7, PLPATTLTGGIFEPSIR-GSVLQLPEMKPTLTPELSFTSQM, (SEQIDNO:5484); XM_539499.4, NOD1, Del, C_7, PLPCAESARPCGHTCL-PACGPT, (SEQIDNO:5485); XM_014114432.1, SLX4, Del, C_7, PLPEGAALARESPERGPLGPACRRAAGQAF, (SEQIDNO:5486); XM_539044.5, BACH2, Del, C_7, PLPGPPAWRDPGACPPPPV, (SEQIDNO:5487); XM_014110676.1, CSRNP3, Ins, C_7, PLPGRQPLGHRVLLVGRRRRRALHQPVPRPQAQP-PAGGIPLVLEGAPPGRVRVPVAR GRPP-PRAPRGEAFESGRQEQTARRVHHVPRGGDGPRV, (SEQIDNO:5488); XM_014119889.1, BRAF, Del, C_7, PLPHCLAHSLM, (SEQIDNO:5489); XM_014115410.1, CRTC2, Ins, C_7, PLPHIDPWSLPPPPPRAPQPPE-FARGPS, (SEQIDNO:5490); XM_014114925.1, ARL8A, Del, C_7, PLPILTLPCSQDSSMRT, (SEQIDNO:5491); XM_014112423.1, KIF7, Del, C_7, PLPLSPPPPPPA WAPSARATGPAPTPPTASCASCRPSPGCPAPPSAK-CATGCAPWRASAAP, (SEQIDNO:5492); XM_005635886.1, SOX7, Del, C_7, PLPNTPALMPWIS, (SEQIDNO:5493); XM_005627317.2, FOXP4, Ins, C_7, PLPPHPAQWTAHCAHTSERQLLP, (SEQIDNO:5495); XM_005622192.2, ELF3, Del, C_7, PLPPPLEPMTIVS, (SEQIDNO:5496); NM_001284456.1, CX3CL1, Del, C_7, PLPPPPPFHTQPQPRTGLTPKADLCGSRETIPRQRIL, (SEQIDNO:5497); XM_846233.4, PPFIA1, Del, C_7, PLPPQDRSA, (SEQIDNO:5498); XM_005620011.2, VAMP2, Del, C_7, PLPPRLGREAPRRPLQT-SPVTGDCSRPRPRWMRWWTS, (SEQIDNO:5499); XM_005631472.2, RE1A, Del, C_7, PLPPRPPKPGKGR, (SEQIDNO:5500); XM_005630688.2, NOTCH2, Del, C_7, PLPQPMLSMHCPSLTCMKCSRWLMVPAL-CFPQLASCCPTTTLLPQATAVQGAWVGS ILSLFRQIG, (SEQIDNO:5501); XM_005618689.2, GAK, Del, C_7, PLPRAAAPGSRRVGPRPRAPRGPPRPSRPPRPVR-SQGLTMLPT, (SEQIDNO:5502); XM_005635865.2, INPP5D, Del, C_7, PLPRRSRPGFSPRGRERRGMILLIT-SPMTST, (SEQIDNO:5503); XM_536182.5, AKAP13, Del, C_7, PLPSAVKVHRLMQPPLAL, (SEQIDNO:5504); XM_014108967.1, PDZD7, Del, C_7, PLP-SHPLSLPGPQGLTGC, (SEQIDNO:5505); XM_545710.3, USH2A, Del, C_7, PLPSPHSHHTPSMCPGRSPRRM, (SEQIDNO:5506); XM_014109374.1, PYGO1, Del, C_7, PLPTLRGNKSTAYFPWV, (SEQIDNO:5507); XM_856804.4, PHF21A, Del, C_7, PLPTPPPLRRPTPPP-PRAAQRTVPRGTRLN, (SEQIDNO:5508); XM_843373.4, AGAP1, Del, C_7, PLPTRPHLSGSSP-SAAPTFSPLGKGVTQTKRRKAWKAERTASGA VEP-SQLNRACC, (SEQIDNO:5509); XM_536288.4, PJA2, Del, C_7, PLPVTARRMPP, (SEQIDNO:5510); XM_014120337.1, BIRC6, Del, C_7, PLQCSVTTDCP, (SEQIDNO:5511); XM_536455.5, CYFIP2, Ins, C_7, PLQDHLQTPGLPGHRSGHGGTAEDCQEL-APRNHSPVRENTDRGDAQDMPLTPT, (SEQIDNO:5512); XM_014116490.1, GAS2L2, Del, C_7, PLQEAAF-QVLQVEVL, (SEQIDNO:5513); XM_005623751.2, BTBD7, Del, C_7, PLQKPCLQIWTLL-WPSIHPCPHHHLHTTPQPPQSITNSKQAGNKDL-PASTLHAHSLIPV IIHCFT-PEQPLKLVPLQSTCQVLKQQHLIAPTPQD, (SEQIDNO:5514); XM_014116630.1, GSK3A, Ins, C_7, PLQLQSWRTLHPAISQRHSHPSSLEVPSGHCLPHSILT-SFK, (SEQIDNO:5515); XM_014113233.1, DNAH9, Del, C_7, PLQLSATSRPR, (SEQIDNO:5516); XM_005634662.2, EDN3, Del, C_7, PLQPDLRGTSRSLWP, (SEQIDNO:5517); XM_014107411.1, WASF3, Del, C_7, PLQPRQSARRRHSHP, (SEQIDNO:5518); XM_005642194.1, AEBP1, Del, C_7, PLQWTITSGLPDPRNPTRTWRQMKRRRS, (SEQIDNO:5519); XM_014118769.1, WFS1, Del, C_7, PLRAP-LAHSLHHRSPRPARGSMPLPRWNRTRG-GRPVLRDQTLPMRLPPLQPGPQVLG ARKGRTEQGP, (SEQIDNO:5520); XM_014118768.1, WFS1, Del, C_7, PLRAPLAHSLHHRSPRPARGSMPLPRWNRTRG-GRPVLRDQTLPMRLPPLQPGPQVLG ARKGRTE-QVRGWGCKLTILSATSAA, (SEQIDNO:5521); XM_014113911.1, RERE, Del, C_7, PLRAPTLLLLSTRA, (SEQIDNO:5522); XM_014115765.1, EFS, Ins, C_7, PLRCPFQPETGISRAQSVRSARGTASRWGMWRH, (SEQIDNO:5524); XM_005616873.2, CD3EAP, Del, C_7, PLRCRNPW, (SEQIDNO:5525); XM_014117108.1, LOC106559343, Del, C-7, PLRPGRRPPS, (SEQIDNO:5526); XM_014110586.1, RREB1, Del, C_7, PLRPPR-PARSSPPRRCSPGTGRSRQPVTGR-SARSSPLGTGTRTPTAPRTTRSATRAWTS TSPAG, (SEQIDNO:5527); XM_014114743.1, AXIN1, Ins, C_7, PLRRRGLRGTAGRTRGEPREHPG, (SEQIDNO:5528); XM_545232.5, EPHB3, Ins, C_7, PLRSCEHHHQPGCSI, (SEQIDNO:5529); XM_014113910.1, RERE, Del, C_7, PLRSLWTLPHSCSNLSKRKTMGSVGSIA, (SEQIDNO:5530); XM_847374.4, HOXD1, Ins, C_7, PLR-SQYHQVWKEPGEPFSGPGALM, (SEQIDNO:5531); XM_546778.4, ANKRD11, Del, C_7, PLR-TEMNCWPHPWREPFPLIWAFPWMPQRTSR-PLPPSSPQSPATWSHWMRAPSARS

SRRNPSSGHIRRPQSRASPAV, (SEQIDNO:5532); XM_014109357.1, NUTM1, Del, C_7, PLRVLPVNS, (SEQIDNO:5533); XM_005627265.2, SRPK1, Del, C_7, PLRWRRASPPASGLPVRAHQPRRPSAPAALAPCSPPGRPASWGRCRARRSATRADGPPAP, (SEQIDNO:5534); XM_014111168.1, SPEN, Del, C_7, PLRWSLRSLF, (SEQIDNO:5535); XM_005617949.2, ATP13A2, Del, C_7, PLSGASLPPSSSCRWNPLQP, (SEQIDNO:5536); XM_014107094.1, HSPG2, Del, C_7, PLSGSNHRPPTWRKGRLWI, (SEQIDNO:5537); XM_005633593.2, COR52H9, Del, C_7, PLSILLSME, (SEQIDNO:5538); XM_540880.5, MAP4K2, Del, C_7, PLSLQRKTLYPALWEPHLHLSQALPTPLCSPLPGLP, (SEQIDNO:5540); XM_014121529.1, THSD7B, Del, C_7, PLSMVGPSVPT, (SEQIDNO:5541); XM_003639867.3, ZFP64, Del, C_7, PLSPRGARARRAR, (SEQIDNO:5542); XM_852921.4, BRD3, Del, C_7, PLSPRRLSLLPPLCQPLLQTSHRSLFPRPPPHLLPRRPSSLWSLPHRLSSRKRV, (SEQIDNO:5543); NM_001002933.1, HCRTR2, Ins, C_7, PLSQMCSGAE, (SEQIDNO:5544); XM_844466.4, MAZ, Del, C_7, PLSRETPPSHSPPV, (SEQIDNO:5545); NM_001097547.2, PADI6, Del, C_7, PLSRWKGKSTP, (SEQIDNO:5546); XM_014118288.1, LENG8, Del, C_7, PLSSCQQPSPLSPPTPRMGLML, (SEQIDNO:5547); XM_014118308.1, PRRC2A, Del, C_7, PLSSPPPLQVWLQLPPW, (SEQIDNO:5548); XM_014118001.1, PHF19, Del, C_7, PLSVSTVCCLTSSSSRKGEFIEEKDQSFCWKMLFPVATLPPPGAPTTTWPASLTSRWM KFRA, (SEQIDNO:5549); XM_005630709.2, BCL9, Del, C_7, PLSWGLLLLRLFTSSLHHFLPRHLDGPPLQNLPFRVPGSLQTIKHPSPWPPQPCWAV, (SEQIDNO:5550); XM_014109795.1, EVA1C, Del, C_7, PLTACLTQLCKYYPGGAMGSRDAKSRSTITISGAPVCQE, (SEQIDNO:5551); XM_005622656.2, CAPN2, Del, C_7, PLTCSGSSRRLCRKAPSSAAP, (SEQIDNO:5553); XM_005623558.2, PLEKHH1, Del, C_7, PLTHLPPTSYGNWTDSSSLLLSHVLPEGQRCC, (SEQIDNO:5554); XM_003431800.2, ZNF16, Del, C_7, PLTISSQIGTPGLRARNFFRRKKFLRIWNPRKKYQKTIPVIFPRCLSLENSVMMY, (SEQIDNO:5555); XM_014115410.1, CRTC2, Del, C_7, PLTPHRPLEPPPATAACPSAP, (SEQIDNO:5556); XM_005626204.2, SBF1, Del, C_7, PLTQASCGPSAQPSTSSGIKRSSRASGQTPCSSGSWCPSRCLRPRPRIHIPPTPTPWTM QISILSSLRPVAPF, (SEQIDNO:5557); XM_849952.3, INTS5, Del, C_7, PLTSVHPHPPMSLLGDLV, (SEQIDNO:5559); XM_545662.6, SLC4A3, Del, C_7, PLTWPVSAVVPHQVQGCHGASSAPRAPGRGSPESLERRAGPGARRPATTCGSGCAP AVPWAAQVARSSRCPPTRRRPRCWAPRTWTT, (SEQIDNO:5560); XM_005632733.2, HAUS8, Del, C_7, PLTWTSRPSMTKVCLERLRN, (SEQIDNO:5561); NM_001002933.1, HCRTR2, Del, C_7, PLVATGHLLRS, (SEQIDNO:5562); XM_532130.5, DNAH8, Del, C_7, PLVLKILPFRVWIQEMRLFPVQERLLLLQTKRVSALQQRLPQL, (SEQIDNO:5563); XM_014113364.1, ARHGEF12, Del, C_7, PLVQTHKARSWSTFVRSRLT, (SEQIDNO:5564); XM_014107649.1, LOC106557788, Del, C_7, PLWGTAGSQPQEPRPPGRGGGAPLLGPPACTQNPGC, (SEQIDNO:5565); XM_531841.5, B3GNT2, Del, C_7, PLWPTGTENKKS, (SEQIDNO:5566); XM_545182.4, ICE1, Del, C_7, PLWYPYHP, (SEQIDNO:5567); XM_014115375.1, EFNA4, Del, C_7, PLYLCGSFHCTLSCGAKDMLSPGPQLSGLS, (SEQIDNO:5568); XM_014117368.1, TRIOBP, Ins, C_7, PLYTSSCVHWSSRCSPGFFTPPPHPV, (SEQIDNO:5569); XM_014114935.1, PPFIA4, Del, C_7, PMAPMLTPTSSS, (SEQIDNO:5570); XM_547389.5, PLXNA2, Del, C_7, PMEGSSTRWSLCSKTEARSSGTWPSPLISATCTSCLRDRSPGSPWNPANSTRPVGNV, (SEQIDNO:5571); XM_547651.5, THOC1, Del, C_7, PMEKDFQRW, (SEQIDNO:5572); XM_014122486.1, TENM4, Del, C_7, PJMEPCTGQT, (SEQIDNO:5573); XM_014113768.1, ACOTL1, Del, C_7, PMPITKAIPLGARSWPGWRTWPPLQPAGCAVPTLR, (SEQIDNO:5574); XM_005639382.2, COL8A1, Del, C_7, PMPMGLRKARTEGQPTRCLPSQLS, (SEQIDNO:5575); NM_001007126.2, DIO1, Ins, C_7, PMPRGGGHDEEPKQPVLRGPTREALRAPGGQDPLQG, (SEQIDNO:5576); XM_534923.5, FKBP4, Del, C_7, PMPRLCLRWSCSSSGERT, (SEQIDNO:5577); XM_005628976.2, GJB4, Del, C_7, PMPSPRESPPRTGTLSS, (SEQIDNO:5579); XM_005634916.2, MYLK2, Del, C_7, PMQRKNPGPHNQRKSLTHPPCRKMPKLLP, (SEQIDNO:5580); XM_014121104.1, CNTF, Del, C_7, PMRLMGYLSLEMVASLRRSCGA, (SEQIDNO:5581); XM_014119548.1, MYPOP, Del, C_7, PMRQAAGRRRRGAPWPRRRRARRRRPPGCASRASRSRRTRS, (SEQIDNO:5582); XM_014119121.1, NTN5, Ins, C_7, PMSLPPPHHGPGV, (SEQIDNO:5583); XM_005618685.2, GAK, Del, C_7, PMTPGTLCSTTSSAPR, (SEQIDNO:5585); XM_014107013.1, PEF1, Del, C_7, PMVEDSMA VGYPQVVAMEGVLPPEGLMDHQLVGDPMGGSPLELQEDYMVVRPRGAPMVSHLQI PTVPSILGLMDRDLLQVSQWTPITVATSPSRS, (SEQIDNO:5586); XM_003639958.3, ATN1, Ins, C_7, PNEVSIFVLW, (SEQIDNO:5587); XM_846736.4, PITPNM1, Ins, C_7, PNHLLWGAQAGKHSLLPTCRHF, (SEQIDNO:5590); XM_005624843.2, KSR1, Ins, C_7, PNHTPAAKAHQAEASADTTPAQPQGLSAAAQLPHTHPEQVP, (SEQIDNO:5591); XM_014108723.1, FAM186B, Del, C_7, PNLHPTLSH, (SEQIDNO:5592); XM_846083.4, SUFU, Ins, C_7, PNMASRANAGLGQIRVPVREHLLQRGPRVLA, (SEQIDNO:5593); XM_014119360.1, CCDC9, Del, C_7, PNMEAGQAWAGQPTAGRTVAGSSLEEELGAVAGEAGAEGPLIFLELEIPQWLTANL RSGRSGGGRTSRR, (SEQIDNO:5594); XM_546088.5, DISC1, Ins, C_7, PNPCWLSGCLYVKL, (SEQIDNO:5595); XM_005616581.2, DYRK1B, Del, C_7, PNPDALVVPHHQPHHHPRS, (SEQIDNO:5596); XM_005622972.2, ADCK3, Ins, C_7, PNPPSGSCRETIPSYADRPQLVQLFL, (SEQIDNO:5597); XM_014116624.1, HOXB3, Del, C_7, PNPPSRPPRTWRAITSARRARCSPWATPPRRPRARSSTVAA, (SEQIDNO:5598); XM_014114048.1, ZFHX3, Del, C_7, PNPSSSSSHRCSRRRPQLSHHPHHSSHRNSSNSNARTKTARR, (SEQIDNO:5599); XM_548149.4, STAC2, Ins, C_7, PNPVAPSLPTTGIYRWGPPSPGPLPLPHPTAPGTAQTGQTAQLPGTRLQESQPL, (SEQIDNO:5600); XM_014118241.1, NOTCH4, Del, C_7, PNPVPMEAPA, (SEQIDNO:5601); XM_014111977.1, IGSF1, Ins, C_7, PNSGPETANPVQRMAGRHGVRSV, (SEQIDNO:5602); XM_014106932.1, LOC106557687, Ins, C_7, PNSGRRTEAWRAGRGPGEPVGPASLLRAAGPSTWTAPSTGPGPAAAGAAGASKRG QVPGPAPMSQRGRRRSGVGSAGQRRQTQGRRR, (SEQIDNO:5603); XM_014116196.1, HGS, Del, C_7, PNSHPLWPSRRLRRALLHRAARPSSSRLT, (SEQIDNO:

5604); XM_005626284.2, FLT4, Ins, C_7, PNSKHHGGDTHH, (SEQIDNO:5605); XM_014110888.1, SPEG, Ins, C_7, PNSPTKAQGPAACPASRAHPTQCPGHPE, (SEQIDNO:5606); XM_014121455.1, PCDH10, Del, C_7, PNSSAPALPYSPSECWTPTTTCPPSTNPSTLCPCPRTRHPARS, (SEQIDNO:5608); XM_003638913.2, PCDH1, Del, C_7, PNTPASSYLTAASPSPPPVRPKSCRTHPSTVTMTVAWRSLRRHPASHPRDPDSVRWL CLRITMNAPPLMAA, (SEQIDNO:5609); XM_003434578.3, RNF214, Ins, C_7, PNTRDSSFQTGVGDKAEWSSDDEKECSGPI, (SEQIDNO:5610); XM_848227.4, C1S, Del, C_7, PNTSSMKI, (SEQIDNO:5611); XM_860093.4, EWSR1, Ins, C_7, PNWILQPGSKSI, (SEQIDNO:5613); XM_003435655.3, NKRF, Ins, C_7, PPAAAVAAPPAAPARASAGAVAL, (SEQIDNO:5614); XM_014122607.1, C21H11orf16, Del, C_7, PPAANCCARAASAVAPWLDLPGGL, (SEQIDNO:5615); XM_014113201.1, MLLT4, Ins, C_7, PPAAPGLRRHLSLHLIPAPlGPSQQYCSQSRPAPTPSKKTRLLPAQPLERTKLLPGICR DSCWHPRCLSGPERKTV, (SEQIDNO:5616); XM_005626257.1, LOC102155231, Ins, C_7, PPAAPRGSGHLWGWIPPPPRPGHCCYRGSDPSSSREYRPHCRTGWSALQP, (SEQIDNO:5617); XM_014115096.1, PROX1, Ins, C_7, PPAATTSPCTSRLSLPPRASPRPPSATPSPFP, (SEQIDNO:5618); XM_005633132.2, DAZAP1, Del, C_7, PPAAVALDEVRTTTCKDSTRTDA, (SEQIDNO:5619); XM_014122263.1, SHC2, Del, C_7, PPAGRPSPPRRSSCGRNPGTNIAR, (SEQIDNO:5620); XM_539768.4, FHDC1, Del, C_7, PPAGTASPGTGPPRGRMRRPPRGARSEKRPRAPPRPALPGAASRRPPRPCAP, (SEQIDNO:5621); XM_014114721.1, CACNA1H, Del, C_7, PPAPGLRPRRAQTPLASWLYARCPCPGCCPCPTTATCSGPWRPPRPHTPAHCGKWTQ RRAQAQPPPAR, (SEQIDNO:5623); XM_014114724.1, CACNAIH, Del, C_7, PPAPGLRPRRAQTPLASWLYARCPCPGCCPCPTTATCSGPWRPPRPHTPAHCGKWTQ RRAQAQPPPVQAR, (SEQIDNO:5624); XM_014121756.1, LOC106560089, Del, C_7, PPAPHPGVVVPCYSSRCRQGTFPGSLAPGLRPGEPAGQGVTPPRVEGASFPEVTGAG GCRLVQATAHFP, (SEQIDNO:5625); XM_003434697.2, CMTM3, Del, C_7, PPAPRGPGSAPSCPRAPSCARAKAASCWPSRASRSSPLSAMWHPRHPPSWQRLCWSS SWPSTSYSLMPCS, (SEQIDNO:5626); XM_541489.6, MED25, Ins, C_7, PPAPTTCPVLAHTASPESSAARSDAAERGSPGPGSPAGPAAQRHGGRHPHGSHL, (SEQIDNO:5627); XM_853531.4, ARPP21, Del, C_7, PPASSPCEGQ, (SEQIDNO:5629); XM_540140.5, GALNT14, Del, C_7, PPASSSPSTTRPAPPCSEPSAAY, (SEQIDNO:5630); XM_005635170.2, CEBPB, Del, C_7, PPASWAAASATT SAPSTSARTWSRWARRRPRRRPQPRTPSRRPRPRPPPRPPPPGSTTTS SPTSSPTTTEARTARRRPSTAT, (SEQIDNO:5631); XM_547146.4, NMRAL1, Ins, C_7, PPAVDSAARSQEAGGGRGARFSPPASPTRAAAGGGGRAGVGVPSASRG, (SEQIDNO:5632); XM_014109869.1, COL18A1, Del, C_7, PPCCLEPHSQLSPGAGALGLLPPRTLWGLGLLITPPR, (SEQIDNO:5633); XM_014116236.1, FAAP100, Del, C_7, PPCCPSRTASACP, (SEQIDNO:5634); XM_014115267.1, ENAH, Ins, C_7, PPCIWIFCGIRVRRQSPFDWTCGCHRRSETEESVPDGGCLFPRRRCEPSLI, (SEQIDNO:5635); XM_848542.4, LURAPI1, Del, C_7, PPCRPPPRPLQPPAPHVAAPAAPWRGWKPSCTSSGRRWLTSEPQMSGSCASCLLSMR ALSPSSG, (SEQIDNO:5636); XM_014117863.1, PAX5, Del, C_7, PPDRAATQHRR, (SEQIDNO:5638); NM_001003008.1, RHPN2, Del, C_7, PPDRWGSCLPGMTPSPGSR, (SEQIDNO:5639); XM_005634296.2, ZBTB47, Del, C_7, PPFILPIPCQGPGPATLKAWSLRPWSGPASPAPCGRGRPEEATSCWLRRRQTHRRPSS RWWRTWRCTSPA, (SEQIDNO:5640); XM_853188.4, RARG, Ins, C_7, PPGAGRRRGRRGNRLRVRGVPSTQLLSKPGRDVRLHGSVRPGPAPAVRGVGARGRL AAQSRGQLLLRGTGVLGLASTRQPAVGGDSEH, (SEQIDNO:5641); XM_005642222.2, KBTBD11, Ins, C_7, PPGARARGRGRGGAGGARPARGPAAAGRADTLQPRRVAVLQLRGRLPAAGSRLRR GGRSVLPALAS, (SEQIDNO:5642); XM_005616615.2, RASGRP4, Ins, C_7, PPGEWLLQPRRADGVPAPGQRHLLQAGPGLPA, (SEQIDNO:5643); NM_001048083.1, ARSA, Ins, C_7, PPGLPPVPGHPVLARPGPLPEPDLLSAVHPL, (SEQIDNO:5644); XM_014114130.1, SRRM3, Del, C_7, PPGLRSGPRAPGRPAPPRPRARTAGTAAQRGRARRAAPAPTRSRGAPAARPPSPARA PRRRGPAAPAARRRPRKP, (SEQIDNO:5645); XM_005618675.2, FGFRL1, Del, C_7, PPGPGSTPNSTRTCTRTRTRTRTHTRTRTWRARSTSTSTSTTSA, (SEQIDNO:5646); XM_014109500.1, CILP, Del, C_7, PPGPLPQALSEEECPQGDSNGLVGVASAG, (SEQIDNO:5647); XM_005631210.2, LRRC55, Ins, C_7, PPGRAAGLPPLGSRGDALGCRHQLPSPLYVP, (SEQIDNO:5649); XM_852751.4, POLR2A, Del, C_7, PPGTAHARCAPSSGCSSESSVRMN, (SEQIDNO:5650); XM_005637420.1, LOC609303, Ins, C_7, PPGWGLAAAP, (SEQIDNO:5651); XM_014110352.1, ZNF683, Ins, C_7, PPHAALRLLLPHHGCAQFADESQ, (SEQIDNO:5652); XM_014110188.1, AHDC1, Del, C_7, PPHGPCFPPGPLPAHLTRPSPTPSPRTHAHPHAGTPAPGAHQSLPRGTTRCPLGQPVPS PRPAAPLLRETATAPDVAGTTGG, (SEQIDNO:5653); XM_014122258.1, DNAH1, Ins, C_7, PPHLPVLGASDPASLLR, (SEQIDNO:5655); XM_014120658.1, LOC100686114, Ins, C_7, PPHMPRGETGSDGSNQALLSVLIALDLQPLQGLPESFWSCWG, (SEQIDNO:5656); XM_014119265.1, C15H12orf74, Del, C_7, PPHPSPQGTQLRASCAHSVYHRARYISGFPYYPSGQGVL, (SEQIDNO:5658); XM_014115490.1, KCTD1, Del, C_7, PPIPPTTTAPSRPRWGTPISSSPKTARSGPT, (SEQIDNO:5659); XM_005635083.2, TOX2, Del, C_7, PPKCCRPSSPCTPCQAWPRS, (SEQIDNO:5660); XM_014114158.1, AUTS2, Ins, C_7, PPKHTASAGARRGPAGPPASGAEAPAAAVPRPAAPSGSPACAGAPLVPGPLPAPLSL QQQ, (SEQIDNO:5661); XM_003639777.3, SYDE1, Del, C_7, PPKPPARSPPAQPGVCP, (SEQIDNO:5662); XM_014114031.1, MTSS1L, Del, C_7, PPKTCWWPSAAGCGSAGPSPTTGRRPASC, (SEQIDNO:5663); XM_014116619.1, SP2, Del, C_7, PPLCLRLTRKPGRRVSLPPSPLWLWRSKWRRC, (SEQIDNO:5665); XM_546572.6, CAMTA2, Del, C7, PPLEGVHPEEAPQSSS, (SEQIDNO:5666); XM_014119807.1, ATG9B, Del, C_7, PPLGCSAILPHLCPRPSWPTSWRSPSCPHGT, (SEQIDNO:5668); XM_014119796.1, KDM7A, Ins, C_7, PPLGGGVGQREPWQERRASPSAPAPAAAGVWASAPPSPPLPSPPQFYRNTTRPGQMS ESPSTGPGRENRLHYSVLFRL, (SEQIDNO:5669); XM_005630123.2, C17H2orf50, Del, C_7, PPLGSRKPRPLGTGCPQPGRQP, (SEQIDNO:5670); XM_014112966.1, TULP4, Ins, C_7, PPLLLPLHRLHPYHQAPNSRSQQHERLCQLPLRGQ, (SEQIDNO:5671); XM_005637152.2, ETV6, Del, C_7, PPLNCCTVLDHLSQPITGLLPTPSSGPSGPPWTT, (SEQIDNO:5672); XM_541835.5, IL17RD, Ins, C_7, PPLPRAGAGEV, (SEQIDNO:5673); XM_005624150.1, CBX4, Ins, C-7, PPLPTCTATELSLPKTE, (SEQIDNO:5674); XM_005625737.2, ZBED4, Ins, C_7, PPLRGQRGERGGEESPASQEHFGLQEAVGCVEALLPVAPGQLQGRVHPLHERVQQG QERQGPGHQLPD, (SEQIDNO:5675); XM_014122450.1, LOC106560164, Ins, C_7, PPLSFSLPKTKRGKTG, (SEQIDNO:5676); XM_014122165.1, CBARP, Ins, C_7, PPLSGQPHQPIPHSRQARGSRGGGRRGRSEPRVPPRAQRRGRAAGI, (SEQIDNO:5677); XM_014106473.1, LOC102155469, Del, C_7, PPLTLSSKGHSAPCRSQSPFPSVLLATGSGRGQPPEGR, (SEQIDNO:5678); XM_014114926.1, LOC102152085, Del, C_7, PPLVCTRCLALK, (SEQIDNO:5679); XM_540000.4, LOC482885, Del, C_7, PPMPCSACTAWRPEASGALPSTP, (SEQIDNO:5680); XM_005635994.1, LOC102152258, Ins, C_7, PPPAAGARGLCPPRPGACAAGLPGLVCGGRGAGGGPRQRGRGRPARDPRGRGWAG VRAPQGARGCAWTGPRARRGQLPGPAPARRPRRRR, (SEQIDNO:5681); XM_005621491.2, GPRC5B, Del, C_7, PPPAPRPPPPNSFPVREGGGSLERGQRPLECGGQRRPCPGRPTRHTGCPAAPGWGLG LCGRVPATEVKLGHYSVENGQAPRSPGRGQRER, (SEQIDNO:5682); XM_005638950.2, SIK1, Ins, C_7, PPPARRRLPGGIGGPAAGHPPAHQPHRGPPSRRHAAPRLCGHGAPAGGL, (SEQIDNO:5684); XM_014107180.1, LOC106557715, Ins, C_7, PPPCPLSGPGLSLQPSEASRRRHPRLRGARGTGRDVRARGKAAGLPASERRRPC, (SEQIDNO:5685); XM_014119801.1, LUZP6, Del, C_7, PPPCSFRLVSLDLEFKHST, (SEQIDNO:5686); XM_014112086.1, LOC106558514, Ins, C_7, PPPELCVPGPRAALELKICVTDLGPPGPPL, (SEQIDNO:5687); XM_014106406.1, LOC102156658, Ins, C_7, PPPGAPPHQLRASDMRRAVAAGRSLAPLPPSHASDLLSRACVQRPGSAADVEEPAA GCGDPGPRGGLSADAR, (SEQIDNO:5688); XM_014112065.1, LOC491446, Del, C_7, PPPGARSR, (SEQIDNO:5689); XM_014116470.1, RARA, Ins, C_7, PPPHLQALLCLSRQIFRLPLWGQRL, (SEQIDNO:5690); XM_539499.4, NOD1, Ins, C_7, PPPLPVPEGRWPGGGRPLQEQGSLSVH, (SEQIDNO:5691); XM_014107689.1, LOC100855783, Ins, C_7, PPPLRPPPPRLGSSHAVCSLAGLRAQQEQEKEEDRFHSLQRLRADLAPPGKSGRELED GDGGGPEPRGHQLRRDAEHAEVRRPGQADP1, (SEQIDNO:5692); XM_005631006.1, COBL, Ins, C-7, PPPLRRRPDPWQDPGEWVQVGPPPHQAPSLPGRAGHQ, (SEQIDNO:5693); XM_005633166.2, LOC102155774, Del, C_7, PPPPARGILGQKAQWPRAS, (SEQIDNO:5694); XM_003434830.3, KCNA3, Del, C_7, PPPPASRTPSSWWRPCASSGSPSSCSCASSPAPAKPPSRGTS, (SEQIDNO:5695); XM_005633811.2, LOC102152567, Del, C_7, PPPPGGGVPGPGPQRRRSTAEGLGPRASGRRGRAPR, (SEQIDNO:5696); XM_014121534.1, VHL, Del, C_7, PPPPGPPFLPGRSERLLEPPEFVTDAVGRY, (SEQIDNO:5697); XM_540529.4, DEAF1, Del, C_7, PPPPPKPCPPPW, (SEQIDNO:5698); XM_014114167.1, GTF2IRD1, Del, C_7, PPPPPPLWPASCTAPRSLTTPQESSSRRRPP AHLPPVTWALAGLGLNPRPLAPKTAVDRSPLGLVVLSSRMSMPRSASCSPSSMTSQR SGTPS, (SEQIDNO:5699); XM_005626204.2, SBF1, Ins, C_7, PPPPRGPCRSAS, (SEQIDNO:5700); XM_014113024.1, WWC1, Ins, C_7, PPPPTSLHT, (SEQIDNO:5701); XM_014116626.1, HSF2, Del, C_7, PPPQESSRGRRYQQTQLLPLVLTQMARVFWFWMNKDLQKKFFLNISSTITWQAL, (SEQIDNO:5702); XM_544960.5, NKX6-1, Del, C_7, PPPRPPRPLRRRPPPRLWAPTTQAA, (SEQIDNO:5703); XM_014120927.1, MAPK8IP1, Del, C_7, PPPRRVAAATRIEIASTIRRTCG, (SEQIDNO:5705); XM_014115697.1, LOC102152805, Ins, C_7, PPPSPLCAPPAALAAPAHLSGGH, (SEQIDNO:5706); NM_001006645.2, KCNA5, Ins, C_7, PPPWARPGDQRQRGPGARLGPHGGASPAADPG, (SEQIDNO:5708); XM_005623942.1, LOC102153864, Del, C_7, PPQALSGTGTGMGTRRTQPQTLRWTRPWTGRSLRTQSRTPRGPALSPAPGDRPRSG WAGEGRSAPPGARKASALSPKPS, (SEQIDNO:5709); XM_005642075.2, LOC100683955, Del, C_7, PPQPPAPAPAAE, (SEQIDNO:5710); XM_846788.3, SLC9A5, Del, C_7, PPQPVQRRSYPGRVGREIWQSTCPRKPPRLCPWTCRQAGTRASRPWRAWHPRPVPR PQL, (SEQIDNO:5711); XM_014118223.1, ZNF865, Del, C_7, PPQTARRRRRQRRPWYMVPCPSHCWGRTRCCSAGPGPVGPGGPAPTSLERHSAAAS VGGASGGVRL, (SEQIDNO:5712); XM_014117280.1, LOC102154639, Del, C_7, PPRAASAR, (SEQIDNO:5713); XM_003434094.4, SIDT1, Del, C_7, PPRAATPATPPGAPISTASTAGW, (SEQIDNO:5714); XM_005618727.2, LOC102156706, Ins, C_7, PPRAHGWGAPRRGRCRRWGQAPGASSWARGLWHRLASPIPRSRAGRTLGLRPRERP PLRAASRLRGWAGRASPG, (SEQIDNO:5715); XM_014108773.1, LOC102154201, Del, C_7, PPRAPHLRGGAPAAGPDGKRPSRSAAGAGRKPEAGVLAHAPSAQGRERVFRRMRRP RRAQSLGAVGVGRSWGAARVE, (SEQIDNO:5716); XM_014115267.1, ENAH, Ins, C_7, PPRASTTPSAPCFRTSTTTPSTPSS, (SEQIDNO:5717); XM_003433939.2, C30H15orf59, Ins, C_7, PPRGPGGRPQAPARPLQAQAPSADQLPPGPRRPRADPEGHKEQ, (SEQIDNO:5718); XM_005631072.2, RIC8A, Ins, C_7, PPRHLAAEHPHPVQGPKLPGPFHQPPEPAGPCLLCRHRLGGVWPGASGHGRCPRVPE VPVQPRAEQPGGTGAGSRGPPGGEARRARGAVSQE, (SEQIDNO:5719); XM_014114530.1, LOC100856086, Ins, C_7, PPRHPPGYRRWGHQWLWVALGGRERLSFQKTRARFHRGCGGCKD, (SEQIDNO:5720); XM_005627318.2, FOXP4, Del, C_7, PPRLLLLSPPFGPLASALPPCTVEALPAGGAVTSSAPPSPQSWPRIMNSTRMPMSGPLS PTPPSSARPFWKPPTGS, (SEQIDNO:5721); XM_014107689.1, LOC100855783, Del, C_7, PPRLLTRRLLSCRTPGPTRTRKRRRPISFPTETPC, (SEQIDNO:5722); XM_005636541.2, ZDHHC8, Del, C_7, PPRPARPAHPPMQAPKLSPSSTRTSQSRHPRWPCKGTTLS, (SEQIDNO:5723); XM_014109382.1, IGDCC4, Ins, C_7, PPRPDLWLQTLLAGGGGRGGGWW, (SEQIDNO:5724); XM_014112353.1, LOC106558589, Del, C_7, PPRPFPSPARPPALRGCAS, (SEQIDNO:5725); XM_014115684.1, LOC106559101, Del, C_7, PPRPVHPAWMHLAGPAGRSNDPDSPAGQDAGAAARRKGAEALSRTWALAPANLPA AARRPGALGDLGAAPPPLRLRQPRV, (SEQIDNO:5726); XM_005619461.2, LOC102153808, Ins, C_7, PPRQDLQDSHALHCQAKISSVDITSTLSSSEPSGQF, (SEQIDNO:5727); XM_014121745.1, ADGRE5, Del, C_7, PPRRWGCAAAWWPDCCTTFSWAPSAG, (SEQIDNO:5728); XM_014116364.1, LOC102155336, Del, C_7, PPRSCTGYGVP, (SEQIDNO:5729); XM_003431507.2, TOMI, Del, C_7, PPSCTTRCSTSSSPGLTRSAAHLT, (SEQIDNO:5731); XM_847603.3, LIMK2, Del, C_7, PPSFPWPPSAANWSLRADLHSQNWRTPLRLSPCTWGSWASRCLQSWRSWTTL, (SEQIDNO:5732); XM_844754.4, PLEKHO1, Del, C_7, PPSFRPTRPSCPGSRTW, (SEQIDNO:5733); XM_005639704.2, ADAMTS16, Ins, C_7, PPSGKPAGLRWGWTPLPHTIQEIHRSAGSRGSPGGPDPEGSGAGESASAQRLEPPAAT KAAFLWKTQEIHAQASQGGSLHPA, (SEQIDNO:5734); XM_843485.5, STK25, Del, C_7, PPSGQAPTASCTRGRPCTAPRSPRSLSRGSRGPSACPRWSGLSSESSRRSTSRAAGAW GHWKSWRMPSAWRRSPVLASRTS, (SEQIDNO:5735); XM_014118664.1, LOC102154884, Del, C_7, PPSGSPLREPRLRWAIARA, (SEQIDNO:5736); XM_005633193.1, TDGF1, Del, C_7, PPSMVATVSTILEKRTVSLCPMTPGCLRDVPCVNAGAAGCTAFGRHFYQGVMAT, (SEQIDNO:5737); XM_543139.5, PDS5B, Ins, C_7, PPSQIRHSLYPCDIF, (SEQIDNO:5738); XM_014121836.1, LOC106560107, Del, C_7, PPSRAAPPASSPTAAWLWVKIGSPSPSLKCTGL, (SEQIDNO:5739); XM_005615409.2, LDLRAD4, Del, C_7, PPSRCPTGRSRRPTRGPAPCSSGTPNSSGSSTASR, (SEQIDNO:5740); XM_542667.4, IRS2, Ins, C_7, PPSSAFARQARWQQRWPPRRLPDPALPGSAAHAPVPGGAADAAQHARVPSAARAQ EPRRVHQH, (SEQIDNO:5741); XM_005617128.2, BEND7, Ins, C_7, PPSSHMHTPPSRKQKQKQKKKKKKKKKVVVLSSTRKQLIRLSP, (SEQIDNO:5742); XM_005640040.2, HIVEP1, Ins, C_7, PPTERKPVI, (SEQIDNO:5743); XM_005642083.2, USP9X, Ins, C_7, PPTESDFIA, (SEQIDNO:5744); XM_846276.4, AKT1S1, Del, C_7, PPTPCPRPQPCPHSSMPSPCLCPCPSGPSRRRGQKHGHRMKRMGRPLRRTWTASRRA CARWCCGRPRTPRSSGTCRGRGSTPATSRS, (SEQIDNO:5745); XM_005629021.1, SLC5A9, Del, C_7, PPTPSQALVQPGCFWPWAGSSSPCTSLPAWSQCHST, (SEQIDNO:5746); XM_005633500.2, NEU3, Del, C_7, PPTPSWPLQRSAPRAGMRMLSTWC, (SEQIDNO:5747); XM_532844.5, SLC25A4, Ins, C_7, PPTPTGPACQQTDQCREAVQRDH, (SEQIDNO:5748); XM_843371.3, LOC606890, Del, C_7, PPTRCSRKSTRWWSSGGRPRAQLPLPPP, (SEQIDNO:5749); XM_014122642.1, FAT3, Ins, C_7, PPVPQRHGFGGPARRL, (SEQIDNO:5751); XM_005639694.1, LOC609445, Ins, C_7, PPVPSEWLVEAPALLPGGGLGHIPHLGCCQLWHLHSLPAT, (SEQIDNO:5752); XM_005626794.2, TMEM8B, Ins, C_7, PPVPVPVPALAPDPSSALVPPPFTNPSPTPVPAPCPVFA, (SEQIDNO:5753); XM_542527.5, IGSF22, Del, C_7, PPVTSLRCGRKTLRSGPSAQRSPSRAPATRWEASPRGRNTSSESGL, (SEQIDNO:5754); XM_532621.6, ARHGEF40, Ins, C_7, PPWEQHSHSGQWRDLRAVPAESCPSPE, (SEQIDNO:5755); XM_005618546.2, LDB2, Del, C_7, PPWGTAALGAVNPPPLRRPNQKAPRPRLPS, (SEQIDNO:5756); XM_005640917.2, SUSD4, Ins, C_7, PQAAGRRPVDPAGAVLRARTAHGRLPRPSDRRCGDP, (SEQIDNO:5757); XM_014122386.1, KIAA1683, Del, C_7, PQAISWHILLPVWQSLGRRGIEPRAPLPVRTAHRSE, (SEQIDNO:5758); XM_014114097.1, KCTD19, Del, C_7, PQALGRGAMQQAWSL, (SEQIDNO:5759); XM_005631410.2, ANKRD13D, Del, C_7, PQALRNSFAWPWSCLRGSRRSRNDGGSRRRKTYRGSCNSRSRST, (SEQIDNO:5760); XM_847571.4, ANKLE1, Del, C_7, PQANGTAAQIRPLSPRLKPLELKTQPWTPPRGLGHYPGPSRDSCLIFNLPRGCQGLQV PHSQCIELPWQTGRQN, (SEQIDNO:5761); XM_014110163.1, MUC13, Del, C_7, PQAPAVLAKELPVKVILPVLA, (SEQIDNO:5762); XM_014107017.1, CHD6, Del, C_7, PQAPPTLKGRCLLLQPPSQPQQPAARPRKPFPARVCLTG, (SEQIDNO:5763); XM_005629454.1, TMEM192, Del, C_7, PQAPREPLLQSPPTAILTGLLTGVPWISPRVLKMTPFWIPTISHIIHYMLILDPDSILFLR SS, (SEQIDNO:5764); XM_005639690.2, NKD2, Del, C_7, PQARTGSPLAAGWRLSSPRTPGEPTRGHLHTPGSPVPNPTPAASAAHTVWTRTQSGE TTTWTWPG, (SEQIDNO:5765); XM_547871.5, DCAF5, Del, C_7, PQASPPIPTLEKTTMITPRSKWMTSPLPLPPPLSAALPRWRFSPTGHLQLPT, (SEQIDNO:5766); XM_014117947.1, KIF12, Del, C_7, PQATLALPSVPEKGVIATGLRPESWRRC, (SEQIDNO:5767); XM_014109614.1, ARID3B, Del, C_7, PQAWAAVPAAAAALTAPRALPRPGAPPAPSRPPAGPS, (SEQIDNO:5768); XM_014121956.1, DOCK3, Del, C_7, PQCLPEACCMVITPYTLTPSTTPWVTPPQPCLPGLCASLLSTLSRPPPPAPSRVWTAAT LHCLAVPAAACPP, (SEQIDNO:5769); XM_014118847.1, ANKRD17, Del, C_7, PQCPLREIPL, (SEQIDNO:5771); XM_014108635.1, ZNF641, Del, C_7, PQCQSAMCALSVGRALADGTTW, (SEQIDNO:5772); XM_014122189.1, HEMK1, Del, C_7, PQCSFLARKLRAESLLWIKEKLPSVLPRRMLRGFGCWTEFGLSPSM, (SEQIDNO:5773); XM_005632499.2, HEMK1, Del, C_7, PQCSFLARKLRSWLSGC, (SEQIDNO:5774); XM_014107603.1, HJURP, Del, C_7, PQDPRLWPCTGVTQRALAAPRP, (SEQIDNO:5775); XM_014114179.1, DTX2, Ins, C_7, PQDRHCLWGPPGLCSIQQALPLWG, (SEQIDNO:5776); XM_544457.2, RAB42, Del, C_7, PQDSSPQVLASV, (SEQIDNO:5777); XM_014121784.1, NBEAL2, Del, C_7, PQDWTPGRLGPRPGTPDTPVPSSARYRAWPGTRAARAPYTTST, (SEQIDNO:5778); XM_005621273.2, FBRS, Del, C_7, PQEPFWGPHLHLCPPPGLVPHLGPLVQPGLTG, (SEQIDNO:5780); XM_014106300.1, FARP1, Del, C_7, PQEPRPPPLKSARAPRRPGAPRAAGRRPEPRGRPPKRRRRTGPPPPPRTGVRRVKLSP RSRAQAP, (SEQIDNO:5781); XM_547000.5, TNRC18, Ins, C_7, PQEREEPQQ, (SEQIDNO:5783); XM_014116626.1, HSF2, Del, C_7, PQESSRGRRYQQTQLLPLVLTQMARVFWFWMNKDLQKKFFLNISSTITWQAL, (SEQIDNO:5784); XM_014111977.1, IGSF1, Del, C_7, PQFGARNCKSGAKDGWQAWSSFCIRRECRNLSSNFMPLGEKPSLQSKEWRIKTKAII AAVLILKSAPSSGLSPVIPWSLS, (SEQIDNO:5785); XM_014120094.1, POU2F2, Ins, C_7, PQFHPLCHSPTPGHHQQHKSQPSRQPLGHRLVGPEPQHGKHNGGVELRAESSPHEQQ PFGHYPSPGLWWNPAPYQP, (SEQIDNO:5786); XM_861140.5, POU2F2, Ins, C_7, PQFHPLCHSPTPGHHQQHKSQPSRQPLGHRLVGPEPQHGPWPLVEPCPLPAL, (SEQIDNO:5787); XM_014120097.1, POU2F2, Ins, C_7, PQFHPLCHSPTPGHHQQHKSQPSRQPLGHRLVGPEPQHGV, (SEQIDNO:5788); XM_547725.4, REM2, Del, C_7, PQGHPRQKQMPHC, (SEQIDNO:5790); XM_014109885.1, PDE5A, Del, C_7, PQGLIMMKGTSARDSWN, (SEQIDNO:5791); XM_014121843.1, APC2, Del, C_7, PQGPQPTPPAAAAMGRRGHCQGWRRRAPRGVASGTRTSHTSCGARCPPPPCH, (SEQIDNO:5792); XM_005629518.1, EZH2, Del, C_7, PQGRRRGNTGCGRHTAERYS, (SEQIDNO:5793); XM_005633132.2, DAZAPC Del, C_7, PQGSLLHLLLQGGQHLWPSLRLRLRPPQT, (SEQIDNO:

5794); XM_014109477.1, STARD9, Del, C_7, PQGSLVAWEVLRNWKL, (SEQIDNO:5795); XM_014110764.1, KCNH7, Del, C_7, PQHPSRRTEVSVLPHNVLNF, (SEQIDNO:5797); XM_005637906.2, TUBGCP2, Del, C_7, PQHQRPGSPSLPS, (SEQIDNO:5798); XM_014118244.1, SYNGAP1, Del, C_7, PQHRPPHPGCRSLRTASSETPQTT, (SEQIDNO:5799); XM_535422.5, FlvLN1, Del, C_7, PQHWHRSACS, (SEQIDNO:5800); XM_014106637.1, DLEC1, Del, C_7, PQIPLPSKFSSLPGAVSCMSPRWWWKVCLARRPAPYGSGAEALMMRDTCHPTSS, (SEQIDNO:5801); XM_846459.4, SMG1, Del, C_7, PQISLLKSSGHLVPHLMNGGESHSLMPGLLQLCLWSDT, (SEQIDNO:5802); XM_005641622.1, SERPINA7, Del, C_7, PQKMPLSIRCHPSMLTLHLTCTGDSLWRPQIGTSSFPL, (SEQIDNO:5803); XM_005616382.1, ZNF541, Del, C_7, PQKRKPVGTPPTPTRGPASLHPLACDLWCPQKPGPPAPSCPTETSCAVL, (SEQIDNO:5804); XM_545710.3, USH2A, Del, C_7, PQKVSEHPSSMQSLPPMQWSTSAPLRSPME, (SEQIDNO:5805); XM_003432782.4, PDE4A, Del, C_7, PQLLAGGDQPEVLP, (SEQIDNO:5806); XM_014113250.1, FOXR1, Ins, C_7, PQLLPPNCTGIKKQFPLWPQRATDLQFHSTTFPLFPDGPGRLEEYRPPQPLLPRQL, (SEQIDNO:5807); XM_005637602.1, HPS1, Del, C_7, PQLMLLRSRSLKTASRHWSLTPQSLPAPEGFSWMPT, (SEQIDNO:5808); XM_005627727.2, PHF10, Del, C_7, PQLPGKWAEGGKTAKRD, (SEQIDNO:5809); XM_014121819.1, CAMSAP3, Del, C_7, PQLPWPPQQPQPLLPGPQWRKRWAPGGGTSLGLSMNAGPS, (SEQIDNO:5810); XM_014110486.1, LOC102156009, Del, C_7, PQLQVNAGPLTARAVAEKDAPH, (SEQIDNO:5811); XM_014106932.1, LOC106557687, Del, C_7, PQLRAQDGGVEGGPRTGRAGRTRLPSSGGRAQHLDSPQHRPGARGRRRSRCQQTRT GARPRPHVPARPPSLGSRERRAAQTNTGPKALAARL, (SEQIDNO:5812); XM_534442.5, PCIF1, Del, C_7, PQLRTSPESDSSQKSSQAAMV, (SEQIDNO:5813); XM_546181.5, ZMIZ1, Ins, C_7, PQLYELHETHSVAQ, (SEQIDNO:5814); XM_003432343.3, LRRN4CL, Ins, C_7, PQLYSPQSRTEEAEAWGHLCRLRGGCKWSWRKQRARGRWGGP, (SEQIDNO:5815); XM_014107816.1, HECTD4, Ins, C_7, PQMAQQVPQTLATSEWRPACS, (SEQIDNO:5816); XM_003433444.3, HIC2, Ins, C_7, PQPAAIHSLRHSGAVSRACGRTQRGPYPPGAPPGQRLR, (SEQIDNO:5817); NM_001205113.1, ALOX5, Del, C_7, PQPCGPHHRRPRVSSPSSRLWTRCQTVAAPAGIWAQYGH, (SEQIDNO:5818); XM_533813.5, DOCK3, Del, C_7, PQPCLPGLCASLLSTLSRPPPPAPSRVWTAATLHCLAVPAAACPP, (SEQIDNO:5819); XM_014107094.1, HSPG2, Ins, C_7, PQPGARLPVTASPGLTS, (SEQIDNO:5820); XM_537364.5, LRP10, Del, C_7, PQPGPLRPDLRSHLLLLPLRP, (SEQIDNO:5821); XM_014121804.1, CACNA1A, Ins, C_7, PQPHCRPSEQKRQPRPTAKKGGREEGGGGRRPWGRRPQAHAPLQLHVYPLYDQPPS PPVPLHPEPALL, (SEQIDNO:5822); XM_014108301.1, CACNA1C, Del, C_7, PQPHPAAEAGPRSLSPPCGWRGLSPTRNSTAASRPSTAAPGLRSPHPVEEVTAPSGEP GRCPSLCPARLGPGAGSSTAVPAASWKRS, (SEQIDNO:5823); XM_005624843.2, KSR1, Del, C-7, PQPHPSCEGTPS, (SEQIDNO:5824); XM_546088.5, DISC1, Del, C_7, PQPLLALRMPLRQALASYGSHLALLGNVEKLKAACHPERLRPLVRAPRRRK, (SEQIDNO:5825); XM_003432681.3, KMT2B, Del, C_7, PQPLLPGLCPRDRCWVCCQW, (SEQIDNO:5826); XM_846736.4, PITPNM1, Del, C_7, PQPPPLGSPGGQAQPPAHLPPLLRLLMAPPVLPALTSRSPASSSLAPRWAWCWLCAK P, (SEQIDNO:5828); XM_546571.4, KIF1C, Del, C_7, PQPQCPLHIPPHTMGSWSHRSPPVPSPRLGLRRPWRGCRRQRRS, (SEQIDNO:5829); XM_542245.5, HEPHL1, Del, C_7, PQPQCPPMKNPARSSSISLARICILGEQKQPWSSSSSLDSSSLSPR, (SEQIDNO:5830); XM_005632690.2, SSBP4, Ins, C_7, PQPQRPHDGASCSASCGPPWLPAPPPWHHGTLPESSGASKHGPDAESDTSTGHGQR WTPELWRWHAAPTQLPRRPRPAHHEHGPWSARPVG, (SEQIDNO:5831); XM_547068.4, TBX6, Del, C_7, PQPQRSFIRSPESA, (SEQIDNO:5832); XM_544699.6, CGNL1, Del, C_7, PQPRIKRRTKSRQPRRR, (SEQIDNO:5833); XM_014106893.1, MAST4, Del, C_7, PQPRSASDVRS, (SEQIDNO:5835); XM_014122378.1, CFD, Del, C_7, PQPRSLVGASWAGARPSPTRGPTWRRCRWTASTCAAASWCRSAGC, (SEQIDNO:5836); XM_538386.5, SH3BP1, Del, C_7, PQPSPLNPGPGALPQRPT, (SEQIDNO:5837); XM_005620701.1, LOC100855981, Del, C_7, PQPTCREWTGARAWPDGLRPGQPSVVPQPKALHQHLEPPSK, (SEQIDNO:5838); XM_005639515.2, LSAMP, Ins, C_7, PQPVAARPAQAALPSPHRTARSQRGL, (SEQIDNO:5840); XM_538715.5, RUSC2, Del, C_7, PQQKMRKEPQSLPLGASSGDISLAPERLSGRPGPQTGSPPTG, (SEQIDNO:5841); XM_014115632.1, RIN3, Del, C_7, PQQLLPRLQRPFLPHPRHLPPTLPPMPQAPQTFQAKHPWQPARGSHGPRQAWAPSGR KR, (SEQIDNO:5842); NM_001003179.1, RRBP1, Del, C_7, PQQSRTLSS, (SEQIDNO:5843); XM_003431676.3, CFB, Del, C_7, PQQTGTVPATLSSL, (SEQIDNO:5844); XM_005638522.1, IGDCC3, Ins, C_7, PQRAGGLCVVHRGPGVLE, (SEQIDNO:5845); XM_014117663.1, AKAP2, Ins, C_7, PQRAPGRPPRGSG, (SEQIDNO:5846); XM_005635245.2, PHACTR3, Del, C_7, PQRAPNIWSQGSALPR, (SEQIDNO:5847); XM_536923.5, LOC479795, Del, C_7, PQRAPQSLSKTRQRMRARTQLC, (SEQIDNO:5848); XM_005624637.2, TMEM92, Del, C_7, PQRGSGRPPLSPHPPMSEIILKPVLPPMEPPPPYSFMP, (SEQIDNO:5849); XM_846500.4, TMEM92, Del, C_7, PQRGSGRPPLSPHPPMSRSF, (SEQIDNO:5850); XM_547143.4, ZNF500, Del, C_7, PQRGSRRPLGQGPAATRRAVRFRGPFWNIEVRVH, (SEQIDNO:5851); XM_003432681.3, KMT2B, Del, C_7, PQRLLPGNGVRRAQNGWCRH, (SEQIDNO:5852); XM_005626050.1, FAM178B, Del, C_7, PQRLPWTLA, (SEQIDNO:5853); XM_541537.5, DHX34, Del, C_7, PQRLRILPPSPSPRRLPCRGPTTARPARRTFCSRPRRCCGTADSTC, (SEQIDNO:5854); XM_005641921.1, LOC100856776, Del, C_7, PQRRGLILQGP, (SEQIDNO:5855); XM_845495.4, DGKZ, Del, C_7, PQRSLMLWRRMGRRVCTRRQPWASAPSATTSWRLGPLS, (SEQIDNO:5856); XM_005632683.2, CRTC1, Del, C_7, PQRTRASRQWGSTLPRRRLCSSTVLVPAPRLTSLPPHLSPIKASPLGAPRNWSSST, (SEQIDNO:5858); XM_005632684.2, CRTC1, Del, C_7, PQRTRASRQWGSTLPRTPPPWAACLGTRTMSSRWRPGRPMLCPTSWSSST, (SEQIDNO:5859); XM_005625714.2, HDAC10, Del, C_7, PQRTRRPCCT, (SEQIDNO:5860); XM_003434181.3, LOC100686305, Del, C_7, PQRWSWIQLWQHSTSTI, (SEQIDNO:5861); XM_549068.5, ZMYM3, Del, C_7, PQRWTTVLRGPLHGMQETRP, (SEQIDNO:5862);

XM_005624295.2, KCNJ16, Del, C_7, PQSEDLTHQTPR-SEEGRLVRLPLSAAVKTPRRPPRLPRMSVRKP-LIRKLS, (SEQIDNO:5864); XM_541627.5, PAK4, Ins, C_7, PQSHEDDSGQPATPTEKPAQGVTIPEGLPGP-PAGA, (SEQIDNO:5865); XM_005630569.1, RAB11FIP5, Del, C_7, PQSLLFHHPLCHPGPATAMGGPAL-HALLCLELGL, (SEQIDNO:5866); XM_005621644.2, ZNF213, Del, C_7, PQSLRRRPLGREQVC, (SEQIDNO:5867); XM_014119601.1, MAP7D1, Del, C_7, PQSPDLLQKGTPPRRRHHHLRCQPWSLTLPQTPLQP, (SEQIDNO:5868); XM_014112559.1, TNIP2, Del, C_7, PQSPRRPPALS, (SEQIDNO:5869); XM_005626612.1, TPD52L3, Del, C_7, PQSPVTPAGSRTLQVWISTL-LAEILSPLATSSTLCTRNWTWTLFM-KIFPSPCRAPRQRL QRAPLNPARLPKQRISQGL-HERSSNPCSLNWRRKL, (SEQIDNO:5870); XM_014106895.1, LOC100683453, Del, C-7, PQSRPG-GAHPRAAPTAHGPQP-WARTVPGTRGSQKPLGQWRPD, (SEQIDNO:5871); XM_014118242.1, SBK3, Del, C_7, PQSSAS-CCHLIPCPCDQLWTPGAWGCFSSALPLLVSLGM, (SEQIDNO:5872); XM_846556.4, CHRDL2, Del, C_7, PQS-TASTMGPCTNTERSSVPMSCSLPACPTSVSSAAVLR-ARSTAVS, (SEQIDNO:5873); XM_845641.5, EPN1, Ins, C_7, PQSWGIRHEWGRGLSG, (SEQIDNO:5874); XM_534785.5, ZNF385A, Del, C_7, PQTGMVQRPVQFPWRMDWVQPRDPQRNSLAPHLL-PAFRRLVKVQPRVKAGLQPQL PCR-GAARKKRKRPSGCSTVLCARWQ, (SEQIDNO:5875); XM_014116465.1, NOS2, Del, C_7, PQTSFYLKPLNLST-SITAPSKRQK, (SEQIDNO:5878); XM_005637736.2, TCF7L2, Del, C_7, PQTSLSALKSSGT, (SEQIDNO:5879); XM_014115361.1, ADAM15, Del, C_7, PQTSPGSRTSS-CQATPVP, (SEQIDNO:5880); XM_548160.4, GPR179, Del, C_7, PQTVSAVTYLKLALRDWLRCARGMLPHL-TAAPKRRSAPGR, (SEQIDNO:5881); XM_014120407.1, FAHD2A, Del, C_7, PQVLVYSGNLQFFSR-RAMKFNVKSKN, (SEQIDNO:5882); XM_543487.4, PLA2G3, Del, C_7, PQVPASRAQPPASLDRSSVL, (SEQIDNO:5883); XM_014117075.1, DENND1A, Del, C_7, PQVRRRSRGTSPVLPLKHPPNCCNH-SAWPPGLQAQAAMPCWPSWTLFTQRGQAVLF PQALQPQM, (SEQIDNO:5884); XM_005636541.2, ZDHHC8, Del, C_7, PQVSLTGSPRAWPAWGLPL-APRGPPPALPGTRSLRRCPAWVGPRTRSQC, (SEQIDNO:5885); XM_003432698.3, ZNF784, Del, C_7, PQVTSSRSR, (SEQIDNO:5886); XM_005623502.2, PLEKHG3, Del, C_7, PQVTWGTLWWWRAPRILRL, (SEQIDNO:5887); XM_548107.3, KRT36, Del, C_7, PQWISTRSWMI, (SEQIDNO:5888); XM_014121835.1, JSRP1, Del, C_7, PQWPPARPPPLCSPPAE-PIGPRRCPRPPVAARPGR-SPSSDCQVPAAVRHPPSSDPQLRS PAPIWAPPSP, (SEQIDNO:5889); XM_003639660.3, B4GALNT4, Del, C_7, PRAAAASRRPRPPPRRAPGAPGR, (SEQIDNO:5892); XM_014106893.1, MAST4, Del, C_7, PRAAGPLRRRP-PRGSLPPPASG, (SEQIDNO:5893); NM_001003009.2, TPO, Ins, C_7, PRAAGQDPGRGPHIQ, (SEQIDNO:5894); XM_014107093.1, PTPRT, Ins, C_7, PRAAGRRGHIPVDQAKCQLNHRGWPHHPEGG-GISHHYRHLG, (SEQIDNO:5895); XM_005634029.2, MBNL2, Del, C_7, PRAARWRTEESLPASIPSRAVVQERT-TASIFILQHI, (SEQIDNO:5896); XM_014117212.1, TBC1D30, Del, C_7, PRAATRKRPSLALSPASNH-CASQPLPGIWGYMVLRKEPQPCTFPT, (SEQIDNO:5897); XM_005630569.1, RAB11FIP5, Ins, C_7, PRACF-STTPSATLGQPLPWGAQPSMLSSAWSSASDFFLPNPW-GASLLPWGLPCPTWG GPRCNYPSLPACASALGDTTS, (SEQIDNO:5898); XM_545640.4, RUFY4, Del, C_7, PRACGNQRGRG-FREPQEQDSAWRTQHPASRDKGSGPRELRRR, (SEQIDNO:5899); XM_014115705.1, CCDC88C, Del, C_7, PRACPWADPGRPPCPRRPTRPPAGP, (SEQIDNO:5900); XM_541492.5, PRR12, Del, C_7, PRACRPQCQP-GACSRSLLPPPLCHTRLLLEPLGWEVRWRRLRAR-GLGWAALRPASG WMRS, (SEQIDNO:5901); XM_005626825.1, GRHPR, Del, C_7, PRAGPR-SPGLRTVRWSSGIQTSQSLPRSWSEVWPGPTASSAS-SRTMWTRGSWTPQEP ISKSSAQCP-WALTIWLWRRSRSAASVWATPQMS, (SEQIDNO:5903); XM_014110256.1, TNK2, Ins, C_7, PRAHPPEAHPPTGRAVSSPLRRGGDRAVAWTRLPSP-GASPGAPVPSRLTOP, (SEQIDNO:5904); XM_005616882.2, AXL, Del, C_7, PRAH-RLRQTPLWGVQGTSPVPEDSPGPFGVSSRFRGSPLR, (SEQIDNO:5905); XM_014118242.1, SBK3, Ins, C_7, PRALPPAAT, (SEQIDNO:5906); XM_005616884.2, MAP3K10, Del, C_7, PRAPASSPG, (SEQIDNO:5907); XM_014110537.1, LOC106558245, Del, C_7, PRAPFSSQHPHGVSFPFSSSFGYSVPWSA, (SEQIDNO:5908); XM_014116397.1, LOC106559250, Del, C_7, PRAPPKPPPAPTRAASPGSWSCWASRT-CPRCGRCSPRSSWPCSCSRCWATRSSCC, (SEQIDNO:5910); XM_005616836.2, LOC102154596, Del, C_7, PRAPPKPPPAPTRAASPVSWSCWASRT-CPRCGRCSPRSSWPCSCSRCWATRSSCC, (SEQIDNO:5911); XM_854614.4, MBD6, Del, C_7, PRAPPQPWSRSLPGLPSVP, (SEQIDNO:5912); XM_548855.5, WWC3, Del, C_7, PRAPPWTRLSFRP-PATRP, (SEQIDNO:5913); XM_005626260.1, ATP6V1B1, Ins, C_7, PRAPQSRGGIANAFVG, (SEQIDNO:5914); XM_846015.3, HOXB2, Del, C_7, PRAPRPRPLPG-GAPRARPRGWSPSRCRKMPSRSARILLSCPTST-SSRSTPVSSCPEASPP ACRARSTARFPF-PRKSWTSSPAPSVPSTCSSL, (SEQIDNO:5915); XM_014116191.1, UNK, Del, C_7, PRAPSGSPQTWKALSSLGSLASPLAAIRRLLA-LRGKTRWELST, (SEQIDNO:5916); XM_014121820.1, LOC106560103, Ins, C_7, PRAPSRPLRAPER-AGRFCRVSRRRAGRWAGSRRLL, (SEQIDNO:5917); XM_014119601.1, MAP7D1, Ins, C_7, PRAQTFSRRGPL-PAAATTTSDVSPGP, (SEQIDNO:5918); XM_014112559.1, TNIP2, Ins, C_7, PRAREDLLP, (SEQIDNO:5919); XM_003432681.3, KMT2B, Ins, C_7, PRARGAGLPPTAAQVSPALRQTATLL, (SEQIDNO:5920); XM_533913.5, RAB3D, Del, C_7, PRARGMQQTRTLTTCLSCCSSATAAWARRP-SCSATRMTPSHLPSLALWASTSRSRRS IVMTRGSS CRSGTRRARSATVQSPPPTTAEPWASC, (SEQIDNO:5921); XM_546631.5, HS3ST3A1, Del, C_7, PRAR-PAPPPPPSRCPAASSGGSC, (SEQIDNO:5922); XM_014112163.1, LOC100856005, Del, C_7, PRAR-PAWSPRGPRRALRRVLTQRALSLETKGTLGGQD, (SEQIDNO:5923); XM_014112161.1, LOC100856005, Del, C_7, PRARPAWSPRGPRRALRRVLTQRGCRGVWGAR-RACG, (SEQIDNO:5925); XM_014109523.1, PML, Del, C_7, PRASELSACRP, (SEQIDNO:5926); XM_541535.6, SLC8A2, Del, C_7, PRASSWTARSWAPRCRAS-WAAWARAPPRPASWTPAAARSSRSSRTSSRSTR-TRTWS SWWASPT TTRCCTSRRAAPSTASRPRGS, (SEQIDNO:5927); XM_541885.4, BSN, Del, C_7, PRATCHPLRMPPQLRS, (SEQIDNO:5928); XM_014114192.1, ZNF853, Del, C_7, PRATWCCRSS-WCCLPWPRPRWWPFPAPRAARL, (SEQIDNO:5929);

XM_005616509.2, DMRTC2, Del, C_7, PRAWSLSPREL-SAALQPVPAAETTESLPTSRATSACASFR-LASVTNVSSSWSAEGSWL PRWPCVGNRRHSSRDIWLRA, (SEQIDNO:5931); XM_014118394.1, LOC484306, Ins, C_7, PRCDLRSAE-PLDPQTEDKCILSLPVRGAPSRAQCVCCSGHSL, (SEQIDNO:5932); XM_014118423.1, LOC611446, Ins, C_7, PRCDLRSAEPLDPQTEDKCILSLPVR-GAPSRAQRVCCSGHSL, (SEQIDNO:5933); XM_005635182.1, NFATC2, Del, C_7, PRCGRRAP-TRRPCLPPRPRPACPATSTRPWSSWGPASRRRAG-ARPPSPSCSCRPPGSS WCQLFPSAASQ, (SEQIDNO:5934); XM_847906.4, PGLYRP2, Ins, C_7, PRCHLCRCWSHISKY, (SEQIDNO:5935); XM_005616406.2, ZC3H4, Del, C_7, PRCLCQCMSHCPRSSCSSSRTCTPVRSPPCLRS, (SEQIDNO:5936); XM_014120347.1, ASAP2, Del, C_7, PRCPHGMLPKIPWLPHRPLQ, (SEQIDNO:5938); NM_001131049.1, DNM1, Del, C_7, PRCPRAPTAPRPGSPADRVRQVRPVLRAPGPPSTS, (SEQIDNO:5939); XM_014117260.1, PPP6R2, Del, C_7, PRCPRQPPGSSPRPPRLRKPPTPQLWPRPPRPPPLPW-PAPPG, (SEQIDNO:5940); XM_848382.3, EBNA1BP2, Del, C_7, PRCRVRTRNLRILWSRTESCRMRFPEAS, (SEQIDNO:5941); XM_014117000.1, HMCN2, Del, C_7, PRCSQARGS, (SEQIDNO:5942); XM_005638641.2, CSPG4, Del, C_7, PRCSRSPGPT-SLHCPASNCGSSSSPCTGPCGERRPLKRGPSAL-SPGKR, (SEQIDNO:5943); XM_014120407.1, FAHD2A, Ins, C_7, PRCWCIQETSSFSQEGR, (SEQIDNO:5944); XM_846534.4, PRCC, Del, C_7, PRCWPPPSPRHCCCPRPPGTPGSSPRRPCRSAWEA-SLPLRASARRRRRELGRGWGCP RPGAPASACPPP-WAVPGPPWAFPSQRRGRSP, (SEQIDNO:5945); XM_014109686.1, SYNJ1, Del, C_7, PRDHLHLQGLGVLHLLEKNSEHPKALEQHGKIL, (SEQIDNO:5946); XM_014109687.1, SYNJ1, Del, C_7, PRDHLHLQGLGVLHLLEKNSEVLEPLPVLGQLGER-WKHPKALEQHGKIL, (SEQIDNO:5947); XM_014109683.1, SYNJ1, Del, C_7, PRDHLHLQHPKA-LEQHGKIL, (SEQIDNO:5948); XM_014109643.1, C30H15orf39, Del, C_7, PRDSRPVPR-SAGLFCRVTARCHPARHPCLSSTMSSAWPRTATTWM-CRPPRTPLSPPR RQPPAGALQRTVGRPWPPGRCPQSP-CAPAERR, (SEQIDNO:5949); XM_014121829.1, TMIGD2, Del, C_7, PRDVAPSPRACEASF, (SEQIDNO:5951); XM_846500.4, TMEM92, Ins, C_7, PREGQDVHL, (SEQIDNO:5952); NM_001130437.2, PABPN1, Del, C_7, PRELRALGLAREPPAARRRRRSRDWSRVTRGTAPLR-TRSWKRSKLESGRWRKKLRS, (SEQIDNO:5953); XM_005632684.2, CRTC1, Ins, C_7, PREPGPAANGDRHYLALLHLGQRVWGLVL, (SEQIDNO:5954); XM_005632682.2, CRTC1, Ins, C_7, PREPGPAANGDRHYLGAGSAAVPC, (SEQIDNO:5955); XM_014120095.1, LOC102155747, Del, C_7, PRESGSGVGGGARSRRPRPLWDPN, (SEQIDNO:5957); XM_005635260.2, OSBPL2, Ins, C_7, PREWDSETQD-VIARPDVYQK, (SEQIDNO:5958); XM_005622972.2, ADCK3, Ins, C_7, PRFLCSHLP, (SEQIDNO:5959); XM_005641877.2, GPR101, Del, C_7, PRFMVGARLPST-SAMPSAP, (SEQIDNO:5960); XM_005623032.2, EMILIN2, Del, C_7, PRFPRTPGN-GRTQASGLSCPRDPRSRCPRQRGRAGQGCPSCPAPPGS, (SEQIDNO:5961); XM_843145.5, PDIA4, Del, C_7, PRFPWLRWMPLRKQTWPRGSRSLAIPR, (SEQIDNO:5962); XM_005629401.2, LOC100855618, Del, C_7, PRGARAAPTWS, (SEQIDNO:5963); XM_014118248.1, LOC106559564, Del, C_7, PRGARLGRARRLRREPA-GANSSGSARGSRA, (SEQIDNO:5964); NM_001003016.2, MCLI, Del, C_7, PRGCCCSRP-PAARRRLKRWKARPPTPSCRPKRS, (SEQIDNO:5965); XM_847216.3, RD3, Del, C_7, PRGCPPG-GRLRWCWRRS, (SEQIDNO:5966); XM_014113861.1, ZNF469, Del, C_7, PRGGAMHRPYHSR-PAGQTAAPSSSTL, (SEQIDNO:5967); XM_014115768.1, SYNJ2, Del, C_7, PRGGGRNRHPQPSTCRCCRA-TASSSRPSPAAPQAATGPLHTCPTRVHLCRHLPASVL PLPQAPKLRAPGRPRQRQPPFWVTIRIPSGAFSITLAF, (SEQIDNO:5968); XM_003434181.3, LOC100686305, Ins, C_7, PRGGHGSSSGSTVPARSRGCSDDRAPGWG, (SEQIDNO:5969); NM_001194984.1, RAN, Ins, C_7, PRGGHGSSSGSTVRARSRGCSDDRAPG, (SEQIDNO:5970); XM_543631.5, CALCOCO1, Del, C_7, PRGGSALFVRSASQPRVIRTPWRTTWMDTSFSAP-RTPLPLS, (SEQIDNO:5971); XM_005641921.1, LOC100856776, Ins, C_7, PRGGVCCSRGPK, (SEQIDNO:5972); XM_005625714.2, HDAC10, Ins, C_7, PRGHAGPAVLERAAGSTVEDAAGGRSFL, (SEQIDNO:5973); XM_014107007.1, DIDO1, Del, C_7, PRGLPHRH-PRCRSHPVRLRHRHRQC, (SEQIDNO:5975); XM_014112439.1, FURIN, Del, C_7, PRGNASLTSSLN-PRTSGSGWRCGRL, (SEQIDNO:5976); XM_539768.4, FHDC1, Del, C_7, PRGPGRPGTAPPSA, (SEQIDNO:5977); XM_014113173.1, DRD2, Del, C_7, PRGPGTVPYHPATTS, (SEQIDNO:5978); XM_536750.5, CDH15, Ins, C_7, PRGPLPLSAESPSPRAYPELEPQPD, (SEQIDNO:5979); XM_014109945.1, WDFY3, Del, C_7, PRGPQVTRSFSITWTT, (SEQIDNO:5980); XM_014122137.1, CPAMD8, Ins, C_7, PRGPR-GAGQGPAQHLQLHGHL-CRGVREDLCSQGHPVCRAPRQTPSDQEDVRGLWG DGACLGGSLLQ, (SEQIDNO:5981); XM_005633132.2, DAZAP1, Ins, C_7, PRGPSSTCYSRGSTSGLPSASVS-GRPRHEQASNGPARLPL, (SEQIDNO:5982); XM_014118655.1, ZC3H3, Ins, C_7, PRGQTSSRIQQFEAPLQ, (SEQIDNO:5983); XM_014111971.1, DUSP9, Del, C_7, PRGRGCCSSTAGAASCTSRRASAGR, (SEQIDNO:5984); XM_005637802.2, TACC2, Del, C_7, PRGRKLLSGP, (SEQIDNO:5985); XM_544644.5, TTBK2, Del, C_7, PRGRVSQPLNSAD, (SEQIDNO:5986); NM_001289434.1, SLC4A3, Del, C_7, PRGRWRLGWS, (SEQIDNO:5987); XM_014122484.1, CCDC34, Del, C_7, PRGSHSTAAAPPCVGRAAR, (SEQIDNO:5989); XM_005636540.2, ZDHHC8, Ins, C_7, PRGYVPPALSRLQPFPRSLGA, (SEQIDNO:5990); XM_014113085.1, SAL13, Del, C_7, PRHAGHPSSTTASHVGRPSPRPAPSRFTSVHTPGRSP-SAAPSAGGHSPQRATSRCIWA RTCGIMPPRGVAAACPWKTPWLC, (SEQIDNO:5991); XM_005632766.2, WIZ, Del, C_7, PRHHWSSLLATSTPS-SAGSVRWNSRGPSLSRRSGCGTYSGTSWR, (SEQIDNO:5993); XM_005617639.1, LCK, Ins, C_7, PRHQADYQQTLGHGSPNCRGHGIH, (SEQIDNO:5994); XM_854174.4, BAG6, Del, C_7, PRHQLWPRSR, (SEQIDNO:5995); XM_005638000.2, PLAG1, Del, C_7, PRHRIFRILQTP, (SEQIDNO:5996); NM_001048101.2, TAPBP, Del, C_7, PRHTASSAASSRCPPRRGGPVA, (SEQIDNO:5997); XM_005640837.2, MIA3, Del, C_7, PRK-AGVARWKGCSHTLKIISHKVTPKIISHKTT, (SEQIDNO:5999); XM_005619439.2, LRIT1, Ins, C_7, PRKALGARAARNLGSEA-WCPGGWGVQQPLLPCGPQAAELSWPCIPCRRAEL-WAE, (SEQIDNO:6000); XM_545954.4, KLF3, Del, C_7, PRKHCCKRIIHQS, (SEQIDNO:6001); XM_014114300.1, DAGLB, Del, C_7, PRKLIWTQS, (SEQIDNO:6002); XM_005631964.2, ZEB2, Del, C_7, PRKTLYYPGRP, (SEQIDNO:6003); XM_847455.4, CHRNB4, Del, C_7, PRLASRSPAGPRPPPPSPMGAPCTL, (SEQIDNO:6004); XM_546499.4, PHLDB1, Del, C_7, PRLCPPKLPGSCRFTAPRWMVRPPAPCPGPAVAPSPPPLVLLPLLRSSAWLLWAGAP PQRVPYLPRMAQAAFLATWRPRCRTLRPSASWPCSRRDSR, (SEQIDNO:6006); XM_547482.5, DUSP27, Del, C_7, PRLEVPRDGRPLARVRRSQKTKRTWRG, (SEQIDNO:6007); XM_539698.4, PTPRQ, Ins, C_7, PRLFCKTVVWCHGEVVMATTPGAKWNYPLLHSLCLG, (SEQIDNO:6008); XM_543973.5, SEMA4G, Del, C_7, PRLHHPHPHRLS, (SEQIDNO:6009); XM_014113210.1, LOC106558749, Del, C_7, PRLHLGRWGANAGPGALGG, (SEQIDNO:6010); XM_005620748.2, ATXNL1, Del, C_7, PRLHPQPTHSTKLLPLPHLGSCHITQVLSHWTLLQAGCPFIIRCPGYLLGTLCMKPLQ QVPAQFLPLRRASLLWKQPLPTDRDSENEI, (SEQIDNO:6011); XM_014113861.1, ZNF469, Del, C_7, PRLKGTAGSTQKSLCPALESSLSLHWT, (SEQIDNO:6012); XM_005624978.1, LRRC3C, Ins, C_7, PRLLHGRRSW, (SEQIDNO:6013); XM_005620601.1, GPR157, Del, C_7, PRLLHPPRQETLRDPDVPQMNFQAP, (SEQIDNO:6014); XM_014114423.1, POLR3E, Del, C_7, PRLLHPQMSRRCSPSGSLET, (SEQIDNO:6015); XM_005615776.2, CEACAM1, Ins, C_7, PRLLLPSRGKPQSLLPHSF, (SEQIDNO:6016); XM_848182.3, C3H4orf48, Del, C_7, PRLPAGSRGRCRRGCCCC, (SEQIDNO:6018); XM_005642274.1, LOC102152225, Del, C_7, PRLPASPDRTVAGAPRVPRP, (SEQIDNO:6020); XM_003639335.2, LMF2, Ins, C_7, PRLPCGQGGEAQASP, (SEQIDNO:6021); XM_005629454.1, TMEM192, Ins, C_7, PRLPENPSCRAPPPRS, (SEQIDNO:6022); XM_014119273.1, LOC106559736, Ins, C_7, PRLPGRQPRLHTPEPEPEPEPEPEPEPAAGGQGGGYLGPGLVSRSALRRRRGRAGASV SSRAAGRGTPDV, (SEQIDNO:6023); XM_014122252.1, ABCA7, Del, C_7, PRLPLRGTQRCSQRRCRRA, (SEQIDNO:6024); XM_548528.6, RGS19, Del, C_7, PRLPPAATPAACAGVAVAAAPGTRSGGVRGGPPGTTSCSPCPAVRRAPRQAPRRCG AGRSRSTS, (SEQIDNO:6025); XM_003433540.4, P3H3, Del, C_7, PRLPTCSTPTVCAPTRPGLGRRPWRCCGRRCGAGRRWAARAGTAGRSARRSRGPRS PRCRSTPRGGTRGPAGRRGPGSACCSALRSAGPSA, (SEQIDNO:6026); XM_535500.5, MYO1E, Del, C_7, PRLQDTIRMESSKTSLCHILMLLETRG, (SEQIDNO:6027); XM_005636226.2, HVCN1, Ins, C_7, PRLQGHIKEALQLPQVSGYHHLPGHSGCPPGAGRAHSGPEDHPG, (SEQIDNO:6028); XM_014116431.1, ILL1, Del, C_7, PRLQPGEASGQPMPFLGGCT, (SEQIDNO:6030); XM_014111656.1, HDAC6, Ins, C_7, PRLQRHLEARC, (SEQIDNO:6031); XM_014117415.1, SHANK3, Del, C_7, PRLRRHPHQPPTTSTRGRPPPSRLRRPRAAPTTLCAPALSPAWRRAWARGPQACMRP GRPWGRCPTPSGRSARAP, (SEQIDNO:6032); XM_005621660.2, KREMEN2, Del, C_7, PRLSAAPAAPRQSSRCRCASASAA, (SEQIDNO:6033); NM_001003291.1, ICAM1, Del, C_7, PRLWKWAHSGLWTALWMGCSQLRRPKSTWR, (SEQIDNO:6034); XM_845262.3, ITGA10, Del, C_7, PRMLGLALPWVPFLI, (SEQIDNO:6035); XM_005620448.2, CHD5, Del, C_7, PRMPSTPTGWCGTSEGRARRSLEPMCPSSCGTCVSRGLMAQRPSRTVCPGRASRGST CSPASGSCH, (SEQIDNO:6036); XM_014107852.1, EP400, Del, C_7, PRMTITSMWIRSCVSRMRALPSQSPSCLPCT, (SEQIDNO:6037); XM_005616594.2, PLEKHG2, Del, C_7, PRNLWAFAGPRELLMPLSTR, (SEQIDNO:6038); XM_543867.5, PRMT8, Del, C_7, PRNPLNPSSQPSLCNVSIMCPLNPAAQDGVRCPSC, (SEQIDNO:6040); XM_014108968.1, PDZD7, Ins, C_7, PRNPSLLAHGPRHPHQLPHRSQQ, (SEQIDNO:6042); XM_005615881.2, LOC102155525, Del, C_7, PRPAAGLRRLPVTPATPFLPMQIPHGPPRPYPA, (SEQIDNO:6043); XM_005628616.2, RAPGEF5, Del, C_7, PRPAAPRVIGDTWSCPGPRRRFWSTF, (SEQIDNO:6044); XM_543274.5, IRS1, Del, C_7, PRPAARRS, (SEQIDNO:6045); XM_547886.5, ITC9, Del, C_7, PRPAASRRSRARRWKPSRSTATTAWQRACSRLSW, (SEQIDNO:6046); XM_014116613.1, SRCIN1, Del, C_7, PRPAASRSPPCWHPRTWGPLGAQPRAPHGRAVVAACHP, (SEQIDNO:6047); XM_014116610.1, SRCIN1, Del, C_7, PRPAASRSPPCWHPRTWGPLGAQPRAPHGRLPQAPGPSASPRSS, (SEQIDNO:6048); XM_005631406.2, SSH3, Del, C_7, PRPAATPRPWGPRRARHPSGEAGSSEGRALQCSVGLSWDCRMEKTMEKQLRPARR QWRDPWVKNSPTGTRQMMGKGSRVPGSRSRVSICISWWSS, (SEQIDNO:6050); XM_860394.4, DLGAP4, Del, C_7, PRPALAASATVARFQVHHA, (SEQIDNO:6051); NM_001081710.2, SSPO, Del, C_7, PRPALCLALPLALGRLSKLPWPVPAPRRPAVPLSSRAAAANARPGAGSATARRRTART AATSTAAAGPACPPHSCVTASRTARMAQTRALTPARG, (SEQIDNO:6052); XM_005635182.1, NFATC2, Del, C_7, PRPALPSSWTP, (SEQIDNO:6053); XM_533664.5, LTBP4, Del, C_7, PRPAPMAGVRTQKVASSASAPQASNPTRLAPSARMWMSVRITWHVLGRSV, (SEQIDNO:6054); XM_014116237.1, BAHCC1, Del, C_7, PRPARPQPLACPPRRITAPKPRRPRGRSPRAKTKPARRSS, (SEQIDNO:6056); XM_014119948.1, PKDLL1, Del, C_7, PRPARRALSPGPLVARATCWAPW, (SEQIDNO:6058); XM_005625727.2, TILLS, Del, C_7, PRPASCAGAHCRPAGPASAAAPSAPRCCRAPASWPWEAAGAAARGTR, (SEQIDNO:6059); XM_014110586.1, RREB1, Del, C_7, PRPATTWPSPGAGRRAWPSPPRIPAAGRSGRRFGRRALARLKLAGALPRPRRRAAPR SRGLRATRARRARRPSCKICPPVPCWPRTGPRRSWEWS, (SEQIDNO:6060); XM_014106264.1, LOC106557546, Del, C_7, PRPFPLRLRPTGYCALGTAERRGR, (SEQIDNO:6062); XM_014116616.1, TBKBP1, Del, C_7, PRPGCRPRPPRCPSRGPTASSTGPAGRSARGAGPSRASGCASRSSRRRRRSGPCPPARP APRRAPSAAPPSARASPSPRRRPPPTPTPSTRSPGRPSTC, (SEQIDNO:6064); XM_542508.5, GALNT18, Del, C_7, PRPGGSWRTPPPRSGALPSSAALSWIGSTSRRLAY, (SEQIDNO:6065); XM_014116627.1, TMEM145, Ins, C_7, PRPGQVRAGQPQLQRGLGVPDEVLLSFGLRPTGLPFPIP, (SEQIDNO:6066); XM_547204.4, LMF1, Del, C_7, PRPGSFCGASGG, (SEQIDNO:6067); XM_014113546.1, DNAH2, Del, C_7, PRPLASTPMRMWPPRSPRPELCLRLCCPCNPRLHPPG, (SEQIDNO:6069); XM_014108893.1, DOCK1, Del, C_7, PRPLLLTRGMFRLHCPARPHLRLLRRRRASRRQWTPESCS, (SEQIDNO:6070); XM_849158.3, ARHGEF18, Ins, C_7, PRPLLPSPT, (SEQIDNO:6071); XM_014115719.1, KIF26A, Del, C_7, PRPLPCASPAWNTRAARLPPR- PRPGA, (SEQIDNO:6072); XM_003639997.2, CALHM3, Ins, C_7, PRPLPLRPPRQPAVGGDG, (SEQIDNO:6073); XM_540094.2, MSGN1, Del, C_7, PRPLPRGCRVGWEAPRARGAGAGAAGCRWPTRCWPSRPPTCRALLAPRPRRAPRSG CRCSGDARPARGRSSG, (SEQIDNO:6074); XM_014121412.1, NCKAP5, Del, C_7, PRPLQTGQAPFSSSLVMTTCHHPHRPSPKPESPVKQQGPSSNPP1, (SEQIDNO:6075); XM_546308.5, PPARGC1B, Del, C_7, PRPLSQPPSPAAAPPSRSNPGPGPNTLPKAPGPSSPS, (SEQIDNO:6076); XM_847571.4, ANKLE1, Ins, C_7, PRPMGLQLRYVLCHRD, (SEQIDNO:6077); XM_005621273.2, FBRS, Ins, C_7, PRPMGPPAPQSSGLSCLGPAP, (SEQIDNO:6078); XM_014116841.1, DPH1, Del, C_7, PRPPGGPSWRRRSPRATLQSRLATVATAETKRERRGLS, (SEQIDNO:6079); XM_014121831.1, TLE6, Del, C_7, PRPPPAPPAPPRAPRKGAQSRAPELRACSPAWPRSLLGEPVHS, (SEQIDNO:6080); XM_003640189.3, FZD5, Del, C_7, PRPPPPPPTTSRCPCRTC, (SEQIDNO:6081); XM_845849.4, BTBDL1, Del, C_7, PRPPPPPPTTTTTTTTRSTRRPGSPWRRWSTRSTTTPKSGGSCSPTSTSSAGRTPAECC ACQTA, (SEQIDNO:6082); XM_014122215.1, LOC484907, Del, C_7, PRPPPSLTLGMRNTSCPPPRS, (SEQIDNO:6083); XM_014110917.1, LOC106558305, Del, C_7, PRPPPVVPPDRA, (SEQIDNO:6084); XM_014121804.1, CACNA1A, Del, C_7, PRPPRTALSSPTPAAPRPTQRRLPGNPTTPQWTSPQPARPPSTTLSSK, (SEQIDNO:6085); XM_014121783.1, PTPN23, Del, C_7, PRPQAPLLWSWPLVLLSTLPLPTLQSWDLCPGRPHSTVW, (SEQIDNO:6086); XM_014110163.1, MUC13, Ins, C_7, PRPQQSLPRSSL, (SEQIDNO:6088); XM_014117950.1, AKNA, Del, C_7, PRPRATAGSLRALPGL, (SEQIDNO:6089); XM_014115697.1, LOC102152805, Del, C_7, PRPREIGCVGRSRQAAAHGALRTAAGSIPGAGLDVQT, (SEQIDNO:6090); XM_014107737.1, ATXN2, Del, C_7, PRPRHPAPPRSAPARPRRAPASPRRARLPAVPARRAGRCMGPSPCR, (SEQIDNO:6093); XM_014109867.1, LOC611835, Del, C_7, PRPRPFAGLPSLARLGPRPRPVGSLERSRVPQPWTHPRSTLRVAFPPATPHSSWAPRL ASSAA, (SEQIDNO:6094); XM_014111713.1, ATP2B3, Del, C_7, PRPRPPTRTTTP, (SEQIDNO:6096); XM_014116941.1, LOC491253, Del, C_7, PRPRQLQTVTGCLQGLCGEWTRLWPAAGLTLGASWQRATAPWAKETRSLTPAPCR QRRRPGL, (SEQIDNO:6097); XM_014122283.1, ZSWIM4, Del, C_7, PRPSGAGAAPRDRRSAMPGPGPCAAGAGPRRCWTSAPSE, (SEQIDNO:6098); XM_014114212.1, LRCH4, Del, C_7, PRPSGPLLVWGASFFS, (SEQIDNO:6099); XM_014119269.1, LOC106559733, Del, C_7, PRPSGVSMEVALTAQAEN, (SEQIDNO:6100); XM_014106893.1, MAST4, Del, C_7, PRPSHPGPAA, (SEQIDNO:6101); XM_857738.4, SPAST, Del, C_7, PRPSLRISGTCTTSPTRCS, (SEQIDNO:6102); XM_005618689.2, GAK, Del, C_7, PRPSRPPRPVRSQGLTMLPT, (SEQIDNO:6104); XM_014119710.1, PPP1R13L, Del, C_7, PRPSTSWAAPLPRAAAPWPRGPRPSSPSAGPRHAPRPPPTTHPWPSGAPYWARAAAL SPRLCALKTT, (SEQIDNO:6105); XM_014110547.1, GABBR1, Del, C_7, PRPTRPWSSRHFASCHRSSSFQSLSSPAWALSWLWSVCPLTSTTLMSVTSRTPSPT, (SEQIDNO:6106); XM_845370.4, ZNF750, Del, C_7, PRPTTITGSSSSTIPTCPFHTGFTDQSLRSPPTVSDSRPSQVFPEIKAHTSWKKLPCSTRP, (SEQIDNO:6107); XM_861784.4, SERTAD1, Del, C_7, PRPWPPVPSWTFLCSSSTTACGRVSRTCGTWYW, (SEQIDNO:6108); XM_005637883.2, NANOS1, Del, C_7, PRPWRSCPAPAT, (SEQIDNO:6109); XM_544498.4, MYOM3, Del, C_7, PRPWRSTGWNTGRRRSTRKSGSTACRWVPRCGGGPSAAARKSISSAPQTTPWQQPW L, (SEQIDNO:6110); XM_005628400.2, AHCYL2, Del, C_7, PRQAAGTLRLQLPPRSGPRPLARALGPPPLSALPPGKCLRRRP, (SEQIDNO:6111); XM_014114982.1, BCAN, Ins, C_7, PRQADVGGGTGVLPGTGCRDCHHGPALCSLGRGPGPLQPGLAGRWQCALSHCHTQ PALRWGPAWCQDALPLPQPDRLSQQAQPLQRVLLPRLCPALRHA, (SEQIDNO:6112); XM_005625909.1, CSF2RB, Del, C_7, PRQAGARSRSLRGPWSTCVCRREGRYSWSRWPR, (SEQIDNO:6113); XM_014108804.1, SORBS1, Del, C_7, PRQARSQTSPASPVRTRPPLGGSPRFPNACLPDTPWRG, (SEQIDNO:6114); XM_850107.5, R3HDM4, Del, C_7, PRQHPASSQRPAAMRPTWRSGMTS, (SEQIDNO:6115); XM_014117947.1, KIF12, Ins, C_7, PRQPWLCQVSQRKES, (SEQIDNO:6117); XM_003639781.3, DCAF15, Del, C_7, PRQRHQLQSLVMSTTPSCITCWGPAKGQNRRTSSRMTRSPCPLW, (SEQIDNO:6118); XM_005625539.2, INHBE, Del, C_7, PRQRWPEPSADYSPEACL, (SEQIDNO:6119); XM_005624061.1, UBALD2, Del, C_7, PRQTLAPSGPRPHPATRLPGSRPPPPRPTVSTTSTTRSPRGPPGRSRGARSRRPWLPW MARD, (SEQIDNO:6120); XM_854849.4, SGK1, Del, C_7, PRQVLLSKSTWDHHPILMLNHLTFTS, (SEQIDNO:6121); XM_014108691.1, PCED1B, Ins, C_7, PRQVLPPAAHAPAAPALSSPPAQAAVPVRSPGCLLFLRPVFPVG, (SEQIDNO:6122); XM_535696.4, ENPEP, Del, C_7, PRRALRPRPRRPGTRGSVPPAKMTAGTGRTSGCRTSSARCTTTWR, (SEQIDNO:6124); XM_843782.2, LGR6, Del, C_7, PRRAPPSPAPHPPARRPAAAKRTASCCRPTARSSGCLPCPGTWTP, (SEQIDNO:6125); XM_014114725.1, CHTF18, Del, C_7, PRRAPRSPLSCGPRGPRMLLLTAASCGPPGRPEIRS, (SEQIDNO:6126); XM_849540.4, XBP1, Del, C_7, PRRASDSASRT, (SEQIDNO:6127); XM_014116465.1, NOS2, Ins, C_7, PRRASTSSH, (SEQIDNO:6128); NM_001003009.2, TPO, Del, C_7, PRRAVERARTAPLAAWCPPSGRRAGPGPWTPHPVGATWRREARH, (SEQIDNO:6129); XM_014116626.1, HSF2, Ins, C_7, PRRAVGGAGTSKRSCFHWCSLKWPEFSGFG, (SEQIDNO:6130); XM_014107665.1, HDAC4, Del, C_7, PRRCPWTSAWTTSLRCPWRSPPSGSSSCSRSYWPSSRSSSSRGRSSSPSSRGSTSSSPG STRPSCTST, (SEQIDNO:6131); XM_005616382.1, ZNF541, Ins, C_7, PRRGSLWGLPPRPRGGQPACTRWPAISGAPRSQVPQLPLAQPRPPALYCEQHRPPED PFSRPGRRGALRWQ, (SEQIDNO:6134); XM_545878.5, TMC3, Del, C_7, PRRIALHS, (SEQIDNO:6136); XM_005630789.1, SEMA6C, Del, C_7, PRRPCPAAAVSTS, (SEQIDNO:6137); XM_005635227.1, APCDDL1, Del, C_7, PRRPCPCAWAAGGSAPGARCAPLCCSSPGSSPSTGTTAPGRDITATSQTPPATSPPSRS TPRAATPGARRPARSSAAPNSCFRSRGPE, (SEQIDNO:6138); XM_843235.4, LOC607355, Del, C_7, PRRPCSSPCPSRTGFCWGPALPTWPRASWRPEGCR, (SEQIDNO:6139); XM_014122482.1, LOC102152187, Del, C_7, PRRPFPSRVREPARPAVSRSSRRAEGHGLHLEKSFAFLLSLFKPLLSEPLEEAWFLLE, (SEQIDNO:6140); XM_003432681.3, KMT2B, Del, C_7, PRRPHPHFLSLSLHPGGPCSFGHLSLPRAKPT, (SEQIDNO:6141); XM_014121829.1, TMIGD2, Ins, C_7, PRRPPGMWPPPPGHVRPPL, (SEQIDNO:6142); XM_542234.5, MAML2, Del, C_7, PRRPPKQPPPQPHRPRQTITITTSSTCSAVAIMVAVVGSTGSSRHKLQPLGTRGTQP, (SEQIDNO:6143); XM_014118793.1, JRK, Del, C_7, PRRPPLCPARPRPAST, (SEQIDNO:6144); XM_014107535.1, KIF13B, Del, C_7, PRRPPRRRTGRPAP, (SEQIDNO:6145); XM_549235.5, LOC492114, Del, C_7, PRRPRPTQTRRPHFPPSPVPADRPRPPLPRDSTRAPPAVGSRPAPSGRRSMPGPPPSPPS PPSPPLPRPALGRLRALRSL, (SEQIDNO:6146); XM_544046.5, BAG3, Ins, C_7, PRRPRRVPPPPAGLHCHSCPPRRRREPTTASSLCLSPAGDTALPNRGGHRGSSEVPVP SAGCGRGNPAR, (SEQIDNO:6147); XM_005639682.1, PAPD7, Del, C_7, PRRPSLITGSR, (SEQIDNO:6148); XM_014112159.1, LOC490881, Del, C_7, PRRPWRGAETGRDCSPSPGRAEAGVPRRRGSPGPNSNQ, (SEQIDNO:6149); XM_005625732.2, ALG12, Ins, C_7, PRRQPADKAGAPGETPWAVL, (SEQIDNO:6150); XM_014114365.1, SETD1A, Del, C_7, PRRQPMAYPMLCTHKGKKAGGHTPGKPTTCLCL, (SEQIDNO:6151); NM_001204439.1, PPAN, Del, C_7, PRRQRGLASRKKRRTKLSISARQWERSPMRTCSRKQPNADSSPGPQARSHEEKSGGQ MEALTTGLQRPRASPSGTRPSWDGEELSGTAGEAKLDHLRK, (SEQIDNO:6152); XM_534305.5, TSC22D2, Del, C_7, PRRRARPPGLGLRPQHSPPPLAVPVFESSSWTTGAGSPTDAADGRAWNTMSGIQTAA S, (SEQIDNO:6153); XM_014111170.1, PLEKHM2, Del, C_7, PRRRERGPAAQPRAASSRSPARWACLSPR, (SEQIDNO:6154); XM_547217.4, PRR35, Del, C_7, PRRRPPGRWPPGS, (SEQIDNO:6155); XM_005640052.2, JARID2, Del, C_7, PRRRPPWRRPCSTGT, (SEQIDNO:6157); XM_014108769.1, ARHGAP22, Ins, C_7, PRRRQQQGGPPGSRAGPWPGRGGRPRRRRRAQRPRRPDPGLRPLLRGSPGPRGAQ GTAVPAEDRVRHEYQKT, (SEQIDNO:6158); XM_014118210.1, CDK19, Del, C_7, PRRRRHHSRTAPRPTGPRAGLAQGPGLQVAACSTARTRASGRCPPARSPAWGPRVP TPAGPSCRQIISTPVLA, (SEQIDNO:6159); XM_531728.4, FAM83F, Del, C_7, PRRRRRPTSSRWSGR, (SEQIDNO:6160); XM_542033.5, IER2, Del, C_7, PRRRRRRARRSRPAAPRTAC, (SEQIDNO:6161); XM_005631006.1, COBL, Del, C_7, PRRRSPRRPAPWCRLALRTGRKTGRAPRVLDGRCHKSLPEALAGGPPS, (SEQIDNO:6162); XM_014121833.1, LMNB2, Del, C_7, PRRSCGRPRTAGALARASGLSWSTLMGRKWP, (SEQIDNO:6163); XM_014110056.1, LOC102151348, Del, C_7, PRRSLPPRNSPDPSSPARPAAATSPRPPPPPLPQWTKQKVAFPRRMTPPRPQGAWPPR LRL, (SEQIDNO:6164); XM_545710.3, USH2A, Ins, C_7, PRRSRSTQVPCSLFHPCSGQHQRP, (SEQIDNO:6165); XM_014120815.1, GRB10, Del, C_7, PRRSVRSPCTSSPSDACRKKTSSSEPRLCRPSPTPSPSSAAPGARRC, (SEQIDNO:6167); XM_014110313.1, TRIO, Del, C_7, PRRTAARGAARARCPWQSPGLGPPRL, (SEQIDNO:6168); XM_849601.5, PLIN5, Del, C_7, PRRTFPRRSPRPPAAPSTP, (SEQIDNO:6169); XM_005621599.2, UBA1D1, Del, C_7, PRRTSPTPPPPASPPRAGLLQPHPRGAHSTTSHSSRPCGLRHPPPRRQTGHPWPPNRPL QNRGPTLRWRLKD, (SEQIDNO:6170); XM_014117449.1, LOC102154536, Del, C_7, PRRVRSATYIGWSGLIGTVPALPLTTEGFWKPGRGLVSLFAIPCVNNVNFIGLLREGIP I, (SEQIDNO:6171); XM_014120865.1, TDRD12, Del, C_7, PRRWSLLFAE, (SEQIDNO:6172); XM_014114472.1, ZSCAN10, Del, C_7, PRSAGSAARASAAAVICCATCWCTPAPGPTRARSVAAASAATPTCCAT, (SEQIDNO:6173); XM_005625433.1, NOTCH1, Del, C_7, PRSAPPMATIVAT, (SEQIDNO:6174); XM_548709.6, DPYSL4, Del, C_7, PRSARTPALPTTSPPCCPAGTCR, (SEQIDNO:6175); XM_857873.4, PTPRF, Del, C_7, PRSCQGSCWATGYSTTVPMRQSPTS, (SEQIDNO:6176); XM_847178.3, PTPRU, Del, C_7, PRSCSARGPPTSSSSSTPTPSLATGRSCARRLSIACPAARGPRCTPSACRPTSCGTLTPT PSTRSAYCSRARVRAAPAARGRPSSAAPNAQNP, (SEQIDNO:6177); XM_014117950.1, AKNA, Del, C_7, PRSCSLRRAGRPRTVQRQLGTE, (SEQIDNO:6178); XM_533102.5, KMT2E, Ins, C_7, PRSEQHGTAPSTPSAPLLLVLLSKPAALCELSEL, (SEQIDNO:6179); XM_014111003.1, MAP2, Del, C_7, PRSGRISPRPRWRLRVSSLAP, (SEQIDNO:6180); XM_849982.3, TLX2, Del, C_7, PRSGRSRARPSPARRCWSWSGASCARSTWPPPRGQRWPRPCA, (SEQIDNO:6181); XM_003640238.3, IKBKG, Del, C_7, PRSHRTSAAPSASIRPLIWTPCRYTSWSASS, (SEQIDNO:6182); XM_014117000.1, HMCN2, Del, C_7, PRSLAPGSRTHRSPWSGTGRPLCGATPRGSPRPG, (SEQIDNO:6183); XM_014107674.1, TRAF3IP1, Del, C_7, PRSLRCQNLKWCPRWT, (SEQIDNO:6184); XM_014110341.1, AIMIL, Del, C_7, PRSLVLLWR, (SEQIDNO:6185); XM_538386.5, SH3BP1, Del, C_7, PRSPACAPPLQPPSHPLALAALWPPRLCPAVWLAATSGPPQCHPPCPPILPSPPGARA GVHRPPPARPPRGHPHPARSL, (SEQIDNO:6186); XM_005621273.2, FBRS, Ins, C_7, PRSPFGGPTSTCARPQA, (SEQIDNO:6187); XM_003434673.2, C5H1orf233, Del, C_7, PRSPPRPPSAWSSQPSRPACGRS, (SEQIDNO:6188); XM_014110953.1, STK36, Ins, C_7, PRSPPSEPATAGAE, (SEQIDNO:6189); XM_014108277.1, LOC106557868, Del, C_7, PRSPQAPAAAALHLFPGKAASPSRGKAVGRAGGSRGPAGEAAEARRAGRSPRRPRA VSEPEALLGELSPASSSGSRKS, (SEQIDNO:6190); XM_014106443.1, MYO16, Del, C_7, PRSPRGARPAEQRGWPAPTCPRRRSRAPRPREARAAPSPRPPTPPGG, (SEQIDNO:6191); XM_014121988.1, WIZ, Del, C_7, PRSPRRACLSLGPWNRWPIG, (SEQIDNO:6193); XM_543178.4, GJA3, Del, C_7, PRSPRRPRSPSGSRPSALPRPPPRDRPPPRATPGRPHWPQTSTRQPCPRPARGTSTCS, (SEQIDNO:6194); XM_005616171.2, TNNT1, Del, C_7, PRSQKGNVWTSMTSTASAWRKICWSCRRSSTCILNSGRKRKRSS1R, (SEQIDNO:6195); XM_005616456.2, GEMIN7, Del, C_7, PRSQRFPKPWGLQ, (SEQIDNO:6196); XM_005622301.2, FCMR, Del, C_7, PRSQSLTTFEFPEHLQ, (SEQIDNO:6197); NM_001003295.2, HSPB1, Del, C_7, PRSRAPPRPPRPPTAARSAGSSAAACRRSGRRPTAGACPWTSTTSPPRS, (SEQIDNO:6198); XM_014106300.1, FARP1, Ins, C_7, PRSRARRP, (SEQIDNO:6199); XM_848173.4, ZFHX4, Del, C_7, PRSRPRWGPGSCPAPGPGPRPCRRPRPRPRRRPRPRRRRRRRRRPRRPRRCSCPCPW TCRSSRPS, (SEQIDNO:6201); XM_014113960.1, FOXL1, Del, C_7, PRSRPTATSRS, (SEQIDNO:6202); XM_014118510.1, ZFPM2, Del, C_7, PRSRRTFPRTLSTTMATSRPPGSPRTR, (SEQIDNO:6203); XM_005628902.2, PABPC4, Del, C_7, PRSRSRCWENVCSHSSKPCIQTWLEKSQACCWRSTTLSCCTCWSPLSLSAPRWMKL WRFYRLIMPRKKLPRRIQKPN, (SEQIDNO:6204); XM_851907.5, PABPC4, Del, C_7, PRSRSRCWENVCSHSSKPCI- QTWLEKSQACCWRSTTLSCCTCWSPLSLSAPRWMKL WRFYRLIMPRKKLPRRWALLLLLPL, (SEQIDNO:6205); XM_003639850.3, VPS16, Del, C_7, PRSRWSGAAVLAAKRGLSWWHGRGV, (SEQIDNO:6206); XM_844054.5, BNIP3, Del, C_7, PRSSCSSTRSARPRSACGTQA, (SEQIDNO:6207); XM_546245.4, FOXI1, Del, C_7, PRSSPRLPHPAPHASTASSPP, (SEQIDNO:6208); XM_014106943.1, RIN2, Del, C_7, PRSSPRRRGTAPSCCPSWSSRSCAR, (SEQIDNO:6209); XM_541408.4, ZNF579, Del, C_7, PRSSSAPPVSTAKTIQPLRWKKKRSTARPTCVDWEAWPP, (SEQIDNO:6210); XM_533117.5, FDXR, Del, C_7, PRSVWWAVDPLASIPPNTC, (SEQIDNO:6211); XM_543112.5, MYT1, Del, C_7, PRSWPCTRTC, (SEQIDNO:6212); XM_849841.4, APOA1BP, Del, C_7, PRSWSSADLEITEETAWSALGTSSSLATSQPFIIPKGRTSHSSPHW, (SEQIDNO:6213); XM_005621574.2, RBFOX1, Del, C_7, PRTASPRSTRPLTPTPLRSTRARPPSPSTR, (SEQIDNO:6216); XM_003431951.3, HIVEP3, Del, C_7, PRTCLASPKSSCPVPPRCP, (SEQIDNO:6217); NM_001287079.1, NCLN, Del, C_7, PRTCRSSRSR, (SEQIDNO:6218); NM_001287078.1, NCLN, Del, C_7, PRTCRSSRSRCRSSRSSWTQ, (SEQIDNO:6219); XM_014118871.1, LOC106559658, Del, C_7, PRTGEMRSLEQNLAPGVSPMSPAPPTPQRLS, (SEQIDNO:6220); XM_014121010.1, MAP3KL1, Ins, C_7, PRTGQLGCADCPWDALPAL, (SEQIDNO:6221); XM_005628976.2, GJB4, Del, C_7, PRTGTLSS, (SEQIDNO:6222); XM_853562.3, R3HDM2, Del, C_7, PRTHPWSSGVTVNITAWTSVGRNLETYTILTVAPRPTLK, (SEQIDNO:6223); XM_014107603.1, HJURP, Ins, C_7, PRTLGCGHVQG, (SEQIDNO:6225); XM_005635367.1, LAMA5, Del, C_7, PRTLRAPHPGPSAPSKTPTSLGAPCLVTWSSPACRPPPGTGSTCRCWCAPTSREDSCS SRPPSQMAAPPWSSS, (SEQIDNO:6226); XM_014113666.1, RAI1, Del, C_7, PRTNWEASSEPPSSLASGWASRHPRRRPAPVTRPPCRWPRIAAPWAPRPRRQTLPAP RARTSAL, (SEQIDNO:6227); XM_539058.4, SIM1, Del, C_7, PRTNWLPLMELGKNTPSVLQTTNSPHQQAKSVTALLLPTLHHVTTSSRERERC, (SEQIDNO:6228); XM_014111262.1, KIRRE1, Del, C_7, PRTPGSTAAPCSCCRPAPRTTSPAEPSTPSRPPPSSGSGTGRSRRAPWPARNC, (SEQIDNO:6229); XM_846145.3, EGR1, Ins, C_7, PRTPVRLPGRVLRPSLLPLRRAHAPHPHPHRPEALPVSHLHAQLQPQ, (SEQIDNO:6230); XM_005624045.1, DNAH17, Del, C_7, PRTPWSMSRPPS, (SEQIDNO:6231); XM_005621046.2, NYAP1, Del, C_7, PRTRLCLTPWYTRQSR, (SEQIDNO:6232); XM_014121712.1, ARHGAP21, Del, C_7, PRTRPWPGLAPGNAAAPKPAAPPQIAPARRPPRR, (SEQIDNO:6233); XM_005633459.2, MYO7A, Del, C_7, PRTTTRLSSGSTTLQASSTMRAKASWRRTGTPCMETSSSWSTPPETSSSSRSSRLMSP WAPRQGSARPHSAASSSGPWSC, (SEQIDNO:6234); XM_005620608.2, SLC12A4, Del, C_7, PRTVKVMRTTWSSWRC, (SEQIDNO:6235); XM_005626938.2, RNF183, Del, C_7, PRTWALPPGLCPFPSPATTLRGSVSATLSSGSLLT, (SEQIDNO:6236); XM_538929.4, PTK7, Del, C_7, PRVCQSPVYGGSMQEPGYPPMAESSKRAMNWCLLVPPRVMLVSTPAMQPTIVLVSG DKMSISLWPLCPHG, (SEQIDNO:6238); XM_005640629.2, TNS1, Del, C_7, PRVLALAAGPSTPAWLPPGVPA, (SEQIDNO:6239); XM_005626612.1, TPD52L3, Ins, C_7, PRVLLHQPGVGPYRFGFPLCWPRFSLRWPPVQLSVPGTGPGLSS, (SEQIDNO:6240); XM_537319.5, ZBTB14, Del, C_7, PRVRRTASRPRRRSGFRRQS, (SEQIDNO:6241); XM_005621644.2, ZNF213, Ins, C_7, PRVSGGGPWGGSRSADREGGRFFLGAGLCPARRQQGF, (SEQIDNO:6242); XM_537395.5, NFATC4, Del, C_7, PRWARGGRGKNWTQRTPRHAAVWPWGSPLPMALPLLAFPGLHPLGLACIRHHPAR PPHLALGRASLPGQ, (SEQIDNO:6243); XM_014114273.1, CPSF4, Del, C_7, PRWEPVWALLGSMR, (SEQIDNO:6244); XM_014107816.1, HECTD4, Ins, C_7, PRWHSRFPRLSLHPSGDLHVHDQTSPVLLSGNHAGETSLCHSLP, (SEQIDNO:6245); XM_014106282.1, STK24, Del, C_7, PRWKEPTANPSRNLLKPV, (SEQIDNO:6246); NM_001008276.1, RHO, Ins, C_7, PRWLVQSPVSLPSGAQVHPRGHAVLMWDRLLHTQARNQQ, (SEQIDNO:6247); XM_005632035.2, RHO, Ins, C_7, PRWLVQVHPRGHAVLMWDRLLHTQARNQQ, (SEQIDNO:6248); XM_014120952.1, ZP1, Del, C_7, PRWPATSLSLGTSWCLTLTSEMGHRAPSCRMAPSVRQSLLRTGHAVGLGVKGAQRS RSHR, (SEQIDNO:6249); XM_005641932.2, MAM1D1, Ins, C_7, PRWPDLTPGLQ, (SEQIDNO:6250); XM_543071.4, NPEPIL, Del, C_7, PRWPSSATPQKEPPRPLHGWAKGSSMTPGVSASKGRPPCLG, (SEQIDNO:6251); XM_005631778.2, MAML3, Del, C_7, PRWPTPTRTR, (SEQIDNO:6252); XM_014117336.L MKL1, Del, C_7, PRYAASRLPVAAPARVLLGPVGWHVRTAPH. (SEQIDNO:6253); XM_014118288.1, LENG8, Ins, C_7, PSAAASSPAPSALQPPAWGSCSEQWPPAWNSPSHTAQPGRACLRPGLWATC1L, (SEQIDNO:6254); XM_014106807.1, DCLK3, Del, C_7, PSAAQRGTRMSSL TSSSWATSNSWPLTGTIFLTLPKIW, (SEQIDNO:6255); XM_005638682.2, SHF, Del, C_7, PSAASLKSCTTTPAASCPSRGPSTCPCSTLWPFGLC, (SEQIDNO:6256); XM_014118741.1, SCRIB, Del, C_7, PSACHWWVLMTCARCRRRKPESCSRRGRS, (SEQIDNO:6257); XM_547396.5, SERTAD4, Ins, C_7, PSAFTELFPPGGF, (SEQIDNO:6258); NM_001003202.1, TJP3, Ins, C_7, PSAGKFSGFQNHLGTRRPEAQQL, (SEQIDNO:6259); XM_014106883.1, PTK6, Del, C_7, PSAHPPHTS, (SEQIDNO:6260); XM_014108635.1, ZNF641, Ins, C_7, PSAKVPCVH, (SEQIDNO:6261); XM_014118847.1, ANKRD17, Ins, C_7, PSALFERYRFNHSSR, (SEQIDNO:6262); XM_846038.3, C17H1orf56, Del, C_7, PSALGSDPPPSFSLAPAPAPAPAPAPVQPLLFGDESGSGWRIFGTVCLQCSQRCNQ, (SEQIDNO:6263); XM_003639867.3, ZFP64, Ins, C_7, PSALGVPERGGRDEPARCPADHSRPGRWGHPAPDAHPHHPRQPPGRLRQPDFHHQF GYYMH, (SEQIDNO:6264); XM_014106638.1, NOD2, Del, C_7, PSALPWPLCCGTSGGLWPCSWTTTLLVTLAWSSCCRASVSARLFTCEITISQTEASVS SSSMLCTASSCRS, (SEQIDNO:6265); XM_005635245.2, PHACTR3, Ins, C_7, PSALRISGLRDPHSPGEEEQQAGHPGQDLQTLEMEEEEKRKTEADDVRAGEEDDRQ ARSGGAHQEGSAGDDGAGC, (SEQIDNO:6266); XM_014109616.1, SNX33, Del, C_7, PSALRLSTAPFLTRAAPMKLWVRCSPSSPRMTSSRCSTRCPSTRACSQISLTSSTCRKA PSPR, (SEQIDNO:6267); XM_014117109.1, ESYT1, Del, C_7, PSAPRCSRTARALLRSIGVEAKGELGWQQRFRAVGGE, (SEQIDNO:6268); XM_005619991.2, EFNB3, Del, C_7, PSAPTMRR, (SEQIDNO:6269); XM_014117108.1, LOC106559343, Ins, C_7, PSARAAGLPRDAGTAAA, (SEQIDNO:6270); XM_014119796.1, KDM7A, Del, C_7, PSARGRCRST, (SEQIDNO:6271); XM_005621365.2, ATXN2L, Del, C-7, PSARTNTSQPQPLR, (SEQIDNO:6272); XM_547204.4, LMF1, Del, C_7, PSASGTWRTTSAPGSGRTRPWMWT, (SEQIDNO:6273); XM_014121956.1, DOCK3, Ins, C_7, PSASPKPAAWSLLPT1, (SEQIDNO:6274); XM_014121827.1, PTPRS, Del, C_7, PSATGRSCGTKSH-PRTSR, (SEQIDNO:6275); XM_005631734.1, MUC5AC, Del, C_7, PSAVLRNRLCQAR-TAAVCPVLYTHPTPVQRAQCTTSSRSSAS-KAAAPPGLCTSPTAR ATVETAPPGTWRPRP, (SEQIDNO:6276); XM_536750.5, CDH15, Del, C_7, PSAYPRTTSASRIPWCRSNRTSSHWAVSSTAS-RGPAWMRSPRACSPLTSSPGRCS, (SEQIDNO:6277); XM_014108022.1, LRRC43, Del, C_7, PSCACWA-VACWPWSPCWRGSHLCPPCATLG, (SEQIDNO:6278); XM_014115762.1, CDH24, Del, C_7, PSCLRAST-SSLWWKRRGQAPWWAGCGPRTQTWGTMPSWHIAS-WTERGLKPSASA QTPRVEMGSSLSARP, (SEQIDNO: 6279); XM_531753.4, BPIFC, Del, C_7, PSCQFLLHCQNAVTLCSMLESPSFSLNLHPLLTL, (SEQIDNO:6280); XM_014116949.1, KCNT1, Ins, C_7, PSCRGNERMAPTWLSCSACHSLQAASSAS-ACWTRCFTSPL, (SEQIDNO:6282); XM_858879.4, EPHX1, Del, C_7, PSCRPAAPQSPC, (SEQIDNO:6283); XM_541489.6, MED25, Del, C_7, PSCTHHLPSPGPHSF-PRELRCQVRCC, (SEQIDNO:6284); XM_005616290.2, MED25, Del, C_7, PSCTHHLPSPGPHSF-PRELRCQWQNERETERATCFEKNGSEPISLWK, (SEQIDNO:6285); XM_005623705.2, TMED8, Ins, C_7, PSD-GASMHLDLCQDERI, (SEQIDNO:6286); XM_014116993.1, NUP214, Ins, C_7, PSEIHCSSQPVPVSLPVTEIL, (SEQIDNO:6287); XM_535042.5, TACC2, Ins, C_7, PSERDTTRAR-GRVSRPQRGD, (SEQIDNO:6288); XM_014121412.1, NCKAP5, Ins, C_7, PSERILCSYYFF, (SEQIDNO:6289); XM_005617055.2, KIAA1462, Ins, C_7, PSESRPRPPD-EDEGDSYDPSRVERV, (SEQIDNO:6290); XM_854764.4, MAP1A, Del, C_7, PSFILHCWEMGSTLLV, (SEQIDNO: 6292); XM_536461.5, FAT2, Del, C_7, PSFREGTVN-KEERTARPCPAWKVALASHLLKVPPVTALTLI-WETGVKWKQGAAQK DTV, (SEQIDNO:6293); XM_014116591.1, NOVA2, Del, C_7, PSGAASPWPRSCLPSTTSPYTPATMSTSHP-SCLTPLWNAPTLLVPTCKSERAHTRLKV ETRPL-TALPPPPVPLQRKANTS, (SEQIDNO:6294); XM_845495.4, DGKZ, Del, C_7, PSGDLGGTRCPPKVKS, (SEQIDNO:6295); XM_014107649.1, LOC106557788, Ins, C_7, PSGEQRGPSPRSRGLPGAGGGRPYSALQPARRTP-GAESGGPRGRFWRAPTSQRP, (SEQIDNO:6296); XM_005640123.2, BTN1A1, Ins, C_7, PSGGDFPGL, (SEQIDNO:6297); XM_547146.4, NMRAL1, Del, C_7, PSGGGLGCKVPGGGRGAGCSVLPSSVSHPGCG-GRWGPGRGRGAER, (SEQIDNO:6298); XM_005624366.2, FMNL1, Ins, C_7, PSGHLGSLAL, (SEQIDNO:6299); XM_545182.4, ICE1, Ins, C_7, PSGILTT-PEHFTFFARTRNLLWRVYRFQ, (SEQIDNO:6300); XM_014119925.1, ZNF672, Del, C_7, PSGRAAVPCA-PAPSGRARCGPTRRGRTRGPCPPCPAPRPSAAR-RAHGPSAATRSHGA AAARPRAPASPQGLRPRRPRT-SAVCAGRASARAPH, (SEQIDNO:6301); NM_001003009.2, TPO, Del, C_7, PSGR-RAGPGPWTPHPVGATWRREARH, (SEQIDNO:6302); XM_548107.3, KRT36, Ins, C_7, PSGSQQDPG, (SEQIDNO:6303); XM_005626260.1, ATP6V1B1, Del, C_7, PSGTAKPWWHCQRFCWLNIALCQQAPLKRGPL-RASCRCPSQRGALWAGA, (SEQIDNO:6304); XM_005642488.1, C1QTNF8, Ins, C_7, PSGTDSSLRP-PAPPGATCGA, (SEQIDNO:6305); XM_003639985.3, INPP5F, Ins, C_7, PSGVHLCR, (SEQIDNO:6306); XM_005621293.2, SRCAP, Ins, C_7, PSHKPPLGLGA, (SEQIDNO:6310); XM_014112912.1, ARIDIB, Del, C_7, PSHPPSEGRSPFLLAQSRRRSQS, (SEQIDNO:6311); XM_538386.5, SH3BP1, Ins, C_7, PSHPPST-PAQEPCLRDR1, (SEQIDNO:6312); XM_014111810.1, PRICKLE3, Del, C_7, PSHPQDSPASLTHPWKMVPLVA-RAPPASASVTLWYPREAHGEP, (SEQIDNO:6313); XM_014113666.1, RAI1, Del, C_7, PSHSPCQGAWANMMTT, (SEQIDNO:6314); XM_014122040.1, BRD4, Del, C_7, PSHSRHPSSST-SPRHGLCTCSPCSSLPTSSSPRRPRASSPRTR-PRASSRRLHSPPSLSRSS SITLHPGTTSRTPILPVT-SEKPPPRL, (SEQIDNO:6315); XM_543689.5, CACNB3, Ins, C_7, PSIASQAEAKAGRACSPL, (SEQIDNO:6317); XM_014111820.1, SLITRK2, Del, C_7, PSIESTSFSS-METS, (SEQIDNO:6318); XM_014112907.1, SEC24C, Del, C_7, PSIFNIWIILANVSMLMTVLSYPWALMN-SWPL, (SEQIDNO:6319); XM_847901.4, HNF1B, Del, C_7, PSIPIPPGFHLRWWSRIPAASVRLPTCLPVN-SAPSKPG, (SEQIDNO:6320); XM_014120097.1, POU2F2, Del, C_7, PSIPSPLSLPHPRPPPTAQIPAL-KAATRPSACRA, (SEQIDNO:6321); XM_014118383.1, UHRF1BP1, Del, C_7, PSIQHLQALSPSL, (SEQIDNO: 6322); XM_005637906.2, TUBGCP2, Ins, C_7, PSI-SAQGRRPCPV, (SEQIDNO:6323); XM_014116482.1, SOCS?, Del, C_7, PSIS-SVRSTGPTQAALQPAFESWRSVVGTGDQ, (SEQIDNO: 6324); XM_014111152.1, HHIPL2, Del, C_7, PSIWSWGF-GASGRWWSARPMQLISTTPRTLRRPSGTFLASALT-TALPSILTATLPFPY, (SEQIDNO:6325); XM_014107872.1, VPS37B, Del, C_7, PSKDSLHSS-CLHTHPLFPRDPRPGCLHTSQASSSS, (SEQIDNO: 6326); NM_001287169.1, SLC7A8, Del, C_7, PSLAFD-SWLPSAYCSSHGSTVPVCGGPPGFKTFSQLGSSWPWP, (SEQIDNO:6327); XM_005632035.2, RHO, Del, C_7, PSLAGPGTSQRACSAHVGSTTTHSSQK-STMSPSSSTCSWSTSPSP, (SEQIDNO:6328); NM_001008276.1, RHO, Del, C_7, PSLAGPVSCLTPLWCSGTSQRACSAHVG-STTTHSSQKSTMSPSSSTCSWSTSPSP, (SEQIDNO: 6329); XM_540216.5, DOK1, Del, C_7, PSLAPRLSAWT-PRSAPTCWRPTRRPAPPGCRPCAETPFRKAAGLWR-LRKTHPSFLPW RCWRTRCIVPPGKDPSSG, (SEQIDNO:6330); XM_003639255.2, LOC100856208, Del, C_7, PSLEQRRTLILVPSSTSLPVCPTYGTSSAS-CSVPLWSLCARPQAI, (SEQIDNO:6332); XM_547068.4, TBX6, Del, C_7, PSLGQIPASRLPWQRATATLIWTLPS-WIASSPGLKLLPAPWPLPQPCPRYPQPWALSR PPQPQRSFIRSPESA, (SEQIDNO:6333); XM_545660.5, INHA, Ins, C_7, PSLGRAASGPLRPPSADQPRP-GAAAALPRLFLRSRAR-GHPLLGGPHAGQAAQRRGED PPLRLPAALAVVS-GRAAPAPEVPRGARRPR, (SEQIDNO:6334); XM_014115267.1, ENAH, Del, C_7, PSLHLDFLRH-PRPKTIAL, (SEQIDNO:6335); XM_005618169.2, ANKRD34B, Del, C_7, PSLIPVSI-TRFPASFLVVRKCLCQQFLCSLKNSKVKKCC, (SEQIDNO:6336); XM_014117542.1, BCL11A, Del, C_7, PSLLCNPPLLPPSPRSSPSRASSAARRSNFRATSWCT-GAATRARSPTSATCATTRARRP AS, (SEQIDNO:6337); XM_005636179.2, SETD1B, Del, C_7, PSLLHPHLHPLL-SPPSCPLRS, (SEQIDNO:6338); XM_849796.4, TCF7L1, Ins, C_7, PSLPAPPPRVPAHSSADLSPLLPSHTPCPPGP-PRAPGPASFLGHQVCPL, (SEQIDNO:6340); XM_014115373.1, DCST1, Ins, C_7, PSLQAPDP-NEAHPHQRDGLLALQG, (SEQIDNO:6341);

XM_014116580.1, PNMAL2, Ins, C_7, PSLRRGGLPASP-PASPRLSVPASQVAERPGGRTEMRVPPARRGPR, (SEQIDNO:6342); XM_005638009.2, CHD7, Del, C_7, PSLR-SPMVAVAVRWESTLACRMKGTGSHSWTVAPCGAPGL-CRCQTRYGPPTSSSH SHSRPSPLHRGL1HRATLSTCS-RWAATWHVGIFPCSSMVSHSRG, (SEQIDNO:6343); XM_539966.5, PLEKHA2, Del, C_7, PSLRVATV, (SEQIDNO:6344); XM_005620646.2, TAF1C, Del, C_7, PSLSLPVATPSPHSPCWSPGVSGGCRSV, (SEQIDNO:6345); XM_005617981.2, PRDM2, Ins, C_7, PSLSSRVDCCHATASTPSHRPSSGPLF, (SEQIDNO:6346); XM_014121529.1, THSD7B, Ins, C_7, PSLWWVPVSQPDRVKSL, (SEQIDNO:6347); XM_541780.5, CAMK1, Del, C_7, PSMTRMMPNSLNRF, (SEQIDNO:6349); XM_014120337.1, BIRC6, Ins, C_7, PSNAVSPQTVHD, (SEQIDNO:6350); XM_532844.5, SLC25A4, Del, C_7, PSNPHRSSM-PANRSVPRSSTKGSLIVW, (SEQIDNO:6351); XM_005639524.2, ARHGAP31, Ins, C_7, PSNSSGG-GASNPAAKGRPRGSRPVQELEDTGVHR-PAEARGQPGGPSPVSGAGGPSRT KGKAKFKECCSGS, (SEQIDNO:6353); XM_005623664.2, PGF, Del, C_7, PSNWPCLLEMAHQRWKWCPSSKCGDAATAGHWR-SWWTSCRSTRMRWSTCSTHPA SPCCA-VVAAAETKTCTVCRWRRPMSPCSPTRHRGRT, (SEQIDNO:6354); XM_014116070.1, PGF, Del, C_7, PSNWPCLLEMAHQRWKWCPSSKCGDAATAGHWR-SWWTSCRSTRMRWSTCSTHPA SPCCA-VVAAAETKTCTVCRWRRPMSPCSS, (SEQIDNO:6355); XM_005616367.2, C1H19orf68, Del, C_7, PSPAARPSSSSS, (SEQIDNO:6356); XM_533813.5, DOCK3, Ins, C_7, PSPACPDSAQVSSPPYPGL-PHQPPVGSGRQQLYTVWQCQQRRVLPERE, (SEQIDNO:6357); XM_005642449.1, ARIH2OS, Ins, C_7, PSPACRGKQGRDPRRTLTGSRSP, (SEQIDNO:6358); XM_848813.4, ACD, Del, C_7, PSPAGPP-PAVGPREKLCTLSPAPGCTSRRMTSEF, (SEQIDNO:6359); XM_844620.4, C5H17orf74, Ins, C_7, PSPAHL-HAAQQDPRRQCRLPGV, (SEQIDNO:6360); XM_014111220.1, ELK4, Del, C_7, PSPAPGPPAATTIYT-PACILPSLSTL, (SEQIDNO:6361); XM_005625737.2, ZBED4, Del, C_7, PSPARTARRTGRRGIPRLPRAL-RAPGGGRLCGSTSTCRPWTTPRPCASTA, (SEQIDNO:6362); XM_014116470.1, RARA, Del, C_7, PSPAST-SLALSVKTNLQATTMGSAPVRAARASSAAASRRTWC-TRVTGTRTVSSIR, (SEQIDNO:6363); XM_014108967.1, PDZD7, Ins, C_7, PSPATPCRSPAPKA, (SEQIDNO:6364); XM_014112392.1, MEF2A, Del, C_7, PSPDRKW-GAPLWTV, (SEQIDNO:6365); XM_005640788.1, NUAK2, Ins, C_7, PSPGAAPP-SQRHPQTQWFSPLSHPSNLAQASWTRC, (SEQIDNO:6367); XM_005640789.2, NUAK2, Ins, C_7, PSPGAAPP-SQRHPQTQWQVLLHSPGAPDPLHLRLPG, (SEQIDNO:6368); XM_005628297.2, SCX, Del, C_7, PSPGREMPRAPSSWREAAEGRGPLL-PAASGAGRRGGGRAGAGEGPPPL, (SEQIDNO:6369); XM_005619930.2, MINK1, Ins, C_7, PSPGR-PRASGPPFPNSAYAEAGGAPGGTAQEPGGTPGPTEA-ICSACTPIPVPAGPAHP KPGCLPSLP, (SEQIDNO:6370); XM_014116619.1, SP2, Del, C_7, PSPHHGNSSPSNLPLSLSVLARIASESCPPKETSFR-FRGHN, (SEQIDNO:6372); XM_544370.5, ZNF366, Del, C_7, PSPITCTSSTEMRV, (SEQIDNO:6373); XM_533193.5, CKAP5, Del, C_7, PSPLPRT-CCTANSLSSGSPGSSSTSTQTWILTRLTLQEA, (SEQIDNO:6374); XM_003640232.3, RAI2, Del, C_7, PSPLT-PRCPPWCPRPPSWCPTL, (SEQIDNO:6375); XM_547735.5, ZFHX2, Del, C_7, PSPMSPQPQRLQSLLNWLLQGRGSPGRLTSCCQAV-LASPPWM, (SEQIDNO:6376); XM_849952.3, INTS5, Ins, C_7, PSPPSTPTLPCPCWGTWSRRCGAGSTAGAV, (SEQIDNO:6377); XM_014107801.1, CCDC92, Del, C_7, PSPPTAAQVSGTAQPASSSTRLMWGWPIASTML-PHHTPSLSWRRWQSTR, (SEQIDNO:6378); XM_005633780.1, LOC102154018, Ins, C_7, PSPPTPP-DASFPASIS, (SEQIDNO:6379); XM_014112086.1, LOC106558514, Del, C_7, PSPRALCSGAQGSP-GAQDLCY, (SEQIDNO:6380); XM_547068.4, TBX6, Ins, C_7, PSPRGPSFAPRSQPEPGQPGAVERVQFCGNRD-DHHQSWEAHVPCLSSVSHWPGP, (SEQIDNO:6381); XM_846419.3, ZNF362, Del, C_7, PSP-SAAAKRSRRRTQGGRLSS, (SEQIDNO:6383); XM_003431800.2, ZNF16, Ins, C_7, PSPSAARLGHQD, (SEQIDNO:6384); XM_545695.2, AVPR1B, Del, C_7, PSPSAPASVGAPGLKAHPKTQRRWTQRPPQRPSPF, (SEQIDNO:6385); XM_014116208.1, ITGB4, Del, C_7, PSPSKMLSA, (SEQIDNO:6386); XM_014109372.1, BCL2L10, Del, C_7, PSPSLSLRPLRSRARL-WAWPLRPEQVRTGFPSEALLGT, (SEQIDNO:6387); XM_014111262.1, KIRRE1, Del, C_7, PSPSPGPKRIQTWGPGLLAPHPRLLSLPRS, (SEQIDNO:6389); XM_005640916.2, KIRRE1, Del, C_7, PSPSPGPKRIQTWS, (SEQIDNO:6390); XM_014119710.1, PPP1R13L, Del, C_7, PSPSPSFHPSP-SHSPRLNRLPQPPSLPHRLGPL, (SEQIDNO:6391); XM_005634655.1, MED12L, Del, C_7, PSPSRPRSPRVR-PLVSKRCSRSS1, (SEQIDNO:6392); XM_014116529.1, NAGS, Del, C_7, PSPSSPPGPRQAARWCSGTSRPF, (SEQIDNO:6393); XM_003639997.2, CALHM3, Del, C_7, PSPSSSAASSPTGSRW, (SEQIDNO:6394); XM_546571.4, KIF1C, Ins, C_7, PSPSVPFTSPRTQWGA-GAIVLPQCRAPDWA, (SEQIDNO:6395); NM_001168461.1, FOXP3, Del, C_7, PSPTPPS-SAGPSWRLLRSSGHSMRSTTGSHACLPSSGT-TLPPGRMPSATI, (SEQIDNO:6396); XM_005627317.2, FOXP4, Del, C_7, PSPTTPCPMD-SPLCSHLGETAPPMRRRQAPTP-STDMESVSGQAVRPCVKTWASLSNT STQSTPWMT-GAQPSAGCRCRWYSSWRSSSPRRVRGCRP, (SEQIDNO:6397); XM_005630840.1, LELP1, Del, C_7, PSPVPSPVLLNAHLPAHPQS, (SEQIDNO:6398); XM_005635865.2, INPP5D, Ins, C_7, PSQEDHVLVSLQGAGKDAG, (SEQIDNO:6399); XM_005621049.2, PILRA, Del, C_7, PSQEEPPGGDPI-LYP, (SEQIDNO:6400); XM_005621048.2, PILRA, Ins, C_7, PSQEEPPGGDPILYPKGL, (SEQIDNO:6401); XM_005636883.1, KMT2D, Del, C_7, PSQGHWAVR-PLLLPPPFSLAAPQPPPACLPLRTGS, (SEQIDNO:6402); XM_014106895.1, LOC100683453, Ins, C_7, PSQGRAE-PTPGPHPPRMVHSPGRGQSPGPEGRRSRLDSGARM, (SEQIDNO:6403); XM_014118232.1, ZNF524, Del, C_7, PSQGRSPRWHRG, (SEQIDNO:6404); XM_014106893.1, MAST4, Ins, C_7, PSQGVPPM, (SEQIDNO:6405); XM_843647.4, PDLIM3, Del, C_7, PSQMCTGCSM-TIGMNLLSLASRALSECSRN, (SEQIDNO:6406); XM_014113564.1, CHD3, Del, C_7, PSQPAFRCPSAAF-SAGWPARARSLTPHRPFPRGPTLHLRDTGRP-SAPHPSGPWPPQAP TTARCLPGSSQPPPTALQCW, (SEQIDNO:6407); XM_546802.6, WFDC1, Del, C_7, PSQRAPRL, (SEQIDNO:6408); XM_005616859.2, BCL2L12, Del, C_7, PSQRRKPYCGSWLPCWRKRLKSSTR-SWPRTPPCVGSWPASPPAPSPAWWSCSLAGR TAL-CPAVHAPPCPAQGLHRLPRSPWPAWPWPWS, (SE- QIDNO:6409); XM_014116608.1, C9H17orf96, Ins, C_7, PSQRTAPPPGTDAPHLEHLQPPRLLPLPPGPGGGG-GRRLRAGILASPAGRR, (SEQIDNO:6410); XM_855303.4, ARHGEF15, Del, C_7, PSRISICPRK-MESKQGTILMKLLQALLQHPWRAGTRRNWRS, (SEQIDNO:6412); XM_003431676.3, CFB, Ins, C_7, PSR-LEPYPPRYHPYD, (SEQIDNO:6413); XM_014122224.1, RFX1, Del, C_7, PSRLP-PLLPPSPNMSLSCRAPSPRHSHQAARNNM, (SEQIDNO:6414); XM_844789.4, CBX6, Del, C_7, PSRL-SPRRCASSIARSSLGSPSETASSST, (SEQIDNO:6415); XM_014120094.1, POU2F2, Del, C_7, PSRLSRICPRPNSC, (SEQIDNO:6416); XM_005623084.2, TXNDC2, Del, C_7, PSRLTP-PILQKKLSHPRKVKSPIPRKKTS, (SEQIDNO:6417); XM_005616542.1, TMEM91, Del, C_7, PSRNLVNPSWGLPFGRRLLQSP, (SEQIDNO:6418); XM_843925.4, DAP, Del, C_7, PSRPCSSQE, (SEQIDNO:6419); XM_548165.4, OSBPL7, Del, C_7, PSRRAMR-SQRTSSSGKT, (SEQIDNO:6421); XM_005640908.2, LOC100685881, Del, C_7, PSRRPAASSSCTPCTPWA, (SEQIDNO:6422); XM_014118210.1, CDK19, Del, C_7, PSRRQPPRRRRHHSR-TAPRPTGPRAGLAQGPGLQVAACSTARTRASGRCP-PARSPAW GPRVPTPAGPSCRQIISTPVLA, (SEQIDNO:6423); XM_548725.4, UNCX, Del, C_7, PSRRRPGQALELPAPPGSPPCAGPQSPAPSPDPARR-RARRRWTWT, (SEQIDNO:6424); XM_003435655.3, NKRF, Del, C_7, PSRRRRCRPSRRPRPSQCWSSGAI-ATKVTGSGLCGAASSVGTCTAIPGLPWTSSSRSPP PGPTTFSWAAGTAHA, (SEQIDNO:6425); XM_853188.4, RARG, Del, C_7, PSRSGAPPGEEGE-SAAGPRCS, (SEQIDNO:6426); XM_014109338.1, DUOX1, Del, C_7, PSRSTSSYLATADAGPCCSR-SPRSMTWCCCLTWRKSGRCWWKTFGGP, (SEQIDNO:6427); XM_014109349.1, DUOX2, Del, C_7, PSRSTSYCPATVDAIPCYSRSPRSMTWCC-CLTLRKSGAPLCSICRTSVCSGLWALTWL R, (SEQIDNO:6428); XM_005640913.1, LOC488620, Del, C_7, PSRWPAASSSYTPCTPWA, (SEQIDNO:6429); XM_014113233.1, DNAH9, Ins, C_7, PSS-CQQRHGRGDDPHGPRGQGAQGPQLEGREGHHGQG-GRFPGLPHQL, (SEQIDNO:6431); XM_014121835.1, JSRP1, Del, C_7, PSSDPQLRSPAPIWAPPSP, (SEQIDNO:6433); XM_014110912.1, BARD1, Ins, C_7, PSSGGSAP, (SEQIDNO:6434); XM_005629808.2, KAT6A, Del, C_7, PSSHSSHRRPPHRHHSPSPSSHSLRPHRSSSPRCHSAV, (SEQIDNO:6435); XM_014112830.1, CNKSR3, Del, C_7, PSSKKAPQPHTGSQGPQRRGSWSGAQTLSGAA-GATSVRISTAAPPSRSRRRGPERSRP PPQRPR-PLQNRPCWSAG, (SEQIDNO:6436); XM_014110273.1, KIAA1407, Del, C_7, PSSLAPTSSSEPRAGKQNP-SAGVTSTTATSSSNS, (SEQIDNO:6438); XM_014114806.1, HIAT1, Del, C_7, PSSLEPVPYCWLCLLPCLFQNIPI, (SEQIDNO:6439); XM_014114365.1, SETD1A, Del, C_7, PSSLHPLLLHPL-LILHTWLPCPLLILPTSGHTSSHRALMGRLPP-STPHLLRHPPTFMTL, (SEQIDNO:6440); XM_531921.4, KDM3B, Del, C_7, PSSLRLQQE, (SEQIDNO:6442); XM_005641757.2, LOC102155093, Del, C_7, PSSLTWVDPAVPSSFRSRIAYGFFR-SHCCWGHLSRSCHPFLWSSCLLCPGFLHLSLCA ATLPWPVRLSYHP, (SEQIDNO:6443); XM_845974.4, KCND3, Ins, C_7, PSSN-PRGGKSASPRQPRPQHEHSFHSQQCCQGLCLV, (SEQIDNO:6444); XM_014122258.1, DNAH1, Del, C_7, PSSPASTGCLGSSFSSALRTPVCSRNAWKPMP-CARTQRLCCCTICTWTACPPRAASSS VSRA, (SEQIDNO:6445); XM_014118376.1, GRM4, Del, C_7, PSSPNRNVWSVSSVLQGALSPSWWPTSFASSRSPR-SATPPQPPT, (SEQIDNO:6446); XM_005638006.2, TOX, Ins, C_7, PSSPPDQPTSSPASQHAAAPATRHAAAP-WEPAPHAGPVCLTLTDHAAGNSSTRLSDY NQSYIH-SCTSGNPSNGVCAFWVQKPSRPAGGLE, (SEQIDNO:6447); XM_005626415.2, AKAP2, Del, C_7, PSSPRMISG, (SEQIDNO:6448); XM_862165.4, ATP2B3, Del, C_7, PSSPRPSCSWCGRPCRT, (SEQIDNO:6449); XM_856636.4, BRPF1, Del, C_7, PSSPSWAPY-VSASGVGAPGPVRAQTATVINPQKTPQWTYQP-MASAAEISQ, (SEQIDNO:6450); XM_005619086.2, ZMIZ1, Del, C_7, PSSPTLRT-CPTTWPPSRNPSVTPCRKLCHTLAVLTSPIP-PYNKVCTSHTPAASQGLHYI TVGLLLLLPSLPGNRHRPLPATIHTVT, (SEQIDNO:6451); XM_005619085.2, ZMIZ1, Del, C_7, PSSPTLRT-CPTTWPPSRNPSVTPCRKLSFQNSQIPMSSSRTWIPLT-CRAIVTMTSCLSLR TT, (SEQIDNO:6452); XM_014121819.1, CAMSAP3, Ins, C_7, PSSRGPL-SNPSPCCQGPSGGRGGPQAGGLHSA, (SEQIDNO:6453); XM_545710.3, USH2A, Del, C_7, PSSRMVT-CLAMRSACRILTSP, (SEQIDNO:6454); XM_014114715.1, UNK1, Del, C_7, PSSRPPSSPSPER-WARRPRPTPWARAPAVRSWPGSGGSWTRPRGRSGN-GRSPGSR, (SEQIDNO:6455); XM_014114719.1, UNK1, Del, C_7, PSSRPPSSPSPERWARRPRPTPWG, (SEQIDNO:6456); XM_014116795.1, PHF12, Ins, C_7, PSSRRWYLGHRSQPTILLT-SAIIRWQGQPRHVIHRKRFNRTLFPSQLYCH-GGPHQLTS SNGC, (SEQIDNO:6457); XM_014107017.1, CHD6, Del, C_7, PSSSTAGMGNLQ, (SEQIDNO:6458); XM_542210.4, GRIN3B, Del, C_7, PSSTPSS-WTSRSSTTKSPSTRTVNC, (SEQIDNO:6459); NM_001287125.1, CDH1, Del, C_7, PSSTQPR-TRDGCLRTRLTSKSLYSK, (SEQIDNO:6460); XM_014116630.1, GSK3A, Del, C_7, PSSTSVLEN-SPSSHLSTPFSSLLT, (SEQIDNO:6461); XM_003432782.4, PDE4A, Ins, C_7, PSSWRVGISRR-SYL, (SEQIDNO:6462); XM_544410.5, SALLI, Del, C_7, PSSYLRAVPATPSFHPTAALPPTLTFWRQR, (SEQIDNO:6463); XM_014116573.1, DACT3, Del, C_7, PSTAGPGALARPARLIWPDAIKSELGPA, (SEQIDNO:6465); XM_014118244.1, SYNGAP1, Ins, C_7, PSTAPPT-PAADH, (SEQIDNO:6466); XM_003432781.3, PDE4A, Del, C_7, PSTCGGSRGPPFVSSSAATPTARSAQSPS-GRHTGP, (SEQIDNO:6467); XM_005638522.1, IGDCC3, Del, C_7, PSTCRRSLCRPPRSGCPGMNPWSTPRRL-LAMSCTSGRLLTPRSWSTRRHSAKAPFSIC, (SEQIDNO:6468); XM_014117439.1, KCTD17, Del, C_7, PSTCTVCCSARRRS, (SEQIDNO:6469); XM_005619461.2, LOC102153808, Del, C_7, PSTDCGGGSLGQHRICFGVKNFVRHTCKTTT, (SEQIDNO:6470); XM_005617918.2, KIAA1522, Ins, C_7, PSTGGQWEGLPQWGQHC, (SEQIDNO:6471); XM_540976.5, ARHGEF4, Del, C_7, PSTGIS-RMWKQPYMP, (SEQIDNO:6472); XM_547530.4, ISG20L2, Del, C_7, PSTGRLTAQRMPLCL, (SEQIDNO:6473); XM_535422.5, FMN1, Ins, C_7, PSTGTAQHAPE, (SEQIDNO:6474); XM_014115765.1, EFS, Del, C_7, PSTLPLPT, (SEQIDNO:6475); XM_003432343.3, LRRN4CL, Del, C_7, PSTLQPAEQN, (SEQIDNO:6476); XM_541835.5, IL17RD, Del, C_7, PSTPESRCWRSL-TRAWC, (SEQIDNO:6477); XM_005624150.1, CBX4, Del, C_7, PSTPHMHSYRALAPEDRVGPYVIPHLE-AAELARFFYAVSPPFPLQDITRGNPRRTSWI PGC, (SE- QIDNO:6478); XM_005616728.2, GRAMD1A, Del, C_7, PSTPSHGPMTASP, (SEQIDNO:6479); XM_005621146.2, SDK1, Del, C_7, PSTPSSTTT, (SEQIDNO:6480); XM_005620012.2, BORCS6, Del, C_7, PSTPTCCGTWSG, (SEQIDNO:6482); NM_001003373.1, C5AR1, Del, C_7, PSTPTMALPPWTPTYLWMSLSTPPSCRSRI, (SEQIDNO:6483); XM_843127.2, SH2D4A, Ins, C_7, PSTQAAVPAPSGVPSAASQNPGSDKDGIELFPGGHHSVVQRGAATSASRLPEGLRHY SALVPRDSYIEESK, (SEQIDNO:6484); XM_014110056.1, LOC102151348, Del, C_7, PSTRMWREPSPCSPSHHSPVTAACSQ, (SEQIDNO:6485); XM_005626061.2, FER1L5, Del, C_7, PSTSGPESLEGMSCAALSGRLPKWT, (SEQIDNO:6486); XM_005620294.2, IGSF9B, Del, C_7, PSTSRPRRVAV, (SEQIDNO:6488); XM_005618506.2, MFSD10, Del, C_7, PSTSRRLRTPA, (SEQIDNO:6489); XM_843488.4, NAV1, Del, C_7, PSTSSKGT, (SEQIDNO:6490); XM_014111044.1, ABI2, Ins, C_7, PSTSSPRRL, (SEQIDNO:6491); XM_005625732.2, ALG12, Del, C_7, PSTSTCRQGWCSWRDAVGRP, (SEQIDNO:6492); XM_014121804.1, CACNA1A, Del, C_7, PSTTLSSK, (SEQIDNO:6493); XM_014120931.1, MUC2, Del, C_7, PSTTTTPACSTPASCPAQAWSVPACRPTRPCAPTRASVSTGGTTPTGFAR, (SEQIDNO:6494); XM_005621773.2, RHBDF1, Ins, C_7, PSTVCGAVPAGHAEDHRPPGPGPGLPRGG, (SEQIDNO:6495); XM_005635260.2, OSBPL2, Del, C_7, PSVHFIQKASIRTSCFTAPSTRS, (SEQIDNO:6496); XM_005632499.2, HEMK1, Ins, C_7, PSVHSSPGN, (SEQIDNO:6497); XM_540177.5, FBLN7, Ins, C_7, PSVLPCSERPSRWQKVWKQVLSGS, (SEQIDNO:6498); XM_005624443.2, CNTNAP1, Del, C_7, PSVPTTALMSPSTSGPRPPQGSSWRIWGALTASGADLMCGWNSTHLGMWSSPSMW GTEMRT, (SEQIDNO:6500); XM_005621271.2, RNF40, Del, C_7, PSVSQLWLLW, (SEQIDNO:6501); XM_014115482.1, DTNA, Del, C_7, PSVWSGCPFCIDWQMWKMSSIRLNVLTATVRV, (SEQIDNO:6502); XM_538279.5, BEST3, Ins, C_7, PSWGPGAPGDSSQRPKEHPHACLWRRPKR, (SEQIDNO:6503); XM_845621.5, MLLT6, Ins, C_7, PTAACRGPGSSLARQQHESHGRGGSSRSSSSSRRTSSPHGPDQPLPQPGGGGWQWPQ RRDR, (SEQIDNO:6506); XM_014122449.1, LOC106560163, Del, C_7, PTAAPPRSEAPRRGHAPSLQRGPAPRTPALD, (SEQIDNO:6507); XM_005623133.1, CTIF, Ins, C_7, PTAERQQRQLSGHAGHGYLGCQHL, (SEQIDNO:6509); XM_014111758.1, RASGRF2, Ins, C_7, PTAGCVQDVLPSEGQKAVLDFSIELKDRSVGPDHLFSIQ, (SEQIDNO:6510); XM_845641.5, EPN1, Ins, C_7, PTAHTEDTRVIPGA, (SEQIDNO:6512); XM_005629454.1, TMEM192, Del, C_7, PTAILTGLLTGVPWISPRVLKMTPFWIPTISHIIHYMLILDPDSILFLRSS, (SEQIDNO:6513); NM_001006650.1, PKD1, Del, C_7, PTALRSSWQRRKPERSRGCMGC, (SEQIDNO:6515); NM_001313776.1, CKM, Del, C_7, PTAPGASAGQWRNSP, (SEQIDNO:6517); XM_014121251.1, LDLRAD3, Del, C_7, PTAPRALGTRSLARPLPAY, (SEQIDNO:6518); XM_014107094.1, HSPG2, Del, C_7, PTARCTAPGYGFPRSHQLILENTYAEWRTRQAPRRPPSSSLSSTAPTRALATP, (SEQIDNO:6519); XM_005636665.1, PAPSS2, Del, C_7, PTASWRPRPGRC, (SEQIDNO:6520); XM_014116196.1, HGS, Ins, C_7, PTATPCGPAAACAGPSCTGQRGPAHLV, (SEQIDNO:6521); XM_014121026.1, SPDYC, Ins, C_7, PTATRARHLHSLYPPEASTMPWAL, (SEQIDNO:6522); XM_005633017.1, KDM4B, Ins, C_7, PTATSQRRAPRGTWRGARAGL, (SEQIDNO:6523); XM_014122125.1, KDM4B, Ins, C_7, PTATSQRRAPRGTWRGARGEAAPHHPHAVRGAAAQHGV, (SEQIDNO:6524); XM_005633018.1, KDM4B, Ins, C_7, PTATSQRRAPRGTWRGARG1, (SEQIDNO:6525); XM_005616892.2, LOC102155339, Del, C_7, PTATTACV, (SEQIDNO:6526); XM_541885.4, BSN, Ins, C_7, PTAVCGQPAAAWAGGAHRCPCHQGQPAPGAGPGPAAGGA, (SEQIDNO:6527); XM_014113859.1, SLC22A31, Del, C_7, PTAWYSPRQLASSRCWALCCCRA, (SEQIDNO:6528); XM_014106909.1, NCOA6, Del, C_7, PTCRPCRATVPRETTSQAMGCLSMHLSVEHPMEIRCPVVRIQAFQSIRMSH, (SEQIDNO:6530); XM_014117984.1, LOC102154618, Ins, C_7, PTCYCRGTQTAPRPLDQQCLSDPLSEPTAEPYQNFI, (SEQIDNO:6531); XM_014116531.1, LOC106559282, Ins, C_7, PTDHRETPTSALLPGPQV, (SEQIDNO:6532); XM_859725.4, WAP1, Del, C_7, PTENMKQVSK, (SEQIDNO:6534); XM_014116271.1, UBE2O, Del, C_7, PTFATSPSAVAA, (SEQIDNO:6535); XM_005626805.1, CCIN, Ins, C_7, PTGGTGLSCLLSSQATVQDSSKDL, (SEQIDNO:6538); XM_538856.5, RXRB, Del, C_7, PTGLPLPSHQLFHGVPWFAPSSSPRILRACQQSPD, (SEQIDNO:6539); XM_005631571.2, C18H11orf84, Del, C_7, PTGLWFCQSPAPPWGGSQRQGVAC, (SEQIDNO:6540); XM_542234.5, MAML2, Ins, C_7, PTGPCCPPDGLPSSRRHSPTAPARLSPSPPAAPAQQWQ, (SEQIDNO:6541); XM_005628076.2, LOC102156955, Del, C_7, PTGPGLPVRCPHCSCNPLCSVIFCQMI, (SEQIDNO:6542); XM_014114179.1, DTX2, Del, C_7, PTGPPLSLGPTRPLLHTASPPSLGLGLHPG, (SEQIDNO:6543); XM_536750.5, CDH15, Del, C_7, PTGPPSTFS, (SEQIDNO:6544); XM_005626257.1, LOC102155231, Del, C_7, PTGSASRLWTPVGVDPAAATTGALLLPGLRPELFPRVPPTLQNGMVRPSAVTVGRQS WL, (SEQIDNO:6545); XM_014111179.1, SOX13, Ins, C-7, PTGWPAANELL, (SEQIDNO:6546); XM_014115709.1, CCNK, Del, C_7, PTHPLPQCPLHQPPSPLLPFLPPLLAIPLLPPPTTPTSHPHPHACPPPTQCPLTLLQAWA CHRPATPLRLSPLEDSHPCPHPSPHPVCLQLGGWGGQPG, (SEQIDNO:6547); XM_014112099.1, LOC106558522, Del, C_7, PTHRGAEYQP, (SEQIDNO:6548); XM_005635892.1, DMTN, Ins, C_7, PTIPRGVGGEPVPWNHLSGFSPKNHRDPPDQPTPFPPS, (SEQIDNO:6550); XM_532087.5, NELFE, Ins, C_7, PTKPQPGPQS, (SEQIDNO:6551); XM_546651.5, MAPK7, Ins, C_7, PTKTSRLPHWSCTAACLPSPWACSSPRQPSGACPWPSSTPDCHP, (SEQIDNO:6552); XM_014114822.1, BCAR3, Del, C_7, PTKYQSHYCCLL, (SEQIDNO:6553); XM_014111054.1, CNPPD1, Del, C_7, PTLDWSPGASWNPAYLLLCHSACRVPLMSPAA, (SEQIDNO:6554); XM_014111411.1, LOC611589, Del, C_7, PTLHLILK, (SEQIDNO:6557); XM_005631547.2, KCNK4, Del, C_7, PTLPGSPCGRGRKADRC, (SEQIDNO:6559); XM_014122488.1, SOCS6, Ins, C_7, PTLTVATSNADQSNPKELQWAHRHRCPRG, (SEQIDNO:6560); XM_005616531.1, CIC, Del, C_7, PTLWGWWNLERVPLPPLRRMPLALQESPGWTVRQRVTTMMPSSPSCLLRSSCPCHP GNAGPSLSVPCQRNETPLQRRMDAAPTSGRRTISGGP, (SEQIDNO:6561); XM_847197.3, SCAND1, Ins, C_7, PTLWRLPTRPGDIPPAFPAVPLPGRRRSAGGVPAAAGALPPVAATRHPHEGADRGDA GAGAAAGHPA, (SEQIDNO:6562); XM_014117185.1, INHBE, Del, C_7, PTMLQPSSTLCSSPTGLWAAST- GRVRR, (SEQ ID NO:6563); XM_014117000.1, HMCN2, Ins, C_7, PTNHRSELGAGHCYRQQQCLPVL, (SEQ ID NO:6565); XM_005630633.2, HIPK1, Ins, C_7, PTPAATRTGRWS, (SEQ ID NO:6566); XM_548413.5, ABL1, Ins, C_7, PTPAGEKD, (SEQ ID NO:6567); XM_005627318.2, FOXP4, Del, C_7, PTPALRGLLKTGTLRRSCQERNCP, (SEQ ID NO:6568); XM_005632724.2, GTPBP3, Del, C_7, PTPARAAW, (SEQ ID NO:6569); XM_014118742.1, SCRIB, Ins, C_7, PTPCHSPQHRGHCQPWRVWAAQAGS, (SEQ ID NO:6571); XM_005626251.1, ANTXR1, Ins, C_7, PTPCTPLPSPTPQCSHPSDSIPTVHPSPSPSRPTSQQGATPLPTSSQAFCL, (SEQ ID NO:6572); NM_001003291.1, ICAM1, Ins, C_7, PTPCYPPDCGSGHTVVCGLHSGWGVPSFGGPSPPGVSRREAALHSPVQKGLPLGHG KCQSKPRRRGYPAAMV, (SEQ ID NO:6573); XM_005638154.2, E2F5, Del, C_7, PTPFLKNRLQILWL, (SEQ ID NO:6574); XM_014115723.1, ADSSL1, Ins, C_7, PTPFVLPVCPPQGARRVHRHSPRACGHFDSNTGGAREPGPAGHGAPGETTVPPHPLS ATMELGWWGPGLVLPGRVGPHSCIRGGTSRAARRIGAGPG, (SEQ ID NO:6575); XM_014122165.1, CBARP, Del, C_7, PTPFWPAPPAHPPLSAG, (SEQ ID NO:6576); XM_849945.3, PGLYRP1, Ins, C_7, PTPGPQGGPESAGLWCGSGKTEPQIPAQRTPGCAADTLSRRPTL, (SEQ ID NO:6578); XM_005628972.2, GJA4, Ins, C_7, PTPGRLLRALCRPGLLLPAHGRGTLVPAVPHLQRALLQRAELGQPDYGGEAGFLQG PPLPGPTPREWPEIPQSPQQLCFQEAVCV, (SEQ ID NO:6579); XM_861377.4, COX11, Ins, C_7, PTPGRYGRALASPVETRCLLWLALEPPWLRGQGRGEGRAPSQAGNEWGRRC, (SEQ ID NO:6580); XM_014112341.1, ADAMTS7, Del, C_7, PTPHHGPHQLRTGQPMAESPRPSLWTPARPRTPHPPRMPAGRWGAGVSAPPPAAWV LSGGPSAAAPAAKRTVPPPAAPSLPAAAT, (SEQ ID NO:6581); XM_014112562.1, FAM193A, Ins, C_7, PTPHHRWLHQRSTQRLQRPRL, (SEQ ID NO:6582); XM_846233.4, PPFIA1, Ins, C_7, PTPHICAHGPLPSAQWALHPTKGPAQPSQGGGQTGGHDSIAGFPGRGTR, (SEQ ID NO:6583); XM_005631375.2, PPFIA1, Ins, C_7, PTPHICAHGPLPSAQWALHPTKGPAQPSQGGGQTGGHDST, (SEQ ID NO:6584); NM_001006645.2, KCNA5, Del, C_7, PTPLGPPGGPTAARPWRPPRAPRWRLSCRGPWLTPSSS, (SEQ ID NO:6585); XM_014116624.1, HOXB3, Ins, C_7, PTPLPGRHAPGGRLPALGVLAAVPGQRRPAGQEQGAQR, (SEQ ID NO:6586); XM_005616581.2, DYRK1B, Ins, C_7, PTPMPWSSPITNL TTTPGADGCEPGGRPFRLLPTSPSACPPAPGCLSPPDSDDRRSSTPPTP, (SEQ ID NO:6587); XM_005628310.2, OPLAH, Del, C_7, PTPPHCSRRVLSFCLSNSSRGVSSRRMR, (SEQ ID NO:6588); XM_003639335.2, LMF2, Del, C_7, PTPPLWPRRRSTGQPLRRTAGLPAKRPPPPLTTAAAALRLLGGKS, (SEQ ID NO:6589); XM_005639705.2, IRX1, Ins, C_7, PTPPQGAHLSPNALLLPLPRRERPRPPAGLARTAVKIALPARARQLAGPAGGDAADP SSPPVGL, (SEQ ID NO:6590); XM_005624035.2, LOC483345, Ins, C_7, PTPPRKGHGPPTGPLDVSAGGWDSRCERWGHAAGQWGHRQRGPRGDLLQWPVGD RV, (SEQ ID NO:6591); XM_014109382.1, IGDCC4, Del, C_7, PTPPRSLATNSTGGRWGPRRRLVVRVPQGATETRPGMWGLSGSRRK, (SEQ ID NO:6592); XM_003639759.3, RBM15B, Ins, C_7, PTPPVLRPGPDLFGRGLDQP, (SEQ ID NO:6593); XM_014114445.1, LOC102155512, Ins, C_7, PTPRGGEGSAAPCPPCVPWACTLGPPHTRRGDCVPTRGLFRVSQQAARLLGSV, (SEQ ID NO:6596); XM_541589.4, CIC, Ins, C_7, PTPRPLHSCHRQV, (SEQ ID NO:6597); XM_005621172.2, MICALL2, Del, C_7, PTPRSAWAQRLQAQQTPQTGPHQQPPRCSRPGRGSSRLLELPPALAQLAGPRLLQMC LLGLTAGSRR, (SEQ ID NO:6599); XM_014117413.1, TLE1, Del, C_7, PTPSSDPASPATHARSTP, (SEQ ID NO:6600); XM_005620885.2, NECAB2, Del, C_7, PTPSWEPWNQGRVLHLSSWTLRRRAWRPRSAAWQS, (SEQ ID NO:6601); XM_537553.5, EV1, Ins, C_7, PTPTPTASRRSTGCQP, (SEQ ID NO:6603); XM_005626204.2, SBF1, Del, C_7, PTPTPWTMQISILSSLRPVAPF, (SEQ ID NO:6604); XM_005625442.1, PRDM12, Ins, C_7, PTPVSNRKAYSGQPTASEDFGPKPPESGEPVAHDAVAGRAQPQCWPLPCPPPGQEFH APRRAASGTVERPV, (SEQ ID NO:6606); XM_545880.5, IL16, Del, C_7, PTPWSSSSQSQSHCRGAPSPPPRPASWECRGPLSQDGSPVGRPSSPTLILSQGCCPHTQ RKPRAPLSRCRANGRGASPCPAPSPGR, (SEQ ID NO:6607); XM_536901.5, BCL7C, Ins, C_7, PTQAHLPKCPRPL, (SEQ ID NO:6608); XM_014106943.1, RIN2, Ins, C_7, PTQAPATRY, (SEQ ID NO:6609); XM_847374.4, HOXD1, Del, C_7, PTQEPVPPSLERTRGALLRPRSPH, (SEQ ID NO:6610); XM_534998.5, PPRC1, Ins, C_7, PTQEVAKIQLQFLWTFPKMLFLFFLLIFFLFFLIFVIQFSKPVPLPIPPTEK, (SEQ ID NO:6611); XM_542667.4, IRS2, Del, C_7, PTQQCLRPAGPVAAALAAPTAS, (SEQ ID NO:6613); XM_014117450.1, LOC106559402, Ins, C_7, PTQQGPPHGPAGPPQLHCPAGPPPPPAGTQRLRRGRAVWA, (SEQ ID NO:6614); XM_005636739.2, ITGA5, Del, C_7, PTQRAWSWIRRVPSTTGYKDGKRQAGARAPRDLRS, (SEQ ID NO:6615); XM_844090.4, INO80, Del, C_7, PTRAAVICWSLWMTQPPQPPSLGPPTLLLP, (SEQ ID NO:6616); NM_001048083.1, ARSA, Del, C_7, PTRASTGSWASRTRTTRALART, (SEQ ID NO:6617); XM_014115355.1, TRIM46, Del, C_7, PTRHLPGTTPSSSGVPMCLPSQAPPAGSGGKR, (SEQ ID NO:6618); XM_005631210.2, LRRC55, Del, C_7, PTRPCCWSPSSWQPG, (SEQ ID NO:6619); XM_014116949.1, KCNT1, Del, C_7, PTRPTSAAPLPYATCCL, (SEQ ID NO:6620); XM_014122642.1, FAT3, Del, C_7, PTRSPTTRIWWARPPPVSLVLLP, (SEQ ID NO:6621); XM_005638950.2, SIK1, Del, C_7, PTSCTPAAPRWHRRPGCWTPTCTSATPWPPVPPPRCPPALWPRGSRRGTVRWRT, (SEQ ID NO:6622); NM_001286964.1, UBE2S, Del, C_7, PTSFAWCIRR, (SEQ ID NO:6623); XM_849543.1, GPR152, Ins, C_7, PTSGPCSPAPAGFCGSPTVRFWGPASAELLRPATGEP, (SEQ ID NO:6624); XM_014114351.1, STX1B, Ins, C_7, PTSHQRLRPGHHPHLGPAPLG, (SEQ ID NO:6625); XM_005633459.2, MYO7A, Del, C_7, PTSLPLPIIAIST, (SEQ ID NO:6626); NM_001110767.1, MYH9, Del, C_7, PTSMPSQTPPTGV, (SEQ ID NO:6627); XM_014115267.1, ENAH, Ins, C_7, PTSPSASRSPPPCIWIFCGIRVRRQSPFDWTCGCHRRSETEESVPDGGCLFPRRRCEPSL I, (SEQ ID NO:6629); XM_005631005.2, ABCA13, Del, C_7, PTSPTPSEPASCTA, (SEQ ID NO:6630); NM_001003247.1, KCNB2, Del, C_7, PTSQGPTSTKEPGGPRS, (SEQ ID NO:6631); XM_545805.5, GABRA5, Del, C_7, PTSQRNRPQQ, (SEQ ID NO:6632); XM_536455.5, CYFIP2, Del, C_7, PTSRPSADSWVTRASQWSWRNC, (SEQ ID NO:6633); XM_537251.5, ASHIL, Ins, C_7, PTSSSFLYACWPFTSQSNQIP, (SEQ ID NO:6634); XM_014121822.1, MYO1F, Del, C_7, PTSSSWSCSLWRESCTWET- SASAKMGITPGWRVWTCWPSPPTCWAS-TAHGCRRSSP AARWTVAGADAVSPSM, (SEQIDNO:6635); XM_005626284.2, FLT4, Del, C_7, PTSTRRRLPPPAPTVARPSPALPTGCP-PLSVSSGTGGHGHPARPSPSAASAGGSRE TTCH-SARTGER, (SEQIDNO:6637); XM_852991.4, DLL4, Del, C_7, PTSWAPTVRRK, (SEQIDNO:6638); XM_541409.5, ZNF628, Ins, C_7, PTTAPALGQPPGLCLPPMREVLPDS-GRPLPPPAQPRGGRRAGVPLWQL, (SEQIDNO:6639); XM_005631742.2, SHANK2, Ins, C_7, PTTAR-QCPACHQGDTTKDLQAVGGRLRGQEPD-SLRPKGKRYQ, (SEQIDNO:6640); XM_014122450.1, LOC106560164, Del, C_7, PTTFILSSKN, (SEQIDNO:6641); XM_014117663.1, AKAP2, Del, C_7, PTTGSRPTAPRFWITMWPERSAT, (SEQIDNO:6642); XM_014111656.1, HDAC6, Del, C_7, PTTPASPRSE-VLRRVPYATPALV, (SEQIDNO:6643); XM_005616464.2, CBLC, Ins, C_7, PTTPSAECVRS, (SEQIDNO:6644); XM_014110091.1, MINA, Del, C_7, PTTRETE-QSFQRQVDGCQGWTAR, (SEQIDNO:6645); XM_014110676.1, CSRNP3, Del, C_7, PTTRPPAPRSS-CAARRPTTAACPAPACTPTAGPATRRWNSTRT, (SEQIDNO:6646); XM_005622745.2, TRIM46, Ins, C_7, PTISFPLPACASLLCVSCAPDRDGCEER-DQDKHEEHGKGASVPSVSRDVQAATGAAL YSQRVPGLCPGGAGPARLYRPLWGPQL, (SEQIDNO:6647); XM_005623336.2, PAX9, Del, C_7, PTTVTFP-PRWRSRECRQPEKVVTLSRLLRS, (SEQIDNO:6648); XM_854614.4, MBD6, Ins, C_7, PTVPPTF-STPYPHSFKFCAAGCQPGSPLGDAPPAL-CPECPPTWTIYLQCHHGNY, (SEQIDNO:6649); XM_536899.5, MYLPF, Del, C_7, PTWEATWT-TRTFATSSRMATPRTRS, (SEQIDNO:6651); XM_014119360.1, CCDC9, Ins, C_7, PTWRPGRHGPGSPQLGGQLRGAASRRSWGPWPER-PGPRVPSSFWSWRYLSG, (SEQIDNO:6653); XM_014122137.1, CPAMD8, Del, C_7, PTWSAGSR-PRSRSASTITWAPVPRCT, (SEQIDNO:6654); XM_005637420.1, LOC609303, Del, C_7, PTWVGSGGSSLARTGKSGLPL, (SEQIDNO:6655); XM_014110880.1, MYO3B, Del, C_7, PTYLHQQMLLTNVWLLSAKTSALSSVEKVAL-GRQRVPT, (SEQIDNO:6656); XM_014121010.1, MAP3K11, Del, C_7, PTYWSTGL-CRLPVGCITCTVRPWCLSSTETSSPTTFCCCSPLKVM-TWTIRP, (SEQIDNO:6657); NM_001136500.1, SLC6A3, Ins, C_7, PVAAHLLPGAGHHPALL, (SEQIDNO:6658); XM_014116209.1, LOC483316, Del, C_7, PVAGPCHCTPGTPGRIWLAVTSCWIS, (SEQIDNO:6659); XM_014116591.1, NOVA2, Ins, C_7, PVARPVPGLGLVFHRQHPHTLPRQCQHHT-PAASHLCGTHRHFWSQPANQSGPTPG, (SEQIDNO:6660); XM_014113331.1, ROBO3, Del, C_7, PVATRSLPCPGRRTVQDSERRREGSRFVEGS, (SEQIDNO:6661); XM_543631.5, CALCOCO1, Ins, C_7, PVEGVPYL, (SEQIDNO:6662); XM_847901.4, HNF1B, Ins, C_7, PVFPYLPVSICDGGHGYQQHQYAYQHVFQ, (SEQIDNO:6663); XM_014112907.1, SEC24C, Ins, C_7, PVFSTGSYWQTCRCL, (SEQIDNO:6664); XM_014107178.1, ZNF512B, Del, C_7, PVGMTGPQE-AETRGRGAPLAGRREPARLLRS, (SEQIDNO:6665); XM_014107177.1, ZNF512B, Del, C_7, PVGMTGPQE-AETRGRGAPLAGRREPARLLR-SPRLGGSLVTRGSGLMRAP, (SEQIDNO:6666); XM_846062.3, DDN, Del, C_7, PVGPARNLGAAL-GWPSQ, (SEQIDNO:6668); XM_005640123.2, BTN1A1, Del, C_7, PVGWGFSWTMNQETSPSTI, (SEQIDNO:6669); XM_848566.4, SLAIN2, Ins, C_7, PVHPGVRGGGPPRLSLGAGRQSRGGGRVGPPGD-EQRPTSGSPLPAGGGRGRLA, (SEQIDNO:6671); XM_005620294.2, IGSF9B, Ins, C_7, PVHRGQGGWQCDHDLHSFWEPQAHCHLAQGGDT-PRC, (SEQIDNO:6672); XM_014116201.1, LOC106559219, Ins, C_7, PVHRGSGPVPGIPGPAPCAL-SPHPGNCLPGPLGGFRSHL, (SEQIDNO:6673); XM_014108388.1, MICAL3, Ins, C_7, PVH-WHEETADTRAWGQPAVLLPT, (SEQIDNO:6674); XM_014108390.1, MICAL3, Ins, C_7, PVHWHEETGLD-KEGVPTELRRQRHVLFLPEAGLRDGKAEC, (SEQIDNO:6675); XM_005639159.2, AFF1, Ins, C_7, PVICTFQPASSSPDTRKQQDSQQ, (SEQIDNO:6676); XM_005623824.2, LOC102153127, Del, C_7, PVIPP-PASATVLGGP, (SEQIDNO:6677); XM_014113682.1, PTPRK, Del, C_7, PVLALSWCIAVLVLDGLAVTS, (SEQIDNO:6678); XM_546606.6, PERI, Del, C_7, PVLRGVPRRGALGVVLGPRLPVRRLLSQRPDWWR, (SEQIDNO:6680); XM_540461.5, TMC8, Del, C_7, PVLRSTSPSSGALS, (SEQIDNO:6681); XM_014109253.1, PCMTD1, Del, C_7, PVLSGNRTWLVFIFDVHLEIS, (SEQIDNO:6682); XM_005617747.2, RPS6KA1, Del, C_7, PVLVPISCSVASASWPLA, (SEQIDNO:6683); NM_001003090.1, COL1A1, Del, C_7, PVLV-VALVMPVLLVPLALLDPLVPPVLPAAVSTSASCP-SHLRRRLTJMAAAATTGPMM PTWSVTVTSR, (SEQIDNO:6684); XM_014114196.1, LOC489893, Del, C_7, PVMERRIAACR, (SEQIDNO:6685); XM_543063.4, FAM210B, Ins, C_7, PVPAAAPARARR-SAAARGPRGQRRPPGPQQNHCDNRQGCQQRTGGK-AKQVTAAEK GLPRVRRRCCVAAHWNLVSLLGHLLHGGFKWCGHVCS-PA, (SEQIDNO:6687); XM_547204.4, LMF1, Ins, C_7, PVPDRSVGLPVADFQNHAWSRPDQDPGRPV-LAGPHLHGLPL, (SEQIDNO:6688); XM_548063.4, ASB16, Del, C_7, PVPGPGSPGHAAAAETQPCTMLCSLVTCNR-SKPCSKMKMLPT, (SEQIDNO:6689); XM_005631208.2, TNKS1BP1, Ins, C_7, PVPGRATGTER-PEQLAWRGWPGGWRAAGEAAGGG-PEPRRCWPGRQGGGPPRLG G, (SEQIDNO:6690); XM_542530.5, NAV2, Ins, C_7, PVPGWHSSAT-GASHSPSPGPASPAGAASAVKSTS, (SEQIDNO:6691); XM_847692.4, FAM214B, Del, C_7, PVPPLFLPLL-SAVPCWATLRNHCCEDALHHLATLRASQQR-LELVDPTAPSMSRCLSL SPSLMFLSKM-PRPPSWVSWT, (SEQIDNO:6693); XM_014107749.1, LOC106557811, Del, C_7, PVPVHRPCLRVVASPSQ, (SEQIDNO:6694); XM_546577.3, BCL6B, Del, C_7, PVQAAQTPRPATGKSTSSSC, (SEQIDNO:6695); XM_014107688.1, KIF1A, Ins, C_7, PVQFSRKGLRLPEQPAVCPPGAPRGRRQRE-GRGEGLPPRGRAGHLSRRRGPRLWL WRPTVRHGQNLL, (SEQIDNO:6696); XM_014107689.1, LOC100855783, Ins, C_7, PVQFSRKGLRLPEQPAVPRPPGAPRGRRQREGRGER-LPPRGRAGHLSRRRGPRLWL WRPTVRHGQNLL, (SEQIDNO:6697); XM_014114089.1, FAM65A, Del, C_7, PVQPVPPHPGWLSQAAGTGRGAAPGGAEAGAAV-AGSERGAQLGQRLVALGLQGH RGGRAGGGW-GAVPDPP, (SEQIDNO:6698); XM_843647.4, PDLIM3, Ins, C_7, PVRCVPDAP, (SEQIDNO:6699); XM_014115482.1, DTNA, Ins, C_7, PVSGLAAPSA, (SEQIDNO:6701); XM_014111820.1, SLITRK2, Ins, C_7, PVSNLPAFPQWKPPDQTVP, (SEQIDNO:6703); XM_005628022.2, GLI4, Del, C_7, PVSRPL- SILHHQGHLDPTTARPGFTCTVVNTGLRMSKPWK, (SEQIDNO:6704); XM_005628021.2, GLI4, Del, C_7, PVSRPLSILHHQGHLDPT-TARPGFTCTVVNTVLTLRCTPSTAAHHRHCRLD, (SEQIDNO:6706); XM_843722.4, MAP3K12, Del, C_7, PVSRTQTVTARNWTTPTVAKPCSLRPPSLH, (SEQIDNO:6707); XM_005625737.2, ZBED4, Del, C_7, PVSYPLKGCSAHPRRTVASASPGSRWNILKN, (SEQIDNO:6708); XM_005619728.2, SIK3, Ins, C_7, PVTAGDHPSTGAR, (SEQIDNO:6709); NM_001003009.2, TPO, Del, C_7, PVTGRPGAGT-PRVVSGVSAQTLRCSGRTERRV, (SEQIDNO:6710); XM_014106929.1, SNPH, Del, C_7, PVTTLGPLLRMG-STVASP, (SEQIDNO:6711); XM_014114029.1, MTSS1L, Ins, C_7, PVVAQRLWLTEVQHVQCPQQW, (SEQIDNO: 6712); XM_542327.5, INPP1L, Del, C_7, PVWER-GAHQMRSLGAHCPLQTFHPHPCQTRPSSCP-PAWILCQGRWSGAAVGVRPV AHHLTRPIQDLHCPQAPHLPALSWGR (SEQIDNO: 6714); XM_014117254.1, NCAPH2, Del, C_7, PVWRRFQDRNARGRVPP-SCRTFTSGTWLPTLTMPTAGGPG-GRARLLQTWRSCTGS M, (SEQIDNO:6715); XM_845091.3, IGFBP4, Del, C_7, PWAAR-SWCGSRAAAVAPLAPWARGCPAGCIPLAAARA-CAATRPGGWRSPCTR (SEQIDNO:6716); XM_846534.4, PRCC, Del, C_7, PWAFPSQRRGRSP, (SEQIDNO:6717); XM_005629174.1, E2F7, Del, C_7, PWAFRAWSCRLPRWARFPCSTLPPCPGRSPLPPAR-SQTRSSSVHARSA, (SEQIDNO:6718); XM_539692.5, E2F7, Del, C_7, PWAFRAWSCRLPRWARFPC-STLPPCPGRSPLPPARSQVRGLCISGCPAWDPRLT-SSSA PQTWLTPSRPRSPPQTRSSSVHARSA, (SEQIDNO:6719); XM_843592.5, CACNAiS, Del, C_7, PWALASSAHTGWPASGWWA, (SEQIDNO:6720); XM_014114909.1, VSIG10L, Del, C_7, PWALGPLLASS-WVPYWAWPS, (SEQIDNO:6721); XM_014116695.1, BZRAP1, Del, C_7, PWARGPRACQRLVGEGGRPLPG-NAPVAGPQNLTWPAASPPSAWKSASNMILRTSRR QAAGASASPAPATSEMGRPGAQPP, (SEQIDNO:6722); XM_005639039.2, C31H21orf58, Del, C_7, PWAST-RPPPCPRGPQSRLGSSSPGPCSLWPPLSSRR-PRPGRPPGDQGGSRRTWWR (SEQIDNO:6723); XM_014119249.1, CSMD2, Del, C_7, PWCWWAPRGGFASQMGRGVAPSPAA, (SEQIDNO: 6725); XM_014107665.1, HDAC4, Del, C_7, PWETRSTWQPSGPWSCPSRTSLPQTWCSCHQALTL-WRATPRPSAATTSPPNVSGT, (SEQIDNO:6726); XM_539847.5, TCAF2, Del, C_7, PWGFTASMPTMIR, (SEQIDNO:6727); XM_014122252.1, ABCA7, Del, C_7, PWGRRMRTWPESGNGWCTGPPRRTCWC, (SEQIDNO:6728); XM_005626210.1, PKDREJ, Del, C_7, PWHCTRIRKDRARSQAPRRKKPKPVTRTQK-TIKIKMPNLSL, (SEQIDNO:6729); XM_014119061.1, IRF5, Del, C_7, PWHPILYPKRMSS-GRPPSSRLWCWALLHQTPACWAPPLATLLAL-GSFSLKSCRACSL GPWLPACPPQANNSCPTC, (SEQIDNO:6730); XM_005641878.2, FGF13, Ins, C_7, PWHTGIHYVTARFHPICGIKEKRVPLSC, (SEQIDNO: 6731); XM_005616269.2, P01D1, Del, C_7, PWIPRR-SPSSSSSWRSIIMWAQHSPCPEHPRHPATPCLSCEP-LESQMRACPSAATSMA LHPTSIPRRPLVLGPSTWVTCSGS, (SEQIDNO:6732); XM_005637886.1, NSMCE4A, Ins, C_7, PWKVDPARA-VHPPPPRPAGDPGTRAWPRCCR, (SEQIDNO:6733); XM_005637634.2, SFXN3, Del, C_7, PWLADLCPLQRWQLPTASTSP, (SEQIDNO:6734); XM_005639752.2, SOX2, Del, C_7, PWLPPPPTPGR-PARPGTSGT, (SEQIDNO:6736); XM_014116209.1, LOC483316, Ins, C-7, PWLVRVTALRGL1AGFGWL, (SEQIDNO:6737); XM_534697.5, WSB2, Del, C_7, PWMTATSTLAP, (SEQIDNO:6738); XM_014122486.1, TENM4, Ins, C_7, PWNPVPDRHRPPTLRLLHGGQLR-CRHGG, (SEQIDNO:6740); XM_005631742.2, SHANK2, Del, C_7, PWNSQIVLIFPTTALLLSPLSRTWSSRRN-TTPPSPPR, (SEQIDNO:6741); XM_846593.4, KLHL38, Ins, C_7, PWQDGRGVARWAALQRP, (SEQIDNO:6746); XM_852173.4, LOC485469, Ins, C_7, PWQVPVPKEGSQ, (SEQIDNO:6747); XM_533370.5, ZNF407, Ins, C_7, PWRGEASLPGL, (SEQIDNO:6748); XM_547389.5, PLXNA2, Ins, C_7, PWRGPVRDGL-CAQRRKPDPPGHGLLH, (SEQIDNO:6749); XM_005622065.1, LOC102151745, Del, C_7, PWRP-STGSCARQLAKSPAHPQRTVAFLPPSVSPPASRNCMS-TLERRSGCCRWCVEGP RLTMGAADPRQKRNRSSAA, (SEQIDNO:6750); XM_014117067.1, RABEPK, Ins, C_7, PWRQPLCSGWPQLFIFTPSW, (SEQIDNO:6751); XM_003433467.3, TARBP2, Del, C_7, PWRR-SPPSPLSSLSAILLAPCRSWWCRRAGGCLSTR, (SEQIDNO:6752); XM_014118654.1, LOC106559636, Del, C_7, PWRSPGSLLPTQGPARGPGPGTRMSPPCP, (SEQIDNO:6753); XM_548447.5, SH2D3C, Del, C_7, PWRTPQQWDPTLLQ, (SEQIDNO:6754); XM_533751.4, LMCD1, Ins, C_7, PWSHPETGSAVHGAHPKREAAS-DRHRGCLLPPTPAHAPAPHLRPGPFSLPWTSGE, (SEQIDNO:6755); XM_005628933.2, ZC3H12A, Del, C_7, PWSPGVGAPPRLPAWSPHPRRRTRRAVT, (SEQIDNO: 6756); XM_014117075.1, DENND1A, Del, C_7, PWSPLLGSERCPWPAQVPGLLRPSRGWP, (SEQIDNO: 6757); XM_541537.5, DHX34, Ins, C_7, PWS-SEMHPLHQHC, (SEQIDNO:6758); XM_014106771.1, XIRP1, Del, C_7, PWTPVWGWGISEARGAPPT-SHRPWKSQCL, (SEQIDNO:6759); XM_541508.4, PLEKHA4, Del, C_7, PWTQLFTKAWRQILC, (SEQIDNO:6760); XM_014108452.1, TNS2, Del, C_7, PWTSCVPSAKPWRRGSVLTHSTWSYCTARGARAS-SASSSPPTCTTARSLQGQTRRW PRLP, (SEQIDNO: 6762); XM_005627762.1, C12H6orf132, Del, C_7, PWTT-SPKTP, (SEQIDNO:6763); XM_014117646.1, LOC106559457, Ins, C_7, PWVAEEPV-VILQGTSWFWQHTTYGQHCLGPR-LYHFTSKASQHTDPVSKRSNAGIAS QPTLEVTVGNSL, (SEQIDNO:6764); XM_014113085.1, SAL13, Del, C_7, PWVLWPPEWTKHALA-VVHPSWVWTKRTPRQEPAGRSHGLLKITRRLALT, (SEQIDNO:6765); XM_005616816.1, LOC102151589, Ins, C_7, PWVPEEPLATLQGASCFWQHTTQ, (SEQIDNO:6766); XM_005616816.1, LOC102151589, Ins, C_7, PWVPEEPMLQGTSRFWQHTTYQQHCLGPR-LYQFPSKVGQHTDPCSDASQPRNRLSA HNWR-SQWATA, (SEQIDNO:6767); XM_005616815.1, LOC102151355, Ins, C_7, PWVPEEPMLQGTSRFWQHT-TYQQHCLGPRLYQFPSKVGQHTDPRS-DASQPRNRLSA HNWRSQWATA, (SEQIDNO:6768); XM_014121804.1, CACNA1A, Del, C_7, PWVWGRSVRPEWLTRGSFAWICLWPTTTPSTSIL-PSWL, (SEQIDNO:6769); XM_014107013.1, PEF1, Ins, C_7, PWWRTVWQWGTPRWWLWRGSCPR-RALWTTSWWGTLWGAPLWNSRRTIWWCGP GGPLWSATSKFLRCPASWALWTGTSSR, (SEQIDNO: 6770); XM_014121664.1, KIAA1257, Del, C_7, PWWWKCMTGTAN, (SEQIDNO:6771); XM_014114672.1, HCFC1R1, Del, C_7, PWYSPHLCPHSGARALSCFSGATLGT, (SEQIDNO:

6772); NM_001097544.1, PAX6, Ins, C_7, PYADPHEQSANGHLGRHFHRTHFPWCVSSSSSWK, (SEQIDNO:6773); XM_854614.4, MBD6, Del, C_7, PYCSPHFQHPLPS, (SEQIDNO:6774); XM_014118768.1, WFS1, Ins, C_7, PYEPLWPTASTTAAPGP-LAAQCHCLGGT-GREGGAPCSGTRRCQCGCPRCSPGPKCSE PGKGGQSR, (SEQIDNO:6775); XM_846855.4, SCAMP3, Del, C_7, PYLLFAQSSPAFSRTSPWRSPKN-FRRLYLPCTISGCAARWPFS, (SEQIDNO:6776); XM_014113546.1, DNAH2, Del, C_7, PYMSNSP-FLRSMRC, (SEQIDNO:6777); NM_001284456.1, CX3CL1, Ins, C_7, PYPHPHHFTHSLREQG, (SEQIDNO:6778); XM_005624035.2, LOC483345, Del, C_7, PYPPQERPWPSHWSSGCVCWWLGLKV, (SEQIDNO:6779); XM_543571.4, LOC486445, Ins, C_7, PYRRRR-PRAPKVRLWTRIPGC (SEQIDNO:6781); XM_005642194.1, AEBP1, Ins, C_7, PYSGLLL-RASQTQETPHGPGDR, (SEQIDNO:6782); XM_005619435.1, LOC610073, Ins, C-7, QAAAASRLP, (SEQIDNO:6783); XM_014119834.1, EPHB6, Ins, C_7, QAALQRGRQVDGSRRGLPLPAGPPAGPRRQGLPSLP, (SEQIDNO:6784); XM_843925.4, DAP, Ins, C_7, QADRVHLRSDRPGRQRLPTSSRPGGSPEAPRLH, (SEQIDNO:6785); XM_005630877.1, LOC102151356, Ins, C_7, QAGLGDCLFERLTLKHD, (SEQIDNO:6786); XM_855303.4, ARHGEF15, Ins, C_7, QAGSRSAL-GRWNPNRGQS, (SEQIDNO:6787); XM_014117194.1, B4GALNT1, Ins, C_7, QAGTAGPRA, (SEQIDNO:6788); XM_005630840.1, LELP1, Ins, C_7, QALCQALSS, (SEQIDNO:6789); XM_538933.4, CRIP3, Ins, C_7, QAQDWPPPGQEKPSPHEDIHWGDFTVPWL, (SEQIDNO:6790); XM_542210.4, GRIN3B, Ins, C_7, QAQRLHHGQVAPRLRSLHRRGL, (SEQIDNO:6791); XM_014116184.1, MTA1, Ins, C_7, QARPREERV-WRARRPDPGQVGPRHQQRLPHHPGQEEL, (SEQIDNO:6792); XM_014117439.1, KCTD17, Ins, C_7, QARVPCAAVPGGGADTDGLHHVRRLAL, (SEQIDNO:6793); XM_014118741.1, SCRIB, Ins, C_7, QARVTGGC, (SEQIDNO:6794); XM_848915.4, C5H16orf70, Ins, C_7, QAWCPPENSRAPL, (SEQIDNO:6795); XM_844279.3, SLITRK5, Ins, C_7, QCCLCRTQPERVSGVKSKTKR, (SEQIDNO:6797); XM_847692.4, FAM214B, Ins, C_7, QCLPCSYPCCQPYPAGQL, (SEQIDNO:6798); XM_014121817.1, LOC106560102, Ins, C_7, QCLRRK-NELFTIYHTSFNGI, (SEQIDNO:6799); XM_548063.4, ASB16, Ins, C_7, QCPGPARQATPLLPRPSRAQCSVLW, (SEQIDNO:6800); XM_846100.3, FAM78B, Ins, C_7, QCTSETQCQRCPGPHVEAQARTTSGCDPS, (SEQIDNO:6801); XM_005617747.2, RPS6KA1, Ins, C_7, QCWCPSAVPWLQLRGHWPDGG, (SEQIDNO:6802); XM_014113682.1, PTPRK, Ins, C_7, QCWPYR-GALQCWCWTDWLLHRDRHHAGHG, (SEQIDNO:6803); XM_005616171.2, TNNT1, Ins, C_7, QDPRRGTCGLR, (SEQIDNO:6804); XM_005620578.2, ZC3H18, Ins, C_7, QEADRQWQRQRQQLQRL, (SEQIDNO:6806); XM_547479.5, GPR161, Ins, C_7, QEKELRDI, (SEQIDNO:6807); XM_005634029.2, MBNL2, Ins, C_7, QELPGGERKSHCLLRFPQG-PLFKRELQVSSSSNTFKNSTRN, (SEQIDNO:6808); XM_005633459.2, MYO7A, Ins, C_7, QEQPRDSVRDQPLCRRRLL, (SEQIDNO:6809); XM_541492.5, PRR12, Ins, C_7, QERAAL-SASPGPAAAASYHPHCATPASCWSLWAGRCAGGG, (SEQIDNO:6810); XM_546816.3, PKD1L2, Ins, C_7, QFIQQCDPQVHSPWGIHCVC, (SEQIDNO:6811); XM_857873.4, PTPRF, Ins, C_7, QGAARGAAGL-PATVPPCR, (SEQIDNO:6812); XM_005624466.2, KCNH4, Ins, C_7, QGLCCLEAP-PASHSPTGNLWTSGPQSPDSGWH, (SEQIDNO:6816); XM_542508.5, GALNT18, Ins, C_7, QGLVEAGELHRPDQEPCPHRLLYRGSAVLPGDWP-TRRRHGGLRRRECRAGDQGMA VWRQRGGPAM-LADCPH, (SEQIDNO:6817); XM_005639618.2, LOC102153772, Ins, C_7, QGPKAAAAARGERAS-RAGGFGPWAAGRRERAALGTASF, (SEQIDNO:6818); XM_005637678.2, WBP1L, Ins, C_7, QGPPGRAEQSLVWAQQKQHETPKHR, (SEQIDNO:6819); XM_014122211.1, REXO1, Ins, C_7, QGPVGHRDQGPWAARLQGGPGH, (SEQIDNO:6820); XM_014117950.1, AKNA, Ins, C_7, QGGQEPRQAASGPCQASDLQVTC, (SEQIDNO:6821); XM_005639813.1, ST6GAL1, Ins, C_7, QGQPGPRQSPGPSQGQVR-GLLPGVEQGQLFQKPHPQATEDLEKLSEHE, (SEQIDNO:6822); XM_005622562.1, RCSD1, Ins, C_7, QGRAGPEW, (SEQIDNO:6823); XM_005620601.1, GPR157, Ins, C_7, QGSCTLQDRRLSGIQTYPR, (SEQIDNO:6824); XM_014120095.1, LOC102155747, Ins, C_7, QGSLGVGLGAGRGHVGRGRSGTPTRAPA-PEPQGGLLLGARK, (SEQIDNO:6825); XM_014116704.1, MTMR4, Ins, C_7, QGTSERGGE-SAGALCSAAG, (SEQIDNO:6826); XM_005634779.2, ISM1, Ins, C_7, QGVGPSSPRPPDF, (SEQIDNO:6827); XM_854764.4, MAP1A, Ins, C_7, QHGGCPFG, (SEQIDNO:6828); XM_005624459.2, STAT3, Ins, C_7, QHL-PRSPRKLDNLISRVTTSDPPTN, (SEQIDNO:6829); XM_861323.3, SRSF10, Ins, C_7, QHLSVRKERGR-RHQV, (SEQIDNO:6830); XM_546506.4, DSCAM11, Ins, C_7, QHPGDEEHHSCRRTGHPHQL, (SEQIDNO:6831); XM_531632.3, NABP2, Ins, C_7, QHPNYPKPAQPHT-CRPSWPLQQPCQ, (SEQIDNO:6833); XM_014108796.1, SORBS1, Ins, C_7, QHPQPAETLT-TAACPCLPGSQIHSQRCAAPQAVASRVHVLPCFLPT-LAPLCGHQDS, (SEQIDNO:6834); XM_014121353.1, RASSF7, Ins, C_7, QHTGPSASGQRRAPRENQPRIPL, (SEQIDNO:6835); XM_014110134.1, ZP1D1, Ins, C_7, QHVWKRRPLCWSHHYSE, (SEQIDNO:6836); XM_014108268.1, GRIN2B, Ins, C_7, QHWHCCH-PRGHFRRGGHQGCPRER, (SEQIDNO:6837); XM_014120153.1, FAT 1, Ins, C_7, QIHHCKSNRENP, (SEQIDNO:6838); XM_003638913.2, PCDH1, Ins, C_7, QIPQQAVTSPPRHLLRHQSGPRAAGPIPAQLL, (SEQIDNO:6839); XM_014108723.1, FAM186B, Ins, C_7, QIYILPSATEPRADAPGQAHYLHEGL, (SEQIDNO:6840); XM_005631571.2, C18H11orf84, Ins, C_7, QLACGSVRVQHHHGGAARGREWHV, (SEQIDNO:6841); XM_005628076.2, LOC102156955, Ins, C_7, QLAQACPSAAPTAPATRFAALFSAR, (SEQIDNO:6843); XM_005616244.2, VSIG10L, Ins, C_7, QLETSRSVSRFKCHGCYPSSQMVFRGLKF, (SEQIDNO:6845); XM_005626204.2, SBF1, Ins, C_7, QLGAPGPAPSRGPGG, (SEQIDNO:6846); XM_014117450.1, LOC106559402, Ins, C_7, QLHCPAGPPPPPPAGTQRLRRGRAVWA, (SEQIDNO:6847); XM_014121831.1, TLE6, Ins, C_7, QLPRGLPGR-ERRAGHRS, (SEQIDNO:6848); XM_532351.5, CYC1, Ins, C_7, QLPVVPPRPPVFPGPHQHPEGLPGI, (SEQIDNO:6849); XM_014122286.1, MAP1S, Ins, C_7, QLPVWGGQPPSRGL, (SEQIDNO:6850); XM_014122103.1, GPR108, Ins, C_7, QLSSPEKQ, (SEQIDNO:6851); XM_005631050.2, DLA-79, Ins, C_7, QNICDPPSH1, (SEQIDNO:6852); XM_005624045.1, DNAH17, Ins, C_7, QPGLQGLPRVHRREPAPRESLPVR- PAPQRRDWLPDSHVREAVPYCPGNAAQRDRLG SGHWRISRGKGESRAGGDPGEGPGDVQHG, (SEQIDNO: 6853); XM_847792.4, IGFBP5, Ins, C_7, QPPGLRAGQRARLRLLHDLRPGR-GAVVRRLHGALRPGAALPPPAGRGEAAARPAAR PRGLPQREELPRASQDRERLP, (SEQIDNO:6855); XM_005620885.2, NECAB2, Ins, C_7, QPQAGSRGTREESSICHPGP, (SEQIDNO:6856); XM_005627318.2, FOXP4, Ins, C_7, QPQHCGAS, (SEQIDNO:6857); XM_005627762.1, C12H6orf132, Ins, C_7, QPRGHGLLSACGLAGSQPDGKASE, (SEQIDNO:6859); NM_001006650.1, PKD1, Ins, C_7, QPRPLHLSRAGLRRELHRPADVYRVPGHLHSHGRDPA, (SEQIDNO:6860); XM_005631547.2, KCNK4, Ins, C_7, QPSPEARAAAGERRTGV, (SEQIDNO:6861); XM_014106880.1, RBBP8NL, Ins, C_7, QPTLRAQPPPGQLPAGLPAPRHGL, (SEQIDNO:6862); XM_005624000.2, GCGR, Ins, C_7, QQAPRPGPARRRRPQQEAAAFQGRRRGGPGPLCRHRPGGHPPWGGRQPLREPAGAP RGPGWGRTQVL, (SEQIDNO:6863); XM_005632456.1, STAB1, Ins, C_7, QQHKAGHLPQGVCLHPRPYWAQRPEERLC, (SEQIDNO:6865); XM_014119462.1, SLFNL1, Ins, C-7, QQHPGAGPAGVPGPGGGHAL, (SEQIDNO:6866); XM_014114822.1, BCAR3, Ins, C_7, QQNISPTTAASCDLNGAPSCHF, (SEQIDNO:6867); XM_014116213.1, SDK2, Ins, C_7, QQPHPWLPGSYSRIFLVCL, (SEQIDNO:6868); XM_005616892.2, LOC102155339, Ins, C_7, QQPLQPVCEPLPCGLSWCSGGGAAPHSLRRGLRV, (SEQIDNO: 6869); XM_014116640.1, FCGBP, Ins, C_7, QQPLRGLCRHLLPGLLRTQRTPAVPRELCRGLPV, (SEQIDNO: 6870); XM_014122285.1, UHRF1, Ins, C_7, QQQQGEGL, (SEQIDNO:6871); XM_005635063.2, LPIN3, Ins, C_7, QQRPVRRGVLTASQRHLPLL, (SEQIDNO:6872); XM_533841.5, PLXNB1, Ins, C_7, QQTIVNRCPCPH, (SEQIDNO:6873); XM_014111404.1, FRMPD3, Ins, C_7, QQWGEKAGDQRGEARGQHGKDGS, (SEQIDNO: 6874); XM_540099.4, SDC1, Ins, C_7, QRDHAAPHHSQGFDRQSHHGPGPCHPPSPQGRAA, (SEQIDNO:6875); XM_005631741.1, KCNQ1, Ins, C_7, QRERGPGGSALQLHQPRALPAQQHPAHLRTANCAPQGSRRGVL, (SEQIDNO:6876); XM_005619042.2, ZSWIM8, Ins, C_7, QRGLQRGCDV, (SEQIDNO:6877); XM_014121822.1, MYO1F, Ins, C_7, QRPAAGPAACGGNPALGKHQLLRRWELRPGGECGPAGLPRLPAGHRQHTAAGEAH QPQDGQSLGRTQ, (SEQIDNO: 6879); XM_003640056.3, RFX7, Ins, C_7, QRPQLGGGSASP-GAWAARDRGQRAATQDQELHLQNCTI, (SEQIDNO: 6880); XM_014113137.1, RPS6KA2, Ins, C_7, QRQCTSSV, (SEQIDNO:6881); XM_014117415.1, SHANK3, Ins, C-7, QRRAALPAALPLHRRAPSGRRRRPHHRPRPAPALPRLCSEAIGERPEPWAFRLHLHPP AHRQAPGPQLAPGPGPGRAGAGSGLPGALPVPHACAQPRR, (SEQIDNO:6882); XM_005636589.2, CLDN5, Ins, C_7, QRRPQIRGCARPAGAADRRR, (SEQIDNO: 6883); XM_005632724.2, GTPBP3, Ins, C_7, QRRQEQPGEPTQPEACVHSVAGAGDHPR-RAGDPRGPGWVPRAAERHGGVAGGRG AGGAG-GRAARPPEAGAG, (SEQIDNO:6884); XM_005628127.1, LOC102154750, Ins, C_7, QRWNSLPILPVQQDGAGRWPPDMVGL, (SEQIDNO:6886); XM_005633023.2, TICAM1, Ins, C_7, QSGADGHPLPRGMH, (SEQIDNO:6887); XM_014116790.1, FAM222B, Ins, C_7, QSLAAWRSEDARLRCPPECDRVYLNYPPFNGGHPAAQPAPG-PEQHRAPDQPVLPDE GRHQHYLSV, (SEQIDNO: 6888); XM_014117011.1, PKN3, Ins, C_7, QSMSPDSSHTPGSCRACLAQ, (SEQIDNO:6889); XM_005636451.2, OSBP2, Ins, C_7, QSQEACPHS, (SEQIDNO:6890); XM_546577.3, BCL6B, Ins, C_7, QSRQPRPQGLQLEKVQVHRAKLSGLPSREPGR-GEEFWSTLPPSPAPQWRRGFQQQW QRQ, (SEQIDNO: 6891); XM_005640730.1, LOC102154007, Ins, C_7, QSSRAVGATPPYPRAARTPPPRRAGLRELPHRPGPR-GLPPLSRAAGTPPPPVVQGRGS HPRHPGP, (SEQIDNO:6892); XM_014118241.1, NOTCH4, Ins, C_7, QTLCPWRPLPEPISWTRDLPVCTWLPG, (SEQIDNO: 6893); XM_003432681.3, KMT2B, Ins, C_7, QTPKGRSLTYSAASCCHLPTRPP, (SEQIDNO:6894); XM_014115762.1, CDH24, Ins, C_7, QVASEPLPVLCGG-NGGARHPGGPAAGPGPRPGGQCPHGI, (SEQIDNO: 6895); XM_005639723.2, BCL6, Ins, C_7, QVHILRLAVPTARGDVPPHRWAHIPRGDGGDPV, (SEQIDNO: 6896); XM_542201.5, PCSK4, Ins, C_7, QVQLLSGT, (SEQIDNO:6897); XM_846419.3, ZNF362, Ins, C_7, QVRARPQKDQGGEPRGAACPRSPLPHPGLRRDCQGGQDIQV, (SEQIDNO:6899); XM_544319.4, PCDH12, Ins, C_7, QVRHQLSQGQCPGLQ, (SEQIDNO:6900); XM_846897.3, TBC1D10C, Ins, C_7, QVSSRLHILPGYPI1, (SEQIDNO:6902); XM_005638951.2, LOC102156742, Ins, C_7, RAAAPGAPPPARWGLWARGAGARCWAGGAWGEEL, (SEQIDNO:6903); XM_005618371.1, MAN2A2, Ins, C_7, RAACHRRPFLLGGGGILRAYSPGGPAI, (SEQIDNO:6904); XM_005629427.2, ACSS3, Ins, C_7, RAAPASSRPHPRLQPSRLLEPLQVFRAGCGLGE, (SEQIDNO:6905); XM_005629401.2, LOC100855618, Ins, C_7, RAAPGPRRPGHELRQRGGA, (SEQIDNO:6906); XM_014115692.1, LOC100687926, Ins, C_7, RAGLRQLLGRGLRCDPSRGPRGSCLHLVAAGPHSAPSR-SAAPIRQQHPSVPSPRLTRP GSGSSARVVGRCIFFKQQQPE, (SEQIDNO:6907); XM_543071.4, NPEP1L, Ins, C_7, RAGRPQPHPRRSHPDHCMGGQRDRL, (SEQIDNO:6908); XM_014117109.1, ESYT1, Ins, C_7, RALPAAPGRPGRCSAP, (SEQIDNO:6909); XM_005625727.2, TTLL8, Ins, C_7, RALPRVPGLTAAQPGLQALPLLLRHGAAGRPLRGPGRRPGR-RHVEPV, (SEQIDNO:6910); XM_014121804.1, CACNA1A, Ins, C_7, RAPAPRLLPGLRLRRGRGPR-GRRRGGAPGRGLRRAAPRATRVLAQDSPGPGPGLRL AFPARPATPQRLLPGRTGQAPRAGLPERPARSLQRD, (SEQIDNO:6911); XM_014119707.1, E2F7, Ins, C_7, RAPQHPGR1, (SEQIDNO:6912); XM_014112944.1, LDB3, Ins, C_7, RAPSVPPGQGHRAAGGALPGQQQDPALRPLQQRHQGPLSGSHGPFLAPGGVQLRLL QDLPGGRVLRGGAEQRLLRALL, (SEQIDNO:6913); XM_540605.4, OR10C10, Ins, C_7, RAPTGLLRHHR-SQYHPALPFCLGYCPHGVSHLSLLYLHPGHNL, (SEQIDNO:6914); XM_014113507.1, ARRB2, Ins, C_7, RAQPTPAPHSPAGPAAEEAGPACPPIFLHNTPEPAL-LCHPAAGPRGHGEGLWSRL, (SEQIDNO:6915); XM_014116870.1, COL5A1, Ins, C_7, RASGAAGSARTS-WREGRDWGRGPDGSPRSPRPPRTLWSSRCRWA-TRASRWNRQPR CRGREG, (SEQIDNO:6918); XM_014109098.1, COL17A1, Ins, C_7, RAS-WSHGTARTSRCPRSCGPSWSPWTARPTRRARTC-WRIVHGQQQLHL, (SEQIDNO:6919); XM_005617936.2, KLHDC7A, Ins, C_7, RATGTRAAGPHPRQLGGPRGRQD, (SEQIDNO:6920); XM_014111810.1, PRICKLE3, Ins, C_7, RATPRTPQPA, (SEQIDNO:6921); XM_014112867.1, COL13A1, Ins, C_7, RATRPPGAEGRKR, (SEQIDNO:6922); XM_849440.4, CYP2R1, Ins, C_7, RAVGAANRQHLLAGGLGRARPRL-HEKAEPGVRRDLQFRSWRYISCGFKWL, (SEQIDNO: 6923); XM_014119446.1, KTI12, Ins, C_7, RAYGSPE-GAL, (SEQIDNO:6925); XM_014121319.1, CDC42BPG, Ins, C_7, RCVYCAAAGRERGRA-GALAAGAGRAAEAAAGLTAKAPSCVHPEGSL, (SEQIDNO:6927); XM_542131.4, ACTL9, Ins, C_7, RDAGAGAHWRPRYGQKEPSEGAPGGAGRCGPER-AALRGLLALPGLRGPLPRGAAP QPAPRGPRGGGG-SAHQTLLRVDRGLHPGLVAGLPVLLGPSGAV, (SEQIDNO:6928); XM_014117695.1, FBN2, Ins, C_7, RDDPTSGRRGLC, (SEQIDNO:6929); XM_003434001.4, COL6A1, Ins, C_7, RDKRHQRLPRPQGRRGRSRRPRR, (SEQIDNO:6930); XM_543112.5, MYT1, Ins, C_7, RDLGHARERAEVPYSGLYGPR-PREQQPQHAQKFVWVSHCCC, (SEQIDNO:6931); XM_005624990.2, CUEDC1, Ins, C_7, RDLGKDFGT, (SEQIDNO:6932); XM_543467.4, RHBDD3, Ins, C_7, RDPAVGSPG, (SEQIDNO:6933); XM_546245.4, FOXI1, Ins, C_7, REAVLASPTRHPMPQQLPLLHDLLCERVE-PSEPPCGNTRTEP, (SEQIDNO:6934); XM_014113173.1, DRD2, Ins, C_7, REDPVQSHTTQPPPADPPRPVP-PRPPQHCRQPRQTREEWACQRPPQDCQDL, (SEQIDNO:6935); XM_544279.5, KLF6, Ins, C_7, REGARRDCGEAR, (SEQIDNO:6936); XM_546181.5, ZMIZ1, Ins, C_7, RETPHAAPPQLYELHETHSVAQ, (SEQIDNO:6938); XM_005622571.1, POGK, Ins, C_7, REVPQWDGNPLPPVRVDDRGLDAGLVGGSVAAE-DGCSTQTAWDADPERLPWPRH, (SEQIDNO:6939); XM_014117695.1, FBN2, Ins, C_7, RFPAEPHWCGLC, (SEQIDNO:6940); XM_005619965.2, ELP5, Ins, C_7, RGACPCSRPATHGASWPRPHGSIEQPGPD, (SEQIDNO:6941); XM_844550.3, ZDHHC23, Ins, C_7, RGAGREPRQGEGGLVRQVPAGATGPRVALPDLRHL-REENGSPLCLDK, (SEQIDNO:6942); XM_005639502.2, ZDHHC23, Ins, C_7, RGAGREPRQGEGGLVRQVPA-GATGPRVALPDLRHLREENGSPLCLLCWRIKSPSNTC PFGLLAHFGVWDHTDLGHHL, (SEQIDNO:6943); XM_003640238.3, IKBKG, Ins, C_7, RGATGLLLPQVPVSGP, (SEQIDNO:6944); XM_005633536.2, ARHGEF17, Ins, C_7, RGCAR-ACGLPCQSPLHTAGPITRGCH, (SEQIDNO:6945); XM_544279.5, KLF6, Ins, C_7, RGCSE-QPRLCLQPGDQQPELRREQRVLRQLRGTFSHH, (SEQIDNO:6946); XM_005630224.2, KIF3C, Ins, C_7, RGE-EQDHEPPFPGL, (SEQIDNO:6947); XM_005623708.1, ISM2, Ins, C_7, RGGVPGAAAGGQGVL, (SEQIDNO:6948); XM_014111262.1, KIRRE1, Ins, C_7, RGHQDRRRPRAPAAGRH-PAQPHLPSLQRQAGRHHHLVPGRDAAGGRRGQHG-TAEG RQERDHRQPAAH, (SEQIDNO:6949); XM_005621779.2, NPRL3, Ins, C_7, RGHRTEPESHP-PIPRSAAAQ, (SEQIDNO:6950); XM_014107131.1, OVOL2, Ins, C_7, RGLPQRRRQQQRRRQQQRG-GAWRRREQLVPARPRARDPRTRRRRGPRRTPGGDAA PGRQVENQVHHRHVQRPSGPQL, (SEQIDNO:6952); XM_005640267.2, XIRP2, Ins, C_7, RGPAAPCP, (SEQIDNO:6955); XM_003431951.3, HIVEP3, Ins, C_7, RGPAWHPQSLRAPSLPGVPEAPRRGAQEGEE-TAEAGQVHMPVLQPALRQAQRAPEA YPLAHGRAALPLRPLRLLLQDQE, (SEQIDNO:6956); XM_849841.4, APOA1BP, Ins, C_7, RGPGHLRTWK, (SEQIDNO:6957); XM_543528.4, SUSD2, Ins, C_7, RGPGL-GALRASQPPVRLRPAVLLHGGRQPAP-DGRLHRRQHPGPRPRLGRAPLPHTTP RARPVPLAL, (SEQIDNO:6958); XM_005626825.1, GRHPR, Ins, C_7, RGPGRARPGCGL, (SEQIDNO:6959); XM_547150.5, SRL, Ins, C_7, RGPGTRANRGGPGRGVL, (SEQIDNO: 6960); XM_014110917.1, LOC106558305, Ins, C_7, RGPRPWFRPTAL, (SEQIDNO:6961); XM_014122283.1, ZSWIM4, Ins, C_7, RGQAEPGLPRGTGGARCRGR-GRARPGPARGAAGPQRQASSRELGLRAG, (SEQIDNO:6962); XM_014107696.1, NEU4, Ins, C_7, RGQAPGALPAF1, (SEQIDNO:6963); XM_537756.4, CPD, Ins, C_7, RGQWSRQQPRP, (SEQIDNO:6964); XM_014111003.1, MAP2, Ins, C_7, RGRAGSRPVHV-GASGCRVWPREGRRPGQRDGDQGEGGQA, (SEQIDNO:6965); XM_014106893.1, MAST4, Ins, C_7, RGRATPVPRPDTC, (SEQIDNO:6966); XM_003639781.3, DCAF15, Ins, C_7, RGRGTSSRAWLCQLHQAVLRAGVQRRDRTGGRVRG, (SEQIDNO:6968); XM_541488.5, PNKP, Ins, C_7, RGSP-PHLPALGRASPCPGPGTLDPGYRPE-VLQKPSGAGRKPQDQDRGSETAGN, (SEQIDNO: 6969); XM_005620790.2, CDH3, Ins, C_7, RGYLHHREGNRLVAVE, (SEQIDNO:6970); XM_005639752.2, SOX2, Ins, C_7, RGYLLLPLQGALPGRGPPGHDQHVPPRRR-GAGARRPQQTAHVPALPERPGARHGH, (SEQIDNO: 6971); NM_001122602.1, IGF2R, Ins, C_7, RHCCLPGER-GAGV, (SEQIDNO:6972); XM_014115303.1, PEAR1, Ins, C_7, RHLRSGLLRALLLRQRHRLLAHRRRLRLQGG-LAAW, (SEQIDNO:6973); XM_546739.5, MEGF6, Ins, C_7, RHLWGELWAEVPLSR, (SEQIDNO:6974); XM_543564.4, THAP7, Ins, C_7, RHQPAPAMQEAML, (SEQIDNO:6975); XM_005623942.1, LOC102153864, Ins, C_7, RHRPCRGRGQGWGPGGH-SPRLCAGHVPGQVVL, (SEQIDNO:6976); XM_014112560.1, FAM193A, Ins, C_7, RHWRHPQSPAAPPSGFCSRLSL, (SEQIDNO:6978); XM_005640917.2, SUSD4, Ins, C_7, RIPRLRGHGHGPGGVRTL, (SEQIDNO:6979); XM_849386.2, TMEM119, Ins, C_7, RKPLCLQCRPQGL, (SEQIDNO:6981); XM_014113940.1, VPS9D1, Ins, C_7, RKRAGQQPCGASLTPGAQLHGCTGQRQLL, (SEQIDNO:6982); XM_014118793.1, JRK, Ins, C_7, RLAAGLPPPLQHQRCRLQRGLRLECCARPHLQPR-LEEAVARGHICRRLVF, (SEQIDNO:6983); NM_001313808.1, TRIB1, Ins, C_7, RLA-LQPAAAARRSGSRRRLRERAGAQPHRRL-PAAAAGGARACVPGAVHPHRPRAA LQGVSY, (SEQIDNO:6984); XM_540000.4, LOC482885, Ins, C_7, RLCHARPAQPGGPRRAEHCLPPRELLQ, (SEQIDNO: 6985); NM_001003150.1, MT4, Ins, C_7, RLCQVCPGLHLQRRLGQVQLLCL, (SEQIDNO:6986); XM_014113410.1, ZBTB16, Ins, C_7, RLE-DREDLPLPVLRV, (SEQIDNO:6987); XM_847443.4, GPN2, Ins, C_7, RLGQDHVLPGHE, (SEQIDNO:6988); XM_537807.5, GTF3C5, Ins, C_7, RLGREPDWPEQGPAPPQCHLCQL, (SEQIDNO:6989); XM_014107689.1, LOC100855783, Ins, C_7, RLGSSHAVCSLAGLRAQQEQEKEEDRFHSLQRL-RADLAPPGKSGRELEDGDGGPE PRGHQLRR DAE-HAEVRRPGQADPL, (SEQIDNO:6990); XM_005625428.2, C9H9orf173, Ins, C_7, RLLHEP-LTCVHRLGHLRPLSRSGCLPRGGLL, (SEQIDNO: 6991); XM_846276.4, AKT1S1, Ins, C_7, RLLRAPGL-SPAHTAVCQVPACVRARLGLQGEEARSTVIG, (SEQIDNO:6993); XM_847603.3, LIMK2, Ins, C_7, RLL-SPGRHLLQTGA, (SEQIDNO:6994); XM_531921.4, KDM3B, Ins, C_7, RLLYVFSRSEEQGQPTQLP, (SEQIDNO:6995); XM_014122369.1, FBN3, Ins, C_7, RLPPQWGHPHL, (SEQIDNO:6996); XM_547741.6, LRRC16B, Ins, C_7, RLVLRTREQPAHSQWLLGGSV, (SEQIDNO:6997); XM_014116373.1, LOC490917, Ins, C_7, RMGDAQGRGQRAPLLLQPRHGRDHLGVALRGL, (SEQIDNO:6998); XM_014116734.1, LHX1, Ins, C_7, RNERGGRVV, (SEQIDNO:6999); XM_014106445.1, COL4A2, Ins, C_7, RNHRVSWVHRK, (SEQIDNO:7000); XM_014109869.1, COL18A1, Ins, C_7, RPAAWNPTLSCHRGQGRLGCSRRGLSGAWAC, (SEQIDNO:7001); XM_003434094.4, SIDT1, Ins, C_7, RPAPRPPRPQRGRRFRPRLRRGGEPQHREHLLLDL-PHPTG, (SEQIDNO:7002); XM_014109365.1, CDAN1, Ins, C_7, RPCRDEAFT, (SEQIDNO:7003); XM_005618546.2, LDB2, Ins, C_7, RPGEQQPLEQ, (SEQIDNO:7005); XM_014116364.1, LOC102155336, Ins, C_7, RPGPARGTGSHDGGGLDGPCAGICDL, (SEQIDNO:7006); XM_014112099.1, LOC106558522, Ins, C_7, RPIAVPSTSPRTLVCPWLSWL, (SEQIDNO:7008); XM_542121.5, LRRC8E, Ins, C_7, RPLAAGAPA-GAQPAPLACQAALLAADLPAGPPEGHLRQVRGAPR-RAPVGVWAAWP GGAAPRGALPPGAGSGSGPREPP-GAEAAQGAVSAEQCQQGAGQRD, (SEQIDNO:7009); XM_850276.3, NCCRP1, Ins, C_7, RPLAPGVPRLPPVWPRGALRPLPAQDQEPEGAR-WAAADKGDRLLRVCAVQGV, (SEQIDNO:7010); XM_014118664.1, LOC102154884, Ins, C_7, RPLGAPSGSPG, (SEQIDNO:7011); XM_014121827.1, PTPRS, Ins, C_7, RPLPDVPAGPSLTQELQGED-DHEDVGPAQLGIS, (SEQIDNO:7012); XM_014113968.1, LOC610373, Ins, C_7, RPPCGIIH, (SEQIDNO:7013); XM_014112065.1, LOC491446, Ins, C_7, RPPGQGAADVFHREVRGRERELAAGQRADGRAL-PAVRRLRPRRGQALRVPGPVGQ, (SEQIDNO:7015); XM_014112341.1, ADAMTS7, Ins, C_7, RPPLFPP-CAVQPL, (SEQIDNO:7016); XM_005621491.2, GPRC5B, Ins, C_7, RPPPPAPRLPTRSPFAKGAAPWSAD-KGPWSVAGSGVPARGPGPRATLAAQLRQDGG LVFAAVYQPQK, (SEQIDNO:7017); NM_001031818.1, COL4A4, Ins, C_7, RPPRETWSPWSCRCHRKSC, (SEQIDNO:7018); XM_014112867.1, COL13A1, Ins, C_7, RPPRPPRKVWTGRNEGRRRTHREPRREGGERGDGT-GRRTGRERRARGEG, (SEQIDNO:7019); XM_014112864.1, COL13A1, Ins, C_7, RPPRPPRKVWT-GRNEGRRRTHREPRREGGERGDGT-GRRTGSRRPNWGERRTRWPR ETRSNRIARPYRA-PGNRRERRARGEG, (SEQIDNO:7020); XM_005628301.1, LOC102155929, Ins, C_7, RPPSGSSGQIPAAPRGISPAARPPASPTAGQPRLGPPS-GISAPPAPRSAHQRLRNIGD, (SEQIDNO:7021); XM_005621001.2, COL26A1, Ins, C_7, RPPWPSRQPGLPSKQPPGRPLLPAASDGQGRRRLT-AGFCCCGHSAGRRPRAPGPPRP SRSPWATWSPRT-PRCTRISGPGWRAGHDGTSW, (SEQIDNO:7022); XM_014118255.1, COL9A1, Ins, C_7, RPPWSSRHR-WHRR, (SEQIDNO:7023); XM_014110056.1, LOC102151348, Ins, C_7, RPQGCGENPAPAAPPTTPQ, (SEQIDNO:7024); XM_005622187.2, LGR6, Ins, C_7, RPRALRLPVSDPPLRSAARGPQVGGQPL-CRARGSPLWEPTSLRGWRTAAQGRGSHA RGWGLVSGQGLAARGPSLCLTLI, (SEQIDNO:7025); XM_845916.4, COL3A1, Ins, C_7, RPRGPGGEERR-PRRDGPRWSLRRSWSCRLPRPPWSPRSTR, (SEQIDNO:7026); XM_005633811.2, LOC102152567, Ins, C_7, RPRPAAASRAR-GRRDAGAPQRASGLGPRAAGDARRAEPRQAPPGAE-GSGGRAPGG QRAGDSPWTPSS, (SEQIDNO:7027); XM_014114446.1, MSLN1, Ins, C_7, RPRP-PHHRDPQHHTWGALPSPHLGPALE, (SEQIDNO:7028); XM_005638009.2, CHD7, Ins, C_7, RPSGPPWWQWRQSDGSLPWHAE, (SEQIDNO:7030); XM_014116870.1, COL5A1, Ins, C_7, RPSRLAGSS-WAKRC, (SEQIDNO:7031); XM_005621001.2, COL26A1, Ins, C_7, RPSRSPWATWSPRTPRCTRISGPG-WRAGHDGTSW, (SEQIDNO:7032); XM_014116870.1, COL5A1, Ins, C_7, RPTRPRGISRGERPGWCRWAHRN-PRETWAPRTSRAGWRERSSW, (SEQIDNO:7033); XM_014114191.1, LOC106558877, Ins, C_7, RPVVPSGPDP, (SEQIDNO:7034); XM_014116209.1, LOC483316, Ins, C_7, RPWHPGPLTASRSTSSPH-TTQQELLR, (SEQIDNO:7035); XM_014111054.1, CNPPD1, Ins, C_7, RPWTGLQVPLGTLPTFF-CATVPAASR, (SEQIDNO:7036); XM_014108204.1, CABIN1, Ins, C_7, RQGQVAPPAQHAKAGHPL-GRHQVPP, (SEQIDNO:7037); XM_014110905.1, LOC106558304, Ins, C_7, RQHPGPALLGARGGREGIL-PLQ, (SEQIDNO:7038); XM_005626061.2, FER1L5, Ins, C_7, RQHQAPKA, (SEQIDNO:7039); XM_546894.5, CDH5, Ins, C_7, RRAAHPPAPEERLDLEPDAHR, (SEQIDNO:7041); XM_014116236.1, FAAP100, Ins, C_7, RRAARAGRHLPAPERAHRG-LAAVPALPWPGCTPHAGCQPTGPRLRPCGHLLGSSPR AAR, (SEQIDNO:7042); XM_005640730.1, LOC102154007, Ins, C_7, RRAGLRELPHRPGPRGLP-PLSRAAGTPPPPVVQGRGSHPRHPGP, (SEQIDNO:7043); XM_014122556.1, MICALCL, Ins, C_7, RRAGQV-LARPRATLQG, (SEQIDNO:7044); XM_005618675.2, FGFRL1, Ins, C_7, RRAQALPQTLHGRAHAHAHA-HALTHALARGGQGPPAPAHPLPVL, (SEQIDNO:7045); XM_014107094.1, HSPG2, Ins, C_7, RRGALIP-STACSCSASSSTFFLLLLL-FLLLSFWAFLSRLSVLSLLQRLLSASWEPLLLAA APSLPGEQGGGLWWEAAVYPLLHSSGAGQPAL, (SEQIDNO:7046); XM_536899.5, MYLPF, Ins, C_7, RRGRQRGLQEHLLRHHAWRRQGPGV, (SEQIDNO:7047); XM_005636795.2, LOC486523, Ins, C_7, RRHPGGHRQPESPHSPEPANRPHHPEGEDGGA-RADQDPQQQVRLLHRQGALPGATE QGPGHQVD-SAPGAGHQDREAEPGAPV, (SEQIDNO:7048); XM_005629703.2, PAXIP1, Ins, C_7, RRKA-MLPAHYFCDWICRQ, (SEQIDNO:7049); XM_014119335.1, MYCL, Ins, C_7, RRKRGSPVLPPQTWQF, (SEQIDNO:7050); XM_533193.5, CKAP5, Ins, C_7, RRLFHGHAAQQTL-SAPGVPGAAPALRPGF, (SEQIDNO:7051); XM_005636665.1, PAPSS2, Ins, C_7, RRLHGAQGL-EGADRLLRLPGEARL, (SEQIDNO:7052); XM_014117963.1, TRAF1, Ins, C_7, RRLPGAGRAQGR-PLCRLSPREREERRGPDLPEVGGRPAVWKPGQPAV-AGEGPA, (SEQIDNO:7053); XM_014117413.1, TLE1, Ins, C_7, RRPHRTRHPPPRTPDQH-PEPRGGGVRRDHQQPHEARVHGREGLRQGLGHQP-PRQQE PRLSARLS EQG, (SEQIDNO:7054); XM_014117428.1, LOC476317, Ins, C-7, RRPHRTRHPP-PRTPDQHPEPRGGGVRRDHQQPHEARVHR-REGLRQGLGHQPPRQQE PRLSA, (SEQIDNO:7055); XM_005618001.1, FBXO6, Ins, C_7, RRPPHPL-PARRPGHAVLGGLVRAPRHQQQHRHWP, (SEQIDNO:7056); XM_014114031.1, MTSS1L, Ins, C_7, RRRHAGGHPPRGAAPQDRHQRQVGAPHLV, (SEQIDNO:7057); XM_003434697.2, CMTM3, Ins, C_7, RRRPGARAPRPPARARLPVLAQRPPPAGRVG-PLVHHLCLLCGILGIRLPGSASAGVPP GPLLPIR, (SEQIDNO:7059); XM_014115096.1, PROX1, Ins, C_7, RRRPPPAPAPVASLCHRGLHHVHLPPPLPPSLDG-LPISESIRCSLRLLLGKRQSLS, (SEQIDNO:7060); XM_005630391.1, DUSP2, Ins, C_7, RRRPRLPAAR-PRAPGAPGPRGAGPGRGAGRGQCLGGRAPARRPR-ARAARRAAAEK KNRLTAPRP-PRRRLRRLPGLLSRPVLGVPRPRHVVCRGREQPL, (SEQIDNO:7061); XM_014111178.1, LOC106558357, Ins, C_7, RRRPRTRRDLRDPAAALGPADTPGPPAAAPL-PRTPRPEVAAPRAPSSWETPRLG, (SEQIDNO:7062); XM_003432767.4, FBLN2, Ins, C_7, RRRQDQLPVHAVPGAAPQLH, (SEQIDNO:7063); XM_005633132.2, DAZAP1, Ins, C_7, RRRQWLWTRSEPQRARIPPVPTL, (SEQIDNO:7064); XM_005615500.2, SASH1, Ins, C_7, RRRRAQPAG, (SEQIDNO:7065); XM_014121251.1, LDLRAD3, Ins, C_7, RRRRGPSGPGAWPGRCPRM, (SEQIDNO:7066); XM_005627563.2, LOC102154910, Ins, C_7, RRSPPVSCSVSILSGRVRRRCGGVCRLPTGDLA-SALLHLRKTGRGRMGVLWARRRM ANPGCSS-CRLIPVQACLENL, (SEQIDNO:7068); XM_014114626.1, LOC106558936, Ins, C_7, RRTEPQLAHRV, (SEQIDNO:7069); XM_014117863.1, PAX5, Ins, C_7, RRTGQLLSTDADRDGAWE, (SEQIDNO:7070); XM_532352.5, SHARPIN, Ins, C_7, RSAHTPDPTTQGGSLLEPWRLSGERGAG-GAPGPGHRGRR, (SEQIDNO:7072); XM_846062.3, DDN, Ins, C_7, RSAPPGTSERPSGGPASRAPSSFSTRAP-GAGGATAPSIRAAAERPRGGVGGALGR, (SEQIDNO:7073); XM_014122593.1, MCM10, Ins, C_7, RSCSQS-GEN, (SEQIDNO:7074); XM_845916.4, COL3A1, Ins, C_7, RSGRAPRRSRACGSPRSPGCQR, (SEQIDNO:7075); XM_014110764.1, KCNH7, Ins, C_7, RSIHQDGPKFQSFLTMS, (SEQIDNO:7076); XM_014111149.1, SLC30A10, Ins, C_7, RSPASGPRQWLCGAQRLSPSGHVPK, (SEQIDNO:7077); NM_001197171.1, COL9A3, Ins, C_7, RSPRATWEAGQGWH, (SEQIDNO:7078); NM_001197171.1, COL9A3, Ins, C_7, RSPR-NAGVQGAHRLQRRSRRGRQGRREGRSWPP-WARWRPWLCGAAGASGTPRSA RAG-WAPRGSGSHRIPRAARDPRSPRESG, (SEQIDNO:7079); XM_005631712.2, EPS8L2, Ins, C_7, RSQLPAGSQGLRTRASHGQVCQDPL, (SEQIDNO:7080); XM_005633593.2, COR52H9, Ins, C_7, RSQSY-CLWSED, (SEQIDNO:7081); XM_005633061.2, ANKRD24, Ins, C_7, RSRDPPWPGQSPA-GAAEAGCQGPQCRGGFV, (SEQIDNO:7082); XM_014114089.1, FAM65A, Ins, C_7, RSSRSRPIPAG, (SEQIDNO:7083); XM_014106444.1, COL4A1, Ins, C_7, RSSRYPWVQWNKG, (SEQIDNO:7084); XM_014116484.1, HOXB4, Ins, C_7, RTGAANL-GAGVGCERGGNERSLYRQQESAPL, (SEQIDNO:7085); XM_014106445.1, COL4A2, Ins, C_7, RTGPAWPQRRAWFPRRCRITWTPRLSRPPRT-PRHSRTNRL, (SEQIDNO:7086); XM_014109943.1, COL16A1, Ins, C_7, RTHGTPGLQGKNRTPWPPRTKG, (SEQIDNO:7087); XM_014106445.1, COL4A2, Ins, C_7, RTPRHSRTNRL, (SEQIDNO:7088); XM_539177.5, COL22A1, Ins, C_7, RTRRTPGFTWRDRLPGKTRAPRADGHTWKGWAGW-STRPARTQGPARRQRRRRSA WKTRP, (SEQIDNO:7089); XM_014113529.1, TNK1, Ins, C_7, RTSPCQSCAPGTPRPAIPT-SLCLQPFSAQPAPQGAASLAQKRTPSRSPLGSIWS, (SEQIDNO:7090); NM_001197171.1, COL9A3, Ins, C_7, RTSRTPRSPRGPP, (SEQIDNO:7091); XM_005616826.1, LOC102153346, Ins, C_7, RTSYLPSCI-PAPKAKVSPAHKPDSGSDAERGSPGPHWRAVAGPA-PRWAAGGGPAYP ARSALPIGRAGD, (SEQIDNO:7092); XM_846492.4, XIRP1, Ins, C_7, RTTGGSPSPKREAHSWFPARGP, (SEQIDNO:7093); XM_014112788.1, LSM11, Ins, C_7, RVGG-GRVSLRGSGSSAGRLTPPAPWRSPPDLCRT, (SEQIDNO:7095); XM_005618215.1, LOC102151979, Ins, C_7, RVNVLPPRSLQCTCRPGIGAPSTPSL, (SEQIDNO:7096); NM_001003373.1, C5AR1, Ins, C_7, RVPRLWHCHPGPQHICG, (SEQIDNO:7097); XM_014106638.1, NOD2, Ins, C_7, RVRCPGLCAAAP-PAACGPAAGPQLCW, (SEQIDNO:7099); XM_005625430.2, NPDC1, Ins, C_7, RVVSTGAHFPL-GAPGRAR, (SEQIDNO:7100); NM_001287169.1, SLC7A8, Ins, C_7, RVWPSTPGCHL-LIAPHMGQLCQCAVGHPGSRHFHSWEAP-GPGPDHHHGSCTDLQRR VFLAGAKECI, (SEQIDNO:7101); XM_014121877.1, MAP4, Ins, C_7, RWGGASHPRGSARSWRPHFSQWPQ, (SEQIDNO:7102); XM_547651.5, THOC1, Ins, C_7, RWRKIFKDG-RAYIKH, (SEQIDNO:7103); XM_014119467.1, SZT2, Ins, C_8, HAGPTAGPI, (SEQIDNO:7104); XM_014121820.1, LOC106560103, Ins, C_8, HASLRTKARPRLPGGELRACQRGAVRALSSWFVPQ-APSPPGCC1HLREVRGGSWRL AGGECL, (SEQIDNO:7105); XM_014111220.1, ELK4, Ins, C_8, HFLRFPLCAGAPQDPHAAAES, (SEQIDNO:7106); XM_005617844.2, ECE1, Ins, C_8, HGECLLLAHQE, (SEQIDNO:7107); XM_014111008.1, NRP2, Ins, C_8, HHHLLRLRALHQVHLRLRPAGGRLLSALRDLQDRL, (SEQIDNO:7108); XM_014115018.1, PAQR6, Ins, C_8, HLCRPLPAWIMLGQRPHLWAGGAEPQPQLPPLLCA-THRLPLRLSPARAAGPRAL, (SEQIDNO:7109); XM_847877.4, NUTM2F, Ins, C_8, HLEL-GGDTLWGRCVSHTRVPGGLCDGTRRTRLGLWGLP-GRPGNLSARPSGCGSATS GPAKCP-GALRKHRAAAPRGWQGGQRSQQPEHCVVAQGLL, (SEQIDNO:7110); XM_541488.5, PNKP, Ins, C_8, HLPALGRASPCPGPGTLDPGYRPE-VLQKPSGAGRKPQDQDRGSETAGN, (SEQIDNO:7111); XM_014107094.1, HSPG2, Ins, C_8, HPDRVLVPHGGRRADPGSELCGG-WAAPGHHHVVQAWRQPSHPTPGPRLPPAAAPH VCG, (SEQIDNO:7113); XM_014119833.1, TRPV5, Ins, C_8, HPFPVPDHIPQQQPPGLGDPSSQHPGT-CESRAGPWRGGWRGQYLSFM, (SEQIDNO:7114); NM_001284456.1, CX3CL1, Ins, C_8, HPGPLHPDPPY-PRSPYPRPPYPHPHHFTHSLREQG, (SEQIDNO:7115); XM_014118871.1, LOC106559658, Ins, C_8, HPRAYGQGGRSCGPHLGRRPGLRAQRAGDGEPPR-GAGAPLEFILEAEAPALGE, (SEQIDNO:7117); XM_014107629.1, APBB3, Ins, C_8, HPRHGRAE, (SEQIDNO:7118); XM_005619266.1, LARP1, Ins, C_8, HPSLATRDQTGACLARPG, (SEQIDNO:7119); XM_014120689.1, SETDB1, Ins, C_8, HPTCPTCTPSVPTGR, (SEQIDNO:7120); XM_005639705.2, IRX1, Ins, C_8, HSQFWGLI-ALSLSLFLPLFPAPRLSLSSPLGGSVVAGLTV, (SEQIDNO:7121); XM_547217.4, PRR35, Ins, C_8, HTPGPRVLPRPAPWPFRRHRQPASGPHG, (SEQIDNO:7122); XM_005638159.2, ESRP1, Ins, C_8, HYSSTT-SAICAPYEC, (SEQIDNO:7123); XM_014110156.1, PVRL3, Ins, C_8, LASKRPSISD, (SEQIDNO:7124); XM_014117851.1, NPR2, Ins, C_8, LGQSPLCL, (SEQIDNO:7126); XM_014119807.1, ATG9B, Ins, C_8, LLGLPIHPTPGLSDSP-SHTPMPPGPSWAADRPSDPRAGL, (SEQIDNO:7127); XM_539044.5, BACH2, Ins, C_8, LLLLLLLLLGELHEE- AGGQRPGGLPGEGASAGIQEPDGDRGLLPGND, (SEQIDNO:7128); XM_005634149.1, SCN5A, Ins, C_8, LLRQRHQGHQR, (SEQIDNO:7129); XM_014115306.1, NES, Ins, C_8, LPAPATDWEAAGSRGYTG, (SEQIDNO:7130); XM_003434606.2, FOXD3, Ins, C_8, LPDPSTPTFGGLHPFAHT, (SEQIDNO:7131); XM_005617044.1, ZNF438, Ins, C_8, LPGGPFRPELCPLCTDAGQEGRPPPTLGAAAL1, (SEQIDNO:7132); XM_844550.3, ZDHHC23, Ins, C_8, LPPPRRGHCL, (SEQIDNO:7133); XM_014113971.1, RLTPR, Ins, C_8, LPSHRPKRRRPQPL, (SEQIDNO:7134); XM_005616836.2, LOC102154596, Ins, C-8, LRQPELRPQ, (SEQIDNO:7135); XM_862201.3, ZFP64, Ins, C_8, LRVQGTNRDPRRKDIQLLLPRLPLQNCSWHERFGPPSENPHGRQTTQM, (SEQIDNO:7136); XM_538777.4, ZNF462, Ins, C_8, LSRNARGSQNVQVQRLCF, (SEQIDNO:7137); NM_001002994.1, SCN5A, Ins, C_8, LVRQRHQGHQR, (SEQIDNO:7138); XM_005635333.1, NKX2-4, Ins, C_8, PAAAALPAPRGGARVGQGRQAVPERGQHAHARPGRPAAARPDARAGARGALAQP ARAARPGGRPGVPGRCGGGLRRRRAGRQPALRQDVV, (SEQIDNO:7139); XM_544073.5, PXDNL, Ins, C_8, PAAATQAGLHGAGGRGRGHPRRPVHAHAHAVGPVSGPRSGPRGACLEHFSLLRRA AV, (SEQIDNO:7140); XM_014107254.1, GMEB2, Ins, C_8, PAAPRCRPPQQHRAELRHAGLGEEGAGQPQVPDGPLSGAVRPRPGSPRAAV, (SEQIDNO:7141); XM_844462.4, SPATC1L, Del, C_8, PAARPRCASCSSTCCPPSSWATRCCCSAACASSPRTTASRSSPG, (SEQIDNO:7142); XM_005620294.2, IGSF9B, Ins, C_8, PAAVTYFGNTSTCTRERCYT, (SEQIDNO:7143); XM_014111268.1, IGSF9, Ins, C_8, PACHRVAALWIPTSHLHPVRPLLSTHRP, (SEQIDNO:7144); XM_548709.6, DPYSL4, Del, C_8, PADAPTSRLCL, (SEQIDNO:7145); XM_014109693.1, LOC106558086, Del, C_8, PAGAIPPRLRGGGAGRRGAARGPGGRGCPLPRRPHPRRGLWDLLGIPRLPA, (SEQIDNO:7146); XM_014108311.1, LOC106557876, Ins, C_8, PAGARAHRRPPAPGRPPARGIPPARRPPALSPAASRSGARAPTNPREQPV, (SEQIDNO:7147); XM_005616395.2, C5AR2, Ins, C_8, PAGVRGGLRGLGRG, (SEQIDNO:7149); XM_005629436.1, AMDHD1, Ins, C_8, PAGVRPRSPPFSPGWVYKSHRSC, (SEQIDNO:7150); XM_541589.4, CIC, Ins, C_8, PAIPPTPRPLHSCHRQV, (SEQIDNO:7152); XM_014111420.1, GAB3, Ins, C_8, PALLPAPRRLGPRAQGAGPRAPHAAPAPPEAEPPVRAAPGRAARGRGGVQKSLPVR PGQREDPES, (SEQIDNO:7153); XM_014113861.1, ZNF469, Del, C_8, PALPPPTIPH, (SEQIDNO:7154); XM_014111293.1, ARHGEF10L, Del, C_8, PAPIYWFLPPVVCQSRLFPAPKI, (SEQIDNO:7157); XM_003433123.4, ZBTB47, Ins, C_8, PAPLLHHCHFGRQDERQQL, (SEQIDNO:7159); XM_014112554.1, ADD1, Del, C_8, PAPLSSLGKEVDVLKSTCYH, (SEQIDNO:7160); NM_001314087.1, KISS1R, Del, C_8, PAPPAELHGLPGRAPAPAAPGSRASVPRAPWG, (SEQIDNO:7161); XM_005638643.2, LOC102157171, Ins, C_8, PAPPAGAT, (SEQIDNO:7162); XM_014110074.1, LOC106558152, Ins, C_8, PAPPPPPAAPGCPGSDLRLRRETSPGT, (SEQIDNO:7163); XM_014113868.1, PLCH2, Del, C_8, PAPPREGPCAPRDLAPK, (SEQIDNO:7164); XM_539741.5, GAS2L3, Del, C_8, PAPPRPGSFPPRGPPARRPRRCCPASLRAKPNRSL, (SEQIDNO:7165); XM_005629418.2, ARTN, Ins, C_8, PAPRPRSPGAPHRQPAG, (SEQIDNO:7166); XM_546201.4, RBP3, Ins, C_8, PAPRRAISGGGVLPH, (SEQIDNO:7167); XM_847581.4, KIAA1024, Ins, C_8, PAPTAQAAQRQLPGGAGVQPAPLPGIPQSPHEEQPSVHGHAADGAGRGEAGPTLLD HRGVHEERGRQGQADCPGPADARIFKP, (SEQIDNO:7169); XM_014116397.1, LOC106559250, Del, C_8, PAPTRAASPGSWSCWASRTCPRCGRCSPRSSWPCSCSRCWATRSSCC, (SEQIDNO:7170); XM_005616836.2, LOC102154596, Del, C_8, PAPTRAASPVSWSCWASRTCPRCGRCSPRSSWPCSCSRCWATRSSCC, (SEQIDNO:7171); XM_014118914.1, LOC106559676, Ins, C_8, PAPVLWSRRDRPTTTQNCQQSPWAAWSRPWVTAAAWQW, (SEQIDNO:7173); XM_005631207.2, SSRP1, Del, C_8, PAQKTRHQDLMS, (SEQIDNO:7174); NM_001003247.1, KCNB2, Del, C_8, PAQPGRCPSPRRTSPSPPRSSSAPSS, (SEQIDNO:7175); XM_847992.3, NCOR2, Del, C_8, PARAPSRGPWHPPAPVTRPSPAPQQRASHPTTPARTSLRRPPRPRTCIGKRLKVNPFPS RNWSSVLWVTMVAATAPTEWSP, (SEQIDNO:7176); XM_005631925.2, MGAT4D, Ins, C_8, PARGCPARAPAAT, (SEQIDNO:7177); XM_014110917.1, LOC106558305, Del, C_8, PARGSARAPPRPPPVVPPDRA, (SEQIDNO:7178); XM_014119242.1, LOC106559725, Del, C-8, PARGTPSGAGPGSGAPRGRAPGSPGPGGRKLWGVNGKKWVVRALRLPLTSLPK, (SEQIDNO:7179); XM_539055.5, PRDM13, Ins, C_8, PARPVAPPGLRGAGGHQA, (SEQIDNO:7180); XM_014108323.1, CECR6, Del, C_8, PARRDPCSCSRSSTEPPAASWARVWTCSTASPWWS, (SEQIDNO:7181); XM_537035.5, RBM15, Ins, C_8, PASATVAP, (SEQIDNO:7182); XM_845787.4, PARP14, Del, C_8, PASWWFSI, (SEQIDNO:7183); XM_545182.4, ICE1, Ins, C_8, PATLARSFGRYTSKDFATSFSSDSFLSLLTYFSYWPDVPLM, (SEQIDNO:7184); XM_536512.5, PDZD2, Ins, C_8, PATVGLPAFSFRFH, (SEQIDNO:7185); XM_014109665.1, LOC102154979, Ins, C_8, PAVFLAYPQPRYVP, (SEQIDNO:7186); XM_005639783.1, CHRD, Ins, C_8, PAWHGGHCPTHSQ, (SEQIDNO:7187); XM_014112341.1, ADAMTS7, Del, C_8, PAWPHALCSPRPPSRPA, (SEQIDNO:7188); XM_014116554.1, LMTK3, Del, C_8, PCASPASPSRLRWRPRGLPPGPPTPGPQAPWRT, (SEQIDNO:7189); XM_005616067.2, ZSCAN18, Ins, C_8, PCCMWTPCQWEAQWVPGVCGR, (SEQIDNO:7190); XM_547145.5, CDIP1, Ins, C_8, PCECRWHLHVSRFLPSSRPPPTHGLLSTRALPTGAVPWPWGPYCHSPGSFGGCHHGD STTRRDL, (SEQIDNO:7191); XM_014110156.1, PVRL3, Del, C_8, PCFKKTFYIRLNTCLCRLSSKKERLAVSSTLMD, (SEQIDNO:7192); XM_545182.4, ICE1, Del, C_8, PCHPCSLLWSLHLQGLRNQFLL, (SEQIDNO:7193); XM_014111268.1, IGSF9, Del, C_8, PCMSSSGCALDSYFPSSSSSASTLHASTLITWGESGCRRGRLSRLRASGRKTRAGTSA ECSSWTSTALKTTLPTAPGCTSP, (SEQIDNO:7194); XM_014118914.1, LOC106559676, Del, C_8, PCPGAVESQGQTHHDSELSAEPLGSLVETVGHRRSLAVVRALHMAHVAWHLLPL, (SEQIDNO:7195); XM_014113536.1, FXR2, Ins, C_8, PCPPAQHKIQRFIYQLSAKRSRQ, (SEQIDNO:7196); XM_014110306.1, GRIN2C, Del, C_8, PCPPVPATAPGSLGPGGLRGAGAGPWG, (SEQIDNO:7197); XM_005618679.1, IDUA, Del, C_8, PCRTARLTAMTSAGTSSSTWPMWVLSLTGASSRSGPTGCWSSSRPGSQLGKA, (SEQIDNO:7198);

XM_014111420.1, GAB3, Ins, C_8, PCSATRACLRRLWGGCGRAQGSVSGMGR, (SEQIDNO:7199); XM_014106254.1, ATP7B, Del, C_8, PCSLCSLPWGGGWNT, (SEQIDNO:7200); XM_014109665.1, LOC102154979, Del, C_8, PCSLPCLSTAPVRPLS, (SEQIDNO:7201); XM_005642410.1, LOC102155373, Ins, C_8, PCSRGRGCAPATS, (SEQIDNO:7202); XM_014107254.1, GMEB2, Del, C_8, PCSSEMPSSSTTSCRTSACWTW, (SEQIDNO:7203); XM_014119467.1, SZT2, Del, C_8, PCWAHSRPYLTGPALWSYISPSTSYSSGMRSYPWTTGRPSY, (SEQIDNO:7204); XM_014113225.1, PITPNM3, Ins, C_8, PCWGRVRVGLARRCELWRGHAPGWSWGSAARPGRGDRCSTSGAAHHLVDAAICL DGPKCPGRVVLAGSPH, (SEQIDNO:7205); XM_005615988.2, LOC610549, Ins, C_8, PDAQHSTDPSASKACGPTGAQPRCCGSGPTPIQPR, (SEQIDNO:7206); XM_014117113.1, RASSF3, Ins, C_8, PDFWKARSQQQRLHEHASHQQHEHRRGSDRGPAQEVSRDREPCQVCTL, (SEQIDNO:7207); XM_005628809.2, PTPRZ1, Del, C-8, PDPLSPPRRR, (SEQIDNO:7208); XM_849485.4, FAM209B, Ins, C_8, PDPRLWVPQGHLLRLPRSPQRLDWTRRERAEPGGLPVSPPSLHPPWRLLQGDPREPP EPPPEASQWPL, (SEQIDNO:7209); XM_542216.5, PALM, Ins, C_8, PDRGLQGREPGGARGPGQRPPGPRHEEAAL, (SEQIDNO: 7210); XM_849910.2, C20H19orf35, Ins, C_8, PDRPAAPAPAPAQEDA VQDPLPAHAQGPQHQPCPGSGWAASEAFPGVPQCGREPGGQ, (SEQIDNO:7211); XM_538528.5, BMP10, Del, C_8, PDTKPTNAVGFATTPWQSTSHPQSTRSSRPWSTSRIPKRLPRSAVCPPS, (SEQIDNO:7212); XM_014121373.1, LOC106560025, Ins, C_8, PEAAPGLPAGSAGPSPPHPPAAPGLPP, (SEQIDNO:7213); XM_547544.4, GON4L, Ins, C_8, PEAQADQGQYFHGEVACSR, (SEQIDNO:7214); XM_014117151.1, SMARCC2, Del, C_8, PEAWAPLNRLGRQGQPWGHSSSNQLEPPSLGQSHQGFPPLDPMAPHRSPTNKLLPQ, (SEQIDNO:7215); XM_014118099.1, NOL8, Ins, C_8, PEESQSAE, (SEQIDNO:7216); XM_005622105.1, RAB40C, Ins, C_8, PEPASELLEEQLQDLL, (SEQIDNO:7217); XM_014109156.1, LOC491694, Ins, C_8, PEPCAPRGAEPRALSGHRDPPDPVQRVQVRAGARGHLPGRGRGVLGEPARAAGGG APPLRGACGGAARGRVGHRV, (SEQIDNO:7218); XM_855027.4, ATP2A1, Ins, C_8, PEPQGAPHQWLALLPLHGNWGLCGCSHCGSCCLVVHVCR, (SEQIDNO:7219); XM_014119431.1, FAM160A1, Ins, C_8, PEQRPPAQQPSVRNRLRGGTG, (SEQIDNO:7220); XM_849712.3, TMEM200B, Ins, C_8, PERAATRGSRRRPGPRPARAAAAPWTRGHGRRPVRFHLRQHAALREPRPGDATAAP GGAAGPGAPAP, (SEQIDNO:7221); XM_546237.5, SH3PXD2B, Ins, C_8, PERIYHQVGRGAAGEGAAEDGAAQRLLTQTSRHDFANDSSQTHTSSPGWQEVRAQT (SEQIDNO:7222); XM_534537.4, LATS2, Ins, C_8, PESDDTLQKQPQRGPI, (SEQIDNO:7223); XM_005625313.2, DPM2, Del, C-8, PFPAPLDSIP, (SEQIDNO:7224); XM_014111220.1, ELK4, Del, C_8, PFPPFPPLCRSPPGPPRRR, (SEQIDNO:7225); XM_546528.5, SIK2, Ins, C_8, PFQPGPVPEPCPGAYHRRADA VQPLPWPLPRAAAAAPASGPWPPSPSTAATAPTTAPSPAGRGHPGTPPVLLPDLRA VRGSIP, (SEQIDNO:7226); XM_537509.5, YLPM1, Ins, C_8, PFSLLCSTSTCLAPPTIVFSHTSSGITSPWGSTRDTSSVSHSSSSTSLQFSKFTGSRET, (SEQIDNO:

7227); XM_005622233.2, HSD11B1, Del, C_8, PFWGSSWPTTTILRMRNSDQRCSKERK, (SEQIDNO:7228); XM_014114435.1, LOC106558903, Ins, C_8, PGAAPGGAPWRCPLEPWSLQERAGSRNLPRRGGPARPGKGPEPSKARILARAPAAAP SRIWQRKWVEGPVRSLQWEGPSTASPQVSHFGGPF, (SEQIDNO:7229); XM_540337.5, MOV10, Ins, C_8, PGAGGRRWPVPASRARVEERAL, (SEQIDNO:7230); XM_003639336.3, SHISA8, Del, C_8, PGAPPTTQTGSAPTTCPWGQRPPAPSVAPGCRAGAA, (SEQIDNO:7231); XM_855027.4, ATP2A1, Del, C_8, PGAPRSPSSV AGSSSATWQLGAMWVQPLWELLPGGSCMQMTGLVSPTAS, (SEQIDNO:7232); XM_540881.6, NRXN2, Ins, C_8, PGARGPHVL, (SEQIDNO:7234); XM_014120154.1, FAT1, Ins, C_8, PGARPSHLLHSKHSKRLQEQPGPQFLRRICH-PRAPGIQHLQPRVWARTPQGRGRLQR GPEPASPAPFQLPFGQRLHPEAQLGLRL, (SEQIDNO: 7235); XM_003639754.2, LIMD1, Ins, C_8, PGEAALPDPYPRPRAWALSCRIEIRSPHPTSGA, (SEQIDNO:7236); XM_548091.5, STAT5A, Ins, C_8, PGEGHHHQ, (SEQIDNO:7237); XM_014111420.1, GAB3, Ins, C_8, PGEQGPQAPEETTATSPGPEEPVHHPGTRISNQDLHCTVQSNQISLSRKKRY, (SEQIDNO:7238); XM_849688.3, LSMEM1, Ins, C_8, PGGAPGHPRPGTRRPGPVLYGADNCADCQPGAGLLRDFSNSSDWKQDG, (SEQIDNO:7240); XM_005619884.2, LOC100688504, Ins, C_8, PGGAPRGPRAQGGGGQEGGSARRREGAGGPHGATPQGRGAPPAPGGGAPPGRGLL PRPFPAPLHLYLRGHRLLDHLLHLHPPAAGL, (SEQIDNO:7241); XM_541178.5, FNDC1, Ins, C_8, PGGEARPSARSWQLPESPTRPAQTPPPQPCHAKPHRGHPGPGAVHHPRPSRPCLHHP YAVLAPAHDELEIPEPSLAPACQIPHQTRL, (SEQIDNO:7242); XM_536612.5, PELP1, Ins, C_8, PGGGAAGGGEPPSRAAASRAY, (SEQIDNO: 7243); XM_014115530.1, GREBL1, Ins, C_8, PGGKDRLLFTVP, (SEQIDNO:7244); XM_014118662.1, ARHGAP39, Ins, C_8, PGGLQQHGGSRAAGRAG, (SEQIDNO:7245); XM_532205.6, CD109, Ins, C_8, PGHREGGAGQDGSQPLCLCPGSRRSL, (SEQIDNO: 7246); XM_005631865.2, WDR33, Ins, C_8, PGIARASRLTRSAGAAPGLFGASTPGWHARAPWTSGTAEPGKRATSISRANTIPAAE NSSAR, (SEQIDNO:7247); XM_546237.5, SH3PXD2B, Del, C_8, PGKNLSSSRKGSCRRGSGRGWSSSEAPHPNLQA, (SEQIDNO:7248); XM_014111162.1, PADI2, Ins, C_8, PGLFWEPLVPPALRSPTP, (SEQIDNO:7249); XM_846534.4, PRCC, Ins, C_8, PGNCPRCLLHR, (SEQIDNO:7250); XM_544381.4, CCDC113, Ins, C_8, PGNSQREATAADQSDPL, (SEQIDNO:7251); XM_005615289.2, NFATC1, Ins, C-8, PGPAATTV, (SEQIDNO:7252); XM_014120434.1, NFATC1, Ins, C_8, PGPAATTVLQPHPPI, (SEQIDNO:7253); XM_014121843.1, APC2, Ins, C_8, PGPGQRPHRPPGQ, (SEQIDNO:7255); XM_847637.3, RUNX3, Del, C_8, PGPPSPGRRHQRPRELEAGKAGPRAAGKGRDEGSGGPRVGGPRPGTSGQGALRRAW AAQPSR, (SEQIDNO:7256); XM_843722.4, MAP3K12, Ins, C_8, PGPTQRGAGPPQYRGLRL, (SEQIDNO:7257); XM_544403.5, IRX3, Del, C_8, PGQPSRPQPCSSRPPPRPPRLTDSSRRR, (SEQIDNO:7258); XM_014121843.1, APC2, Del, C_8, PGRPPGTGTGRGARAAAGWGWSCPFAGRRAPALSSTAAAPARREGTEGTEGTGRCS LCASRRPPRRPCTASTTTPTRIHPWPWHPRGDRPPSPGP, (SEQIDNO:7259); XM_014110676.1, CSRNP3, Ins, C_8, PGRVRVPVARGRPPPRAPRGEAFESGRQEQ-

TARRVHHVPRGGDGPRV, (SEQIDNO:7260); XM_014113331.1, ROBO3, Ins, C_8, PGSDSGLGG, (SEQIDNO:7261); XM_849833.4, RPS6KA4, Del, C_8, PGSGPWHRTCCSGYFARTPR-SUWVQGPRGHRKSRTTPSSRVWIGPLWLPGKFQPHSDHRSARSWM, (SEQIDNO:7262); XM_843399.4, ADM2, Del, C_8, PGSPQPVPLPAA, (SEQIDNO:7263); XM_014119322.1, MACF1, Ins, C_8, PGSQTAYFSE, (SEQIDNO:7264); XM_014114200.1, SRRT, Del, C_8, PGWAASQRLTWVCHHR, (SEQIDNO:7265); XM_005616351.2, SULT2B1, Ins, C_8, PGWIRAPPPV, (SEQIDNO:7266); XM_005616395.2, C5AR2, Del, C_8, PGWSAWWTTGARPWLRAPWRPPALCAAS-WGRWWSWPAATVPCCAGPPRTAGPW AWPSCWAFLSAGPPTNCWGW, (SEQIDNO:7267); XM_005640282.2, LRP2, Del, C_8, PHAGVCTEEIAILMRMTSPNASVP-VATWENIVK, (SEQIDNO:7268); XM_014114207.1, GIGYF1, Del, C_8, PHCWATWTRSG, (SEQIDNO:7269); XM_005635161.2, STAU1, Ins, C_8, PHEELCDQGVGWGVCGGR, (SEQIDNO:7270); XM_538777.4, ZNF462, Del, C_8, PHHPRHQTSVLSF-TIANTVPTVIGQLWECLSTTRKDTQR, (SEQIDNO:7272); XM_005621273.2, FBRS, Del, C_8, PHHPTIPPCS-PLAPPCPHPHPCCRCQGTLGPQMLTPFLSRT, (SEQIDNO:7273); XM_005639159.2, AFFI, Del, C_8, PHLCHPHPHPPRSQPSLHKRGQGGKLIP-PAKTLPKVPVVARATTKTLPLPSTEK, (SEQIDNO:7274); XM_014119783.1, SSPO, Ins, C_8, PHLCPGRGD-HAGARELLSHLPPSDSGRPAFPGAAYHGD, (SEQIDNO:7276); XM_860394.4, DLGAP4, Del, C_8, PHLHPQPPAPALGWAPTPTMSSGAPGLL, (SEQIDNO:7277); XM_539768.4, FHDCI, Del, C_8, PHLHSPG-GLRPHLPLRDYPQPLT, (SEQIDNO:7278); XM_546606.6, PERI, Del, C_8, PHLPLLPSRLSSSPTLSRCSPLGEAPSLLPLPLQLG-PLQPSLPRS, (SEQIDNO:7279); XM_549021.5, FGDI, Del, C_8, PHLSPFPLHHHAPCLQT-PEWPRAWPPGWKPAPVLQQYPH, (SEQIDNO:7280); XM_540889.5, RCOR2, Del, C_8, PHLSSALLWLP-PATVPAPAHSLHPP, (SEQIDNO:7281); XM_005616609.2, HNRNP1, Del, C_8, PHLTTKGEGW AHQWGVTVGAQVATAPSMGTPHPLPHHPSMAPTP-TALCSWSMAWINLR, (SEQIDNO:7282); XM_005631954.2, R3HDM1, Del, C_8, PHPCPPGNQSLLLAILPQAILSASLCCSSR-DIFSSPHHRCQPVTVLQATITPVNLSIAQSL LSITIHI, (SEQIDNO:7283); XM_005628329.2, LOC102154101, Del, C_8, PHPEEQLGMP, (SEQIDNO:7284); XM_014120825.1, GLI3, Del, C_8, PHPEIRAAIHSPGR-LAGRLREPLGSRRTSATLPQSGKNASK, (SEQIDNO:7285); XM_014118244.1, SYNGAP1, Del, C_8, PHPGCRSLRTASSETPQTT, (SEQIDNO:7286); XM_014110154.1, THEMIS2, Del, C_8, PHPGPPKVRVSVGRRNKATRRKAASLLNS, (SEQIDNO:7287); XM_005623660.2, LTBP2, Ins, C_8, PHPGPQPAALRKQHRRHRGPA, (SEQIDNO:7288); XM_014119050.1, LOC106559698, Del, C_8, PHPHPP-PLPPN, (SEQIDNO:7289); NM_001033992.1, DAGI, Del, C_8, PHPLRPPWRARAPVPRT, (SEQIDNO:7290); XM_014116598.1, SIX5, Del, C_8, PHPNTGPPNPDS-PEPPPPHPPPLLPPGPSIPAPLLPCRTPT-PRGCSWGLRQGARRMRG WRPSRRF, (SEQIDNO:7292); XM_014121497.1, LOC476151, Del, C_8, PHPPHYLHRQRHLKQCKTVQ, (SEQIDNO:7293); XM_005628317.2, GPT, Del, C_8, PHPPPPPTPRGRRR-GRRCWRSWRQRRSSRSRCSTSPRASAATR-CRAPCTPSLACSCPP APCSALRN, (SEQIDNO:7294); XM_005622126.1, LOC102154422, Del, C_8, PHPRPLP-WETFLCSGCGFVHPASRQATCLL, (SEQIDNO:7295); XM_014107347.1, LOC102155751, Del, C_8, PHPRQAWGPARE, (SEQIDNO:7296); XM_534998.5, PPRCI, Del, C_8, PHQQCPWYLVLLAPMLCPPLAM-CLGYLLQPQSHLIAPAVPMGPWDGVQGCNTLHSGLLCHHLLCL, (SEQIDNO:7297); XM_005620138.2, SLC5A10, Del, C_8, PHRESRLRT-SPGGPWLRMCWWERKQVIARH-PRNMLFGPVCVASMPFCSCVSTSSST PTLP, (SEQIDNO:7298); XM_005616756.1, LOC102155403, Del, C_8, PHRGPLLPPHPGVPSCL-PRPHTHEGHGGQGRHTISSVPSPRSPLWSHSHHTQG, (SEQIDNO:7299); XM_005619036.2, SYNPO2L, Del, C_8, PHRGPPLCPATCQPPVPPALHAPRAP-SQPQVPCTSQPPIVLLRQEEPPSPPPPLALLP, (SEQIDNO:7300); XM_005636081.1, SFSWAP, Del, C_8, PHRGSTWPLTTAPCLLVWLCLALLG, (SEQIDNO:7301); XM_014116569.1, GLTSCR1, Del, C_8, PHRLLGPSRW, (SEQIDNO:7302); XM_014113517.1, DVL2, Del, C_8, PHRYPPCHRRGPAASGTLGLRP-STLTCPAAGRTWSLRRKPSQWCPCGGNGLVGETA GATGLVDPRGWSATWPGMRAPQPL, (SEQIDNO:7303); XM_014113515.1, DVL2, Del, C_8, PHRYPPCHRRGPAASGTLGLRP-STLTCPAAGRTWSLRRKPSQWCPCGGNGLVGETA VSTQGATGLVDPRGWSATWPGMRAPQPL, (SEQIDNO:7305); XM_014113516.1, DVL2, Del, C_8, PHRYPPCHRRGPAASGTLGLRP-STLTCPAAGRTWSLRRKPSQWCPCGGNGLVGETA VSTVGATGLVDPRGWSATWPGMRAPQPL, (SEQIDNO:7306); XM_546582.5, DVL2, Del, C_8, PHRYPPCHRRGPAASGTLGLRP-STLTCPAAGRTWSLRRKPSQWCPCGGNGLVGETA VSTVQGATGLVDPRGWSATWPGMRAPQPL, (SEQIDNO:7307); XM_844295.4, TNKS, Del, C_8, PHSAPAWPRGPPQPPQRRAAWPPSPPRGTA, (SEQIDNO:7308); XM_014115299.1, ARHGEFI1, Del, C_8, PHSASRGPDLCRILNSRNMPPRSFGIC, (SEQIDNO:7309); XM_537794.5, RABL6, Del, C_8, PHSPSPLWPPSD, (SEQIDNO:7310); XM_005620440.2, TP73, Del, C_8, PHTAQQPGPTWGPWAPEFSTT-TATPFQPAAR, (SEQIDNO:7311); XM_005642273.1, LOC102152155, Del, C_8, PHTPRGGGDRGGGVWRR-GLTLPTGPTAPTRGGRATPKGSLNLRAGTR, (SEQIDNO:7312); XM_014121497.1, LOC476151, Del, C_8, PHYLHRQRHLKQCKTVQ, (SEQIDNO:7313); NM_001003339.1, CYP2E1, Del, C_8, PITNSVSFPARA, (SEQIDNO:7314); XM_014120785.1, ATXN7L1, Del, C_8, PITVCLCTTQTMG, (SEQIDNO:7315); XM_854451.4, ATXN2L, Del, C_8, PKARCPRVGCIHSQLPHPHPIPTSDTPKFNLIPPSSSP-STPRGT, (SEQIDNO:7316); XM_005621365.2, ATXN2L, Del, C_8, PKARCPRVGCLHSQLPHPH-PIPTSDTPKVSSLARRLDFQEEPMTGFVSSR, (SEQIDNO:7317); XM_005621364.2, ATXN2L, Del, C_8, PKARCPRVGCLHSQLPHPHPIPTSDTPKYVG-WAEATVAAARGLLLALSFASLRPRSV VIQQPPSPLPPQLSVTPTVS, (SEQIDNO:7319); XM_860802.4, CACNA1G, Ins, C_8, PKERRAESLWFSL, (SEQIDNO:7320); XM_005626438.2, SRFBP1, Del, C_8, PKKCCYRRKINMKLIRV, (SEQIDNO:7321); XM_534035.5, PRKCDBP, Ins, C_8, PKKTRSR-GRGELRRGAGGVPGPAAAAHRVAEGTE-PAKGLVRPQRPGLADTHAGQA APPWARPER, (SEQIDNO:7322); XM_014111339.1, KDM5C, Del, C_8, PKPCPLLAAPAPRRTR-

MAWSLRWPLQAPQPLSLLCLLSCMCPAHSSHLSNSC, (SEQIDNO:7323); XM_005616816.1, LOC102151589, Ins, C_8, PKPQHFSMWKRHHHKGLCVQARAC-FPLTEHQGLAWPHDLTFSCKKQHRDLSASMH F, (SEQIDNO:7324); XM_005616815.1, LOC102151355, Ins, C_8, PKPQHFSVWKRHHHKGLCVQARACFPLTEH-QGLAWPHDLTFSCKKQHRDLSASMH F, (SEQIDNO: 7325); XM_014115739.1, TIAM2, Ins, C_8, PKPVPASGGVPG, (SEQIDNO:7326); XM_544671.4, SHC4, Del, C_8, PKPVSLGLGPHL-CRSSQARWGTGQPS, (SEQIDNO:7327); XM_005630690.2, LOC100683419, Del, C_8, PKR-PARPIQAFIFPPYPHWLAFPRHHCPQLHPASCLSAP-LALPSLAAVRHLWSPWQRL SRSCRC-CRNNWEKVSAPSILLPQLHCQATI, (SEQIDNO:7328); XM_014120602.1, LOC100683419, Del, C_8, PKR-PARPIQVSAPSILLPQLHCQATI, (SEQIDNO:7329); XM_545655.5, FAM134A, Del, C_8, PKTCWAPLRP-SQGKT, (SEQIDNO:7330); XM_014119273.1, LOC106559736, Del, C_8, PLAAASAARPGP, (SEQIDNO:7331); XM_844430.3, C2H1orf158, Del, C_8, PLACTLSRAS, (SEQIDNO:7332); XM_005625495.2, SMARCC2, Del, C_8, PLDPMAPHRSPTNKLLPQ, (SEQIDNO:7333); XM_005638159.2, ESRP1, Del, C_8, PLFQYYLSNLCPLRMLETVYAFAVFPMRPPLKTS, (SEQIDNO:7334); XM_014111420.1, GAB3, Del, C_8, PLFRHSCLSPPVVGWVWSSSGVGFWDGSLKER-ERTDAPRQVR, (SEQIDNO:7335); XM_014119807.1, ATG9B, Del, C_8, PLGAPNPPHPWPQ, (SEQIDNO: 7336); XM_014112436.1, CIB1, Ins, C_8, PLGFASSSEI-PAAAAAPPRASL, (SEQIDNO:7338); XM_003638937.3, HCRTR1, Del, C_8, PLGPGPSWLR, (SEQIDNO:7339); XM_540834.4, TMEM151A, Del, C_8, PLGRCPAGPRCPGWPRWTSPSWSGT-SAPTGSWYPATRRPWSWVPAPVPTSVAASAA VAP-SAAIRCPLPGPVGPACLSAAAACLWEL-GAGPHQGSSGA, (SEQIDNO:7340); XM_005619960.2, DVL2, Del, C_8, PLHPLSHQQCSPQGPLLSETWAL-CPQN, (SEQIDNO:7341); XM_014108280.1, LOC106557869, Del, C_8, PLHPPHAWPQGAWSSTG-PADLCPQVALGCQEAPGRSRDREATAP, (SEQIDNO: 7342); XM_005636179.2, SETD1B, Del, C_8, PLHSQR-PRLVSHPHPSCHRCHPSPQGCFP, (SEQIDNO:7343); XM_854467.4, CLIP1, Ins, C_8, PLHTPRQSERGAPVL, (SEQIDNO:7344); XM_005623432.2, KTN1, Del, C_8, PLKQLPQRRNQDRRSLKMEAMTRIKRWKLL-WHLQKSKNHYPSSKRLNKKVDQERR KFLQR-SKRQKNIYW, (SEQIDNO:7345); XM_005616718.2, LSR, Ins, C_8, PLLGDGLPGLAGAEA, (SEQIDNO: 7346); XM_014113225.1, PITPNM3, Del, C_8, PLLGPSPRWAGQKV, (SEQIDNO:7347); XM_005616067.2, ZSCAN18, Del, C_8, PLLHVDPVPMGGSVGSRGVWQVMVPCSLRRRD, (SEQIDNO:7348); XM_005642410.1, LOC102155373, Del, C_8, PLLSRSWMCPSHLLT, (SEQIDNO:7350); XM_014122116.1, SUGP2, Del, C_8, PLMASRARQPK-MAQQVHLPYHRPPQGPASLGRGSVASP, (SEQIDNO: 7351); XM_014121497.1, LOC476151, Del, C_8, PLPHPLPSQALQLRRCRLLLYLPLLLLLHPRCL-GRPHPQWFSTQD, (SEQIDNO:7353); XM_014113536.1, FXR2, Del, C_8, PLPPGPAQDTTLHLSAQC, (SEQIDNO: 7354); XM_005621674.2, SRRM2, Del, C_8, PLPPGTGPCTTGSGCRRPGAAAPTATS-SATCPWCGAAGVSGLTTRERRNCGAWRLP W, (SEQIDNO:7355); XM_014120934.1, LOC106559977, Ins, C_8, PLPPPRAAPV, (SEQIDNO:7356); XM_845621.5, MLLT6, Del, C_8, PLPQPLSPQRQTSLSRRWSSLALGP-SCASPPPPPARPGPGPRPLETISLPTFRGLGPQQA PTSGCPH, (SEQIDNO:7357); XM_005616928.2, COMMD3, Del, C_8, PLPSRIIRIP, (SEQIDNO:7358); XM_014114995.1, LOC106558989, Del, C_8, PLPVLLLGPLGQDSSSSHPPHHSPR, (SEQIDNO:7359); XM_849996.3, CDX1, Del, C_8, PLQPMK-SPPPQLGHPWGACAPALLASWGPPPQCRSRRSICH, (SEQIDNO:7360); NM_001003339.1, CYP2E1, Ins, C_8, PLQTLCRSPLGL, (SEQIDNO:7361); XM_014106885.1, ACSS2, Del, C_8, PLRGHAQMCRVS, (SEQIDNO:7362); XM_014112610.1, CLNK, Del, C_8, PLRGSAFLKSRKGPGK, (SEQIDNO:7363); XM_014121352.1, LOC611811, Del, C_8, PLRLC-CLQPPTSPSTTTACTLEPQVPSESLRRDQHHTPCPISR-PAEIRTACPSQLGWGS CPPLPCT, (SEQIDNO:7364); XM_543975.5, LZTS2, Del, C_8, PLRMRPCCTVSWKESSTTVRQSCSSCGTVWTRVR, (SEQIDNO:7365); XM_014122539.1, FRMD4A, Del, C_8, PLRSPWRGSGRCTIPATTMTSPP, (SEQIDNO:7366); XM_005629445.2, FREM3, Del, C_8, PLRSTGPPGAH, (SEQIDNO:7367); XM_546528.5, SIK2, Del, C_8, PLSAWPRP, (SEQIDNO:7369); XM_014110909.1, RAPH1, Del, C_8, PLSCFLINRKLVTEV-VIYRAMQRCGEDPLPLPPRETRIPSSQETG, (SEQIDNO:7370); XM_005626284.2, FLT4, Del, C_8, PLSVSSGTGGHGHPARPSPSAASAGGSRETTCHSARTGER, (SEQIDNO:7372); XM_844883.3, RANGRF, Del, C_8, PLTIGYLLVLKICHFCPGAWVTLNSW, (SEQIDNO:7373); XM_005616718.2, LSR, Del, C_8, PLTRRRTPRPRGSGGLRRTWP, (SEQIDNO:7374); XM_005633032.2, HDGFRP2, Del, C_8, PLT-STPSSSLVHTKQPSWDPRTCFLTTNVKISTGNP-TRGKASMRDCGRSRTIPTPATV LLCR, (SEQIDNO: 7375); NM_001103219.2, MLPH, Ins, C_8, PLVPSLSGHRQPAGPVCPGPHAWSSCRGRLPG-GRRPGGGGC, (SEQIDNO:7376); NM_001013846.1, CCKBR, Del, C_8, PMGVAGRRAGWLAR-TATAATCSFRARVRPWSCPR, (SEQIDNO:7377); XM_014114772.1, CELSR2, Del, C_8, PMPIFCTAYWR-GLAAAPLKSLRLTLALGSSEPVAPWIGKK, (SEQIDNO:7378); XM_005640282.2, LRP2, Ins, C_8, PMQVYVRRKLLF, (SEQIDNO:7379); XM_548376.6, NACC2, Del, C_8, PMSCPPLCPSRC, (SEQIDNO:7380); XM_014115113.1, KIAA1614, Del, C_8, PMWESQPGLHPGTEVYHQSGQQGTWTGT-PASPCRTQSRTGPLVPSRSLC, (SEQIDNO:7381); XM_014118314.1, BAG6, Ins, C_8, PNHQSPEGHPNFP-PERGTRGHDAHEYPRFRHTAWWSSECSHWP-PRTPWSWPDPGLH HPAALPAP, (SEQIDNO:7382); XM_014111339.1, KDM5C, Ins, C_8, PNPAHYWQPQHPGEPEWLGACAGHFRPLSPFLYSVS-SAACALPTAATSATVV, (SEQIDNO:7383); XM_014117646.1, LOC106559457, Del, C_8, PPAPAP-PELPAGHARP, (SEQIDNO:7385); XM_014116201.1, LOC106559219, Del, C_8, PPARLLQPSPWTRGDRPALV, (SEQIDNO:7386); XM_014115167.1, BRINP2, Del, C_8, PPASRPWTGCSPTAAPSTAPRSTLTSWSAT-GRVSPPGTGSTGSLPVGK, (SEQIDNO:7387); XM_014111408.1, KAZN, Ins, C_8, PPCGPASGQGE-PLPLPAALRHLRRICRRRRPVVHAKRHQLPSAP-DTLPLQRRQSRPST EEPAQPHCTVTRGS, (SEQIDNO: 7388); XM_014115306.1, NES, Del, C_8, PPCSSHRLGGSRFQRLYRLKPRWPSLPASCQDQRSL-GASNERPVQASPLRMLPLWPH PSALITLV, (SEQIDNO:7389); XM_005619566.2, FLI1, Ins, C_8, PPDL-HARHFLQLVWSGVTILDLPHGGDLPQPQRAPPP, (SEQIDNO:7390); XM_846419.3, ZNF362, Ins, C_8, PPGLHQDNPGPRPAWPPQVRARPQKDQGGEPR-GAACPRSPLPHPGLRRDCQGGQDI QV, (SEQIDNO:7391); XM_014112341.1, ADAMTS7, Ins, C_8, PPGPTPSARLVPRAGGQHEQRHRGRPRVGPVGACVC, (SEQIDNO:7392); XM_847877.4, NUTM2F, Del, C_8, PPGTRRGHSVGALRVPHPCSWRPL, (SEQIDNO:7393); XM_014119833.1, TRPV5, Del, C_8, PPLPCPGPHPTAAATGAGRSFVATPWDM, (SEQIDNO:7394); XM_014115018.1, PAQR6, Del, C_8, PPLPSFASLDYAGAEATPVGRRR, (SEQIDNO:7395); XM_014111293.1, ARHGEF10L, Ins, C_8, PPPFTGSFLQWCARAGSSQLPRSRNQLCTLFPTPR-SAMSHW, (SEQIDNO:7396); XM_014118871.1, LOC106559658, Del, C_8, PPPGLRAGGPELWAPPGP-PAGSAGAAGRGWGAP-TRSRCSPGIHFGSRGACSRRMSPA AR, (SEQIDNO:7397); XM_547146.4, NMRAL1, Del, C_8, PPPGPLGPQFPRRLAWQTRSWWWWCSGPQVL-REAPWPGRSWKMGRLEFEW, (SEQIDNO:7398); XM_005624049.2, TNRC6C, Ins, C_8, PPPGPRPA, (SEQIDNO:7399); XM_014121373.1, LOC106560025, Del, C_8, PPPGWAQHLHPPPAGPGAAVGRQGGGGRRCP-GAQVHRRRLPAGHRHRGCGAGRG GGPLGASRP-TRAAPPPSKA VGASFQGRGSRTSGVLVR-SAQPAAAGP, (SEQIDNO:7401); XM_005636179.2, SETD1B, Ins, C_8, PPPPPAAPAAARPFGREEEP-PLEKLQVDD, (SEQIDNO:7402); XM_539044.5, BACH2, Del, C_8, PPPPPPPPPRRIARGGRRAATRGAS-RRGGLRWNPGARR, (SEQIDNO:7403); XM_005628850.2, YBX1, Del, C_8, PPPPPSAPPTPSPA-PRAAAQGAAARAASHRRRLPAGTRRSSQRRFWEQ, (SEQIDNO:7404); XM_014118223.1, ZNF865, Del, C_8, PPPPTRPRNIQRPPSRSPRLPSLPALTSCLPTPPPQ-TARRRRRQRRPWYMVPCPSHCWG RTRCCSAGPGPVGPGGPAPTSLERHSAAASVG-GASGGVRL, (SEQIDNO:7406); XM_005626259.1, FIGLA, Del, C_8, PPPPWSRSPSWASRRPRCWRT-CCGSSSGRCPSWLPSAGSSGCRRAATRPPRTCSWCS RSGAGPTPRSASR, (SEQIDNO:7407); XM_014116364.1, LOC102155336, Ins, C_8, PPPRPGPARGTGSHDGGGLDGPCAGICDL, (SEQIDNO:7408); XM_005639946.1, ATP11B, Ins, C_8, PPPSSGCAQPPTAAARARPLGPRRPLSSRPGAGPGAG-GRARSYK, (SEQIDNO:7410); XM_014108311.1, LOC106557876, Ins, C_8, PPPTPRLFPRPTSP-PAAAGAPGHQAARDRRGEAVPGRGVLRGSSS-CQLCSRVT, (SEQIDNO:7411); XM_014108675.1, IFF01, Del, C_8, PPPWLSATTWAPTSTCSRP, (SEQIDNO:7412); XM_014121888.1, MAP4, Ins, C_8, PPPWRPQR-RHPGSWLPVPGCFL, (SEQIDNO:7413); XM_005619266.1, LARPI, Del, C_8, PPQPGNQRPNRSLPGTTRMRHRV, (SEQIDNO:7414); XM_014113971.1, RLTPR, Del, C_8, PPQPQTKEAAAPTP, (SEQIDNO:7415); XM_003434606.2, FOXD3, Del, C_8, PPRPLNTDLRRPP-PLRAHLGWRSKLAARPPARRE, (SEQIDNO:7416); NM_001284456.1, CX3CL1, Del, C_8, PPRPPP-PRPSLPTLPLPTP-PLPPPPPFHTQPQRTGLTPKADLCGSRETIPRQRIL, (SEQIDNO:7417); NM_001314087.1, KISSIR, Ins, C_8, PPRPRSCTAWALGAPQPPPRRGAERASPGRPGV, (SEQIDNO:7418); XM_005620971.2, MLXIP1, Del, C_8, PPSLPWLLPLPCCRKNLSSLPDSPSLP-SHLPQEECPHCLLPLPSHRPHSLAQALPLPPSP, (SEQIDNO:7419); XM_014111008.1, NRP2, Del, C_8, PPSSPPAPCSTSSSPPTTPGRGQASLCA-TRSSSRQALKTVQKTSQAPMGPSNPLGFLRST HTTWI-APLPSWPNPRWRSSCSS, (SEQIDNO:7420); XM_005634149.1, SCN5A, Del, C_8, PPTTASPGP-PAITRRCGRPTTAAARTSPTCPRPQTGTASLSC, (SEQIDNO:7421); XM_014109693.1, LOC106558086, Ins, C_8, PPVPSRRGCGGEARGGAELRAGRAAGAAPS-LAARTRAAASAGTSSGFRASRPDLSRF SATWQPARPPPRGKSMEQSVATSPWSV, (SEQIDNO:7422); XM_014110917.1, LOC106558305, Ins, C_8, PPVVPPAPPRGPRPWFRPTAL, (SEQIDNO:7423); XM_005616816.1, LOC102151589, Del, C_8, PQATALLHVETPPPQRSVCPSSCVFPSYRAPGPCLA-TRPHF, (SEQIDNO:7424); XM_005616815.1, LOC102151355, Del, C_8, PQATALLR-VETPPPQRSVCPSSCVFPSYRAPGPCLATRPHF, (SEQIDNO:7425); XM_014122046.1, SMARCA4, Del, C_8, PQDPQACPLGCQVSPPEGLPSLGLKDPWRMLLP-PRAHLRS, (SEQIDNO:7426); XM_005622734.2, HCN3, Del, C_8, PQEEVDGD, (SEQIDNO:7427); XM_005624035.2, LOC483345, Del, C_8, PQERPWPSH-WSSGCVCWWLGLKV, (SEQIDNO:7428); XM_005630746.2, CIART, Ins, C_8, PQFPRYHFL, (SEQIDNO:7429); XM_014108913.1, SH3PXD2A, Del, C_8, PQHLLASPRRPRRGQWAPRRARTPP, (SEQIDNO:7430); XM_849191.4, MCOLN1, Del, C_8, PQKRKT-SAVGSNTSS, (SEQIDNO:7431); XM_014118314.1, BAG6, Del, C_8, PQLPMRRQLPLVLGR-PRPWLPLLPLSSLQPRGL-PRQGQLPPQPPVTRGSSEFPTRAWN PWS, (SEQIDNO:7432); XM_540739.5, FNBP4, Del, C_8, PQNPLLPPLLPLL1, (SEQIDNO:7433); XM_844462.4, SPATC1L, Ins, C_8, PQPGRAAQAAHRRAAPQVPGR-LAAAAQLPVRARQGRPQAALRLV, (SEQIDNO:7434); XM_005616850.2, CACNG8, Del, C_8, PQPPARPR-PRCPGGGPRPPGCPWSSWSR, (SEQIDNO:7435); XM_014118314.1, BAG6, Del, C_8, PQPPVTRGSSEFP-TRAWNPWS, (SEQIDNO:7436); XM_005620593.2, LOC102153713, Del, C_8, PQPRGWWEGLRHTLRRQG-GRLMRDWARAAE, (SEQIDNO:7437); XM_014117950.1, AKNA, Del, C_8, PQPR-PACPGRPGTPSS, (SEQIDNO:7438); XM_014113873.1, PRDM16, Del, C_8, PQPSTTPAWASTSTSHPGHT-PAACPSRRLHLPSPHSPRASRASSLHPCTPGRLCYL-PRR CSRAP, (SEQIDNO:7439); XM_546149.4, ADAMTS14, Del, C_8, PQPTEAACVPGPCSNTR-CATARSVRGPTRTSGPSNVPSATPTTSTRMP-STAGSPMSLK MMPRSVS, (SEQIDNO:7440); XM_014117109.1, ESYT1, Del, C_8, PQPTPPSAPRCSR-TARALLRSIGVEAKGELGWQQRFRAVGGE, (SEQIDNO:7441); XM_014113377.1, PHLDB1, Del, C_8, PQQTTQQDSR, (SEQIDNO:7442); XM_014113536.1, FXR2, Del, C_8, PQQVP-GAAAPAAAAQMRTGPSWMGAWSLMGPV, (SEQIDNO:7443); XM_005627781.1, AIM1, Del, C_8, PQRPHQSHRIRYLTHSPQLSHLTGLLPPSLHPKARV-FELP, (SEQIDNO:7444); XM_014122403.1, PLK5, Del, C_8, PQRPPTSACCASLCPSGRCCCSSATGRCRSAA-GATGLTWC, (SEQIDNO:7445); XM_003435094.2, HOMEZ, Del, C_8, PQSHYLLVVVSRSQYLI, (SEQIDNO:7447); XM_862201.3, ZFP64, Del, C_8, PQSPRNKP, (SEQIDNO:7448); XM_014115739.1, TIAM2, Del, C_8, PQTSPSFWRSSWITSKRIQPMISAM-SLMSQVA, (SEQIDNO:7449); XM_848403.4, STX5, Del, C_8, PQWPWSLPLPTPCPAEIGPRSSCL-PASPCRAVRMESRQISQLCVLSGSVANLPSWPSA LGKTSATHLPSWRS, (SEQIDNO:7450); XM_545071.5, DCBLD2, Del, C_8, PQWWGHTTLCSPELTAAPP-PAPSMIPQKAGSQVRVPRTNWCTRCRRAHRRYQGRG GMVNVMSLKKFS, (SEQIDNO:7451); XM_846858.4, PDE2A, Ins, C_8, PRAAPGRESPRGCGLPEAAGLQWTGPLKSAREAL-GQAGGSTGS, (SEQIDNO:7452); XM_014111420.1, GAB3, Del, C_8, PRAPPRAPTARPARPGSRTPRPARR-PRAPRSRATCPSGARTRSPRARRRPEESPCPAW TT, (SEQIDNO:7453); XM_005622105.1, RAB40C, Del, C_8, PRARLRTARGATARSP, (SEQIDNO:7454); XM_014109869.1, COL18A1, Del, C_8, PRAR-TRRRRRRRTSPAWEPRS, (SEQIDNO:7455); XM_005629418.2, ARTN, Del, C_8, PRASAPLRPWCSP-SATCRVAPTSWCASASAAARAAGRAPRTT, (SEQIDNO:7456); XM_014109156.1, LOC491694, Del, C_8, PRAVRSPWG, (SEQIDNO:7457); XM_544073.5, PXDNL, Del, C_8, PRCRHPGWSPRSWRPRPR-SPPTTGTRTCSCSGASFWTTIWATRCLP, (SEQIDNO:7459); XM_005615988.2, LOC610549, Del, C_8, PRC-STFHRPLCKQSLWPHRCPAQVLRVRAHTHTASLSRPLL-WRQLGRV, (SEQIDNO:7460); XM_005616196.2, FAM71E2, Ins, C_8, PREDTCGG, (SEQIDNO:7461); XM_014121820.1, LOC106560103, Del, C_8, PRFLTNE-SPSTSSRRRASCVPEGRCQSPFLL-VCPPSPKPSRLLPSPAGSPRGQLEACGG RVP, (SEQIDNO:7462); XM_852361.4, TCF20, Del, C_8, PRGAALAISMGARGMWASFKHSTLPLVVCLIISRITR-GLSLQGVLSTNSRLPASSSSR YSS, (SEQIDNO:7463); XM_005636752.2, HOXC4, Ins, C_8, PRGLVCRQRRL-PRG, (SEQIDNO:7464); XM_005629711.2, NOMI, Del, C_8, PRGPGPPQPQPQPLPPLGNGLFWRPTRRRTGRS-ESWSGASA, (SEQIDNO:7465); XM_005630690.2, LOC100683419, Ins, C_8, PRGQPGPSRPSFSLHIHTG, (SEQIDNO:7468); XM_014108311.1, LOC106557876, Del, C_8, PRGRARAPTPAGSGAPTRAGNPPSPPA-PRFVSGGVALRRSRSHKSP, (SEQIDNO:7469); XM_014114367.1, FBXL19, Ins, C_8, PRGRAWAPQKKGEGGRE, (SEQIDNO:7470); XM_536612.5, PELP1, Del, C_8, PRGRGRGRW-GAPQPCRRLKSLLKKSPQLPQLCWKR-GLRVGGTKCQSPRRRLRQKT WRPRWRQRRQPCRRRSRMTRLPCWLTSSIVPLMTT-SHHRPQSLIP, (SEQIDNO:7471); XM_005616451.2, NKPD1, Ins, C_8, PRHKRSRPCPRDGPVRSGCRACP-WARQRSPPAPGLGAGGQAETPGL, (SEQIDNO:7472); XM_536512.5, PDZD2, Del, C_8, PRHRGPPSLQF, (SEQIDNO:7473); XM_540739.5, FNBP4, Ins, C_8, PRIPSSPPSSPSSCRRW, (SEQIDNO:7474); XM_005624035.2, LOC483345, Ins, C_8, PRKGHGPPTG-PLDVSAGGWDSRCER-WGHAAGQWGHRQRGPRGDLLQWPVGDRV, (SEQIDNO:7475); XM_014110676.1, CSRNP3, Del, C_8, PRKGSCPRCTGTATSPSTPRRSL, (SEQIDNO:7476); XM_846534.4, PRCC, Del, C_8, PRKLPQMPPSSMTKHLSGCRARGTEGGRRST-LWRLKGMTSSVGPSSG, (SEQIDNO:7477); XM_005616351.2, SULT2B1, Del, C_8, PRLDPSPSTR, (SEQIDNO:7478); XM_014117113.1, RASSF3, Del, C_8, PRLLESSLPAATAA, (SEQIDNO:7479); XM_537035.5, RBM15, Del, C_8, PRLRHRCPVSWRESETIRSMRE-CARRTAWSPGWELEQVLLLSEKWMRSHPRTISELT GRFSWAT, (SEQIDNO:7480); XM_003431951.3, HIVEP3, Del, C_8, PRPAPPPWTAAAPWAAWPRPPLAS-RPGGGTCPGSPGPVGAPPSPQEVGGPGHFHASP RTGAPQAL, (SEQIDNO:7482); XM_014110497.1, LOC106558231, Del, C_8, PRPAPTPLRKRR, (SEQIDNO:7483); XM_546111.5, CCDC6, Del, C_8, PRPARRPP-PRRSRRTPPPSL, (SEQIDNO:7484); XM_005615289.2, NFATC1, Del, C_8, PRPCCDHS, (SEQIDNO:7485); XM_014120434.1, NFATC1, Del, C_8, PRPCCDHSPAAP-PAHLRWARSSTDCRRLRGASLQPPGLCRRPRCVRT-VIIVWPPFP, (SEQIDNO:7486); XM_014118223.1, ZNF865, Del, C_8, PRPCPPVPPPRLLLLELPPWPP-PLRRGPVPLPGWACPLPRRGAARAHLPARSAGRSSR SPATSTSTRSSTPARSPSPVPCAARASTAGRASSGT, (SEQIDNO:7487); XM_849485.4, FAM209B, Del, C_8, PRPPALGPTGTLAPSAPLTSTSGLDT, (SEQIDNO:7488); XM_005638643.2, LOC102157171, Del, C_8, PRPPGWSHLTRASSWASPAPRAPWDLLARASGLSAL-CGEPSRSPGSVLLCPAPAPPR ALTVLQAVWPPPCSHALLLPRAL-TAFLCLLPSRAPGPCL, (SEQIDNO:7489); XM_005642274.1, LOC102152225, Del, C_8, PRPPRL-PASPDRTVAGAPRVPRP, (SEQIDNO:7491); XM_546201.4, RBP3, Del, C_8, PRPPSCHLRRRCPT-SLKPCSKPRCCPAGWATCASTPWRSWRRSRPSGR-SWCSWCGR G, (SEQIDNO:7492); XM_542216.5, PALM, Del, C_8, PRPRAPGKRTRWGPRPRPATPRT-STRRSSAVNAAPSC, (SEQIDNO:7495); XM_005629436.1, AMDHD1, Del, C_8, PRPRGPRSP-PRRGSSAQPALLPGMGL, (SEQIDNO:7496); XM_849736.4, FBXO28, Del, C_8, PRPRPR-PRSRAPRRPQPRRWLPTSCLKTTRWWRCPS, (SEQIDNO:7497); XM_014115699.1, IRF2BP1, Del, C_8, PRPRPWDPIPTGPPRPSQPLRTARPPWPPSCRWQTL-WARRTRRRTAAPCTPPLRPPGA TAAARCHRPPCPGSAAWHHGTGT, (SEQIDNO:7498); XM_544370.5, ZNF366, Del, C_8, PRPRRRPRAGPRPR-RAPTAWT, (SEQIDNO:7499); XM_014121843.1, APC2, Del, C_8, PRPRSAAPPPSWAVMWTGLVPPRRP-PLFPSSTKAWGWLRGAFPPAGTAPPAARPVC PPSTTCPAPWCQPPLTWLQRKPPPLPLPASWN, (SEQIDNO:7500); XM_003433123.4, ZBTB47, Del, C_8, PRPSSPPLPLRAAG, (SEQIDNO:7502); XM_005631293.2, CHRM4, Del, C_8, PRRAPWP-TRTLPTSPAPAAPRTTPRNDQPRSCPPRRPPRLPCP-PRPYSRGPSTPRPNGP RSRL, (SEQIDNO:7503); XM_014118099.1, NOL8, Del, C_8, PRRESKCRMRHLLHLQL, (SEQIDNO:7504); XM_005621365.2, ATXN2L, Ins, C_8, PRRGAPEW-GACTLSFHTLTLSLHRTPPR, (SEQIDNO:7505); XM_005621364.2, ATXN2L, Ins, C_8, PRRGAPEW-GACTLSFHTLTLSLHRTPPSM, (SEQIDNO:7506); XM_854451.4, ATXN2L, Ins, C_8, PRRGAPEW-GACTLSFHTLTLSLHRTPPSSISSLPAAPLPPPGEL, (SEQIDNO:7507); XM_849191.4, MCOLN1, Ins, C_8, PRR-GRPPPSAQILLHESL, (SEQIDNO:7508); XM_005629436.1, AMDHD1, Del, C_8, PRRGS-SAQPALLPGMG1, (SEQIDNO:7509); XM_005635333.1, NKX2-4, Del, C_8, PRRRRPPRAAWRCPCWSRTAS-RARTGPARPRPARPARSRPPRRPRRSSRSSRPARPRC TPRGPAWRPWTLRRGTSAAACWAPTCSTAGRG, (SEQIDNO:7510); XM_005622101.1, LOC102155632, Del, C_8, PRRRRRRRRRPCGHTARSALRPRPRDDATAR-GRLSR, (SEQIDNO:7511); XM_541178.5, FNDC1, Del, C_8, PRRRSAPLRPLLAAPREPHSPRPDTPTAAL-PRQAPPWAPRPGCGTPPAPLPSMPPPPLC CPCASA, (SEQIDNO:7512); XM_014117950.1, AKNA, Del, C_8, PRRRWSSWGL, (SEQIDNO:7513); XM_005622734.2, HCN3, Ins, C_8, PRRRWTA TRTSGPPSLSLPTLSAS-TGSWGWFSWVQGLGK, (SEQIDNO:7514); XM_005620294.2, IGSF9B, Del, C_8, PRRRYLLRE-HIHLHPGTLLHLRGWRL, (SEQIDNO:7515); XM_849688.3, LSMEM1, Del, C_8, PRRSSRTPATRD-TAAGACSLWG, (SEQIDNO:7517); XM_014114459.1, LOC106558910, Ins, C_8, PRRVPPPRLPAQAGSAGD- PLAHLAGGPGWAGGISS, (SEQIDNO:7518); XM_014114435.1, LOC106558903, Del, C_8, PRSCPWRCPLEVPPGALESTGTGWEQEPSQERGP-SQAWEGA, (SEQIDNO:7519); XM_540337.5, MOV10, Del, C_8, PRSGRKKMACPCK, (SEQIDNO:7520); XM_014115300.1, ARHGEFI1, Del, C_8, PRSMSWWH, (SEQIDNO:7521); XM_547544.4, GON4L, Del, C-8, PRSPSRPGTVLSWRSCMQ, (SEQIDNO:7522); XM_005629754.2, GBX1, Ins, C_8, PRSSEICAG, (SEQIDNO:7523); XM_005632636.2, SLC6A20, Ins, C_8, PRTGRHWTAG-GLLHHVHPPGGPGDFHHTLLQEEGRHAPRGL, (SEQIDNO:7524); XM_014111162.1, PADI2, Del, C_8, PRTLLGAPCPTCPSVPHPMTRSLCLPTARPQLR-PRPSA, (SEQIDNO:7525); XM_014122046.1, SMARCA4, Ins, C_8, PRTLRRAPWDARSAPR-RASQALA, (SEQIDNO:7526); XM_539055.5, PRDM13, Del, C_8, PRTPRRPSRPAGRGRASSLKCICHT-CLRRRRRPL, (SEQIDNO:7527); XM_014122376.1, POLR2E, Ins, C_8, PRTSAGGKDHPAQ, (SEQIDNO:7528); XM_014107801.1, CCDC92, Del, C_8, PRTSCLKRPAAA, (SEQIDNO:7529); NM_001002994.1, SCN5A, Del, C_8, PRTTASPGPPAITRRCGRPTTAAART-SPTCPRPQTGTASLSC, (SEQIDNO:7530); XM_843722.4, MAP3K12, Del, C_8, PRTYPEGSRAPPVSRTQTVTARNWTTPTVAK-PCSLRPPSLH, (SEQIDNO:7531); XM_014119322.1, MACF1, Del, C_8, PRVPDCLLLRVNPSAAGL, (SEQIDNO:7532); XM_014114207.1, GIGYF1, Ins, C_8, PRWHLPWQGQHSEPRPRPW, (SEQIDNO:7534); XM_531943.5, ADAMTS1L, Del, C_8, PRWPC-PLASTCPASAARCGPRPPRGRPWGALAGRTASPP-SCGRSRPPSSCRPPRWSRT SGRRWPWPAAR-SACSCTARP, (SEQIDNO:7535); XM_014115712.1, SLC25A29, Ins, C_8, PSAGRPDL-GRRVTRGHRAPSRAGPRAAAGAPPPGPGGPH-TRRGCGRRACGTPI, (SEQIDNO:7536); XM_014122539.1, FRMD4A, Ins, C_8, PSAVPGGA-PADALSPQRL, (SEQIDNO:7537); XM_014113199.1, ZBTB4, Ins, C_8, PSGGDRPVPCPRRPAPAQ, (SEQIDNO:7538); XM_545071.5, DCBLD2, Ins, C_8, PSGG-GIQHSALQN, (SEQIDNO:7539); XM_003638937.3, HCRTR1, Ins, C_8, PSGPGLPG, (SEQIDNO:7540); XM_848403.4, STX5, Ins, C_8, PSGPGPSPSQHHVL-PRSDPGVPVCLQVPAEPSEWNPDK, (SEQIDNO:7541); XM_005615674.1, LOC102154183, Ins, C_8, PSGPPAD-GAAGSSAGHPPARRAHLRRRGPARP, (SEQIDNO:7542); XM_005627781.1, AIM1, Ins, C_8, PSGRTKATGYVI, (SEQIDNO:7544); XM_014107094.1, HSPG2, Del, C_8, PSGSSPRPPRWSKGRPWI, (SEQIDNO:7545); XM_005622233.2, HSD11B1, Ins, C_8, PSGVLLGLLLLFCE, (SEQIDNO:7546); XM_005630772.2, SETDB1, Del, C_8, PSHLPHLY-PLCPHRQVTMTAWKVSLPNLGSR, (SEQIDNO:7547); XM_014120689.1, SETDB1, Del, C_8, PSHLPHLY-PLCPHRQVTMTWKVSLPNLGSR, (SEQIDNO:7548); XM_541589.4, CIC, Del, C_8, PSHPPHPPAPPQLPQAG, (SEQIDNO:7549); XM_014113536.1, FXR2, Ins, C_8, PSKCQAPPLPPPPHR, (SEQIDNO:7550); XM_005639783.1, CHRD, Del, C_8, PSLAWGALPYS-LSVTQRTL-CIFCCSSVDCWNPGVGDQPRFPCGSRFYTRGSYC-ESCR PMPQSRSQALLRSCPT, (SEQIDNO:7551); XM_014110466.1, CHRD, Del, C_8, PSLAWGALPYS-LSVTQRTLCIFCCSSVDCWNPGVGVSGMGQV, (SEQIDNO:7552); XM_855866.4, VTA1, Del, C_8, PSLRAY-SII, (SEQIDNO:7553); XM_546149.4, ADAMTS14, Ins, C_8, PSLRRPPVFRAHVPIPGVQQRGVSGALRGLPG-PAMCQAQLLLHPPECQAQLDPL, (SEQIDNO:7554); XM_005634658.1, LOC102156928, Del, C_8, PSLSGGQAWDRTMESWSLR-SPTHCLPTLDPRRLHPWGPFYLEFGDIPGVAGQH-PRAP KTTTTTTK, (SEQIDNO:7555); XM_844430.3, C2H1orf158, Ins, C_8, PSPAPCPAP1, (SEQIDNO:7556); XM_005620593.2, LOC102153713, Ins, C_8, PSPGAG-GRAFVTPSAARGVA, (SEQIDNO:7558); XM_005631925.2, MGAT4D, Del, C_8, PSPGLSRAGPR-SHVTVRPELGWRGRAPSVPHGGTEPWQGPAWP-PRGPRVAWARPA RPSWGRVGAARFPV, (SEQIDNO:7559); XM_846492.4, XIRP1, Ins, C_8, PSPGRSAAATAQGVLLQVPPAETSQRAPPPLQAHPP, (SEQIDNO:7560); XM_014122358.1, KCNN1, Del, C_8, PSPHLAQASRWWWPRASQPGLHLAVPGGSPR-TRKKKKMMKRMRQAGGGTQGRPQ MWATAWAIGGHSLRSGSASATMPSSSACSALL, (SEQIDNO:7561); XM_005639946.1, ATP11B, Del, C_8, PSPLLRLRPAPDRCRARQAPRPAPPPFVTSGGGAGRR-GAGPEL, (SEQIDNO:7562); XM_014119273.1, LOC106559736, Ins, C_8, PSPPPRPPARGRSIWPRSV, (SEQIDNO:7563); XM_005625313.2, DPM2, Ins, C_8, PSPPPSTLFPRESRRTAGPAM-PLETTFPGMQGGGGTLLSWDT, (SEQIDNO:7564); XM_542201.5, PCSK4, Del, C_8, PSPPQSATPGATVA-VPRLWY, (SEQIDNO:7565); XM_539694.5, NAV3, Del, C_8, PSPPVQAPVMVGRMTMPFLSLVTRKVLTVV, (SEQIDNO:7566); XM_005621674.2, SRRM2, Ins, C_8, PSPRARGHVQRDRAADAPGQRHQRLRPAQPVP-GAGPPG, (SEQIDNO:7567); XM_014114995.1, LOC106558989, Ins, C_8, PSPSSSSALWAR-TAALPTLLTILPGNNYPHL, (SEQIDNO:7568); XM_014121497.1, LOC476151, Ins, C_8, PSPTPSP-PRPCS, (SEQIDNO:7569); NM_001081710.2, SSPO, Del, C_8, PSPVPRTR (SEQIDNO:7570); XM_005623660.2, LTBP2, Del, C_8, PSPWTSASSAA, (SEQIDNO:7571); XM_014117109.1, ESYT1, Ins, C_8, PSQAARALPSLLL-DGHPAWGSEG-PLPLGDRADLRGSVCPDNPGRVHRIRPSLPRARG PPVPTPGQHGSRGAPPSQPPRALPAAPGRPGRCSAP, (SEQIDNO:7572); XM_005626284.2, FLT4, Ins, C_8, PSQCPVALAAMDTLQDLHQAQPQPAAAER-PHATVPGLARGDHPGCREPHREPGHL DRVCGGEE, (SEQIDNO:7573); XM_014117109.1, ESYT1, Ins, C_8, PSQPPRALPAAPGRPGRCSAP, (SEQIDNO:7574); XM_014113123.1, FYB, Del, C_8, PSRSPCLPCLPWAH-RHPNPADLPTLT, (SEQIDNO:7575); XM_541488.5, PNKP, Del, C_8, PSSCPRTGKPLSWAGDP, (SEQIDNO:7576); XM_540739.5, FNBP4, Ins, C_8, PSSPSSCRRW, (SEQIDNO:7577); XM_014114276.1, LOC100687089, Del, C_8, PSSPYSGLTTSLALPFFCL, (SEQIDNO:7578); XM_847581.4, KIAA1024, Del, C_8, PSTDCPSSPKTAS-WWSRCSARTPTRHPSKPT, (SEQIDNO:7579); XM_005619960.2, DVL2, Ins, C_8, PSTPCPTS-SAAPRGPSCQRPGLCAPRTDS, (SEQIDNO:7580); XM_014108280.1, LOC106557869, Ins, C_8, PSTRLTLGHRELGAAPGPQICVHRWPSAARRPL-GAAGTEKPRPL, (SEQIDNO:7581); XM_844550.3, ZDHHC23, Del, C_8, PSTTPPRTLS, (SEQIDNO:7582); XM_005630746.2, CIART, Del, C_8, PSVPQVPF-PLAMVL, (SEQIDNO:7583); XM_005617044.1, ZNF438, Del, C_8, PSWGPIQA, (SEQIDNO:7584); XM_005632562.2, USP19, Del, C_8, PSWLRQP-PRQKLRNSSGYHH, (SEQIDNO:7585); XM_846419.3, ZNF362, Del, C_8, PSWTPSRQSRATACLAPPSP-SAAAKRSRRRTQGGRLSS, (SEQIDNO:7586);

XM_014115299.1, ARHGEF11, Ins, C_8, PTAHHGAQTSAGS, (SEQIDNO:7587); XM_005641102.1, ARHGAP6, Del, C_8, PTATATPTLCGSPRVTSPGTACRAAACA, (SEQIDNO:7588); XM_014113517.1, DVL2, Ins, C_8, PTATPPATGEDQRHRGL, (SEQIDNO:7589); XM_546606.6, PERI, Ins, C_8, PTCHYSLPGCRPALPSPGVLPSGRLPVSCLCPYSWAPCSLPCPARDPNGGLGAS, (SEQIDNO:7590); XM_860394.4, DLGAP4, Ins, C_8, PTCTPSRLPQPWGGHRHQLCQAGLLVYSDPQPRP, (SEQIDNO:7591); XM_005639159.2, AFF1, Ins, C_8, PTCVILILILPEASQACTKEAKAGS, (SEQIDNO:7592); XM_005619036.2, SYNPO2L, Ins, C_8, PTGAHPSAQPRASLRFPQHSTLLGPRHSHKFPVHPSPQSSCYARRSPRAPRPL, (SEQIDNO:7593); XM_005636081.1, SFSWAP, Ins, C_8, PTGGRRGHLLQHPACWCGCA, (SEQIDNO:7594); XM_014106590.1, TRAK1, Del, C_8, PTHLCRHPRPPRPPLSSSARALPMTTSWPPSRPAPS, (SEQIDNO:7596); XM_005632636.2, SLC6A20, Del, C_8, PTHWPSLDCWWPPPPCASPWWPWGLSSHAASRGRETRPPWP, (SEQIDNO:7597); XM_005619042.2, ZSWIM8, Del, C_8, PTLMMSNGCWGWQQSWE, (SEQIDNO:7598); XM_014111408.1, KAZN, Del, C_8, PTLRTGKRSG, (SEQIDNO:7599); NM_001033992.1, DAG1, Ins, C_8, PTLYGPHGGQGLPSQEHDPVPVAPSLRAPL, (SEQIDNO:7600); XM_534998.5, PPRC1, Ins, C_8, PTNSAPGIWYSWHLCCAPHLQCALGTSSSPSPTL, (SEQIDNO:7601); XM_005622126.1, LOC102154422, Ins, C_8, PTPARSPGRRFSAAAAGSCTRLPARPHACSKTCTPEPPRGARSPRRPICSRLSWPGAFP GHLSVATGNKM, (SEQIDNO:7602); XM_014113545.1, KDM6B, Ins, C_8, PTPAWPSH, (SEQIDNO:7603); XM_014108306.1, LOC610488, Ins, C_8, PTPGGSDGRNRAGGDRAAVLPLF, (SEQIDNO:7604); XM_547064.5, INO80E, Del, C_8, PTPHSLLTTWPCSCPSPAP, (SEQIDNO:7606); XM_005628329.2, LOC102154101, Ins, C_8, PTPKSSWGCPK, (SEQIDNO:7608); XM_014116569.1, GLTSCR1, Ins, C_8, PTPPAPPIPAPRGAAAPSSPPSSRLHLLWRGLHGYVHQAASPYAS, (SEQIDNO:7609); XM_014116364.1, LOC102155336, Del, C_8, PTPPRSCTGYGVP, (SEQIDNO:7610); XM_014121497.1, LOC476151, Ins, C_8, PTPPTTSIVRDT, (SEQIDNO:7611); XM_537794.5, RABL6, Ins, C_8, PTPQAPCGLLQTEE, (SEQIDNO:7612); XM_005616451.2, NKPD1, Del, C_8, PTPQTEPAMPPGRSGQVRVPSMSVGTPAKPTSPGTGRRGASRDPWP, (SEQIDNO:7613); XM_014120825.1, GLI3, Ins, C_8, PTPRFGQPFTVQVAWPADSGSPWGAEGPQQHYLKAGRMPPSESCQGREAHADISAK PWW, (SEQIDNO: 7614); XM_540363.4, GLI3, Ins, C_8, PTPRFGQPFTVQVAWPADSGSPWGAEGPQQHYLKAGRMPPSESCQGREAHDISAKP WW, (SEQIDNO: 7615); XM_005623834.1, LOC480441, Del, C_8, PTPRIRGRPKGSSA, (SEQIDNO:7616); XM_546245.4, FOXI1, Del, C_8, PTPTCGSTGLP, (SEQIDNO:7618); XM_014119050.1, LOC106559698, Ins, C_8, PTPTPRRCPQM, (SEQIDNO:7620); XM_014116598.1, SIX5, Ins, C_8, PTPTRAPRTQTARSPPPPPTPPPCCPPAPPSPPPSSPAGPRPRGAAPGVCGRGRGG, (SEQIDNO:7621); XM_014107347.1, LOC102155751, Ins, C_8, PTPVRLGVPPGSDTLPHGSSSKSERGPIPP, (SEQIDNO:7622); XM_005615728.2, VASP, Ins, C_8, PTPWCVPLRGLCGRARSRGRPTPCAPSPHSTRHQWWGNRGPRSCSSHCRSQTQESQ QARGGLRGAPSP, (SEQIDNO:7623); XM_014110154.1, THEMIS2, Ins, C_8, PTQAPQKSGSQWAEETKQQGEKRPVF, (SEQIDNO:7624); XM_547735.5, ZFHX2, Del, C_8, PTQCPTKQPALLPKPF, (SEQIDNO:7625); XM_014114459.1, LOC106558910, Del, C_8, PTQGPPSAASCTSWVRRGPPGSPGGRPGLGGGHLVLMMGGTWAR, (SEQIDNO:7626); XM_844295.4, TNKS, Ins, C_8, PTQPRPGPGDHPSLPNGGRPGPLRLPAARPSAAGGGWQSGSARQASIPGAG, (SEQIDNO:7627); XM_005619566.2, FLI1, Del, C_8, PTRPPCPSLPPACLERRHNTGPPPRGGSTPTPTCPATLTPTCPHT, (SEQIDNO:7628); XM_014121261.1, BRSK2, Ins, C_8, PTSARTELGCWA, (SEQIDNO:7629); XM_846858.4, PDE2A, Del, C_8, PTSCPRKGKSERLWSPGSGWAAMDWAPQICQGSPWPGWWLHWLLTAKCWSCRW WTRRLGLWRPSSWCTVAS, (SEQIDNO:7630); XM_540889.5, RCOR2, Ins, C_8, PTSHPPCSGCLPPQCPPRPTASTHPDWSPSGASSTLTV, (SEQIDNO:7631); XM_014121888.1, MAP4, Del, C_8, PTSLAAPAQAPGLLAPCPGLLS, (SEQIDNO:7632); XM_005616609.2, HNRNP1, Ins, C_8, PTSLRREKDGPTSGGSPSGPKSLRPPVWAPPTPSPTTRVWPPRRQPCAHGLWLGSI, (SEQIDNO:7633); XM_005616893.2, LRFN3, Ins, C_8, PTSPASQQHQL, (SEQIDNO:7634); XM_538777.4, ZNF462, Ins, C_8, PTTPATRPQY, (SEQIDNO:7637); XM_005621273.2, FBRS, Ins, C_8, PTTPPPLLVLPWPHPAPTPTPAAGARAPWGLRC, (SEQIDNO:7638); XM_014121497.1, LOC476151, Ins, C_8, PITSIVRDT, (SEQIDNO:7639); XM_005636179.2, SETD1B, Del, C_8, PITITSSPRRSPALRARGGTTIGEVTS, (SEQIDNO:7640); XM_014117924.1, LOC481671, Ins, C_8, PITTITKPH, (SEQIDNO:7641); XM_014117969.1, SEMA4D, Ins, C_8, PVAPARENVRPHRWAACRPGHGIWDDGGIRTGPQDHLGAQRGAAGEVSRARHLQL LGVAAK, (SEQIDNO:7642); XM_014116554.1, LMTK3, Ins, C_8, PVLLPLLRLACAGDPGASRPGPRRPARRPRGEL, (SEQIDNO:7643); XM_539694.5, NAV3, Ins, C_8, PVLQFRPQ, (SEQIDNO:7644); XM_005632319.2, DAG1, Ins, C_8, PVLQYAPHPTGGESPSPPS, (SEQIDNO:7645); XM_005629424.1, ZNF219, Del, C_8, PVLRRRGRRAPGCRGPRSG, (SEQIDNO:7646); XM_005642274.1, LOC102152225, Ins, C_8, PVPPACPRPPTARSRARRACRAPNSALRGPKPASPLLGVLPPPWPPWLGGGVPGRSA LGPPRKGRREARGGCWGGASLRVCGRAFSGEPVA, (SEQIDNO:7648); XM_005638708.1, LOC102154051, Ins, C_8, PVPPGESIGVGRRPLRSAARPSEATAAGSSSMGMFSSAPKNTPYP, (SEQIDNO:7649); XM_540881.6, NRXN2, Del, C_8, PWGPGPPRPLSRGGPRPCAPA, (SEQIDNO:7651); XM_005642274.1, LOC102152225, Ins, C_8, PWPPWLGGGVPGRSALGPPRKGRREARGGCWGGASLRVCGRAFSGEPVA, (SEQIDNO:7652); XM_014119467.1, SZT2, Ins, C_8, PWRPSAPEGPQCYPGRLRVNLASGSGASPNLGPSAPQIHL, (SEQIDNO: 7653); XM_014117848.1, NPR2, Del, C_8, PWTIPPVPLTWTTHPVIKPHFPLWRLWPWAQESPSSCLVFPASSFSES, (SEQIDNO:7654); XM_014117851.1, NPR2, Del, C_8, PWTIPPVPLTWTTHPVIKPHFPLWRLWPWAQESPSSCLVFPASSFSVLTES, (SEQIDNO:7655); XM_014117150.1, SMARCC2, Ins, C_8, PWTPWPLTVPQPTNSSRNDARGSARQRAPRRGG, (SEQIDNO:7656); XM_014117151.1, SMARCC2, Ins, C_8, PWTPWPLTVPQPTNSSRNDARGSARQRAPRRGGPEPCHCGSCSGQPPAQCQPTARPR YPSASRPH GPEPRHSHPCATSTV, (SEQIDNO:7657); XM_005625495.2, SMARCC2, Ins, C_8, PWTPWPLTVPQPTNSSRNDARGSAR

QRAPRRGGPRYPSASRPHGPEPRHSHPCATST V, (SEQ ID NO:7658); XM_014113123.1, FYB, Ins, C_8, QAEAPASPVYLGPTATQTQQTSQR, (SEQ ID NO:7659); XM_014114200.1, SRRT, Ins, C_8, QAGQHRRD, (SEQ ID NO:7661); XM_005634658.1, LOC102156928, Ins, C_8, QASPGVKPGTERWRVGAYAALLTVSQR, (SEQ ID NO:7662); XM_014115113.1, KIAA1614, Ins, C_8, QCGNPSLDSILGQRCTTRAASRGRGLGLRHLPAGLRAEQDLWSQAGVCAEPQA, (SEQ ID NO:7663); XM_014114772.1, CELSR2, Ins, C_8, QCQYSVPPIGGAWRQPL, (SEQ ID NO:7664); XM_005619930.2, MINK1, Ins, C_8, QGASEDLLHCCRAQHQWGRRGPAHSGCPRQTSQQLRLANLSAKAGRAGHPQVSRA PRSAPWPAQRL, (SEQ ID NO:7665); XM_014117950.1, AKNA, Ins, C_8, QGDGGAVGVCKASRLPCIR-GQRWLPPGPGQSRGNSSRPYPAAPPPGHQDC-SIPPEQS DQLGGKWHL, (SEQ ID NO:7666); XM_014112550.1, ADD1, Ins, C_8, QHPCQAWGRPATGAHFRRGQ, (SEQ ID NO:7667); XM_014112554.1, ADDI, Ins, C_8, QHPCQAWGRRWMC, (SEQ ID NO:7668); NM_001003247.L KCNB2, Ins, C_8, QHSPAAARHHGGLLPHRPAAHQHHPPRRDPLPGRQALLGAEGSAHCQGPSKGLSPR FPKQKLFPFSSRERRSFTEI, (SEQ ID NO:7669); XM_005628809.2, PTPRZ1, Ins, C_8, QIPSVLHADGD, (SEQ ID NO:7670); XM_005626438.2, SRFBP1, Ins, C_8, QKSVVTGGR, (SEQ ID NO:7671); XM_547735.5, ZFHX2, Ins, C_8, QLNAQRSSPHCCQSPSRKLWL, (SEQ ID NO:7672); XM_005631207.2, SSRP1, Ins, C_8, QLRRLGIRI, (SEQ ID NO:7673); XM_014109393.1, LOC100686862, Ins, C_8, QLRVRRGWAA, (SEQ ID NO:7674); XM_014106590.1, TRAK1, Ins, C_8, QLTYADTHVLPALL, (SEQ ID NO:7675); XM_847992.3, NCOR2, Ins, C_8, QQGLRAAAPGTPRLQSLGHRPHPSKEPRTP-PRRPGPACAARLDHGPASGKDSK, (SEQ ID NO:7678); XM_005641102.1, ARHGAP6, Ins, C_8, QQPQP-PLRCVEVRG, (SEQ ID NO:7679); XM_005623834.1, LOC480441, Ins, C_8, QRPGYVAVRKVHRL, (SEQ ID NO:7680); XM_005629424.1, ZNF219, Ins, C_8, QSSAGGGGGLRAAGGPGAV, (SEQ ID NO:7681); NM_001013846.1, CCKBR, Ins, C_8, QWELPAG-GRAGWRGRRRLLRAASALASDP-GAVRADRAHSWARRWPPALPGQAVG QEARGADAAGDRRAFFPVLVATV, (SEQ ID NO:7682); XM_003432577.3, ERF, Ins, C_8, RAPQARARRGSRGGAVHASQAALQAALE, (SEQ ID NO:7683); XM_005629711.2, NOM1, Ins, C_8, RGDQAPRSRSRSHCRRSETGSSGGQRGGGPGDPKAGAVPR-LEQAQKEGRRQLRAAE LCPRWARLHPRSPGVWKK, (SEQ ID NO:7685); XM_014106952.1, RTEL1, Ins, C_8, RGGAGTRPPHLVRPT, (SEQ ID NO:7686); XM_003431951.3, HIVEP3, Ins, C_8, RGLRPRPGPQQLRGLPGRGLRSLPGPEEAPVRGAQDQSGLPRALRKWGARGTSTPAP GQGPPKRL, (SEQ ID NO:7687); XM_005629436.1, AMDHD1, Ins, C_8, RGRADPGAPPAGVRPRSPPFSPGWVYKSHRSC, (SEQ ID NO:7689); XM_546111.5, CCDC6, Ins, C_8, RGRRAARPLAAAGAPPLPAL, (SEQ ID NO:7690); XM_544403.5, IRX3, Ins, C_8, RGSRRAPSPAALARRR-GRRGSQTRLGAAEQVPRLDQPAVPRPAAGPTPAPALPARLG PSTPAGTSRSRGPPGRGRCCLRSACGARGRSRSL, (SEQ ID NO:7691); XM_547146.4, NMRAL1, Ins, C_8, RLPGLWGRSSRGGSHGR-REAGGGGVRGHRCSGRLRGPDAPGRWDV, (SEQ ID NO:7693); XM_014113186.1, NCAM1, Ins, C_8, RPAGGPRHRRPGPRARPARRRREEPGRGSRGPH, (SEQ ID NO:7694); XM_014119242.1, LOC106559725, Ins, C_8, RPAGPRAARDRAAGRPEG-GRRGPPGRAAGNSGE, (SEQ ID NO:7695); XM_014121373.1, LOC106560025, Ins, C_8, RPRAGPSTCTRPLRDPAQQ, (SEQ ID NO:7696); XM_014108675.1, IFFO1, Ins, C_8, RRHGSPQRPGLQHQRAQDPEPPLPLLPGQGA-RAGAPQPAAREAAAAGAGGG, (SEQ ID NO:7698); XM_014115167.1, BRINP2, Ins, C_8, RRPAAPGLAAHR-PRPLPPRPGVR, (SEQ ID NO:7699); XM_545655.5, FAM134A, Ins, C_8, RRPAGPPSGPLKARPRLGRG-GRCGSQGNLASALVPPSFCEHALQWG-GLSHRWSAAV PGRTSGDTEPRGSEW, (SEQ ID NO:7700); XM_005628850.2, YBX1, Ins, C_8, RRPRPQRRRHQARHHGQRRRERRPGR-PHIGGACRRGQEGHRNEGFGNSKMVQCKK RIWFHQQE, (SEQ ID NO:7701); XM_003639988.3, MMP21, Ins, C_8, RRRRPGPGRAQVPEGQRAA-GQRAPGRGHPGGHEQAALRGPRHPGPAAPRRPAAPQ ALPAAAAAARGPAA, (SEQ ID NO:7703); XM_548709.6, DPYSL4, Ins, C_8, RRTLQHHVSVL, (SEQ ID NO:7704); XM_005632287.2, LOC102152377, Ins, C_8, RTQRTGR-SWGEAEPRAAGARRGADRGRVLAPRHTHP-FLSRGVAPAPQG, (SEQ ID NO:7706); XM_014107494.1, RHOBTB2, Ins, C_9, HHCGAR-SPVQQRGVPRPPPGGPAVCGCHTGAAGAGAHL-CPQDLPLHLVLQVLRPVP HGPK, (SEQ ID NO:7708); XM_014111415.1, LOC612200, Ins, C_9, HHGQPELQGSPGLRDPRGGSRYFAC, (SEQ ID NO:7709); XM_005634658.1, LOC102156928, Ins, C_9, HPGSAGGPQSRTPRRAQGPAVSPAAPNARRTGR-PETPPPPQCPTPRCAHRPQSSRPRS APPPR-SARRPQGPTPRI, (SEQ ID NO:7710); XM_014121183.1, MADD, Ins, C_9, HSASQHWQVERGQAS-DRNWRGVSAPANL, (SEQ ID NO:7711); XM_014116237.1, BAHCC1, Del, C_9, PAAPRRHHVPA-PRALYPSAPLAAPGPAPGCPAPRTRAGRAGG-PEPTSVRWNQTCLL DTPALP, (SEQ ID NO:7713); XM_014116598.1, SIX5, Ins, C_9, PALPPWTSDPTLLGHISAPPTPTRAPRTQTAR-SPPPPPTPPPCCPPAPPSPPPSSPAGPRP RGAAPGVCGRGRGG, (SEQ ID NO:7714); XM_014121819.1, CAMSAP3, Del, C_9, PAPLRCWPFWRGGAPCPRCPSALCRRRT, (SEQ ID NO:7715); XM_014114459.1, LOC106558910, Ins, C_9, PAPRPASGTPRGRPPRAPARPSHGGPAP-DAAPAAGDLPGSCPTPPSAPRGPPPRRVPPP RLPAQAGSAGDPLAHLAGGPGWAGGISS, (SEQ ID NO:7716); XM_014120235.1, TMEM214, Ins, C_9, PAPRPL-SACHYPSSNPDDKHPL, (SEQ ID NO:7717); XM_540485.6, ARL16, Ins, C_9, PDAAHGGHRPDRHRGPEEDHHPGAG-GLHGPHLAQLLWRLPLSPVHDGCRQPHSAV RIL-CATPGSSFCRRTRRSISPDTLQ, (SEQ ID NO:7718); XM_014120232.1, LOC106559875, Ins, C_9, PEASR-GAQPPSRRPPLAQQADL, (SEQ ID NO:7719); XM_005624164.1, SLC16A5, Del, C_9, PFPGPPPPP, (SEQ ID NO:7720); XM_014110159.1, LOC106558165, Del, C_9, PFRGARGRV, (SEQ ID NO:7721); XM_014114181.1, RASA4B, Ins, C_9, PGALSALHITPSHWGAGL-RALLGWVDWGPEARPCPPV, (SEQ ID NO:7723); XM_005640418.2, AAMP, Ins, C_9, PGDPELPW, (SEQ ID NO:7724); XM_014116573.1, DACT3, Ins, C_9, PGFPPWGRPGPKNC, (SEQ ID NO:7725); XM_005634649.1, CHST2, Ins, C_9, PGGAAPRTHPPGP-PYSVPPSCRRRGGPRRCSRRRRRGRGGRGGRG-GRGPSPQWHS GPRGWRRQEAVGVRVHHVAL-

GLIVLR, (SEQIDNO:7726); XM_014114582.1, LYRM1, Del, C_9, PGGLVRPGLPDLPDQRRPRLSKAPGAASS, (SEQIDNO:7727); XM_014117590.1, LOC102151723, Del, C_9, PGSAGLGGHLAAVASRRTPRTPAC, (SEQIDNO:7728); XM_005638643.2, LOC102157171, Del, C_9, PGSPAVPPRCQASTRALAPSPAPEWRQGGRV, (SEQIDNO:7729); XM_014118308.1, PRRC2A, Del, C_9, PHLAERAALRPAGALAQAAVVVGSLQRNQGPLPAGLGL, (SEQIDNO:7730); XM_536612.5, PELP1, Del, C_9, PHLLPLCRALWPCRRHSWYPRRLLVEEDPLPWRKT, (SEQIDNO:7731); XM_014118223.1, ZNF865, Del, C_9, PHRPSLMLPSPPRNGASSTSLDTSTFLGI, (SEQIDNO:7732); XM_005632764.2, WIZ, Del, C_9, PHRRPRRPS, (SEQIDNO:7733); XM_014111168.1, SPEN, Ins, C_9, PITSCTRRTL, (SEQIDNO:7734); XM_014115022.1, SKOR2, Del, C_9, PKSRAPSATTRPRRRRRPR (SEQIDNO:7735); XM_014107007.1, DIDO1, Del, C_9, PLATSWAQGGRIPVSLKDPEAKHQISCQDPGGCSLSSSRSRG, (SEQIDNO:7736); XM_854614.4, MBD6, Del, C_9, PLGDPALP, (SEQIDNO:7737); XM_014112383.C ADAMTS17, Del, C_9, PLGQEALTAWEPVWSMLSARTCPALRACPASETSSARHMTA, (SEQIDNO:7738); XM_541489.6, MED25, Del, C_9, PLLDPSFGLRTLGPTPNCGVSSSTHLRLRLGCPHPKLPSTTSSHQGLQHCCHHTRAW GNPSWGPPSCTHHLPSPGPHSFPRELRCQVRCC, (SEQIDNO:7739); XM_005642172.2, RAB40B, Ins, C_9, PLSSSRTQKAGPGHHCPGLGGGGAVHTEDVPGAAAHPRPRVPVQHVCSAPGQP, (SEQIDNO:7740); XM_014111569.1, NLGN3, Del, C_9, PMTHCASLHCLTTR (SEQIDNO:7741); XM_541409.5, ZNF628, Del, C_9, PNLAKPLPQWASPQLPPPRWYKWYPLALHLEV, (SEQIDNO:7742); XM_014119102.1, LOC102153462, Del, C_9, PPARARCGRTRGGLGGCCARCARGAPRETLGASSPGGCGPATRQGHSSALS, (SEQIDNO:7743); XM_005628643.2, LOC102153462, Del, C_9, PPARARCGRTRGGLGGCCARCARGAPRETLGASSPGGCGPATRQVGHGRLALRSPE DPAPPG, (SEQIDNO:7744); XM_014114176.1, LOC489812, Del, C_9, PPPGPALAQP, (SEQIDNO:7745); XM_014109694.1, DONSON, Del, C_9, PPPPPPPILMVKPDAKLT, (SEQIDNO:7746); XM_005635892.1, DMTN, Del, C_9, PPPPSARPPARWRAPPGPGTHAHSHRPPFTLPSNHLPPLGASAPPAAPVFPALPPASW PRWTTRCWATRTWLPSPRTRPSWTSSGLTS, (SEQIDNO:7747); XM_014120095.1, LOC102155747, Del, C_9, PPQAPTPTPPSRSSARRIPETANPARLTAQRRSGGAPHPAFCTPKSGRRRAPPRESGSG VGGGARSRRPRPLWDPN, (SEQIDNO:7748); XM_538915.5, FRS3, Ins, C_9, PPQQQQRGPF, (SEQIDNO:7749); XM_005637416.1, KCNH3, Del, C_9, PPRAQPAGALLRPSGGGQSAHPRPRAAEKDASPRR (SEQIDNO:7750); XM_005634658.1, LOC102156928, Del, C_9, PPRQRRRSAEPDAPQSSRSCSVPRSAQRPQNRTPGNAPPPAVPDAPLRPPPAELEAPQ CPPPPQRPTPAGPDAPH, (SEQIDNO:7751); XM_014121188.1, MADD, Del, C_9, PQCLPALASRTWTGVRQKLERA, (SEQIDNO:7752); XM_855872.4, MADD, Del, C_9, PQCLPALASRTWTGVRQKLERGLKRCCGPTA, (SEQIDNO:7753); XM_014121190.1, MADD, Del, C_9, PQCLPALASRTWTGVRQKLERGQCAGEPMTIHTSSPNMAFPLRRRMMSRGKVTLPD SANMSMAIGLKRCCGPTA, (SEQIDNO:7755); XM_547535.6, SMG5, Del, C_9, PQGRAASPRRRSSIPSGFTGLWWRLCIDSTSSFATKLLIKKCLNQRTLA, (SEQIDNO:7756); XM_014121934.1, PRAM1, Del, C_9, PQPSPHCPLAPGMSRASEEPQPQPQL, (SEQIDNO:7757); XM_005640437.2, LOC102152812, Del, C_9, PQRDLRSSPRGPW AWSECPWHPGLSSLLRPLSYHPGWRSRPPQAQPPNLSRPDPLPARPSSNFSPSDGTPS PSSQCNKMVQAGGPRTWWA, (SEQIDNO:7758); XM_539202.5, FAM83H, Del, C_9, PQRGRARHLTLSPRGAPPLPTRSGKGAPPRPSRSAGPARCPPCPSAGPAQCPPCPSAG PASPLPSPRSPPRPAPRRSRRAAPWRCCARAPCASASC, (SEQIDNO:7759); XM_014116598.1, SIX5, Del, C_9, PRAAPLDK, (SEQIDNO:7760); XM_014122404.1, PSPN, Del, C_9, PRAPRTPSSFPPRCHLPSAAPCPLQVAAHAEPWPARASCGACPCLWPSWVWATRRR RRSPSATVRAAAPAACAPSTA, (SEQIDNO:7761); XM_014118922.1, TEAD2, Ins, C_9, PRECGRPAD1, (SEQIDNO:7762); XM_539202.5, FAM83H, Ins, C_9, PRGAAPGTSP, (SEQIDNO:7763); XM_547535.6, SMG5, Ins, C_9, PRGEQRARGEGPPYQAALPGCGGGCASTRPHPLQQNCLSRSV, (SEQIDNO:7764); XM_014120232.1, LOC106559875, Del, C_9, PRGLPRGPAAVPPPAARATGGSVGLQRRRAPGTRRTGGAAGQAPRTAHSPRGP, (SEQIDNO:7765); XM_540485.6, ARL16, Del, C_9, PRRGPRWAPT, (SEQIDNO:7768); XM_005622091.2, CASKIN1, Del, C_9, PRRPRRRAPAASWTTSAACSTTWPTSWTPCWS, (SEQIDNO:7769); XM_005631712.2, EPS8L2, Del, C_9, PRTRPPSPSSATAVTPQPARTGWARRCRSVSQASAVGSRRMRSPEPCWPRR, (SEQIDNO: 7771); XM_848355.4, PDZD4, Del, C_9, PSAMSIMTRRSSWRAARRRQTVWTSWSMRRWSCTRPATGTS, (SEQIDNO:7772); XM_014118661.1, C13H8orf82, Ins, C_9, PSASLRQRPGPRRASRAGGGTSWLLSPGPTFSTGLPVPGPRPGRSARQDHRRV, (SEQIDNO: 7773); XM_014110159.1, LOC106558165, Ins, C_9, PSGVLGGGL, (SEQIDNO:7774); XM_005634093.2, F7, Ins, C_9, PSLPHPGGSPGCPAPAKARQLVPGGAAGRLPGERVPGGAVLL, (SEQIDNO:7775); XM_014107494.1, RHOBTB2, Del, C_9, PSLWCPIPRPAARSAPPTSWRTRCVRMSYWCCRSGCASLPTRSTSPPRPPSSTTCSSW T, (SEQIDNO:7776); XM_005642172.2, RAB40B, Del, C_9, PSQLLEDSEGRPGSPLPGAGGRGSRSY, (SEQIDNO:7779); XM_014111415.1, LOC612200, Del, C_9, PSRAARAPRLPGAT, (SEQIDNO:7780); XM_540906.5, B3GAT3, Ins, C_9, PSRHPGSRVLC, (SEQIDNO:7781); XM_014118922.1, TEAD2, Del, C-9, PSRVWTSGRSMTSSQRKRVAFGSCTIAGPLTPSSWSSSGRTSTGARVARR, (SEQIDNO:7782); XM_005632764.2, WIZ, Ins, C_9, PTAGQEGQAEGRGYGQPLGEAGPLGRRSRRHFLGL, (SEQIDNO:7783); XM_005627098.2, ATAT1, Del, C_9, PTHTPSKSVFSLQEVAQAVPPNGCIPS, (SEQIDNO:7784); XM_005628317.2, GPT, Del, C_9, PTPRGRRRGRRCWRSWRQRRSSRSRCSTSPRASAATRCRAPCTPSLACSCPPAPCSAL RN, (SEQIDNO:7785); XM_003639258.3, DOC2B, Del, C_9, PTPRRKTRTPRVKIPTPPKIVLPWARWISACSTTRKTTPSTVPSARPRA, (SEQIDNO:7786); XM_014118308.1, PRRC2A, Ins, C_9, PTSQREPH, (SEQIDNO:7787); XM_536612.5, PELP1, Ins, C_9, PTSSPCAGPCGPAAATVGTRGDSWWRRTPCPGGRPDGY, (SEQIDNO:7788); XM_848028.5, ZCCHC24, Del, C_9, PTTCATCASTKDTTSRTVPRHAPKARV, (SEQIDNO:7789); XM_538915.5, FRS3, Del, C_9, PTTTTTTRALLSARPSPSAPMRTSVRGCGQGRAGD, (SEQIDNO:7790); XM_541409.5, ZNF628, Ins, C_9, PTWPSLCPSGHLHSSHLPDGTSGTHWRCTWRYDPTGPTLHPDCPDSARSPAGAYIL, (SE- QIDNO:7791); XM_014118661.1, C13H8orf82, Del, C_9, PVRVPAAAPGAAQGEPGRGRD, (SEQIDNO:7792); XM_014112383.1, ADAMTS17, Ins, C_9, PWARRHSLLGSQCGACCLREPALP, (SEQIDNO:7793); XM_014114181.1, RASA4B, Del, C_9, PWCAFSSSHHSVSLGSGA, (SEQIDNO:7794); XM_854614.4, MBD6, Ins, C_9, PWGTRPSPSPRRA, (SEQIDNO:7795); XM_014107007.1, DIDO1, Ins, C_9, PWPLRGPKGAASQSV, (SEQIDNO:7796); XM_005631712.2, EPS8L2, Ins, C_9, QGPGPHPLPALRQ, (SEQIDNO:7798); XM_005627098.2, ATAT1, Ins, C_9, QHTHLQSQYFHYRR, (SEQIDNO:7799); XM_014117108.1, LOC106559343, Ins, C_9, QLPHVQLPPSCPSTAPWLPGRTRQGKTGHSAPGPRRTASGHSHLTSSL, (SEQIDNO:7800); XM_848028.5, ZCCHC24, Ins, C_9, QLPVPPVLQQRTLHQGLSPGTPQRRGSDPVPGQKALFRRVQVSQVQEKMDERELLG QHGAGVH, (SEQIDNO:7801); XM_014121819.1, CAMSAP3, Ins, C_9, QPLCAAGPSGEEGHRARAARAPCAGGGPEAPAYPHGRPPPCSPDHPAAAGED, (SEQIDNO:7802); XM_003639258.3, DOC2B, Ins, C_9, QPPGGKPGPRGLKFRRLQKLYCPGHAGFQPALRPGKQRPPLYHQQGQGPEADGPQR ASRPLCQAASAARSQ, (SEQIDNO:7803); XM_014112276.1, COL4A3BP, Ins, C_9, RAGAGTPPFPAPRALTPAPGRFLRRGSGSGGWSPARLSRLHVG, (SEQIDNO:7804); XM_005638643.2, LOC102157171, Ins, C_9, RGHRPSPRAVRPPPGLWHLLRLQSGGREAES EEEGEGGWRPPEAPNSC, (SEQIDNO:7805); XM_014116237.1, BAHCC1, Ins, C_9, RLPPDATTSQRPVHFIRLPLWQPRARLQAARLRGQERGGLAGRSRPQCVGTRPACWI HLPCHDQLGLLHVPRRALF, (SEQIDNO:7806); XM_014120095.1, LOC102155747, Ins, C_9, RPRPLLPPRRPALLLGGSPRRQTPRGSRRNAEAAALLTRPSAPQNPDADGPPQGSLGV GLGAGRGHVGRGRSGTPTRAPAPEPQGGLLLGARK, (SEQIDNO:7809); XM_014109694.1, DONSON, Ins, C_9, RPRPRPRF, (SEQIDNO:7810); XM_005629431.1, LOC102155312, Ins, C_9, RQARPRRLPAVTHRAPGSCAR, (SEQIDNO:7811); XM_014119102.1, LOC102153462, Ins, C_9, RRRGPGAAAPGAASEDAARAAPGVRPGRPWVLPPRAGADPRPGRVIPVPSLDEA, (SEQIDNO:7812); XM_005628643.2, LOC102153462, Ins, C_9, RRRGPGAAAPGAASEDAARAAPGVRPGRPWVLPPRAGADPRPGRW ATDASRFAVPRTPPRPDDLRVIPVPSLDEA, (SEQIDNO:7813); XM_005642085.2, LOC102156583, Ins, G_10, ADGPRPLCSSPWPP, (SEQIDNO:7814); XM_014113210.1, LOC106558749, Ins, G_10, AVRGHWALLGWAEGLELGRPGRLGGPRAA, (SEQIDNO:7815); XM_532250.5, QRS1L, Ins, G_10, EGDRTLSTP, (SEQIDNO:7816); XM_014109665.1, LOC102154979, Del, G_10, GAAGGRVPGGRAHLGCG, (SEQIDNO:7817); XM_005642273.1, LOC102152155, Del, G_10, GAGARAHGRGTTATGQGASPLPAAAWTGHVAWRPPPHTPRGGGDRGGGVWRRGL TLPTGPTAPTRGGGRATPKGSLNLRAGTR, (SEQIDNO:7818); XM_014107649.1, LOC106557788, Del, G_10, GAPLLGPPACTQNPGC, (SEQIDNO:7819); XM_014118269.1, LOC106559574, Ins, G_10, GAQRGAGGA, (SEQIDNO:7820); XM_539574.5, ZFP69B, Del, G-10, GASSCCSSSSSPCPRRPARG, (SEQIDNO:7821); XM_014116262.1, LOC491550, Ins, G_10, GCRRPEGAGGRRGRRTSPRHPLVSWDLFFPHSGPSLPAKPRQQPAQGLCSQLEPFAR SWAANERVPAGARGHGRKGDRSSRGDSGAQW, (SEQIDNO:7822); XM_014121835.1, JSRP1, Del, G_10, GEGPARGWGGVS, (SEQIDNO:7823); XM_014117116.1, CPM, Del, G_10, GIQGRSPRVPQPTGAPEGGPASWGGGVQGAPEEPRPRGEEGCGEPPRSPGLVREEGP WHGRRRRQVLRAGRPPRRVGPPQPPGRPTPAA, (SEQIDNO:7828); XM_014109665.1, LOC102154979, Ins, G_10, GLRGAEFRGVEPTWAAAEVVSPGL, (SEQIDNO:7829); XM_014122482.1, LOC102152187, Del, G_10, GLSERGPPRRPFPSRVREPARPAVSRSSRRAEGHGLHLEKSFAFLLSLFKPLLSEPLEE AWFLLE, (SEQIDNO:7830); XM_003639170.3, SLC27A3, Del, G_10, GPAGKGRVPAHARSRGRG, (SEQIDNO:7831); XM_005642273.1, LOC102152155, Ins, G_10, GRAHAHTDAARLPPGRGRAPSRRPRGPGTWRGDPPRTPHGVAGTEAAESGGGD, (SEQIDNO:7832); XM_014107649.1, LOC106557788, Ins, G_10, GRPYSALQPARRTPGAESGGPRGRFWRAPTSQRP, (SEQIDNO:7833); XM_848566.4, SLAIN2, Ins, G_10, GRVGPPGDEQRPTSGSPLPAGGGRGRLA, (SEQIDNO:7834); XM_014113210.1, LOC106558749, Del, G_10, GSARPLGPAGVGRGSGAGQAREAGRASSSLTGDRGQGTGWLPPPTGQIRGALGQ, (SEQIDNO:7835); XM_848566.4, SLAIN2, Del, G_10, GSGRAPGGRTTTNFGKPPPCWRRARAACLTRWSRCGPTSWSGCRAGRRRRRAGCIH HQRKN, (SEQIDNO:7836); XM_014121826.1, LOC106560105, Ins, G_11, GCIISSPRWPSGSARSRCADDVSSTWASLGLFVLFSY APALFSGGLLRSRS, (SEQIDNO: 7839); XM_005635998.1, DTYMK, Del, G_11, GLLSGAPAAQTAGAASATRAAAASGPGEAPAEAASSGSRGFGSRPRPRTKGRPSAPR AAPLCSGPARPGPRLRSALCFLGR, (SEQIDNO:7840); XM_014121826.1, LOC106560105, Del, G_11, GJMYYFISQVAFRLSSIQMCRRCF, (SEQIDNO:7841); XM_005633247.1, C20H19orf24, Del, G_11, GPGAAPPSGSAAPRHPAWPRAASVLRGPGLPAGRQGPGVPPLGAGPERRRGRGRGG RGGRGRAGTARGLAGPRRRP, (SEQIDNO:7842); XM_541564.5, MARK4, Ins, G_11, GRGCAEWAPRLSHAGPRGHPPAHWAAPPHHQPLHQADLQTDQKGHRRT, (SEQIDNO:7843); XM_545270.2, LOC488146, Del, G_11, GRGQKNVLDSLIRLCLVSRGQKKIAESANFLISLKKM, (SEQIDNO: 7844); XM_014111178.1, LOC106558357, Del, G_11, GRPNRQKAPRTT, (SEQIDNO:7845); XM_014120239.1, SOS1, Del, G_11, GVRKDLREKGAQERGKELVPRSRDKFIRLLSLVTMLFNMLKN, (SEQIDNO:7846); XM_014110071.1, LOC100683502, Ins, G_12, ALGARAQGNGDPLI, (SEQIDNO:7848); XM_005619076.1, LOC102154314, Del, G_12, GCASGTRRAESALGKN, (SEQIDNO:7849); XM_005621522.2, NTAN1, Ins, G_12, GETWAPNVPSRLDYISHKAPAPAPGYF, (SEQIDNO: 7850); XM_014121838.1, BTBD2, Ins, G_12, GRGVGIARVRPPLATFLLEASASSARGRCVLCAGPGAPDSGPGTGGRAEGHQAPL, (SEQIDNO:7851); XM_005621522.2, NTAN1, Del, G_12, GRNLGAERSLAVGLHLPQGPRPRPRVFLARGEGPASRSRAAPGATP, (SEQIDNO:7852); XM_014110071.1, LOC100683502, Del, G_12, GSGSTGPGEWGPSHLRERTRREEDRPAEFMESAISGPLILRRGGVLGRGVGALPAGA ALRPPEGAAAPGSQS, (SEQIDNO:7853); XM_014120227.1, CMPK2, Del, G_12, GVSPSFLKLKQCSTWLTSARSRSRRGSSRSLSSKDWMPLVKPL, (SEQIDNO:7855); XM_005621005.2, CLDN15, Del, G_13, GASRDSLSSPACHSQCVSHLPR, (SEQIDNO:7856);

XM_005621005.2, CLDN15, Ins, G_13, GLP-GIPCPLQLATPSACLTFPV, (SEQIDNO:7858); XM_014106531.1, LOC106557613, Del, G_14, GARLAAHRRRGPGLWGPPLDATVRGPA, (SEQIDNO:7859); XM_542564.5, RCBTB2, Ins, G_14, GPKAELCPRVWK, (SEQIDNO:7861); XM_014111206.1, SRM, Del, G_14, GQARPDCHSPPARATATCWCWTA, (SEQIDNO:7862); XM_014111206.1, SRM, Ins, G_14, GRPGPTVTRPQQELRQRAGAGRRDPVHRAGRVLLPGD-DREPAAVQPPRPPQGADHR GRRRGRPAG-GAEALVRGVRGAVRDRRGRHPGL, (SEQIDNO:7863); XM_005619450.1, PWWP2A, Del, G_14, GTIRQTRTS, (SEQIDNO:7864); XM_542564.5, RCBTB2, Del, G_14, GTKGGALPSSLEVTPGPR, (SEQIDNO:7865); XM_014110360.1, P1D1, Del, G-15, GAMHLL-CREVAPGHCLPFQALPTSTTAACWEGATAK, (SEQIDNO:7866); XM_014110360.1, P1D1, Ins, G_15, GRCTCSAERLLQVTVSRSRLCQHQRPQHAGKARQR-NECACAGHGDGPFGHGRTGV PRWPLRPRP-PAAVLQGCPWLSF, (SEQIDNO:7867); XM_005623909.1, LOC102152283, Ins, G_16, DDAQGAAD, (SEQIDNO:7868); XM_005620429.2, MMEL1, Ins, G_7, AAAAAAPGDRRPGGPGP-PLCCQQQREAADTLS, (SEQIDNO:7870); XM_014115697.1, LOC102152805, Ins, G-7, AAAGSGLRGSAAG, (SEQIDNO:7872); XM_849768.4, FAM83E, Ins, G_7, AAAGSQPPPCGPP-PLCGPHVPAATRRPVGPTLGCLPSI, (SEQIDNO:7873); XM_005617274.2, PURA, Ins, G_7, AAARDAGAGLQAGGHPEQALLPGREAERQG-PLPEDR, (SEQIDNO:7874); XM_005638695.2, C2CD4A, Ins, G_7, AAGAAEPRAVGCRV, (SEQIDNO:7875); XM_543461.5, MN1, Ins, G_7, AAGAAGARILWR-PAAAPRPPGRPPPPPTSPPLWGQLRRPGPG-GLVPARGSPTWVRRR RRRPGQPAALRGGL, (SEQIDNO:7876); XM_014107348.1, AMER2, Ins, G_7, AAGAGRGSPGAPGRP-GAAPWGGPAGRRRPQPPQPRGPPRRLGRRRRRPRP, (SEQIDNO:7877); XM_850395.3, USF2, Ins, G_7, AAGCDPGGCGWGRPAPRPHCRLCAPRARSAL-PAGRNPKSLQQWRQPGS, (SEQIDNO:7878); XM_005626608.1, SIL1, Ins, G_7, AAGPQEPGTGQGHR-GAGRACGHSAL, (SEQIDNO:7880); XM_005629424.1, ZNF219, Ins, G_7, AAGSAAHAPRRGPRARRTCRG-GAGQARGAGRERAVSWRDSARRRPRSHGEGLPLL WKVFPLSASP, (SEQIDNO:7881); XM_539200.2, PYCR1, Ins, G_7, AAGSHHERRGGCHVPGQGAQQEV, (SEQIDNO:7882); XM_014118662.1, ARHGAP39, Ins, G_7, AALAQPAAVRAGARRPRVLPRAEAV-ALPEEGRAGELLPAAGAAAQSCRRLAAVVP T1R1, (SEQIDNO:7883); XM_014112681.1, DGKQ, Ins, G_7, AALRHPHRPGLLLPGHPSQGHARAGGRRAL-GAGPRAHDHLGRRPQGPHAQEDQAE AQEVRGPQGCPSRRGARP, (SEQIDNO:7884); XM_014108067.1, RNF152, Ins, G_7, AAPGGGGGGAR-QAGRGEKLHLVRGVHCDPCGLRPGLPPGHRAAQHVLHF, (SEQIDNO:7885); XM_543229.5, TRIM35, Ins, G_7, AAQLAGGRGAAAPGRRCRGPLAQLLPRHPLRLL-VRVPHAGGGGGPLRDLGPSHIAS GPGHPSPPAR-GAGV, (SEQIDNO:7886); XM_005617510.2, KIFC3, Ins, G_7, AARCGPHGA, (SEQIDNO:7887); XM_533246.4, NUDT22, Ins, G_7, AARGAGAG, (SEQIDNO:7888); XM_005631571.2, C18H11orf84, Ins, G_7, AARGREWHV, (SEQIDNO:7889); XM_014122123.1, CELSR3, Ins, G_7, AASCPVPG, (SEQIDNO:7890); XM_536856.5, PLOD3, Ins, G_7, AASPPGASGCVCRTIYPIPAPL-PAAAAAPGLPP, (SEQIDNO:7891); XM_844169.5, ARHGEF25, Ins, G_7, AAVLPRSRETCLPLRANCHLQ, (SEQIDNO:7892); XM_005630824.2, LINGO4, Ins, G_7, ACCFFLLWRRRPSPHCLLDEASGGLAGKGWE-SEGPRGWDAGDPLSAATGQRGLRL HGQQCRWE, (SEQIDNO:7893); XM_014115361.1, ADAM15, Ins, G_7, ACGHQLCPMLLRLPPLSAPSRGSWGPCRWH, (SEQIDNO:7895); XM_005622091.2, CASKIN1, Ins, G_7, ACRSWPRCGGWCHPAAVSRSSQG, (SEQIDNO:7896); XM_005620597.2, NOL9, Ins, G_7, ACSPSSRAGGK, (SEQIDNO:7897); XM_014116795.1, PHF12, Ins, G_7, ADGANPSSAGSPQDGRGRKAESEA, (SEQIDNO:7898); XM_014109646.1, LMANL1, Ins, G_7, ADLVGRHRDPLRLLGRGHPAEPCHPRAGQ, (SEQIDNO:7899); XM_005638627.2, LMANL1, Ins, G_7, ADLVGRHRDPLRLLGRGHPEPCHPRAGQ, (SEQIDNO:7900); XM_014118167.1, SPDEF, Ins, G_7, ADPGGALPGAGAVHGGGRGA, (SEQIDNO:7901); XM_535292.4, SLC12A3, Ins, G_7, ADQQDGPGEKSDHFPVEQVPTGIP, (SEQIDNO:7902); XM_005637247.2, IFF01, Ins, G_7, AEA-GAQGCHRGGHLPVGK, (SEQIDNO:7903); XM_005633056.2, UBXN6, Ins, G_7, AEVVGGGQPGLQRVRAGALGPPDLLVGRSCAR-RHQGGWGRTQLIYSETGAPGSHR EALM, (SEQIDNO:7904); XM_542952.5, HCK, Ins, G_7, AFELRRSGL-PAGGGAGAQDGVYEVQVSPGQRQGLKN, (SEQIDNO:7905); XM_005619991.2, EFNB3, Ins, G_7, AGAALAGRGRGWGCHVLA-ETAGQAFGESPPWSWLLREGRVSGPGQRKWH-GASGG, (SEQIDNO:7906); XM_005621751.2, CAPN15, Ins, G_7, AGACRAASGAAQRGGGGGGGLGG-GAAKGGGSREWLGLPALHAAQHAGGQLLLCL RGP-PETLAAQNTPRGPGGP, (SEQIDNO:7907); XM_535876.5, FL3A1, Ins, G_7, AGAPRSQPARLSS-CYKYSPVQGEMGHQ, (SEQIDNO:7908); XM_854895.4, SH3BP5L, Ins, G_7, AGDPAGGASG, (SEQIDNO:7909); XM_005624167.2, OTOP3, Ins, G_7, AGGALFGGL, (SEQIDNO:7912); XM_005621663.2, FLYWCH1, Ins, G_7, AGGPEAAGADPQPGPEGRLRSP-PASGVPEDVPWGQVPGVRVLPLQEGEGGGGEVL DVPGPGPAGLPQPGHHPGPAGDGDA, (SEQIDNO:7913); XM_003432153.3, EMILIN1, Ins, G_7, AGGPGQAAQCP, (SEQIDNO:7915); XM_845621.5, MLLT6, Ins, G_7, AGGQRGPAPQWAPGGVEWGCRPQPC-GLEPGWRGPHAAAARLS, (SEQIDNO:7916); XM_540483.3, TSPAN10, Ins, G_7, AGGRRSEPGRLPGCPL, (SEQIDNO:7917); XM_005623069.1, LRRC30, Ins, G_7, AGHA-LQLPEGQKAPL, (SEQIDNO:7919); XM_005638641.2, CSPG4, Ins, G_7, AGHRGLPPPPGTPPGPGLG-GRQRLPPGLHGGSQHQRPEAGAPGSLADSQHG-GRLQP GGRRVRGGHLRHL, (SEQIDNO:7920); XM_537179.5, PAPPA2, Ins, G_7, AGKPPGRTQ, (SEQIDNO:7921); XM_014108780.1, LOC106557931, Ins, G_7, AGLLYGIWTPALPSRAGVPAAALAQSAASR, (SEQIDNO:7922); XM_014112067.1, LOC106558506, Ins, G_7, AGPGPRGAEPGGGARSLTRAARPSARAPGGGG-GRSRPRGA11, (SEQIDNO:7923); XM_014116135.1, FAM181A, Ins, G_7, AGPQGGTSL, (SEQIDNO:7924); XM_005620316.2, PLD2, Ins, G_7, AGPRLRPLG, (SEQIDNO:7925); XM_005621134.2, ZNF316, Ins, G_7, AGRARGSG, (SEQIDNO:7926); XM_005623080.2, MTCL1, Ins, G_7, AGRERGWCRAFP, (SEQIDNO:7927); XM_003435111.3, NFATC4, Ins, G_7, AGRGFRGGG-GRPCSRMPQHPHHLHLSHA, (SEQIDNO:7928); XM_014122369.1, FBN3, Ins, G_7, AGRGR- GRPSVRGHPRAQHLLWSPGAGLLRP-PLPWRGHQIRVLLC, (SEQ ID NO:7929); NM_001286967.1, ARHGAP18, Ins, G_7, AGRQGAGGGHVQP, (SEQ ID NO:7930); NM_001145174.1, CA9, Ins, G_7, AGRVGRL-SAGGSRRKQCL, (SEQ ID NO:7931); XM_014107657.1, GPC1, Ins, G_7, AGSCGRRGCPDLGHGGLEL-PRWGRRGQPWMPPRTKSLCAVSSYAFVY, (SEQ ID NO:7932); XM_014111418.1, LOC106558412, Ins, G_7, AGSLQAPDDLLGRLCALGPGWAPG, (SEQ ID NO:7933); XM_005635420.2, UFM1, Ins, G_7, AGVARPRAS-RRRRRGCRSAGLHDVEGFL, (SEQ ID NO:7934); XM_014118775.1, LIMCH1, Ins, G_7, AHGGTSSPVRRQRCRRSPEAPTAGASWDQSEA-GGAALCQSQAVQ, (SEQ ID NO:7935); XM_014115724.1, CEP170B, Ins, G_7, ALAHAPGL-RAALRQCGTPLPSGPGLHGAVPAGGLPGRPARP, (SEQ ID NO:7937); XM_537686.5, COIL, Ins, G_7, ALAPGRERAPGTRQRLPQS, (SEQ ID NO:7938); XM_014117279.1, TRMU, Ins, G_7, ANERFCQENSC, (SEQ ID NO:7941); XM_014114446.1, MSLN1, Ins, G_7, APAAAQRL, (SEQ ID NO:7942); XM_014120227.1, CMPK2, Ins, G_7, APA-PAPGPSFYIPVAQGPAQTRPGSAAHSESRGEDA, (SEQ ID NO:7943); XM_843818.3, LST1, Ins, G_7, APAPGCAHSVRLSVSASSESEEAGEELGPALRARAPL-RISAAHALP, (SEQ ID NO:7944); XM_005618879.1, PRF1, Ins, G_7, APEGSGLGPRLWLG, (SEQ ID NO:7945); XM_539851.4, EPHA1, Ins, G_7, APGCE-VQRGVFTVPGSSGGRGALPALRGKCALFPRSQRAH-GASRARQRP, (SEQ ID NO:7946); XM_860329.4, KLHL42, Ins, G_7, APGPSPLPRGAPVHAQV, (SEQ ID NO:7948); XM_849651.4, RINI, Ins, G_7, APGRWGLQGQSQSRGQQRRV, (SEQ ID NO:7949); XM_005639039.2, C31H21orf58, Ins, G_7, APGSGGFSAAGAPCR, (SEQ ID NO:7950); XM_014121604.1, FRMD4B, Ins, G_7, APLSWKQWGLQSFCGRPGRWLR, (SEQ ID NO:7951); XM_014112188.1, LOC106558557, Ins, G_7, APPAAETH-LLCRLHDPALLLQLPGVHRMRAPGLHGLR-PLRGHLPPPALPSHHDHGA LRPAGGLLLRQRLLH-LYDQGVLCLQGHLLWLQRPEPLLL, (SEQ ID NO:7952); XM_543313.3, OR12C12, Ins, G_7, APPAAETHLL-CRLHDPALLLQLPGVHRMRAPGLHGLRPLRGHLPP-PALPSHHDHGA LRPAGGLLLRQRLLH-LYDQGVLCLQGHVLWLQRPEPLLL, (SEQ ID NO:7953); XM_014109156.1, LOC491694, Ins, G_7, APPLRGACG-GAARGRVGHRV, (SEQ ID NO:7954); XM_005640594.2, PIKFYVE, Ins, G_7, APRTRYSQQFGRCV, (SEQ ID NO:7956); XM_005630590.1, ADI1, Ins, G_7, AQAGGLGDP-PRPPCGAQASSAAAVGC, (SEQ ID NO:7957); XM_847033.4, FSD2, Ins, G_7, AQCKERPRD-DLHHWQLLSPE, (SEQ ID NO:7958); XM_014122252.1, ABCA7, Ins, G_7, AQCPQNADQPGKADAN-TERRRQSSPASTQRPSARPTTP, (SEQ ID NO:7959); XM_014116304.1, OTOP2, Ins, G_7, AQPSPC-SAHDCPAHLPECVHHREPPSGTTRG, (SEQ ID NO:7960); XM_014107187.1, LOC106557718, Ins, G_7, AQRGGEGAAGRDPPGAPSLRNQGAAARAPP-PARVPAHQVGK, (SEQ ID NO:7961); XM_014107007.1, DIDO1, Ins, G_7, AQRSSTTPV, (SEQ ID NO:7962); XM_546502.5, MPZL2, Ins, G_7, ARA-VCVLLPCGSLQTHEWAFQGSGGLGREP, (SEQ ID NO:7964); XM_014120943.1, NAALADL1, Ins, G_7, ARCGT-PIRSLRSPGNPTGPPGLCQPGNRRRFHEATGSGHQIR-RHHRADPIWGHRTWG QGCQRCQTWGRWGVGVHGPRRHQ, (SEQ ID NO:7965); XM_014121803.1, PALM3, Ins, G_7, AREQPLRGHRRGGQGPKGCTDQLT, (SEQ ID NO:7966); XM_543945.5, TLL2, Ins, G_7, ARGALG-GRPGLLGAGRRGRRGAAAGALPRPVQSRCLLGRY-CLR, (SEQ ID NO:7968); XM_005621756.2, PDIA2, Ins, G_7, ARGGAPRGGEGP, (SEQ ID NO:7969); XM_541952.2, NXNL1, Ins, G_7, ARGGGRRRGPVL, (SEQ ID NO:7970); XM_539681.5, SLC39A2, Ins, G_7, ARLGPGCVRRRGCRHLSVRHLPRSSAPGTGQPRGP-SAQVGLCSCRVRLHGLHRLVG L, (SEQ ID NO:7972); XM_005638718.1, MAN2C1, Ins, G_7, ARPAGVSQP-GARGAAAHQRPPAVPTDPQSEGVWRK-GRASTFRSTAMAVLQMVDLL VSGGA-DHPGGMGGSGSSPSLGK, (SEQ ID NO:7973); XM_014121804.1, CACNA1A, Ins, G_7, ARPERP-PLLPTGPRWRPDGS, (SEQ ID NO:7974); XM_005629742.1, C16H7orf73, Ins, G_7, ARPRPHSPCRP, (SEQ ID NO:7975); XM_005629656.2, ZNF775, Ins, G_7, ARRAPPVHLQRVRQELLL-VVGAHHPPAHPHGRAALSVPRVRPPLQPEAQP-DAASAQ PHGRAALPVHRVRPRL, (SEQ ID NO:7976); XM_014108419.1, MAP3K12, Ins, G_7, ARRGTLSLG-GLPSSPAWAPPRP-PATQDVFIVPGSAVSSTGSPGPRGHRGSRGSWLTTS SPGRHPAK, (SEQ ID NO:7978); XM_848174.4, NAT8L, Ins, G_7, ARRVHPRVPRGRAGGGAPHLLR-RHHGAHPQHGLPRPAAAPAHAAALRPAGRALFC PDPLAAADVPGASRAAGPALLLQPEGGPGLPGLR-FAHGHG, (SEQ ID NO:7979); XM_534578.5, SFTPC, Ins, G_7, ARSPAAPGPAGACGHHCHLLHWLHWHRSV, (SEQ ID NO:7980); XM_859534.4, WNK3, Ins, G_7, ARVPSTVGRNFRNTTTVCSNSYSIWGTIPARNEFT-GISSFISAESICNPSWSQM, (SEQ ID NO:7981); XM_547829.5, TMEM260, Ins, G_7, ASCPGGAAALRGPARRLGRVRRRGRRVHPHAAP1G-AGGRLGGTDHSRT, (SEQ ID NO:7983); XM_005621587.2, UBN1, Ins, G_7, ASEGASPEA, (SEQ ID NO:7984); XM_014107808.1, LOC478038, Ins, G_7, ASILLCLHRLRHRHPICIVLL, (SEQ ID NO:7985); XM_014112419.1, POLG, Ins, G_7, ASLREGAS-RTVRQG, (SEQ ID NO:7986); XM_014113773.1, GLIS1, Ins, G_7, ASQAGPAWPHHGEPRGQFAA, (SEQ ID NO:7987); XM_003435196.3, MRC2, Ins, G_7, ASQSLLI-LQCQSSCPALEVGLPESALQPGHHAVPGHR-LAGYQHHSIPGHVRV, (SEQ ID NO:7988); XM_014113182.1, JAK1, Ins, G_7, ASRSLHAPEK, (SEQ ID NO:7990); XM_005627636.2, MDN1, Ins, G_7, ATA-SETDVKGQGRN, (SEQ ID NO:7991); XM_005632929.2, ARHGEF18, Ins, G_7, ATASTQPGGNGDTAWT-SHRRNG, (SEQ ID NO:7992); XM_843844.3, ADAMTS2, Ins, G_7, ATGPGHRGPAGQPG, (SEQ ID NO:7993); XM_014114365.1, SETD1A, Ins, G_7, ATPAPYTPFTP-FLRTPK, (SEQ ID NO:7994); XM_849704.4, CECRI, Ins, G_7, AVGADPTGRAGQREAHGPQEG, (SEQ ID NO:7995); XM_014115762.1, CDH24, Ins, G_7, AVGQHYSD-SHPQRRQRQPPQVASEPLPVLCGGNNGAR-HPGGPAAGPGPRPGGQCPH GI, (SEQ ID NO:7996); XM_545627.5, CPS1, Ins, G_7, AVHWSGRRI, (SEQ ID NO:7997); XM_005632803.2, CC2D1A, Ins, G_7, AVQDGSGTGHSPAEAGRPGDSMRGPGDP, (SEQ ID NO:8000); XM_005636303.2, MSI1, Ins, G_7, AVSEHHGGGREAIF, (SEQ ID NO:8001); XM_546604.4, ALOX12B, Ins, G_7, AVSQGHVPGSARLC, (SEQ ID NO:8002); XM_014114800.1, COL11A1, Ins, G_7, AWFIWCQR (SEQ ID NO:8003); XM_014106951.1, RTEL1, Ins, G_7, AWGLSVLGSHPP, (SEQ ID NO:8004); XM_005629104.2, B4GALT2, Ins, G_7, DAGARVQGRAPSLPAALSRGRHPLL, (SEQ ID NO:

8005); XM_535200.5, PITRM1, Ins, G_7, DDRVAPRAARRRASGHVRAGCAFLIFLP, (SEQIDNO: 8007); XM_014111291.1, CD84, Ins, G_7, DGCFTGAPCRGGASE, (SEQIDNO:8008); XM_014112349.1, BOD1L1, Ins, G_7, DGGLGCGPPSPPVGRGWRTGGRRDGSGRMRPGVRGARRRGRGESAGRFLAWEEGL RGEGLCAKCQSESGACLPEPEATC, (SEQIDNO:8009); XM_539968.5, ADGRA2, Ins, G_7, DGGPRGGGAGAHGLLGHPCPPPPN, (SEQIDNO:8010); XM_005616884.2, MAP3K10, Ins, G_7, DGQGVGHDPHGARLDRGVRLRGGGR (SEQIDNO: 8011); XM_014118260.1, KHDC1L, Ins, G_7, DGTRLVAFWGTGEGGPGTLAGHQPLPWACAGTLGVVTGDQRGAEW, (SEQIDNO:8012); XM_532946.5, COX7A2L, Ins, G_7, DHLLPDCSLHGFAAQKQM, (SEQIDNO:8013); XM_547113.5, ABCC6, Ins, G_7, DLDRRGPHRTRGAAHAALQNHHHPPGPHAVPRLSADEPRHAGRAHG, (SEQIDNO:8014); XM_005620375.2, SCNN1D, Ins, G_7, DLPASSPTTLPGALAGVLAEEL, (SEQIDNO:8015); XM_005619566.2, FLI1, Ins, G_7, DLPQPQRAPPP, (SEQIDNO:8016); XM_541795.5, BHLHE40, Ins, G_7, DLQETIRPGSQSHGLQGETQLPGQRL, (SEQIDNO: 8017); XM_005636656.1, LOC102153039, Ins, G_7, DLSRSPLSCGQGSPASGVEGRRSSRRRNLSSHQAADHRGPRAPSRQVPPSHQVPVLSG DPPLAPEDQ, (SEQIDNO:8018); XM_539687.3, LOC482570, Ins, G_7, DNPLHIADLPHHHAALLWS, (SEQIDNO:8019); XM_005627365.1, PTCRA, Ins, G_7, DPALPAPQRAGRCTAVSRSLRPQARPQPPPPALAAVGGTPGAPEPRLGGGEALYPPS LGLVLV, (SEQIDNO:8020); XM_014119273.1, LOC106559736, Ins, G_7, DPGGLPQPQRNRKTWEEQNLEPRRRDCPGRRGPGRAGDAA, (SEQIDNO:8021); XM_844620.4, C5H17orf74, Ins, G_7, DPGQPATSLSLPLP, (SEQIDNO:8022); XM_539219.5, FOXH1, Ins, G_7, DQQAPTPFP, (SEQIDNO:8023); XM_014111086.1, MDH1B, Ins, G_7, DRGAHKAFQDSVSSCSPRPKLSVRDPGPRAQFTVRLRHAVVARKPPRRDSCPRGGF NMAKFVLAGVVKRSV, (SEQIDNO:8024); XM_014108010.1, MYO18B, Ins, G_7, DSRDSSWPPGQH, (SEQIDNO:8025); XM_005616462.2, PVRL2, Ins, G_7, DTAGAAAASCWGVLGLHLAEGEEEKEEPWRRRRRRRRRRRRQQWRRILRSKNSGV WEWGPSLLDTNRPWSPEARRQG, (SEQIDNO:8026); XM_014116586.1, LOC612190, Ins, G_7, DYCSWDAGTL, (SEQIDNO:8027); XM_005629015.1, LOC102155600, Ins, G_7, EAGPHLPTP, (SEQIDNO:8028); XM_014106386.1, LOC102156659, Ins, G_7, EAGRGAGAALFYARGVSRQPGGSKTLRENRVFPPGR, (SEQIDNO:8029); XM_014109693.1, LOC106558086, Ins, G_7, EARGGAELRAGRAAGAAPSLAARTRAAASAGTSSGFRASRPDLSRFSATWQPARPP PRGKSMEQSVATSPWSV, (SEQIDNO:8031); XM_541606.3, LOC484492, Ins, G_7, EASPWSHTNTLPGECAASPY, (SEQIDNO:8032); XM_005642072.1, LOC102152098, Ins, G_7, EDAAGAAGGPVAEDGCGEPVRQR, (SEQIDNO:8034); XM_014118249.1, PGC, Ins, G_7, EDGGPEHPGLQLAVRPQ, (SEQIDNO:8035); XM_005619697.2, LOC102155606, Ins, G_7, EELRPESLRRPLWGTQV, (SEQIDNO:8037); XM_014107187.1, LOC106557718, Ins, G_7, EGAAGRDPPGAPSLRNQGAAARAPPPARVPAHQVGK, (SEQIDNO:8038); XM_014110158.1, LOC106558164, Ins, G_7, EGEEQAGAEKKSWKGKEPALFPHFWLPFRGQCPRTPLPLQPHPRALLASLSSSLPVA RSPETVSDTPVSV, (SEQIDNO: 8039); XM_544572.6, MASP2, Ins, G_7, EGHGEHALRWLRRWGQGQLQRGQWGGISVSRQ, (SEQIDNO:8040); XM_005623182.2, TSHR, Ins, G_7, EGVSFSPL, (SEQIDNO:8041); XM_005620976.2, FKBP6, Ins, G_7, EHAEPKGPARGQRFRPVTV, (SEQIDNO:8042); XM_005616334.2, BCAT2, Ins, G_7, ELWAHSTCAARGEEEGL, (SEQIDNO:8043); XM_005624150.1, CBX4, Ins, G_7, EPGRRAPR, (SEQIDNO:8044); XM_014117924.1, LOC481671, Ins, G_7, EPHLQCRGWWTCPSRTSPPTTTTTKPH, (SEQIDNO:8045); XM_005628380.1, CPA1, Ins, G_7, EQTPCHLDRHRHPFPGVGHPGQRGLVCKEDHTRLWPGLHTHSHS, (SEQIDNO:8047); XM_003431951.3, HIVEP3, Ins, G_7, EQTRPFTSWQP, (SEQIDNO:8048); XM_005617189.2, WDR37, Ins, G_7, ERGREGAPSL, (SEQIDNO:8049); XM_005630224.2, KIF3C, Ins, G_7, ERQDHHGGHSGASFSQLRREPLHPALCQQGQEHQEQAPGERGSQGHAAAGIPGGDR PPEGPAGEEGDAGKAAPEEEQPQEEGCVGPGWVPGGVSDRGLGG, (SEQIDNO: 8050); XM_535078.5, LYN, Ins, G_7, ESAASKANRLFCPDCRGNGIHREKELHPPRSTSSKRSGF, (SEQIDNO:8051); XM_014112781.1, ANTXR1, Ins, G_7, ESCPGRFHELPGSQLLLCGPLLSCYClHEGAQGDPSLWKRGVP, (SEQIDNO:8052); XM_014118297.1, MDC1, Ins, G_7, ESGQLSGRGFPLGD, (SEQIDNO:8053); XM_005627533.2, SLC17A5, Ins, G_7, ETAARIWDPWHCCLYPVHSHCCRFWSWSPHCTQGTRRIRRGCYISSYACHVVFMGS PS, (SEQIDNO:8054); XM_014117000.1, HMCN2, Ins, G_7, ETADREGGPKG, (SEQIDNO:8055); XM_8475 1 7.4, C25H2orf57, Ins, G_7, EVPRLQPLHGQRGGQLYALHDQPAGRRRGVHQLPGRRPRVV, (SEQIDNO: 8056); XM_005641746.2, LOC102154334, Del, G_7, GAAATAAATRRRRRSPRSSRTRPPQPPRGRSPRTRSSASSAACSPGWS, (SEQIDNO:8060); XM_846765.3, TRIM65, Del, G_7, GAAATRRAPSAGSPSPTWPSCAEMWRSAPCSR, (SEQIDNO:8061); XM_543686.5, WNT1, Del, G_7, GAAATTSTSAASSAGSLWTPGRRGGTCASS, (SEQIDNO:8062); XM_849485.4, FAM209B, Del, G_7, GAACVPALAAPALEAAPGRPPGAS, (SEQIDNO:8064); XM_540228.5, EGR4, Del, G_7, GAADLGSPAALWRSEEPPPEAGPGEQGRLGPPTPFPEVSTWSQQPRCLGL, (SEQIDNO:8065); XM_548143.3, PNMT, Del, G_7, GAAEGWGEGGRRARAARTRPECLPLGH, (SEQIDNO: 8066); XM_003639488.2, NUPL2, Del, G_7, GAAEIKKSHLLVPSILELQLAGTGGLDCPRTHLLHPVLMGRKMKRNFWKEL, (SEQIDNO:8067); XM_014107257.1, ARFGAP1, Del, G_7, GAAGRAEPRPPRRLRRRPCRLTRAGTTRTG, (SEQIDNO:8069); XM_005630590.1, ADI1, Del, G_7, GAAGRLRGARW, (SEQIDNO:8070); XM_014107476.1, HAND2, Ins, G_7, GAAGRRAPGPRGAAPGEAPGHR, (SEQIDNO:8071); XM_542654.5, NALCN, Del, G_7, GAAGRTPRTPGSPRGRSDSGGCPQHQNQ, (SEQIDNO:8072); XM_014118917.1, WNT16, Del, G_7, GAALMMSSMACGSAESS, (SEQIDNO:8073); XM_005616826.1, LOC102153346, Del, G_7, GAALPAAPRARWITHSASVRSAPAPSPPDCTAPRATPGGGCGQRSPDPSTPGLA, (SEQIDNO:8074); XM_005616764.2, LOC102156806, Del, G_7, GAARPPEGPAAAAHRSRTPRAPGPHQSQPRP, (SEQIDNO:8075); XM_014107943.1, SGSM1, Del, G_7, GAARQRSTARWTVGTISQKSPRWKVSSLPWLL- WPWPLLPTMRRPLCLPAASPTLQS SWTCTR, (SEQIDNO:8076); XM_005622125.1, SYDE2, Del, G_7, GAARRGLPLSPELRSLAAQTHLPLTARPPSAA, (SEQIDNO:8077); NM_001025398.2, SCN1B, Del, G_7, GAAWRWTQRPRPCTG, (SEQIDNO:8078); XM_005616765.2, PEPD, Del, G_7, GACATAPTPASVAVVRIQLCCTTDTPGPPTTGPSRMETCACSTWVASITASLLTSRAR SRPTASSPRTRRPSMRRCCGAAVLS, (SEQIDNO:8079); XM_014110527.1, LOC106558240, Del, G_7, GACELRGAAPGPAGSPPTRVDLWTPSTPVAGSGLGRRFSGCSGRARPRSPAAPPRQT R, (SEQIDNO:8080); XM_014107657.1, GPC1, Del, G_7, GACGAQGRAHRRLCGPAALWGAGGGSGRSA, (SEQIDNO:8081); XM_538028.5, TIMM17B, Del, G_7, GACSPPSTVAWCACGAKKIPGIPLPAEH, (SEQIDNO:8082); XM_014119127.1, LOC102151792, Del, G_7, GACSPSTPRAAWGTRWVSTPPFTPWPR, (SEQIDNO:8083); XM_014111997.1, LOC106558481, Del, G_7, GAEARRRAGP, (SEQIDNO:8085); XM_546956.5, NYAP1, Ins, G_7, GAEQGLWNGGPVPHGQDPAAGARDRRGCLCQHLLRPCHRQCRDTRGGRRGDGRC DIWGRLGSAEEGPVWREEGKRAGHRGRGWCPGLEWQCRGSRQGGA, (SEQIDNO:8086); XM_005621046.2, NYAP1, Ins, G_7, GAEQGLWNGGPVPHGQDPAAGARDRRGCLCQHLLRPCHRQCRDTRGGRRGDGRC DIWGRLGSAEEGPVWREEGKRAGQGRGWCPGLEWQCRGSRQGGA, (SEQIDNO:8087); XM_014119242.1, LOC106559725, Del, G_7, GAEWGWPEPGSE, (SEQIDNO:8088); XM_005631271.2, LRP4, Del, G_7, GAFCGIMYA, (SEQIDNO:8089); XM_843553.5, FAM171A2, Del, G_7, GAGARRRSAARSPSRCCSTSPPWRSSTGSCRL, (SEQIDNO:8090); XM_005625992.1, SLC9A2, Del, G_7, GAGGFVTSQAQW, (SEQIDNO:8091); XM_014117996.1, C11H9orf152, Del, G_7, GAGGGKRRPRGPSKCQKPGGRLSSRDACVRGGGCSLGALPTGSPPRLRTPRRQL, (SEQIDNO:8093); XM_005616888.2, CAPN12, Del, G_7, GAGGQQERGARRGGGASPSALSFCHSSSATGGA, (SEQIDNO:8095); XM_005630590.1, ADI1, Del, G_7, GAGGRPWGPPATPVRSAGLLRSGSWMLTNMRMIQN, (SEQIDNO:8096); XM_014111404.1, FRMPD3, Del, G_7, GAGLRSLRHQCPASRGGRGTESP, (SEQIDNO:8097); XM_014111629.1, ARHGAP6, Del, G_7, GAGPALRGPACAARPTSGAAEGRSRPHPRQSST, (SEQIDNO:8099); XM_014114474.1, LOC106558921, Del, G_7, GAGPLLLPGGRTEDTRTASGASCWLGICHQGASSSSPTSECPPGP, (SEQIDNO:8101); XM_537253.5, MTX1, Del, G_7, GAGPRGGGRKRRGRCFRARGRARWRRPWSCTAGRGAGGYRQWTWTAWPC, (SEQIDNO:8102); XM_005620069.1, CDRT4, Del, G_7, GAGRDQNKVFGPSV, (SEQIDNO:8103); XM_014120406.1, GPAT2, Del, G_7, GAGRGAYPYLNY, (SEQIDNO:8104); XM_005625164.1, PPP1R26, Del, G_7, GAGRPVSSAHP, (SEQIDNO:8105); XM_541952.2, NXNL1, Del, G_7, GAGRRAAPGTCS, (SEQIDNO:8106); XM_014119253.1, LOC106559727, Ins, G_7, GAGRSAANSERAVPSAGSVRPAPNCGGRRACPGPRVPRSWAALGCAALRGRGAGR PNVPRGPGGRGRDRGRSS, (SEQIDNO:8107); XM_003431554.4, LOC481426, Del, G_7, GAGSACGTSRNRTGTTGRAA, (SEQIDNO:8108); XM_537674.5, MYCBPAP, Del, G_7, GAGSPGCRAASLSPVPRRRVTQSRPGRHHEVSKEGVPPQNVYSQILGGRRSL, (SEQIDNO:8109); XM_003638869.3, ZNF367, Ins, G_7, GAGTAAAAHPHQPRLQRLHGVPVALGRERAQRDAQPRGRGGRRLGRLARRRRAPG TPKPGRAPARRLGR, (SEQIDNO:8110); XM_014119531.1, CCDC61, Del, G_7, GAGVEAVLPAPRPRPQVVACHVSTPQPL, (SEQIDNO:8111); XM_005632677.2, HOMER3, Ins, G_7, GAHQSSPGARCPPGAPKSPRQRQWPRRRETVP, (SEQIDNO:8113); XM_014121988.1, WIZ, Del, G_7, GAKRPMNSRSWRRCGSPRPGSGRSPPWYPGPPRHHWSSLLATSTPSSAGSVRWNSR GPSLSRRSGCGTYSGTSWR, (SEQIDNO:8114); XM_014121817.1, LOC106560102, Del, G_7, GALHTRGAGAGTCWLWLRASSSSVRQALMGLWCPSLTFPHMKIPHG, (SEQIDNO:8118); XM_005639814.2, MASP1, Del, G_7, GALKNVAASRSMGSTQRSPTMWTGCGNRWAPHKVWGTSKWNG, (SEQIDNO:8119); XM_014117894.1, ABCA1, Del, G_7, GALPTCKMWWSRRSSGC, (SEQIDNO:8121); XM_543042.5, KCNB1, Del, G_7, GALQLLSLDWSVPHSWTGLY, (SEQIDNO:8122); XM_003432584.4, SAMD4B, Del, G_7, GALQSWALGRLGQAGRTSHPGKMDMCPSTHPAQCRQPSTVLGATQMQVSLAKFTP AR, (SEQIDNO:8123); XM_014120042.1, MEGF8, Del, G_7, GALTAACRSAQPTAAAMAPVPRPWDHAVVSLASWDVPVTCTCGRTRALAGGTM, (SEQIDNO:8124); XM_540302.4, ADAMTSL4, Del, G_7, GALWAIRRSC, (SEQIDNO:8125); XM_014114011.1, ZNRF1, Ins, G_7, GALWPLHPRLPGHRRLGEGARRRRVCVRLHLCPWQWLPGDRRRSP, (SEQIDNO:8126); XM_845262.3, ITGA10, Del, G_7, GALYCGSKRVTTFSPHGQPWKMSSPLLSRTMQPTWVTLFPPCFCGVDAASFSQGLL GLDTEERSSPSSLRKMGL, (SEQIDNO:8127); XM_014117418.1, CELSR1, Del, G_7, GAMGSRIRPLSPGLPRGITATTPTRIASCPWMSRAAHTPPPTRQTVRTMGWRLRTNG TQLGALSTAPPKWMPQPTTSRPAGPTRAWRGATARSLETSRA, (SEQIDNO:8128); XM_003431951.3, HIVEP3, Del, G_7, GANASFHQLAALNSPWRPSSKKG, (SEQIDNO:8129); XM_532155.4, AARS2, Del, G_7, GAPAAGRSHPSPLRPRPPPCETPS, (SEQIDNO:8130); XM_549367.5, IRAK1, Del, G_7, GAPARSRAGAVAQGPS, (SEQIDNO:8131); XM_014114417.1, XYLT1, Del, G_7, GAPASCPHTCRACETSWR, (SEQIDNO:8132); XM_548229.6, EPX, Del, G_7, GAPCHWLLFHFRSRPMIPASGTRGTASPSSARHPHAPRTGTKSETSSTRSPPSWTPAW CTAARTLWPLGFET, (SEQIDNO:8133); XM_014116184.1, MTA1, Del, G_7, GAPCPPSSGGG, (SEQIDNO:8134); XM_843371.3, LOC606890, Ins, G_7, GAPERSSRYHHRDQHPR, (SEQIDNO:8135); XM_014113853.1, SKI, Del, G_7, GAPGAATAPAERPSGGRGRAAPSGAERHRAGPSGAERGRAAPSGAERGRVPGGRGR AEPNRGRAEPSSWRAGPKAAESKRAAGCRRRWSSST, (SEQIDNO:8136); XM_014109910.1, KHDRBS1, Del, G_7, GAPGPRPPRSHHRCCRPRPRAPTRRWAVRRRPRCCPPQPLPPSRWSRRTSTCPNSWP RRTRSTRPSLTPCSY, (SEQIDNO:8137); XM_005636328.2, ACACB, Del, G_7, GAPGWSWTPPSTPCA, (SEQIDNO:8138); XM_005627166.1, EHMT2, Del, G_7, GAPIEEEVGPGAYSLFPEPRRPGLPNFLAG, (SEQIDNO:8139); XM_014116165.1, KIF25, Del, G_7, GAPPAAEPRPGPRGPSSPRSRCMPSCSSWTWRVASVQNIHCTSSPCGWVFARS, (SEQIDNO:8141); XM_005634379.2, PLCL2, Del, G_7, GAPPAGPCPPPRARPSAPRAP, (SEQIDNO:8142); XM_014122402.1, C2CD4C, Del, G_7, GAPPRPTGVTGCPGRRRGPS, (SEQIDNO:8143); XM_014107553.1, DGKD, Del, G_7, GAPRKMTLLQLRRLMIRSWRWLLCLAVCRWPSLVSLSCSITESPSVAR, (SEQIDNO:8144); XM_014112772.1, LOC106558673, Del, G_7, GAPRPVQVGVTGRGRGRERLSRRRSPRAGYGAVPAKARGYPRRCFLRPRKICLLS, (SEQIDNO:8145); XM_005620295.2, ADAMTS15, Del, G_7, GAPRTPGSRGSFCRSQRSGRTFTST, (SEQIDNO:8146); XM_014118740.1, EEF1D, Del, G_7, GAPSWFRWAMASASCRSSAWWRTTRWGQTCWRRRSPSSRSTCRVWTLLLSTRS, (SEQIDNO:8147); XM_014116133.1, UNC79, Del, G_7, GAPTPARRKKKQLSVTYVSLVFSAISLLVNSWRDWLLKKKAGWWSPQTVLRIASFLPDQTSL, (SEQIDNO:8148); XM_541408.4, ZNF579, Del, G_7, GAQEPLGRPCPAQPVAASSASPTTSPATG, (SEQIDNO:8149); XM_005619042.2, ZSWIM8, Del, G_7, GAQGLSRLQWQRQQ, (SEQIDNO:8150); XM_014112419.1, POLG, Del, G_7, GAQNQKCSISWRALPCLTPHVPRCWAAASAAPWSPRLSRGSL, (SEQIDNO:8152); XM_014116358.1, LOC102156823, Del, G_7, GAQRHVRSGSL, (SEQIDNO:8153); XM_847877.4, NUTM2F, Del, G_7, GAQTLQGRRPSLGPTSGALGSRPRPRPWGRFTPHSLQREGVTPFRWGAGGSATAAS, (SEQIDNO:8155); XM_005629920.2, HTRA4, Del, G_7, GARAAARRGRRCAAATGAPTPACASCAPRTARRVSGARSRPCRC, (SEQIDNO:8156); XM_014120956.1, NRXN2, Del, G_7, GARAAPPPWPGP, (SEQIDNO:8157); XM_014117074.1, LOC491341, Del, G_7, GARAARPAPTPAAPRPVPAAAATRAPTAASSAAARPPPA, (SEQIDNO:8158); XM_014116485.1, RSAD1, Del, G_7, GARAHAAPLPSFRRRGPAGRAPRAPVRPGRVSAASPSPGAVALLGAAPTWRLAAP, (SEQIDNO:8159); XM_003639503.3, COL8A2, Ins, G_7, GARAPGGAWAPR, (SEQIDNO:8160); XM_847007.4, HGH1, Del, G_7, GARARARRGAGCLPQRRGCRRPARRRRWRRCCPSWRPGPGRTCGPRRCGTCWR, (SEQIDNO:8161); XM_005617189.2, WDR37, Del, G_7, GAREGGGSESLTGVLSFLRTL, (SEQIDNO:8162); XM_849651.4, RINI, Del, G_7, GAREMGPSRSKPVPRTAEESLRQLLKGPREVWARPGRALLSQGGQRLRQQRS, (SEQIDNO:8163); XM_014109869.1, COL18A1, Del, G_7, GARGAGELGGPSRSRR, (SEQIDNO:8164); XM_005620976.2, FKBP6, Del, G_7, GARGAQGSCKGTTLPASHRMRG, (SEQIDNO:8166); XM_003432297.3, LRRC17, Del, G_7, GARGPPARPTRTSTRSTWTVRKGNWFTCCPTGLRICCTCCWPGTRSAY, (SEQIDNO:8167); XM_014122263.1, SHC2, Del, G_7, GARGPRTPPPPPSGSARAASSTSRRTAGCTPTPGSWGPGSPTSCGTWAASKSSAPCALWILTLAPR, (SEQIDNO:8168); XM_005627878.2, SYBU, Del, G_7, GARIPSTTSEPCSGAAAWSPCIRCAAPPSTSKP, (SEQIDNO:8169); NM_001110801.1, MAPT, Del, G_7, GARISTKTAMWMSPRPRTPLRPRSPRVRRAPQPEAGHPPTPLPEEPLASPVFQLRVPS ASLSISSPTSPQRSRRQSPPGPAQGPRWKGRPRPPSSPSTWR, (SEQIDNO:8170); XM_005616850.2, CACNG8, Ins, G_7, GARLPHAAQRLPQGGGRRRHGHGHRAARRARARPARARRAGPRDPGQGGRRLQH QHAQQENHAGV, (SEQIDNO:8171); XM_005624150.1, CBX4, Del, G_7, GARPPSTPLTCPPPPPSLSPRSSCWTRIWTSP, (SEQIDNO:8172); XM_005637620.2, WNT8B, Del, G_7, GARRTNPGENP, (SEQIDNO:8174); XM_005618689.2, GAK, Del, G_7, GARSASSQTSRTPPPRSSSLLPITQKEIWTSLTSHLELL, (SEQIDNO:8175); XM_003639660.3, B4GALNT4, Del, G_7, GARTGSSWTGSCRQGWRWNGSD, (SEQIDNO:8177); XM_014109869.1, COL18A1, Del, G_7, GASCGRAATASSPG, (SEQIDNO:8178); XM_005625164.1, PPP1R26, Del, G_7, GASGARETTGQRARTPRKACPSQVFPRCCPHSYSTLERVSPGGAGRPVSSAHP, (SEQIDNO:8179); XM_005616415.2, LOC102151906, Del, G_7, GASGEWFVETPPRMLSF, (SEQIDNO:8180); XM_014121228.1, BSCL2, Del, G_7, GASGPDTASPCR, (SEQIDNO:8181); XM_014116698.1, RNF43, Del, G_7, GASQSPHQPLSPRT, (SEQIDNO:8184); XM_014117924.1, LOC481671, Del, G_7, GASSAMQGLVDLPQQDIPPHHHHYQTPLRRREWKQESRSRMMTWALVFF, (SEQIDNO:8185); XM_005627795.1, DLL1, Del, G_7, GASSATRT, (SEQIDNO:8186); XM_014118331.1, VWA7, Del, G_7, GASTRTAHPRASLPTTCFTSRLQNWPFWPPSKPSAS, (SEQIDNO:8187); XM_538101.4, TNMD, Del, G_7, GASTSGRRHPKKHMTWSTLSTAMERRRRFTWKLIL, (SEQIDNO:8188); XM_014107619.1, ECEL1, Del, G_7, GASTTAPAICCTGGRRLPTAASCARRSASSTCTTISLSTTSG, (SEQIDNO:8189); XM_005639643.2, CCDC80, Del, G_7, GATAALPRPRPGRPKSTRSSRSSRSSRSPRRRRGRS, (SEQIDNO:8190); XM_014120910.1, RTN4RL2, Del, G_7, GATAARTSAASRRARARPARRPRTPAAPRSRPGCPALCSASCSWRPTTS, (SEQIDNO:8191); XM_014120777.1, LOC102153599, Ins, G_7, GATADRWAAGPTRGAPGAHIAASDASPQTQNSRITSELEEQPT, (SEQIDNO:8192); XM_005620829.2, KCTD19, Del, G_7, GATLRVLPRRNAPQSTSHRNLKPKTLLSPLCKNSSPW, (SEQIDNO:8193); XM_005616783.2, TSHZ3, Del, G_7, GATPASTPPTSCPT, (SEQIDNO:8194); XM_533945.4, SAFB2, Del, G_7, GATPPTKG, (SEQIDNO:8195); XM_533428.5, HECA, Del, G_7, GATSTHRCSSCGAWTCPSCSLTSPGIS, (SEQIDNO:8197); XM_005639316.1, METTL14, Del, G_7, GAVEEHTEVAFHLD, (SEQIDNO:8198); XM_005619370.2, C9, Del, G_7, GAVISGAARADA, (SEQIDNO:8199); XM_014120655.1, FAM98C, Del, G_7, GAVQMSWRLPCPPGRAEERMVVGGRQAARAGVARRRRS, (SEQIDNO:8200); XM_014120866.1, MYBPC3, Del, G_7, GAVTSAPVTSMAWQPRAQGTL, (SEQIDNO:8201); XM_014121842.1, LOC106560109, Del, G_7, GAWPRGEERAGARGGRKCASRARGGAPPRPEAEVAPRRRPRFCWRAGVRRAGGG ASPGGGAGFPGNGAPAPC, (SEQIDNO:8202); XM_005632563.2, USP19, Del, G_7, GAWRPQLHEVQWVVQRLPCRQVQPLWIQHHQEAPLTPSQDRRKLGLWRRKNPSLG LRTRGWMVWLPVRPWSM, (SEQIDNO:8203); XM_014121980.1, USP19, Del, G_7, GAWRPQLHEWVVQRLPCRQVQPLWIQHHQEAPLTPSQDRRKLGLWRRKNPSLGLR TRGWMVWLPVRPWSM, (SEQIDNO:8204); XM_855303.4, ARHGEF15, Ins, G_7, GCALHLTSPLHPPLPAALQ, (SEQIDNO:8205); XM_014112681.1, DGKQ, Del, G_7, GCAPASASPRAPTSGSPFSRPRPCRWTASPGCRPPGT, (SEQIDNO:8206); XM_005620429.2, MMEL1, Del, G_7, GCCCCCSW, (SEQIDNO:8207); XM_005636016.2, NOS1, Ins, G_7, GCCGAERPHPGRRHHPRSQRPALGGPEL, (SEQIDNO:8208); XM_003433995.4, ADAMTS1, Del, G_7, GCCLTRAVIL, (SEQIDNO:8209); XM_844169.5, ARHGEF25, Del, G_7, GCCPPEVERDVSSSSSKLSSSVRPWEEEYGVEHRPDMCTRTASR, (SEQIDNO:8210); XM_549068.5, Z:MYM3, Del, G_7, GCFIKPPPPQRWTTVLRGPLHGMQETRP, (SEQIDNO:8211); XM_014122123.1, CELSR3, Del, G_7, GCFLPSSRLSAEVPGSLRT1, (SEQIDNO:8212); XM_014115697.1, LOC102152805, Del, G_7, GCGGIRPPPRKRGWMITGT-SPSLTLLGKPPGLWSRWGAETATPR-PAQSRRPSVGFGPT CSQSSDTTMAPRRTRRRWG-GRRRRPAGGWRVPWGG, (SEQIDNO:8213); XM_843907.4, GPR37L1, Ins, G_7, GCGPALRQARG, (SEQIDNO:8214); XM_535634.4, COQ2, Del, G_7, GCGSWRGRGCGGSAPWPRRARLARSALGTRGLRS-GRNRAGVGSAYRPLRW, (SEQIDNO:8215); XM_014116542.1, WNK4, Del, G_7, GCHPAPL-SPISACPRLLPSPSHVLALAATFPRE-TAMPQMQHQALVMWEKGWHA, (SEQIDNO:8216); XM_542175.4, GIPC3, Ins, G_7, GCHRGGSAQRI, (SEQIDNO:8217); XM_536148.4, ALDH9A1, Ins, G_7, GCHRPAPVSAP, (SEQIDNO:8218); XM_543480.5, PES1, Ins, G_7, GCILGQVSVHWGYC (SEQIDNO:8219); XM_014108967.1, PDZD7, Ins, G_7, GCLPQWGPAGWL-RACGSGWREPGAAITEAPSFPDKLDVKDKVLLD-SLCHLLTAPHL PGQGDVGRKPRSGAWDWWTLSHVPYSAPKH, (SEQIDNO:8221); XM_543229.5, TRIM35, Del, G_7, GCPAGGWAWCGCARTPVPRA TRTAATTTPAQASGT-CAARRGWRGTTA, (SEQIDNO:8222); XM_544457.2, RAB42, Ins, G_7, GCPAHPQDPSPQGPPK-TAAPRSLPVL, (SEQIDNO:8223); XM_545627.5, CPS1, Del, G_7, GCPLVRQENLITQDHKL, (SEQIDNO:8225); XM_548997.5, PPP1R3F, Del, G_7, GCPPAIPWAYSRTET, (SEQIDNO:8226); XM_005618879.1, PRF1, Ins, G_7, GCPPAPAPGTDRLARPGLGLPA-PRGQGQGQLHRGCGQGSSQQHPQRLARGAGCVSQ AQHQCACEHGRLALQGGRLRCPEDPPGQVQLQH, (SEQIDNO:8227); NM_001012395.1, UTRN, Ins, G_7, GCPSLTAPV, (SEQIDNO:8229); XM_546604.4, ALOX12B, Del, G_7, GCQPGACPWVCKALLR, (SEQIDNO:8230); XM_005641483.2, NHSL2, Ins, G_7, GCQQVPGAVTVCAHGLWHHGCL, (SEQIDNO:8231); XM_533246.4, NUDT22, Del, G_7, GCQRSRCGLS, (SEQIDNO:8232); NM_001003264.1, SRP72, Del, G_7, GCRCLRSGVK, (SEQIDNO:8233); XM_005625810.2, FAM109B, Ins, G-7, GCRD-SADPQWRWPKVLVCPQRQPAVLL, (SEQIDNO:8234); XM_005638928.1, ABCG1, Ins, G_7, GCRGEPFSLAPAL, (SEQIDNO:8235); XM_014107476.1, HAND2, Del, G_7, GCRRAPGPRA, (SEQIDNO:8236); XM_005626608.1, SIL1, Del, G_7, GCRSSGAWYR-PRAQRCWPCVWSLCFMTWSLKRCLPRRRLN, (SEQIDNO:8237); XM_014106882.1, COL20A1, Ins, G_7, GCRVGVQHG, (SEQIDNO:8238); XM_014116992.1, PRRC2B, Del, G_7, GCSGRGASTAAARGAAV-AGGCGTLGSPKTSLGPSRGGGSPARRTVRAP-STKSFQSG GGSEARRTGAKARFWSARAAP, (SEQIDNO:8239); XM_005626236.1, LOC102152123, Ins, G_7, GCSPAPPSPDRDRGRGHTAGSRPSVVG-GRAAPGPRVPAPPRAARRFAGLQTGPEL, (SEQIDNO:8240); XM_005632803.2, CC2D1A, Del, G_7, GCSRRI-GYWAQPS, (SEQIDNO:8241); XM_005617274.2, PURA, Del, G_7, GCSTRRRSWPPSGWTSRTSASTWT, (SEQIDNO:8242); XM_849768.4, FAM83E, Del, G_7, GCSWLPTPTVWSAAALWPPCPRRHPTARWPNAWL-PAEYLRVTGRRPRPPQGRR, (SEQIDNO:8243); XM_014118366.1, PHF1, Ins, G_7, GCTEEG-PLCPGHAGHEAVTAIWTKGARLGRWTSEQPTAEL-LLLWWPWGVEPENVA VPELPAVVP, (SEQIDNO:8244); XM_014109906.1, ANK2, Ins, G_7, GCTNLKITMQHNRWNHPSTMGRHYRNYAFNICQ, (SEQIDNO:8245); NM_001289435.1, SLC4A3, Del, G_7, GCVGSSGCPGSRLPPSARSRT, (SEQIDNO:8246); XM_847615.4, SLC16A8, Del, G_7, GCWPR-RAWSWHPSPRASWSCT (SEQIDNO:8247); XM_005637591.2, UBTD1, Ins, G_7, GCWQGRGGREG, (SEQIDNO:8248); XM_544061.5, ZRANB1, Del, G_7, GCWWPCRRVPGGGTTPWSRRW, (SEQIDNO:8249); XM_014114474.1, LOC106558921, Del, G_7, GDAEL-QTLPGTQGAACQQGSRTPASSRSWGPSGI, (SEQIDNO:8250); XM_005632217.2, SRGAP3, Ins, G_7, GDGPDIEKTM, (SEQIDNO:8251); XM_003432747.3, SRGAP3, Ins, G_7, GDGPSAVTIRWSGHPQAPKR-GRHPQPTPGPGSQHRHATPGRRLPQQPPQNPSHPGED REP, (SEQIDNO:8252); XM_005616301.1, TSKS, Ins, G_7, GDHPGQGDHEEKEGRVVPRGGASDVP, (SEQIDNO:8253); XM_005616302.1, TSKS, Ins, G_7, GDHPGQGDHEEKEGRVVPRVGLSHPVGDGP-SAQHCLQQSTSPTGGASDVP, (SEQIDNO:8254); XM_005626758.2, FAM214B, Ins, G_7, GDIPR-GLPGIHLFPSSWCL, (SEQIDNO:8255); XM_849131.4, NHLRC4, Del, G_7, GDPGACTAPRTACSS, (SEQIDNO:8256); XM_003639777.3, SYDE1, Del, G_7, GDQTSCGWTTPST, (SEQIDNO:8257); XM_014122053.1, FLNB, Del, G_7, GDTTFQRAPLRFKLALKQACRKFVH-GALAFMVGLSGGQQTSW, (SEQIDNO:8259); XM_548847.4, STS, Del, G_7, GDTTQARSPP-PLLHCTCPRGTCA, (SEQIDNO:8260); XM_014111463.1, LOC106558415, Del, G_7, GEAHSPSGHLALAT, (SEQIDNO:8261); XM_539681.5, SLC39A2, Del, G_7, GEAWPRLC, (SEQIDNO:8262); XM_014116204.1, TMC6, Del, G_7, GEGAAP-WARGGWLPGGTGARPGPALRPPLPPERRAGP, (SEQIDNO:8263); XM_014122470.1, LOC102156231, Del, G_7, GEGGGGGGPPSW AARGRERASPSQRALAAAP-PRAPPCGPRPSAPGAQSAAAARPGPALRREAAD-SASAP RRALGPHPGARRSGGAGWSASGCGG-GRAAAA, (SEQIDNO:8265); XM_014110905.1, LOC106558304, Del, G_7, GEGTRGTAGGPAR, (SEQIDNO:8266); XM_844406.4, NLGN2, Del, G_7, GEGVPVAAPRAAQAWASAASGRNAFRW, (SEQIDNO:8267); XM_014122111.1, RBM6, Del, G_7, GEIFHLLIS-RAEIHHSWTSGVGTYIL-GIFGIEKDHQWTTGVEMVLLWIIEVERHLT, (SEQIDNO:8268); XM_014108564.1, HDAC7, Del, G_7, GELGTLCCFPWPRAVTGPCPGLSR-PRLRLPPCRLQSPPVRPVSCPAQKHLPGCCRSPQ GWSTTR, (SEQIDNO:8269); XM_547829.5, TMEM260, Del, G_7, GELPGWGRGAP-GACAAAWPCSPPWPPCSPSRCPPRCRGETRGN, (SEQIDNO:8270); XM_014112781.1, ANTXR1, Del, G_7, GELPWAVPRAAWISAPAVWSSAVMLLLT, (SEQIDNO:8271); XM_538049.4, SMC1A, Ins, G_7, GENSGGSGLA-LCHPQLQASPLLRPG, (SEQIDNO:8272); XM_014111168.1, SPEN, Del, G_7, GEPEEPP-PLPTPPPQAAAAAASASAPASRR, (SEQIDNO:8273); XM_005622132.2, ERICH3, Del, G_7, GEQGSGRPPG-GRRSPRPLRGDSGRREGPAL-GAQHLRPEQQRIPGRLQWS, (SEQIDNO:8274); XM_536894.5, EIF3B, Del, G_7, GERNSNKSRD-SATKGFSSLTSHLVKDTW, (SEQIDNO:8275); XM_005628025.2, RHPN1, Del, G_7, GFCGARRSVGVGRQLLHEPAPGPSLAGAARPRGA-RAEGGCPHSP, (SEQIDNO:8277); XM_014112916.1, ZNF503, Ins, G_7, GFGREVRIPGTERHLPAI-HAQDRQPQLQRVGLLARRHAAFGR-GRPGGQGRQEGPRR GRRRRRQQGLRGRLGRRGTR-GAGARPDQLRRRD, (SEQIDNO:8278); XM_544410.5, SALL1, Ins, G_7, GFGSDIQSRRENHQRRFFGDPLPF, (SEQIDNO:8279); XM_547113.5, ABCC6, Del, G_7, GFGSTGSPSHTWGCTRCAPESPSSPRTPRCSPALCG, (SEQIDNO:8280); XM_846580.3, LCAT, Ins, G_7, GFHQAHAGLGLR, (SEQIDNO:8281); XM_533169.4, MPEG1, Del, G_7, GFLSIRASPSRPGSRASPTTWWP, (SEQIDNO:8283); XM_014114562.1, LOC479817, Del, G_7, GFLSPRFSCM, (SEQIDNO:8284); NM_001253744.1, KRT15, Ins, G_7, GFPLGWGRRLWWGESLRGWWKPQYFSFFC, (SEQIDNO:8285); XM_005642089.2, CACNAIF, Ins, G_7, GFQFQTVQCTPGWIPWPQEKLWGFHFHH-PRRRKFSAQGNQRARESGGGRGNSHQR LWPQQALLPR, (SEQIDNO:8286); XM_005621273.2, FBRS, Ins, G_7, GFQWGHWGARGQL, (SEQIDNO: 8287); NM_001284496.2, TAP1, Ins, G_7, GFRGRGPPAS-RLPGLRDAPPPAPAGPVGSLQSWGNGHSILHWPPH, (SEQIDNO:8288); XM_014112916.1, ZNF503, Del, G_7, GFRPRSPDSGYRAPPASHSRPGQAAPAPARRPARQE-ACCLRPGAARRARTTRRTPTW AAAAAPARAP-GAPRPKGDPRGWRTAGSAAAEGLMWT, (SEQIDNO: 8289); XM_014112350.1, UCHL1, Del, G_7, GFVPVWRRRPRSPSLGVAPAPPAQAPEVRQAGAL, (SEQIDNO:8290); XM_538306.5, KLHDC7B, Del, G_7, GFWSPQQHLHSRHLAR, (SEQIDNO:8291); XM_005622611.1, CNST, Ins, G_7, GGAALQRRGPA-GAARPALGRLRG, (SEQIDNO:8293); XM_014111486.1, PTCHD2, Del, G_7, GGADAAPRPPPRPRPIRAGPAE-GPRAGTTRART, (SEQIDNO:8294); XM_14121983.1, ADGRL1, Del, G_7, GGAGPPTFLTS-ALPWSLLPSRGWLQSSCAQGPCRRCWSPLPHTSRNT-SLAHGARTRC RQATVSTS CPGSRTARTR, (SEQIDNO: 8295); XM_014109693.1, LOC106558086, Del, G_7, GGAGRRGAARGPGGRGCPLPRRPHPRRGLGWDLL-GIPRLPA, (SEQIDNO:8296); XM_848801.3, THAP10, Ins, G_7, GGAPGGPRGPARPAPEPSPLRAARG-PEEGRARTDYM, (SEQIDNO:8297); XM_014111368.1, F8A1, Ins, G_7, GGARRGRGRGTRAR-RARRRRRRRRRGPGARGRGLPGPLPAGVEQAA, (SEQIDNO:8298); XM_005624150.1, CBX4, Del, G_7, GGCRGPCQACSSPPSTPHMHSYRALAPE-DRVGPYVIPHLEAAELARFFYAVSPPFPLQ DITRGN-PRRTSWIPGC, (SEQIDNO:8299); XM_543127.5, FREM2, Ins, G_7, GGEH-CAQAQFCGHDDGGGGSVCPDRPDPRHAGGGGCR-VAP, (SEQIDNO:8300); XM_014111418.1, LOC106558412, Del, G_7, GGEPSSPRRPAGPAL-RAWAWVGPGVSRAQGALAYSLLRANL-GRGPAGECGP, (SEQIDNO:8301); XM_005635420.2, UFM1, Del, G_7, GGGGAAPGEQAASAGVSVRGAPR-CRRFPLRSR, (SEQIDNO:8304); XM_005628669.2, LOC102151330, Del, G_7, GGGGEPDLSFLFAA, (SEQIDNO:8306); XM_014116598.1, SIX5, Ins, G_7, GGGGGGGDRRRGGGSAPAPADFAGGRG, (SEQIDNO: 8307); XM_014106692.1, NPHP3, Ins, G_7, GGGGGGGGGGGGRAGVADPRGGRRRAARG, (SEQIDNO:8309); XM_858973.3, DDHD1, Ins, G_7, GGGGGGRRRRRGPRLRLLPARCGARARDGGAGEH-RAGVCAGRPLRGGCDPRRVLP GVLEPS, (SEQIDNO: 8310); XM_014112065.1, LOC491446, Ins, G_7, GGGHCPGLGGLSRGGSLPRGSPARLSFPPGRAHL-HLLWGTRLRPMACDPRVPRLHV ALGV, (SEQIDNO: 8312); XM_005634257.2, CSRNP1, Ins, G_7, GGGPRQPQLFPPR, (SEQIDNO:8313); XM_014107591.1, AADAT, Del, G_7, GGGRGGRP, (SEQIDNO:8314); XM_005623276.2, NFATC4, Ins, G_7, GGGRPCSRMPQHPHHLHLSHA, (SEQIDNO:8315); XM_014109054.1, SORCS3, Ins, G_7, GGGRRA-PAAQHLVRADRGLGPQSGHGALVGTQQQRY-TYPDEAV, (SEQIDNO:8316); XM_014118260.1, KHDC1L, Ins, G_7, GGHGKEGLQQEAMVDCI, (SEQIDNO:8317); XM_547541.5, UBQLN4, Ins, G_7, GGHRRIGDQPGAPDSLEPLWDQCG, (SEQIDNO:8318); XM_014117140.1, IKZF4, Ins, G_7, GGIPPSGPPAPAT-SHHCGGPAQPCLRQRGPQAAGGVTAGHPR-PLQGSAPGGGREW, (SEQIDNO:8319); XM_014114294.1, TECPR1, Del, G_7, GGKSQTSP-WAACPYGLCLCRARCGTERTSATPTPKAH-RGPSWTPQGRRCRSAVGPT TSCGSRSGR-GRPWSGKESTGTIPKEVPGP, (SEQIDNO:8320); XM_014107522.1, BMP1, Ins, G_7, GGLRVGHCGRRRLRR-GAGVPDLRGGGGDRLWLRLHGALRWL, (SEQIDNO: 8321); XM_543274.5, IRS1, Ins, G_7, GGPGGQRWRQQRGGYETPQFGF1, (SEQIDNO:8322); XM_532352.5, SHARPIN, Del, G_7, GGPGPLD-HASAAEPPGRVGPGPSGTGRLA-LRPSGVGRNPKRAAPVSGRPRRSEPRAH GSAAG-PEMGWRRPRARARPPCCWRCRPR, (SEQIDNO:8323); XM_005616718.2, LSR, Ins, G_7, GGPPAGLSGLGR-GRLRVPLSQHLVRSPCQCHPGDCIRSLPRGDPIPAGD-PALHLPIDH NPYGTHRDLEVQVFLPRPYRRCCLLP-SQC, (SEQIDNO:8324); XM_847517.4, C25H2orf57, Del, G_7, GGPSTPAFAWPTRRTAICAP, (SEQIDNO:8326); XM_005623080.2, MTC1L, Del, G_7, GGQGARLVQSLSLTPPGTSPRVSP, (SEQIDNO:8327); XM_005621134.2, ZNF316, Del, G_7, GGQGTWIRLRWSWRRTRTWRTRWQRSRV, (SEQIDNO:8328); XM_862898.3, LOC611145, Ins, G_7, GGRAAPAGPRPWSKEALSSPLLRPGPPPPGALPRLAT-PASAALSESGSPRAPPAPSRTL PQGPETPVPGM, (SEQIDNO:8330); XM_862887.2, PRR23A, Ins, G_7, GGRAAPAPAGPRPWSKEALSSPLLRPGPPPPGALPR-LATPASAALSESGSPRAPPAPS RTLPQGPETPVPGM, (SEQIDNO:8331); XM_540538.1, RAG1, Del, G_7, GGRASPCCR, (SEQIDNO:8332); XM_014116569.1, GLTSCR1, Ins, G_7, GGRLPFRDLGAGVLLPVLLL-VLLRRLLPGRR, (SEQIDNO:8333); XM_005630813.2, SNX27, Ins, G_7, GGRPGRGAQGGPHPGGERREC, (SEQIDNO:8334); XM_854895.4, SH3BP5L, Del, G_7, GGR-PRRGSFGLRL, (SEQIDNO:8335); XM_014122606.1, ST5, Ins, G_7, GGRPTPGEGRQWLH, (SEQIDNO:8336); XM_005629015.1, LOC102155600, Del, G_7, GGRTP-PADALRSWGEGPC, (SEQIDNO:8337); XM_014120941.1, DRAP1, Ins, G-7, GGRTVVFGVRTPR-PLPCPPGVRVPSPLSRENLSR, (SEQIDNO:8338); XM_014117368.1, TRIOBP, Del, G_7, GGRVRRSLQER-RALTDLWRVRVAAGGRALA, (SEQIDNO:8339); XM_005637247.2, IFFO1, Del, G_7, GGSGSARLPSRRTPPCRKVMGPASPMGMRRRAQP-SASTRRCSACSTS, (SEQIDNO:8341); XM_005632813.2, NACCI, Ins, G_7, GGSGSSGGGSRGCGE-WAQHVRADQPGHLERLYQRQPWLLPQ, (SEQIDNO: 8342); XM_544572.6, MASP2, Del, G_7, GGSRRTC-FALA, (SEQIDNO:8343); XM_014107265.1, HELZ2, Ins, G_7, GHAAGAAQCHPAAWLPGTESAA VHGGTRLHPLPGARGAAGQLLPGPDAPGRAR-PLSRRGRVLPRVGALLLGVGHRRR LGE, (SEQIDNO: 8345); XM_847967.4, UBC, Ins, G_7, GHADLREDLDG, (SEQIDNO:8346); XM_005616765.2, PEPD, Ins, G_7, GHAPQLLHLHLWQW, (SEQIDNO:8347); XM_005616462.2, PVRL2, Del, G_7, GHCWCCCFLLGGPWPSSC, (SEQIDNO:8348); XM_005618689.2, GAK, Ins, G_7, GHGAPLHKPQGHLLQGHPVCCQLRKRRFGHLLHHI, (SEQIDNO:8349); XM_014110368.1, LPP, Ins, G_7, GHGLCLYATARTSA, (SEQIDNO:8350); XM_005627878.2, SYBU, Ins, G_7, GHGSRLQHRSPAPGLLRGRPAFAAPHRLPHQNL, (SEQIDNO:8351); XM_538279.5, BEST3, Del, G_7, GHHLRGSRKGPEPGSSP, (SEQIDNO:8352); XM_537234.5, PYCR2, Ins, G_7, GHHPCPALPREWGLPLPAHQCCGGLLHPHTRAAVHG, (SEQIDNO:8353); XM_005632658.2, HAPLN4, Ins, G_7, GHHRLALPLPL, (SEQIDNO:8354); XM_014121228.1, BSCL2, Ins, G_7, GHLAPTPLLLAGKHPKKRQFPEASTAKDLSPSSRAPRPGGVNTAVRHHRGR, (SEQIDNO:8355); XM_005631612.2, BSCL2, Ins, G_7, GHLAPTPLLLAGKHPKKRQFPEASTAKDLSPSSRHRAPRPGGVNTAVRHHRGR, (SEQIDNO:8356); XM_005637953.2, SULF1, Ins, G_7, GHLHQRFCDYPHVLPLPVLHAHRKICAQPQCLHQQ, (SEQIDNO:8357); XM_014119783.1, SSPO, Ins, G_7, GHPLHPGPCRGQPWGPLLCHTAVPAAGRLS, (SEQIDNO:8359); XM_005630240.1, AGBL5, Del, G_7, GHQLPSAALPLPLTMSSTCGPDQTVLKQNLRMGTGLGSTSVSGEELQGNSSRSTL, (SEQIDNO:8360); XM_014118331.1, VWA7, Ins, G_7, GHQQGQHIPGLLSPPHASPPGCKTGPSGLHPSLQPPEKPPGRQGFL, (SEQIDNO:8361); XM_540475.4, NPTX1, Ins, G_7, GHQVDIRSLSPDQL, (SEQIDNO:8362); XM_543740.5, YARS2, Ins, G_7, GHRAPRRPQRPPQGARGAGAGAGAGERARPPPRPRGRGG, (SEQIDNO:8363); XM_014116695.1, BZRAP1, Del, G_7, GHRARETRCGVSSPRESNS, (SEQIDNO:8364); XM_014119669.1, ADPRHL2, Ins, G_7, GHRHHSHHGRGHCWCLLWDGAGARELAAKL, (SEQIDNO:8365); XM_014112419.1, POLG, Ins, G_7, GHRIRNVQ, (SEQIDNO:8366); XM_005632929.2, ARHGEF18, Del, G_7, GHSQHPARWERGHSLDQSQEKWMKPTLCF, (SEQIDNO:8368); XM_005629920.2, HTRA4, Ins, G_7, GHVRLPGDGGGGVRQRRAHLPQPVRAARPEPRGASPGRAPGRAGAEGRLRGARGLECRPAPEPVQLPRGGGGEGGALRGAPAAVPQVTS, (SEQIDNO:8369); XM_005622757.2, EFNA3, Del, G_7, GHWETGMRCTGTAPTSTCDERATRCR, (SEQIDNO:8370); XM_014113772.1, GLIS1, Ins, G_7, GHWPASMPVGGLLRGL, (SEQIDNO:8371); XM_005623080.2, MTC1L, Ins, G_7, GHWRHKRGSLRTRAQQVALRPLQAPPRLCGGRAAPPRKCPLRPPGFCLLAARPADV QEHE, (SEQIDNO:8372); XM_541491.5, SCAFI, Del, G_7, GIGTETGTEIGTGTGHPRRLGLPRSQRPPRGPRQSHRSAAAQALRRPHAPLPPGR, (SEQIDNO:8373); XM_005626080.2, EPAS1, Del, G_7, GIHQAAALHIRYGKG, (SEQIDNO:8374); XM_005616334.2, BCAT2, Del, G_7, GIMGPQYLCSKRRRRGAVNRSSGCTGRTTSSPRWAP, (SEQIDNO:8375); XM_005634338.2, EOMES, Del, G_7, GIMLFTQLP, (SEQIDNO:8376); XM_005630240.1, AGBL5, Ins, G_7, GISSHQQHCLFP, (SEQIDNO:8377); XM_014113963.1, HSF4, Del, G_7, GKARPGWPWPQTSVIFA, (SEQIDNO:8378); NM_001048121.1, HSF4, Del, G_7, GKARPGWPWPQTSVTSA, (SEQIDNO:8379); XM_005620267.1, LDLRAD1, Del, G_7, GKATAPSAACAGEPASLPSCCSCW, (SEQIDNO:8380); XM_846313.4, CENPB, Del, G_7, GKERSWGRKRRWKRRVMLMTVMKRRRKRRKRAPLRGWRPRTGPRG, (SEQIDNO:8381); NM_001048128.1, RING1, Del, G_7, GKESLGRERGMERM, (SEQIDNO:8382); XM_005625506.1, TIMELESS, Del, G_7, GKGLLVRKNS, (SEQIDNO:8383); XM_005637906.2, TUBGCP2, Del, G_7, GKGPRSTSR, (SEQIDNO:8384); XM_005641785.2, PRR32, Ins, G_7, GKGQQWGHRERWQ, (SEQIDNO:8385); XM_014114950.1, LOC100856175, Del, G_7, GKQVTGMVWGVLGELGQGVR, (SEQIDNO:8387); XM_005625037.2, PNPLA7, Ins, G_7, GKRLCPGWHHPGPGRVWHPCGHGRRDNWGLHGCPVLRGAELQPDPDPGQGVG, (SEQIDNO:8388); XM_005629022.2, SLC5A9, Del, G_7, GKRQSAAARPRSGRQARAGGVAGCWGPGSAGSPDTPSQH, (SEQIDNO:8389); XM_005628665.2, JAZF1, Del, G_7, GKRSPSPARFLDVKRDTRM, (SEQIDNO:8390); XM_005637080.2, PDE3A, Del, G_7, GKRSSSSGWASGRIACCRSRPRGWCSAAWPPRHGWC, (SEQIDNO:8391); XM_003435196.3, MRC2, Del, G_7, GKSESPHPAMPVFLPSAGSGSPGIGSSTWAPCSAWAQAGRVPTPQHPW ACTSVTGRH, (SEQIDNO:8392); XM_005637916.2, SPRN, Del, G_7, GLAAAPGEGCAGARGGPRGCA, (SEQIDNO:8393); XM_003433278.3, SPATA25, Del, G_7, GLAGRYYSGLSMADTTTNSPMQGSQRAWAGRMAAPEAELPSWVAPAGLGPCCCV GCHQGFYRCPPRQGGRRPAPSLTSASLPWP, (SEQIDNO:8394); XM_005619964.2, PHF23, Del, G_7, GLALGCLGGLGQLLGTGKRGLELRRARNGS, (SEQIDNO:8395); XM_014114474.1, LOC106558921, Ins, G_7, GLAPFFSLVDGRRTPGQRPEQAAG, (SEQIDNO:8396); XM_005632900.2, RAVER1, Ins, G_7, GLAPGAATPAREATTSAAATAWPLWG, (SEQIDNO:8397); XM_005641605.2, TCEA14, Del, G_7, GLCGCKKVYRTPSTRGAQGN, (SEQIDNO:8399); XM_005633211.2, MAST1, Ins, G_7, GLCHPAEEHRGTACGDGPHVLR, (SEQIDNO:8400); XM_845262.3, ITGA10, Ins, G_7, GLCIVARRGSPPFPPTDSPGR, (SEQIDNO:8401); XM_014117894.1, ABCA1, Ins, G_7, GLCLLARCGGAGDHQGADGHREENWRLCATDALPLLRR, (SEQIDNO:8402); XM_014114637.1, LOC102151838, Ins, G_7, GLECGSYGEGMFVVSSLPIMAG, (SEQIDNO:8403); XM_003432297.3, LRRC17, Ins, G_7, GLGAPLRGLHVPPREVLGLSGKETGLRAARLASGSAAHAAGQEQDPHIEGQDVFQV, (SEQIDNO:8404); XM_534308.5, IGSF10, Del, G_7, GLGDLSLFTPVVPSSFRIPKLQILGSTNAQQGTHLVAIMQQLTFR, (SEQIDNO:8405); XM_014106904.1, MMP15, Ins, G_7, GLGGSPDSECAAGAGAGAGARAAGSQRSADSAGAAGALP, (SEQIDNO:8406); XM_005616888.2, CAPN12, Ins, G_7, GLGGSRSVGPGEGGAHPQVHCPSVTHPAQPAAPEGPGPHLPHRGLPCVPAAGGRTA GIREVAAGPWGGAHRDCLGSEVACPRLPPEQPADPGPH, (SEQIDNO:8407); XM_014107847.1, EP400, Ins, G_7, GLGLWDDVPTTPHQPLQDCGAPGPLQPSSHICGECRGTKGP, (SEQIDNO:8408); XM_014106951.1, RTEL1, Del, G_7, GLGPVSPTRFTSTLMLVTTGRVLGRMPGAARLPESQGRC, (SEQIDNO:8409); XM_014106952.1, RTEL1, Del, G_7, GLGPVSPTRFTSTLMLVTTGRVLGRMPGAARLPESQS, (SEQIDNO:8410); XM_014107981.1, ARAP3, Del, G_7, GLGRAGRPLCRKP, (SEQIDNO:8411); XM_014113859.1, SLC22A31, Ins, G_7, GLGRLFPCPLRGSLGAV, (SEQIDNO:8412); XM_014116991.1, PRRC2B, Del, G_7, GLGRRPLGQVVVTLLPVMRANRMGRL, (SEQIDNO:8413); NM_001346058.1, KRT23, Del, G_7, GLGVSASPFPSAHQGVCLLEGLGDLEKAIPSRVQVGRK, (SEQIDNO:8414); XM_014115372.1, DCST1, Ins, G_7, GLHACPASSENHWSPEQLLGDSGGIKQHALPAPAHGSGCQGLSEGRTPHGPAAVPLP APGLRLPTSEGHRSLLLPQAREEEDPVPLQ, (SE- QIDNO:8415); XM_538573.4, GRM6, Ins, G_7, GLHCPVHQDSQGTKARRIQ, (SEQIDNO:8416); XM_005636883.1, KMT2D, Del, G_7, GLHFLVRAPLRDPVFTQ, (SEQIDNO:8417); XM_005633560.2, ART1, Del, G_7, GLHLHPCRTSQPSSLGRIPSSASGLAL-GHLSRAIPSSPGRRRC, (SEQIDNO:8418); XM_005621226.2, SLC5A2, Ins, G_7, GLHPHGLR, (SEQIDNO:8419); NM_001007142.2, SLC5A2, Ins, G_7, GLHPHGLRLP, (SEQIDNO:8420); XM_005631198.2, CTNND1, Del, G_7, GLHPLTGDSQSCLR, (SEQIDNO:8421); XM_014122787.1, SAAL1, Ins, G_7, GLHREHRLQQALGLRGPQRVHPDC, (SEQIDNO:8422); XM_003639638.3, POGZ, Del, G_7, GLKSHMSGLCVSCSGTT, (SEQIDNO:8423); XM_845299.4, LOC608319, Ins, G_7, GLKSYPREKLSSLGAESLGSSPGTSHLPPNLWGSAAWE-EQEVFLGSIGKQTVQAHRP LPEEIWAQEDTGV-GASGGDRRRQ, (SEQIDNO:8424); XM_535802.5, NDUFS6, Del, G_7, GLLATRKCT, (SEQIDNO:8425); XM_014109663.1, LOC102154979, Ins, G_7, GLLEEL-GAGEEGSRGCGRGGLPERRPGTRSHSPGG-GAAVDWVEWGVPPGEREAGG RRRWPLQ, (SEQIDNO:8426); XM_005636328.2, ACACB, Ins, G_7, GLLGGRGL1HQPLVHRNVCRQGEQGKYSGARGHS-GD, (SEQIDNO:8427); XM_014121693.1, GRIP2, Del, G_7, GLLPGVTC, (SEQIDNO:8428); XM_005625541.1, GLI1, Ins, G_7, GLLQGAEAFQGSVHAGGA-HAQAYGREAAQVYV, (SEQIDNO:8429); XM_005626855.2, CORO2A, Ins, G_7, GLLRHSPASDG-KIGPPLPKGLRAQRERLRHQVESF, (SEQIDNO:8430); XM_005639100.2, FRAS1, Del, G_7, GLMGLKVLM, (SEQIDNO:8431); XM_005625008.2, PTGS1, Del, G_7, GLMVERSRPSGNMEQGEGLSGEIFWKMQE, (SEQIDNO:8432); XM_014121831.1, TLE6, Del, G_7, GLPAAGIRVHGSRLEPWTPLEDPGLCPEPAAP-PAQDLGPVHASRLRDVGLRKAFWV HN, (SEQIDNO:8433); XM_014116184.1, MTA1, Ins, G_7, GLPA-PRQAAEDELDRRPR, (SEQIDNO:8434); XM_005623126.2, LIPG, Ins, G_7, GLPARLWTQ, (SEQIDNO:8435); XM_541696.5, LGI4, Ins, G_7, GLPAVGPARPRPAPGAHPSPGPAAAAAAQ, (SEQIDNO:8436); XM_014116133.1, UNC79, Ins, G_7, GLPHLPEGRKSN, (SEQIDNO:8437); XM_005632383.2, KCTD6, Ins, G_7, GLPHSSRPSRQLLH, (SEQIDNO:8438); XM_005642089.2, CACNA1F, Del, G_7, GLPIPDSPVYPRLDPMATGEALGVSFSPSPKKEVLSTREPK-SKRIRRRKRKFPPKTLAT TGSPT, (SEQIDNO:8440); XM_546641.5, TRPV2, Ins, G_7, GLPLGGPAMVLLEAS-SVHLDLLRGQLL, (SEQIDNO:8441); XM_005627200.2, ZBTB22, Del, G_7, GLPLGSCCWRQMSCAMTAGTRGVLW-FLGLGSSGGPPTHPPASCHRNTGYM, (SEQIDNO:8442); XM_014114199.1, SRRT, Del, G_7, GLPLRN-PLRKGTQQRSMWSEMKN, (SEQIDNO:8443); XM_536148.4, ALDH9A1, Del, G_7, GLPPASS-CVSTLTWPKSPSPEACPPA, (SEQIDNO:8444); XM_546739.5, MEGF6, Ins, G_7, GLPPGPGRL, (SEQIDNO:8445); XM_014119249.1, CSMD2, Ins, G_7, GLPQPAQRKLLRSQQSRPHREQQQQPLLGLPQRRL-REQRSLRHRLHRKPTGVLF, (SEQIDNO:8447); XM_014119707.1, E2F7, Del, G_7, GLPQTRSSSVHARSA, (SEQIDNO:8448); XM_005629174.1, E2F7, Del, G_7, GLPQVSCPP-WAFRAWSCRLPRWARFPCSTLPPCPGRSPLPPAR-SQTRSSSVHARSA, (SEQIDNO:8449); XM_014106366.1, TBC1D4, Ins, G_7, GLPRAQKKAS-RAHPGRFWP, (SEQIDNO:8451); XM_539968.5, ADGRA2, Del, G_7, GLPSAPTPSTSL, (SEQIDNO:8452); XM_014113773.1, GLIS1, Del, G_7, GLPSGPGLAPPPR-RATRAVCSLKPAGRGAS, (SEQIDNO:8453); XM_014108967.1, PDZD7, Del, G_7, GLPSSVGPCR-LASSLWQWMERAWSSYH, (SEQIDNO:8454); XM_014108966.1, PDZD7, Del, G_7, GLPSSVGPCSYH, (SEQIDNO:8455); XM_849485.4, FAM209B, Ins, G_7, GLPVSPPSLHPPWRLLQGDPREPPEPPPEASQWPL, (SEQIDNO:8456); XM_014118740.1, EEF1D, Ins, G_7, GLQAGSGGLWHPQAADPVRGGGRQGGDR-PAGGGDHQVRGARAECGHCCFQQDL, (SEQIDNO:8457); XM_014106882.1, COL20A1, Del, G_7, GLQGG-GAARINTKLPRSRASGWLGTGGFRGLGGDLQARG-QMWGSQEGPWWLLAH QEG, (SEQIDNO:8458); XM_014108010.1, MYO18B, Del, G_7, GLQGLLVAPR-PALRTQPQRPRSPGLRVLGTQAWCY, (SEQIDNO:8459); XM_005622091.2, CASKIN1, Del, G_7, GLQI-MATLWRMVPPGSGLEVQPRVRRVRRAHPWPGWR-PVPRSRGASEPSRASRRTS SSS, (SEQIDNO:8460); XM_005626236.1, LOC102152123, Del, G_7, GLQPRA-PEPRS, (SEQIDNO:8461); XM_014119335.1, MYCL, Del, G_7, GLQREVPKKRLWRETPQRKRKKWMKRL, (SEQIDNO:8462); XM_533945.4, SAFB2, Ins, G_7, GLRLRQKDE, (SEQIDNO:8465); NM_001253741.1, KRT14, Ins, G_7, GLRPGGRLWRRLQQQQQLWWGPG, (SEQIDNO:8466); XM_548101.3, KRT16, Ins, G_7, GLRPGGRLWRWLQQQQQLWWGPG, (SEQIDNO:8467); XM_548143.3, PNMT, Ins, G_7, GLRRAGGR-VAGVPGPPARAPSACRSDTKGDWRGAHRAR-SPGRPQARPPPPQRRG GRGTRGT, (SEQIDNO:8468); XM_014120910.1, RTN4RL2, Ins, G_7, GLRRRGPAR-RADVPGRGLPGAPGLPRPRALGRAAQPSALPPAP-GAPPPL, (SEQIDNO:8469); NM_001287152.1, PIGR, Del, G_7, GLRSSTRAGSHCMKSQAMAPTRSSST-SSPPTMLASTGV, (SEQIDNO:8470); XM_545865.4, CRTC3, Del, G_7, GLRTPPLDWGRSL, (SEQIDNO:8471); XM_541157.5, MTRF1L, Del, G_7, GLSCWRRPNC, (SEQIDNO:8472); XM_533169.4, MPEG1, Ins, G_7, GLSGMHPALGEGGRPAVPNL-GAEEPPHWCFLLPLWLLPHPPAIPGPRGGLQPPGVPA QVHPPRLLQDGVRRRVPGGEG, (SEQIDNO:8473); XM_540709.1, OR14DL1, Del, G_7, GLSMQQYSFSS-CINYPSVASMLLITLCVICFPC, (SEQIDNO:8474); XM_014116336.1, LOC102156711, Ins, G_7, GLSPALL-PAQPPRAPQAPSPGPGTLPPPWGAALSFHHC, (SEQIDNO:8475); XM_538389.4, CARD10, Del, G_7, GLSPMTRAQMACPSLGTAGLGPWCGGCSRGR-GLPGWSRESHGQRLLAWRGQAWK VRSSREPCP-GARCPRSPS, (SEQIDNO:8476); XM_540228.5, EGR4, Ins, G_7, GLSRFLLPGGACTHAPSWPQLQR, (SEQIDNO:8477); XM_547872.5, EXD2, Del, G_7, GLSYGKASSGGGGIKRALTLGSSGFGSSKHPVGD-SCPLQRRTSCAPVPPEPHGRRGSS EQRW, (SEQIDNO:8478); XM_014120548.1, GRHL1, Del, G_7, GLTDSL-SPRS, (SEQIDNO:8479); XM_005624875.2, SEZ6, Del, G_7, GLTRCPWPTSLSY, (SEQIDNO:8480); XM_844392.4, ABCF3, Del, G_7, GLTSTAPFSRNS-SAVRASS, (SEQIDNO:8481); XM_005619376.2, EGFLAM, Ins, G_7, GLTVPLQPGQRWCDLLR-RYCYTVSSVLWPLLCNL, (SEQIDNO:8482); XM_014114800.1, COL11A1, Del, G_7, GLVHLVPKVRVVTQVLRALVVFKVHLVQREN-LEKGVVQVLMEEEECQENLEQREI GDLMDFQVCQVTKVTGANGAPKAPLVLLEKME, (SEQIDNO:8483); XM_014121616.1, IL17RE, Ins, G_7, GLVLPPGAEIQKVT, (SEQIDNO:8484); NM_001253744.1, KRT15, Del, G_7, GLVVVLGVAS-VEGLVVVLAEASEVALEVALVGVMAAALVTTVVAM-VASSLAMRR SPCRTSTTAWPPTWTRCTPWRRP-TATWR, (SEQIDNO:8485); XM_535893.4, RANBP9, Ins, G_7, GLWEQTKRQNS, (SEQIDNO:8486); XM_005628325.2, LRRC66, Del, G_7, GLYVPVRTVI-PEGL, (SEQIDNO:8489); XM_533901.5, GCDH, Del, G_7, GMGFLMSIM, (SEQIDNO:8491); XM_005630824.2, LINGO4, Del, G_7, GMLFFPALETETQPPLSPG, (SEQIDNO:8492); XM_014122055.1, IFRD2, Del, G_7, GMPWMSRAS-RRTLRRS, (SEQIDNO:8493); XM_005631472.2, RE1A, Del, G_7, GMRSSCSVTRCRKRTLKCISRDQAGRPEAP-FLKLMYTDK, (SEQIDNO:8494); XM_014111170.1, PLEKHM2, Del, G_7, GMVTALSAAQAWGGRPRTP-PLRPPRRRERGPAAQPRAASSRSPARWACLSPR, (SEQIDNO:8496); XM_543480.5, PES1, Del, G_7, GMYPGT-SLCALGLHMMSQTPASPTRLSTGLGSRPLFLAGTM-CSLSGCLTV, (SEQIDNO:8498); XM_014117000.1, HMCN2, Del, G_7, GNCRSRRWT, (SEQIDNO:8499); XM_014114843.1, EPHX4, Ins, G_7, GND-CLANRHLLSRNGDEAYCY, (SEQIDNO:8500); XM_014114365.1, SETD1A, Del, G_7, GNPR-PLHPLHPLPSNPEVSLNR, (SEQIDNO:8501); XM_014120131.1, SORBS2, Del, G_7, GNRFRLCIT-ILLGMKMSWSSEKVMSLM, (SEQIDNO:8502); XM_005624372.2, HEXIM1, Del, G_7, GNR-SPRPSLSHSHVLIPRPTSWGLLLRGARRRGDSSRD-SWARKNIGDAPPRRSGIGNR TTS, (SEQIDNO:8504); XM_005624466.2, KCNH4, Del, G_7, GPAASSST-TASPRPCGTASSSLPPSTLRSPSPTMSASWAM-MIPPSLRDTPLSATSPWRC SSSWISS, (SEQIDNO:8505); XM_539219.5, FOXH1, Del, G_7, GPAGPHPFPLSTEPGL-STYCRLPQTPGGCPVGVTGPHSGGSCPPPTCP-STLPMW, (SEQIDNO:8508); XM_014107173.1, PCED1A, Del, G_7, GPAGSGLDTQTD, (SEQIDNO:8509); XM_536708.5, ATAD3A, Ins, G_7, GPAGSQGQMEQL, (SEQIDNO:8510); XM_005631320.1, LOC483656, Ins, G_7, GPALPQL-PHPRALL, (SEQIDNO:8511); XM_014117074.1, LOC491341, Ins, G_7, GPALRGPRRPLPPRALCPRPL-PRAPRRPLRVPLLARLRL, (SEQIDNO:8512); XM_014118328.1, DDAH2, Del, G_7, GPALWWPVAATQPKRLSGRWQC, (SEQIDNO:8513); XM_546222.4, SIMC1, Del, G_7, GPARAGRGGSAGPCRGPPALCPAGPWTSLT, (SEQIDNO:8514); XM_005624044.2, CYTH1, Ins, G_7, GPARGAAPESV, (SEQIDNO:8515); XM_014112406.1, NMBR, Del, G_7, GPARTFCPPRTGPAPSSPSAA, (SEQIDNO:8516); XM_014121804.1, CACNA1A, Del, G_7, GPARTPSPPPNWTQVEA, (SEQIDNO:8517); XM_014106771.1, XIRP1, Del, G_7, GPASGRR-SWCLASFPGSSAKCCAGQMWTSRGCWFRRTQRAS-SALSH, (SEQIDNO:8519); XM_005620375.2, SCNN1D, Del, G_7, GPASLIPHNAPGSPGRSPC, (SEQIDNO:8520); XM_005629656.2, ZNF775, Del, G_7, GPASPASSSAT-SAARASLGGRRSPSTSASTRASGPIRAPSAAAASAR-SPT, (SEQIDNO:8521); XM_531734.5, GTPBP1, Ins, G_7, GPASQSEVPGGLRDSCQRLL, (SEQIDNO:8522); XM_546739.5, MEGF6, Del, G_7, GPASRAW-TAVTAPRAGLGSSAMRLVLQTPSGR-TAASPAAVRTVGPATL, (SEQIDNO:8523); NM_001005760.1, LIFR, Del, G_7, GPATSHRCTSPSLL1, (SEQIDNO:8524); XM_014113162.1, MYO10, Ins, G_7, GPAVSRRPLRLRPGR1, (SEQIDNO:8526); XM_858228.3, EMC10, Del, G_7, GPCCSQPCVLL-PRGPRRRRRRP, (SEQIDNO:8527); XM_847431.4, LOXL3, Ins, G_7, GPCGGELCARPSLRSVQ, (SEQIDNO:8528); XM_005632900.2, RAVER1, Del, G_7, GPCPRSCHPGEGSHHLCCRHCLAP1GVTGKP, (SEQIDNO:8529); XM_014106275.1, PCDH17, Del, G_7, GPCPSSWRRTTTTSTPW, (SEQIDNO:8530); XM_014113162.1, MYO10, Del, G_7, GPCRQQTAT-TTTTGTTMRTAPPPPAAA, (SEQIDNO:8532); XM_014121817.1, LOC106560102, Ins, G-7, GPCTP-GAPARAPAGSGCEPPPRLCARH, (SEQIDNO:8533); XM_014108308.1, LOC106557874, Del, G_7, GPCVAARGKGPCRACALWGL, (SEQIDNO:8534); XM_014121155.1, CD6, Del, G_7, GPDGRLSEN, (SEQIDNO:8535); XM_003431554.4, LOC481426, Ins, G_7, GPDLPAGRQETGPGRLGERPEGHGVCAALGKE-CEPVVARIAHSGLRPRRPPFVRLPG DALSE, (SEQIDNO:8536); XM_844284.4, MLX, Del, G_7, GPEDE-GIPCSPQRSPRPSGPGAAEKTALTPRVPRWNMPTAI-TAWTPGFL, (SEQIDNO:8537); XM_003431813.2, GLI4, Ins, G_7, GPEDPSEEPAP, (SEQIDNO:8538); XM_014114499.1, FAM57B, Del, G_7, GPELRAAPGP-WRAAICTRSSSWCSTTPSWCSYASRCLWCGVKARE-ISF, (SEQIDNO:8540); XM_850179.4, ALDH4A1, Del, G_7, GPEPLEPMTSQAGPTTSCGGRRPRSSRRPTSL-WAIGATPTCS, (SEQIDNO:8541); XM_005622264.1, LOC100855804, Ins, G_7, GPEQGKTERSHKDSVGQW-DRPGGSWGQQWARWSWGPGVSRRESF, (SEQIDNO:8542); XM_845505.2, TLX1, Ins, G_7, GPERCGGDP-GARA, (SEQIDNO:8543); XM_548256.5, MMP28, Ins, G_7, GPGARLPAPPGRSALRRRRALVPEPPPRPQPVR-GAGARDRPHARAGALPRAARAHG ALLQEAGPR-RAAQLGRRAGRAGPVWKAPGGLSSHPAPRKAVH, (SEQIDNO:8544); XM_014114446.1, MSLN1, Del, G_7, GPGCGSAPLTCCSSGSWCVTWTRPASRLQTPVCWRT-CSAAAGSLPPSKPPSTRC, (SEQIDNO:8545); XM_014117147.1, ZC3H10, Del, G_7, GPGCLTGTAMP-TALGAAVEALEAVAMRRPVGQGQAVAGPAQJMPS-VETS, (SEQIDNO:8546); XM_005631695.2, TMEM132A, Ins, G_7, GPGGGDRAHWL, (SEQIDNO:8547); XM_539936.4, MNX1, Del, G_7, GPGISPHPS, (SEQIDNO:8550); XM_531653.5, XRCC6BP1, Del, G_7, GPGKGSSPASSPTTRGASGCS, (SEQIDNO:8551); XM_014120762.1, NAMPT, Del, G_7, GPGPGA-TRAARGQPPPPEPQRPRARPGARARRLLTINSTH-PIQVKFIPTLNAVKRRQKT PK, (SEQIDNO:8552); XM_014119666.1, EML2, Ins, G_7, GPGPGWGWG-GRRWLWRGDGGARPGLLRPLRHVLAASILQR, (SEQIDNO:8553); XM_539881.5, TMEM178B, Ins, G_7, GPGPHANLGILLYLGPFCPTCPEDQLP, (SEQIDNO:8554); XM_005626996.1, KLF4, Ins, G_7, GPGR-GAGRRRWRRRRRRRPPLQPGARAPSHG-PLQPGGHQRREPLGRLRG, (SEQIDNO:8556); XM_014121926.1, SLC25A23, Ins, G_7, GPGRR-GAAAALGSPLRGAGQ, (SEQIDNO:8557); XM_014109896.1, LOC106558120, Del, G_7, GPGRWP-SASSKGCAAQILAPPPPRMAADCRPRSDGEKER-AAIPMDAVPGRGKRKRL QV, (SEQIDNO:8558); XM_014119531.1, CCDC61, Ins, G_7, GPGSRPSCPPLA-LAHR, (SEQIDNO:8559); XM_005635974.2, PASK, Ins, G_7, GPGSRRGHPGRLGSWRLPPPFP-PASANSDSGSGKHPKRKLISP, (SEQIDNO:8560); XM_005628670.2, TRIL, Del, G_7, GPGTGPPGSS-WATAAL, (SEQIDNO:8561); NM_001003016.2, MCLI, Del, G_7, GPGWGPAAAAPPLREGGFWLRGRR-PRPDGREGEGKPVR, (SEQIDNO:8564); XM_857445.4, SLC6A9, Ins, G-7, GPHHHGFLQQVPQQLLPGQHYHQHH, (SEQIDNO:

8565); XM_003434804.3, PRRT2, Ins, G_7, GPHHHRLLRHQLRRV, (SEQIDNO:8566); XM_014116730.1, ARHGAP33, Del, G_7, GPHPHPPRTQHAS-WPWPWLSGLSRWPRDRANRSMGAPLLLPTPLS-TAHCHWRWAV SPQGPQGLGQPPIP, (SEQIDNO:8567); XM_540643.3, LOC483524, Ins, G_7, GPHQRIHDD-CYCWN, (SEQIDNO:8568); XM_005616765.2, PEPD, Ins, G_7, GPHRGGRRGDRQWHGTADLCAPHGGGD, (SEQIDNO:8569); XM_005619266.1, LARP1, Ins, G_7, GPHRQPHLTCQDECRAGQGH, (SEQIDNO:8570); XM_847576.4, ZNF428, Ins, G_7, GPISSGPPCSPT-PRPPSPALPALWPLTPWGGPTRHPTL-PALLPCYSPPGSSSP, (SEQIDNO:8571); XM_005617918.2, KIAA1522, Ins, G_7, GPITQL-PRLSSG, (SEQIDNO:8572); XM_005630511.2, SEMA4F, Ins, G_7, GPLCCHCEKLPGDGADYLPGCGSHRGLDS-DRDLAVLA, (SEQIDNO:8573); XM_005616796.2, C1H19orf12, Del, G_7, GPLGACWARG, (SEQIDNO:8574); XM_005631690.2, CD5, Ins, G_7, GPLG-GLRVPGETERLQLTVPGPAG-GLHREKLVHSVQPELELEPEPKPLGGT, (SEQIDNO:8575); XM_005627795.1, DLL1, Ins, G_7, GPLLQPGPELLHPPQALQEWGHLYQHRAGKLHLLL-PARVLGGQL, (SEQIDNO:8578); XM_014119273.1, LOC106559736, Ins, G_7, GPLPRPAAGPPAPRQDS-GRSSQSPLPRPSPEGGGAGGDPGGLPQPQRNRKTWE-EQNL EPRRRDCPGRRGPGRAGDAA, (SEQIDNO:8579); XM_546739.5, MEGF6, Ins, G_7, GPLQPGYGAVPVPSRENWG, (SEQIDNO:8580); XM_005636656.1, LOC102153039, Del, G_7, GPLQVASQLWARQPGFWG, (SEQIDNO:8581); XM_014116698.1, RNF43, Ins, G_7, GPLRAPTSL-SAPGLDCTPRLPDFSPLQYQP-GIPLVPRGPPTDLWTSRPRQEAATRFFRP LLLKF-TASVVVSDSTPVPGSTPTRRGAF, (SEQIDNO:8582); XM_533428.5, HECA, Ins, G_7, GPLRRT-GAVPAAPGPVRAAHSHPQA, (SEQIDNO:8583); XM_014116933.1, SNAPC4, Del, G_7, GPLTPRDCQ, (SEQIDNO:8584); XM_548229.6, EPX, Ins, G_7, GPLVTGSSSTSDPAQ, (SEQIDNO:8585); XM_014107094.1, HSPG2, Ins, G_7, GPMPAT-GRCSPAGGPGASSSEHSTPRWLPLPAVPGQWEPT-SLLLLVS, (SEQIDNO:8586); XM_014120943.1, NAALADL1, Del, G_7, GPMWYPHTQPTLPREPHRAS-WSMPTREQKKIS, (SEQIDNO:8587); XM_005621642.2, LOC610677, Ins, G_7, GPPGAADRGQPAGVRT-GRAGSRLPGAPQGLPGDPQLAAAAALPAGL, (SEQIDNO:8589); XM_014109663.1, LOC102154979, Del, G_7, GPPGGVGCWGGGKQGLR, (SEQIDNO:8590); XM_542974.5, GDF5, Del, G_7, GPPMPGPRGAPGR-REA, (SEQIDNO:8591); XM_005640594.2, PIKFYVE, Del, G_7, GPPNSIQPAVRKMCLMDICWGPQIAK, (SEQIDNO:8592); XM_003639638.3, POGZ, Del, G_7, GPPQLSLKSFRLL, (SEQIDNO:8593); XM_543740.5, YARS2, Del, G_7, GPPRASETPAAAPR-SARRWRRSRCGGTRAPSAEAS-RPWRLITSGSSPTGGPGEASRS WTTRPGTRGSTWWTS, (SEQIDNO:8594); XM_860534.5, EEPD1, Del, G_7, GPPRLSPPALP, (SEQIDNO:8595); XM_540475.4, NPTX1, Del, G_7, GPPSGHSKPVARST, (SEQIDNO:8596); XM_537234.5, PYCR2, Del, G_7, GPPSMPCTS, (SEQIDNO:8597); XM_005637953.2, SULF1, Del, G-7, GPPSPTLL, (SEQIDNO:8598); XM_005616412.1, PRKD2, Del, G_7, GPQGGPVGRELRLPGAGKPPSARP, (SEQIDNO:8599); XM_845299.4, LOC608319, Del, G_7, GPQKLPKGEAF-LPGGRESRQLPWNQPPSPQSLGFRCLGGTRGIP-WFHREANSPSTPA APGRNLGPGGHGSRSQWW, (SEQIDNO:8600); XM_005637227.2, PIANP, Ins, G_7, GPQLCQSWISAPGLWFCSPPWAGNPTPQLRFHAG, (SEQIDNO:8601); XM_003639769.2, MISP, Del, G_7, GPQSSPRRPPSSGRSGWPRSGKRT-CGSGGGCGRPTPSRSWCRSPAGRC, (SEQIDNO:8602); XM_536612.5, PELP1, Del, G_7, GPQVRRCCPTCSVIS-PRRLTL, (SEQIDNO:8603); XM_005619991.2, EFNB3, Del, G_7, GPRAGAVRHLLPQTCFSLVTGQTWI-CASPSSSRSIALTSGAMSSARTTITT, (SEQIDNO:8604); XM_537649.5, CASC3, Del, G_7, GPRALRSRNVRVK-MASRAMLFCRIMKVQKTLKVKKGSIVKRKTPK, (SEQIDNO:8605); XM_005627365.1, PTCRA, Del, G_7, GPRAPRAPAGRQVHRRLPQPPPAGTPSAPAACTGR-SWGHARSPGAQAGRRGGSLPT ELGPGAR, (SEQIDNO:8607); XM_538784.5, MUSK, Del, G_7, GPRAPRGAP, (SEQIDNO:8608); XM_005622207.1, LOC102151417, Del, G_7, GPRARDTRAPRVAAR-PAGRGGPGTGPATRSS, (SEQIDNO:8609); XM_005630590.1, ADI1, Ins, G_7, GPRGACA-GRAGSGVHGGAQAGGLGDPPRPPCGAQAS-SAAAVGC, (SEQIDNO:8610); XM_005616412.1, PRKD2, Ins, G_7, GPRGAQWAGS, (SEQIDNO:8611); XM_540228.5, EGR4, Ins, G_7, GPRIW-GARLRFGEARSRLPRPVPASKGASAPRPLSQR, (SEQIDNO:8613); XM_847877.4, NUTM2F, Ins, G_7, GPRPCREDAPPWGPPQGLWAAGQGQGRGAASPL-TASKEKV, (SEQIDNO:8614); XM_005640564.1, ABI2, Del, G_7, GPRPLLMASLLQLPLLFLPLPLQVILFSSTV, (SEQIDNO:8615); XM_014115724.1, CEP170B, Del, G_7, GPRPRPGAPRGPSAVWDAAPVWPRTSWR-SACGRAPRPPGPALTRHPQHHRPPRHPV GPAPWPRR-PRHHPPPTPS, (SEQIDNO:8616); XM_014118775.1, LIMCH1, Del, G_7, GPRRHQLPSPKTEMPSKSR-SADGWSKLGSE, (SEQIDNO:8617); XM_005621756.2, PDIA2, Del, G_7, GPRRSPSRRRRSLRRMGSWC, (SEQIDNO:8618); XM_005631271.2, LRP4, Ins, G_7, GPSAGSCMHEDRHSVYPGQLGLPG, (SEQIDNO:8619); XM_005624035.2, LOC483345, Del, G_7, GPSAVSRWSSAPST, (SEQIDNO:8620); XM_014119242.1, LOC106559725, Ins, G_7, GPSGAGQSLDPSD, (SEQIDNO:8621); XM_005626753.2, PIGO, Ins, G_7, GPS-GRSVPRVLICGVRVQASPPRFRAPFK, (SEQIDNO:8622); XM_005626749.2, PIGO, Ins, G_7, GPS-GRSVPRVLICGVRVQASPPRFRAPFKDAEDLGAAL-PGLGQLPLLRRHCPLHQWL PAHSFGTHQP, (SEQIDNO:8623); XM_014118308.1, PRRC2A, Ins, G_7, GPSLQAPST, (SEQIDNO:8624); XM_014112998.1, UNC5A, Ins, G_7, GPSPSGPQCLQDPLPH-SAKDHYQPRPAL, (SEQIDNO:8625); XM_014111712.1, LOC106558448, Ins, G_7, GPSQGRRCLLFSGAIYPPPPT-PRAL, (SEQIDNO:8626); XM_014114499.1, FAM57B, Ins, G_7, GPSSGQHLGRGARLSAQGVPHGAPPR-RHGARMLPAVCGVASRQGRFLSRLLADG, (SEQIDNO:8627); XM_003435252.3, CDK12, Ins, G_7, GPS-SIFCLWKALSGAYKSPAKRGKRERSSLL, (SEQIDNO:8628); XM_546502.5, MPZL2, Del, G_7, GPSSLCSTTMWIPSNP, (SEQIDNO:8629); XM_005626855.2, CORO2A, Del, G_7, GPSSSFPCIR-RENWTPTTQRSAGTKGTS, (SEQIDNO:8630); NM_001007142.2, SLC5A2, Del, G_7, GPSSS-WVTPSMKWEGIQGFSTNTWGQ, (SEQIDNO:8631); XM_005621226.2, SLC5A2, Del, G_7, GPSSSWVTVGS-SAGGGGARRLSHRALSGGAETSCISSMVVLGTVLA-LAPGLLTTLPS QPSMKWEGIQGFSTNTWGQ, (SE- QIDNO:8632); XM_005631690.2, CDS, Del, G_7, GPTGRTQSSR, (SEQIDNO:8634); XM_014116730.1, ARHGAP33, Ins, G_7, GPTPTPQEPSTPHGPGPG, (SEQIDNO:8636); XM_540482.5, NPLOC4, Del, G_7, GPTRGNLLPWRTSVARLNQGARDTFRGLTASVL-SASQVPSR, (SEQIDNO:8637); XM_546946.5, ACHE, Del, G_7, GPVAMTQSWSPA, (SEQIDNO:8639); XM_014120762.1, NAMPT, Ins, G_7, GPVLARPERPEVSPRQSRSVPGPGRELERAGYSL, (SEQIDNO:8640); XM_538028.5, TIMM17B, Ins, G_7, GPVLHHRLWPGAPAGQRRSLEFHYQRSIDWGCAGCPQWPIGHGGL-SNDGGHPLGS HRGCWHPPYS-LYCPAVPQCTPVLGGPQPATP, (SEQIDNO:8641); XM_847033.4, FSD2, Del, G_7, GPVQGATP, (SEQIDNO:8642); XM_014107619.1, ECEL1, Ins, G_7, GPVR-PLRQSV ALVDGGFLQPL-PAQGGVHRPPVRQFHCLQPAGERKAHPW, (SEQIDNO:8643); XM_014106406.1, LOC102156658, Del, G_7, GPVSRCALILLSGESKTGVQL-GRKRKPLGGQGLTSRVRSGSLTPGGRYTCA, (SEQIDNO:8644); XM_014117418.1, CELSR1, Ins, G_7, GPWGAGFVLCPQDYQEASRPRLRLG, (SEQIDNO:8646); XM_548256.5, MMP28, Del, G_7, GPWGTPSCPA-GAKRTSTATSAGP, (SEQIDNO:8647); XM_014121791.1, NOTCH3, Del, G_7, GPWNQCPLRR-TRRRTRQPASSQT, (SEQIDNO:8648); XM_860329.4, KLHL42, Del, G_7, GPWPLTPTKGSPRPCSGMRR, (SEQIDNO:8649); XM_014113859.1, SLC22A31, Del, G_7, GPWQAFSLPSTWLAWSCVTPPTAWYSPRQLASSRC-WALCCCRA, (SEQIDNO:8650); XM_014106904.1, MMP15, Del, G_7, GPWRKPRL, (SEQIDNO:8651); XM_005639316.1, METTL14, Ins, G_7, GPWRSTQRWLSTSI, (SEQIDNO:8652); XM_005639039.2, C31H21orf58, Del, G_7, GPWVGWLLRGRCSLQMI, (SEQIDNO:8653); XM_005640095.2, HISTIH1T, Del, G_7, GQAHRRLL-VVAGRPKAPKTNSPGRAQARPPLGNPRRPSPGST-SRRSTRGRRCPRS, (SEQIDNO:8655); XM_014114526.1, KIAA0556, Ins, G_7, GQALHPGRLVG, (SEQIDNO:8656); XM_538101.4, TNMD, Ins, G_7, GQALLAGDTQKNI, (SEQIDNO:8657); XM_014113517.1, DVL2, Del, G_7, GQAVQGGPRNGPL-SPSPAAAVSLSPPAVGAASG-GAGSRVGLVMGALPLPEARQGVS PISEPTLG-SIPMGHPRGWPSPIIP, (SEQIDNO:8659); XM_005625037.2, PNPLA7, Del, G_7, GQEAVPR-LASSGPWQSVASLWTWSEGHLLGPSWVPCTPRSGT-TARSGSGPRSGLRT, (SEQIDNO:8661); XM_005620069.1, CDRT4, Ins, G_7, GQEEIRTRYLDL-RYEELFSDGGD, (SEQIDNO:8662); XM_003434552.1, OR10S1, Del, G_7, GQERGSLRSSTQSSLPCSTLSSTL-CATRRSSGLCKDF, (SEQIDNO:8663); XM_005628314.1, CPSF1, Ins, G_7, GQEWGSPGARGR-GRGAGAAGTPPSGPCTLR, (SEQIDNO:8664); NM_001110801.1, MAPT, Ins, G_7, GQGFRRRPRCG, (SEQIDNO:8666); XM_005641667.2, LOC102152628, Ins, G_7, GQGGREHSRSLSASGGTC, (SEQIDNO:8667); XM_533429.5, TXLNB, Del, G_7, GQGLM-PRKSVVFTML, (SEQIDNO:8668); XM_014121191.1, MADD, Del, G_7, GQGPVGRKDPVLLVPQKRLAL-RAQRVACPCSLPVLTLPPLM, (SEQIDNO:8669); XM_859534.4, WNK3, Del, G_7, GQGTQYSG, (SEQIDNO:8672); XM_003639620.3, SV2A, Ins, G_7, GQHCILERAGRVDR, (SEQIDNO:8673); XM_005641281.2, SLC9A7, Ins, G_7, GQHSDCK-WLLRLPHGLHKPRGQSENKEQLRGGAGPSPGNGR-PAGV, (SEQIDNO:8674); XM_534578.5, SFTPC, Del, G_7, GQKPSSAWPCRSVWAPLPPSPLAPLAS, (SEQIDNO:8675); XM_005633536.2, ARHGEF17, Del, G_7, GQLSVWPR, (SEQIDNO:8676); XM_003433503.3, LOC100683813, Del, G_7, GQPEEATGPGASPCAP-PEASRRSRSTRAS, (SEQIDNO:8677); XM_005633207.1, SAMD1, Del, G_7, GQPLLPLGPTPHPLCLCPQENQPCPGLMEPPLAVLL-GAKRSRLTLSSGR, (SEQIDNO:8678); XM_014109631.1, ITGA11, Ins, G_7, GQPPADAEGLPH, (SEQIDNO:8679); XM_014116554.1, LMTK3, Del, G_7, GQPRRKGSLDRGLPPSPPTR-ERPGHPQTRVPTHCRGPGRSRPL, (SEQIDNO:8681); XM_539968.5, ADGRA2, Del, G_7, GQQPGRPSRRPVRAAACTTARPTATRAAAATARASS, (SEQIDNO:8682); XM_003639488.2, NUPL2, Ins, G_7, GQQRSRKAIFWFLRFWSFN, (SEQIDNO:8683); XM_014121803.1, PALM3, Del, G_7, GQRAATQRPQER-RAGA, (SEQIDNO:8684); XM_014110417.1, SLITRK3, Del, G_7, GQRAHHLMSSRPLGAPCHFLC, (SEQIDNO:8685); XM_014107943.1, SGSM1, Ins, G_7, GQRGREA-QPGGQWGQSLRRARDGKSLPCPGFSGRGHFCQQ, (SEQIDNO:8686); XM_014111997.1, LOC106558481, Ins, G_7, GQRRGGGRGL, (SEQIDNO:8687); XM_541491.5, SCAF1, Del, G_7, GQRRRRRKRKKRRRRRRSSSLPPPQP-PAQLQRPQALPLARGPQPATQGQKMDRP PVSP-SCPRCPHPCPGTCLLVWTAPPAVSWP, (SEQIDNO:8689); XM_014120101.1, XKR5, Del, G_7, GQRWQVPH, (SEQIDNO:8690); XM_014114308.1, LOC102151519, Ins, G_7, GQRWWEDTAPEDKHIGAGRSACRRE-ALQVLRV, (SEQIDNO:8691); XM_014107197.1, TMEM230, Del, G_7, GQTEPFLS, (SEQIDNO:8693); XM_014109600.1, TYRO3, Del, G_7, GQWGPPPVTIGTSSALGG, (SEQIDNO:8694); XM_854764.4, MAP1A, Ins, G_7, GQWNSPSQAWP, (SEQIDNO:8695); XM_014111684.1, PLXNB3, Ins, G_7, GRAADPSQGHGPGRGAAAPAVGVAGGHSG-GAGCRC, (SEQIDNO:8696); XM_544915.6, PWP2, Ins, G_7, GRAAGQPGLQVRAPPVPLQGL-RAQRLLLSRWQEVRCHKRQPRSDVPRPWEEAGVQ RVCPGQNLLWAVR, (SEQIDNO:8697); NM_001286967.1, ARHGAP18, Del, G_7, GRAARGGRR-PRPAVNMASAR, (SEQIDNO:8698); XM_014120910.1, RTN4RL2, Ins, G_7, GRAHGGRLLGGLRRRGPARRAD-VPGRGLPGAPGLPRPRALGRAAQPSALPPAPGAP PP1, (SEQIDNO:8700); XM_014120941.1, DRAP1, Del, G_7, GRAHRGVRGTNAPPPSVPSRRPGPQPSLPGEPLSLAP-STPFGDGGDRVRVFCPLPRRG SRRSCKLTKRL-GRWRRQCLSSSPGRSSCS, (SEQIDNO:8701); XM_547541.5, UBQLN4, Del, G_7, GRAPEDRGPARC-TRQSRTPLGSMRLAWGQGCSTAQR-CRPSSSRSLKTPN, (SEQIDNO:8703); XM_014112067.1, LOC106558506, Del, G_7, GRARAPRGRA WRRRAL-PHPSCAPQCTRARRRRRPLPPPRRAPLSGWASA-DREQEECG, (SEQIDNO:8704); XM_005623080.2, MTCL1, Del, G_7, GRARGARRSPHCWGPSTRG, (SEQIDNO:8705); XM_539936.4, MNX1, Ins, G-7, GRASAPTPV, (SEQIDNO:8707); XM_846645.3, CCDC184, Ins, G_7, GRATCGAPRPARHYPAAAGGR-GLSV, (SEQIDNO:8708); XM_005618215.1, LOC102151979, Ins, G_7, GRAVLAAKA, (SEQIDNO:8709); XM_538245.6, LRP1, Del, G_7, GRCIGRTGGQTR, (SEQIDNO:8710); XM_535876.5, FL3A1, Del, G_7, GRCPEESTCKTIFMLQIFTCSRRDGTPIKWTTTLT-SMKTTS, (SEQIDNO:8711); XM_005642072.1, LOC102152098, Del, G_7, GRCRWRSWRTRGRRWL-WRARPTALRFFSFPQVKI, (SEQIDNO:8712);

XM_543042.5, KCNB1, Ins, G_7, GRCSCCRWTGVCHTLGQACTESRVLHLHHSKC, (SEQIDNO: 8713); XM_005628665.2, JAZF1, Ins, G_7, GREALRLPGSWM, (SEQIDNO:8714); XM_537179.5, PAPPA2, Del, G_7, GREAPRQDTVSQMPQGAWL, (SEQIDNO:8715); XM_005620161.2, RAI1, Ins, G_7, GREGGGGRGPLQPLQEDVFSQED, (SEQIDNO:8716); XM_536894.5, EIF3B, Ins, G_7, GREIQTNPEIQPPRGSAH, (SEQIDNO:8717); XM_014113085.1, SAL13, Del, G_7, GRFLTRHCQRASRTPWTLSCLTTTRRQRPSAATMMTRTRTPWRTTPSYRSRPATRPS HSWPTPAPARPHHPPSSPASPP, (SEQIDNO:8718); XM_546596.5, FXR2, Ins, G_7, GRGAGTARRGARLQRGLLQGLCEGCP, (SEQIDNO:8719); XM_014112349.1, BOD1L1, Del, G_7, GRGAGVRPAEPSGGERMEDRWPQRWKWKDAARSAWCTAAGKGRVRRALPRVGR GAPRGRTLCQMSE, (SEQIDNO:8720); XM_005639081.2, SHROOM3, Ins, G_7, GRGAPARAQRPPPRGTATGGPSPEGAARRR, (SEQIDNO:8721); XM_014122263.1, SHC2, Ins, G_7, GRGAPGRRRRRRVDPQGQLHPQAGARLAAPRRQGPGARGLIHRAVHGLHRSPPLH ALSGF, (SEQIDNO: 8723); XM_005637620.2, WNT8B, Ins, G_7, GRGAQTREKIL, (SEQIDNO:8724); XM_014119803.1, LOC102156916, Ins, G_7, GRGARGARGARGA, (SEQIDNO:8725); XM_005623276.2, NFATC4, Del, G_7, GRGEAVFSNAPASASPPSLPRLTRRPRWRTTRMPGETAPPGITPRRKALGATERQGA RAGAPSSAPALAAAACPRGASSPTLPTRQPCTQPATRWSPS, (SEQIDNO:8726); XM_014114657.1, DNAJA3, Ins, G_7, GRGGGFAEPQAERQYLRAFPGRSGLRGTADIDTRCQLQRSKKLPFCLYCLLPHELPF GQRGLLPDTRSAPKCQPEGDQESLLPAGQEIPPGHK, (SEQIDNO:8727); XM_541491.5, SCAF1, Ins, G_7, GRGGGGGRGGRRGGGGGGGAAACHHHSHQHSCSGPKHCP, (SEQIDNO:8728); XM_546031.5, MBLAC2, Ins, G_7, GRGGPAPAGRGHPRALRPLRGPLPVRPGGGASRRGRGAGSRGQL, (SEQIDNO:8729); XM_014109869.1, COL18A1, Ins, G_7, GRGGGPGSWGALPGAGGDAGEVSGAWGQGPQAAGHPRAPRKWRKRGRRESVADPG PLSRRPAPLRPPPARG, (SEQIDNO:8730); XM_005638695.2, C2CD4A, Del, G_7, GRGGRGGRRAPRRRVPR, (SEQIDNO:8732); XM_005624842.2, KSR1, Ins, G_7, GRGGRGRGPRGRGQPGAAAVRAAPEAHRHLHRQPARAAHQVRGVQRPHPAGDPD PGGKAGPVHLQTAAVQAECGSWREDPRAQQLPPFQ, (SEQIDNO:8733); XM_005638695.2, C2CD4A, Del, G_7, GRGGRRAPRRRVPR, (SEQIDNO:8734); XM_014120406.1, GPAT2, Ins, G_7, GRGGVHTLT, (SEQIDNO:8735); XM_005623276.2, NFATC4, Del, G_7, GRGKNWTQRTPRHAAVWPWGSPLPMALPLLAFPGLHPLGLACIRHHPARPPHLALG RASLPGQ, (SEQIDNO:8736); XM_003639660.3, B4GALNT4, Ins, G_7, GRGLGAPGQGPAGRAGGGTAPTEEFLPPLPLQAGHVGHAQPEGLPRGEPV, (SEQIDNO:8737); XM_014121842.1, LOC106560109, Ins, G_7, GRGPAGRSGQEPGEAGSVRHVPGAGLRRDRKRKWLLGGARGSAGARA, (SEQIDNO: 8738); XM_014110905.1, LOC106558304, Ins, G_7, GRGPGGPRGDRPGEPGSARWATRRDGSAGRPLFRP, (SEQIDNO:8739); XM_005622956.2, LOC102153244, Del, G_7, GRGPPKERANQARRSLQELS, (SEQIDNO: 8740); XM_848801.3, THAP10, Del, G_7, GRGPRRTPRPSPPRPRAQPAARGPGPGGGPRPHRLHVKMKLNKHKSLLINLIVSLQY LLTVKKAQCIKVHSCL, (SEQIDNO:8741); XM_005634649.1, CHST2, Ins, G_7, GRGPSPQWHSGPRGWRRQEAVGVRVHHVALGLIVLR, (SEQIDNO:8742); XM_540364.3, INHBA, Ins, G_7, GRGQGAVPQTFPHAAGPPV, (SEQIDNO:8743); XM_014116204.1, TMC6, Ins, G_7, GRGQRPGHAAGGSREGLGPVPVQP, (SEQIDNO:8744); XM_843208.4, SPATA24, Del, G_7, GRGRCVSPSINCGT, (SEQIDNO: 8745); XM_005637906.2, TUBGCP2, Ins, G_7, GRGRGLHRDDAEEPDPERDDHRVRAQRQG, (SEQIDNO: 8746); XM_538784.5, MUSK, Ins, G_7, GRGRRGERL, (SEQIDNO:8748); XM_537768.5, RILP, Ins, G_7, GRGRTEAEVRAGNRRRWSSGDP, (SEQIDNO:8749); XM_014106881.1, LOC106557667, Del, G_7, GRGSFISWFRSFP, (SEQIDNO:8750); XM_014112065.1, LOC491446, Del, G7, GRGSLPGARGALPWGVAAPGLSSAAVLPPGACAPSPSLGDPPAADGL, (SEQIDNO:8751); XM_005629427.2, ACSS3, Ins, G_7, GRGSPAQRPPPPRAAPASSRPHPRLQPSRLLEPLQVFRAGCGLGE, (SEQIDNO:8752); XM_537674.5, MYCBPAP, Del, G-7, GRGVAGVSRSLVVPGPAAQGHAISARAAP, (SEQIDNO:8753); XM_005623182.2, TSHR, Del, G_7, GRGVLLPPVSATRRMTSESPARISTASPPYHPARRL, (SEQIDNO:8754); XM_014119248.1, DLGAP3, Ins, G_7, GRGWGRQQHLPQDVPWPGPLRHL, (SEQIDNO:8755); XM_005626758.2, FAM214B, Del, G_7, GRHPPGSTRYPSFPLQLVPLSLIGP, (SEQIDNO:8756); XM_014122402.1, C2CD4C, Ins, G_7, GRHQGQRG, (SEQIDNO:8757); XM_014111463.1, LOC106558415, Ins, G_7, GRHTAPAGTWPLPPKCPTALQMHRVPQGPRGLHPGHPNPHVRG, (SEQIDNO:8758); XM_538049.4, SMC1A, Del, G_7, GRKQWRLWPCSLPSTATSQPPSSSWMRSMLPWITPTLARWQITSRSSRLATSRPSSSL SRRSSTPRLRASLESTPSKGTV, (SEQIDNO:8762); XM 005624449.2, MLX, Ins, G_7, GRKTRGFLAVPKGPPALRAPGLQRRQLSPRACQGGICLQR, (SEQIDNO:8763); XM_014116165.1, KIF25, Ins, G_7, GRLLRQSPGRVPGGPAAQGAGACQAAARGPGG, (SEQIDNO:8764); XM_005632180.2, PRRT3, Del, G_7, GRLPRPVPALGARRRLWAAAPRVARGCPAAAWGPRRRRASWTCGRRRPST, (SEQIDNO:8765); NM_001005760.1, LIFR, Ins, G_7, GRLQATDAPPRHFYCRRPRCRGRPR, (SEQIDNO:8766); XM_005640955.1, LOC488614, Ins, G_7, GRLSHLSDRDCTDIQGLLLQPQPRQTLLLPHADSGEAGLYRQQPH, (SEQIDNO:8767); XM_542654.5, NALCN, Ins, G_7, GRPAGLRGPREAPEEDRTVAAALSTKTNKPLSVFGQLTICRAHNNEIRSVQNEPHDR HGVVWFRG, (SEQIDNO:8768); XM_014112772.1, LOC106558673, Ins, G_7, GRPAQCKLE, (SEQIDNO: 8769); XM_005616850.2, CACNG8, Del, G_7, GRPASSRCTTPSRRRAAASRSRSPGRPPRPRPPRPRPPRRPPGPWPRRPPPPTPTRSTG KPRRC, (SEQIDNO: 8770); XM_005639649.2, SEMA5B, Del, G_7, GRPCTPGRACGGWARACRSAAQRPLPSRRRSRRATPRAASKCGATPRGRRGCR, (SEQIDNO:8771); XM_014109910.1, KHDRBS1, Ins, G_7, GRPGLARHAATTAAAALGHGPRRDGGRSGADPAAAPLSHCLRQDGAGEQVPARTH GREGLARPVLHSRHAATDGRN, (SEQIDNO:8772); NM_001201331.1, MBOAT4, Ins, G_7, GRPGLSCYGSLCCAGLHPCSVCHGSDLLAGPTGCPQVGFPLSDGLADAVSPGAAVY, (SEQIDNO:8773); XM_005616764.2, LOC102156806, Ins, G_7, GRPGPQRALRQPLTVPERREHPAPTKASRGL, (SEQIDNO:8774); XM_005621041.2, FBXO24, Del, G_7, GRPKPVRSTSARSTVAPPCRIAWKR, (SEQIDNO:

8775); XM_014108780.1, LOC106557931, DEl, G_7, GRPLIWNLDPGAPLQGWCPGRGPGAVRRLPLGAREEEETQPAARAAGGPRLSPLGG RRAEGAG, (SEQIDNO:8776); XM_005616873.2, CD3EAP, Del, G_7, GRPPGPERAGSEGHPRAPTPHGRSRTRPRPLVPRGLRRGSSGSGYWG, (SEQIDNO:8777); XM_540520.5, PTDSS2, Ins, G_7, GRPPQHRVRGVRRRHQHLLLASPHPDCALHPHLCAWLRDSAGGDAPGHSL, (SEQIDNO:8778); XM_843371.3, LOC606890, Del, G_7, GRPRAQLPLPPP, (SEQIDNO:8781); XM_003640189.3, FZD5, Del, G_7, GRPRGPSAPPGPRRCASAASPSCPS, (SEQIDNO:8782); XM_005638627.2, LMAN1L, Del, G_7, GRPRGTASGSSSTPRPRTPRALSSACWPVMGTLASSRTGTEPAASWAPAAGTSATCH DPSRHGSRTGGTGCVCP, (SEQIDNO:8783); XM_014109646.1, LMANL1, Del, G_7, GRPRGTASGSSSTPRPRTPSRALSSACWPVMGTLASSRTGTEPAASWAPAAGTSATC HDPSRHGSRTGGTGCVCP, (SEQIDNO:8784); XM_005620267.1, LDLRAD1, Ins, G_7, GRPRPPLLLAPGSLPLCLLAAPAGDSRSPDRPGYHPWTPTTHTRGPGLCDANKQDRL PVPRPEELHPSQRGL, (SEQIDNO:8785); XM_014108067.1, RNF152, Del, G_7, GRPRRRRRRSQTGGARRKAPPGPGCAL, (SEQIDNO:8786); XM_005616884.2, MAP3K10, Del, G_7, GRPRSGARPPRGPSGPRCSTTRRRAMRS, (SEQIDNO:8787); XM005640052.2, JARID2, Del, G_7, GRPSPPGTPSMASRSVAG, (SEQIDNO:8788); XM_014107197.1, TMEM230, Ins, G_7, GRPSRSCPDHWHSGVPARILPPAHCLLCFQRLPGLLLR, (SEQIDNO:8789); XM_005630813.2, SNX27, Del, G_7, GRPTGPGCARGTASWR, (SEQIDNO:8790); XM_543274.5, IRS1, Del, G_7, GRPWGAAVAAAARRI, (SEQIDNO:8791); XM_014113517.1, DVL2, Ins, G_7, GRPYREARGTGP, (SEQIDNO:8792); XM_014122606.1, ST5, Del, G_7, GRQAHPWRGKAVAPLSQGPLEIARALSCCHPRAPLIPL, (SEQIDNO:8793); XM_014114950.1, LOC100856175, Del, G_7, GRQALETAQETMGEGVQAPR, (SEQIDNO:8794); XM_542974.5, GDF5, Ins, G_7, GRQCQGQGGHRADGRPDTAQEG, (SEQIDNO:8795); XM_540482.5, NPLOC4, Ins, G_7, GRQGEICCPGEHQLQD, (SEQIDNO:8796); XM_014112352.1, LOC102153630, Ins, G_7, GRQGVRSSREERQQESGRGKARERALTFGGAVLGAADEK, (SEQIDNO:8797); XM_549367.5, IRAK1, Ins, G_7, GRQPGAELGRWPRAPADSCGRITVEQLRVIAATADRHQPGPTEDGAEAGLVRGRGP GQPAAAVL, (SEQIDNO:8798); XM_014114417.1, XYLT1, Ins, G_7, GRQPPVHIPAEHARPPGDDRLAMGLLHQPQRSRLPHQDE, (SEQIDNO:8799); XM_005632813.2, NACCI, Del, G_7, GRQRQQRWRQQGVW, (SEQIDNO:8800); XM_005617510.2, KIFC3, Del, G_7, GRQVWPPWCIGWWRPCPSCRRRKLGYRRSWQPFRRGWPSKTVTSKPHPPSCRTRW KT, (SEQIDNO:8801); XM_005633206.2, LOC102152641, Ins, G_7, GRRAGPVGTAGRADRAGAGHQQ, (SEQIDNO:8802); XM_003432153.3, EMILIN1, Del, G_7, GRRAWAGGSVPLTAPCCSWRTSFTSSV, (SEQIDNO:8803); NM_001048128.1, RING1, Ins, G_7, GRRAWGGRGGWRGCELRLRP, (SEQIDNO:8804); XM_014119253.1, LOC106559727, Del, G_7, GRREERGK, (SEQIDNO:8805); XM_014107257.1, ARFGAP1, Ins, G_7, GRRGGQSQDRQEGCAAGRAG, (SEQIDNO:8806); NM_001048121.1, HSF4, Ins, G_7, GRRGRAGPGPKRV, (SEQIDNO:8807); XM_846313.4, CENPB, Ins, G_7, GRRGVGGGRGGGRGG, (SEQIDNO:8808); XM_539968.5, ADGRA2, Del, G_7, GRRPAGRGSRSPRAPGASLPPATQLICTIGAERTRVWPRRTARGRPAPGTGSGRCAG GQQPGRPSRRPVRAAACTTARPTATRAAAATARASS, (SEQIDNO:8810); XM_014110496.1, LDLRAP1, Ins, G_7, GRRPASQAARELDRHSGDTARGNALQPQVPGHDAGGAAQG, (SEQIDNO:8811); XM_014109054.1, SORCS3, Del, G_7, GRRPKSSGCPAPRSR, (SEQIDNO:8812); XM_005639643.2, CCDC80, Ins, G_7, GRRPRSQGQGQGGQKAREAREAREAREAREGEEEEAEKREGRQVAQGEEGKG, (SEQIDNO:8813); XM_005641746.2, LOC102154334, Ins, G_7, GRRRRRRRRGGGGGAPAAAGRGLRSRRGAAAPGPAAAPPPRLVHPVGAEGAGERF PTRSIP, (SEQIDNO:8815); XM_014106692.1, NPHP3, Del, G_7, GRRRRRRRRGRGPGRGR, (SEQIDNO:8816); XM_005640095.2, HISTIHiT, Ins, G_7, GRRTEGCL, (SEQIDNO:8820); XM_543127.5, FREM2, Del, G_7, GRRTLRPSPVLWP, (SEQIDNO:8821); XM_014122475.1, SYT9, Del, G_7, GRRTVPMASVYSAKSQSQPRRPGIIQSEDNSTCQTQTSISSSFKNRNS, (SEQIDNO:8822); XM_014119666.1, EML2, Ins, G_7, GRRWLWRGDGGARPGLLRPLRHVLAASILQR, (SEQIDNO:8823); XM_014116598.1, SIX5, Del, G_7, GRRWRRRRPKKRRRKRASSCRLCRRPRVRRRPRPRPGPGRAKRRRERRARDPRASP GRPPRPLPSRPRASASRPSRWRASARRCYRRATPAA, (SEQIDNO: 8824); XM_005620294.2, IGSF9B, Del, G_7, GRSCCGRSPPRRRYLLREHIHLHPGTLLHLRGWRL, (SEQIDNO:8826); XM_005633056.2, UBXN6, Del, G_7, GRSCRRRTAWPSTSAGWCPRPS, (SEQIDNO:8827); XM_003434552.1, OR10S1, Ins, G_7, GRSGGPCGLLHNRHSHAQPFHLHSAQQGGQAGSAKTFEPRPAGVPVRQPAPL, (SEQIDNO:8828); XM_533011.5, RSBN1, Del, G_7, GRSGHLNVCLWVKWLRRSERCA, (SEQIDNO:8829); XM_538306.5, KLHDC7B, Del, G_7, GRSGTPTPC, (SEQIDNO:8830); XM_005622611.1, CNST, Del, G_7, GRSRSAAPRPRGSCPPSPGTPARMTAACSCLSRGPAEMWPQ, (SEQIDNO:8831); XM_014117371.1, TMPRSS6, Del, G_7, GRSSLTAG, (SEQIDNO:8832); XM_535292.4, SLC12A3, Del, G_7, GRSTGWTRREKRSFPC, (SEQIDNO:8833); XM_014118581.1, TMEM74, Ins, G_7, GRSVLFANDVYVERGAVSSQQVCLFQRVCKTLRFFQLQDENLH, (SEQIDNO:8834); XM_005616884.2, MAP3K10, Ins, G_7, GRTEQGAGRPPGAPSCAGQLGCAGGPGHELPTQ, (SEQIDNO:8835); XM_014118662.1, ARHGAP39, Del, G_7, GRTRPACSSSRRSPTAPCSSPSGGRRPS, (SEQIDNO: 8836); XM_014121783.1, PTPN23, Ins, G_7, GRTTPASCRSALCPSSPVLRTRDGPGGSASHDHCG, (SEQIDNO: 8837); XM_536512.5, PDZD2, Del, G_7, GRVAASRGTAAPGRGGAAP, (SEQIDNO:8839); XM_858228.3, EMC10, Ins, G_7, GRVAHSPASCCPGAHAAAAGGL, (SEQIDNO:8840); XM_014117996.1, C11H9orf152, Ins, G_7, GRVGESGDQGGRANARSLGGGCPPGMRV, (SEQIDNO:8841); XM_014119127.1, LUC102151792, Ins, G_7, GRVHHQLQGPPGEPDG, (SEQIDNO:8842); XM_014121191.1, MADD, Ins, G_7, GRVPWEGRTPCYLCPRRDWH, (SEQIDNO:8843); XM_005630877.1, LOC102151356, Del, G_7, GRVSCVRAPGAPAAPIGSPALRGGRRGGPRGAVSARGWESSQEPGDRLPPPARPPRA PRPRP, (SEQIDNO:8844); XM_005617924.2, LOC102154107, Ins, G_7, GRVSGFGC, (SEQIDNO:8845); XM_014121835.1, JSRP1, Del, G_7, GRVSPSGLEGAPPQWPPARPPPLCSP- PAEPIGPRRCPRPPVAARPGRSPSSDCQVPAAV RHPPSSDPQLRSPAPIWAPPSP, (SEQIDNO:8846); XM_005616796.2, C1H19orf12, Ins, G_7, GRWGPVGRVDDKRTVSADSSDPDAAAAL, (SEQIDNO:8847); XM_014119866.1, ADNP2, Del, G_7, GRWLMMMLFRF, (SEQIDNO:8848); XM_005629424.1, ZNF219, Del, G_7, GRWLRCTRAPPRAPGSPHLPRGRRPGPRRRKRTGC, (SEQIDNO:8849); XM_005629104.2, B4GALT2, Del, G_7, GRWSACARPCSFSACCTFSWPSSSTLTSTPSTWPS-SAASAPVALPAPSTQLPAAAPTS PGPTPRP-PARGSPRLPAPVLAPRLPSCLPVPTRRLVLWAGC, (SEQIDNO:8850); XM_541885.4, BSN, Del, G_7, GSAASRPLSSIARAAMAMSWTWAKALT-PAWSGSLSWRWRA, (SEQIDNO:8851); XM_014107981.1, ARAP3, Ins, G_7, GSAELGGRSAGSRN, (SEQIDNO:8852); XM_014111700.1, LOC102153373, Ins, G_7, GSAKFGAPR-PAAPGPRGPPGRAPAPSGCRSSRRPSVRGQRRPGPH-PAPSGQHLAAGR QRGVSWARAPPAAGARH, (SEQIDNO:8853); XM_003639620.3, SV2A, Del, G_7, GSALHPGTRWTC, (SEQIDNO:8854); XM_538573.4, GRM6, Del, G_7, GSALPSPSRFPGNQSQENSIR, (SEQIDNO:8855); XM_005640836.2, MIA3, Del, G_7, GSAPHLPRLTCLRDRSLLR, (SEQIDNO:8856); XM_005637080.2, PDE3A, Ins, G_7, GSARPARAGRRGGSLAVAPGRGGGAQLRGRRDMAGAE-AEAGRPHGRRD, (SEQIDNO:8857); XM_005616765.2, PEPD, Del, G_7, GSASRRTSW, (SEQIDNO:8858); XM_014112350.1, UCHLI, Ins, G_7, GSCPFGGGGPVPRRLVLPPLPLRRHPKCVRPALYSR-GLGGSARCFSRCLGSGSSRAPP RCSSSRWRSTPRC, (SEQIDNO:8859); XM_537686.5, COIL, Del, G_7, GSCPRPRARAWY, (SEQIDNO:8860); XM_843818.3, LST1, Del, G_7, GSCSWLCSFCPPVCVGFIGK, (SEQIDNO:8861); XM_014120777.1, LOC102153599, Del, G_7, GSDCGSLGGGPDPRCPRRSHRRL, (SEQIDNO:8862); XM_005633536.2, ARHGEF17, Ins, G_7, GSFPCGQGELSCIPSQSGRLPWQQPLFQHRDPQG, (SEQIDNO:8864); XM_541606.3, LOC484492, Del, G_7, GSFPLVPHQYPSWGMCCKSVLMPLFSLL, (SEQIDNO:8865); XM_533169.4, MPEG1, Del, G_7, GSFRNAPSSR-GRRPPSCAKPWSRGTPSLVLSPAPLATPPSTCYPR-STRRATTTWSAGA SAPSSSSARRCAKTCSGWRRLNLGLFGV, (SEQIDNO:8867); XM_548206.3, WFIKKN2, Ins, G_7, GSGCDHLGERPQRHGLPRGRVPEAPRQRGLRRGAD-PLALRRAGQQLPHLHLRPLPP QPEPL, (SEQIDNO:8868); XM_005635711.2, CCAR2, Del, G_7, GSGLPLW-MASTPRATRRC, (SEQIDNO:8870); XM_014121211.1, TRMT112, Del, G_7, GSGLTASPERGAGRPEMT, (SEQIDNO:8871); XM_014120700.1, MTMR11, Ins, G_7, GSGPEFQHRPPEGGARP-GALWTKVRPEDWDAGAQELSA, (SEQIDNO:8873); XM_538841.5, SKIV2L, Del, G_7, GSGPGSWRS, (SEQIDNO:8874); XM_541491.5, SCAF1, Ins, G_7, GSGPRQGQR, (SEQIDNO:8875); XM_005629022.2, SLC5A9, Ins, G_7, GSGRVLQPGP-GAAGRPVQAVWQAAGGLALRAPRTPRASTEPRGRG-CAQPGTDQHR RGAALEKRLRRPGH-PAAGHQRLPVGLLCV, (SEQIDNO:8876); XM_005617043.2, ZNF438, Del, G_7, GSHFLANLNP, (SEQIDNO:8877); XM_542293.5, CAPN5, Ins, G_7, GSHQRLHQGGDSSSRHGGPPCVWPGEGPRVCHH, (SEQIDNO:8879); XM_005636883.1, KMT2D, Ins, G_7, GSISWSGPPSETPFLPSK, (SEQIDNO:8880); XM_548355.4, NDOR1, Del, G_7, GSLALMPLT-TLPDSSGHCASRVRHGP, (SEQIDNO:8881); XM_014109402.1, TP53BP1, Ins, G_7, GSLCEAAPFKCP, (SEQIDNO:8882); XM_003435632.3, MORF4L2, Ins, G_7, GSLCREPPFRISEEDQKEQTEDTWKR, (SEQIDNO:8883); XM_005633810.2, OTOG, Ins, G_7, GSLHTICCPTEEHHGEDGHPVQASVPALLDIWPCPG-YAHRTHTCCGPHSCYLGT, (SEQIDNO:8884); XM_843959.4, LY6G5B, Del, G_7, GSLNAWVTWPPCP, (SEQIDNO:8885); XM_536856.5, PLOD3, Del, G_7, GSLPPGCFWLCL, (SEQIDNO:8886); XM_014119706.1, E2F7, Ins, G_7, GSLRSAAPPGH-SVHGPAVSHAGPVSRALLSHRAQAGLLCRRRA-PRCGACAFRGAQP GIHGSPPHRPHKRG, (SEQIDNO:8887); XM_003433650.1, VENTX, Ins, G_7, GSLRSRQGVQQRGAPARCGRGGGQVFRSVCAP-DAHGWVGQGRGRPAGAPRAHGL HRRAAQHPGERL-PAAPLPGPPGAPAPGP, (SEQIDNO:8888); XM_005639548.2, FBXO40, Del, G_7, GSMWNSTVSV, (SEQIDNO:8889); XM_844641.4, C6H7orf43, Del, G_7, GSNPLKGPRRA, (SEQIDNO:8890); XM_005638718.1, MAN2C1, Del, G_7, GSPGGGVPARGSGRSGP-SAATCGPH, (SEQIDNO:8891); XM_014116168.1, XRCC3, Del, G_7, GSPRGPSA, (SEQIDNO:8892); XM_005619964.2, PHF23, Ins, G_7, GSPSPRAANTP, (SEQIDNO:8893); XM_005624539.1, MS1L, Del, G_7, GSQRPRAPAAVPDPSIRRCCPFR-RALSWRRPKSLRPGLGTRVGRLPQLPPPRTRRDPH HYLCRGRHPSRPPPPPGPWRPARADGRV, (SEQIDNO: 8894); XM_005631571.2, C18Hllorf84, Del, G_7, GSQRQGVAC, (SEQIDNO:8895); XM_003639963.2, SLC48A1, Del, G_7, GSQVCWRCGCW, (SEQIDNO:8896); XM_847066.4, PAXBP1, Del, G_7, GSRCRARGCRRLPR, (SEQIDNO:8897); XM_014119335.1, MYCL, Ins, G_7, GSRERSPRRGSGERRPRGKGRSG, (SEQIDNO:8898); XM_014117421.1, LOC106559393, Ins, G_7, GSRIGKTSVKGAPGGSAGEASLL, (SEQIDNO:8900); XM_005636092.2, TMEM132D, Ins, G_7, GSRLHAPVPACHGAGLDPVCGRGGGRPRRAPGP-PAGLRLAGGHHGASE, (SEQIDNO:8901); XM_014121831.1, TLE6, Ins, G_7, GSRLLGSG-STAPVWSPGRP, (SEQIDNO:8902); XM_003638869.3, ZNF367, Del, G_7, GSRNRRRRSSPPAPASATSWCTR-GAGARTRTT, (SEQIDNO:8904); XM_544960.5, NKX6-1, Del, G_7, GSRPWAAPHSSSQPPPPMASTTS, (SEQIDNO:8905); XM_014107348.1, AMER2, Del, G_7, GSRRRPGKPRSPGPPGSCALGRAGRPTT-PAAPAAPGTAPATRKAAAAAAPLTPAPST RPQTRRQSLFVSCFLT, (SEQIDNO:8906); XM_005619097.2, LOC102151313, Del, G_7, GSRRWRVRTWTPGLRTRPKTPRAKRTARFWM, (SEQIDNO:8908); XM_014114950.1, LOC100856175, Ins, G_7, GSRSQGWFGGSWENWARG, (SEQIDNO:8910); XM_014112188.1, LOC106558557, Del, G_7, GSSCSRN-SSPLPAA, (SEQIDNO:8911); XM_014120407.1, FAHD2A, Del, G_7, GSSISTPLTPHCPRR, (SEQIDNO:8912); XM_014114292.1, KLK8, Del, G_7, GSSLKTTGSSQQPTVKKGSTQYAWGITA, (SEQIDNO:8913); NM_001037345.1, CYP2A13, Del, G_7, GSSLQDPPHCPSSEITCS, (SEQIDNO:8915); XM_005616252.2, KLK12, Del, G_7, GSSLTAGGSSQLL-TAVAAGTGCAWGSIASAGWTGRRRFGEVASP, (SEQIDNO:8916); XM_539968.5, ADGRA2, Ins, G_7, GSSRGARAAVQ, (SEQIDNO:8917); XM_003434804.3, PRRT2, Del, G_7, GSSSSSPPASST, (SEQIDNO:8918); XM_014120227.1, CMPK2, Del, G_7, GSSTCPRPII-LYTSGPGTCSNPTWFCCSQ, (SEQIDNO:8919); XM_005627878.2, SYBU, Del, G_7, GST- GAAVSWWISWPWLPPWSPPFCGHSVLGGGARIPSTT-SEPCSGAAAWSPCIRCAA PPSTSKP, (SEQIDNO:8920); XM_005619566.2, FLI1, Del, G_7, GSTPTPTCPATLTPTCPHT, (SEQIDNO:8921); XM_005626080.2, EPAS1, Ins, G_7, GSTRQQHFTSGME-KDEEPQGQRELPFDSRQTAECKHPQ, (SEQIDNO: 8922); XM_540643.3, LOC483524, Del, G_7, GST-SKNTR, (SEQIDNO:8923); XM_546641.5, TRPV2, Del, G_7, GSTSWWASYGTSGGVVCSSGSPSWTATLNCSS-WSRPCSQCCPRDCVSWPWSGTCLC LCLPWCWAG, (SEQIDNO:8924); XM_005625012.2, PTGS1, Del, G_7, GSVAPSLGGLMVERSRPSGNMEQGEGLSGE-IFWKMQE, (SEQIDNO:8925); XM_854764.4, MAP1A, Del, G_7, GSVELTIPGLAMTHPLSLNQTLAHPLLALM-CAWLTLRGSVQNLEG, (SEQIDNO:8926); XM_014116300.1, LOC100856218, Del, G_7, GSVM-RAEIDTWCRWPSCP, (SEQIDNO:8927); XM_014111404.1, FRMPD3, Del, G_7, GSVWEHPTIGS, (SEQIDNO:8928); XM_844620.4, C5H17orf74, Del, G_7, GSWPACHLPLSTSPLSCAACPSAWRPSQN, (SEQIDNO:8929); XM_535802.5, NDUFS6, Ins, G_7, GSWPPESVHKPGQRNKNGDVRLLWTAVQTSPSL, (SEQTDNO:8930); XM_014115404.1, HAX1, Del, G_7, GSWRVIQEVNPPNQHQTGAPRDLLVCLMICGL, (SEQIDNO:8931); XM_005620294.2, IGSF9B, Del, G_7, GTAAPARLA WTPGGTSPSPGPGPAPGRP-GAPSPVYIKWCYSRPGSRLSPKAP, (SEQIDNO:8933); XM_541287.5, TMEM2, Del, G_7, GTAPRRSWMA-FLFITASHGASPCMGQMAC, (SEQIDNO:8934); XM_005619266.1, LARP1, Del, G_7, GTAQATTPHVPR, (SEQIDNO:8935); XM_014114308.1, LOC102151519, Del, G_7, GTAVVGRHCPRR, (SEQIDNO:8936); XM_005624044.2, CYTH1, Del, G_7, GTCPRSCSG-ICMRA, (SEQIDNO:8938); XM_005624372.2, HEXIM1, Ins, G_7, GTEARGRASRTAMS, (SEQIDNO:8939); XM_536371.4, TET1, Ins, G_7, GTEIGIKPTSPRKCNQK, (SEQIDNO:8940); XM_846645.3, CCDC184, Del, G_7, GTGHLWSPSTRPTLPCCSWRARPLC, (SEQIDNO:8941); XM_014114637.1, LOC102151838, Del, G_7, GTGMWVLWRRDVCGFISPHHGRVV, (SEQIDNO:8943); XM_014119666.1, EML2, Del, G_7, GTGPRLGLGGPAVAVAGRWRSAARPSAASTTR-PRCFNTATMTICRARAAWRWTTA CRRWSSGCSCRKTSSRS, (SEQIDNO:8944); XM_005630084.1, LOC102155720, Del, G_7, GTGPR-SQPTSRSRATGCGGKAAGMRLPRVRGRATLR-GAVRPNGTCILSINLKDMKT VMLTGQVRAAAS, (SEQIDNO:8945); XM_014114526.1, KIAA0556, Del, G_7, GTGPTPGPARGLRTGSRG, (SEQIDNO:8946); XM_005636328.2, ACACB, Del, G_7, GTGSLRRCSSPT-MASLP, (SEQIDNO:8948); XM_546286.5, GRIA1, Del, G_7, GTIQVSRIGHISSLQS, (SEQIDNO:8949); XM_536612.5, PELP1, Del, G_7, GTKCQSPRRRLRQKTWR-PRWRQRRQPCRRRSRMTRLPCWLTSSIVPLMTT-SHHRPQ SLIP, (SEQIDNO:8950); XM_535893.4, RANBP9, Del, G_7, GTLGANKTPEFIARSLHASRST-FARLREGWSRQSQVAKTN, (SEQIDNO:8951); XM_014120234.1, GAREML, Ins, G_7, GTLPF-STWTPQGL, (SEQIDNO:8952); XM_014115372.1, DCST1, Del, G_7, GTPCLPGFFGKPLEP, (SEQIDNO:8953); XM_014121604.1, FRMD4B, Del, G_7, GTPFLEA-VGAPELLREARKMA, (SEQIDNO:8954); XM_014122053.1, FLNB, Ins, G_7, GTPHSKEPL, (SEQIDNO:8955); XM_005630224.2, KIF3C, Del, G_7, GTPRPSWWPLWGQLLTATTRASPPCALPTGPRTSRT-SPG, (SEQIDNO:8957); XM_014119249.1, CSMD2, Del, G_7, GTPSARSKEASTVPAIPAASRAAATASSWP-SAATPP, (SEQIDNO:8958); XM_005620393.2, MIB2, Del, G_7, GTQGPCSCCPGSRPQASRAAGS, (SEQIDNO:8960); XM_005622264.1, LOC100855804, Del, G_7, GTRAGKDRKEPQGQCGAVGPARREL-GTAVGQVVLGPGRIPERELLAPR, (SEQIDNO:8961); XM_014107317.1, NKX2-2, Del, G_7, GTRARSGSGGCSSPRHRPTSWSGASGSSGTCRRP-SASTWPASSASRPRRSRSGSRTTA TR, (SEQIDNO:8962); XM_005626996.1, KLF4, Del, G_7, GTRAWR-RAAAV AAAAAAAASSTAGSPCPLPRPPSTWRTSTT, (SEQIDNO:8963); XM_014107265.1, HELZ2, Del, G_7, GTRCRCSSVPPCSVASWHRVCSCARWHPASP-SAWSTWSGW AAASWTRCPRPCETAVPTWPST-PACGGPSAPWSRPPAPSWRVTPSRCST, (SEQIDNO:8964); XM_003639777.3, SYDE1, Ins, G_7, GTRLPAAGPHLPPRTRGGPAAAGTGAGVGPG-CAEAPALRPGHCAPTHSLPRVPGPA TGRASGAP-GAVVCQADAVRAAGSPRHR, (SEQIDNO:8965); XM_014120910.1, RTN4RL2, Del, G_7, GTRPRRTTTG-GATAARTSAASRRARARPARRPRTPAAPRSRPGCPAL-CSASCSWRPT TS, (SEQIDNO:8966); XM_546031.5, MBLAC2, Del, G_7, GTRRAGPCWPWPPTCTSTTP-GASTSSTGWRCITPRPRRWLAGTTLRR, (SEQIDNO:8967); XM_005641667.2, LOC102152628, Del, G_7, GTRRQRTQPFSLSLRRHLLMPCGQQQVPLSPLLRM-HPWQPMRR, (SEQIDNO:8968); XM_548847.4, STS, Ins, G_7, GTRRRPGARLPCCIAHVHGAHAREPWADVP-SCQRV, (SEQIDNO:8969); XM_005631505.2, CI8HIlorf85, Del, G_7, GTRRR-SWRSSQPGPASVTCVAFRAT, (SEQIDNO:8970); XM_014114474.1, LOC106558921, Ins, G_7, GTRSSRLCPGPKGQPASREAGPLPALVHGDHRA1, (SEQIDNO:8971); XM_540364.3, INHBA, Del, G_7, GTRTRSSPTDLSSCCRPASLKTTLIGGGGGAWSVTAR-STSAVRNSSL, (SEQIDNO:8972); NM_001197119.1, TMEM132C, Del, G_7, GTSCRTSPWT-SPTSRRRWSCPGRGAAWGPATWCRRPGA, (SEQIDNO:8973); XM_014116594.1, DMWD, Del, G_7, GTSPAAPPPAAGWTQPRCWALRCAHASTRCHCSSPS-CARRSPRSASRSSSSWRTASS PPARRASSVPGPGRAR-RASPPNQATPRVAQWC, (SEQIDNO:8974); XM_005632383.2, KCTD6, Del, G_7, GTSPQLETLKAIT-SLIEMDLFSDMFSTS, (SEQIDNO:8975); XM_005623126.2, LIPG, Del, G_7, GTSSQAVDSMMCWAQSHMEQSRRW, (SEQIDNO:8976); XM_005620290.1, LOC489267, Del, G_7, GTSSRSSGAPSTTSECPGRTGGTACGS, (SEQIDNO:8977); XM_543329.4, ANO7, Ins, G_7, GTTRCGPGRRPVVLPTRQGTRVPRRRPGLSSPSGH-SGLGARV, (SEQIDNO:8978); XM_843610.4, DPP7, Del, G_7, GTTSEVPATSSSPTGTWTPGQGVGSGVT, (SEQIDNO:8979); XM_853562.3, R3HDM2, Del, G_7, GTTVGLLRTAATRTSLPCTPSWLCFPAPWLPRMPP-FASTTL, (SEQIDNO:8980); XM_853836.4, TCERG1, Del, G_7, GTVSDSTRGSSGWLNSRP, (SEQIDNO:8981); XM_005634486.1, A4GNT, Ins, G_7, GTWEAGSR, (SEQIDNO:8982); XM_846693.4, GINS2, Del, G_7, GTWGLLTLVYQWKCLCGWRLT, (SEQIDNO:8983); XM_546596.5, FXR2, Del, G_7, GTWSRDCPSR-CAAPTGPSTRAL, (SEQIDNO:8985); XM_005636092.2, TMEM132D, Del, G_7, GVAAARSSTSMPWCGS, (SEQIDNO:8987); XM_847066.4, PAXBP1, Ins, G_7, GVAAGPGAAAAFRADPGLGGRGRGLLPGRRGAR-QRAEAAQEAAGEQRGAAGQPA ELPGRGGRK, (SEQIDNO:8988); XM_005629462.2, NOS3, Del, G-7, GVALLTGPGSCPPSLAASPLFSIRRWSTMSCPRP- SAIRQTRGRGVHPRVPASPGRKPL RKWPMR, (SEQ ID NO:8989); XM_003435632.3, MORF4L2, Del, G_7, GVALQRTPLQDQ, (SEQ ID NO:8990); XM_014109104.1, PAX2, Ins, G_7, GVCERPAPARRGEAAHRGAGPPGRAALRHIPAAARQPRLCQQNPGQVL, (SEQ ID NO:8991); XM_014114716.1, UNK1, Del, G_7, GVCGSVARTGSRLVLPGDGRLRRREPGRWVLH, (SEQ ID NO:8992); XM_014118709.1, PTP4A3, Del, G_7, GVEAVAQRSFPPEGQSRQGQGLLRLSKTQPREWFFCFLAVWLGRVTQPL, (SEQ ID NO:8993); NM_001003264.1, SRP72, Ins, G_7, GVGACALE, (SEQ ID NO:8994); XM_014120700.1, MTMR11, Del, G_7, GVGARVSTSPPRRWSQTWGSLDQSPSRGLGCWSPGVVSLAVTWLRDASQGSRS, (SEQ ID NO: 8995); XM_014111649.1, LOC106558441, Del, G_7, GVGGAVQAPTGMLQPRPVAWLPRFPVLIAEL, (SEQ ID NO:8996); XM_014113230.1, STX8, Del, G_7, GVGGRTLPRAPQPRLPQGRPRRRAGWSPGSGGRGGAVRRPGRCPEPCIGSHRTAGIS RPARIRAGGCGLPRTPPDSPGLPGQVQAE, (SEQ ID NO: 8997); XM_014121616.1, IL17RE, Del, G_7, GVGSTSWCRNTKSHISSGSVGDTRCQHMLRGS, (SEQ ID NO: 8999); XM_014121618.1, IL17RE, Del, G_7, GVGSTSWCRNTKSHISSGSVGDTRCQHMLRHLSQGAAL, (SEQ ID NO:9000); XM_005637591.2, UBTD1, Del, G_7, GVLAGKGWERGLTTAWL, (SEQ ID NO:9001); XM_003639260.3, MYO1C, Del, G_7, GVLCVTGCCRATLCWRPLEMPRPSGMITPAGLGSTWMYSLTSRVLPWVATSSVTSW KSPEWCTRTTGRETSTSSTSCWKGARRRCCAGWA, (SEQ ID NO:9002); XM_005640836.2, MIA3, Ins, G_7, GVLPTSHG, (SEQ ID NO:9003); XM_005636016.2, NOS1, Del, G_7, GVLRSRAASSRPATSSSQSTASPWWT, (SEQ ID NO:9004); XM_005620597.2, NOL9, Del, G_7, GVLSFFQGGRKVRTRSARNLAGRGPWYRVLLLAGSAV, (SEQ ID NO:9005); XM_003639746.2, STAB1, Ins, G_7, GVPARHMCPRLQRPLL, (SEQ ID NO:9006); XM_548997.5, PPP1R3F, Ins, G_7, GVPQPSPGHTHGPRPDLEVAWP, (SEQ ID NO:9008); NM_001253744.1, KRT15, Del, G_7, GVPSGLGEAALVGGVSTGVVEAAVFQLLLLDLFPRGQEGAMGVA, (SEQ ID NO:9009); XM_005618879.1, PRF1, Del, G_7, GVPSSACPWH, (SEQ ID NO:9010); XM_846580.3, LCAT, Del, G_7, GVPSSPCWSWPQVTTRASRSCPASS, (SEQ ID NO:9011); XM_005621273.2, FBRS, Del, G_7, GVPVGPLGSQGTALIGSLAGPLGIGPENGPISGEGKRPPPVILWKLDTYVMQKAIWM RGSPMMTSTHPLLSQPAKPRAPTAPSMGTVKQNSP, (SEQ ID NO:9012); XM_005630554.2, TET3, Del, G_7, GVPWLLSPSIRKRRGLSPLGRRWPCPQTQQSPCPPTPTRRSLAPTAAGS, (SEQ ID NO:9013); XM_005625810.2, FAM109B, Del, G_7, GVQGLRRPPVALAEGAGLSSKATCCSPLRVGRAGPR, (SEQ ID NO:9014); NM_001284496.2, TAP1, Del, G_7, GVQGTRSAGF, (SEQ ID NO:9015); XM_005640052.2, JARID2, Ins, G_7, GVQVHRARRQWPQGQWQVEPKVMH, (SEQ ID NO:9016); XM_542952.5, HCK, Del, G_7, GVRAAKIRAARRRRSGRPGWGV, (SEQ ID NO:9017); XM_014116004.1, GALNT16, Del, G_7, GVRILSSPSGCGCAVGAWRSCPAAGWATSSGNGTPTTSLRAMPSPISGIPSALQRCG WMNTSSITTRPGPQPSGRPLAAWPRGLSRGRR, (SEQ ID NO:9018); XM_843907.4, GPR37L1, Del, G_7, GVRPRTQAGTGLRPRGSRAGPEEALRTRRPRGCSSMCPRTGPSTPGPSTRLTCSPPSP, (SEQ ID NO:9020); XM_014115077.1, LOC611716, Del, G_7, GVSGPREGGWAQVGVGWTHRQASVSPKGPCRRMQSMSSACRNQ, (SEQ ID NO: 9021); XM_014111404.1, FRMPD3, Ins, G_7, GVSGSTQLSEADAPLQYQRTGSG, (SEQ ID NO:9023); XM_548354.4, RNF208, Del, G_7, GVSRRAAATRPSGSTVGPRAPAMCGTRCLPAPSC, (SEQ ID NO:9024); XM_542293.5, CAPN5, Del, G_7, GVSSAPPSRR, (SEQ ID NO:9025); XM_014116730.1, ARHGAP33, Del, G_7, GVSTTEGPCTGMGGKEGRGLVPHPPTPLPAGPSTLRVRPGATA, (SEQ ID NO:9026); XM_847645.3, TMEM38A, Del, G_7, GVTITMTTMAGPMVAVGPARHTQPCLLSPKRS, (SEQ ID NO:9027); XM_014119248.1, DLGAP3, Del, G_7, GVTPLGARTGRFPAAGCGAAATSKPWGMRRAETQTAAPRRLPKPWPGASPPAAPPV WTRPGSTAVSRPGSIPGAPSLATAVPSPPDSSVRS, (SEQ ID NO: 9028); XM_005631208.2, TNKS IBP1, Del, G_7, GVTSALASSPSPRPPSARASEIGAVTSARRLPREATSLASSVTTGQVVLP, (SEQ ID NO:9030); XM_005635711.2, CCAR2, Ins, G_7, GVVSLFGWPRPQGRPAGASPHCHSLCASPDWH, (SEQ ID NO:9031); XM_014121211.1, TRMT112, Ins, G_7, GVVSPPAQSEGRDARR, (SEQ ID NO:9032); XM_545865.4, CRTC3, Del, G_7, GVWGAGPRAGAGRRAAVGERRAAARGRPEGEGEASRAPGGNHKQLAGGRRGF SFSAHPPPAAGARRGRGEPGAP, (SEQ ID NO:9033); XM_014118297.1, MDC1, Del, G_7, GVWPAQWQRLPTW, (SEQ ID NO: 9034); XM_536512.5, PDZD2, Ins, G_7, GVWRRLGALLPRGGGGQPRDGHRQTPQGAGCRRASDRGPGGSRGTFSGPTSSGRW KRKFPPRGARHGQPDARPEEGLGSCWPAPPATVGLPAFSFRFH, (SEQ ID NO:9035); XM_005616718.2, LSR, Del, G-7, GWAPGRPLGAGARSSSGASFSAPCAQPLPVPSR, (SEQ ID NO:9036); NM_001346058.1, KRT23, Ins, G_7, GWGCPHLPFLQLTKVSASWRALGI, (SEQ ID NO:9039); XM_005634337.2, EOMES, Del, G_7, GWGFLVPASVPTSTCATGLCGSNSTATKPR, (SEQ ID NO:9040); XM_014111649.1, LOC106558441, Ins, G_7, GWGGLCRRPRGCSSPGPWPGSRGSLC, (SEQ ID NO:9041); XM_014113212.1, LOC106558751, Del, G_7, GWGGTRLN, (SEQ ID NO:9042); XM_014112782.1, LOC106558678, Ins, G_7, GWGQLSAPRPPGHPRASPQSPVPALHGLPGTHPRPGAAVRGGTLCLPGSSGSRGGLD AAQAPTSRGWSLICGCPRLASSRNSARRPGARTNG, (SEQ ID NO:9043); XM_014122630.1, FAM160A2, Ins, G_7, GWLRTPARASTTS, (SEQ ID NO:9045); NM_001145174.1, CA9, Del, G_7, GWPCWPPFCRRVQKKTVPMSSCCHIWKKSLKKTQRLGSQDWMYPRCCPLTSAATS AMRGL, (SEQ ID NO:9046); XM_862887.2, PRR23A, Del, G-7, GWPGRARARGPPALVQRGSLLSATSTWTPTSWSPSPARHSSLCRPLRVRVPTCAPSA LQDPPPRPGDACSRN, (SEQ ID NO:9047); XM_862898.3, LOC611145, Del, G_7, GWPGRARGPPALVQRGSLLSATSTWTPTSWSPSPARHSSLCRPLRVRVPTCAPSALQ DPPPRPGDACSRN, (SEQ ID NO: 9048); XM_845621.5, MLLT6, Del, G_7, GWRAAGPCPSMGSWGG, (SEQ ID NO:9049); XM_005619991.2, EFNB3, Del, G_7, GWRCSCWAWQGLGVPCVGGDGGPSLRRVATLVLAPSGGEGLWAWAAEVAWGLG RLSLGS, (SEQ ID NO: 9050); XM_014122483.1, LOC106560169, Del, G_7, GWRGGAVERLDVAWTPSWAGRRPPASFPSYPRARSA, (SEQ ID NO:9051); XM_005617934.2, PAX7, Del, G_7, GWRRPPQPRTPAQPTEPATASPATRTAS, (SEQ ID NO:9052); XM_005621026.2, SLC12A9, Ins, G_7, GWSLLHDQPDPGA, (SEQ ID NO:9053); XM_538325.3, TRMU, Del, G_7, GWTAQWPRCC, (SEQIDNO:9054); XM_005623069.1, LRRC30, Del, G_7, GWTCSSVT, (SEQIDNO:9056); XM_005638641.2, CSPG4, Del, G_7, GWTQRPPATSRNTAWAWPRGPSTSPSWAAWRISASTARGRGSGKPR, (SEQIDNO:9057); XM_014111291.1, CD84, Del, G_7, GWVFYRSSLPGRSQ, (SEQIDNO:9058); XM_005624167.2, OTOP3, Del, G_7, GWWSSIWRP, (SEQIDNO:9059); XM_014117140.1, IKZF4, Del, G_7, GWYPSLRAPRPSHLPPLWWAGPALPTPKRTPSRRRGYCGAPQAPPRKCSGWWARV VSP, (SEQIDNO:9060); XM_534537.4, LATS2, Ins, G_7, GYDEPADPDGGIP, (SEQIDNO:9061); NM_001287152.1, PIGR, Ins, G_7, GYGAVRGQARTA, (SEQIDNO:9062); XM_005627200.2, ZBTB22, Ins, G_7, GYLWEAAAGGR, (SEQIDNO:9063); XM_548318.5, HIC1, Del, G_7, GYPASPAPTARASSTSPRASLLWPDSRQNS, (SEQIDNO:9064); XM_005624150.1, CBX4, Ins, G_7, VAVGDRVRPAAAPPPLPTCTATELSLPKTE, (SEQIDNO:9066); XM_014112641.1, NWD2, Ins, G_7, VCEVPSNLGHGSRNGHGRQ, (SEQIDNO:9067); XM_005633560.2, ART1, Ins, G_7, VCICIPAERRSPAVWGGYLLRHLDLPWGTYQGLFLLPRGGGGADPPLRDLPGDQCQ, (SEQIDNO:9068); XM_547872.5, EXD2, Ins, G_7, VCPMERHPAAAEE, (SEQIDNO:9069); XM_845621.5, MLLT6, Ins, G_7, VEWGCRPQPCGLEPGWRGPHAAAARLS, (SEQIDNO:9070); XM_005618685.2, GAK, Ins, G_7, VGGLGRGAGPRSCCRRRPACRPQCPRELDQVSEPGPVC, (SEQIDNO:9071); XM_005618689.2, GAK, Ins, G_7, VGGLGRGAGPRSCCRRSLLLCRRPACRPQCPRELDQVSEPGPVC, (SEQIDNO:9072); XM_005623276.2, NFATC4, Ins, G_7, VGGRTGLRGRPAMLPSGPGGAPSLWRCPYWHSPASTPSAWHAFATTPPGPLTWHLG EPACPVSEAGGAGRGFRGGGGRPCSRMPQHPHHLHLSHA, (SEQIDNO:9073); XM_014114294.1, TECPR1, Ins, G_7, VGNHRRARGPPVRMGCVSAGQGVVQRGRQPPQPRRLIVVPHGHPRGGGADQLWAP RPPVGHALGGAGLGPGRNQQEQSQRKFLVHSGASHL, (SEQIDNO:9075); XM_014121983.1, ADGRL1, Ins, G_7, VGRGPPPF, (SEQIDNO:9076); XM_843208.4, SPATA24, Ins, G_7, VGVGVSRLRSTAGRDRISGGTDPAAEERDGSPGRKFCQ, (SEQIDNO:9077); XM_005634338.2, EOMES, Ins, G_7, VLCFLHNSL, (SEQIDNO:9078); XM_843185.4, ATP12A, Ins, G_7, VLHPSVDRSHPVLDCVWDPVLHE, (SEQIDNO:9079); XM_014120548.1, GRHL1, Ins, G_7, VLQTHSHRDL, (SEQIDNO:9081); XM_005624466.2, KCNH4, Ins, G_7, VPLPPPPLQRPQGRVGRPHPPCHLLRCGHRPLQCLLLGR, (SEQIDNO:9082); XM_003639890.1, LOC100856687, Ins, G_7, VPPAAETHLLCRLHDPAVLLQLPGVHRMRAPGLHGLRPLRGHLPPPALPSHHDHGA LRPAGGLLLRQRLLHLYDQGVLCLQGHVLWLQRPEPLLL, (SEQIDNO:9083); XM_014116198.1, RAC3, Ins, G_7, VPRAPSPQGRDSVA, (SEQIDNO:9084); XM_014122205.1, LOC106560134, Ins, G_7, VQCLSLLLCGNQEAGPGQSSCGLSPVSLGNS, (SEQIDNO:9085); XM_014121155.1, CD6, Ins, G_7, VQMDACRRTESAGQVCVRVFTSGCHSPKNLLRSPDSSPI, (SEQIDNO:9086); XM_541287.5, TMEM2, Ins, G_7, VQPRDVRGWPFYSSQLLTVHHRAWDKWPAD, (SEQIDNO:9087); XM_005628594.2, HDAC9, Ins, G_7, VQSDSKMLWSFDEAIDDIG, (SEQIDNO:9088); XM_531653.5, XRCC6BP1, Ins, G_7, VRARAPLQRLLQRPGVPAAAPEDAGDKSLCQTSA, (SEQIDNO:9089); XM_014111629.1, ARHGAP6, Ins, G_7, VRGLPSGVPRVQHAPHPGRQKVGAGRTQGRAVLDSEQRRRPHRE, (SEQIDNO:9090); XM_545627.5, CPS1, Ins, G_7, VRLRNLSH, (SEQIDNO:9091); NM_001103215.1, COL6A3, Ins, G_7, VRPEHWLGPELCPCQPLHRSWRQQDPRTRAAALAPAHSRAV, (SEQIDNO:9092); XM_014112406.1, NMBR, Ins, G_7, VRPGLSARLGRDRRQVRHPLRDPVPLPAHHRRGLAGQHHAGEDLHHHQRHEERPQ HLHL, (SEQIDNO:9093); XM_014109896.1, LOC106558120, Ins, G_7, VRVGGRLPAPRAALRRSWLPHLPGWRPIADQGATGKRKEQPYLWTPSPEEEKGSAC KFKG, (SEQIDNO:9094); XM_005633207.1, SAMD1, Ins, G_7, VSLCCHWARLPIPCAFAPRKTSPARG, (SEQIDNO:9096); XM_014116695.1, BZRAP1, Ins, G_7, VTGHERQGVGSPLQGKATPKETGLWEKGV, (SEQIDNO:9097); XM_540709.1, OR14DL1, Ins, G_7, VYPCSNTASLHVSTTLLWPQCY, (SEQIDNO:9099); XM_005641605.2, TCEA14, Ins, G_7, VYVDAKKFTGPLPPEGPKGTEGWVQGPTEGL, (SEQIDNO:9100); XM_005615822.1, RASEF, Ins, G_8, AAASRGSPPARARARARARLSVGGARPRRRRGRGRGRGRGRRGRAGGRLGSG EPRPGLAGLPGATRRRGQIHPQKRTS, (SEQIDNO:9101); XM_844530.4, GAS6, Ins, G_8, AALRQRCQRVWPAERGLQPHLFQQAGQLPLCLLQRLRALP, (SEQIDNO:9102); XM_005620318.2, PLSCR3, Ins, G_8, AAPRSPHRCR, (SEQIDNO:9103); XM_014111383.1, RBM10, Ins, G_8, AGAQAQPHWPPRFPPRRGLSGPGLSAPPMGGSGPF, (SEQIDNO:9104); XM_005638688.1, MYO5A, Ins, G_8, AGARAGVGPLVPWSPAVRYLRATPRALFGSMPPASAGRASCFRIAFEGSVLSLLYRR QYF, (SEQIDNO:9105); XM_005642352.1, LOC102157319, Ins, G_8, AGFCRGSHSCRAQPRT1, (SEQIDNO:9106); XM_014116572.1, LOC106559285, Ins, G_8, AGGERDPRSQTPDALAAGEGASCALDARARRGGPVAGREEAPRAGAKGGPCRPAT APGRAPGTRAPT, (SEQIDNO:9107); XM_005616888.2, CAPN12, Ins, G_8, AHPQVHCPSVTHPAQPAAPEGPGPHLPHRGLPCVPAAGGRTAGIREVAAGPWGGAH RDCLGSEVACPRLPPEQPADPGPH, (SEQIDNO:9108); XM_014117109.1, ESYT1, Ins, G_8, AHTRPLLGAAAAAAPATRGQAPGRPGRAPGPGGPGAADRVVPR, (SEQIDNO:9109); XM_546961.5, GAL3ST4, Ins, G_8, ALPEEATRPAAPTALGPIPEIGCIILPTPAATCVPEDS, (SEQIDNO:9110); XM_858955.4, GLYR1, Ins, G_8, ALSGSPSLRESAAV, (SEQIDNO:9111); XM_003639258.3, DOC2B, Ins, G_8, APPQPPGGKPGPRGLKFRRLQKLYCPGHAGFQPALRPGKQRPPLYHQQGQGPEADG PQRASRPLCQAASAARSQ, (SEQIDNO:9112); XM_859724.4, NRAP, Ins, G_8, ARGCGARRESEGGREPRRHRDSARQKEEGSAVV, (SEQIDNO:9113); XM_005630524.2, PCGF1, Ins, G_8, DAGARSGD, (SEQIDNO:9114); XM_005619129.2, GPRIN2, Ins, G_8, DVPVQVPQGAPRALPLLCPPLGSRRVRHGACCQDQGRVDHDFGQ, (SEQIDNO:9116); XM_005628195.2, PDGFRA, Ins, G_8, EPKPARGPKVFRNYGDFPSGTPDLRLSPRRAQPNPLPAFITLDPSK, (SEQIDNO:9117); XM_014120653.1, PRKAB2, Ins, G_8, ERHGAKVFSCRGCRRPRPFKGAQDHGGEYGRPQRLQPAGPQAPWGQRVCIMATGF GGLRKAHTAGSAHCYPMV, (SEQIDNO:9118); XM_014107586.1, GALNTL6, Ins, G_8, ESNCAFVLQMPNS1, (SEQIDNO:9119); XM_538860.5, RGL2, Del, G_8, GAALTSSATSGSGWTPRPPTFLSPWPSPAIPLLTPRMSWCSSLTTWPNS, (SEQIDNO:9120); XM_014117556.1, LOC102156852, Del, G_8, GAEEAAARRAAGPERRCNPSRGPRPLPAGPS, (SEQIDNO:

9121); XM_0141 19807.1, ATG9B, Del, G_8, GAEGGQGGGETWGQVPCLSSPYPCLLFLLLLVGGLAEGGFPSSLCPLPPTQEAPLPL WPWDHPAQRCRPRGPLTLATAPSPPGQHRHSL, (SEQIDNO:9122); XM_858955.4, GLYR1, Del, G_8, GAFWKPQSQGISSCLMMGCW, (SEQIDNO:9123); XM_014115679.1, NPAS3, Del, G_8, GAGAGARGARAAGAAAGARARARAAAPARPTPCCTLGTWRRCRGCRRATSCSRW CTG, (SEQIDNO:9124); XM_014112777.1, LOC102154969, Del, G_8, GAGAHGRSGAPALGARAEGEEAAAAAAEVEAASWKGDRVQDGVESWRFPGLRWK LERCFYLQALRMRS, (SEQIDNO:9125); XM_547168.3, CLDN6, Del, G_8, GAGAQVIIWPDTQHLPHMPPLRVPPSTPLRIMS, (SEQIDNO:9126); XM_005619129.2, GPRIN2, Del, G_8, GAGGGARFEPSCSPCGALAAAAAPAPPPS, (SEQIDNO:9127); XM_005625650.2, NXPH4, Ins, G_8, GAGGGRAGRPLRGRAGSAGGQGVPRLQLPRGV, (SEQIDNO:9128); XM_014114294.1, TECPR1, Del, G_8, GAGITSLSGPMPPEPSGAGPRRQPLTGVGSRASPARRRGWLEPRRRPVALSAA, (SEQIDNO:9129); XM_005628806.2, CPED1, Del, G_8, GAGLCRSLSTLRELSPRARPLVLRRTGCVAPGPPGLSPWPAGLPWAAPGRRP, (SEQIDNO:9130); XM_539064.5, LIN28B, Ins, G_8, GAGLHLTALPPGGQVRGLRMAGQVIPRRFLSKGICSAGGTKQKGAFCSKKEKDL, (SEQIDNO:9131); XM_005615669.2, TNFRSF11A, Del, G_8, GAGNPSWLPRKVDLCPSAPTAWAFRPRVQQMGPASPWTGLTSGFPAP, (SEQIDNO:9132); XM_848851.3, FAMIO1B, Del, G_8, GAGSARRPPGRWSPTRRRAPRPRIQHLSPAHWPLPAHQGCALCPLVKEWSLIPYRQR K, (SEQIDNO:9133); XM_014118915.1, CTTNBP2, Del, G_8, GAGTRGAALPPRRGAQLPAGGGPRGSPQPGRGGEGRGGGATGQRPGERGCRVPLA KLASLHRKLSGKIDFSFFARKTKKSLMWTPSVNQSSGCSSA, (SEQIDNO:9135); XM_005628195.2, PDGFRA, Del, G_8, GAKACSGTESFPELWGLPFWHS, (SEQIDNO:9136); XM_005619219.2, KCNIP1, Del, G_8, GAKKKHSNKTTPRFSPMEMPACMPITSSTPSTPPRQAP, (SEQIDNO:9137); XM_536395.5, VCL, Del, G_8, GAKPNFALRRKSQNHIRVLLSLPCP, (SEQIDNO:9138); XM_014144471., METRN, Del, G_8, GALAPSSSWAGATLGRPGWAVHLTSRSSAEPTQLPTPAASTSARWPWT, (SEQIDNO:9139); XM_005632929.2, ARHGEF18, Del, G_8, GALCPPPPCHCPPPRSARKKAARKTSSSS, (SEQIDNO:9140); XM_014106895.1, LOC100683453, Del, G_8, GALGTWHWTRHAARAPSDPGNTPWGSPSPGIRRAGPRGGPPQSRPGGAHPRAAPTA HGPQPWARTVPGTRGSQKPLGQWRPD, (SEQIDNO:9141); XM_532350.5, GPAA1, Del, G_8, GALNLVLLSSQHRVWGWPRLWRLC, (SEQIDNO:9142); XM_548255.6, TAF15, Del, G_8, GAMEETAVVAGATVETEVAATEETEVGAAMEETEEAMEAKWEEETTTEMISATDH T, (SEQIDNO:9143); XM_542166.4, ZBTB7A, Del, G_8, GAMGAPGPPPRAASRPDLP, (SEQIDNO:9144); XM_005628310.2, OPLAH, Del, G_8, GAPASSSGLASLWWGLSPQEPILAPPATARGAP, (SEQIDNO:9145); NM_001131049.1, DNM1, Ins, G_8, GAPRALQAGGFP, (SEQIDNO:9146); XM_014116623.1, HOXB2, Del, G_8, GAPRARPRGWSPSRCRKMPSRSARILLSCPTSTSSRSTPVSSCPEASPPACRARSTARF PFPRKSWTSSPAPSVPSTCSSL, (SEQIDNO:9147); XM_845159.3, PBX2, Del, G_8, GAQPQLLQLLQPPGAACPLTTPLSTPTTAANLPRSATSTTQSWRSMSRPVTSSRPTS, (SEQIDNO:9148); XM_014114946.1, PTPN7, Del, G_8, GAREHGRPPGLWGEP, (SEQIDNO:9149); XM_535406.5, FBXO2, Del, G_8, GARGGASVPSLPLLGCAPRTPRPTQTRGPSPPPAAPLERAPRSDPPSR, (SEQIDNO:9150); XM_014117986.1, LOC106559521, Del, G_8, GARKPRPEPRELANSWRGLGHPRPPQSHL, (SEQIDNO:9151); XM_532334.4, KCNQ3, Del, G_8, GARRRRATRSAKWGWRRATRSKSPWRSGPGRTKTGPCCWRAAAATRGCGGPRRA SGSWPRPP, (SEQIDNO:9153); XM_543651.3, KRT82, Del, G_8, GASEPWAAWAPGACATWASGGPGWPPGAACLASGTEWGPSPDPRPASPPSPSTRAC WSHSSWR STRLCRG, (SEQIDNO:9154); XM_005618715.2, MYL5, Del, G_8, GASGPRGHPPTSFPTLSRPRSRSSRRRSR, (SEQIDNO:9155); XM_005616888.2, CAPN12, Del, G_8, GASPSALSFCHSSSATGGA, (SEQIDNO:9156); XM_531943.5, ADAMTS1L, Del, G_8, GASRAGQFPVWRRTSRGMSPQWKSGNACTPLRCPSCSPATFLTVLNGWHRSGLRAR (SEQIDNO:9157); XM_005628310.2, OPLAH, Del, G_8, GATGTQRTPCHHRGRPSTSPPSLSGAASTSTAGPRRPC, (SEQIDNO:9158); XM_005626996.1, KLF4, Del, G_8, GAVLFLSQVRNPTTVIGTAVGGNSPARTN, (SEQIDNO:9159); XM_014111649.1, LOC106558441, Del, G_8, GAVQAPTGMLQPRPVAWLPRFPVLIAEL, (SEQIDNO:9160); XM_014111170.1, PLEKHM2, Ins, G_8, GAVRWLSEGQHHGSAPRLPGHPRRPAVPGAERRERG, (SEQIDNO:9161); XM_005616263.1, LRRC4B, Del, G_8, GAWAGTVTWPCPPWSATISTITITWRPPSRRTIAATPAAGAAGARAPRGSTPSTNLCS SRVAPRRMCKRRRS, (SEQIDNO:9162); XM_846128.4, HOXB7, Del, G_8, GAWRARVQPASTRPATGSSRVPSTCTARPLSRTSPGCVPATPPRRRAPRSRGTRTWR PRVTSGSTPGCEAQGRTESEAARPTPATRPWSWRRSFTTIAT, (SEQIDNO:9163); XM_014114365.1, SETD1A, Del, G_8, GCPCPSRCKPRC, (SEQIDNO:9165); XM 014114498.1, C6H16orf92, Del, G_8, GCPQLPVPSSFSLPSLQSCAQNGSRL, (SEQIDNO:9166); XM_539064.5, LIN28B, Del, G_8, GCRAAPHRPSPRRPGSRSQNGRAGHPKTLPQQGHLQCRRNQAKRGL1FKKGKRP, (SEQIDNO:9167); XM_005620318.2, PLSCR3, Del, G_8, GCSKKPSQMQMTSACSSLWIWT, (SEQIDNO:9168); XM_547555.4, EFNA4, Ins, G_8, GCSQPPLSLAALAAPNSASPASSL, (SEQIDNO:9169); XM_014112314.1, ACAN, Ins, G_8, GCVPLPPRLRPL1TD1, (SEQIDNO:9170); XM_014119028.1, NRF1, Del, G_8, GDRSSCLGKPQQLSEHLLESKMLMDWSRSL, (SEQIDNO:9173); XM_014119037.1, NRF1, Del, G_8, GDRSSCLGKPQQLSEHLLESKMLMVPTSF, (SEQIDNO:9174); XM_014110056.1, LOC102151348, Del, G_8, GEEGEMAQNVGTLSPSRRAAGTPPGMRRLTTSPPTRSS, (SEQIDNO:9175); NM_001003009.2, TPO, Del, G_8, GEHSPSWASRCWWPSRAASSPSSSEAGTSCGDRAERPVSLAS WRRAGAWWTAPSST P, (SEQIDNO:9177); XM_538859.5, WDR46, Del, G_8, GEISGKRPPGKMTKSGRALSNSHRSKRRKPSP, (SEQIDNO:9178); XM_854614.4, MBD6, Del, G_8, GELRHPSRRLLVP, (SEQIDNO:9179); XM_005629758.2, PSD3, Del, G_8, GEMMISLGMGMQRTPLMCTAPSLKLFW TTLRYTT TVLNPWRHYIQNPIAILALTCPSL R, (SEQIDNO:9180); XM_005629149.1, TPPP2, Ins, G_8, GEPADRHQQVHGQPQGAFRREWQGQRHRRPGRGDRQLRLCNAPPDGEQEKHCHV SEERNAA, (SEQIDNO:9182); NM_001284460.1, HTRA2, Del, G_8, GFTRGRDPC, (SEQIDNO:9184); XM_005626238.1, EPCAM, Ins, G_8, GGAGAEGP- PRGVGGRPPPPHLLPPGAGRWPRMCASRGHRWLRG-GRAARTCAGAGP GPQRLARCPLVMYL, (SEQIDNO: 9185); XM_014118903.1, LOC102156909, Ins, G_8, GGGAARPGSLTVTRGAAPSGAAPARRGPRTVSR-GRRSRPLGLERQACRRPAAADTG RGRGGQRTA-SAEAGRCCNLRPRLRTAPS, (SEQIDNO:9187); XM_005641356.2, SHROOM4, Ins, G-8, GGG-GAATPVFQFRNHWYECPPSRRGPGAATILGLWSFGG-SKAGPAKLSGRARVL, (SEQIDNO:9188); XM_532250.5, QRS1L, Ins, G_8, GGGGEGDRTLSTP, (SEQIDNO:9189); XM_005626232.1, LOC102151375, Del, G_8, GGGGLKIAQQPGAEATAGANKR-GAQRPSLESDPCNTQEASGSARLAPAPGGRGKED SRARSRAPPPPHTPALSPSSGATTRAPP, (SEQIDNO: 9190); XM_014112752.1, TRIM67, Ins, G_8, GGGGWKRIGPLPPAFSLAV, (SEQIDNO:9191); XM_005638688.1, MYOSA, Del, G_8, GGGTGRGRSPG-PLVPGSSLPACNP, (SEQIDNO:9194); XM_014111383.1, RBM10, Del, G_8, GGGTGTAPLAPQVS-PETGTFGTGTFGPTNGRIWPFLRRRRRRRSPVTSSC, (SEQIDNO:9195); XM_014106932.1, LOC106557687, Ins, G_8, GGNKQTSPWT, (SEQIDNO:9196); XM_005627459.2, C12H6orf141, Ins, G_8, GGR-GRRPGRLPRRLPRDPPGRRRAGL, (SEQIDNO:9197); XM_005615822.1, RASEF, Del, G_8, GGRQPGLPAGPR-PRPRPRPAQRRRRPTPKTAARTRARTRARARATGTR-GRPPGVGR APARPGGTSRSDSATRPNSS-PEKNKLAPCI, (SEQIDNO:9198); XM_014116572.1, LOC106559285, Del, G_8, GGRRKGSALPDPGRPGRG-GRGV VRPGRARPTRGTSRRAGGSAQG-GRQRRSLPTCDG PGKGSGNAGSDLRASSKPQGPR, (SEQIDNO:9199); XM_014121384.1, MYO7B, Del, G_8, GGSNYPAQVVSPALLSPLTWLPGLWRTPGQAPS, (SEQIDNO:9201); XM_847261.3, FOXA1, Del, G_8, GGSWILGRELNSS, (SEQIDNO:9202); XM_005625313.2, DPM2, Ins, G_8, GGTLLSWDT, (SEQIDNO:9203); XM_014120933.1, LOC100687378, Del, G_8, GHCPLHTSLPTAGHCPPVPTAGSLPTAHL-AAPLDPWYKGSPQCA, (SEQIDNO:9205); XM_537262.4, DENND4B, Ins, G_8, GHGGGAAPPAG-GLLRDSRACRERSSHSRGDTGSRTQWAPAPSPAS-RAHHRHGGHCS GTGRGSAPGLHLHPVLRWGP-PLGTQCRALGWNAARHLLPQGP, (SEQIDNO:9206); XM_846128.4, HOXB7, Ins, G_8, GHGGPECSRRLR-GRLRARAEFLQHALRAL, (SEQIDNO:9207); XM_531943.5, ADAMTS1L, Ins, G_8, GHPEPGSFLCGGGHPGACHLSGRVEMHVHP, (SEQIDNO:9208); XM_014116616.1, TBKBP1, Ins, G_8, GHVLRLPLCPHHSLWGHQGAAGRPGKGECHPPTP-SQSLRDQVPTDQRLWRGARLLP V, (SEQIDNO:9209); XM_537179.5, PAPPA2, Del, G_8, GIALRMATIFVGT-WAHWSSGQLPFHKATSNTVLSIQLEWEN, (SEQIDNO:9210); XM_538859.5, WDR46, Ins, G_8, GKFLEKGPPVK, (SEQIDNO:9211); XM_005624024.1, CCDC40, Del, G_8, GKKWGPWILKSRG, (SEQIDNO:9212); XM_005629705.2, INSIGI, Del, G-8, GLAA-LAAAPRAAGTTTWCDGAWCCSRWGSCWPWCSTC-CRCSGTSRCSPRRSSPPSS RRPGGSRRAAGRRPLWWACCTPASTVTWENHTSL-RESGPA, (SEQIDNO:9213); XM_014111649.1, LOC106558441, Ins, G_8, GLCRR-PRGCSSPGPWPGSRGSLC, (SEQIDNO:9215); XM_014112314.1, ACAN, Del, G_8, GLCSTTAQAP-PATH, (SEQIDNO:9216); XM_005624124.2, CD300LF, Del, G_8, GLEGSRCGGCRAS, (SEQIDNO:9217); XM_014117986.1, LOC106559521, Ins, G_8, GLGN-RAPSRES, (SEQIDNO:9218); XM_014114294.1, TECPR1, Ins, G_8, GLGSHHCPGQCHQSLQEQVPGDSH, (SEQIDNO:9219); XM_014113657.1, SOGA3, Ins, G_8, GLLEGRM-PAV, (SEQIDNO:9221); XM_538741.5, SHB, Ins, G_8, GLLGRPHLEPDGLRWQETAQQVCRLGRGGER-GRQEGQGDHC, (SEQIDNO:9222); XM_005628310.2, OPLAH, Ins, G_8, GLPPLLQVWPLCGGA, (SEQIDNO:9223); NM_001284453.1, PSMB7, Ins, G_8, GLQGWHSS-WSRYKGN, (SEQIDNO:9224); XM_005628310.2, OPLAH, Ins, G_8, GLRGPRGPRATIGVAPAHPRLP, (SEQIDNO:9225); XM_014116869.1, CAMSAP1, Ins, G_8, GLRGRAAGVQGCRPPETAVGPSGGGWGLWGGG-NAA, (SEQIDNO:9226); XM_549094.4, FGF16, Ins, G_8, GLRLLGLGSARLLLVCGERAHS, (SEQIDNO:9227); XM_845159.3, PBX2, Ins, G_8, GLSRSCCSCCSLR-GRRVP, (SEQIDNO:9228); XM_014119359.1, CCDC9, Del, G_8, GLTLSGCAAAWSRSGRAAGPAWAALAT, (SEQIDNO:9229); XM_548255.6, TAF15, Ins, G_8, GLWRRPRWWRGLRWRPRWRLRRRQKWGRLWRR-PRRLWRQNGRKKRLQK, (SEQIDNO:9230); XM_545391.3, LOC488269, Del, G_8, GPAPPRRALRRP-PRRPRSPPRPQEPKRPKAPRRRKRPSPRRR-PRALRRPKL, (SEQIDNO:9232); XM_538741.5, SHB, Del, G_8, GPARAAAPGARRPAVARNCSTSVPPRPRR-RAGPARRTR, (SEQIDNO:9233); XM_005616622.2, SPRED3, Del, G_8, GPARGTTSSTGSAFGTRKPPWSVP, (SEQIDNO:9234); XM_014109368.1, LOC106558038, Ins, G_8, GPATPPPFGFGVCCFRCGIFTGGFWARLTEW-LRAPRCRQRRAFPLSSGCGRDRTRPR SPSR-ERPSWAAGARWVGPSWAHCSP, (SEQIDNO:9236); XM_005632929.2, ARHGEF18, Ins, G_8, GPCAPLPLA-TAHHPAQQGRKQQGRRHLLL, (SEQIDNO:9237); XM_005616205.2, LOC476396, Del, G_8, GPCRRMQSMSSECRNQ, (SEQIDNO:9238); XM_005619129.2, GPRIN2, Ins, G_8, GPEG-PASSRHAVPAAP, (SEQIDNO:9239); XM_547168.3, CLDN6, Ins, G_8, GPELKSLYGPILSICRTCH-LSVCPRVPH, (SEQIDNO:9240); XM_014111152.1, HHIPL2, Ins, G_8, GPEWLGPQAPC1, (SEQIDNO:9241); XM_005626996.1, KLF4, Ins, G_8, GPFSSSPR, (SEQIDNO:9242); XM_014120955.1, NRXN2, Del, G_8, GPGEEEPAMCTSQRKARRSLWRPSKAMSSSATTCRI-TRSRAARTRSLWPSAPCSATG, (SEQIDNO:9243); XM_014118248.1, LOC106559564, Del, G_8, GPGPA-PRALRAPPARGPSHLALKVSPSAACP-PRLWQLVPSSGVRPRAAPAAPSRTPP AARP, (SEQIDNO:9245); XM_014113209.1, ADAMTS8, Del, G_8, GPGPGAARGCAAASSRAPWTARPGRWRPSACAGA, (SEQIDNO:9246); XM_005615669.2, TNFRSF11A, Ins, G_8, GPGTPRGFPEKWT-SAPVRLRHGPSARGCSRWGRPAPGRG, (SEQIDNO:9249); XM_547055.4, TBC1D10B, Ins, G_8, GPLSTSS-CPQG, (SEQIDNO:9251); XM_005616622.2, SPRED3, Ins, G_8, GPPGALRHPRGAPSGPENHLGVYPEARL-GLQQSEPHFSSLEPG, (SEQIDNO:9252); XM_005618715.2, MYL5, Ins, G_8, GPPGPE-GILQRLFQL, (SEQIDNO:9253); XM_542234.5, MAML2, Del, G_8, GPPGRGSLEGARSPRGCTAPSWSACGLGLP-SAASTT, (SEQIDNO:9254); XM_844466.4, MAZ, Del, G_8, GPPPLSRETPPSHSPPV, (SEQIDNO:9255); XM_014118241.1, NOTCH4, Ins, G_8, GPPQTLCPWR-PLPEPISWTRDLPVCTWLPG, (SEQIDNO:9257); XM_014121544.1, TTL13, Ins, G_8, GPQTAAQQAGGL, (SEQIDNO:9259); XM_542234.5, MAML2, Ins, G_8, GPRGGAPWRGLGHPEGAQRHRGAPAGSDCHLPPAP-PELRRPL, (SEQIDNO:9260); XM_014109368.1, LOC106558038, Del, G_8, GPRHAAPLRVWGLLF, (SE- QIDNO:9261); XM_005616802.2, PLEKHF1, Del, G_8, GPSAGPPVGTTRTPTRTRRAEGTATGPATWSST-PRACPGQPFTA, (SEQIDNO:9262); XM_003638990.3, SYNPO2L, Del, G_8, GPSRGNLYRCPRSEDGAR-LAEQDSERGTSFWPSMGSPAPASPMPVP, (SEQIDNO: 9263); XM_546961.5, GAL3ST4, Del, G_8, GPSRR-GYQACSSDSPWPHP, (SEQIDNO:9264); XM_547737.5, JPH4, Del, G_8, GPVNRQRN, (SEQIDNO:9265); XM_014119783.1, SSPO, Ins, G_8, GPVPEEPQLLKP-PAQERGCPLCWGEAPVSALQPLAL, (SEQIDNO:9266); XM_005641468.2, ITGB1BP2, Del, G_8, GPVTTQN-SWRG, (SEQIDNO:9267); XM_537262.4, DENND4B, Del, G_8, GPWRRSGPPGWWITS, (SEQIDNO:9269); XM_005628806.2, CPED1, Ins, G_8, GQASVAR-SPHSGNCPHVQGPSCSGVPGVWRPDPLASPR-GRQVSRGPRRAAALSEAW S, (SEQIDNO:9270); XM_003639170.3, SLC27A3, Del, G_8, GQGPGGRPA-GALLATFDFLGRKGAGGGPAGKGRVPAHARSRGRG, (SEQIDNO:9271); XM_005621751.2, CAPN15, Ins, G_8, GQHEGGRRCL, (SEQIDNO:9272); XM_005625443.2, FUBP3, Ins, G_8, GQQSCPTPSSQGS, (SEQIDNO:9273); XM_859724.4, NRAP, Del, G_8, GQRLWSPQRIRGGT, (SEQIDNO:9274); XM_005619219.2, KCNIP1, Ins, G_8, GQRRNIQTKPRPGFPPWRCQHVCPLPL-PRLRHHPDRLREVRGLCNCSVNFTERNRP, (SEQIDNO:9275); XM_014106959.1, ADCY7, Ins, G_8, GQSKWPCSWHLCQP, (SEQIDNO:9276); XM_003638990.3, SYNPO2L, Ins, G_8, GRAEETFTGVQDPKTEPGWQSRT-PREGPAFGHQWGLLHQPLPCQCHEPHRCLRESA YPHSAAGRG, (SEQIDNO:9277); XM_014106932.1, LOC106557687, Del, G_8, GREQTNKPLDVIGH-GIRQSSQSPAHGLVRGRRGHLGRRCRRVSQGR-GRAGPRPPRA RPAGGRASGVRAPLRG-GAPRPPTAVRRPPGVRSGPGSLRDRLM, (SEQIDNO:9279); XM_014120955.1, NRXN2, Ins, G_8, GRERRSRRCAPANERQGGVCGDLQRQ, (SEQIDNO:9280); XM_005619419.2, GOLPH3, Del, G_8, GRGAGGGFHLHEDVARNPTALWSP, (SEQIDNO:9281); XM_848851.3, FAM101B, Ins, G_8, GRGAL-GGPRDAGARRGGEPRGPESST-SPQPTGLCLLTKAVPSVLW, (SEQIDNO:9282); XM_014118866.1, LOC102157316, Del, G_8, GRGGA-RACGLGLVLTPGPQETAAGTEGGGSTAQSPASGAED-EQVAACLRPSHQTKE VTSLWPKG, (SEQIDNO:9283); XM_005616263.1, LRRC4B, Ins, G_8, GRGRGQSPGPARPGARPPQPPPLRG-GRLQGALQRQPQRRGLRGQGPPGAQLHPRTS ALQEWLQGECARDADL, (SEQIDNO:9285); XM_014115679.1, NPAS3, Ins, G_8, GRGRGRGGGRGRR-GRRRGRGRGRGRRPRRGQLLAVHWGPGGAAE-VAGGGQRRAPAG AQGDGDPGRHQHGGAE-GLHHRHHPLRARRGDPGHAGQPAAQRARC, (SEQIDNO:9287); XM_014116573.1, DACT3, Ins, G_8, GRGRPSSPPPLPQPGPGPWHVRRA, (SEQIDNO:9288); XM_005625313.2, DPM2, Del, G_8, GRHPPVLGHVVAGPPTDYDSRRAPRLRAGKPRIRI-RAAASGWGVRSRGTWPRGQTR WWDSASSPLA, (SEQIDNO:9290); XM_545391.3, LOC488269, Ins, G_8, GRHPQEER, (SEQIDNO:9291); XM_005621006.2, TRIM56, Ins, G_8, GRHRGASHGPVPGLCG, (SEQIDNO:9292); XM_014116623.1, HOXB2, Ins, G_8, GRLARGRGVGARAVAGRCLPGAPGFSFPARPQLLR-GRLLSPAVRRPLPQPAGLARQP GSLFR-GRAGLLHQHPLCHRPAVPL, (SEQIDNO:9293); XM_844466.4, MAZ, Ins, G_8, GRPPCPGRRPPATAHLL, (SEQIDNO:9294); NM_001131049.1, DNM1, Del, G_8, GRPPCPPGRGLPLTPSVLP-PRCPRAPTAPRPGSPADRVRQVRPVLRAPGPPSTS, (SEQIDNO:9295); XM_005617051.2, SVIL, Del, G_8, GRPPRMSGSLPSRRF, (SEQIDNO:9296); XM_847680.4, CHERP, Ins, G_8, GRPRQVGPVQGCGRGPGRSIRE-LPPEQELLLHRPHEGQGRVQV, (SEQIDNO:9298); XM_546016.5, ELL2, Del, G_8, GRRACGRS-SATGCRAGGWDRTTSRCCM, (SEQIDNO:9299); XM_014110056.1, LOC102151348, Ins, G_8, GRRGR-WHRM, (SEQIDNO:9301); XM_005638682.2, SHF, Ins, G_8, GRRRRWGQAGAPRAGLPSPRTLPGRAPCTTPGHPGRL-PAAEGARLRRPLLWGAVQL RCCPGHPHRPR-PHAAPAPRLASPPPYTG, (SEQIDNO:9305); XM_005641356.2, SHROOM4, Del, G_8, GRRRSCHP-SISVQKPLV, (SEQIDNO:9306); XM_005624024.1, CCDC40, Ins, G_8, GRSGAPGS, (SEQIDNO:9307); XM_014108010.1, MYO18B, Ins, G_8, GRSPRGGQSR-RASQCTWEVR, (SEQIDNO:9308); XM_005616802.2, PLEKHFI, Ins, G_8, GRVRGLQWGRRGLRRGQGGRR-GRRLAQPRGVLRLGRVLVSLSRL, (SEQIDNO:9309); XM_542166.4, ZBTB7A, Ins, G_8, GRWGRRGPRRGQLRGRTCL, (SEQIDNO:9311); XM_533258.5, SLC22A6, Del, G_8, GSAASSKSRSLWWSSPCS, (SEQIDNO:9312); XM_014106959.1, ADCY7, Del, G_8, GSEQVAMQLAPL-PALTAPVAPSTAWRPSPGPATTSPAPASSSSASCWST-SCSCPGW, (SEQIDNO:9313); XM_544921.5, AIRE, Del, G_8, GSFILPASSKTPVGGRTGPVAAA, (SEQIDNO:9314); XM_014114463.1, LOC106558915, Ins, G_8, GSGAGARTGSCPLHCRTSAELRGHKSLVRCLPSN, (SEQIDNO:9315); XM_014117109.1, ESYT1, Del, G_8, GSHTAPPRRRSCGSACHTRTGPRTPRPGPRAR-WARCS, (SEQIDNO:9316); NM_001284460.1, HTRA2, Ins, G_8, GSLGEGTPADP, (SEQIDNO:9317); XM_547541.5, UBQLN4, Ins, G_8, GSLPWGWGGTPQ-CYCIHTLWLWGHLGPGQPGPRLRQLHGAAAA-DAETADVQS, (SEQIDNO:9318); XM_854614.4, MBD6, Ins, G_8, GSSATPPGGF, (SEQIDNO:9320); XM_014111170.1, PLEKHM2, Del, G_8, GSSAVA-VGGPTPRIGPTPSRSSSPTGRAWS, (SEQIDNO:9321); XM_014121544.1, TTL13, Del, G_8, GSSDCSTAS-WWALRPCRPQARP, (SEQIDNO:9322); XM_549094.4, FGF16, Del, G_8, GSSPPWTGICTASPRLWGTCP, (SEQIDNO:9323); XM_005628039.2, CCDC166, Del, G_8, GTALSRRCRSARSTCSARTRCSRRSWAPARRAW-TRCCGTTPSWTPRRCACARRTGS TPATRARA-PAAAPAPWCGWTSSTART, (SEQIDNO:9324); XM_014119028.1, NRF1, Ins, G_8, GTDRPVWGNRSS-CRSTYWSPRC, (SEQIDNO:9326); XM_014108010.1, MYO18B, Del, G_8, GTLPERWAKQA-SIPVHLGSQVSPGPR, (SEQIDNO:9327); XM_014118241.1, NOTCH4, Del, G_8, GTPPNPVP-MEAPA, (SEQIDNO:9328); XM_014120653.1, PRKAB2, Del, G_8, GTPRRQSLLVPRVPAATPL, (SEQIDNO:9329); XM_014116573.1, DACT3, Del, G_8, GTRAPQLPSPP-STAGPGALARPARLIWPDAIKSELGPA, (SEQIDNO:9330); XM_005625634.2, KCNC2, Ins, G_8, GTRVLLR-PAPGRVRLCAQLLPHRQAALPGRRVRAALRGGAG-LLGHRRDGRGALLL DDLPAAPRRRGGARHLRD-ARPPGWRPRRRRPGGQEAGH, (SEQIDNO:9331); XM_847680.4, CHERP, Del, G-8, GTSETSGT-STRVWAWPWTIHTRTTAGTRATPSSPA, (SEQIDNO:9332); XM_005640347.2, HOXD3, Del, G_8, GVAASLLA, (SEQIDNO:9333); XM_005639284.2, NEU-ROG2, Del, G_8, GVAEACRGRSSPRRCC, (SEQIDNO:9334); XM_005634924.1, ASXL1, Del, G_8, GVARVEVAAGPPMREVAEAAAVVMVVRPVATL-SPVEPRTPLESVRQNSEHNYCRL VL, (SEQIDNO:9335); XM_014122211.1, REXO1, Del, G_8, GVAVPWST-SPRL, (SEQIDNO:9336); XM_014114200.1, SRRT, Del, G_8, GVGALLMAPLSPGATQTSTSCSTMFCLSRPD-FLTGPPPGWAASQRLTWVCHHR, (SEQIDNO:9337); XM_003434769.3, SRRT, Del, G_8, GVGALLMAPLSP-GATQTSTSCSTMFCLSRPGWAASQRLTWVCHHR, (SEQIDNO:9338); XM_014114463.1, LOC106558915, Del, G_8, GVGSWSAHRILSLALPNLSGTAWPQVPGAV-SAIQLEDRLRLP, (SEQIDNO:9339); XM_547555.4, EFNA4, Del, G_8, GVLSAPSVSCCSCCSQFCVSCEFS, (SEQIDNO:9340); XM_544921.5, AIRE, Ins, G_8, GVLYSQQVRRPQWGEEQDP, (SEQIDNO:9341); XM_005642274.1, LOC102152225, Ins, G_8, GVPGR-SALGPPRKGRREARGGCWG-GASLRVCGRAFSGEPVA, (SEQIDNO:9342); XM_014114498.1, C6H16or192, Ins, G_8, GVPSSQF-PALSLFPPSRAVLRMAPGYDITEPPPL, (SEQIDNO:9344); XM_005628921.2, GJA9, Del, G_8, GWGLKCL-GIGEDWSKNSVSWNKGN, (SEQIDNO:9346); XM_003434769.3, SRRT, Ins, G_8, GWGPYLWPPSAL-GPPRRPHHAAPCSAYPGQAGQHRRD, (SEQIDNO:9347); XM_014114200.1, SRRT, Ins, G_8, GWGPYLWPP-SALGPPRRPHHAAPCSAYPGQTS, (SEQIDNO:9348); XM_005642352.1, LOC102157319, Del, G_8, GWILSRKPQL, (SEQIDNO:9349); XM_005624124.2, CD300LF, Ins, G_8, GWKGAGVEVAEQAERGKPREA-QSLCPSREEDLGFLSKVLQPQEGDLCYANL, (SEQIDNO:9350); XM_005634924.1, ASXL1, Ins, G_8, GWPGWRWRRGHR, (SEQIDNO:9351); XM_005640347.2, HOXD3, Ins, G_8, GWQPASWPEL-RAAATTTPSSTATSAPILTHQSWRWSACQEGQG-WAQCFGLLSHHQ QADLPLDER-VPTELQAKEQLCHCRRELRG, (SEQIDNO:9353); XM_005639284.2, NEUROG2, Ins, G_8, GWRRPAG-GALPRDGAAEPGRR, (SEQIDNO:9354); XM_014112752.1, TRIM67, Del, G_8, GWWRLEEDWT-SPTCLFSGS, (SEQIDNO:9355); XM_005617051.2, SVIL, Ins, G_8, VGHPECQEASHLEGSRK, (SEQIDNO:9356); XM_005616205.2, LOC476396, Ins, G_8, VPAGECRV, (SEQIDNO:9357); XM_536395.5, VCL, Ins, G_8, VQNQILLSGGNRRITFVCFCLYLAPEQRLC, (SEQIDNO:9358); XM_014120933.1, LOC100687378, Ins, G_8, VTAHCTPHCPLQVTAHLCPLPTLLPP, (SEQIDNO:9359); XM_005631747.1, SARTI, Ins, G_9, AGSGGKYHPGGVKKTPWGERGGRDDGGGQHRR-RHRAAAAAPGAQKTQAPERRW REQRWRTSE-AESGAWGRARGRAARDRSRDTQRRARAGARPG, (SEQIDNO:9360); XM_543055.4, SALL4, Ins, G_9, AKPHFPEGWWLPREWDPRAGVRDPEITAAGGEH-RQGHHRPQRMSHLPPGLELPKLP QDAL-PHPHRGEAVPV, (SEQIDNO:9361); XM_014116267.1, TMEM235, Del, G_9, GAAASVRVCARVCSCVCK-RVWVCPCVQESVHATRTSSIPGKATGSSGPRER, (SEQIDNO:9363); XM_014106250.1, LOC102153261, Del, G_9, GAAPPWPSLSLPAGP-PAPSARWWFSYQTMTAASQKCLRNTCTMRSHSS, (SEQIDNO:9365); XM_005642470.2, MED4, Del, G_9, GAARARRAGTARGSGCCLRWRTWRSCRENL, (SEQIDNO:9366); XM_014112086.1, LOC106558514, Del, G_9, GAGGVGCVSLAGLLSSQQLSSSPSEPRGCLWSFPGP-FLYVPPRPRLLGVWWERQLYP GLLRLLNRHWRD-SWGLGGT, (SEQIDNO:9367); XM_005635935.2, LOC102152569, Del, G_9, GALGTHCR-VARPSPGCPYRAPGRRGSGPRPGRQCS-PEKPTWGPGRPPHLCALYWSP, (SEQIDNO:9369); XM_005635268.2, OGFR, Del, G_9, GAPRSGPGRPSGPVPSPRGPRWPRR, (SEQIDNO:9371); XM_014107474.1, LOC477353, Del, G_9, GARCP-SASGLGRPVCHL, (SEQIDNO:9372); XM_014118660.1, RECQL4, Del, G_9, GARTPAVSPRRCRSPAAGGRT, (SEQIDNO:9373); XM_005633826.2, ATP7B1, Del, G_9. GASRPSWRPWVTRR, (SEQIDNO:9374); XM_014117894.1, ABCA1, Del, G_9, GASRSSP-STGTRTTTTKPSLVATARTKMLAASMTILRLLIAMI, (SEQIDNO:9375); XM_014121026.1, SPDYC, Del, G_9, GASSSSCPPNCN, (SEQIDNO:9376); XM_014113230.1, STX8, Del, G_9, GAVRRPGRCPEPCIGSHRTAGISR-PARIRAGGCGLPRTPPDSPGLPGQVQAE, (SEQIDNO:9377); XM_014114924.1, LOC607201, Del, G_9, GAWRAPGPWWRGWVAPASRH, (SEQIDNO:9378); XM_014106278.1, LOC106557553, Del, G_9, GEVKGPQESKEDRHRLPTYSLPGPARPQGRPLP-PAEWNPSTPGASPVTTVRIRVEMT AGVLTCFV, (SEQIDNO:9379); XM_536395.5, VCL, Ins, G_9, GFSPGGVQNQILLSGGNRRITFVCFCLYLAPEQRLC, (SEQIDNO:9380); XM_014117418.1, CELSR1, Ins, G_9, GGAVGSRRPAQSGAVVRSGGLRRGPR-GASGGGGQTARGPPTGGV, (SEQIDNO:9381); XM_014119249.1, CSMD2, Ins, G_9, GGDEVQGPNPEALDHSGFMAAL, (SEQIDNO:9382); XM_003639950.2, NCKAP5L, Ins, G_9, GGPRGQEGRLGLPLNPHPIQNV, (SEQIDNO:9383); XM_014120095.1, LOC102155747, Ins, G_9, GHCRG-GRAPGDCAVASATAARGRELGRAGAAVRPTR, (SEQIDNO:9384); XM_014107474.1, LOC477353, Ins, G_9, GHGALRHQASEGQFATCDSFRPQVPHRESRS, (SEQIDNO:9385); XM_539311.4, ADAMTS3, Del, G_9, GKAGNTGPGTGGSSGNSWAT-GAGFSPSWKGPNPSWTTRTGPGSGRTTAGPATGCPA PTSGKRALE, (SEQIDNO:9386); XM_014118660.1, RECQL4, Ins, G_9, GLGRPPCLPADAGAQLL-GAALESGSDAEASRRRLCARLCGGRGRLRGEA, (SEQIDNO:93 87); XM_014106250.1, LOC102153261, Ins, G_9, GLHRLGPRCLCLQGRLLRQQGGGFLTKR, (SEQIDNO:9388); XM_014121026.1, SPDYC, Ins, G_9, GLPHHPAPPTATRARHLHSLYPPEASTMPWAL, (SEQIDNO:9389); XM_014122483.1, LOC106560169, Ins, G_9, GLQEPVGAPSSARRSRPG-GRRTQEARVQLLPPGPAPPLVAEPGAAR-SAAAAWILQSA DEDGAATSGGDGGAGP, (SEQIDNO:9390); XM_014112072.1, LOC100688285, Ins, G_9, GLRGGTLGAAIGPRRDGAPCAPPGASAARPRSST-HAAMRARRGGRAGARGCRQPPG AAVHC, (SEQIDNO:9392); XM_014119640.1, TMEM55B, Del, G_9, GPAAGAPQPPFPVQRSPRSPRDTRPCSRARTRPPTRP, (SEQIDNO:9393); XM_014122483.1, LOC106560169, Del, G_9, GPAGAGGGALERTE-VEAWRTQDAGSSGPAAASGPRPAARR, (SEQIDNO:9394); XM_014114365.1, SETD1A, Del, G_9, GPAL-REKKLGPPPAQLHLPAPAPRPQRPPTRACPSLNIAAWI-PASRCC, (SEQIDNO:9395); XM_847576.4, ZNF428, Ins, G_9, GPGGPISSGPPCSPTPRPPSPALPALWPLTPWGGP-TRHPTLPALLPCYSPPGSSSP, (SEQIDNO:9396); XM_014117894.1, ABCA1, Ins, G_9, GPQDQVPQLVRGQQLQSPLWWQRHGRRCWQLL, (SEQIDNO:9397); XM_005635935.2, LOC102152569, Ins, G_9, GPWGRIAGWRGRPQDAHTAPPGDEAP-AHVPGDSAARRSRRGAQGALHTFALCIGV RRPQRKVGERRPRAWRRPASRVPTT, (SEQIDNO:9398); XM_005633826.2, ATP7B, Ins, G_9, GQAVLPGDPG, (SEQIDNO:9399); XM_014116516.1, DBF4B, Del, G_9, GQLFSVVLGPLTSLSPST, (SEQIDNO:9401); XM_543055.4, SALL4, Del, G_9, GQTTLPRGLVASKGVGPPSRGQRP, (SEQIDNO:9403); XM_003639950.2, NCKAP5L, Del, G_9, GRAPRAGGTTGAPPQPSSYSKC, (SEQIDNO:9404); XM_005635268.2, OGFR, Ins, G_9, GRPGAGRGGRAALSPAPGAQGGRGGEEEKEGGPGPGRRRPGGRRGRRRGGARGGR GARGAGVR, (SEQIDNO:9405); XM_014113503.1, CHRNE, Del, G_9, GRRALAPQLADVQCRGGGLRLRRGRRRRDHQQNRHRHRGLHG, (SEQIDNO:9406); XM_014117418.1, CELSR1, Del, G_9, GRRSGVEASCPERGGGQERGAAPGAAGGFRRRRPDSPRTSDGGC, (SEQIDNO:9408); XM_014106278.1, LOC106557553, Ins, G_9, GRSKVRKRAKKTGTGCQPTASRVPPGLRVGPCLLPSGIHPPRGPLLSRLCESVWR, (SEQIDNO:9409); XM_014115006.1, LOC106558992, Ins, G_9, GRWAAGGSPGAQGQRRSRPRRGRR, (SEQIDNO:9410); XM_014107345.1, LOC106557740, Del, G_9, GSGSRGAKDTFSNARVTPEPSRMKREAGGLAEPWAEDCCFPRVGSLTGPLPFGGFRC HRCSQRRGPRSAGSVRAFGTHPGAS, (SEQIDNO:9411); XM_014117984.1, LOC102154618, Ins, G_9, GSRNHGDGGRLGGATGSRTSAQGRTDRTGQGADHGGR, (SEQIDNO:9412); XM_003640010.2, LOC100856502, Del, G_9, GSWRYFIK, (SEQIDNO:9413); XM_014107345.1, LOC106557740, Ins, G_9, GVEAAAQRTHFQTLVLPPSPRE, (SEQIDNO:9414); XM_545414.4, PRSS16, Del, G_9, GVFARAVSRSRSAGRRRPQPSQRWNDGCTRAGRLARRCGRSWAPAHLWTEPRTRR SCWGRCRPWWGAPCSTTRRPGCR, (SEQIDNO:9415); XM_005642085.2, LOC102156583, Ins, G_9, GWGGGGADGPRPLCSSPWPP, (SEQIDNO:9417); XM_014121460.1, SLC35F5, Del, T_10, FALCGFWQICRIKKHFQTHRLL, (SEQIDNO:9418); XM_014116451.1, RDM1, Del, T_10, FCFFVFFFFFCP (SEQIDNO:9419); XM_014109369.1, MYEF2, Del, T_10, FFPFWQQQLQQRKHQGSFLL, (SEQIDNO:9420); XM_847990.3, OR7C2, Ins, T_10, FHCIWMPGQFTPDRNGL, (SEQIDNO:9421); XM_005630624.2, PHTF1, Ins, T_10, FHDVCGRENI, (SEQIDNO:9422); XM_014121429.1, SPATA5, Ins, T_10, FKRQLPWKNSLYL, (SEQIDNO:9423); XM_014120710.1, GOLPH3L, Del, T_10, FPKVRLGTPSNYSTS, (SEQIDNO:9424); XM_014121429.1, SPATA5, Del, T_10, FQKAIALEKFTL1, (SEQIDNO:9426); XM_847990.3, OR7C2, Del, T_10, FSLYLDAWTIYS, (SEQIDNO:9427); XM_014116451.1, RDM1, Ins, T_10, FVFLFFFFFFVLKILHVP, (SEQIDNO:9428); XM_542851.5, LEKR1, Del, T_10, LEMQPSGKRYPCALGLHLGGRGLRAAGG, (SEQIDNO:9431); XM_014121460.1, SLC35F5, Ins, T_10, LLCVVSGKFVVSRSTFRHTGCYS, (SEQIDNO:9432); XM_014109369.1, MYEF2, Ins, T_10, SFLFGNSSCSSGNIRALFSFRI, (SEQIDNO:9433); XM_014106795.1, LEKR1, Ins, T_10, WKCSHPGSAIPVPWDCTWGAGGSVLQDSRCKHAVKKSTK, (SEQIDNO:9434); XM_005634607.2, LEKR1, Ins, T_10, WKCSHPGSAIPVPWDCTWGAGGSVLQIILLQNSLTVFWEIMDRHIPMHALPEEIQKD SRCKHAVKKSTK, (SEQIDNO:9435); XM_542851.5, LEKR1, Ins, T_10, WKCSHPGSAIPVPWDCTWGAGGSVLQVGRP, (SEQIDNO:9436); XM_538839.5, SLC44A4, Ins, T_11, FHRSHPGAG, (SEQIDNO:9437); XM_014116709.1, LOC106559303, Del, T_11, FIIIEFILVRNPMDVKFVLRHF, (SEQIDNO:9438); XM_014108558.1, LOC106557908, Del, T_11, FLSLSLSLSLSLFLFLFLY, (SEQIDNO:9439); XM_014112116.1, NUDT12, Del, T_11, FSISLFLRKKCLL, (SEQIDNO:9440); XM_014108558.1, LOC106557908, Ins, T_11, FSLSLSLSLSLSFFFFFFIKRLQKKPPTLRDDRRGQFYESHPGLWKILLL, (SEQIDNO:9441); XM_538839.5, SLC44A4, Del, T_11, FSPVASRGWVDTLKTPPSTTTGCPSWSPSWGPMSSPAASSVFLACVWTHSSSVSWKT WRGTTARRTGPTTCPKPFSRS, (SEQIDNO:9442); XM_014113348.1, LOC100688741, Del, T_12, FAFLSFLSATC, (SEQIDNO:9443); XM_014116778.1, LOC102156959, Del, T_12, FFFLFFFFFF, (SEQIDNO:9444); XM_014107785.1, ZNF891, Ins, T_12, FKRKFLTWVKTCFFKESFHQ, (SEQIDNO:9445); XM_005624998.1, LOC100687222, Del, T_12, LTGHNLGGKKTSPLLNPHMLK, (SEQIDNO:9446); XM_014116778.1, LOC102156959, Ins, T_12, SFFFFFFFF1, (SEQIDNO:9447); XM_005637886.1, NSMCE4A, Ins, T_13, LHRKPGGYTECQRQINRGP, (SEQIDNO:9448); XM_014106263.1, NEK5, Del, T_14, LARMEWLQSLWTLG, (SEQIDNO:9449); XM_005624991.1, MED13, Del, T_16, FFPCPPFPTLLQP, (SEQIDNO:9451); XM_005624991.1, MED13, Ins, T_16, SFLVPRFRLFFNRSLVFNLCSLSGRILPFPG, (SEQIDNO:9452); XM_014115014.1, DEGS1, Ins, T_17, FLLYSKVSRDKVLDET, (SEQIDNO:9453); XM_014115014.1, DEGS1, Del, T_17, FPSLQQSIQR, (SEQIDNO:9454); XM_014116451.1, RDM1, Ins, T_18, FVLKILHVP, (SEQIDNO:9455); XM_005635625.2, CBR4, Del, T_22, FSLGVLGFCFFFLSLGASVV, (SEQIDNO:9457); XM_005630622.2, CTSK, Del, T_22, FTALKDSHVKLNT, (SEQIDNO:9458); XM_005630622.2, CTSK, Ins, T_22, LLPSKTVM, (SEQIDNO:9459); XM_014109132.1, TDRD1, Del, T_24, FVYWECCLLCLCLCLPAILLLGWVVLFFSLSSSSQINLA, (SEQIDNO:9460); XM_014109132.1, TDRD1, Ins, T_24, LFIGNVVSCASVFVCLPFFC, (SEQIDNO:9461); XM_005618433.2, MORF4L1, Del, T_25, LLLQVSEYCAFMGLFFMKQSV, (SEQIDNO:9462); XM_545128.5, SLC15A2, Ins, T_7, CAPAGPDAGTKSSSGSYLHPAV, (SEQIDNO:9463); XM_005616820.1, TMC1, Ins, T_7, CASCRCASRTLLGNNGGTGICAADCF, (SEQIDNO:9464); XM_539698.4, PTPRQ, Ins, T_7, CCCKNCKRTWSFQYSFLLHR, (SEQ1DNO:9465); XM_847422.4, YIF1A, Ins, T_7, CCGHSLCGQEAGAPGLPLHTPELGSAVQS, (SEQIDNO:9466); XM_014109476.1, STARD9, Ins, T-7, CCSEQTFSFN, (SEQIDNO:9467); XM_005639633.1, ATP13A3, Ins, T_7, CCVCDYFVCFHITHHVASSCLY, (SEQIDNO:9468); XM_014114990.1, DIEXF, Ins, T_7, CEQDFASVS, (SEQIDNO:9469); XM_846061.4, CPB2, Ins, T_7, CERIRCKQCESSFTRQHHPIQSLGGRSERSYPTANLQQHPQPPDLLLLL, (SEQIDNO:9470); XM_005628406.2, SMO, Ins, T_7, CGEHWLVGPVYGRRSPGDCLPCRWHHETWGAHLQ, (SEQIDNO:9471); XM_005630852.2, LOC100686848, Ins, T_7, CGFYCCKWSVSSASTFNLQLHWVLCLCGLPWICIWMAQLSVV, (SEQIDNO:9472); XM_005632588.1, PFKFB4, Ins, T_7, CGVHLCGS, (SEQIDNO:9474); XM_005626092.1, LHCGR, Ins, T_7, CHLSCLQNAPHHSNQL, (SEQIDNO:9475); XM_005631833.2, LOC483842, Ins, T_7, CHNECKNE, (SEQIDNO:9476); XM_014122642.1, FAT3, Ins, T_7, CHQYQNRFDHNNFKEIGSRTAGRTFSRGDCDGWRLLSQTIHHLGGGSGFG, (SE- QIDNO:9477); XM_533782.4, DENND6A, Ins, T_7, CKNTPALATHYSNRRP, (SEQIDNO:9478); XM_544956.5, THAP9, Ins, T_7, CKQGIRIFASSVAASYHWQTE, (SEQIDNO:9479); XM_549283.3, ADGRG4, Ins, T_7, CLGTCEDLFLISFCHFQHVARIPHFHVLLRNEGECAGAVADTLLLRVVTTG, (SEQIDNO:9480); XM_014109908.1, ANK2, Ins, T_7, CLQRKPTSSLCQGT, (SEQIDNO:9481); XM_014109884.1, EGF, Ins, T_7, CNVPFWESDLLFNMEKEDNLDS, (SEQIDNO:9482); XM_542919.5, SLC4A11, Ins, T_7, CQRQPRGAAQPGC, (SEQIDNO:9483); XM_014114457.1, OPYD, Ins, T_7, CQVDPKCH, (SEQIDNO:9484); XM_532487.2, ITGB8, Ins, T_7, CRRICPPAKLPAGSSPVPSGGLGAFSCSWTGPK, (SEQIDNO:9485); XM_005617468.2, BDP1, Ins, T_7, CSFASESSC, (SEQIDNO:9486); XM_005630848.2, SLC16A1, Ins, T_7, CSFYCCKWSVSSASTFILQLHWVLCLCGLLWICVWMAQLSVV, (SEQIDNO:9487); XM_005637418.1, COR8S14, Ins, T_7, CSHLLPHTV, (SEQIDNO:9488); XM_005627566.2, BCKDHB, Ins, T_7, CSLPRNQGGCTQKPFPGQGTSFVMHRG, (SEQIDNO:9489); XM_014106638.1, NOD2, Ins, T-7, CSPVPCAQH, (SEQIDNO:9490); XM_846025.3, ADAMTS5, Ins, T_7, CSQEVHPKSQLSHQPCQQ, (SEQIDNO:9491); XM_014118470.1, POLH, Ins, T_7, CSSGTAAKSSFEE, (SEQIDNO:9492); XM_541002.4, PTPN4, Ins, T_7, CTLFYIRFKISVLWKN, (SEQIDNO:9493); XM_548259.5, PEX12, Ins, T_7, CTTTSIHPREGSASFTTAEAGWSSARSTYSSGHTGSGAQAS, (SEQIDNO:9494); XM_014118588.1, CSMD3, Ins, T_7, CTYICRIWILSL, (SEQIDNO:9495); XM_014119192.1, VWDE, Ins, T_7, CVLTTAHSGMYGILCRSYF, (SEQIDNO:9496); XM_014110567.1, ATXN1, Ins, T_7, CVWTGMLLSRENQPALRPAVLQALRWGRLHLADPQEPEERLC, (SEQIDNO:9497); XM_014118473.1, MRPL14, Ins, T_7, CWALGPLHSCKQSIQPAQFQHHWELQCNSEDDAGPCGGQQCPGEYSVPSPSSLHPC L, (SEQIDNO:9498); XM_014111411.1, LOC611589, Ins, T_7, CWCLLLSIFGRCDLWGFKQNIPQGVRYCANKPIKRFRKRTIGNS, (SEQIDNO:9499); XM_544475.5, NUDC, Ins, T_7, CWRRGDGREAHHTDLQPP, (SEQIDNO:9500); XM_014114453.1, NTNG1, Ins, T_7, CWTMATQYGFSLRTAGYNQETQRFLYSHRPEDKAFETSGWGNICR, (SEQIDNO:9501); XM_538213.3, LOC481092, Ins, T_7, CYISWGNRILPLGFYVL, (SEQIDNO:9502); NM_001313886.1, LOC100683286, Ins, T_7, CYISWGNRVLSLGFYVL, (SEQIDNO:9503); XM_014117454.1, ARHGAP25, Del, T_7, FAEIRMCTQWPPC, (SEQIDNO:9505); XM_005631134.2, HIPK3, Del, T_7, FAEKQRFLILVGD, (SEQIDNO:9506); XM_014111169.1, LOC610561, Ins, T_7, FAFFWQCGPHVPTLLCHLLLIGYSHCSGLCSFVSLLQPHHL, (SEQIDNO:9507); XM_540660.3, LOC483540, Ins, T_7, FAFHPYLLHHSGR, (SEQIDNO:9508); XM_014115201.1, KIFAP3, Del, T_7, FAFLAFLSFMDLSLTIKLELYV, (SEQIDNO:9509); XM_014113716.1, ALG6, Del, T_7, FAFYLASVLKKA, (SEQIDNO:9510); XM_005625977.2, RANBP2, Del, T_7, FAIVQNCFVLM, (SEQIDNO:9512); XM_003433059.3, SPRY2, Ins, T_7, FALFMVLPSSQGLP, (SEQIDNO:9513); XM_014113929.1, CENPBD1, Del, T_7, FALLKNTVPRIISPIKHCSS, (SEQIDNO:9514); XM_014112649.1, RBPJ, Del, T_7, FALLLVCILWAVDGRKKKNKWNGMVVLNKSLNHVHLLE, (SEQIDNO:9515); XM_005628714.2, BBS9, Del, T_7, FALRIMDRFDS, (SEQIDNO:9516); XM_846518.4, C4BPB, Del, T_7, FAMPLWSGTPPFPHVSWATVLSLCW, (SEQIDNO:9517); XM_005634703.2, LOC606793, Del, T_7, FAPLLLQPNLGNLSSLC, (SEQIDNO:9518); XM_014119800.1, LOC106559804, Ins, T_7, FAPMPAASQTRGTLASWPGTRGSPGPRTTVLRLPAASATGGRAEKAMGMPEGTRGR QWARAAFWVGDSGQPCLLEGSPGGPPPPRPAAGAYRISCC, (SEQIDNO:9519); XM_014120611.1, AP4B1, Del, T_7, FAPTRSPTTSSCRRWRCCVSW, (SEQIDNO:9520); XM_014116753.1, LIG3, Ins, T_7, FARVACGTLQWAL, (SEQIDNO:9521); XM_014119949.1, TBXAS1, Del, T_7, FARVSGKAKWSSESYMDLCVGTILVAGCLLLSLSQT, (SEQIDNO:9522); XM_014118520.1, LRP12, Del, T_7, FASQEIFIVKTIGVCLKAGCVILRMTAVMAAMRRIAQLLCLPES, (SEQIDNO:9523); XM_014117160.1, APOF, Del, T_7, FATSCCTLWMSFHMETGQTFPHL, (SEQIDNO:9524); XM_014110296.1, GRAMD1C, Ins, T_7, FAVASSVECDAVSEAVKDRICCSVLLPSPSPRREIFTFSL, (SEQIDNO:9525); XM_014118505.1, ADGRF2, Del, T_7, FAVKRNGTRSLKPAGLLMPSTSLRQIYIQLNHSKEIQKSVSMPECLRLSQTC, (SEQIDNO:9526); XM_014115233.1, EXO1, Del, T_7, FAVLWILPTVYL, (SEQIDNO:9527); XM_005624276.2, GNA13, Ins, T_7, FAVSPYHKSTVGRQWHTECL, (SEQIDNO:9528); XM_005640538.2, CFLAR, Del, T_7, FCAGTLLQMLLHLLSGTFWIF, (SEQIDNO:9529); XM_014111169.1, LOC610561, Del, T_7, FCFFLAMWPSCTYASLPPTPYSGIQSLLWPLQFCLPSSTPSFIA, (SEQIDNO:9530); XM_005631715.2, RCN1, Del, T_7, FCFLFFFF, (SEQIDNO:9531); XM_003433951.2, LOC100684620, Del, T_7, FCFLLYFT, (SEQIDNO:9532); XM_005630716.2, CD160, Ins, T_7, FCFSHRDRELHRGSTETYRTARVQSQ, (SEQIDNO:9533); XM_003433948.1, LOC100684112, Del, T_7, FCFSPHACFCTSGLLPHLQLIKICSLWILLSSLP, (SEQIDNO:9534); XM_540660.3, LOC483540, Del, T_7, FCFSPLFTSPLWQVTGA, (SEQIDNO:9535); XM_014119604.1, TMPO, Del, T_7, FCFWSIKLWKPTKEIRSVVFFLMTLVNPS, (SEQIDNO:9536); XM_014118650.1, CWH43, Del, T_7, FCGCLLVWDY, (SEQIDNO:9537); XM_005642440.1, LOC100688648, Del. T_7, FCHVRKNKCQNHQRRTEENRNMGIRIMKMLSSS, (SEQIDNO:9538); XM_014108289.1, LOC102156424, Del, T_7, FCIWLWAYVSSAKVAFCSVV, (SEQIDNO:9539); XM_014107328.1, PARP4, Del, T_7, FCLFLKEFLLLVHPEGLTFITILILLFIFKIL, (SEQIDNO:9540); XM_545339.4, GCM2, Del, T_7, FCLGHLAAMNWQLLVTQIQAHIPPFIRILAMSLMTQTGFI, (SEQIDNO:9541); XM_014113785.1, ZCCHC2, Del, T_7, FCLRLLMQTDWCMTQSWGAKPTTACSRWRDLGGSILCTQHRT, (SEQIDNO:9542); XM_003433059.3, SPRY2, Del, T_7, FCLVYGVTFQPRVALSCARGVMTGLTGLDAAVKTQTQFAAKFPLSHPGTLKNQH, (SEQIDNO:9543); NM_001286967.1, ARHGAP18, Del, T_7, FCMKLEEILENAALMTTRT, (SEQIDNO:9544); XM_005636714.2, ASUN, Del, T_7, FCMSLAVLDPF, (SEQIDNO:9545); XM_005632290.2, NUP210, Del, T_7, FCPAFLASSHPCHLPGQRWPV, (SEQIDNO:9546); XM_014113223.1, DYNC2H1, Del, T_7, FCQQETQIPSSHQMQPPSLQRLTSLQQEVGCEDSFWL, (SEQIDNO:9548); XM_547742.5, NRL, Del, T_7, FCRCTPRKPAPEWHCLPAPWLWNMSMTLT, (SEQIDNO:9549); XM_005633637.2, TRIM66, Del, T_7, FCSAFLQGDPRWPGTAPSARRRGQRISCAP- TATAGCAAHAQRSTGMAPPLGAHSFR GPTRDHQE, (SEQIDNO:9550); XM_014120068.1, RAB11FIP1, Ins, T_7, FCSSVQFWPDTCPF, (SEQIDNO:9551); XM_005640646.2, RQCD1, Del, T_7, FCTPFCTLSAKHDPLNIFD, (SEQIDNO:9553); XM_014110028.1, TSPAN5, Ins, T_7, FCVPGNYFLPGAHCWGSGICFQRLDQRPAVFLYKQQHQSVQR, (SEQIDNO:9554); XM_544884.5, KCNJ15, Del, T_7, FCWLLSWSLRP, (SEQIDNO:9555); XM_014110333.1, SLC12A7, Ins, T_7, FDLHLPQRSHHPGRDGGG, (SEQIDNO:9557); XM_005637629.2, SLF2, Ins, T_7, FDNTRLSYLCLSLCPVSCTCVKVAVSDDVGSYRLYCVCADFKYIDGNND, (SEQIDNO:9558); XM_005615336.2, CDH19, Ins, T_7, FDPGSETAKEANSIS, (SEQIDNO:9559); XM_014120725.1, LOC607038, Del, T_7, FDVALPKMQYIIARMVATVKWTCTCVGNVKSAD, (SEQIDNO:9560); XM_005639030.2, PRMT2, Ins, T_7, FEAQVQPHFEARRLSV, (SEQIDNO:9561); XM_005635818.2, SP140, Ins, T_7, FEDSILLLY, (SEQIDNO:9562); NM_001145170.1, CA2, Ins, T_7, FEDWWCQSRPTKNP, (SEQIDNO:9563); XM_014116438.1, ABCA6, Ins, T_7, FEEKMGSWILLKFVQK, (SEQIDNO:9564); XM_014122642.1, FAT3, Ins, T_7, FEGPRWWWENDFLHCESDRCG, (SEQIDNO:9565); XM_014110533.1, LOC488248, Del, T_7, FEIRTLAKITSSTRIRITCGHARICASIKEACS, (SEQIDNO:9566); NM_001313773.1, RPGRIP1, Ins, T_7, FELPSRGFSSA, (SEQIDNO:9567); XM_014111835.1, ZMAT1, Ins, T_7, FEMFVRLS, (SEQIDNO:9568); XM_532205.6, CD109, Ins, T_7, FESSLYYQR, (SEQIDNO:9569); XM_014110011.1, INTS12, Ins, T_7, FESTRLLTFKE, (SEQIDNO:9570); XM_005633847.2, KPNA3, Ins, T_7, FETSPFTTSEC1, (SEQIDNO:9571); XM_005615672.2, LOC483960, Del, T_7, FEWSFLTLPQDEQMLTISSMKLKGLERIY, (SEQIDNO:9572); XM_849082.4, TMEM182, Ins, T_7, FFACWITIPGYWSTYSNTSL, (SEQIDNO:9573); XM_005620968.2, WBSCR22, Ins, T_7, FFALLCAGSWSPGRPAAIPGELRAVGANYDPGHQGWLHWWRGCGLPQ, (SEQIDNO:9574); XM_849728.3, MYCT1, Del, T_7, FFCLFYFLWILWLITQQV, (SEQIDNO:9575); XM_005633797.1, COR52E4, Ins, T_7, FFHDTPFWSKHPPLYPYPFS, (SEQIDNO:9576); XM_005623261.2, TM9SF1, Ins, T_7, FFPKVHPLYLC, (SEQIDNO:9577); XM_005636001.2, PPP1CC, Del, T_7, FFSEETMNVPASIEFMDFTMNVKEDITLNYGKLSQTALTVYR, (SEQIDNO:9578); NM_001003033.1, PPP1CC, Del, T_7, FFSEETMNVSASIEFMDFTMNVKEDITLNYGKLSQTALTVYR, (SEQIDNO:9579); XM_005635807.1, TRIP12, Ins, T_7, FFTTSWRRAHWKSRTSG, (SEQIDNO:9580); XM_532457.5, CYP51A1, Ins, T_7, FGAEENAKKWP, (SEQIDNO:9581); XM_536257.5, KLB, Del, T_7, FGALGLEHFKWKGIGRQMEKDPLYGIISSTHTLKMSTA, (SEQIDNO:9582); XM_005632409.2, ASB14, Ins, T_7, FGCQHLPLRKCQFSSSQWLQSECQEF, (SEQIDNO:9583); XM_003640306.1, LOC100855565, Ins, T_7, FGDIPVGLDRQPPHYHCNQLGPSPTVPHVLLLEAPLSSGPLLHLCHSPPVHHKFTYEQ WLHFLCPVHSSGVLLHSSGLIRSGHPHSDVL, (SEQIDNO:9584); XM_014112077.1, MAN2A1, Del, T_7, FGDRIGIWDLAQIFFAT, (SEQIDNO:9585); XM_003432273.2, LOC100683523, Ins, T_7, FGDWVLAMWAGEFCDTHSAGSHTHSLWAQPNQPLSL, (SEQIDNO:9586); XM_003639984.3, BTAF1, Ins, T_7, FGEGSSMAGSN, (SEQIDNO:9587); XM_539359.3, OR2T2, Ins, T_7, FGGCHSQCGHDSTHPC, (SEQIDNO:9589); XM_843573.4, DARS, Ins, T_7, FGIAQCSSDVNVPPGS, (SEQIDNO:9591); XM_014119713.1, FHDC1, Del, T_7, FGKPFQRSKFVAKPTSGLWPPGSSITTRLIQRPLRNSLGSKKILPSLPFLGEEEL, (SEQIDNO:9592); XM_014115860.1, CTAGE5, Ins, T_7, FGKPVKRREI, (SEQIDNO:9593); XM_005616941.2, CUL2, Ins, T_7, FGKSRTAFAQESSGV, (SEQIDNO:9594); XM_534336.5, CSRP2BP, Del, T_7, FGLALTCLSA YSIQTSVLLSFIKKSSLPLASWYLM, (SEQIDNO:9595); XM_014107454.1, UGT1A6, Ins, T_7, FGLKSIKRQS, (SEQIDNO:9596); XM_005630347.2, CEBPZ, Del, T_7, FGLVSRKKILNQKCLVPF, (SEQIDNO:9597); XM_533578.4, NLRP9, Ins, T_7, FGLWLVVVPGGAQKGRILEI, (SEQIDNO:9598); XM_014119438.1, C15H12orf29, Del, T_7, FGMLRKTSNLFQSAGYQRRK, (SEQIDNO:9599); XM_005638131.2, FSBP, Del, T_7, FGMSVENTLGHN, (SEQIDNO:9600); XM_844183.4, ESRRG, Ins, T_7, FGNAGGQGL, (SEQIDNO:9601); XM_537895.5, LOC480777, Del, T_7, FGNFMNVLRSSVKM, (SEQIDNO:9602); XM_845265.4, UTS2B, Ins, T_7, FGNGAWTAISYPRK, (SEQIDNO:9603); XM_005621497.2, TMC5, Del, T_7, FGNQTIPELRTLQTFGGNLITQSLRMVVIMALLRLQKLPERCSAEHLHSGPHCVIGVM ALWGSLGERMKITLKTLQ, (SEQIDNO:9604); XM_003640134.2, OTOL1, Ins, T_7, FGNRWYGHSSKDHTTYQIYEEI, (SEQIDNO:9605); XM_014119195.1, MTERF1, Del, T_7, FGPVTTET, (SEQIDNO:9606); XM_014119721.1, ENPP1, Del, T_7, FGQDQMWKLKEFSQTSIKCIMVQYHLKKGF, (SEQIDNO:9607); XM_003435483.1, FOXR2, Del, T_7, FGQLQMAGKTPSATISVSWAALRRHQSIFRMGPM, (SEQIDNO:9608); XM_014122196.1, DOCK6, Ins, T_7, FGRDPRRPQTLQAS, (SEQIDNO:9609); XM_845208.4, HECTD1, Ins, T_7, FGSASKTWCNQQSINFGRSFL, (SEQIDNO:9610); XM_014118865.1, UTRN, Ins, T_7, FGSNGKRSQITLPNGGILYTYNIWGRCTRLHKGAEE, (SEQIDNO:9611); NM_001012395.1, UTRN, Ins, T_7, FGSNGKRSQITLPNGGILYTYNTWGRCTRLHKGTEE, (SEQIDNO:9612); XM_847187.3, TXNDC12, Ins, T_7, FGSQWQGAS, (SEQIDNO:9613); XM_005624856.2, KIAA0100, Del, T_7, FGSRMSALSFSNTSKLWKLIACGFPANSLAMICHAMWHCALEKYVSGRTYRRFLAF LPHFPKALGYIKRNCLSVHPY, (SEQIDNO:9614); XM_005639633.1, ATP13A3, Del, T_7, FGSSSNLGMKYGIHNQMMQREAYIGILLHICTMKLNLIRVIYKIMKIPQCFLSPVFSTS, (SEQIDNO:9615); XM_536122.5, RAB3GAP2, Del, T_7, FGSVCMEKALPRICVTLWSQLDLALSCCCLCS, (SEQIDNO:9616); XM_005627518.2, PHF3, Del, T_7, FGTPMLNIRTNTEV, (SEQIDNO:9617); XM_005639761.2, B3GNT5, Del, T_7, FGTQSIITL, (SEQIDNO:9618); XM_014119897.1, ZNF283, Del, T_7, FGVQALLNMR, (SEQIDNO:9619); XM_536500.4, NUP155, Ins, T_7, FGWKRWLFI, (SEQIDNO:9620); XM_014119539.1, ABCE1, Ins, T_7, FGWLRSNRKLEIQRCLTCF, (SEQIDNO:9621); XM_014112250.1, PAPD4, Ins, T_7, FGWVLFKWIWYPEQ, (SEQIDNO:9622); XM_540733.1, LOC483613, Ins, T_7, FHALLRWH, (SEQIDNO:9623); XM_541402.3, LOC484287, Del, T_7, FHAYMRLRRKTL, (SEQIDNO:9624); XM_005629095.2, KLF18, Ins, T_7, FHEPKGDV, (SEQIDNO:9625); XM_533330.4, SLC35F5, Del, T_7, FHFLLQLSYAIIIGIL, (SEQIDNO:9626); NM_001003027.1, AFP, Ins, T_7, FHFPTKFF, (SEQIDNO:9627); XM_005635483.2, USP1L, Ins, T_7, FHFSIKFFSK, (SEQIDNO:9628); XM_014109484.1, TMEM87A, Ins, T_7, FHGDVYCICPVWCSVAGMVCLLLERSPENS- VLDWCCHLLGNA, (SEQ ID NO:9629); XM_003639544.3, EN2, Ins, T_7, FHGQLLAARVRPEEQPGDVLCRRGRRKRRRRRGRRRGRRGRRRRR-GRRRAAPGV GPRGPAERARGARGGRAS-WRRRRRHSG, (SEQ ID NO:9630); XM_003431626.3, FNIP1, Del, T_7, FHIFLSLKAT, (SEQ ID NO:9631); XM_005637011.2, TMTC1, Ins, T_7, FHKRKPTKRAESSG, (SEQ ID NO:9632); XM_005628579.2, AGMO, Ins, T_7, FHLHCFLGSQKHETTCLQPFEI, (SEQ ID NO:9633); XM_014108701.1, LOC611536, Ins, T_7, FHLTSQCLFYCKLFGEQGQLLSFWLESLPVQLLSSS, (SEQ ID NO:9635); XM_014115681.1, RALGAPA1, Del, T_7, FHLVCLVPQCLLWILL, (SEQ ID NO:9636); XM_014106710.1, SLC4A7, Ins, T_7, FHNIFSVFIPQAI, (SEQ ID NO:9637); XM_014118177.1, BVES, Ins, T_7, FHNWVGYSNYTSPSYDTS, (SEQ ID NO:9638); XM_005638361.2, CTDSPL2, Del, T_7, FHQQIKMEHQDPIPQDRLWKLKK, (SEQ ID NO:9639); XM_547829.5, TMEM260, Ins, T_7, FHRFQAFWLICWRNPCCGGVFIFSSNMAVVHCSRGF, (SEQ ID NO:9640); XM_014114384.1, TNNBK, Ins, T_7, FHSAAHCSILWT, (SEQ ID NO:9641); XM_005639144.2, ARHGAP24, Ins, T_7, FHVWGADSGTEEN-RERKHNMDPV, (SEQ ID NO:9643); NM_001003106.1, CTLA4, Del, T_7, FIAFLSQLFL, (SEQ ID NO:9644); XM_849878.4, ZDHHC14, Del, T_7, FICLFYLCLF, (SEQ ID NO:9645); XM_005639457.2, CD47, Ins, T_7, FICWWTSAHYSCHCRSHSFRPR, (SEQ ID NO:9646); XM_847055.3, LOC609729, Ins, T_7, FIFGVHINCDGKPPHHGHCDL, (SEQ ID NO:9647); XM_014109438.1, MYO9A, Del, T_7, FIFPNKTH, (SEQ ID NO:9648); XM_533330.4, SLC35F5, Ins, T_7, FIFYCNSLMPL, (SEQ ID NO:9649); NM_001172235.1, UGCG, Ins, T_7, FIGIMGPYYKLENWSLQIALWRHSRGNSRCI, (SEQ ID NO:9650); XM_005633841.2, ALG11, Del, T_7, FIHYSSLG, (SEQ ID NO:9651); XM_003433028.1, LOC100685902, Ins, T_7, FIICFDTPLSAEAEFSRSCI-QSPKYLYFPSHPNFILLHCHC-CHFYYPQCNNDSSPHPSSA, (SEQ ID NO:9652); XM_005638476.2, VPS13C, Del, T_7, FIIDKIMALY, (SEQ ID NO:9653); XM_547308.5, LPAR3, Del, T_7, FIIGATQTLPMSGQERSW, (SEQ ID NO:9654); XM_005627902.2, TBC1D31, Del, T_7, FIIGITWI, (SEQ ID NO:9655); XM_535047.6, PSTK, Del, T_7, FIMRKITLSGNIFQSHT, (SEQ ID NO:9656); XM_005624915.2, GEMIN4, Del, T_7, FIPRYSVTFCTSWPCSPTRCASRCMSWPWKSSPAMKP, (SEQ ID NO:9657); XM_005627580.2, DOPEY1, Ins, T_7, FIQFWVISSSCKCCHVCEANVAESVRDILLAFG, (SEQ ID NO:9658); XM_005631925.2, MGAT4D, Del, T_7, FIQTYYLSHSQLRTREN, (SEQ ID NO:9659); XM_544123.3, TRPA1, Ins, T_7, FIQYIWILQRSDPNLPTEKELYVGSGQCS, (SEQ ID NO:9660); XM_014111169.1, LOC610561, Del, T_7, FIRPRTSS, (SEQ ID NO:9661); XM_005622851.2, EPG5, Del, T_7, FISFGYPHWTLKALVCSQNGVLTWLI, (SEQ ID NO:9662); XM_014109687.1, SYNJ1, Del, T_7, FISMEVKSKDARVVLFEQTAWTVLIEQIVCRHSLA, (SEQ ID NO:9663); XM_533983.5, CCDC81, Ins, T_7, FITIHFHQTKCGIYFQRNWGPCD, (SEQ ID NO:9664); XM_856309.4, KDELR2, Ins, T_7, FITMYKDFFTQRNL, (SEQ ID NO:9665); XM_005633788.1, OR52E1, Ins, T_7, FIYDPQVWPEYTTLYPHPFG, (SEQ ID NO:9667); XM_014122769.1, RIC3, Ins, T_7, FNINSI, (SEQ ID NO:9668); XM_847424.4, GLIPR1L1, Ins, T_7, FKGNKKLEKYEKYPDWNPQGTAPQHISCNPLCL, (SEQ ID NO:9669); XM_005636226.2, HVCN1, Ins, T_7, FKIICLPLGVLSPQI, (SEQ ID NO:9670); XM_014119270.1, LOC102151283, Del, T_7, FKKQKLSLPNIMRK, (SEQ ID NO:9671); XM_005622271.2, CAMSAP2, Del, T_7, FKLRICPMILRMLSCTGLIR, (SEQ ID NO:9672); XM_005628968.1, ZMYM6, Ins, T_7, FKPKAFRLGQVFS, (SEQ ID NO:9673); XM_534667.5, RNF34, Ins, T_7, FKPYSPFCYCVFISGRLYGWRPDLGIWSSGTGTK, (SEQ ID NO:9674); XM_014113138.1, C4H5orf42, Ins, T_7, FKQEHRPKCMGPLYL-STFSSVFINPVLGYEIQTRCGTFGKADLKYYKAFADSATTGS VILREAFG, (SEQ ID NO:9675); XM_014109139.1, CFAP43, Ins, T_7, FKRSSKVPK, (SEQ ID NO:9676); XM_005626122.2, PAPOLG, Del, T_7, FKSIDIILY, (SEQ ID NO:9677); XM_003435457.4, FANCB, Ins, T_7, FKSRRSFK, (SEQ ID NO:9678); XM_014116723.1, RNFT1, Ins, T_7, FKSYIGPFKLLGSTLDCWNYRLHSEIPLHGLKMPYFVDAFFHHAF, (SEQ ID NO:9679); XM_014108367.1, LOC611565, Del, T_7, FKTTRSNASPIVGMLE, (SEQ ID NO:9680); XM_862279.4, G3BP1, Del, T_7, FKVMGMWWSY-ALTVAGNYPILVLLCLMILSLFKRSLATGPSCSEVRSA, (SEQ ID NO:9681); XM_547621.5, B4GALT6, Ins, T_7, FLASDSNAPEAEVGICLLCH, (SEQ ID NO:9682); XM_014107880.1, SSH1, Del, T_7, FLAYLHIITS-ESMMKRQQTFLPTGTKHTIL, (SEQ ID NO:9683); XM_003639673.1, LOC100856189, Ins, T_7, FLCHYIIHFKKSLSRRKTQSPLYLWISYHGYS-FIFWAFHLCLP, (SEQ ID NO:9685); XM_849082.4, TMEM182, Del, T_7, FLCLLDYYSWLLVDIFKYIT, (SEQ ID NO:9686); XM_014110908.1, LOC100686469, Del, T_7, FLCLPLSASEDSTKLESHHLRLPDKLQEFR-GLLQLKKKMVIFQTL, (SEQ ID NO:9687); XM_844911.2, LOC608017, Ins, T_7, FLCNKCNDGMLFAGNNGL, (SEQ ID NO:9688); XM_003434058.3, LOC100684793, Ins, T_7, FLCNQCNDRMLFAGNNGL, (SEQ ID NO:9689); XM_545065.3, OR5H2, Ins, T_7, FLCNQYNDGMLFAGNNGL, (SEQ ID NO:9690); XM_014110028.1, TSPAN5, Del, T_7, FLCSWELFSSWSSLLGFWHLFSKTGSKTSCISL, (SEQ ID NO:9691); XM_014112224.1, ADGRV1, Del, T_7, FLDKVTQQSTLLSKLMTHQK, (SEQ ID NO:9693); XM_005640225.2, 42436, Del, T_7, FLEDLARIP, (SEQ ID NO:9695); XM_014109449.1, ZNF106, Del, T_7, FLENTQIP, (SEQ ID NO:9696); XM_014115269.1, DNAH14, Del, T_7, FLEQHFQQQIKLPWRKQYLLQHNSWAYNNGQLRKRKSYSFIINCRLVLV, (SEQ ID NO:9697); XM_014117392.1, KIAA1033, Ins, T_7, FLFESNSIFQSFY, (SEQ ID NO:9698); XM_005633595.2, LOC100685491, Ins, T_7, FLFHPPLWPPSTSSCPHCTCKSLPSCAPCSQPPGLWH, (SEQ ID NO:9699); XM_005638667.1, LOC487459, Ins, T_7, FLFILCWNYLRKPLHYVNSDF, (SEQ ID NO:9700); XM_846785.4, BTBD10, Ins, T_7, FLFLCVYLGIY, (SEQ ID NO:9701); XM_005618393.2, BTBD1, Ins, T_7, FLFQLPWQ, (SEQ ID NO:9702); XM_014121827.1, PTPRS, Ins, T_7, FLFYFLYRGLAHAIRQVDVWGRRPDA, (SEQ ID NO:9704); XM_536170.5, MCEE, Del, T_7, FLGFRHRFQK, (SEQ ID NO:9705); XM_005617241.1, SLC6A2, Ins, T_7, FLGGWIWSPDCICQLQQI, (SEQ ID NO:9706); XM_533741.5, SLC6A11, Ins, T_7, FLGNSSGTIHE, (SEQ ID NO:9707); XM_537209.4, MPC2, Ins, T_7, FLGSNYEMGVGVCRIG, (SEQ ID NO:9708); XM_005635807.1, TRIP12, Del, T_7, FLHHFLEKSPLEE, (SEQ ID NO:9709); NM_001164486.1, SELENOI, Del, T_7, FLHVCYSFCLQHGSFSRLQIF, (SEQIDNO:9710); XM_014119426.1, FNIP2, Del, T_7, FLIFPCLNLT, (SEQIDNO:9711); XM_005641570.2, ARMCX1, Ins, T_7, FLIQRIWSVC, (SEQIDNO:9713); XM_014119702.1, CFAP54, Del, T_7, FLKPFMRYPRFFMEKTCLPQY-PLAVRLLEK, (SEQIDNO:9714); XM_014120068.1, RAB11FIP1, Del, T_7, FLLFCPVLARHLSLLNW-GIVQRHHPLNLLLSSLSHLPLWLPFPH-PRQLKTGPPQTRAR PVLKNHLCSIRQNC, (SEQIDNO: 9715); XM_005625434.1, QSOX2, Ins, T_7, FLLFEVVAGCEEKIDFVA, (SEQIDNO:9716); XM_843974.3, NEMP1, Ins, T_7, FLLFKREIE, (SEQIDNO:9717); NM_001145507.1, CAFA-T2R43, Del, T_7, FLLLLFLMSM, (SEQIDNO:9718); XM_005641635.2, TBC1D8B, Ins, T_7, FLLLVFELSSIEVP, (SEQIDNO:9719); NM_001003176.1, RPE65, Ins, T_7, FLLPRSGGH, (SEQIDNO:9720); XM_847656.3, LOC610217, Ins, T_7, FLLQPPFWTCITLCSYSLVYHLSACAACP, (SEQIDNO:9721); XM_014117993.1, LOC100685402, Ins, T_7, FLLYVYPLHHLENELSYRETQSLFHLLSTSDRG-DHILWYHLLHVCQAQVSRPPRE, (SEQIDNO:9723); XM_539781.2, ASICS, Ins, T_7, FLMEY-RVQSRPSSGNQVQLLWL, (SEQIDNO:9724); XM_859377.4, UPF3B, Del, T_7, FLMILVCILICMPEHT-STLKTKRTLFCSGIALMVMYSLTIKVRNILL, (SEQIDNO:9725); XM_005637170.2, KLRB1, Del, T_7, FLMLPTLGKTV, (SEQIDNO:9726); XM_003639673.1, LOC100856189, Del, T_7, FLMSLYYSL, (SEQIDNO:9727); XM_014109384.1, DIS3L, Del, T_7, FLNCENVLKPKASS, (SEQIDNO:9728); XM_536110.5, CFH, Del, T_7, FLNMNLHMSWLQ, (SEQIDNO:9729); XM_014115842.1, BAZ1A, Ins, T_7, FLPDCHLPGDS, (SEQIDNO:9730); XM_849282.4, CLRN3, Ins, T_7, FLPEGPIPAKTGGEKAHGICSKRWNSIL, (SEQIDNO:9731); XM_005618617.2, UGDH, Del, T_7, FLPILTM-PLKKLILYLFL, (SEQIDNO:9732); XM_014115614.1, LOC100688957, Ins, T_7, FLPPDSCGEPHYHHYLIPT-SPPPHPYVLLPQQPLPAGPLLHY, (SEQIDNO:9733); NM_001122645.1, D102, Ins, T_7, FLQLPLPGT1, (SEQIDNO:9734); XM_014108246.1, NR4A1, Ins, T_7, FLQPPYWSQSQPCPEPLEAVPLTGHLPAGGERK-LFHIHGFPGPGAHFSTPRRPRDAGR TGAFGQG-PERGPQWKRGPLCRVWGQRFVPALRRPHLRGL, (SEQIDNO:9735); XM_005639098.2, CNOT6L, Del, T_7, FLQSHVPKSCLSRRESMWMVVQYSSKQKNLHWCK-SIQWNLTKWQWLIQMDPKLC, (SEQIDNO:9736); XM_014112771.1, DNA2, Del, T_7, FLRDLCWWGI-INSFLPWC, (SEQIDNO:9737); XM_005620968.2, WBSCR22, Del, T_7, FLRFTLCWFMEPGPSC-SYTRRTPSSWS, (SEQIDNO:9738); XM_005641854.2, ZNF75D, Del, T_7, FLRKNGNY, (SEQIDNO:9740); XM_014118099.1, NOL8, Del, T_7, FLRMMKDLVVLIYSGEEWEVILAGILGRLEQTTCE-WTVGRNIKMPKGE, (SEQIDNO:9741); XM_003435449.1, LOC100684897, Ins, T_7, FLRYRTWCS, (SEQIDNO:9742); XM_005619828.2, ACAT1, Ins, T_7, FLSALRWYF, (SEQIDNO:9743); XM_003640298.1, LOC100855846, Ins, T_7, FLSFCCSHSPCSHFLSPWSYTQKDAVSEDGWSL, (SEQIDNO:9744); XM_014110308.1, MORC1, Del, T_7, FLSISYHQDLATHLWRILQQVLSWSSAQSR, (SEQIDNO:9745); XM_014109103.1, PAX2, Ins, T_7, FLSLPSRARGCEPARGGVCERPAPARRGEAAHR-GAGPPGRAALRHIPAAARQPRLCQ QNPGQVL, (SEQIDNO:9746); XM_005642111.1, LOC609849, Del, T_7, FLSMGFLRT, (SEQIDNO:9747); XM_014118880.1, LOC482344, Ins, T_7, FLSMSPGCSHPLWLIPQY, (SEQIDNO:9748); XM_534842.3, LOC477647, Ins, T_7, FLSSPTVS, (SEQIDNO:9749); XM_005615356.2, PIGN, Ins, T_7, FLTFIRNRYKWTCSPTNIEGI, (SEQIDNO:9750); XM_538554.3, LVRN, Del, T_7, FLTFYIM-SSVKITPWCLELCP, (SEQIDNO:9751); NM_001003176.1, RPE65, Del, T_7, FLTSEEWRSLTM-PLLTSTQ, (SEQIDNO:9752); XM_014116675.1, AKAP1, Del, T_7, FLVKSMLAVRTDRWRPALWS, (SEQIDNO:9754); XM_005627538.2, FILIP1, Del, T_7, FLVPLSFLP, (SEQIDNO:9755); XM_014111483.1, LOC611979, Del, T_7, FLVSGFLLKSTVW, (SEQIDNO:9756); XM_014109103.1, PAX2, Del, T_7, FLVSPQQGTGV, (SEQIDNO:9757); XM_005625665.2, THADA, Del, T_7, FLVSQNSIPFFSNSWKL, (SEQIDNO:9758); XM_846785.4, BTBD10, Del, T_7, FLVSVCLPWHILK, (SEQIDNO:9759); XM_014120908.1, SERPINGI, Ins, T_7, FLWLCSRIL, (SEQIDNO:9760); XM_541402.3, LOC484287, Ins, T_7, FLWPFKKKPNKRTGRYFVL, (SEQIDNO:9761); XM_014109417.1, LOC100688948, Ins, T_7, FLWSNHVCLYMATPQFPDGQISCSL, (SEQIDNO:9762); XM_546110.4, SLC16A9, Ins, T_7, FLWYCCR-TRMWFTVHGNSDHYVPVF, (SEQIDNO:9763); XM_005639817.2, RTP4, Ins, T_7, FLYL-CKQILGSRKIKI, (SEQIDNO:9764); XM_005615676.2, LOC102154335, Del, T_7, FLY-LKTLLPGHLSLKVELISLERSRSNKRIRGST-FLPTWQNWL, (SEQIDNO:9765); XM_014110864.1, GALNT3, Ins, T_7, FLYNIFDFNAKRSKY-SIFQRGIKDGKKYKQKQDV, (SEQIDNO:9766); XM_535048.6, ACADSB, Ins, T_7, FLYPRDRGISQSRCI-CRVGL, (SEQIDNO:9767); XM_014107795.1, LOC487177, Del, T_7, FMAMKRLVGHLHLMNSQEKLK, (SEQIDNO:9768); XM_005622466.2, SOAT1, Del, T_7, FMCTT-SLKGSAPPCFGISNRSPSALAFWSYVYLTPSCQVC, (SEQIDNO:9769); XM_014122375.1, DNAH12, Del, T_7, FMLLYKRERNLVLLVGIFHTDLMNPTYASVSDNY-SYL, (SEQIDNO:9770); NM_001013852.1, VN1R4, Del, T_7, FMPSHPFVRFVCLF, (SEQIDNO:9773); XM_005634064.2, CCDC168, Del, T_7, FMPVYQQIHWRLYPKLFAGLFPQEL, (SEQIDNO:9774); NM_001031630.1, TERT, Del, T_7, FMSRKPRFKRTDSSSTGRASGASYRA, (SEQIDNO:9776); XM_005622414.2, SHCBP1L, Del, T_7, FMTFFGETGMMKKVVRITLL, (SEQIDNO:9777); XM_005642125.2, FRMD7, Del, T_7, FMWTDH-PRCPDGLQSWQRKMTGQTAVWSPL, (SEQIDNO:9778); XM_005618857.2, SPHAR, Del, T_7, FNALDI-FLKSQNMKEILRLNYFLDLTGRTFDSMSHLW, (SEQIDNO:9779); XM_539875.1, COR9A7, Ins, T_7, FNGCVHYCWFFDPYNHLLHLHHFHHPQDSLSL-WAEESLFYVCVPLHLCRDRVWHL LVPL-CETQANTGSRV, (SEQIDNO:9780); XM_005626598.1, PKD2L2, Ins, T_7, FNKPMYIDFWDGKP-TYVLLKQSYVIFIFGHFCAW, (SEQIDNO:9781); XM_014108769.1, ARHGAP22, Ins, T_7, FNLGKPDCWGKR, (SEQIDNO:9782); XM_005624950.2, MNT, Ins, T_7, FNLQILFCKYFGKH, (SEQIDNO:9783); XM_014119189.1, ABCB4, Ins, T_7, FNPDWSLQCGTGCSMY, (SEQIDNO:9784); XM_014115134.1, TSEN15, Del, T_7, FNRAADGAAILA-LRLPLQPIPGACGAKPWVDS, (SEQIDNO:9785); XM_005638404.2, TRPM7, Ins, T_7, FNRRRSKETT, (SEQIDNO:9786); XM_005642422.1, OVCH1, Ins, T_7, FNSKISTGL, (SEQIDNO:9787); XM_005625561.2, LRIG3, Del, T_7, FPAMYSLICKHLAS, (SEQIDNO:9788); XM_003640168.3, ABT1, Ins, T_7, FPARGRVREA- QEEGSVSLSHGREKAVQVQQGLHRGLGGVPGQASSQACGGQSSQHAHGSPKAQPLPLRPMESQVPAPFHVVPPQRTSCL, (SEQIDNO:9789); XM_014119565.1, LRRC41, Ins, T_7, FPCSTWDH, (SEQIDNO:9790); XM_005627957.1, SECTHRC1, Ins, T_7, FPEQTEGDRGGGGPV, (SEQIDNO:9791); XM_534842.3, LOC477647, Del, T_7, FPFLTYCLLAKFGLFFP, (SEQIDNO:9792); XM_014112679.1, GRM1, Ins, T_7, FPGDLFGDVPSS, (SEQIDNO:9794); XM_014119262.1, SLC6A15, Ins, T_7, FPGTCCGSKNPARKHWCVELHKP, (SEQIDNO:9795); XM_547724.5, SLC7A7, Ins, T_7, FPHGLLALDHLPGGRGTLQGYHQIPHRDWDWPFRVGPLLPQQQGGKKQKNSLGPKNCSIHYMVPPGPMYVSCCRDGFGRWRRDAQATRSQV, (SEQIDNO:9796); XM_014109990.1, SPARCL1, Ins, T_7, FPIHFGNCSCNPDKCKVPV, (SEQIDNO:9798); XM_014109991.1, SPARCLI, Ins, T_7, FPIHFGNCSCNPG, (SEQIDNO:9799); XM_014118880.1, LOC482344, Del, T_7, FPIHVARMFSSFVAYPSVLRKERQ, (SEQIDNO:9800); XM_844651.4, SETD9, Ins, T_7, FPIHWKPNF, (SEQIDNO:9801); XM_005638791.2, LTN1, Del, T_7, FPKASTVCFYLFW, (SEQIDNO:9802); XM_014119702.1, CFAP54, Del, T_7, FPKIHLFPKCWNMKEIRELMLENLPIDSSWIT, (SEQIDNO:9803); XM_005637172.1, LOC611455, Del, T_7, FPLGIVRTTAMKYVNNLLKSWETVVLLKLLIQKSSNSTVQDFSCHFIPL, (SEQIDNO:9804); XM_003434058.3, LOC100684793, Del, T_7, FPLQSVQRQNAFCWQQWLMIAMWPYANH, (SEQIDNO:9805); XM_546110.4, SLC16A9, Del, T_7, FPMVLLSDSDVVYCTRQQ, (SEQIDNO:9807); NM_001284438.1, DEFB126, Ins, T_7, FPPDSLGLRSFIFEKV, (SEQIDNO:9808); NM_001017521.1, cOR52P3, Ins, T_7, FPPGHPRSGTISPVALTPRVLPGHSHNCGQHYHPGCCCH, (SEQIDNO:9809); XM_533692.5, TMEM147, Del, T_7, FPPGKAASMTSSGSS, (SEQIDNO:9810); XM_005630827.2, THEM5, Ins, T_7, FPPIREEVHLSFPTWPLPGGGPRLDPSGLSGCTERPCGKDRGPEALHVLHRPEQGPAD GLCQVLRYLPSAAARRGITPV, (SEQIDNO:9811); XM_845796.3, THEM5, Ins, T_7, FPPIREEVHLSFPTWPLPGGGPRVCTWRLPGYHDGRDFF, (SEQIDNO:9812); XM_005628322.1, SLC30A9, Ins, T_7, FPPRMAEFSDVEKLFTRDLLWASVPSRAESSEVVLHKRAERRTGVADSQSGKSTIVR, (SEQIDNO:9813); XM_005638791.2, LTNI, Ins, T_7, FPRHPQFAFTSFGDCYRRKQRYI, (SEQIDNO:9814); XM_014106286.1, MYCBP2, Del, T_7, FPRKQQCKNKICRSCEEGQAYTR, (SEQIDNO:9815); XM_014119142.1, LSM8, Ins, T_7, FPRLKKPRGNTERV, (SEQIDNO:9816); XM_014106285.1, MYCBP2, Del, T_7, FPRNLKLILMTFSKI, (SEQIDNO:9817); XM_005628579.2, AGMO, Del, T_7, FPSALLSGESEA, (SEQIDNO:9818); XM_014108246.1, NR4A1, Del, T_7, FPSAPLLVPVPALPRAP, (SEQIDNO:9819); XM_005626363.1, TYRP1, Ins, T_7, FPSDLGSIPKRVCHC, (SEQIDNO:9820); XM_847656.3, LOC610217, Del, T_7, FPSSATVLDMYHPMFIFSCLPSICLCRLPLTPLSMV, (SEQIDNO:9822); NM_001005870.1, RXFP2, Ins, T_7, FPSSKQCLEPNPLHSHNQLFQGQVETAAAQTSEENFQN, (SEQIDNO:9823); XM_003433032.1, LOC100688267, Ins, T_7, FPSSWVYRKFPPSSDVL, (SEQIDNO:9824); XM_535467.5, SLC12A1, Ins, T_7, FPSSYWDSCWCQYLRRFGGSPRCHPQRNHAGHFHHHCR-LYRSCYLCRGLCGPRCY RKHE, (SEQIDNO:9825); XM_005638811.2, LOC102153645, Del, T_7, FPSVLISPVSVNLQCIIDLRTVCPVILAHRSTSLMAVSHRTSSPVGIDH, (SEQIDNO:9826); XM_005629214.2, TMTC3, Ins, T_7, FPSWICCC, (SEQIDNO:9827); NM_001013846.1, CCKBR, Ins, T_7, FPVLVATV, (SEQIDNO:9828); XM_014117525.1, NRXN1, Ins, T_7, FPVQDNIPRWTDSI, (SEQIDNO:9830); XM_005640499.2, BOL1, Ins, T_7, FPVWVCKRSEDCK, (SEQIDNO:9831); XM_014116442.1, ABCA5, Ins, T_7, FPVWVINIFCFNADTSF, (SEQIDNO:9832); XM_014113241.1, RAVER2, Del, T_7, FPVYINLCFASLHRMKAVMLVALQ, (SEQIDNO:9833); XM_005617241.1, SLC6A2, Del, T_7, FPWGLDLES, (SEQIDNO:9834); XM_014109139.1, CFAP43, Del, T_7, FQEIVKST, (SEQIDNO:9837); XM_014113264.1, LOC100684019, Del, T_7, FQEQLNMSSKILYMTQKDTRCSSVI, (SEQIDNO:9838); XM_014118218.1, REV3L, Del, T_7, FQIQVLRVVIHLKIACLLNIIHLILIQ, (SEQIDNO:9839); XM_014120726.1, LOC607038, Del, T_7, FQIVHTLKISDMWKNKNQFYTFCTNIQKFIIRKTYNILLIS, (SEQIDNO:9840); XM_014119702.1, CFAP54, Del, T_7, FQKALETKLLHIHFML, (SEQIDNO:9841); XM_014119702.1, CFAP54, Ins, T_7, FQKSTYFRNVGT, (SEQIDNO:9842); XM_003433214.2, LOC100685852, Del, T_7, FQLEEEPLSSAGYSLC, (SEQIDNO:9843); XM_005637157.2, LOC100683403, Del, T_7, FQLLKYWSRTIHP, (SEQIDNO:9844); XM_005642422.1, OVCH1, Del, T_7, FQLQDIHWIIEENWNVLGCSECHQAVWQN, (SEQIDNO:9845); XM_005640284.2, LRP2, Del, T_7, FQLTLVVSTSKKSFLLMIQRI, (SEQIDNO:9846); XM_852855.4, FLRT3, Ins, T_7, FQPSQLNRTVPGTEFPDCCTSKPSRHKPEEALSSR, (SEQIDNO:9847); XM_536110.5, CFH, Del, T_7, FQQSMEIRQHVLM, (SEQIDNO:9848); XM_005619936.2, RNASEK, Ins, T_7, FQRPFRCADRGRSFHRERF, (SEQIDNO:9850); XM_843679.5, SON, Ins, T_7, FQSEYCCSKANSTKKPGNINKRISCVIWISTSKKRSR, (SEQIDNO:9851); XM_014109787.1, DOPEY2, Ins, T_7, FQSFAAKNISPAFDFIVAHNGL, (SEQIDNO:9852); XM_014110705.1, GRB14, Del, T_7, FQSIWCLLQLKPMVKYPPHRFCRCF, (SEQIDNO:9853); XM_005642434.2, LOC100686288, Del, T_7, FQWKNTKEH, (SEQIDNO:9856); XM_014120154.1, FAT1, Del, T_7, FQYILKQVLSQRRQGNWTESSKMNN, (SEQIDNO:9857); XM_005615345.2, VPS4B, Del, T_7, FQYLPLTLSLSG, (SEQIDNO:9858); XM_005641432.1, YIPF6, Del, T_7, FRASVCWVTVYFP, (SEQIDNO:9859); XM_005618243.2, TLR10, Del, T_7, FRAVRKLRF, (SEQIDNO:9860); XM_534289.5, SLC25A36, Del, T_7, FRHCLWLFKKKVMGLFTVV, (SEQIDNO:9861); XM_005628880.2, TMCO2, Del, T_7, FRLCWSAQMGIFSQFKTIISSCPWVCKREF, (SEQIDNO:9862); XM_005635818.2, SP140, Del, T_7, FRRFHIIIILKRFLKT, (SEQIDNO:9863); XM_014112169.1, LOC100856170, Del, T_7, FRSKSLYYSL, (SEQIDNO:9865); XM_005631507.2, ATG2A, Del, T_7, FRSLMPPRMGPSAPVTSTISDRASRGPVPVAMSD, (SEQIDNO:9866); XM_005639030.2, PRMT2, Del, T_7, FRSPSTTTF, (SEQIDNO:9867); XM_005639390.2, LOC487951, Ins, T_7, FRSRLHSDRSSNMVGRLFHDGHSPDAEKKENALHPGL, (SEQIDNO:9868); XM_014116442.1, ABCA5, Ins, T_7, FRSSDFYVFGASLF, (SEQIDNO:9869); XM_533578.4, NLRP9, Del, T_7, FRTLACCGTWRSSKRKNSGNLRSSSNKNLCN- LASSQSHGLS, (SEQIDNO:9870); XM_014118865.1, UTRN, Del, T_7, FRVERQKVTNYITQWWNIVYLQHLGKMYETSQRC, (SEQIDNO:9871); NM_001012395.1, UTRN, Del, T_7, FRVERQKVTNYITQWWNIVYLQHLGKMYETSQRY, (SEQIDNO:9872); XM_014107486.1, LOC100688473, Ins, T_7, FRVSRCHEFQRESEESHLPLGGTFILPLFFKNCFGSCI, (SEQIDNO:9873); XM_005635896.2, LOC100688622, Ins, T_7, FRVSRCHEFQRESVESHLPLRGTFILPLFF, (SEQIDNO:9874); XM_005640282.2, LRP2, Ins, T_7, FRYIKRHDL, (SEQIDNO:9875); XM_005635025.2, RBL1, Ins, T_7, FRYISKSI, (SEQIDNO:9876); XM_014110908.1, LOC100686469, Ins, T_7, FSACLCQPQRIQPNWKAIT, (SEQIDNO:9877); XM_005637170.2, KLRB1, Ins, T_7, FSCFQHLERQSN, (SEQIDNO:9878); XM_014116442.1, ABCA5, Del, T_7, FSCMGYHLYFLL, (SEQIDNO:9879); XM_005639368.1, LOC100856070, Del, T_7, FSCTLDQICLNKGIKISQLLFCLQ, (SEQIDNO:9880); NM_001013846.1, CCKBR, Del, T_7, FSCVGCHCIVPTRGVPSTALVHTAHFQERQSLSSTC, (SEQIDNO:9882); XM_005622962.2, NPHS2, Del, T_7, FSFFPALIPTTRLTFVSKLWRYPFMRL, (SEQIDNO:9885); XM_014108715.1, C27H12orf40, Del, T_7, FSFFSLVKLIILIPWSPN, (SEQIDNO:9886); XM_014121827.1, PTPRS, Del, T_7, FSFLLLSLPWARPCHTSSGCLGPKT, (SEQIDNO:9887); XM_005642072.1, LOC102152098, Del, T_7, FSFPQVKI, (SEQIDNO:9888); XM_005618393.2, BTBD1, Del, T_7, FSFSAPLAIIMALQ, (SEQIDNO:9890); XM_005641779.2, STAG2, Del, T_7, FSFWKVSCMSMQHTLWIACGTVLPSY, (SEQIDNO:9891); XM_014109050.1, R3HCC1L, Del, T_7, FSFYFIWN, (SEQIDNO:9892); XM_014114796.1, LOC612019, Del, T_7, FSFYFRMLMIGMGHQIIMG, (SEQIDNO:9893); XM_848418.4, GPR137C, Ins, T_7, FSGELDLCNVSPRRCPRKSVEMDCVCSSIN, (SEQIDNO:9894); XM_845544.4, C6H7orf61, Del, T_7, FSGNTKLSQPSWNTMTPGKVL, (SEQIDNO:9895); XM_005642434.2, LOC100686288, Ins, T_7, FSGRTPRSIDPVLHF, (SEQIDNO:9896); XM_849291.3, PRPF8, Del, T_7, FSGSQQMRLGT, (SEQIDNO:9897); XM_005642102.1, LOC102156483, Del, T_7, FSIFMGLAGECPLALSAS, (SEQIDNO:9898); XM_005638424.2, FAM214A Ins, T_7, FSIKCLAECFSWCYSTKYSLQNQCC, (SEQIDNO:9899); XM_005626363.1, TYRP1, Del, T_7, FSIRPGLNSQESVPLLRP, (SEQIDNO:9900); XM_542156.5, CHAF1A, Del, T_7, FSKGRCLWWSCRISWLRNLLKPSLQRHLHTRACPLRVRCWSLALKKTLFLATHPGV LPLLPAHLRGSLLPKSSTAVPGPSPPPHLSAE, (SEQIDNO:9901); XM_005641813.2, ARHGAP36, Ins, T_7, FSKRPGRSPRTQSGPQDEDDIDTQSVGAGASEAARDCLPRTRGQTFPL, (SEQIDNO:9902); XM_005639098.2, CNOT6L, Ins, T_7, FSKVTCQNHV, (SEQIDNO:9903); XM_003640055.1, LOC100856122, Del, T_7, FSLCYMSSLCWETFS, (SEQIDNO:9904); XM_534842.3, LOC477647, Ins, T_7, FSLEIYLCS, (SEQIDNO:9905); XM_014107412.1, MICU2, Del, T_7, FSLPLKIKTSIGKM, (SEQIDNO:9906); XM_005639817.2, RTP4, Del, T_7, FSLPLQANTWKQKDQN, (SEQIDNO:9907); XM_014114384.1, TNNI3K, Del, T_7, FSLRCTLQHTMDMNR, (SEQIDNO:9908); XM_005638667.1, LOC487459, Del, T_7, FSLYSMLELS, (SEQIDNO:9910); NM_001164486.1, SELENOI, Ins, T_7, FSMFAIHFVYSMDPSVAFRYFRVAS, (SEQIDNO:9911); XM_014111106.1, ALS2CR11, Del, T_7, FSNIISLIEDNQKKN, (SEQIDNO:9912); NM_001048097.1, PTGFR, Ins, T_7, FSNLHDSGNLVKQPCHCYSHEGLSEI, (SEQIDNO:9913); XM_844651.4, SETD9, Del, T_7, FSNPLETHLFLDAWMGYSLMEMTKEYQKLYTDLAMGGIDLVPSK, (SEQIDNO:9914); XM_547829.5, TMEM260, Del, T_7, FSPFSGFLAHMLEESLLRGCFHFLV, (SEQIDNO:9915); XM_014118577.1, PKHD1L1, Del, T_7, FSPHFSVWMST, (SEQIDNO:9916); XM_014117993.1, LOC100685402, Del, T_7, FSPICLSSTPS, (SEQIDNO:9917); XM_538762.4, LOC481640, Del, T_7, FSPICSSSTPS, (SEQIDNO:9918); NM_001122645.1, DIO2, Del, T_7, FSPTASSWHSMTRSFSSSTWCCC, (SEQIDNO:9919); XM_005630975.2, RELN, Del, T_7, FSQELQLSIAVSQKATLFISTEMKEVSSILPPPGM, (SEQIDNO:9921); XM_014116442.1, ABCA5, Del, T_7, FSQFRFLCFWCIALLKMLWFPSNLFQTYIS, (SEQIDNO:9922); XM_014106710.1, SLC4A7, Del, T_7, FSQHFFC1HSSSNLRLSGIFLPRCDRQSVILLYFSQ, (SEQIDNO:9923); XM_005629214.2, TMTC3, Del, T_7, FSQLDLLLLSEYYMFLAWGSVFW, (SEQIDNO:9924); XM_014118177.1, BVES, Del, T_7, FSQLGWLFQLHFTFI, (SEQIDNO:9925); XM_005626214.1, PMM1, Del, T_7, FSQRQPMRR, (SEQIDNO:9927); XM_014116978.1, DDX31, Del, T_7, FSQVVSWWSSTTTSSSRPCRAAQGPWRQDGHHLPPHN, (SEQIDNO:9928); XM_005633004.2, CATSPERD, Del, T_7, FSREIISEVVSFHFPSLHQ, (SEQIDNO:9929); XM_005623486.2, SYNE2, Del, T_7, FSRNLLLTCC, (SEQIDNO:9930); XM_005627957.1, CTHRC1, Del, T_7, FSRTDRGGQRRWWTCIMECAYKDLQGCLGEMEALGPMAFLVPLGSQVEMDSKEK RGNA, (SEQIDNO:9931); XM_014108700.1, LOC611536, Del, T_7, FSSHFSVLVLLQIVW, (SEQIDNO:9932); XM_014108701.1, LOC611536, Del, T_7, FSSHFSVLVLLQIVWGAGAVAVLLAGEPSSPTAIFLLMTTRPGLRVKGTARVWGLT WPPSAQKLS, (SEQIDNO:9933); XM_014115000.1, MRI, Ins, T_7, FSSHHYNVLLAERAVGSVDGGELHAWALGEKHHISPACI, (SEQIDNO:9934); XM_005635476.2, PDS5B, Del, T_7, FSSILTKMAYW, (SEQIDNO:9935); XM_534154.5, RNF219, Del, T_7, FSSLHLTKK, (SEQIDNO:9936); XM_005626899.2, FKTN, Del, T_7, FSSMKRLTICGMEALRPKQEKNLNTCFPSLHCAGLSL, (SEQIDNO:9937); XM_003640168.3, ABT1, Del, T_7, FSSPRTGS, (SEQIDNO:9938); XM_014115507.1, PIEZO2, Ins, T_7, FSSRDRRTGTRGRSLCQINLPVPIPRNHDQMD, (SEQIDNO:9939); XM_849282.4, CLRN3, Del, T_7, FSSRRPDTSENRRRESPWNLLQEMEFYS, (SEQIDNO:9940); XM_014117525.1, NRXN1, Del, T_7, FSSSRQHP, (SEQIDNO:9941); XM_014111846.1, PRDX4, Del, T_7, FSSTPLISPLCVQLKSSPMELKNSNR, (SEQIDNO:9942); XM_005630827.2, THEM5, Del, T_7, FSTHPRRSPSVFSNLAPTWRGPPA, (SEQIDNO:9944); XM_845796.3, THEM5, Del, T_7, FSTHPRRSPSVFSNLAPTWRGPPGLHMEAPWLP, (SEQIDNO:9945); XM_005615724.2, TJP2, Del, T_7, FSTQTLDKVSKP, (SEQIDNO:9946); XM_005619936.2, RNASEK Del, T_7, FSTSIPLC, (SEQIDNO:9947); XM_541064.5, DSEL, Del, T_7, FSTVVIFSTSEFLQPTSIFLKLNLKLTHLWTPVNGRHLISTVCISVCSEAGCSP, (SEQIDNO:9948); XM_014117497.1, FER1L5, Ins, T_7, FSTYAVQLYLFNTELLGHELDQT, (SEQIDNO:9949); XM_546437.4, COR8C4, Del, T_7, FSVSLPILSAMC, (SEQIDNO:9950); XM_014122259.1, DNAH1, Del, T_7, FSVYLTWPTWTPCTSTPWSGFSTSSAQASP- TRRGQTT, (SEQIDNO:9951); XM_533741.5, SLC6A11, Del, T_7, FSWKQLWDNSRVRVALRVGGK-FALYLKASAMQHK, (SEQIDNO:9952); XM_014119262.1, SLC6A15, Del, T_7, FSWNLL-WVKESGEEALVCGIT, (SEQIDNO:9953); XM_014120569.1, PTGFRN, Del, T_7, FSYRFIDL, (SEQIDNO:9956); XM_005641570.2, ARMCX1, Del, T_7, FSYSKNLECVLRKSRH, (SEQIDNO:9957); XM_014109991.1, SPARCL1, Del, T_7, FSYTFWELQLQSRLKNLLY, (SEQIDNO:9958); XM_014109990.1, SPARCL1, Del, T_7, FSYTFWELQLQSRQMQGSCLIIPNQLLIL, (SEQIDNO:9959); XM_014110047.1, BANK1, Ins, T_7, FTCEKRSNPIISLGELLFLGFGIAEFKLL, (SEQIDNO:9961); XM_005631620.2, MTA2, Del, T_7, FTHWCLTLCRRHF, (SEQIDNO:9962); XM_005640869.2, LOC478984, Del, T_7, FTIILSTTFQQQQVNTMAPTSAGGLSGRKTSLRRL, (SEQIDNO:9963); XM_014121804.1, CACNA1A, Del, T_7, FTKRRGGCVSTSAAWSKLRPSTGLCSVW, (SEQIDNO:9964); XM_014107997.1, KNTC1, Del, T_7, FTLQIFNF, (SEQIDNO:9965); XM_014114799.1, ECT2L, Ins, T_7, FTMLQITIKVCPRLFRKDASGQTGFLYSVT-TLHFSIYLFLPESKRSVCSCTSQLALEVY N, (SEQIDNO:9966); XM_005624150.1, CBX4, Ins, T_7, FTPCPLPFLCKI, (SEQIDNO:9967); XM_005635222.2, LOC477273, Ins, T_7, FTRKQIKFSSGAF, (SEQIDNO:9968); XM_536312.4, CMYA5, Del, T_7, FTRTYMNKQLERKTRKRRQLLKVTV, (SEQIDNO:9969); XM_014114127.1, CCT6A, Del, T_7, FTRVQKR-ERNS, (SEQIDNO:9970); XM_014118383.1, UHRF1BP1, Ins, T_7, FTSCFPDGFPTPSTQYPPSPEA, (SEQIDNO:9971); XM_005629907.2, LEPROTL1, Del, T_7, FTSFHLFHTA, (SEQIDNO:9972); XM_014110652.1, SLC17A2, Del, T_7, FTSHLDKQKSKTGPKRRPLPAF, (SEQIDNO:9973); XM_014111380.1, DNAJC16, Del, T_7, FTSLLTLSGGAPLMRSNCTFHTT, (SEQIDNO:9974); XM_005620301.1, OR16A12, Del, T_7, FTTSSAALSVC-STR, (SEQIDNO:9975); XM_014107594.1, FZD3, Del, T_7, FTVVGKKR, (SEQIDNO:9977); XM_014115681.1, RALGAPA1, Ins, T_7, FTWFAWCHNAYYGFYCSSW, (SEQIDNO:9978); XM_534129.3, LACC1, Ins, T_7, FTWIYYKNRWNILHPNS, (SEQIDNO:9979); XM_003638904.3, LYPLA2, Ins, T_7, FTWTWRHRAQLG, (SEQIDNO:9980); XM_014109945.1, WDFY3, Del, T_7, FTYQNSCSIPT-TLI, (SEQIDNO:9981); XM_014118650.1, CWH43, Ins, T_7, FVAACWCGTIRIRTTT, (SEQIDNO:9982); XM_014118899.1, CASD1, Del, T_7, FVDSSSYRRFKTNQDI, (SEQIDNO:9983); XM_014117404.1, RANBP2, Del, T_7, FVESAVILMRT-MEMGKIFSQNFKKFRTLRNPRMRK, (SEQIDNO:9984); XM_014119043.1, PEX1, Ins, T_7, FVEYQSAAE-DHNTSPSRSYGKRRKQ, (SEQIDNO:9985); XM_005631715.2, RCN1, Ins, T_7, FVFCFFFSKLQEDR, (SEQIDNO:9986); XM_014116451.1, RDM1, Del, T_7, FVFFFFFCP, (SEQIDNO:9987); XM_014108289.1, LOC102156424, Ins, T_7, FVFGCGLMCLLQRWLFVQ, (SEQIDNO:9988); XM_014119604.1, TMPO, Ins, T_7, FVFGLSSYGNQPRKSVQ, (SEQIDNO:9989); XM_003433948.1, LOC100684112, Ins, T_7, FVFHPMHVSVRLAFSPTFN, (SEQIDNO:9990); XM_005619626.2, LOC489325, Ins, T_7, FVFLLFL-NAMC, (SEQIDNO:9991); XM_003433951.2, LOC100684620, Ins, T_7, FVFYYILHSKYARKP-SHCGHYHLRPSLTFTYVFFAGKSFHHRHRCF, (SEQIDNO:9992); XM_544884.5, KCNJ15, Ins, T_7, FVGCSAGHYDPD, (SEQIDNO:9993); XM_005627651.2, MANEA, Del, T_7, FVISSTSCLSQVWAQDI, (SEQIDNO:9994); XM_005638132.2, RAD54B, Ins, T_7, FVKFKSWWCGT, (SEQIDNO:9995); XM_014116854.1, ITGAE, Del, T_7, FVLLSFRWPPLSLSRNWWWVSQRS, (SEQIDNO:9996); XM_848171.2, LOC610635, Del, T_7, FVLVLECTSALLLPRTPTRVQWPQ, (SEQIDNO:9997); XM_848256.3, LOC484896, Del, T_7, FVLVLECTSAP-LLPRAPTRVQLPQ, (SEQIDNO:9998); XM_014110082.1, LOC487944, Del, T_7, FVMFFHYSNSPVLTLISMNC, (SEQIDNO:9999); XM_535270.5, TNPO1, Del, T_7, FVMLLHR-GLTQKMHI, (SEQIDNO:10000); XM_014118893.1, LOC482235, Del, T_7, FVMSLPFSFSHAPTHCYLKG, (SEQIDNO:10001); XM_014110085.1, LOC100687081, Del, T_7, FVNFFHYSNSPVLTLISMNC, (SEQIDNO:10002); XM_014113223.1, DYNC2H1, Ins, T_7, FVNKKPKSLHPTRCSLHHYRG, (SEQIDNO:10003); XM_014109133.1, TDRD1, Del, T_7, FVNSYRVDISSLNFRHPLVSTVVKC1HAQIFIQPMSV-VHDSQRMISGTVPLF, (SEQIDNO:10005); XM_005640538.2, CFLAR, Ins, T_7, FVPGRCCRCC-STYCQGPSGYFK, (SEQIDNO:10006); XM_005640646.2, RQCD1, Ins, T_7, FVPL-FAHCQQNTTL, (SEQIDNO:10007); XM_014112169.1, LOC100856170, Ins, T_7, FVRSHYIIHFKKSLS-GRKTQSPLYLWISHHSYSFIFWAFHLCLP, (SEQIDNO:10008); XM_014111215.1, ZBED6, Del, T_7, FVSTKAL-RIC, (SEQIDNO:10009); XM_014110084.1, LOC100685107, Del, T_7, FVTFFPSIDSLVLTLLSMN, (SEQIDNO:10010); XM_014110202.1, ABHD10, Del, T_7, FVVFCFVVLF, (SEQIDNO:10011); XM_847331.4, CEPT1, Del, T_7, FVVLLGHLCSIVHT-GRRMFLEHCDLE, (SEQIDNO:10012); XM_005621786.2, CEPT1, Del, T_7, FVVLLGHLC-SIVHTGRRMFLEHCDLEYSMLQSPRS, (SEQIDNO:10013); XM_843573.4, DARS, Del, T_7, FWDCTMFVRRQCSPGILNDSLL, (SEQIDNO:10014); XM_014107257.1, ARFGAP1, Ins, T_7, FWESGGHVGQAPGGPELPEQRWGPPPEPHRG-PELLGELREHGPCQGPQVPEQRQLD VRRRL-GREEELGQLGCVGLGLRVQQ, (SEQIDNO:10015); XM_014108734.1, LOC100687078, Del, T_7, FWFLKWSQW, (SEQIDNO:10016); XM_546450.3, OR28D07, Del, T_7, FWGTCLCLT, (SEQIDNO:10017); XM_005627189.2, LOC481728, Del, T_7, FWIMKTMT-FLSMT, (SEQIDNO:10018); XM_847187.3, TXNDC12, Del, T_7, FWIPVARCILKSSMRMETPATSISMSVLSKL-FRG, (SEQIDNO:10019); XM_844183.4, ESRRG, Del, T_7, FWKCWRPRS, (SEQIDNO:10020); XM_014119672.1, OTOGL, Del, T_7, FWKINLHTSFGRQGST, (SEQIDNO:10021); XM_005616941.2, CUL2, Del, T_7, FWKITYGICTRE-FWSLKSKYLLCHGIGRNIAKVQTIWTACI-GISTLSLLKRIN, (SEQIDNO:10022); XM_845265.4, UTS2B, Del, T_7, FWKWCMDGHILPKEMNCFQQK-KIQIARNYCWIY, (SEQIDNO:10023); XM_536500.4, NUP155, Del, T_7, FWLEKMAVYMK, (SEQIDNO:10024); XM_005625825.2, XRCC6, Del, T_7, FWLMVLGPCLNLRVKLN, (SEQIDNO:10025); XM_014111948.1, TSPAN6, Del, T_7, FWLNWSLPS, (SEQIDNO:10026); XM_005632409.2, ASB14, Del, T_7, FWLSALAS, (SEQIDNO:10027); XM_014119539.1, ABCE1, Del, T_7, FWMATFQQKT, (SEQIDNO:10028); XM_014120560.1, PIP5K1A, Del, T_7, FWMLTCTMLCVRPYSVTVWCCRASR, (SEQIDNO:10029); XM_014122642.1, FAT3, Del, T_7, FWMMSMIVPQLSFPVAIV, (SEQIDNO:10030);

XM_014122196.1, DOCK6, Del, T_7, FWQRSQKTPNSSGIITSCGSVSRTSARSVRMPCGRTRP, (SEQIDNO:10031); XM_003640134.2, OTOL1, Del, T_7, FWQSLVWTQ, (SEQIDNO:10032); XM_003639984.3, BTAF1, Del, T_7, FWRRFFHGWEQLMTISNRRVQLKHLHV, (SEQIDNO:10033); XM_014111351.1, DMD, Ins, T_7, FWSSCKRP, (SEQIDNO:10034); XM_005621541.1, CLEC16A, Del, T_7, FWTCLKTNTGA, (SEQIDNO:10035); XM_005638158.1, KIAA1429, Ins, T_7, FWTHTTFRAAASTIAHANNSGY, (SEQIDNO:10036); XM_005628358.2, TRIM58, Del, T_7, FWTMKQVKSPFTM, (SEQIDNO:10037); XM_014106943.1, RIN2, Del, T_7, FWTRKAARRP, (SEQIDNO:10038); XM_848657.4, TRIM38, Del, T_7, FWTVILELYPFTT, (SEQIDNO:10039); XM_539359.3, OR2T2, Del, T_7, FWWLSQPMWS, (SEQIDNO:10040); XM_005631191.1, LOC483467, Del, T_7, FWWWASMTSFLS, (SEQIDNO:10041); XM_005624150.1, CBX4, Del, T_7, FYAVSPPFPLQDITRGNPRRTSWIPGC, (SEQIDNO:10042); XM_014114799.1, ECT2L, Del, T_7, FYDAPNHN, (SEQIDNO:10043); XM_847055.3, LOC609729, Del, T_7, FYFWCTHQL, (SEQIDNO:10044); XM_014108288.1, GXYLT1, Del, T_7, FYGLSMIFGLY, (SEQIDNO:10046); XM_533983.5, CCDC81, Del, T_7, FYHDPFSSNKMWNLLSKELGSL, (SEQIDNO:10047); XM_014120337.1, BIRC6, Del, T_7, FYIMLIEYLSFH, (SEQIDNO:10048); XM_005626134.2, C1OH2orf74, Del, T_7, FYINVPKAKLKRQKKFLV, (SEQIDNO:10050); XM_005635896.2, LOC100688622, Del, T_7, FYIVRICLGTQH, (SEQIDNO:10051); XM_014107486.1, LOC100688473, Del, T_7, FYIVRICMQN, (SEQIDNO:10052); XM_014122769.1, RIC3, Del, T_7, FYIYYIFYLSFQRGKLLQRIGNALLPQLETPTGKLPISSLFNCKKN, (SEQIDNO:10053); XM_005635222.2, LOC477273, Del, T_7, FYKKTDQIFQWCFLNISHRLW, (SEQIDNO:10054); XM_014107218.1, COMMD7, Del, T_7, FYKTCMTF, (SEQIDNO:10055); XM_003432392.1, LOC100687724, Del, T_7, FYLFVDPMK, (SEQIDNO:10056); XM_003640185.3, TMEM237, Del, T_7, FYLIGQAWILVKS, (SEQIDNO:10057); XM_014108759.1, ZFAND4, Del, T_7, FYLPVVLE, (SEQIDNO:10058); XM_003638904.3, LYPLA2, Del, T_7, FYMDLETQGTAGLTPSPPSGSLTSSTSVPMHPGSL, (SEQIDNO:10059); XM_534129.3, LACC1, Del, T_7, FYMDLLQEQVEYLTSQLLVHSISSVVPNGEIPRWWFKKICVGWGMLLDLTWRNFTE, (SEQIDNO:10060); XM_544123.3, TRPA1, Del, T_7, FYPVYLDTAKK, (SEQIDNO:10061); NM_001172235.1, UGCG, Del, T_7, FYRHYGTLL, (SEQIDNO:10062); XM_014116024.1, PCNX, Ins, T_7, FYSTKSLSGKCNIHHFICSTCEILGERL, (SEQIDNO:10063); XM_005627580.2, DOPEY1, Del, T_7, FYTVLGYFLFLQMLPCL, (SEQIDNO:10064); XM_005627466.1, PKHD1, Del, T_7, FYWGTEVPPSFFWLYSTMNFRTPVFS, (SEQIDNO:10065); XM_533381.4, TMX3, Del, T_7, FYWIWLSVKDLYKIWMNRLKIIGKMTFGL, (SEQIDNO:10066); XM_856309.4, KDELR2, Del, T_7, FYYYVQRFFYTKKL, (SEQIDNO:10067); XM_005636644.2, LIPJ, Del, T_7, LAAKTSSLIPHLKDLLVQSCVR, (SEQIDNO:10068); XM_014110801.1, CCDC141, Del, T_7, LAALIRHLMYLGESKLTLSSLNQKV, (SEQIDNO:10069); XM_003434547.1, LOC100687427, Del, T_7, LAFLNAMC, (SEQIDNO:10070); XM_014111151.1, MFN2, Del, T_7, LAGRATGRA1, (SEQIDNO:10071); XM_005626218.2, BAIAP2L2, Del, T_7, LAGTRGGKRKKHET, (SEQIDNO:10072); XM_549283.3, ADGRG4, Del, T_7, LAKLHCLRPEMSQKH, (SEQIDNO:10073); NM_001002952.1, EPB41L5, Ins, T_7, LAQDNQIGF, (SEQIDNO:10075); XM_014119721.1, ENPP1, Ins, T_7, LARIRCGN, (SEQIDNO:10076); XM_005630949.2, BCAP29, Ins, T_7, LASVETSGYPYYSIG, (SEQIDNO:10077); XM_532924.5, SLC30A6, Del, T_7, LASYYRNLDL, (SEQIDNO:10078); XM_005641414.2, AMER1, Del, T-7, LAVSAVTGKARSLGLKKVS, (SEQIDNO:10079); XM_003639076.3, SYCE1L, Del, T_7, LAVVLQGARQLRPRVGKWRASWSP, (SEQIDNO:10080); XM_005630844.1, LRIG2, Del, T_7, LAWITWKN, (SEQIDNO:10081); XM_014122003.1, LOC403903, Del, T_7, LCFLDVWIVSSWL, (SEQIDNO:10082); XM_005642125.2, FRMD7, Ins, T_7, LCGQTTPGAQTVSNHGRGK, (SEQIDNO:10083); NM_001031630.1, TERT, Ins, T_7, LCHGNHVSKEPTLLLPEERLEPVTEHRNQTTLQ, (SEQIDNO:10084); XM_005616820.1, TMC1, Del, T_7, LCILQMCLEDPAGKQWWDRNLCG, (SEQIDNO:10085); XM_014110567.1, ATXN1, Del, T_7, LCLDRAGHLAVQREPASSSTCRAPSSPLGTSASR, (SEQIDNO:10086); XM_005634064.2, CCDC168, Ins, T_7, LCLYTSRFTGDYTPNCSLDYSPKNFKEDKLQSSSGGKDFKFFRYMDFIQKVLGVPLG VLQSS, (SEQIDNO:10087); NM_001013852.1, VN1R4, Ins, T_7, LCPLIHLSDLSVFFKYLKSVDGEHVCILYYVFSFSQPLCAHEL, (SEQIDNO:10088); XM_005615845.2, CARNMT1, Del, T_7, LCSFLPTLYSTDVLKLINISFIPGSISLAITGGQLIRFDPSLSPMLTPTVFLLVTFP, (SEQIDNO:10089); XM_545128.5, SLC15A2, Del, T_7, LCSSRTRCRY, (SEQIDNO:10090); XM_014119192.1, VWDE, Del, T_7, LCTYYSPLRDVWDIVQKLFLMQNYTHVTLMKLKLEVTVFVSC11HCHHHPQEGRKL WWS, (SEQIDNO:10091); XM_005629133.1, LOC100686641, Ins, T_7, LDDFKFLALIYSFLLHHGVLYSGLESCVEGPFCSWTKKSFLYLWVPSGCGFTVLWLS DGHVSEPDI, (SEQIDNO:10092); XM_005625619.2, BEST3, Del, T_7, LDFIGYSSSGEGASTNYCTGNLLSLLFFTRP, (SEQIDNO:10093); XM_014113223.1, DYNC2H1, Del, T_7, LDLSSITLHIEFSKTCILS, (SEQIDNO:10094); XM_536737.4, SLC25A33, Del, T_7, LDLWQLLQFLRDVLPASLIHMKS, (SEQIDNO:10095); XM_003432360.1, LOC100685932, Del, T_7, LDQDSLSICTPALAILWARTR, (SEQIDNO:10096); XM_014118119.1, PHIP, Del, T_7, LDQVSQRKYQNWSSILTKLTVSSFPTLATDL, (SEQIDNO:10097); XM_003435483.1, FOXR2, Ins, T_7, LDSSKWLEKHHPPQSLFPGQL, (SEQIDNO:10098); XM_005637041.2, TM7SF3, Del, T_7, LDTDSGKQNYFS, (SEQIDNO:10099); XM_014112641.1, NWD2, Ins, T_7, LEAGHRTMHGELTGDLRYHSQAREVQSPQYAAIFVNQWCSFHLGYRYNHGHVQHR, (SEQIDNO:10100); XM_014111447.1, VPS13D, Del, T_7, LELVPLTTMQ, (SEQIDNO:10102); XM_531814.5, MSH6, Del, T_7, LEMTLYPMTF, (SEQIDNO:10103); XM_014112077.1, MAN2A1, Ins, T_7, LETELGSGIWHRYFLPHDALLQL, (SEQIDNO:10105); XM_536122.5, RAB3GAP2, Ins, T_7, LEVFAWRKLYRGYVSHSGVSWT, (SEQIDNO:10106); XM_005631218.2, LOC483596, Del, T_7, LEVLKASCLL, (SEQIDNO:10107); XM_848405.1, LOC483573, Del, T_7, LEVLMSSCLL, (SEQIDNO:10108); XM_014116451.1, RDM1, Ins, T_7, LFFFFFFVLKILHVP, (SEQIDNO:10109); XM_544974.4, PKD2, Del, T_7, LFFTMWWKRYWKFVFTSYTISGVSGIVWML, (SE- QIDNO:10110); XM_005633841.2, ALG11, Ins, T_7, LFIIPPWANSLWNFMCMSVRYPLGNQTAATEKERVSINQQKWEEANGGCIFSSILQC RWRRRKSFVVCLKGPAEKV, (SEQIDNO:10111); XM_003433052.3, ALG11, Ins, T_7, LFIIPPWANSLWNFMCMSVRYPLGNQTAATEKERVSINQQKWEEANGGCIFSSILQC RWRRRKSFVVCLKGPAEKVP, (SEQIDNO:10112); XM_014118470.1, POLH, Del, T_7, LFKWNSGKILI, (SEQIDNO:10113); XM_539788.5, FSTL5, Del, T_7, LFLLPHSSSPT, (SEQIDNO:10114); XM_005637418.1, COR8S14, Del, T_7, LFPPSPTHS, (SEQIDNO:10115); XM_846025.3, ADAMTS5, Del, T_7, LFPRSPPKKSTQSPAMPAIKWGRTLHSCSG, (SEQIDNO:10116); XM_537050.5, SLC30A7, Del, T_7, LFSQKELREH, (SEQIDNO:10117); XM_014121504.1, MGAT5, Del, T_7, LFTSVRLKIGVLIYLGEQKIPTKKLIIIHWRKFVRILIFSTA, (SEQIDNO:10118); XM_848171.2, LOC610635, Ins, T_7, LFWSWSVPQLCCSPELPHECSGLSDVHSGHTHAEPLHLQPEEQRHKEGSEKSHWGSS DV, (SEQIDNO:10119); XM_848256.3, LOC484896, Ins, T_7, LFWSWSVPQLRCSPELPLECSCLSDVYSGHTHAKPLHLQPEEQRHKESSEKILWGSS DV, (SEQIDNO:10120); XM_005627622.2, SRSF12, Del, T_7, LGLRTCAVSLVDMAL, (SEQIDNO:10121); XM_005639633.1, ATP13A3, Ins, T_7, LGQAATLV, (SEQIDNO:10122); XM_536257.5, KLB, Ins, T_7, LGRWDWSISSGRELEDRWKRTLYMGSFHPHTP, (SEQIDNO:10123); XM_540672.2, OR16F12, Del, T_7, LGSLQMWSVSCWLSWLMTGM, (SEQIDNO:10124); XM_005641635.2, TBC1D8B, Del, T_7, LGSPKKKP, (SEQIDNO:10126); XM_005621497.2, TMC5, Ins, T_7, LGTRLSQS, (SEQIDNO:10127); XM_014110652.1, SLC17A2, Ins, T_7, LHHIWTSRNPRLGQREDPYPP1, (SEQIDNO:10129); XM_014120096.1, LOC102152484, Ins, T_7, LHHSLCIRYNL, (SEQIDNO:10130); XM_844450.4, LOC486076, Del, T_7, LHLLCHMSLAILWVCGMMKKRVNVQTMCA, (SEQIDNO:10131); XM_014119262.1, SLC6A15, Del, T_7, LHLSWQHWWCLQFWALKQML, (SEQIDNO:10132); XM_005634703.2, LOC606793, Ins, T_7, LHLYCCNQTLEI, (SEQIDNO:10133); XM_014118588.1, CSMD3, Del, T_7, LHLYLQDLDFIFINKGLHPKHSIQDVQFMKITMAKQLLRTPCMTPTQSQWKERQYDL IPT, (SEQIDNO:10134); XM_005629907.2, LEPROTL1, Ins, T_7, LHPFTYSILHSEKISG, (SEQIDNO:10135); XM_005624950.2, MNT, Ins, T_7, LHQNFFNLQILFCKYFGKH, (SEQIDNO:10136); XM_014113358.1, SC5D, Del, T_7, LHRTSIQPHGLRMTSSDKLLVS, (SEQIDNO:10137); XM_014107997.1, KNTC1, Ins, T_7, LHYKSSTFKNSTSD, (SEQIDNO:10138); XM_537465.5, DHRS7, Del, T_7, LIASGLNLLSTQV, (SEQIDNO:10139); XM_014121811.1, LOC102153907, Del, T_7, LIFLDVWTVYS, (SEQIDNO:10140); XM_005630352.2, RMDN2, Del, T_7, LIFNQVGITSLIQMK, (SEQIDNO:10141); XM_005639074.2, ART3, Del, T_7, LIKKVKKLF, (SEQIDNO:10142); XM_005639026.2, MCM3AP, Del, T_7, LITRLQPWPGRRGKACIKTWLSFGTRRK, (SEQIDNO:10144); XM_014118396.1, STK38, Del, T_7, LKALTGNISERDLLQYLLKSKALMIPQTSMNFQNLIFLSQQ, (SEQIDNO:10145); XM_005627278.2, STK38, Del, T_7, LKALTGNISERDLLQYLLKSKALMIPQTSMNFQNLIFLSQQLQVITLRLTTRTKTGSSS ITHTSALRA, (SEQIDNO:10146); XM_547836.5, DAAM1, Del, T_7, LKCSEMKMS, (SEQIDNO:10147); XM_005624898.2, EFCAB5, Del, T_7, LKDWRQKPRKCSRK, (SEQIDNO:10148); XM_003639988.3, MMP21, Del, T_7, LKEINTGDTTVTRIRPTQKMNKETSTPN, (SEQIDNO:10149); XM_014111020.1, INO80D, Del, T_7, LKERMETSFQLPKRPRNLNGPYRL, (SEQIDNO:10150); NM_001011556.1, CLN5, Del, T_7, LKGLMISTGRKMGR, (SEQIDNO:10151); XM_005639064.2, USO1, Del, T_7, LKKAHIFNV, (SEQIDNO:10153); XM_005627752.1, LOC100856021, Del, T_7, LKKTVTLK, (SEQIDNO:10156); XM_003639382.3, DENND4C, Del, T_7, LKLSENFSCLSTNFLCLDHILFPLKSIFHTSCKTSLFLHHKDQESLYSFQSMMH, (SEQIDNO:10157); XM_005623314.2, ARHGAP5, Del, T_7, LKMRLSRN, (SEQIDNO:10158); XM_014109787.1, DOPEY2, Del, T_7, LKNIPRIF, (SEQIDNO:10159); XM_005626455.2, CSNK1G3, Del, T_7, LKNQTMTT, (SEQIDNO:10160); XM_535470.5, COPS2, Del, T_7, LKPSRIMMNREVQDEPLA, (SEQIDNO:10161); XM_005627773.1, SH3BGRL2, Del, T_7, LKQRKATQSIHS, (SEQIDNO:10162); XM_539791.4, TLL1, Del, T_7, LKRKTSVPSRTAGAASSAA, (SEQIDNO:10163); NM_001171748.1, RBM12, Del, T_7, LKSWILWKIVFILLMDPMGKQLVKAL, (SEQIDNO:10164); XM_014112366.1, MPHOSPH10, Del, T_7, LKTLILMKMKENCLEVKNLSQVKVPETSNTKTSLIQLKVMKT, (SEQIDNO:10165); XM_014112702.1, ADGB, Del, T_7, LKTLKERLNYHHH, (SEQIDNO:10166); XM_005623082.2, ANKRD12, Del, T_7, LKVMRLKICF, (SEQIDNO:10167); XM_014110041.1, PAPSS1, Del, T_7, LKYLLMLLCMFVNRGMSKDSTKKHGLEKLKASLVSILSMKNQKLLNWC, (SEQIDNO:10168); NM_001289066.1, MME, Del, T_7, LLARMIRTL, (SEQIDNO:10169); XM_847415.3, CLPX, Del, T_7, LLCYLKQTQRKA, (SEQIDNO:10170); XM_544475.5, NUDC, Del, T_7, LLEEKRGWQRSSSHRPSTTITSWHRRPDGRRELGRRLSGGRRPRGQPGWPKRPNQRP LGPRSRS, (SEQIDNO:10172); XM_847331.4, CEPT1, Ins, T_7, LLFCWDNVLLCTLADVCFW'NIAIWNN, (SEQIDNO:10173); XM_014110202.1, ABHD10, Ins, T_7, LLFFVLLFCFRIGGFHLMLKKALLFPNYILPKRI, (SEQIDNO:10174); XM_003434558.1, LOC100686309, Del, T_7, LLFLNAMC, (SEQIDNO:10175); XM_014113716.1, ALG6, Ins, T_7, LLFTWQVF, (SEQIDNO:10176); XM_014118473.1, MRPL14, Del, T_7, LLGSGAPSLMQAEHSASAVSAPIGASVQFRR, (SEQIDNO:10177); XM_005617468.2, BDP1, Del, T_7, LLICFRKFLLKKRKENKNLLKIRA, (SEQIDNO:10178); XM_532271.4, NT5DC1, Del, T_7, LLIQCRDWKTQKTHWSTPGLVRESVLTAQSQFQVLKQ, (SEQIDNO:10179); XM_535002.5, NT5C2, Del, T_7, LLIVLDIPAVKQDLKMGTSSCLTEVCSRM, (SEQIDNO:10180); XM_014119240.1, LOC106559724, Del, T_7, LLIVLDIPAVKQDLKMGTSSCLTEVCSRV, (SEQIDNO:10181); XM_005630079.2, EIF2AK2, Del, T_7, LLKNLNSVRSTERYLSIMNCLRKDLHIT, (SEQIDNO:10182); XM_014120611.1, AP4B1, Ins, T_7, LLLGAPLHQVAEGGGAV, (SEQIDNO:10183); XM_005621973.2, CLCA4, Del, T_7, LLLMKPRITASLMPLEPLHQETLIFPNSLFSLKVRD, (SEQIDNO:10184); XM_014109476.1, STARD9, Del, T_7, LLLRTNIFFHLLAQKYVNLKIKLEF, (SEQIDNO:10185); XM_532299.5, DCAF13, Del, T_7, LLLVMTKL, (SEQIDNO:10186); XM_849440.4, CYP2R1, Del, T_7, LLMLLKHTKVDLLTLNN, (SEQIDNO:10187); XM_014113265.1, LOC100684019, Del, T_7, LLMNSWLGSLRTQITKQW, (SEQIDNO:10188); XM_005634400.2, METTL6, Del, T_7, LLMN- SWLGSLRTQVTKKW, (SEQIDNO:10189); XM_532373.5, LNX1, Del, T_7, LLNPLSKEHQHTMTEELDAETFFWLSMVEVHQE, (SEQIDNO:10190); XM_014115910.1, CNIH1, Ins, T_7, LLPIRHDLCFGELL, (SEQIDNO:10191); XM_014117160.1, APOF, Ins, T_7, LLPPAAPCGCHFTWKLDKHSLIFEILDTFLRLLVLPDSAPKVPAWLHLHGSSAQVPG GLATGDCPGESWLPG, (SEQIDNO:10192); NM_001003126.C RPGR, Del, T_7, LLPSVRLSSFLLDLILQLH, (SEQIDNO:10193); XM_546085.4, PCNXL2, Ins, T_7, LLQFSDCILHNNQIGQLSPTPHV, (SEQIDNO:10194); XM_005626107.2, PSME4, Del, T_7, LLRISTMMQL, (SEQIDNO:10195); XM_014110190.1, SENP5, Del, T_7, LLRQSPVWLLKMLVLCPLK, (SEQIDNO:10196); XM_005627566.2, BCKDHB, Del, T_7, LLTAQESRWLYPEALSRPRDFFCHA, (SEQIDNO: 10197); XM_005624315.2, BRCA1, Del, T_7, LLTIQVLVSLKSASTLAFEEKK, (SEQIDNO:10198); XM_014112077.1, MAN2A1, Del, T_7, LLTLTEMIITGVATLHPDPFTNEWIGYWNPI, (SEQIDNO:10199); XM_014109945.1, WDFY3, Ins, T_7, LLTRIPVFQQL, (SEQIDNO:10200); XM_014111411.1, LOC611589, Del, T_7, LLVFTPQHFWKM, (SEQIDNO:10201); XM_014107594.1, FZD3, Del, T_7, LLWLAVFGG, (SEQIDNO:10202); XM_538213.3, LOC481092, Del, T_7, LLYFLGQQNFTSWLLCPMTAMLPYANPCIT, (SEQIDNO:10204); NM_001313886.1, LOC100683286, Del, T_7, LLYFLGQQSFISWLLCPMTAMLPYANPCII, (SEQIDNO:10205); XM_014116993.1, NUP214, Del, T_7, LMFAHFQMRLNSKNAHLPIISF, (SEQIDNO:10207); XM_532688.5, GATB, Del, T_7, LMHLCLELSRFSTGGA, (SEQIDNO:10208); XM_003640123.2, OSBPLL1, Del, T_7, LMLDIPNYNQ, (SEQIDNO:10209); XM_014112420.1, TICRR, Del, T_7, LMLWILYYIRFTIHLKIQLPALLLFQSGPNRSLAALIPGMQLLWRSGFLPPTLVVPVQ V, (SEQIDNO:10210); XM_005621512.2, SMG1, Del, T_7, LMMIITGRC, (SEQIDNO:10211); XM_014115004.1, TPR, Del, T_7, LMMKTELFQVLQLLWFHIVLMDLLKQFIPHKLLVFLDSGLGHLKICHKQVQVTLILA NLLLKEA, (SEQIDNO:10212); XM_014108770.1, VSTM4, Del, T_7, LMMSGPGGQWHLMSMRLSHG, (SEQIDNO:10213); XM_014109752.1, ROBO1, Del, T_7, LMNFKEQIVKLNLPKP, (SEQIDNO:10214); XM_005615683.2, LOC102155259, Del, T_7, LMNSPSWSSQESQEITQFVRKNSAVI, (SEQIDNO: 10215); XM_005619718.1, TMPRSS4, Del, T_7, LMRSSFQPPHSGSSDGALRSRMEERCPTPCYRHLSSSLTTLGAMQRTHTRGKSPK, (SEQIDNO:10216); XM_014109091.1, KIF20B, Del, T_7, LMVKGKYA, (SEQIDNO:10217); XM_005619074.1, SAMD8, Del, T_7, LNAMLMVQYLMNIVGHFQNQQ, (SEQIDNO:10218); XM_014115839.1, BAZ1A, Del, T_7, LNEPFCATVLCGVVL, (SEQIDNO:10219); XM_005637939.2, SGK3, Del, T_7, LNHSAGLILYKRGFHHHLILMWQDQMISGTLMQRLQKKQFRILCVYLLTIL, (SEQIDNO:10220); XM_005628968.1, ZMYM6, Del, T_7, LNKNLLKWNVKIVL, (SEQIDNO:10221); XM_863015.4, NLK, Del, T_7, LNMIMYSLPLTYSNLHTLTILKKYMLSQN, (SEQIDNO:10222); XM_536271.5, ZCCHC4, Del, T_7, LNPEFVSFFQASACWITR, (SEQIDNO:10223); XM_859089.4, LOC608729, Del, T_7, LNSMRKLK, (SEQIDNO:10224); XM_005640494.1, SF3B1, Del, T_7, LNTSGNTEWLWTEEITDS, (SEQIDNO:10225); XM_014118520.1, LRP12, Ins, T_7, LPARKFSL, (SEQIDNO:10226); XM_005626675.1, KLHL9, Del, T_7, LPATLTVRWCCKASTSSE, (SEQIDNO:10227); XM_014111483.1, LOC611979, Del, T_7, LPAVSRLFIFLCMRFITS, (SEQIDNO:10228); XM_014109770.1, LOC100856716, Del, T_7, LPCGNLIEAP, (SEQIDNO:10229); XM_014119949.1, TBXAS1, Ins, T_7, LPGFLGKPNGAQKAIWTSVWVLSWSPDVYCYL, (SEQIDNO: 10230); XM_005625788.2, ARFGAP3, Del, T_7, LPLMFLLR, (SEQIDNO:10232); XM_532487.2, ITGB8, Del, T_7, LPPHLSACKTAGRVQPRSFGRPGCF, (SEQIDNO:10233); XM_549080.1, CDX4, Del, T_7, LPPYLLFIDFSLLRYSRS, (SEQIDNO:10234); XM_843302.3, COR6C33, Del, T_7, LPSFWGQLNFIF, (SEQIDNO:10235); XM_014122642.1, FAT3, Del, T_7, LPSIPKQV, (SEQIDNO:10236); XM_014109908.1, ANK2, Del, T_7, LPSKKTDFLSLSRYVIRLRNLAGDYHL, (SEQIDNO:10237); XM_005626092.1, LHCGR, Del, T_7, LPSQLPSKCPSSQ, (SEQIDNO: 10238); XM_014112649.1, RBPJ, Ins, T_7, LPSSLCVSYGQWMEEKKRTNGTGWLF, (SEQIDNO: 10239); XM_014109096.1, GFRA1, Del, TJ7, LPTANLSQGLPAAV, (SEQIDNO:10240); XM_014107852.1, EP400, Del, T_7, LPTSLAMKATGVLILWL, (SEQIDNO:10241); XM_014109446.1, PIGB, Ins, T_7, LPVKLLVHMVLLYQNSYKHHGNCSYYNCSFLLSFGRFKVYEQCQVLLPGGTCLHNS SHSSHSMDTFGLQTFLARTKKA, (SEQIDNO:10242); XM_014118274.1, MED23, Del, T_7, LQALIQFRELGVKTYFRPS, (SEQIDNO:10243); XM_846518.4, C4BPB, Ins, T_7, LQCLSGVERPRSHMSVGPLSCPCAGEW, (SEQIDNO:10244); XM_014109884.1, EGF, Del, T_7, LQCPFLGIRSSIQHGKRRQFG, (SEQIDNO:10245); XM_014114127.1, CCT6A, Ins, T_7, LQECRRERETRKS, (SEQIDNO: 10246); XM_848323.4, EYS, Del, T_7, LQHWMSSNLSWRRNITELLPST, (SEQIDNO:10248); XM_014118114.1, SENP6, Del, T_7, LQKFHLKKPIADLLPVQEPMKRASKEVVCKKKTKLKMCPLNLKYNLKTNKNSSFLM MMKKLERIIPSSWAL, (SEQIDNO:10249); XM_014110829.1, METTL8, Del, T_7, LQKGKSTICSARLG, (SEQIDNO:10250); XM_533782.4, DENND6A, Del, T_7, LQKHSSTGHTLFE, (SEQIDNO: 10251); XM_538482.4, MSH2, Del, T_7, LQKIFIRT, (SEQIDNO:10252); XM_005635695.2, DOCKS, Del, T_7, LQKSTCRSTPKTRRRLSC, (SEQIDNO:10253); XM_005630848.2, SLC16A1, Del, T_7, LQLLLLQMECVIC, (SEQIDNO:10254); XM_014121460.1, SLC35F5, Del, T_7, LQMLKVTLLLAQQIRL, (SEQIDNO:10255); XM_014117483.1, LIPT1, Del, T_7, LQPKKSMIECRI, (SEQIDNO:10256); XM_005635381.2, PARP4, Del, T_7, LQQKIMKHQNF, (SEQIDNO:10257); XM_005631134.2, HIPK3, Ins, T_7, LQRNRDFSFWLEIKDTRRT, (SEQIDNO:10258); XM_014117454.1, ARHGAP25, Ins, T_7, LQRYGCAHSGLPVKALPPRPPRASGSLEPVRGVPAMWAAHECG, (SEQIDNO:10259); XM_005625977.2, RANBP2, Ins, T_7, LQSCKIVSF, (SEQIDNO:10260); XM_014118505.1, ADGRF2, Ins, T_7, LQSKEMAQDH, (SEQIDNO:10261); XM_005618200.2, LOC479005, Del, T_7, LQVRTVEIMRR, (SEQIDNO:10262); XM_014109072.1, OBFC1, Ins, T_7, LQWASNKAGRDLGNCNWKERKRCFLQLWSG, (SEQIDNO: 10263); XM_014106313.1, DOCK9, Del, T_7, LQYLKSAYTSSSTWGSDI, (SEQIDNO:10264); XM_005636642.2, RNLS, Del, T_7, LQYVKVTL, (SEQIDNO:10265); XM_005641660.1, NXT2, Del, T_7, LRC- CLLVSSRSIC, (SEQIDNO:10266); XM_005623940.2, TDRD9, Del, T_7, LRCLLGSILMDTGTK, (SEQIDNO:10267); XM_014113993.1, CENPN, Del, T_7, LRCLLSSSRSNRA, (SEQIDNO:10268); XM_014108707.1, PTPRO, Del, T_7, LREKQYLITGCQEYVIVILLFSWYLKQLLIKVLLWSTVASVMNPNSIELPLIHLEISRF VL, (SEQIDNO:10269); XM_014112476.1, CEMIP, Del, T_7, LRGAGVTVESLFMSSTPKQRQSSILTGLTPIDP, (SEQIDNO:10270); XM_014109535.1, CSNK1G1, Del, T_7, LRGKGRRLPSATS, (SEQIDNO:10271); NM_001003359.1, CAMP, Del, T_7, LRIFSPGRRSP, (SEQIDNO:10272); XM_014107454.1, UGT1A6, Del, T_7, LRKAHNAPVPFLMFLDLSPCCQMP, (SEQIDNO:10273); XM_014106997.1, GPCPD1, Del, T_7, LRKISVNM, (SEQIDNO:10274); XM_014114836.1, EVI5, Del, T_7, LRKKIALDRRFYLM, (SEQIDNO:10275); XM_014118151.1, ANKRD6, Del, T_7, LRLFLPRWKSGMKGRLKKLEAKPVRKPSKTRPP, (SEQIDNO:10276); XM_005630852.2, LOC100686848, Del, T_7, LRLLLLQMECVIC, (SEQIDNO:10277); XM_014120310.1, FAM228B, Del, T_7, LRLPFHHFVTL, (SEQIDNO:10278); XM_005622856.2, RIT2, Del, T_7, LRPLRPSDSALMMPFMVS, (SEQIDNO:10279); XM_005633843.2, SERPINE3, Del, T_7, LRRIGHSSFS, (SEQIDNO:10280); XM_014110499.1, GMDS, Ins, T_7, LRSPRHSPQAMV, (SEQIDNO:10281); XM_005637412.1, LOC100683250, Del, T_7, LRTTSAASRLSWMGSIWRRTSCRER, (SEQIDNO:10282); XM_014110866.1, NR4A2, Del, T_7, LSARYKKTQNTCV, (SEQIDNO:10283); XM_005631925.2, MGAT4D, Ins, T_7, LSKHITSHTVN, (SEQIDNO:10284); XM_005626903.2, IKBKAP, Del, T_7, LSMTLRLLQISHHLQYMMNFYC, (SEQIDNO:10285); XM_014120533.1, PLB1, Ins, T_7, LSPPQRLGCPA, (SEQIDNO:10287); XM_005618818.2, SPRTN, Del, T_7, LSRKSKYKVVEMIQSGVHILQLQLRIPAVHPARTGWSIVLFVRMKCWSLRLMSTWT GALKVVASKSKV, (SEQIDNO:10288); XM_003435516.2, LOC100688842, Del, T_7, LSRLTENVLKSLLRHQ, (SEQIDNO:10289); XM_536337.5, LYST, Ins, T_7, LSSRVLSQP, (SEQIDNO:10290); XM_005616833.2, LOC100685462, Del, T_7, LSSVFLWKECHRPELQIQADLSQRFILAICVSQWRKTSCTWLNTKELTLA, (SEQIDNO:10291); XM_003432377.1, LOC100685331, Del, T_7, LSSWGPLNVSFSPQWPMIAMLLSVILCITQWLCPQDSAVPSSLGPI, (SEQIDNO:10292); NM_001025269.1, HACD1, Del, T_7, LSSYILSGLLVNSLQYMLPYHM, (SEQIDNO:10293); XM_014109133.1, TDRD1, Ins, T_7, LSTATEWT, (SEQIDNO:10294); XM_542919.5, SLC4A11, Del, T_7, LSTSTSRCSPARLLRVTRLAAVGSYTPPAST, (SEQIDNO:10295); XM_014120191.1, NEIL3, Del, T_7, LSVLLRRQSSAIFSSGQKTDQE, (SEQIDNO:10296); XM_014112256.1, WDR41, Del, T_7, LTCGDLDE, (SEQIDNO:10297); XM_014112364.1, FAN1, Del, T_7, LTMHHLLNLPALFVVKWCQGMT, (SEQIDNO:10298); XM_005620205.2, DNAJC6, Del, T_7, LTNREMDVVLTVMY, (SEQIDNO:10299); XM_536312.4, Clv1YA5, Del, T_7, LTPSRRTVVKMRKG, (SEQIDNO:10300); NM_001003081.1, ABCC2, Del, T_7, LTQHPQVGL, (SEQIDNO:10301); XM_534842.3, LOC477647, Del, T_7, LTSFIIQKQDPCFLLFLPI, (SEQIDNO:10302); XM_014117490.1, VWA3B, Del, T_7, LTSLLTAPFAMLMGSLM, (SEQIDNO:10303); XM_014117620.1, ZNF879, Del, T_7, LTSSWGKPT, (SEQIDNO:10304); NM_001286853.1, RWDD4, Del, T_7, LTTPYHRL, (SEQIDNO:10305); XM_014106801.1, LOC610614, Del, T_7, LTVQEEGDPMFISI, (SEQIDNO:10306); XM_005635727.1, NUDT18, Ins, T_7, LVEGDGGRPTKPALTEASGIIGRPSQQI, (SEQIDNO:10307); XM_005638437.1, NEDD4, Del, T_7, LVEIYLLTAPPIEVCQTGILLHVTFFQEVQVPFLLSRMTWSMD, (SEQIDNO:10308); XM_845745.2, TRIM4, Ins, T_7, LVESISIFSHPSSDWWEM, (SEQIDNO:10309); XM_003434546.1, LOC100687264, Del, T_7, LVFLKLMC, (SEQIDNO:10310); XM_540715.3, OR08D06, Del, T_7, LVLLRLSSLQ, (SEQIDNO:10311); NM_001003198.1, PLA2G7, Del, T_7, LVLVNILEHPGLWAKY, (SEQIDNO:10312); XM_848492.2, OR10H12, Del, T_7, LVPLRSSSWWPWPMTDMQPSADPFTIWSS, (SEQIDNO:10313); XM_005634821.2, PANK2, Del, T_7, LVSAVFLLAVPLLKKLLKWHLVEIAPKWIN, (SEQIDNO:10314); XM_005627533.2, SLC17A5, Del, T_7, LVSSFSMHYV, (SEQIDNO:10315); XM_014116529.1, NAGS, Del, T_7, LVVGRCWELLSQPLMPAMVASSQWRPTCYSGAWSRAAFPSCAPSGRRPHAVRCSST RWR, (SEQIDNO:10316); XM_847748.2, LOC483503, Del, T_7, LVVLLRSVFLVSL, (SEQIDNO:10317); XM_014118082.1, DST, Del, T_7, LVVNFISQKTWQI, (SEQIDNO:10318); XM_534250.5, PP2D1, Del, T_7, LVYLMDIMVPQQQT, (SEQIDNO:10319); XM_014121999.1, LOC100685490, Del, T_7, LWFLEAWTLSSLL, (SEQIDNO:10320); XM_005628406.2, SMO, Del, T_7, LWGALAGWPSLWTALAGRLSAVQMAP, (SEQIDNO:10321); XM_014117196.1, LOC106559354, Del, T_7, LWILMQNSLNLPIRKERVSGISLKKMYLL, (SEQIDNO:10323); XM_846595.3, NDNF, Del, T_7, LWLKKTILHYQSQ, (SEQIDNO:10324); XM_005638321.2, UBR1, Del, T_7, LWRWNTKNSLLWNL, (SEQIDNO:10326); XM_005632588.1, PFKFB4, Del, T_7, LWSPSVWILRS, (SEQIDNO:10327); XM_014118899.1, CASD1, Ins, T_7, LWTPHLIVDSRQIKTL, (SEQIDNO:10328); NM_001003167.1, CE9, Ins, T_7, LYDDRLLADSDRLYAVQTNFWL, (SEQIDNO:10329); XM_014114561.1, LOC479816, Ins, T_7, LYHYYLFDMCFILCQDFQ, (SEQIDNO:10330); XM_003432842.1, LOC100686724, Ins, T_7, LYKFRSVP, (SEQIDNO:10331); XM_014121800.1, LOC106560098, Ins, T_7, LYKPRSIP, (SEQIDNO:10332); XM_539577.5, ZMPSTE24, Del, T_7, LYMPGCSH, (SEQIDNO:10333); XM_548259.5, PEX12, Del, T_7, LYNNFDTS, (SEQIDNO:10334); XM_005624915.2, GEMIN4, Ins, T_7, LYPGILSRSAHHGHAPPRGVRAAVCLGLGNPHLL, (SEQIDNO:10335); XM_542001.5, OR10A12, Del, T_7, LYSLLSQTSLSSV, (SEQIDNO:10336); XM_014109438.1, MYO9A, Ins, T_7, LYSPTRPTENKFPTRYKYPEKQAIRR, (SEQIDNO:10337); XM_849878.4, ZDHHC14, Ins, T_7, LYVYFISVFSDSLYICIRYHPRHSSFTTDRIPQCS, (SEQIDNO:10338); XM_014113785.1, ZCCHC2, Ins, T_7, SASDSLCKRTGA, (SEQIDNO:10339); XM_005633637.2, TRIM66, Ins, T_7, SAVLFYRAIQDGQELLRVQGEEGSAYPVHLLQPLAVQLMHRGAPAWPRPWGPTLSA GPQGTTRSEQWFWGLRLVLSSTHTGSAQAILRDL, (SEQIDNO:10340); XM_014122375.1, DNAH12, Ins, T_7, SCSCTREKEIWSSWLEYSIRI, (SEQIDNO:10341); XM_545477.5, KCNJ3, Ins, T_7, SCYLLRRRVL, (SEQIDNO:10342); XM_005633800.2, LOC485325, Ins, T_7, SDGHPRFRGKPALDSIATVCPLCPCCNGQCHHHLHHLD, (SEQIDNO:10343); XM_005633799.2, LOC610911, Ins, T_7, SDGHPRFRGKPALDSIATVCPLCPCCNGQCHRHLHHLD, (SEQIDNO:10344); XM_005630347.2, CEBPZ, Ins, T_7, SDLYQEKRY, (SE- QIDNO:10345); XM_534289.5, SLC25A36, Ins, T_7, SDTVFGCSRRRLWVSLPWSNNSSGETDSKHSHY-DGHL, (SEQIDNO:10346); XM_005641432.1, YIPF6, Ins, T_7, SEPLCAGLLYTSLDSG-NAGLPVGAFGRARTSQLHGPTFCCDCDVCLVYSS-LYSFSC, (SEQIDNO:10347); XM_005625258.2, SH3GLB2, Ins, T_7, SFAIEPQCDSGTRLPFSAE-GQKALE, (SEQIDNO:10348); XM_005628880.2, TMCO2, Ins, T_7, SGFAGQPRWESSPNSRQ, (SEQIDNO: 10349); XM_014106943.1, RIN2, Ins, T_7, SGR-GRQREDLDRRPASPGPGAP, (SEQIDNO:10350); XM_005626285.2, CNOT6, Ins, T_7, SGRTERTWL, (SEQIDNO:10351); XM_541064.5, DSEL, Ins, T_7, SGSFRSFYEGIVHSKGPSGMDLFNAVQ, (SEQIDNO: 10352); XM_533692.5, TMEM147, Ins, T_7, SHLGRRHL, (SEQIDNO:10353); XM_005638811.2, LOC102153645, Ins, T_7, SHQFLSLQFLSTFNAS, (SEQIDNO:10354); XM_014109050.1, R3HCC1L, Ins, T_7, SHSILFGTDI-VFLFFGGYFRNYKLHA, (SEQIDNO:10355); XM_014108759.1, ZFAND4, Ins, T_7, SICPWYWNEWK, (SEQIDNO:10356); XM_005627466.1, PKHD1, Ins, T_7, SIGEQKYLQASFGCILP, (SEQIDNO:10357); XM_862279.4, G3BP1, Ins, T_7, SKLWECGGATH, (SEQIDNO:10358); XM_014119702.1, CFAP54, Ins, T_7, SKRLWRPSCCTYISCFKWQKYLQL, (SEQIDNO: 10359); XM_005635055.2, RALGAPB, Ins, T_7, SLCH-CAGSRNVWKTCLGTTTLPFTQRSKSKSEAFCT, (SEQIDNO:10360); XM_003638951.1, LOC100856766, Ins, T_7, SLQFLHLRNLIHNSMHSQILVQYNNWRQHYYV, (SEQIDNO:10361); XM_533564.5, HIATLi, Ins, T_7, SLSQTGHRFWIC, (SEQIDNO:10362); XM_005642102.1, LOC102156483, Ins, T_7, SLYSWGWQGSVHWHCPPLE-CLPGHHHQPQELQVGSA, (SEQIDNO:10363); XM_014106286.1, MYCBP2, Ins, T_7, SPGSNNAR-TRYAVLARRARHIQGSEDGTFRSQHQKLP, (SEQIDNO:10364); XM_014111818.1, LOC100683280, Ins, T_7, SPQFLHLRNLIHNSMHSQILVQYNNWRQHYYV, (SEQIDNO:10365); NM_001197142.1, CALCR, Ins, T_7, SPVHDGMQLFLDAL, (SEQIDNO:10366); NM_001287163.1, HIF1A, Ins, T_7, SQNEVYPN, (SEQIDNO:10368); XM_535696.4, ENPEP, Ins, T_7, SQNKPRSYWVLSCKL, (SEQIDNO:10369); XM_014119705.1, GRB14, Ins, T_7, SRAYGVFCN, (SEQIDNO:10370); XM_014108367.1, LOC611565, Ins, T_7, SRLPEATLLP, (SEQIDNO:10371); XM_014119270.1, LOC102151283, Ins, T_7, SRSKNSHCPTL, (SEQIDNO:10372); XM_014110987.1, FN1, Ins, T_7, SSIL-YSWLLRQWETLSDKPTMGAHLPGKCLGLYLLR-REPRL, (SEQIDNO:10373); XM_849728.3, MYCT1, Ins, T_7, SSVYSISCGYYG, (SEQIDNO:10374); XM_845820.3, USP50, Ins, T_7, STRHTDLE, (SEQIDNO:10375); XM_005636667.2, LIPN, Ins, T_7, STSEFRNQEI-FRYQRFLSKHGEGTFHQNLQQ, (SEQIDNO:10376); XM_014115134.1, TSEN15, Ins, T_7, STVQQMEQPFWP, (SEQIDNO:10377); XM_005631726.1, LOC100684610, Ins, T_7, SVFPVLHR, (SEQIDNO:10378); XM_014109449.1, ZNF106, Ins, T_7, SWR-TRKSLEQTHYRRESWVLYNQIAKFMSSCFKRE, (SEQIDNO:10379); XM_014115269.1, DNAH14, Ins, T_7, SWSNIFNSKSNCLGESNNCNTTVGLTTMASSEK-ENHTVL, (SEQIDNO:10380); XM_533782.4, DENND6A, Ins, T_7, SYCAQTNSTRVF, (SEQIDNO:10381); XM_843248.3, CCDC54, Ins, T_7, WFLKRRNN-STI, (SEQIDNO:10382); XM_005627533.2, SLC17A5, Ins, T_7, WFLRSLCITCESECCISGYGRFKYNFSR, (SEQIDNO:10383); XM_540672.2, OR16F12, Ins, T_7, WGL-CRCGVSHVGCHGL, (SEQIDNO:10384); XM_534200.5, ACSS1, Ins, T_7, WHCPSAHGREGKGRGGW, (SEQIDNO:10385); XM_014117864.1, PLGRKT, Ins, T_7, WHCSHLFNSWGNKKEEASLPLPYYSIKLYLHLPV, (SEQIDNO:10386); XM_014118119.1, PHIP, Ins, T_7, WIRSARENIRIGVPY, (SEQIDNO:10387); XM_003432360.1, LOC100685932, Ins, T_7, WIRTLCLY-APQHWQFCGPGQDSISLLYSGDPDVESSNLQSE-EQGNQRCP, (SEQIDNO:10388); XM_005623379.1, SOS2, Ins, T_7, WNIFNKYSEN, (SEQIDNO:10390); XM_014111447.1, VPS13D, Ins, T_7, WNWFHCRQPCNEGAA, (SEQIDNO:10391); XM_005641236.2, CFAP47, Ins, T_7, WRK-SYLRFDRFYSDSKKKFTWFL, (SEQIDNO:10393); XM_005634821.2, PANK2, Ins, T_7, WSLLSSYWLYHF, (SEQIDNO:10394); XM_014113223.1, DYNC2H1, Ins, T_7, WTCLQLLYI, (SEQIDNO:10395); XM_005637041.2, TM7SF3, Ins, T_7, WTQILEN-RIIFHRFYLHGILLLHTDYKTDTY, (SEQIDNO: 10396); XM_536737.4, SLC25A33, Ins, T_7, WTYGSCCNF, (SEQIDNO:10397); XM_014118530.1, NIPAL2, Ins, T_7, WVFSVVPWCVFGHKKSRKGTSATVLH, (SEQIDNO: 10398); XM_014116529.1, NAGS, Ins, T_7, WWWVGAGSC, (SEQIDNO:10399); XM_005615845.2, CARNMT1, Ins, T_7, YALFFQLCTQQMF, (SEQIDNO: 10400); XM_540640.3, LOC483521, Ins, T_7, YCH-GDYRILHAGCNGL, (SEQIDNO:10401); XM_005629350.1, ARFIPi, Ins, T_7, YCQCEHFGE, (SEQIDNO:10402); XM_003432856.3, LOC100684808, Ins, T_7, YDFCRDGWFPPDRDGL, (SEQIDNO:10403); XM_014106493.1, TTC21A, Ins, T_7, YDSRAGGGEGA VLQRRSHQLRTGLEVQSSCQPRYWLQARFQL-LEGQEICGRH, (SEQIDNO:10404); XM_014110792.1, CALCR1, Ins, T_7, YDSRRSRIRGEH, (SEQIDNO: 10405); XM_005638321.2, UBR1, Ins, T_7, YGDGIQKIL-CYGICEVL, (SEQIDNO:10406); XM_014121999.1, LOC100685490, Ins, T_7, YGFWRHGHFPPYCDGL, (SEQIDNO:10407); NM_001025269.1, HACD1, Ins, T_7, YHLISCRGCW, (SEQIDNO:10408); XM_539577.5, ZMP-STE24, Ins, T_7, YICLAVHISCFSGACHDLC, (SEQIDNO:10409); XM_014119262.1, SLC6A15, Ins, T_7, YICPGNTGGVCSSGL, (SEQIDNO:10410); XM_538482.4, MSH2, Ins, T_7, YKRYLSGLEPVIER-QKGRTGE, (SEQIDNO:10412); XM_005618818.2, SPRTN, Ins, T_7, YQERASTKWWK, (SEQIDNO:10414); XM_014111483.1, LOC611979, Ins, T_7, YQQFHGCLSFYVCGSLLLDQTSNHWHCKHH-FILWVHDGYGPDFLPFHRDDWIFFLF LVSY, (SEQIDNO:10415); XM_005626675.1, KLHL9, Ins, T_7, YQQHSQFGGAARLRPAQSRRLAL, (SEQIDNO:10416); XM_014119016.1, LOC106559695, Ins, T_7, YQRQPKVRAVQSST, (SEQIDNO:10417); XM_005636091.2, PIWIL1, Ins, T_7, YREPGSE-KWQCFSHTL, (SEQIDNO:10418); XM_005635695.2, DOCK5, Ins, T_7, YRKVLAGAPRRPGED, (SEQIDNO: 10419); XM_539788.5, FSTL5, Ins, T_7, YSCYHTHHHPHKVWNSSQR, (SEQIDNO:10420); XM_544974.4, PKD2, Ins, T_7, YSLLCGGRDIGNSYS-QATLFQEFLELSGCCDHCAVSGRYRN, (SEQIDNO: 10421); XM_542001.5, OR10A12, Ins, T_7, YTLC-CLRLLCPQCDGL, (SEQIDNO:10422); XM_014113358.1, SC5D, Ins, T_7, YTVHLSSLMV, (SEQIDNO:10423); XM_014107594.1, FZD3, Ins, T_7, YYGWQCLVGNSYHHMVLGSCAKVG, (SEQIDNO: 10424); XM_005640422.1, AOX4, Ins, T_8, CEWKKGHREEC, (SEQIDNO:10426); XM_005619365.2, MROH2B, Ins, T_8, CGRNKKEHD- FIPSPPLGS, (SEQIDNO:10427); XM_005637524.2, SLC16A12, Ins, T_8, CGVPVVLHSGLCTNSLDPFHCRLCDHALCSTWECCQ, (SEQIDNO:10428); XM_005637525.1, SLC16A12, Ins, T_8, CGVPVVLHSGLCTNSLDPFHCRLCDHALWSWICAVLLSSYCHGWQVFQQTESSRLWDCHVGKWHWHLHIGSCGSTPY, (SEQIDNO:10429); XM_534660.5, VPS33A, Ins, T_8, CQTQARTNGYNC, (SEQIDNO:10431); XM_005631724.1, LOC100683738, Ins, T_8, CSLHFHVC, (SEQIDNO:10432); XM_014112004.1, LOC106558487, Ins, T_8, CSLHLHVC, (SEQIDNO:10433); XM_535242.6, PLK2, Ins, T_8, FAGLHSRQTLF, (SEQIDNO:10434); XM_005630997.2, PHTF2, Ins, T_8, FALCSRKNL, (SEQIDNO:10435); XM_005623425.2, FBXO34, Ins, T_8, FATGSTPVGLFPVE, (SEQIDNO:10436); XM_003639076.3, SYCEIL, Del, T_8, FCFVFLAVVLQGARQLRPRVGKWRASWSP, (SEQIDNO:10437); XM_005635599.2, UGT1A6, Del, T_8, FCGTFHVI, (SEQIDNO:10438); XM_005623425.2, FBXO34, Del, T_8, FCHRVNASRAVPS, (SEQIDNO:10439); XM_535242.6, PLK2, Del, T_8, FCRASLQTDSLLAVVIQFQISTCQARLRISLRKQLLLFLVAKKTKQDILTHIIECLKKMKKFTSLGMI, (SEQIDNO:10440); XM_005627752.1, LOC100856021, Ins, T_8, FCSCYYSGSRQRSSQSHPI, (SEQIDNO:10441); XM_005631219.2, LOC483600, Ins, T_8, FDHLCGHGVWQHAHCGHYHLQSHAGFPHVLFPGQLVLY, (SEQIDNO:10442); XM_014106743.1, XRN1, Ins, T_8, FEEKWGSSIPAKQSWRKHDVRNFSECRIR, (SEQIDNO:10443); XM_005638410.2, DMXL2, Ins, T_8, FELCDVQFSMGPSR, (SEQIDNO:10444); XM_014106798.1, SCN11A, Ins, T_8, FERLWERPDSRIRF, (SEQIDNO:10445); XM_005618433.2, MORF4L1, Ins, T_8, FFFFFFFFFYSYR, (SEQIDNO:10446); XM_537979.5, PHEX, Del, T_8, FGEQNILDL, (SEQIDNO:10448); XM_853830.5, GABRA2, Del, T_8, FGKNGKMNG, (SEQIDNO:10450); XM_848093.2, LOC610566, Ins, T_8, FHCVWMPGQFTPDRDGL, (SEQIDNO:10451); XM_546489.5, DPAGT1, Ins, T_8, FHHLGIALP, (SEQIDNO:10452); XM_844785.5, HMGCS2, Del, T_8, FHLECPRMLLQDPPWRSWCLVCQTCQNVSPPGSVCPLRSSQK, (SEQIDNO:10453); XM_014109153.1, KNDC1, Ins, T_8, FHQNFKPPVSAQLQFASLAKLLGGRAPAASGVPGQVLQGGARSMAVQK, (SEQIDNO:10454); XM_014111407.1, DOCK11, Ins, T_8, FICCGPFDFSRFKS, (SEQIDNO:10455); XM_005625919.2, APOL6, Del, T_8, FIFFSFTEAHL, (SEQIDNO:10456); NM_001145496.1, TAS2R42, Ins, T_8, FILEQEDHKVYHVGRLCLSFKPLTNFDSGKQQAETDSLEGTVAS, (SEQIDNO:10457); XM_005625919.2, APOL6, Ins, T_8, FILFYFLFSFFFFFLFFFLSPKLIL, (SEQIDNO:10458); XM_005621511.2, SMG1, Del, T_8, FILIAKLAKTG, (SEQIDNO:10459); XM_014111215.1, ZBED6, Del, T_8, FILILSTSQELCVTYVKEV, (SEQIDNO:10460); XM_014119746.1, DDX60, Ins, T_8, FIQLRRCRKKGCKLEVFPVAKASNAKASQS, (SEQIDNO:10461); XM_005639946.1, ATP11B, Del, T_8, FIRMCALSHPNFYISSTVCFLNKHCMTACT, (SEQIDNO:10462); XM_003434870.3, MEIOB, Ins, T_8, FITQSKGRIEN, (SEQIDNO:10463); XM_014114821.1, ABCD3, Ins, T_8, FKTHTDSENHGP, (SEQIDNO:10464); XM_546033.5, TMEM161B, Ins, T_8, FLCESNGSLDCDRKLSGIWT, (SEQIDNO:10465); XM_003639666.1, LOC100856789, Ins, T_8, FLCQHGSH, (SEQIDNO:10466); XM_014121896.1, LOC106560121, Ins, T_8, FLCVWMPGQFTPDRDGL, (SEQIDNO:10467); XM_542650.5, GPR18, Ins, T_8, FLDSPVHHDWVLLNHHS, (SEQIDNO:10468); XM_014109163.1, CNGB3, Del, T_8, FLEFLCSPA, (SEQIDNO:10469); XM_005618433.2, MORF4L1, Del, T_8, FLFFFFFFFFLLLQVSEYCAFMGLFFMKQSV, (SEQIDNO:10470); XM_005634584.2, MBNL1, Del, T_8, FLFFLSFSFSFFFPIVW, (SEQIDNO:10471); XM_847870.2, LOC610378, Ins, T_8, FLFHSQIWILYSIIHTYHPVQPLPTGSTFLQSSCLWGEDQTHPRESSKNVPLQRPGL, (SEQIDNO:10472); NM_001003040.2, RP1, Del, T_8, FLGLYTDLRFVLIILLNFSVLGK, (SEQIDNO:10473); XM_005628231.2, THEGL, Del, T_8, FLGRESEIFLGLKNNGEPQIEDCFGGIKILFALSPILL, (SEQIDNO:10474); XM_005617430.2, IPO11, Del, T_8, FLHFLMRWHINLIRRWTSFWEI, (SEQIDNO:10475); XM_535555.4, GBE1, Del, T_8, FLKILNIMSVPFLFWCTFRAEWASSCRMWICPT, (SEQIDNO:10476); XM_005635688.1, PPP2R2A, Del, T_8, FLKSSPRFPM, (SEQIDNO:10478); XM_005622402.2, RGS1L, Del, T_8, FLKWRSFVPGRQPALTSSTGARHTRIKNLLLSPWLSTLFGVEETTPS, (SEQIDNO:10479); XM_005622401.1, RGS1L, Del, T_8, FLKWRSLMIW, (SEQIDNO:10480); XM_014113248.1, LOC100686868, Ins, T_8, FLLLFLCLF, (SEQIDNO:10481); XM_005627752.1, LOC100856021, Del, T_8, FLQLLLLWIQTALIPISSYLRIENKFL, (SEQIDNO:10482); XM_014107422.1, LOC606856, Ins, T_8, FLRCSSSSICRRDSTIFF, (SEQIDNO:10483); XM_014109416.1, KATNBL1, Del, T_8, FLRFLRIMKQWHRFCSAGI, (SEQIDNO:10484); XM_852029.5, HNRNPH1, Del, T_8, FLTAKFKMGLKVFVSSTPEKADRVARLLLNLNQKMKSNWP, (SEQIDNO:10485); XM_545235.4, TMEM41A, Ins, T_8, FLTVFETFPHDTKLVLEPLGSDSEHPDCAVLLLCSARSDPVQFYLCADRLHPVNSDLSGCSFLLGNGLQAFGHCLGGLSSWNPH, (SEQIDNO:10486); XM_005638907.2, TTC3, Del, T_8, FLVMEPLLRSLILAS, (SEQIDNO:10487); XM_014110076.1, LOC100684714, Ins, T_8, FLYNWCNHRMFSAGNNGI, (SEQIDNO:10488); XM_014113145.1, SPEF2, Del, T_8, FMALTTLGQNFSMHIISVRLMPRLH, (SEQIDNO:10489); XM_541240.4, SAMD3, Ins, T_8, FMETSSQRSL, (SEQIDNO:10490); XM_005628829.2, TLR2, Del, T_8, FPCGVLNIWTYLITSYLTYHPPGSGPFLH, (SEQIDNO:10491); XM_847870.2, LOC610378, Del, T_8, FPFSLTDLDLIFHHTYISPCPTFTYWFHLSSILLSMG, (SEQIDNO:10492); XM_847631.3, COR6M4, Ins, T_8, FPGDSGVYPPGSDVL, (SEQIDNO:10493); XM_014122716.1, PLEKHA7, Ins, T_8, FPGEIADTEGSLED, (SEQIDNO:10494); XM_014115682.1, TTC6, Ins, T_8, FPKKICII, (SEQIDNO:10495); XM_542656.5, FGF14, Del, T_8, FPKWAFWPSRSAGRDLRIPSSRV, (SEQIDNO:10496); XM_003639706.3, RIF1, Del, T_8, FPNMQIHLSLLFMIALLRLEKMLLM, (SEQIDNO:10497); XM_858691.4, OSBPL3, Del, T_8, FPNRSATIHLSLHVMLSLEILFSGKM, (SEQIDNO:10498); XM_847080.1, LOC483451, Ins, T_8, FPPCWRGGCIFFVSDGIGSICGHLQAPALCDHYE, (SEQIDNO:10499); XM_005624332.2, TRPV1, Ins, T_8, FPRDSIFPAEAAIAEDLVCGQLQ, (SEQIDNO:10500); XM_005640932.2, KCTD3, Ins, T_8, FQFAEWKNFNTSR, (SEQIDNO:10501); XM_005638410.2, DMXL2, Del, T_8, FQIHKYRSTKIQILIAGLFYI, (SEQIDNO:10502); XM_005620874.1, CCDC79, Del, T_8, FQIHLHYVQI, (SEQIDNO:10503); XM_005621973.2, CLCA4, Ins, T_8, FQKCINTNS, (SEQIDNO:10504); XM_846828.3, LOC609558, Del, T_8, FQPCYLLFT, (SEQIDNO:10505); XM_005633892.2, LRRC63, Del, T_8, FQRIFLVE, (SEQIDNO:10506); XM_847239.5, MMP17, Ins, T_8, FQRKVLLAADPGWAPGVTAAGTDAPL-LAGPAAAAGQRGRCVRAHQ, (SEQIDNO:10507); XM_542656.5, FGF14, Ins, T_8, FQSGLFGPQEAQVEIS-GSPAQGYSDQVILQARLLLANAPRWSSRWNQG, (SEQIDNO:10508); XM_850372.4, C4H5orf22, Del, T_8, FQSRIPSKKCSLRKSTKSYKSCTSLKSLVPT, (SEQIDNO:10509); XM_003639706.3, RIF1, Ins, T_8, FQTCKYTYHCCS, (SEQIDNO:10510); XM_544113.5, PREX2, Del, T_8, FRMRKWKDQI, (SEQIDNO:10511); XM_014119371.1, DCLK2, Ins, T_8, FRRHACKNHL, (SEQIDNO:10512); XM_014110313.1, TRIO, Ins, T_8, FRRVGEVP, (SEQIDNO:10513); XM_858691.4, OSBPL3, Ins, T_8, FRTGQPPSTYLCMSC, (SEQIDNO:10514); XM_014111692.1, DDX26B, Ins, T_8, FRTIYFNYHHRWKQVNKYCWCSRRASSSFEFSSARK, (SEQIDNO:10515); XM_005638410.2, DMXL2, Ins, T_8, FRYTNTGAPRSKFL, (SEQIDNO:10516); XM_014115196.1, FMO2, Del, T_8, FSASMVLIHQH, (SEQIDNO:10517); XM_014116303.1, LOC106557537, Del, T_8, FSDIGYLTLPFCLDPYIKRPRKPPMAP, (SEQIDNO:10518); XM_005624332.2, TRPV1, Del, T_8, FSEGFNISCRGGHR, (SEQIDNO:10519); NM_001024633.1, HTR2B, Del, T_8, FSFCLCGVP-FLLQM, (SEQIDNO:10520); XM_014116439.1, ABCA6, Del, T_8, FSFQCFYFCM, (SEQIDNO:10522); XM_005617468.2, BDP1, Ins, T_8, FSHQHGRN, (SEQIDNO:10523); XM_847239.5, MMP17, Del, T_8, FSKESTSGG, (SEQIDNO:10524); XM_005627788.2, KIAA1919, Del, T_8, FSLCFLRKAQGRRKPKHLLR-GLEELNTTMPFFASFFCSSFSTLEPR, (SEQIDNO:10525); XM_848093.2, LOC610566, Del, T_8, FSLCLDAWTNS, (SEQIDNO:10526); XM_014110076.1, LOC100684714, Del, T_8, FSLQLVQPQNVFCWQQWH-MIAMWPYASLYFIQ, (SEQIDNO:10527); XM_005626210.1, PKDREJ, Ins, T_8, FSLRFRRGLRH-LARKGLLREKRVQSAQLCFKMHNRAH-RAFLPEELLGHWHNPVLLV EP, (SEQIDNO:10528); XM_003639666.1, LOC100856789, Del, T_8, FSL-SAWVSLSASF, (SEQIDNO:10529); XM_846828.3, LOC609558, Ins, T_8, FSMSFLLRVYTRRQICIT-FLHNSFHILCLWTESHICTSNICVSNPCFSC-STVTDTSITSGP QPSQTAASCFASHTAT, (SEQIDNO:10530); XM_536172.5, TARSL2, Del, T_8, FSMISVLEAAFFFPEEPSFIIHLWISYER-SITDVTSQKCSLPTCSTANSGKPQATGSITAR TCLPLILKRILLLLSP, (SEQIDNO:10531); XM_859725.4, WAP1, Del, T_8, FSPPTENMKQVSK, (SEQIDNO:10532); XM_003639813.3, LPAR6, Del, T_8, FSPPTFRRTIPQQPALKNFQKPHGKHISQGL, (SEQIDNO:10533); XM_546489.5, DPAGT1, Del, T_8, FSPPWDCSTITGTHHRCLWEIPSVTLLA, (SEQIDNO:10534); XM_850372.4, C4H5orf22, Ins, T_8, FSQESLQRNVHSGRVQNLTRVVPV, (SEQIDNO:10535); XM_014112871.1, IPCEF1, Del, T_8, FSQLRM-HRK, (SEQIDNO:10536); XM_014122716.1, PLEKHA7, Del, T_8, FSRRNRRYRRISGGLKMSLQA, (SEQIDNO:10537); XM_014107422.1, LOC606856, Del, T_8, FSSMFFFEYM, (SEQIDNO:10538); XM_014113248.1, LOC100686868, Del, T_8, FSSVSLSFLNPISCQR-WHMTAMSPSVNHCCTRSPCLLRCVYSS-CWVFMGWGCLGL, (SEQIDNO:10539); XM_847080.1, LOC483451, Del, T_8, FSTLLEGWMYFLCQ, (SEQIDNO:10540); XM_84763 1.3, COR6M4, Del, T_8, FSWGQWSLSSWQ, (SEQIDNO:10541); XM_014115742.1, ZNF566, Del, T_8, FSWNQDVR-PRNYF, (SEQIDNO:10542); XM_005626919.1, LUC100856036, Del, T_8, FSWRVFLDTRS, (SEQIDNO:10543); XM_014118505.1, ADGRF2, Del, T_8, FTSLCFSGCLPRHSLSSMES, (SEQIDNO:10546); XM_014119817.1, GALNTL5, Ins, T_8, FTTAWSEIC-CLWQH, (SEQIDNO:10547); XM_003435094.2, HOMEZ, Ins, T_8, FTVPVGTA, (SEQIDNO:10548); XM_005634570.2, P2RY14, Ins, T_8, FVDLFLHCY-HEENLQVPP, (SEQIDNO:10549); XM_005634758.2, DSTN, Ins, T_8, FVGTRTSSSEK, (SEQIDNO:10550); XM_005638125.2, TMEM67, Del, T_8, FWRSWDSRT, (SEQIDNO:10551); NM_001003040.2, RPI, Ins, T_8, FWVYTQISGLSL, (SEQIDNO:10553); NM_001145496.1, TAS2R42, Del, T_8, FYFGTRR-SQSLSCWPFMSFLQATH, (SEQIDNO:10554); XM_005625919.2, APOL6, Del, T_8, FYFILFFIL-FLFLFFIFFSFTEAHL, (SEQIDNO:10555); XM_541240.4, SAMD3, Del, T_8, FYGNELSKIAL-NMFGDP, (SEQIDNO:10556); XM_003434870.3, MEIOB, Del, T_8, FYHTEQGAD, (SEQIDNO:10557); XM_003435094.2, HOMEZ, Del, T_8, FYSASGHGVRI-TIN, (SEQIDNO:10558); XM_005622224.2, GRM7, Del, T_8, LALLSQRKSSTYKLPHLQSP, (SEQIDNO:10559); XM_014111169.1, LOC610561, Del, T_8, LAMWPSC-TYASLPPTPYSGIQSLLWPLQFCLPSSTPSFIA, (SEQIDNO:10560); XM_014111131.1, ABCA12, Del, T_8, LASIPLFPCQWCTFFPRKSLMIRL, (SEQIDNO:10561); XM_014119240.1, LOC106559724, Del, T_8, LATLRNCSALLMILHSLPGDLFLIHYMEIF, (SEQIDNO:10562); XM_005638158.1, KIAA1429, Del, T_8, LCRNMKQQIC, (SEQIDNO:10563); XM_005624333.2, TRPV1, Del, T_8, LCSHCSCWGPWCCTSAT-TRSTWPLWCSPWPWAGPTCSTTPAASSRWASMLL, (SEQIDNO:10564); XM_003434545.2, LOC100687027, Del, T_8, LDQQHSCILNILLLDLWSREKFLQC-SILMWDPCSIP, (SEQIDNO:10565); XM_005629703.2, PAXIP1, Del, T_8, LESLRVSPRCRPQTGAPCGLCSLST-GATASCTSTRNAHIWLFQNQKGRNTNAR, (SEQIDNO:10566); XM_005625919.2, APOL6, Ins, T_8, LFF-FLSPKLIL, (SEQIDNO:10567); XM_014112004.1, LOC106558487, Del, T_8, LFPAFACMLDLFLTCPLISL, (SEQIDNO:10568); XM_005631724.1, LOC100683738, Del, T_8, LFPAFSCMLDLFLTCPLIS1, (SEQIDNO:10569); XM_005634571.2, GPR171, Ins, T_8, LFSFPCWNYWERICNLGFRTKQDKSQVCE-HILDQFADSRFPAHPGITSENRCRPGSGT LEAE-DLPLPSDSLPHVH, (SEQIDNO:10570); XM_005623887.2, JAG2, Del, T_8, LGGPAGRRGCPSHT-GAPGWRIVTAATAWTATGTAARCGVAISLACW-PAGPNP, (SEQIDNO:10571); XM_537979.5, PHEX, Ins, T_8, LGNRISSISELWSYRSNCWT, (SEQIDNO:10572); XM_014118895.1, TMEM243, Del, T_8, LKRRYANAL-GIVTIPSLLLLFLLLSS, (SEQIDNO:10573); XM_005641803.2, SLC25A14, Del, T_8, LLHTSSSRGFKS, (SEQIDNO:10574); NM_001003247.1, KCNB2, Del, T_8, LLRIDv1PMLSSPVSQRRFGGPPSP, (SEQIDNO:10576); XM_005632123.2, NR2C2, Del, T_8, LLVSLAMCR, (SEQIDNO:10577); XM_005627906.2, ATAD2, Del, T_8, LMKSMVWLQYDQAG-KIRFTVPLFPPC, (SEQIDNO:10578); XM_547466.4, FMO4, Del, T_8, LNWCEINRLEFPLI, (SEQIDNO:10579); XM_014118505.1, ADGRF2, Ins, T_8, LPLCVFL-DACQGTPYPLWNPDCFPYGAQISTGGSSLFGWLRGP-SAHCCCHGCCHGA QKGLPTA, (SEQIDNO:10580); XM_549109.5, RPS6KA6, Del, T_8, LQMLTGIDYIEEKFNLLSNLLLENQMIL-FVLILSLLQKHLKILLVCQLVLTLINSSKDS ALLQRLLQRNIKSLLSQVQMCYQLFR, (SEQIDNO: 10581); XM_014112065.1, LOC491446, Del, T_8, LRIL-SIYPRETQR, (SEQIDNO:10582); XM_014109046.1, CSGALNACT2, Del, T_8, LRRQTLWNIDM, (SEQIDNO: 10584); XM_005641091.2, LOC102152866, Ins, T_8, LSPEILPKHHRKSGCSGN, (SEQIDNO:10585); XM_533302.6, EXOSC9, Del, T_8, LTLNSLRWLLQLLN-LAGSQISW, (SEQIDNO:10587); NM_001003232.1, CANX, Del, T_8, LTTLLFVGIEE, (SEQIDNO:10588); XM_005628742.2, TMEM168, Del, T_8, LVFLQQRF, (SEQIDNO:10589); XM_014109446.1, PIGB, Del, T_8, LVNGPWFSITF, (SEQIDNO:10590); XM_014115783.1, ZNF793, Ins, T_8, LWESLH-SEVTPQRTSKNTYWRETLCVQ, (SEQIDNO:10591); XM_005637524.2, SLC16A12, Del, T_8, LWSSSRTSL-RIMHKQLGSIPL, (SEQIDNO:10592); XM_548761.3, COR52AB3, Ins, T_8, SELSIPAV, (SEQIDNO:10593); NM_001024633.1, HTR2B, Ins, T_8, SLFAY-VVSLFYYKCNFSFV, (SEQIDNO:10594); XM_014116439.1, ABCA6, Ins, T_8, SLFNAFIFVCSK-LNGNLYHKRNCVCFGYIHARLCSFTCLPNICDI-LYFSQDEKK, (SEQIDNO:10595); XM_005620874.1, CCDC79, Ins, T_8, SRSNIMFRYNR, (SEQIDNO:10597); XM_003639813.3, LPAR6, Ins, T_8, SVHPHSGEQFHSSLL, (SEQIDNO:10598); XM_005623887.2, JAG2, Ins, T_8, WEALLVAGVALR-TRELLGGGL, (SEQIDNO:10599); XM_005632224.2, GRM7, Ins, T_8, WHCSVSGKALHTNYHTYNLHEPK-CISGSGDAIHAESVHHHFPP, (SEQIDNO:10600); XM_014111131.1, ABCA12, Ins, T_8, WHQFHCFLVSGVLSFQGKA, (SEQIDNO:10601); XM_003434545.2, LOC100687027, Ins, T_8, WISSIHVS, (SEQIDNO:10602); XM_014119240.1, LOC106559724, Ins, T_8, WLPSGTAQLCL, (SEQIDNO:10603); XM_005629703.2, PAXIP1, Ins, T_8, WNHCVSLPGVVHRQERLVGFAHFLRGRL-PAAPQQEMHTSGCSRTKRGEIRMRVKES KYQNCYP, (SEQIDNO:10604); XM_014111169.1, LOC610561, Ins, T_8, WQCGPHVPTLLCHLLLI-LGYSHCSGLCSFVSLLQPHHL, (SEQIDNO:10605); XM_846475.4, NDST3, Ins, T_8, WQQLKLLVAQAHL-HRCCFLLVRKEADTVLGQVHSCGYR, (SEQIDNO: 10606); XM_014109446.1, PIGB, Ins, T_8, WSMDLGSV, (SEQIDNO:10607); XM_005633659.2, TMEM41B, Ins, T_8, YWDFSRCCTSLFCSN, (SEQIDNO:10609); XM_005632123.2, NR2C2, Ins, T_8, YWSH-WQCVDRQHNPLHPQDGDSRV, (SEQIDNO:10610); XM_005641803.2, SLC25A 14, Ins, T_8, YYI-RAAQEASNL, (SEQIDNO:10611); XM_847748.2, LOC483503, Ins, T_9, CGLNKSIAAPGCSLCDIS-LGLSCYSSGKCGDDHPHLVGSPTPHTYVLFS, (SEQIDNO:10612); XM_005620886.2, ADAMTS18, Ins, T_9, CNVRQSERRNSLLPKQTRCLY, (SEQIDNO:10613); XM_849368.3, DPY19L4, Ins, T_9, FAIDTVFFITFLY-FSVNYLFSFYDASYF, (SEQIDNO:10614); XM_014110417.1, SLITRK3, Ins, T_9, FCCLCCCRPLCL-CAATAPEEAAL, (SEQIDNO:10615); XM_849037.4, TSPAN18, Del, T_9, FCSSSSSSWRSSRRPSWPSSSG-KISLASPSPRSSPSTTRATMTQTSSPPPGTPS, (SEQIDNO:10617); XM_547308.5, LPAR3, Ins, T_9, FEFSSHRSSDQKQKVSFPLLLPVG, (SEQIDNO:10618); XM_536488.5, C6, Ins, T_9, FEKRSGTQVYH, (SEQIDNO:10619); XM_005627395.2, XPO5, Ins, T_9, FGKCDQPDVSDIR, (SEQIDNO:10620); XM_014120987.1, LOC100684857, Ins, T_9, FGRKHN-FLLFMCHTGSFLHDLHH, (SEQIDNO:10621); XM_014110073.1, GABRR3, Del, T_9, FIS-DITGKMRGSPFLAQQTKA, (SEQIDNO:10622); XM_003435295.1, SLFN5, Del, T_9, FLEA-GLWTLVYQRSRE, (SEQIDNO:10623); XM_014111218.1, ZC3H11A, Ins, T_9, FLFYMYQR, (SEQIDNO:10624); XM_014110515.1, ZNF165, Del, T_9, FLGFQSMHMDKRYSGERWYLLDQYL-VSTCSQWTPMPFMVLQHPFFWTVIRKVKT MDLCQSWTFVKKLNHKEFYQEEFQD-SCRKDLLSLKTSVSLQAG, (SEQIDNO:10625); XM_005635440.2, EXOSC8, Ins, T_9, FLPASRV-SKDCGTSGVLQEIFERELPS, (SEQIDNO:10626); XM_005625919.2, APOL6, Ins, T_9, FLSPKLIL, (SEQIDNO:10627); XM_014118398.1, KCTD20, Ins, T_9, FLVKQTVQDSESKHERSSWQ, (SEQIDNO:10628); XM_014114900.1, SRSF11, Del, T_9, FMLLVYFV-VIHLCQSHPVSALLSSMIRTQQLWHSI, (SEQIDNO: 10629); XM_014109749.1, ITSN1, Del, T_9, FNLGYLNLF, (SEQIDNO:10630); XM_014106443.1, MYO16, Ins, T_9, FPEAIWISLFIG, (SEQIDNO:10631); XM_005623772.2, SERPINA3, Del, T_9, FPER-SAHWSLFVSTDPFCSAYTTKIRRTSSSGARSPTPIKP, (SEQIDNO:10632); XM_014118021.1, MCHR2, Ins, T_9, FPFAFDFGVLYFNFMLYLGDVSTE, (SEQIDNO:10633); XM_540560.5, ELP4, Del, T_9, FQKNYPQLLI, (SEQIDNO:10634); XM_005639096.2, CCNG2, Ins, T_9, FQLQSGTDTVLSIL, (SEQIDNO:10635); XM_014106522.1, FOXL2, Ins, T_9, FQSPLEKTLQYQQNTTT, (SEQIDNO:10636); XM_003638934.3, ABCC11, Del, T_9, FRCLRHP-STCSRGWRTTAAPLCSPTFSPLFRA, (SEQIDNO: 10637); XM_005623772.2, SERPINA3, Ins, T_9, FRKDRPTGHCSFQQTLSVLHTPQRY-GEHPLLGQGHQPQSSL, (SEQIDNO:10638); XM_536488.5, C6, Del, T_9, FRKKKWNTGVPL-TRCPRNTKVPFCREQRNPYP, (SEQIDNO:10639); XM_005625919.2, APOL6, Del, T_9, FSFTEAHL, (SEQIDNO:10640); XM_014118398.1, KCTD20, Del, T_9, FSGQADSSGFRIQA, (SEQIDNO:10641); XM_014111218.1, ZC3H11A, Del, T_9, FSILHVPKVTAVPSVTVKLH, (SEQIDNO:10642); XM_003435295.1, SLFN5, Ins, T_9, FSKLGCGHW-SIREAGSNL, (SEQIDNO:10643); XM_014106522.1, FOXL2, Del, T_9, FSKSTRKNTTISAKYNNMN, (SEQIDNO:10644); XM_014118812.1, CLOCK, Ins, T_9, FSNHDRWKHNICV, (SEQIDNO:10645); XM_014106443.1, MYO16, Del, T_9, FSRSHLDFS-LYWMKKVR, (SEQIDNO:10646); XM_005635440.2, EXOSC8, Del, T_9, FSSRFACLKGLWNLWSITGDF, (SEQIDNO:10647); XM_005639096.2, CCNG2, Del, T_9, FSTSKWHRHCAFHL, (SEQIDNO:10648); XM_005637816.2, FAM24B, Del, T_9, FTAGIHRTWKT, (SEQIDNO:10649); XM_014106247.1, LOC102155967, Del, T_9, FTGTLITEVSYSAFILATHSGVQHLSSYLDL, (SEQIDNO:10650); XM_014120987.1, LOC100684857, Del, T_9, FWKKTQFLIIYVPHRELST, (SEQIDNO: 10651); XM_542618.5, FBXL3, Del, T-9, FYMKRN-LIHSFGMKYLPPIFTLGDQ, (SEQIDNO:10652); XM_531662.5, TMBIM4, Del, T_9, FYTLSLYGH-LYMKVLP, (SEQIDNO:10653); XM_014115464.1, ZNF396, Ins, T_9, LFFKIYFYRESGVWQGGGQK-EREFQADSPL, (SEQIDNO:10654); XM_005615357.1, PIGN, Del, T_9, LHHLSCFLNLNS, (SEQIDNO:10656); XM_005618779.2, RYR2, Del, T_9, LLLISLTLLWGSKH, (SEQIDNO:10657); XM_005637816.2, FAM24B, Ins, T_9, LLRAFIEHGRLRG, (SEQIDNO:10658); XM_014116728.1, INTS2, Del, T_9, LSHL-SYLRVQSIWRKLQMYFVFYKQSSLPCFL, (SEQIDNO: 10659); XM_014110073.1, GABRR3, Ins, T_9, LSQTLLER, (SEQIDNO:10660); XM_532552.5, UTP11L, Del, T_9, LTPKRKLSSLILPLT, (SEQIDNO:10661); XM_014109749.1, ITSN1, Ins, T_9, SIWVTSTCFSTDM-GAS, (SEQIDNO:10662); XM_540560.5, ELP4, Ins, T_9, SRKIIPNS, (SEQIDNO:10663); XM_014110515.1, ZNF165, Ins, T_9, SSGSSPCTWTRDIQEKGGTFWTST, (SEQIDNO:10664); and XM_849037.4, TSPAN18, Ins, T_9, SVHPHHLLGGALGGHPGLHLQGK-SHSRVLHQGAHQALPGQQ, (SEQIDNO:10665).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Screening Human Cancer Patients for Vaccine Candidates

The peptide sequence of the FSP array was from our human or dog FS database. It includes the most of the MS FS antigens (homopolymer size >6 nt, peptide size >9 a.a) and potential FSP caused by mis-splicing of each exon. All FS antigens were segmented into 10 to 15 a.a long peptides. The array was synthesized by Nimblegen with photolithography. There were about 400K peptides of each FSP array, including ~14 K MS FSPs.

Figure 8A:
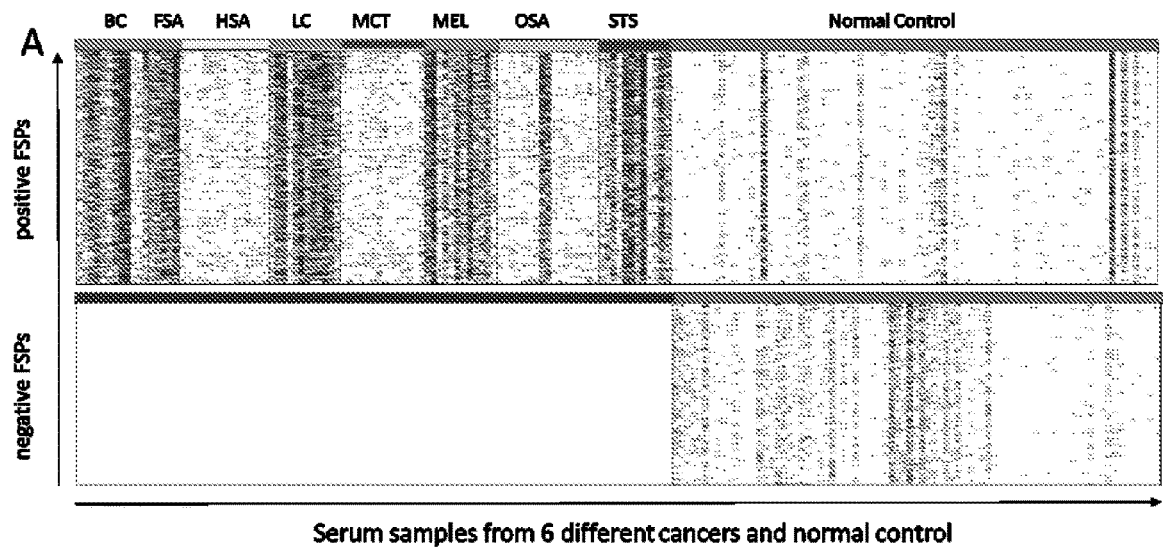
FIG. 8A, FIG. 8B, and FIG. 8C show 400K FSP array screen antibody reactive in cancer patient and examples of using the SPCV system identify FS antigens for personalized cancer vaccine.
Figure 8B:
Figure 8C:
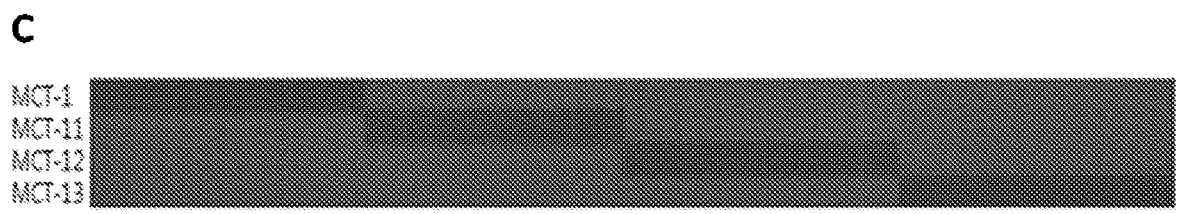

Total 96 cancer serum from 8 different cancers and 81 non-cancer normal controls were analyzed with the 400K array (FIG. 8A and FIG. 8B). Cancer patients had much higher IgG reactive to the FSPs. However, there is still a small portion FSPs don't have IgG positive reactive in cancers (FIG. 8A). It was determined that positive IgG reactive FSPs have better protection (FIG. 9, FIG. 10, FIG. 11). Based on the IgG reactivity to FSPs, 20 best reactive FS antigens can be selected for each cancer patient as personalized cancer vaccine. (FIG. 8B and FIG. 8C).

Example 2: Screening Dog Cancer Patients For Vaccine Candidates

Blood from dogs with various cancers was used to screen vaccine candidate peptides. 830 spotted peptides corresponding to 374 different FS antigens from 209 genes in dogs. Sera from dogs with 8 different cancers, (N=116), including mammary cancer, were compared to sera from dogs without cancer (N=52). Results of the screen are shown in FIG. 9. Red spots indicate the normalized florescent value of the peptide was 5 fold higher than in the corresponding sample. There were a total 487 FS peptides had at least one example of 5 fold higher reactivity. The dogs with cancer also showed higher antibody reactive to the FS peptide. Each type of cancer has its own reactive profile, as well as each individual dogs.

Figure 13A:
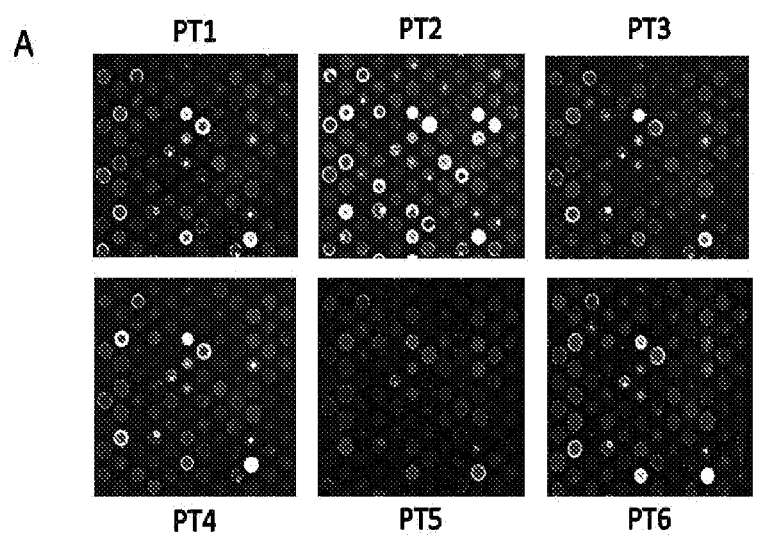
FIG. 13A and FIG. 13B shows data identifying personal reactive FS antigens and detection of the T cell responses to some of these FS antigens in the same dog.
Figure 13B:
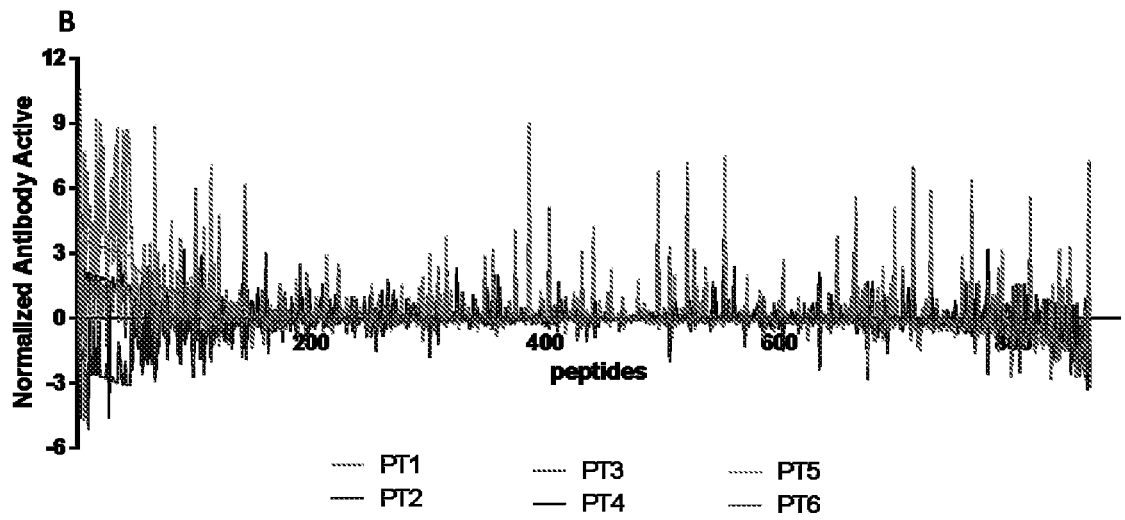

Data from individual dogs is shown in FIG. 13A and FIG. 13B. Screening of 6 dogs with cancer for specific cancer vaccine candidates. In FIG. 13A, a corner of the scanned FS array of each cancer dog analysis is shown. In FIG. 13A, data is shown of normalized antibody active to each peptide of each cancer dog. These data showed that each dog has personal highly reactive FS peptides.

Figure 14:
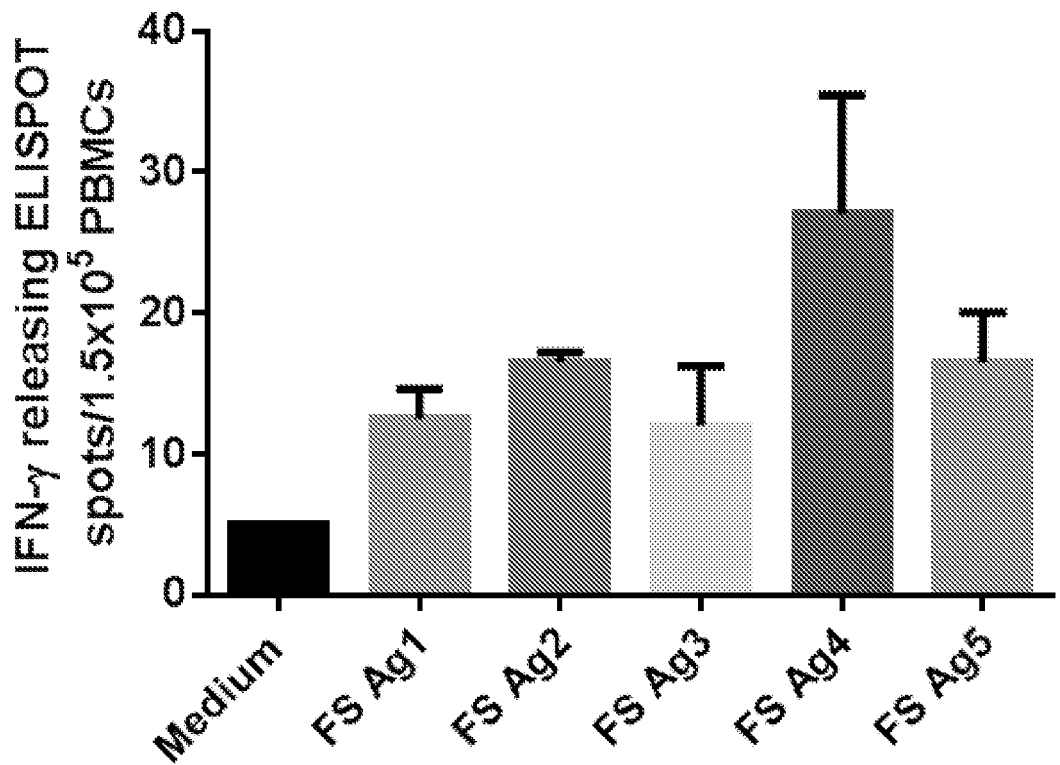
FIG. 14 shows data identifying personal reactive FS antigens and detection of the T cell responses to some of these FS antigens in the sanle dog. For a specific dog screened using the arrays in FIG. 9, 5 FS antigens that were highly antibody reactive were tested in ELI-Spot assays. PBMCs from the dog's blood were purified, stimulated with pooled peptides from each FS antigen candidates and the number of positive cells counted. The number for positive for each FS antigen stimulant is shown. As can be seen all 5 FS antigens showed significant T-cell reactivity compare to the medium control.

T-cell reactivity was determined for candidate vaccine peptides. For a specific dog screened using the arrays in FIG. 13A and FIG. 13B, 5 FS antigens that were highly antibody reactive were tested in ELI-Spot assays. PBMCs from the dogs' blood were purified, stimulated with pooled peptides from each FS antigen candidates and the number of positive cells counted. The number for positive for each FS antigen stimulant is shown. As can be seen all 5 FS antigens showed significant T-cell reactivity compared to the medium control (FIG. 14).

Example 3: Cancer Vaccine for Dogs

Figure 15A:
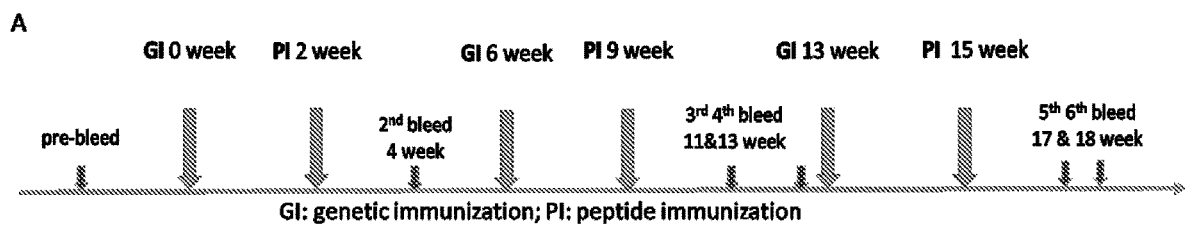
FIG. 15A, FIG. 15B, and FIG. 15C show the result of the dog cancer vaccine safety trial.
Figure 15B:
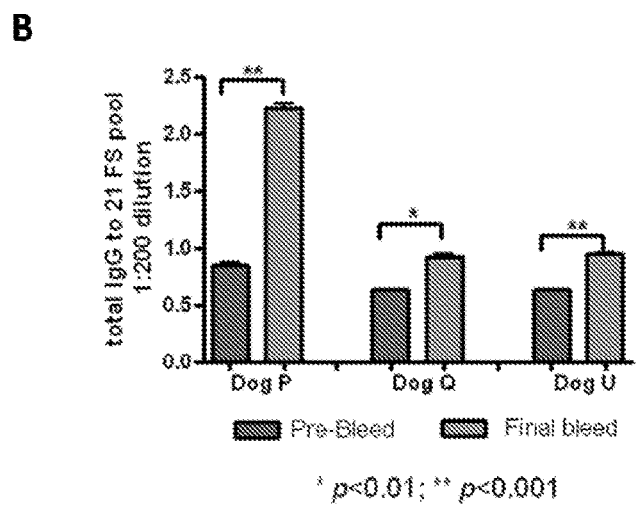
Figure 15C:
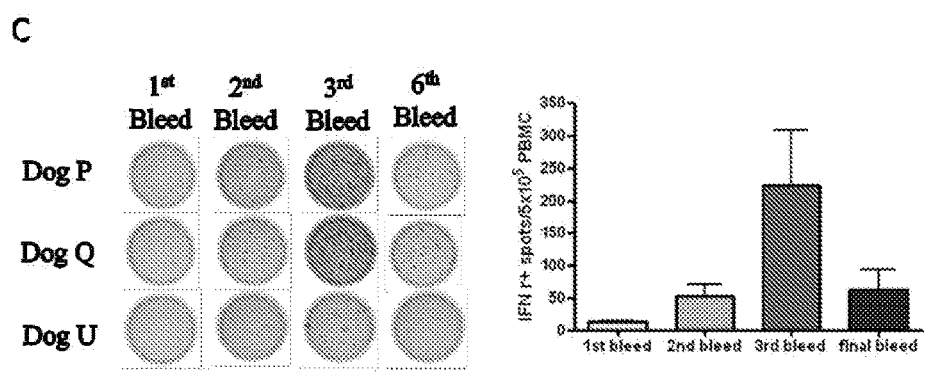

A safety trial of FS peptide based cancer vaccine was conducted in dogs. The cancer vaccine was formulated with 21 FS antigens. Three healthy dogs were immunized with the vaccine according to the timeline shown in FIG. 15A. An ELISA analysis was conducted on the antibody reactivity of the immunization, shown in FIG. 15B. ELISPOT analysis was conducted to measure the specific IFNγ releasing PBMCs to the vaccine antigens after immunization, shown in FIG. 15C. Standard clinicopathologic analysis showed the vaccine is safe for these three dogs.

Example 4: Frameshift Peptide Vaccines Protect Against Cancer

Figure 16A:
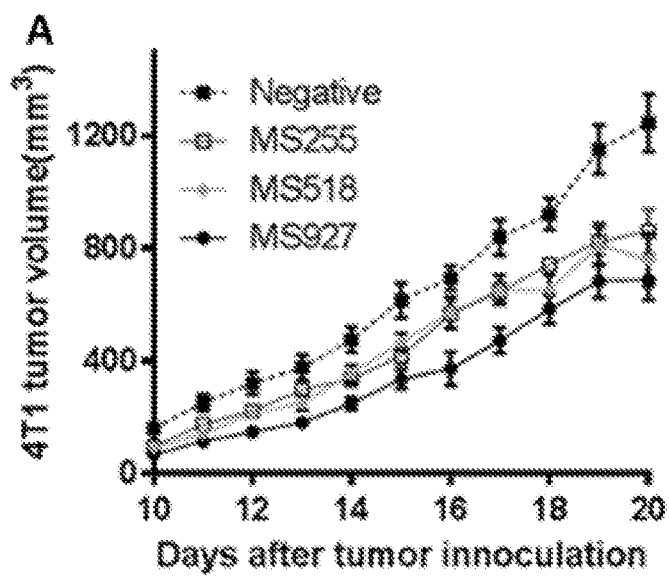
FIG. 16A and FIG. 16B show that FSPs have significant protection as vaccine candidates in different mouse tumor model.
Figure 16B:
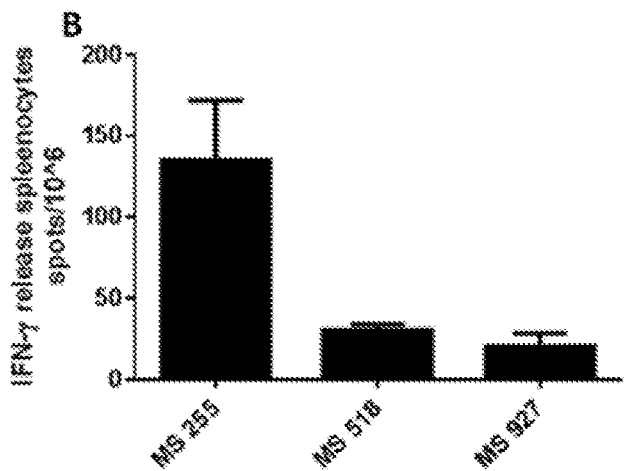

To determine whether any MS Indel event could produce a FS in any constitutive gene and could therefore be a protective antigen against most or all tumor types, three predicted MS FSs in mouse genes were selected using the criteria of FS peptide length and predicted H2-D epitopes (Table 3). Each FS peptide was tested individually in the 4T1-BALB/c mouse breast tumor model with the prophylactic vaccination of gene vaccine/peptide boost. Each FS peptide vaccination significantly slowed the tumor growth compared to the mock immunized mice (FIG. 16A). Each FS antigen can elicit specific IFNγ releasing splenocytes (FIG. 16B). These results indicate that any FSs produced by MS can confer protection. Peptides tested are listed in Table 1.

TABLE 3

The three MS FSPs (SEQ ID NOS 10666-10668, respectively, in order of appearance) with predicted H2-D epitopes for the vaccine test.

| Gene ID | MS type | FS type | FS size | FS peptide (Kd/Ld > 20) |
|---|---|---|---|---|
| MS0518 | 10A | Del | 59 aa | TLCMEVMLRWNTRELGY-LYLQLCFLNTHFLHTSQEEKLLTL-GRFLTWTSRCGSFVIRPL (SEQ ID NO: 10666) |
| MS7927 | 9A | Del | 33 aa | ICMSPPLLWATLQAPETTSAACKASYRPEG-LYL (SEQ ID NO: 10667) |
| MS2255 | 9A | Ins | 25 aa | YFSCDKRCIKHYAGNKSLLTFSGY (SEQ ID NO: 10668) |

In another demonstration, two different pools of mouse FS antigen of the different MS length were selected (Table 4) and tested in the same mouse tumor model. Both FS pooled vaccine significantly retarded tumor growth comparing to the control group (FIG. 17A and FIG. 171B).

TABLE 4

Two pools of the FS antigens from the different MS length.

| Ag ID | Ref Gene | MS type | INDEL | peptide size (aa) |
|---|---|---|---|---|
| Short MS pool | | | | |
| Mus385 | NM_146792.2 | 8T | Deletion | 32 |
| Mus392 | NM_029998.3 | 8T | Deletion | 51 |
| Mus023 | NM_147003.1 | 8T | Insertion | 19 |
| Mus263 | NM_001114663.1 | 8A | Insertion | 20 |
| Mus942 | NM_001081355.3 | 8A | Insertion | 37 |
| Mus671 | NM_001163189.1 | 8A | Insertion | 49 |
| Mus334 | NM_130448.3 | 8A | Deletion | 29 |
| Mus051 | NM_033618.3 | 8A | Insertion | 26 |
| Mus587 | NM_001081302.1 | 8A | Insertion | 32 |
| MS255 | NM_010086.4 | 9A | Insertion | 24 |
| MS927 | NM_053009.3 | 9A | Deletion | 33 |
| MS518 | NM_153511.3 | 10A | Deletion | 59 |
| Long MS pool | | | | |
| Mus487 | NM_001109759.1 | 10A | Deletion | 44 |
| Mus413 | NM_027009.2 | 10A | Deletion | 27 |
| Mus274 | NM_001081345.2 | 10A | Insertion | 14 |
| Mus694 | NM_028787.4 | 10T | Insertion | 45 |
| Mus281 | NM_001160399.1 | 11A | Deletion | 39 |
| Mus951 | NM_025441.3 | 11A | Deletion | 36 |
| Mus461 | NM_001033226.4 | 13T | Deletion | 22 |
| Mus528 | NM_001034881.3 | 14T | Deletion | 54 |
| Mus414 | NM_028664.1 | 18T | Deletion | 28 |

The FS vaccine was also tested in a mouse ovarian cancer model (ID8-C57BL6). A pool of FSP from 10 MS FS and 3 mis-splicing FS was immunized, as well as a pool of peptides from the point DNA mutation if the 1D8 cells were immunized the mice after the tumor cell injection. Both vaccines showed the significant protection comparing to the control mice which were immunized with PBS (FIG. 18). The same sets of the vaccines combined with immune checkpoint treatment also showed the significant protection. This experiment shows our FS variants have the same protection as the neo-antigens from the DNA mutations.

Example 5: Personalized Vaccine Test in Mouse Tumor Models

Protection by personalized pool FS neoantigens was tested in the 4T1 BALB/c tumor model (FIG. 19). Serum from BALB/c mice (n=10/group) were collected two days previous and 7-days post subcutaneous injection of 4T1 tumor cells (500 cells/mouse). Both sera were run on microarray slides containing peptides for human FS neoantigens and the 10 mouse homologs neoantigens with higher median normalized signal on the array were selected as targets for the vaccines formulations for each mice. Mice were vaccinated subcutaneously on days 12 and 19. For the immunization group with the combined immunotherapy, the antibody treatment, anti-PD-L1 and CTLA-4, were administrated intraperitoneally on days 12, 15, 19, 22. Control group (non-treated) was immunized with PBS at the same schedule as the vaccine groups. Non-reactive groups were immunized with FS antigens without signal in the microarray before and after tumor challenge, and followed the same vaccine regimen as the other groups. The test shows that the personalized positive FSPs selected from the FSP array have significant protection as a vaccine. It also shows again that the negative IgG reactive FSPs don't have the protection.

The personalized cancer vaccine was also tested in a spontaneous mouse breast tumor model (FIG. 20). Female FVB/N mice (n=22) were evaluated weekly for the presence of palpable tumor, when tumor was detected sample blood was collected and run on microarray slides containing peptides for human FS neoantigens. The 10 mouse homologs neoantigens with higher median normalized signal compared to age matched FVB/NJ samples on the array were selected as targets for the vaccines formulations for each mice. Mice were vaccinated subcutaneously with pool of FS peptide with minimum two doses and maximum seven doses, as needed to maintain tumor control, with intervals 1-2 weeks between doses. Each vaccine dose was followed by checkpoint inhibitor treatment (antibody anti-PD-L1 and anti-CTLA-4) (CPI), two doses, three days a part. As control groups, animals were immunized with PBS (non-treated) at the same schedule as the vaccine groups or only with CPI treatment (CPI only), twice per animal. Personalized FS vaccine conferred 68.2% of protection. Both personalized cancer vaccine tests with our SPCV system showed significant protection in two different mouse tumor models. It suggests the SPCV system may also work with human cancer treatment.

Example 5: Personalized Cancer Vaccine

An individual presenting with histologically confirmed stage 1 mammary cancer is in need of treatment. A blood sample is obtained from the individual and serum from the blood sample is applied to a peptide array having approximately 20,000 spotted FS peptides. After incubation, the array is washed and the patient's bound antibodies are detected using a fluorescently labeled secondary antibody. FS peptides are found to bind specifically to the patient's sera and not to sera from healthy individuals.

These reactive FS peptides are prepared in a vaccine preparation including a poly I:C adjuvant and administered to the individual with a checkpoint inhibitor or combination of checkpoint inhibitors after receiving a lumpectomy surgery. The individual is monitored for mammary cancer recurrence and is cancer-free for five years.

Example 6: Clinical Trial for a Personalized Cancer Vaccine

Ten individuals presenting with histologically confirmed stage 1 mammary cancer are in need of treatment. Blood samples are obtained from each individual and serum from the blood samples were applied to peptide arrays having approximately 20,000 spotted FS peptides. After incubation, the arrays are washed and the patients' bound antibodies are detected using a fluorescently labeled secondary antibody. FS peptides are found to specifically bind to the patients' sera but not to sera from healthy individuals. Reactive FS peptides are prepared in a vaccine preparation for each patient including a poly I:C adjuvant. The FS vaccine components are chosen from pre-synthesized reagents. Each individual is given their vaccine after receiving lumpectomy surgery. Vaccinated individuals are monitored for manlmary cancer recurrence and nine of the ten individuals remain cancer free for five years. Ten individuals receive a lumpectomy surgery only and six of the ten individuals remain cancer free for five years. This Example demonstrates that a personalized cancer vaccine provides increased efficacy in mammary cancer treatment compared to lumpectomy surgery only.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11484581B2). An electronic copy of the "Sequence Listing" will also be available from the USPTO upon request and payment of the fee set forth in 37 CFR 1.19(b)(3).

What is claimed is:

1. A method of treating an individual in need of treatment for a cancer, the method comprising:
    a) contacting a biological sample from the individual with a frameshift peptide (FSP) array, wherein the FSP array comprises a first population of peptides encoded by a frameshifted mRNA created in a splicing error or a transcription insertion or deletion error, wherein the first population of peptides comprising the peptide sequence of SEQ ID NO: 1;
    b) identifying peptides in the FSP array that are immunoreactive with the biological sample;
    c) preparing a vaccine composition comprising the immunoreactive peptides identified in step b) or a nucleic acid sequence encoding the immunoreactive peptides; and
    d) administering an effective amount of the vaccine composition to the individual, thereby treating the cancer, wherein the individual is a canine.

2. The method of claim 1, comprising obtaining the biological sample from the individual.

3. The method of claim 1, wherein treating the cancer comprises reducing tumor size, inhibiting tumor growth, reducing tumor burden, increasing survival, or increasing cancer-free survival.

4. The method of claim 1, wherein administering the vaccine composition elicits an immune response in the individual against the cancer.

5. The method of claim 1, wherein the immunoreactive peptides are a subpopulation of the first population of peptides.

6. The method of claim 1, wherein the identified peptide elicits a positive response in an antibody assay or a T cell assay performed on the biological sample from the individual.

7. The method of claim 1, wherein the biological sample is selected from the group consisting of blood, plasma, serum, thymus, bone marrow, spleen, lymph node, bronchoalveolar lavage, breast, central nervous system, cerebrospinal fluid, eye, tears, gastrointestinal tract, saliva, feces, urine, heart, kidney, liver, lung, muscle, pancreas, peripheral nervous system, saliva, skin, thyroid, trachea, and tumor.

8. The method of claim 1, wherein the biological sample comprises cells selected from B cells, T cells, CD4+ T cells, CD8+ T cells, Thl 7 cells, and combinations thereof.

9. The method of claim 1, wherein the biological sample comprises an antibody.

10. The method of claim 1, wherein identifying comprises determining immunoreactivity of the first population of peptides to the biological sample using antibody reactivity using an antibody assay selected from the group consisting of ELISA, radio-immunoassay, western blot, surface plasmon resonance, immunostaining, immunoprecipitation, mass spectrometry, phage display, ELISPOT, flow cytometry, cytometric bead array, immunohistochemistry, high density array, microarray, delayed-type hypersensitivity (DTH), and combinations thereof.

11. The method of claim 1, wherein identifying comprises determining immunoreactivity of the first population of peptides to the biological sample using a T cell response using an assay selected from the group consisting of proliferation assay, 3H-thymidine assay, BrdU assay, CFSE assay, cytokine secretion assay, ELISA assay, ELISPOT assay, intracellular staining assay, quantitative rtPCR assay, cytometric bead array assay, cytotoxicity assay, 51-chromium assay, degranulation assay, granulysin assay, granzyme A assay, granzyme B assay, and perforin assay.

12. The method of claim 1, wherein the first population of peptides comprises peptides encoded by a frameshifted mRNA expressed by a cancer cell.

13. The method of claim 1, wherein the first population of peptides is bound to a substrate.

14. The method of claim 1, wherein the vaccine composition comprises a pharmaceutically acceptable adjuvant or excipient.

15. The method of claim 14, wherein the adjuvant is selected from the group consisting of ABM2, AS01B, AS02, AS02A, Adjumer, Adjuvax, Algammulin, Alum, Aluminum phosphate, Aluminum potassium sulfate, *Bordetella pertussis*, Calcitriol, Chitosan, Cholera toxin, CpG, Dibutyl phthalate, Dimethyldioctadecylammonium bromide (DDA), Freund's adjuvant, Freund's complete, Freund's incomplete (IFA), GM-CSF, GMDP, Gamma Inulin, Glycerol, HBSS (Hank's Balanced Salt Solution), IL-12, IL-2, Imiquimod, InterferonGamma, ISCOM, Lipid Core Peptide (LCP), Lipofectin, Lipopolysaccharide (LPS), Liposomes, MF59, MLP+TDM, Monophosphoryl lipid A, Montanide IMS-1313, Montanide ISA 206, Montanide ISA 720, Montanide ISA-51, Montanide ISA-50, nor-MDP, Oil-in-water emulsion, Pl005 (non-ionic copolymer), Pam3Cys (lipoprotein), Pertussis toxin, Poloxamer, QS21, RaLPS, Ribi, Saponin, Seppic ISA 720, Soybean Oil, Squalene, Syntex Adjuvant Formulation (SAF), Synthetic polynucleotides (poly IC/poly AU), TiterMax Tomatine, Vaxfectin, XtendIII, and Zymosan.

16. The method of claim 1, wherein the vaccine is administered via a route selected from the group consisting of subcutaneous, intradermal, intramuscular, intranasal, intravenous, and sublingual.

17. The method of claim 1, wherein the individual is a dog.

18. The method of claim 1, wherein the cancer is selected from the group consisting of Acute lymphoblastic leukemia, Acute monocytic leukemia, Acute myeloid leukemia, Acute promyelocytic leukemia, Adenocarcinoma, Adult T-cell leukemia, Astrocytoma, Bladder cancer, Bone Cancer, Brain Tumor, Breast Cancer, Burkitt's lymphoma, Carcinoma, Cervical Cancer, Chronic Lymphocytic Leukemia, Chronic myelogenous leukemia, Colon Cancer, Colorectal cancer, Endometrial cancer, Glioblastoma multiforme, Glioma, Hepatocellular carcinoma, Hodgkin's lymphoma, Inflammatory breast cancer, Kidney Cancer, Leukemia, Lung cancer, Lymphoma, Malignant Mesothelioma, Medulloblastoma, Melanoma, Multiple myeloma, Neuroblastoma, Non-Hodgkin Lymphoma, Non-Small Cell Lung Cancer, Ovarian Cancer, Pancreatic Cancer, Pituitary tumor, Prostate cancer, Retinoblastoma, Skin Cancer, Small Cell Lung Cancer, Squamous cell carcinoma, Stomach cancer, T-cell leukemia, T-cell lymphoma, Thyroid cancer, and Wilms' tumor.

\* \* \* \* \*

UNITED STATES PATENT AND TRADEMARK OFFICE
CERTIFICATE OF CORRECTION

| | | |
|---|---|---|
| PATENT NO. | : 11,484,581 B2 | Page 1 of 12 |
| APPLICATION NO. | : 16/617889 | |
| DATED | : November 1, 2022 | |
| INVENTOR(S) | : Johnston et al. | |

It is certified that error appears in the above-identified patent and that said Letters Patent is hereby corrected as shown below:

In the Drawings

On Sheet 10 of 17, FIG. 13B, Y-Axis, Line 2, delete "Normallzed Antlbody Actlve" and insert --Normalized Antibody Active--.

On Sheet 12 of 17, FIG. 16A, X-Axis, Line 2, delete "innoculation" and insert --inoculation--.

On Sheet 12 of 17, FIG. 17A, Line 3 (Approx.), delete "Contorl" and insert --Control--.

On Sheet 13 of 17, FIG. 17B, Line 3 (Approx.), delete "Contorl" and insert --Control--.

In the Specification

In Column 2, Line 55, delete "XtendIII," and insert --Xtend III,--.

In Column 4, Line 55, delete "XtendIII," and insert --Xtend III,--.

In Column 6, Line 18, delete "XtendIII," and insert --Xtend III,--.

In Column 7, Line 61, delete "XtendIII," and insert --Xtend III,--.

In Column 9, Line 14, delete "II" and insert --I/II--.

In Column 10, Line 49, delete "sanle" and insert --same--.

In Column 13, Line 11, delete "and or" and insert --and/or--.

In Column 18, Line 18, delete "RNA" and insert --RNA.--.

In Column 20, Line 20, delete "(IFN-7)" and insert --(IFN-γ)--.

Signed and Sealed this
Eighteenth Day of April, 2023

Katherine Kelly Vidal
*Director of the United States Patent and Trademark Office*

CERTIFICATE OF CORRECTION (continued)
U.S. Pat. No. 11,484,581 B2

In Column 20, Line 20, delete "ethylcarvazole" and insert --ethylcarbazole--.

In Column 20, Line 31, delete "SI$\leq$2." and insert --SI$\geq$2.--.

In Column 20, Line 54, delete "tmle" and insert --tune--.

In Column 21, Line 54, delete "alcoHO1," and insert --alcohol,--.

In Column 23, Line 54, delete "SEQ IDNO: 1-10665." and insert --SEQ ID NO: 1-10665.--.

In Column 24, Lines 48-49, delete "antibacteRIA1," and insert --antibacterial,--.

In Column 25, Line 7, delete "XtendIII," and insert --Xtend III,--.

In Column 28, Line 9, delete "XtendIII," and insert --Xtend III,--.

In Column 29, Line 26, delete "gem1" and insert --germ--.

In Column 29, Line 58, delete "InvoMng" and insert --Involving--.

In Column 31, Line 35, delete "Acanthoina," and insert --Acanthoma,--.

In Column 33, Line 13, delete "Sezaiy" and insert --Sezary--.

In Column 33, Line 17, delete "wart." and insert --wart,--.

In Column 33, Line 23, delete "lymphocyle" and insert --lymphocyte--.

In Column 34, Line 16, delete "LH" and insert --LH,--.

In Column 35, Line 54, delete "A-13," and insert --A_13,--.

In Column 38, Line 17, delete "ClH," and insert --C1H,--.

In Column 38, Line 66, delete "MK167," and insert --MKI67,--.

In Column 41, Line 59, delete "XM 005639666.2," and insert --XM_005639666.2,--.

In Column 44, Line 17, delete "XM 014110659.1," and insert --XM_014110659.1,--.

In Column 45, Line 23, delete "A-7," and insert --A_7,--.

In Column 45, Line 38, delete "A-7," and insert --A_7,--.

In Column 45, Line 65, delete "A-7," and insert --A_7,--.

CERTIFICATE OF CORRECTION (continued)
U.S. Pat. No. 11,484,581 B2

In Column 46, Line 8, delete "LUC100683727," and insert --LOC100683727,--.

In Column 46, Line 55, delete "PiS," and insert --PLS,--.

In Column 47, Line 44, delete "A-7," and insert --A_7,--.

In Column 48, Line 47, delete "IPOS," and insert --IP05,--.

In Column 49, Line 51, delete "MK167," and insert --MKI67,--.

In Column 50, Line 1, delete "A-7," and insert --A_7,--.

In Column 50, Line 24, delete "TL1," and insert --TLI,--.

In Column 50, Line 30, delete "A-7," and insert --A_7,--.

In Column 50, Line 39, delete "A-7," and insert --A_7,--.

In Column 50, Line 57, delete "A-7," and insert --A_7,--.

In Column 54, Line 39, delete "XM 534297.5," and insert --XM_534297.5,--.

In Column 55, Line 43, delete "XM_005616994.2." and insert --XM_005616994.2,--.

In Column 56, Line 34, delete "C1IH" and insert --CLLH--.

In Column 60, Line 2, delete "QV" and insert --QV,--.

In Column 64, Line 25, delete "A-7," and insert --A_7,--.

In Column 64, Line 40, delete "XM 005624024.1," and insert --XM_005624024.1,--.

In Column 66, Line 36, delete "C1H-" and insert --CLH- --.

In Column 67, Line 11, delete "A-7," and insert --A_7,--.

In Column 67, Line 39, delete "C5H11orf141," and insert --C5H1orf141,--.

In Column 67, Line 40, delete "XM 005640597.2," and insert --XM_005640597.2,--.

In Column 68, Line 39, delete "A-7," and insert --A_7,--.

In Column 69, Line 56, delete "A-7," and insert --A_7,--.

In Column 75, Line 10, delete "A-7," and insert --A_7,--.

CERTIFICATE OF CORRECTION (continued)
U.S. Pat. No. 11,484,581 B2

In Column 77, Line 27, delete "A-7," and insert --A_7,--.

In Column 81, Line 54, delete "A-7," and insert --A_7,--.

In Column 83, Line 27, delete "PIPSK1A," and insert --PIP5K1A,--.

In Column 87, Line 15, delete "RHQ" and insert --RIIQ--.

In Column 87, Line 42, delete "FBX015," and insert --FBXO15,--.

In Column 88, Line 8, delete "MK167," and insert --MKI67,--.

In Column 88, Line 58, delete "A-7," and insert --A_7,--.

In Column 88, Line 67, delete "HlLL" and insert --HILL--.

In Column 90, Line 27, delete "A-7," and insert --A_7,--.

In Column 92, Line 54, delete "A-7," and insert --A_7,--.

In Column 93, Line 48, delete "CIS," and insert --CLS,--.

In Column 97, Line 17, delete "A-7," and insert --A_7,--.

In Column 97, Line 28, delete "A-7," and insert --A_7,--.

In Column 99, Line 25, delete "C16H2orf73," and insert --C10H2orf73,--.

In Column 100, Line 3, delete "A-7," and insert --A_7,--.

In Column 101, Line 35, delete "PTI" and insert --PTT--.

In Column 101, Line 49, delete "HI1," and insert --HL,--.

In Column 107, Line 35, delete "A-7," and insert --A_7,--.

In Column 110, Line 1, delete "SIL," and insert --SLL,--.

In Column 110, Line 14, delete "A-7," and insert --A_7,--.

In Column 110, Line 40, delete "A-7," and insert --A_7,--.

In Column 110, Line 63, delete "A-7," and insert --A_7,--.

In Column 111, Line 10, delete "ATP6VOD2," and insert --ATP6V0D2,--.

CERTIFICATE OF CORRECTION (continued)
U.S. Pat. No. 11,484,581 B2

In Column 112, Line 16, delete "A-8," and insert --A_8,--.

In Column 113, Line 39, delete "A-8," and insert --A_8,--.

In Column 114, Line 16, delete "G1H" and insert --GIH--.

In Column 114, Lines 64-65, delete "XM 005626849.2," and insert --XM_005626849.2,--.

In Column 115, Line 32, delete "A-8," and insert --A_8,--.

In Column 116, Line 17, delete "XM__005637551.2," and insert --XM_005637551.2,--.

In Column 116, Line 22, delete "A-8," and insert --A_8,--.

In Column 116, Line 57, delete "A-8," and insert --A_8,--.

In Column 117, Line 35, delete "CSNKIG3," and insert --CSNK1G3,--.

In Column 118, Line 15, delete "ID1," and insert --LDL,--.

In Column 118, Line 48, delete "FIA," and insert --FLA,--.

In Column 118, Line 61, delete "KHC" and insert --KIIC--.

In Column 119, Line 1, delete "TR." and insert --TR,--.

In Column 119, Line 13, delete "XM-850195.4," and insert --XM_850195.4,--.

In Column 120, Line 58, delete "A-8," and insert --A_8,--.

In Column 121, Line 17, delete "A-8," and insert --A_8,--.

In Column 121, Line 39, delete "XM-014108520.1," and insert --XM_014108520.1,--.

In Column 123, Line 9, delete "SSI," and insert --SSL,--.

In Column 123, Line 47, delete "A-8," and insert --A_8,--.

In Column 124, Line 25, delete "A-8," and insert --A_8,--.

In Column 126, Line 19, delete "PDSSB," and insert --PDS5B,--.

In Column 126, Line 45, delete "A-8," and insert --A_8,--.

In Column 127, Line 37, delete "A-8," and insert --A_8,--.

CERTIFICATE OF CORRECTION (continued)
U.S. Pat. No. 11,484,581 B2

In Column 127, Line 46, delete "A-8," and insert --A_8,--.

In Column 128, Line 19, delete "A-8," and insert --A_8,--.

In Column 128, Line 39, delete "A-8," and insert --A_8,--.

In Column 129, Line 67, delete "A-8," and insert --A_8,--.

In Column 130, Line 18, delete "AS8," and insert --A_8,--.

In Column 130, Line 25, delete "A-8," and insert --A_8,--.

In Column 130, Line 27, delete "A-8," and insert --A_8,--.

In Column 130, Line 50, delete "A-8," and insert --A_8,--.

In Column 131, Line 37, delete "A-8," and insert --A_8,--.

In Column 131, Line 54, delete "A-9," and insert --A_9,--.

In Column 132, Line 39, delete "DYNCII2," and insert --DYNC1I2,--.

In Column 133, Line 55, delete "A-9," and insert --A_9,--.

In Column 134, Lines 32-33, delete "XM 005637736.2," and insert --XM_005637736.2,--.

In Column 134, Line 36, delete "A-9," and insert --A_9,--.

In Column 135, Line 45, delete "PDSSB," and insert --PDS5B,--.

In Column 136, Line 29, delete "A-9," and insert --A_9,--.

In Column 136, Line 59, delete "ATI," and insert --ATL,--.

In Column 137, Line 54, delete "C_I0," and insert --C_10,--.

In Column 139, Line 23, delete "C-11," and insert --C_11,--.

In Column 139, Line 31, delete "C11," and insert --C_11,--.

In Column 140, Line 34, delete "LW" and insert --LW,--.

In Column 144, Line 47, delete "LURAPIL," and insert --LURAP1L,--.

In Column 146, Line 61, delete "C-7," and insert --C_7,--.

CERTIFICATE OF CORRECTION (continued)
U.S. Pat. No. 11,484,581 B2

In Column 147, Line 15, delete "C-7," and insert --C_7,--.

In Column 148, Line 39, delete "PDSSB," and insert --PDS5B,--.

In Column 149, Line 3, delete "COLSA1," and insert --COL5A1,--.

In Column 152, Line 51, delete "DOCKI," and insert --DOCK1,--.

In Column 155, Line 57, delete "C-7," and insert --C_7,--.

In Column 156, Line 2, delete "C-7," and insert --C_7,--.

In Column 156, Line 17, delete "C-7," and insert --C_7,--.

In Column 159, Line 58, delete "C-7," and insert --C_7,--.

In Column 161, Line 11, delete "XM 014119834.1," and insert --XM_014119834.1,--.

In Column 161, Line 28, delete "C-7," and insert --C_7,--.

In Column 162, Line 38, delete "C-7," and insert --C_7,--.

In Column 165, Line 24, delete "XM_U14116817.1," and insert --XM_014116817.1,--.

In Column 167, Line 30, delete "XM 543989.5," and insert --XM_543989.5,--.

In Column 168, Line 66, delete "C-7," and insert --C_7,--.

In Column 170, Line 30, delete "INPPSK," and insert --INPP5K,--.

In Column 171, Line 35, delete "Q VFA1T" and insert --QVFAIT--.

In Column 171, Line 38, delete "CSNKlE," and insert --CSNK1E,--.

In Column 171, Line 45, delete "ClW" and insert --CIW--.

In Column 173, Line 16, delete "UBE20," and insert --UBE2O,--.

In Column 173, Line 27, delete "C-7," and insert --C_7,--.

In Column 174, Line 54, delete "C-7," and insert --C_7,--.

In Column 177, Line 9, delete "L CLRI" and insert --LCLRI--.

In Column 178, Line 57, delete "C7," and insert --C_7,--.

CERTIFICATE OF CORRECTION (continued)
U.S. Pat. No. 11,484,581 B2

In Column 179, Line 5, delete "C-7," and insert --C_7,--.

In Column 179, Line 51, delete "C-7," and insert --C_7,--.

In Column 182, Line 2, delete "ClE" and insert --CIE--.

In Column 183, Line 64, delete "C-7," and insert --C_7,--.

In Column 184, Line 54, delete "LlL" and insert --LLL--.

In Column 185, Line 17, delete "C-7," and insert --C_7,--.

In Column 196, Line 24, delete "NPEPlL," and insert --NPEPL1,--.

In Column 196, Line 67, delete "C-7," and insert --C_7,--.

In Column 198, Line 4, delete "ARIDIB," and insert --ARID1B,--.

In Column 204, Line 20, delete "UBE2O," and insert --UBE2O,--.

In Column 204, Line 38, delete "C-7," and insert --C_7,--.

In Column 206, Line 34, delete "IN080," and insert --INO80,--.

In Column 209, Line 34, delete "CACNAiS," and insert --CACNA1S,--.

In Column 209, Line 60, delete "P01D1," and insert --POLD1,--.

In Column 210, Line 3, delete "C-7," and insert --C_7,--.

In Column 211, Line 20, delete "C-7," and insert --C_7,--.

In Column 212, Line 44, delete "FAT 1," and insert --FAT1,--.

In Column 213, Line 23, delete "C-7," and insert --C_7,--.

In Column 213, Line 52, delete "C-7," and insert --C_7,--.

In Column 218, Line 57, delete "C-7," and insert --C_7,--.

In Column 221, Line 12, delete "C-8," and insert --C_8,--.

In Column 221, Line 57, delete "KISSIR," and insert --KISS1R,--.

In Column 222, Line 25, delete "C-8," and insert --C_8,--.

CERTIFICATE OF CORRECTION (continued)
U.S. Pat. No. 11,484,581 B2

In Column 223, Line 21, delete "C-8," and insert --C_8,--.

In Column 223, Line 57, delete "QT" and insert --QT,--.

In Column 223, Line 59, delete "C-8," and insert --C_8,--.

In Column 224, Line 52, delete "C-8," and insert --C_8,--.

In Column 226, Line 38, delete "ARHGEFI1," and insert --ARHGEF11,--.

In Column 226, Line 52, delete "ClH" and insert --CLH--.

In Column 229, Line 47, delete "IFF01," and insert --IFFO1,--.

In Column 229, Line 60, delete "KISSIR," and insert --KISS1R,--.

In Column 233, Line 6, delete "ARHGEFI1," and insert --ARHGEF11,--.

In Column 233, Line 7, delete "C-8," and insert --C_8,--.

In Column 240, Line 46, delete "C-9," and insert --C_9,--.

In Column 241, Line 63, delete "G-10," and insert --G_10,--.

In Column 243, Line 15, delete "G-15," and insert --G_15,--.

In Column 243, Line 25, delete "G-7," and insert --G_7,--.

In Column 244, Line 20, delete "IFF01," and insert --IFFO1,--.

In Column 248, Line 27, delete "YCl" and insert --YCL--.

In Column 253, Line 39, delete "G-7," and insert --G_7,--.

In Column 254, Line 1, delete "CT" and insert --CT,--.

In Column 255, Line 9, delete "CACNAIF," and insert --CACNA1F,--.

In Column 255, Line 27, delete "XM_14121983.1," and insert --XM_014121983.1,--.

In Column 256, Line 46, delete "G-7," and insert --G_7,--.

In Column 259, Line 28, delete "GLIl," and insert --GLI1,--.

In Column 262, Line 10, delete "G-7," and insert --G_7,--.

CERTIFICATE OF CORRECTION (continued)
U.S. Pat. No. 11,484,581 B2

In Column 262, Line 66, delete "G-7," and insert --G_7,--.

In Column 263, Line 64, delete "G-7," and insert --G_7,--.

In Column 265, Line 36, delete "HISTIH1T," and insert --HIST1H1T,--.

In Column 266, Line 57, delete "G-7," and insert --G_7,--.

In Column 267, Line 22, delete "LIH" and insert --LLH--.

In Column 268, Line 15 (Approx.), delete "G7," and insert --G_7,--.

In Column 268, Line 20, delete "G-7," and insert --G_7,--.

In Column 268, Lines 34-35, delete "XM 005624449.2," and insert --XM_005624449.2,--.

In Column 269, Line 27, delete "XM005640052.2," and insert --XM_005640052.2,--.

In Column 270, Line 17, delete "HISTIHiT," and insert --HIST1H1T,--.

In Column 270, Line 58, delete "LUC102151792," and insert --LOC102151792,--.

In Column 270, Line 63, delete "PlG" and insert --PLG--.

In Column 272, Line 29, delete "C18Hllorf84," and insert --C18H11orf84,--.

In Column 273, Line 23, delete "(SEQTDNO:8930);" and insert --(SEQIDNO:8930);--.

In Column 274, Line 30, delete "CI8Hllorf85," and insert --CI8H11orf85,--.

In Column 274, Line 66, delete "G-7," and insert --G_7,--.

In Column 276, Line 15, delete "TNKS IBP1," and insert --TNKS1BP1,--.

In Column 276, Line 32, delete "G-7," and insert --G_7,--.

In Column 276, Line 51, delete "G-7," and insert --G_7,--.

In Column 278, Line 30, delete "MYOSA," and insert --MYO5A,--.

In Column 279, Line 29, delete "FAMIO1B," and insert --FAMl0lB,--.

In Column 280, Line 19, delete "AR" and insert --AR,--.

In Column 280, Line 36, delete "XM 014114498.1," and insert --XM_014114498.1,--.

CERTIFICATE OF CORRECTION (continued)
U.S. Pat. No. 11,484,581 B2

In Column 281, Line 7, delete "G-8," and insert --G_8,--.

In Column 281, Line 17, delete "MYOSA," and insert --MYO5A,--.

In Column 281, Line 56, delete "INSIGI," and insert --INSIG1,--.

In Column 281, Line 56, delete "G-8," and insert --G_8,--.

In Column 284, Line 62, delete "G-8," and insert --G_8,--.

In Column 286, Line 7, delete "ATP7B1," and insert --ATP7B,--.

In Column 286, Line 7, delete "G_9." and insert --G_9,--.

In Column 288, Line 46, delete "(SEQ1DNO:9465);" and insert --(SEQIDNO:9465);--.

In Column 288, Line 49, delete "T-7," and insert --T_7,--.

In Column 289, Line 22, delete "T-7," and insert --T_7,--.

In Column 290, Line 44, delete "Del." and insert --Del,--.

In Column 293, Line 66, delete "GLIPRiL1," and insert --GLIPR1L1,--.

In Column 295, Line 39, delete "D102," and insert --DIO2,--.

In Column 296, Line 16, delete "SERPINGI," and insert --SERPING1,--.

In Column 298, Line 20, delete "NIIH" and insert --NIIII--.

In Column 301, Line 38, delete "OR16A12," and insert --OR16Al2,--.

In Column 302, Line 53, delete "CHG" and insert --CIIG--.

In Column 304, Line 10, delete "T-7," and insert --T_7,--.

In Column 306, Line 45, delete "PlG" and insert --PLG--.

In Column 308, Line 21, delete "TJ7," and insert --T_7,--.

In Column 310, Line 48, delete "OR10A12," and insert --OR10Al2,--.

In Column 311, Line 30, delete "HIATLi," and insert --HIATL1,--.

In Column 312, Line 19, delete "(SEQIDNO: 10396);" and insert --(SEQIDNO:10396);--.

CERTIFICATE OF CORRECTION (continued)
U.S. Pat. No. 11,484,581 B2

In Column 312, Line 28, delete "ARFIPi," and insert --ARFIP1,--.

In Column 312, Line 60, delete "OR10A12," and insert --OR10Al2,--.

In Column 316, Line 4, delete "LUC100856036," and insert --LOC100856036,--.

In Column 319, Line 3, delete "T-9," and insert --T_9,--.

In Column 321, Line 22, delete "171B)." and insert --17B).--.

In Column 321, Line 54, delete "1D8" and insert --ID8--.

In the Claims

In Column 323, Claim 1, Line 47, delete "comprising" and insert --comprises--.

In Column 324, Claim 4, Line 5, delete "manlmary" and insert --mammary--.

In Column 324, Claim 8, Line 55, delete "Thl 7" and insert --Th17--.

In Column 324, Claim 10, Lines 62-63, delete "plasm on" and insert --plasmon--.

In Column 325, Claim 15, Line 28, delete "InterferonGamma," and insert --Interferon Gamma,--.

In Column 326, Claim 15, Line 5, delete "XtendIII," and insert --Xtend III,--.